US012195733B2

(12) United States Patent
Abudayyeh et al.

(10) Patent No.: US 12,195,733 B2
(45) Date of Patent: Jan. 14, 2025

(54) SYSTEMS, METHODS, AND COMPOSITIONS FOR SITE-SPECIFIC GENETIC ENGINEERING USING PROGRAMMABLE ADDITION VIA SITE-SPECIFIC TARGETING ELEMENTS (PASTE)

(71) Applicant: Massachusetts Institute of Technology, Cambridge, MA (US)

(72) Inventors: Omar Abudayyeh, Cambridge, MA (US); Jonathan Gootenberg, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 18/487,610

(22) Filed: Oct. 16, 2023

(65) Prior Publication Data

US 2024/0076662 A1 Mar. 7, 2024

Related U.S. Application Data

(63) Continuation of application No. 18/066,223, filed on Dec. 14, 2022, now Pat. No. 11,827,881, which is a continuation of application No. 17/649,308, filed on Jan. 28, 2022, now Pat. No. 11,572,556, which is a continuation of application No. 17/451,734, filed on Oct. 21, 2021, now abandoned.

(60) Provisional application No. 63/222,550, filed on Jul. 16, 2021, provisional application No. 63/094,803, filed on Oct. 21, 2020.

(51) Int. Cl.

| | |
|---|---|
| *C12N 15/85* | (2006.01) |
| *A61K 31/7105* | (2006.01) |
| *C12N 9/12* | (2006.01) |
| *C12N 9/22* | (2006.01) |
| *C12N 15/10* | (2006.01) |
| *C12N 15/11* | (2006.01) |
| *C12N 15/113* | (2010.01) |
| *C12N 15/90* | (2006.01) |

(52) U.S. Cl.
CPC ........ *C12N 15/111* (2013.01); *A61K 31/7105* (2013.01); *C12N 9/1276* (2013.01); *C12N 9/22* (2013.01); *C12N 15/102* (2013.01); *C12N 15/113* (2013.01); *C12N 15/85* (2013.01); *C12N 15/907* (2013.01); *C12N 2310/20* (2017.05); *C12N 2310/3519* (2013.01); *C12Y 207/07049* (2013.01)

(58) Field of Classification Search
None
See application file for complete search history.

(56) References Cited

U.S. PATENT DOCUMENTS

| | | |
|---|---|---|
| 9,023,649 B2 | 5/2015 | Mali et al. |
| 9,914,939 B2 | 3/2018 | Church et al. |
| 10,113,163 B2 | 10/2018 | Liu et al. |
| 10,125,361 B2 | 11/2018 | May et al. |
| 11,193,123 B2 | 12/2021 | Halperin |
| 11,299,731 B1 | 4/2022 | Held |
| 11,352,623 B2 | 6/2022 | Halperin |
| 11,447,770 B1 | 9/2022 | Liu et al. |
| 11,572,556 B2 | 2/2023 | Abudayyeh |
| 2011/0059502 A1 | 3/2011 | Chalasani |
| 2014/0186958 A1 | 7/2014 | Zhang et al. |
| 2014/0349400 A1 | 11/2014 | Noah et al. |
| 2015/0071898 A1 | 3/2015 | Liu et al. |
| 2018/0230464 A1 | 8/2018 | Zhong |
| 2019/0055543 A1 | 2/2019 | Tran et al. |
| 2019/0062734 A1 | 2/2019 | Cotta-Ramusino et al. |
| 2019/0330619 A1 | 10/2019 | Smith et al. |
| 2020/0109398 A1 | 4/2020 | Rubens |
| 2022/0119848 A1 | 4/2022 | Doudna |
| 2022/0145293 A1 | 5/2022 | Abudayyeh et al. |
| 2022/0154224 A1 | 5/2022 | Abudayyeh et al. |
| 2023/0135673 A1 | 5/2023 | Abudayyeh et al. |
| 2023/0279391 A1 | 9/2023 | Abudayyeh et al. |

FOREIGN PATENT DOCUMENTS

| | | |
|---|---|---|
| WO | 2015035139 A2 | 3/2015 |
| WO | 2015195798 A1 | 12/2015 |
| WO | 2016205728 A1 | 12/2016 |
| WO | 2017151719 A1 | 9/2017 |
| WO | 2018049161 A1 | 3/2018 |
| WO | 2018049168 A1 | 3/2018 |
| WO | 20180165629 A1 | 9/2018 |
| WO | 2019051097 A1 | 3/2019 |

(Continued)

OTHER PUBLICATIONS

Burke, W. D. et al., Molecular Biology and Evolution 2003, 20(8), 1260-1270).
Wang et al., 2010, Genome Res. 20, 19-27.
Bannert and Kurth, 2006, Proc. Natl. Acad. USA 101, 14572-14579.
Lander et al., 2001, Nature 409, 860-921; Hua-Van et al., 2011, Biol. Dir. 6, 19.
Graham et al. (1973) Virology, 52: 456.
Anzalone et al., Programmable Large DNA Deletion, Replacement, Integration, and Inversion with Twin Prime Editing and Site-Specific Recombinases, https://doi.org/10.1101/2021.11.01.466790.

(Continued)

*Primary Examiner* — Celine X Qian
(74) *Attorney, Agent, or Firm* — Lathrop GPM LLP; Laura A. Labeots

(57) ABSTRACT

This disclosure provides systems, methods, and compositions for site-specific genetic engineering using Programmable Addition via Site-Specific Targeting Elements (PASTE). PASTE comprises the addition of an integration site into a target genome followed by the insertion of one or more genes of interest or one or more nucleic acid sequences of interest at the site. PASTE combines gene editing technologies and integrase technologies to achieve unidirectional incorporation of genes in a genome for the treatment of diseases and diagnosis of disease.

23 Claims, 145 Drawing Sheets

Specification includes a Sequence Listing.

(56) References Cited

FOREIGN PATENT DOCUMENTS

| | | | |
|---|---|---|---|
| WO | 2019118935 | A1 | 6/2019 |
| WO | 2020047124 | A1 | 3/2020 |
| WO | 2020191153 | A2 | 9/2020 |
| WO | 2020191171 | A1 | 9/2020 |
| WO | 2020191233 | A1 | 9/2020 |
| WO | 2020191234 | A1 | 9/2020 |
| WO | 2020191239 | A1 | 9/2020 |
| WO | 2020191242 | A1 | 9/2020 |
| WO | 2020191243 | A1 | 9/2020 |
| WO | 2020191245 | A1 | 9/2020 |
| WO | 2020191246 | A1 | 9/2020 |
| WO | 2020191248 | A1 | 9/2020 |
| WO | 2020191249 | A1 | 9/2020 |
| WO | 2020247587 | A1 | 12/2020 |
| WO | 2021046243 | A2 | 3/2021 |
| WO | 2021072328 | A1 | 4/2021 |
| WO | 2021138469 | A1 | 7/2021 |
| WO | 2021188840 | A1 | 9/2021 |
| WO | 2021226558 | A1 | 11/2021 |
| WO | 2022067130 | A2 | 3/2022 |
| WO | 2022087235 | A1 | 4/2022 |
| WO | 2022098885 | A1 | 5/2022 |

OTHER PUBLICATIONS

Gaj, et al., Genome-Editing Technologies: Principles and Applications, Cold Spring Harbor Perspectives in Biology 2016;8:a023754.

Ata-Abadi, "Construction of a new minicircle DNA carrying an enhanced green florescent protein reporter gene for efficient expression into mammalian cell lines", Mol. Biol. Rep., 2015, 42: 1175-1185.

Anzalone, A., et al., "Programmable deletion, replacement, integration and inversion of large DNA sequences with twin prime editing," Nat. Biotechnol., 2022, 40(5):731-740.

Chen, P., et al., "Enhanced prime editing systems by manipulating cellular determinants of editing outcomes," Cell, 2021, 184(22):5635-5652.e29.

Guilinger, J., et al., "Fusion of catalytically inactive Cas9 to FokI nuclease improves the specificity of genome modification," Nat. Biotechnol., 2014, 32(6):577-582.

Halperin, S., et al., "CRISPR-guided DNA polymerases enable diversification of all nucleotides in a tunable window," Nature, 2018, 560(7717):248-252. doi: 10.1038/s41586-018-0384-8.

Ioannidi, E., et al., "Drag-and-drop genome insertion without DNA cleavage with CRISPR-directed integrases," bioRxiv, 2021. doi: 10.1101/2021.11.01.466786.

Jiang, T., et al., "Deletion and replacement of long genomic sequences using prime editing," Nat. Biotechnol., 2022, 40(2):227-234.

Krzywkowski, T., et al., "Limited reverse transcriptase activity of phi29 DNA polymerase," Nucleic Acids Res., 2018, 46(7):3625-3632.

Lee, H. K., et al., "Simultaneous targeting of linked loci in mouse embryos using base editing," Sci. Rep., 2019, 9(1):1662.

Lin, Q., et al., "High-efficiency prime editing with optimized, paired pegRNAs in plants," Nat. Biotechnol., 2021, 39(8):923-927.

Marzec, M., et al., "Prime Editing: A New Way for Genome Editing," Trends Cell Biol., 2020, 30(4):257-259.

Mohr, G., et al., "A Reverse Transcriptase-Cas1 Fusion Protein Contains a Cas6 Domain Required for Both CRISPR RNA Biogenesis and RNA Spacer Acquisition," Molecular Cell, 2018, 72(4):700-714, available at https://doi.org/10.1016/j.molcel.2018.09.013.

Nelson, J., et al., "Engineered pegRNAs improve prime editing efficiency," Nat. Biotechnol., 2022, 40(3):402-410. https://doi.org/10.1038/s41587-021-01039-7.

Pallarès-Masmitjà, M., et al., "Find and cut-and-transfer (FiCAT) mammalian genome engineering," Nat. Commun., 2021, 12(1):7071. https://doi.org/10.1038/s41467-021-27183-x.

Ran, F. A., et al., "Double Nicking by RNA-Guided CRISPR Cas9 for Enhanced Genome Editing Specificity," Cell, 2013, 154(6):1380-89.

Sharon, E., et al., "Functional Genetic Variants Revealed by Massively Parallel Precise Genome Editing," Cell, 2018, 175(2):544-557.e16.

Su, Y., et al., "Human DNA polymerase n has reverse transcriptase activity in cellular environments," J. Biol. Chem., 2019, 294(15):6073-6081.

Wang, J., et al., "Efficient targeted insertion of large DNA fragments without DNA donors," Nat. Methods, 2022, 19(3):331-340. https://doi.org/10.1038/s41592-022-01399-1.

Wang, Z., et al., "Optimized paired-sgRNA/Cas9 cloning and expression cassette triggers high-efficiency multiplex genome editing in kiwifruit," Plant Biotechnol. J., 2018, 16(8):1424-1433.

Xu, W., et al., "Multiplex Nucleotide Editing by High-Fidelity Cas9 Variants with Improved Efficiency in Rice," BMC Plant Biol., 2019, 19(1):511.

Yang, L., et al., "One Prime for All Editing," Cell, 2019, 179(7):1448-1450.

Flotte Human Gene Therapy, 2019, vol. 30, No. 2, pp. 1445-1446). (Year: 2019).

Anzalone et al., Nature 2019, vol. 576, 149-157, and methods and supplement. (Year: 2019).

Anzalone et al., Programmable Deletion, Replacement, Integration and Inversion of Large DNA Sequences with Twin Prime Editing, Nature Biotechnology, Dec. 9, 2021.

Innis et al., A Novel Bxb1 Integrase RMCE System for High Fidelity Site-Specific Integration of mAb Expression Cassette in CHO Cells, Biotechnology and BioEngineering, John Wiley, Hoboken, USA, vol. 114, No. 8, Mar. 14, 2017, pp. 1837-1846.

Merrick, et al., Serine Integrases: Advancing Synthetic Biology, ACS Synthetic Biology, vol. 7, No. 2, Jan. 9, 2018, pp. 299-310.

Lee et al., Conditional Targeting of Ispd Using Paired Cas9 Nickase and a Single DNA Template in Mice, FEBS Open Bio, vol. 4, No. 1, Jul. 1, 2014, pp. 637-642.

PCT Application No. PCT/US2021/056006, International Search Report and Written Opinion, dated Feb. 23, 2022, 20 pages.

Maeder et al., Development of a Gene-Editing Approach to Restore Vision Loss in Leber Congenital Amaurosis Type 10, Letters, Nature Medicine, 25, 229-233 (2019).

Anzalone, et al., Genome Editing with CRISPR-Cas Nucleases, Base Editors, Transposases and Prime Editors, Nat. Biotechnol. 38, 824-844 (2020).

Jiang et al., Deletion and Replacement of Long Genomic Sequences Using Prime Editing. Nat. Biotechnol. 1-8 (2021).

Hsu, P. D., Lander, E. S. & Zhang, F. Development and applications of CRISPR-Cas9 for genome engineering. Cell 157, 1262-1278 (2014).

Wright, A. V., Nuñez, J. K. & Doudna, J. A. Biology and Applications of CRISPR Systems: Harnessing Nature's Toolbox for Genome Engineering. Cell 164, 29-44 (2016).

Nami, F. et al. Strategies for In Vivo Genome Editing in Nondividing Cells. Trends Biotechnol. 36, 770-786 (2018).

Suzuki, K. et al. In vivo genome editing via CRISPR/Cas9 mediated homology-independent targeted integration. Nature 540, 144-149 (2016).

Mali, P. et al. RNA-guided human genome engineering via Cas9. Science 339, 823-826 (2013).

Cong, L. et al. Multiplex genome engineering using CRISPR/Cas systems. Science 339, 819-823 (2013).

Rouet, P., Smih, F. & Jasin, M. Introduction of double-strand breaks into the genome of mouse cells by expression of a rare-cutting endonuclease. Mol. Cell. Biol. 14, 8096-8106 (1994).

Rudin, N., Sugarman, E. & Haber, J. E. Genetic and physical analysis of double-strand break repair and recombination in *Saccharomyces cerevisiae*. Genetics 122, 519-534 (1989).

Chapman, J. R., Taylor, M. R. G. & Boulton, S. J. Playing the end game: DNA double-strand break repair pathway choice. Mol. Cell 47, 497-510 (2012).

Geisinger, J. M. & Stearns, T. CRISPR/Cas9 treatment causes extended TP53-dependent cell cycle arrest in human cells. Nucleic Acids Res. 48, 9067-9081 (2020).

Wang, H. et al. Development of a Self-Restricting CRISPR-Cas9 System to Reduce Off-Target Effects. Mol Ther Methods Clin Dev 18, 390-401 (2020).

(56) References Cited

OTHER PUBLICATIONS

Kanca, O. et al. An efficient CRISPR-based strategy to insert small and large fragments of DNA using short homology arms. Elife 8, (2019).
Gaudelli, N. M. et al. Programmable base editing of A•T to G•C in genomic ONA without DNA cleavage. Nature 551, 464-471 (2017).
Komor, A. C., Kim, Y. B., Packer, M. S., Zuris, J. A. & Liu, D. R. Programmable editing of a target base in genomic DNA without double-stranded DNA cleavage. Nature 533, 420-424 (2016).
Rees, H. A. & Liu, D. R. Base editing: precision chemistry on the genome and transcriptome of living cells. Nat. Rev. Genet. 19, 770-788 (2018).
Anzalone, A. V. et al. Search-and-replace genome editing without double-strand breaks or donor DNA. Nature 576, 149-157 (2019).
Ivics, Z., Hackett, P. B., Plasterk, R. H. & Izsvák, Z. Molecular reconstruction of Sleeping Beauty, a Tc1-like transposon from fish, and its transposition in human cells. Cell 91, 501-510 (1997).
Choi, J. et al. Precise genomic deletions using paired prime editing. Nat. Biotechnol. 1-9 (2021).
Calos, M. P. The C31 Integrase System for Gene Therapy. Curr. Gene Ther. 6, 633-645 (2006).
Mulholland, C. B. et al. A modular open platform for systematic functional studies under physiological conditions. Nucleic Acids Res. 43, e112 (2015).
Ehrhardt, A., Engler, J. A., Xu, H., Cherry, A. M. & Kay, M. A. Molecular Analysis of Chromosomal Rearrangements in Mammalian Cells After øC31-Mediated Integration. Hum. Gene Ther. 17, 1077-1094 (2006).
Liu, J., Jeppesen, I., Nielsen, K. & Jensen, T. G. Phi c31 integrase induces chromosomal aberrations in primary human fibroblasts. Gene Ther. 13, 1188-1190 (2006).
Kovac, A. et al. RNA-guided retargeting of Sleeping Beauty transposition in human cells. Elife 9, (2020).
Ma, S. et al. Enhancing site-specific DNA integration by a Cas9 nuclease fused with a DNA donor-binding domain. Nucleic Acids Res. 48, 10590-10601 (2020).
Chen, S. P. & Wang, H. H. An Engineered Cas-Transposon System for Programmable and Site-Directed DNA Transpositions. CRISPR J 2, 376-394 (2019).
Bhatt, S. & Chalmers, R. Targeted DNA transposition using a dCas9-transposase fusion protein. bioRxiv 571653 (2019) doi:10.1101/571653.
Hew, B. E., Sato, R., Mauro, D., Stoytchev, I. & Owens, J. B. RNA-guided piggyBac transposition in human cells. Synth. Biol. 4, ysz018 (2019).
Chaikind, B., Bessen, J. L., Thompson, D. B., Hu, J. H. & Liu, D. R. A programmable Cas9- serine recombinase fusion protein that operates on DNA sequences in mammalian cells. Nucleic Acids Res. 44, 9758-9770 (2016).
Akopian, A., He, J., Boocock, M. R. & Stark, W. M. Chimeric recombinases with designed DNA sequence recognition. Proc. Natl. Acad. Sci. U. S. A. 100, 8688-8691 (2003).
Gordley, R. M., Smith, J. D., Gräslund, T. & Barbas, C. F., 3rd. Evolution of programmable zinc finger-recombinases with activity in human cells. J. Mol. Biol. 367, 802-813 (2007).
Mercer, A. C., Gaj, T., Fuller, R. P. & Barbas, C. F., 3rd. Chimeric TALE recombinases with programmable DNA sequence specificity. Nucleic Acids Res. 40, 11163-11172 (2012).
Gersbach, C. A., Gaj, T., Gordley, R. M., Mercer, A. C. & Barbas, C. F. Targeted plasmid integration into the human genome by an engineered zinc-finger recombinase. Nucleic Acids Res. 39, 7868-7878 (2011).
Prorocic, M. M. et al. Zinc-finger recombinase activities in vitro. Nucleic Acids Res. 39, 9316-9328 (2011).
Zhang, Q., Azarin, S. M. & Sarkar, C. A. Model-guided engineering of DNA sequences with predictable site-specific recombination rates. bioRxiv 2021.08.02.454698 (2021) doi:10.1101/2021.08.02.454698.

Peters, J. E., Makarova, K. S., Shmakov, S. & Koonin, E. V. Recruitment of CRISPR-Cas systems by Tn7-like transposons. Proc. Natl. Acad. Sci. U. S. A. 114, E7358-E7366 (2017).
Strecker, J. et al. RNA-guided DNA insertion with CRISPR-associated transposases. Science (2019) doi:10.1126/science.aax9181.
Klompe, S. E., Vo, P. L. H., Halpin-Healy, T. S. & Sternberg, S. H. Transposon-encoded CRISPR-Cas systems direct RNA-guided DNA integration. Nature 1 (2019).
Xu, Z. et al. Accuracy and efficiency define Bxb1 integrase as the best of fifteen candidate serine recombinases for the integration of DNA into the human genome. BMC Biotechnol. 13, 87 (2013).
Kay, M. A., He, C.-Y. & Chen, Z.-Y. A robust system for production of minicircle DNA vectors. Nat. Biotechnol. 28, 1287-1289 (2010).
Oscorbin, I. P., Wong, P. F., Boyarskikh, U. A., Khrapov, E. A. & Filipenko, M. L. The attachment of a DNA-binding Sso7d-like protein improves processivity and resistance to inhibitors of M-MuLV reverse transcriptase. FEBS Lett. 594, 4338-4356 (2020).
Ghosh, P., Kim, A. I. & Hatfull, G. F. The orientation of mycobacteriophage Bxb1 integration is solely dependent on the central dinucleotide of attP and attB. Mol. Cell 12, 1101-1111 (2003).
Keravala, A. et al. A diversity of serine phage integrases mediate site-specific recombination in mammalian cells. Molecular Genetics and Genomics vol. 276 (2006).
Singh, S., Ghosh, P. & Hatfull, G. F. Attachment site selection and identity in Bxb1 serine integrase-mediated site-specific recombination. PLoS Genet. 9, e1003490 (2013).
Jusiak, B. et al. Comparison of Integrases Identifies Bxb1-GA Mutant as the Most Efficient Site-Specific Integrase System in Mammalian Cells. ACS Synth. Biol. 8, 16-24 (2019).
Schwinn, M. K. et al. CRISPR-Mediated Tagging of Endogenous Proteins with a Luminescent Peptide. ACS Chem. Biol. 13, 467-474 (2018).
Lin, S., Staahl, B. T., Alla, R. K. & Doudna, J. A. Enhanced homology-directed human genome engineering by controlled timing of CRISPR/Cas9 delivery. Elife 3, e04766 (2014).
Schnepp, B. C., Jensen, R. L., Chen, C.-L., Johnson, P. R. & Clark, K. R. Characterization of adeno-associated virus genomes isolated from human tissues. J. Virol. 79, 14793-14803 (2005).
Wold, W. S. M. & Toth, K. Adenovirus vectors for gene therapy, vaccination and cancer gene therapy. Curr. Gene Ther. 13, 421-433 (2013).
Wesselhoeft, R. A., Kowalski, P. S. & Anderson, D. G. Engineering circular RNA for potent and stable translation in eukaryotic cells. Nat. Commun. 9, 2629 (2018).
Azuma, H. et al. Robust expansion of human hepatocytes in Fah-/-/Rag2-/-/112rg-/-mice. Nat. Biotechnol. 25, 903-910 (2007).
Bateman, A. et al. UniProt: the universal protein knowledgebase in 2021. Nucleic Acids Res. (2020).
Amberger, J. S., Bocchini, C. A., Schiettecatte, F., Scott, A. F. & Hamosh, A. OMIM.org: Online Mendelian Inheritance in Man (OMIM®), an online catalog of human genes and genetic disorders. Nucleic Acids Res. 43, D789-98 (2015).
Ruan, J. et al. Efficient Gene Editing at Major CFTR Mutation Loci. Mol. Ther. Nucleic Acids 16, 73-81 (2019).
Mackay, D. S. et al. Screening of a large cohort of leber congenital amaurosis and retinitis pigmentosa patients identifies novel LCA5 mutations and new genotype-phenotype correlations. Hum. Mutat. 34, 1537-1546 (2013).
Marson, F. A. L., Bertuzzo, C. S. & Ribeiro, J. D. Classification of CFTR mutation classes. The Lancet. Respiratory medicine vol. 4 e37-e38 (2016).
Eyquem, J. et al. Targeting a CAR to the TRAC locus with CRISPR/Cas9 enhances tumour rejection. Nature 543, 113-117 (2017).
Tareen, A. & Kinney, J. B. Logomaker: beautiful sequence logos in Python. Bioinformatics 36, 2272-2274 (2020).
Su, Q., Sena-Esteves, M. & Gao, G. Purification of the recombinant Adenovirus by cesium chloride gradient centrifugation. Cold Spring Harb. Protoc. 2019, db.prot095547 (2019).
Brown et al., "Serine recombinases as tools for genome engineering." Methods, 2011; 53(4):372-9.

(56) References Cited

OTHER PUBLICATIONS

Hirano et al., "Site-specific recombinases as tools for heterologous gene integration." Appl. Microbiol. Biotechnol. 2011; 92(2):227-39.
Chavez and Calos, "Therapeutic applications of the φC31 integrase system." Curr. Gene Ther. 2011; 11(5):375-81.
Turan and Bode, "Site-specific recombinases: from tag-and-target- to tag-and-exchange-based genomic modifications." FASEB J. 2011; 25(12):4088-107.
Venken and Bellen, "Genome-wide manipulations of Drosophila melanogaster with transposons, Flp recombinase, and φC31 integrase." Methods Mol. Biol. 2012; 859:203-28.
Murphy, "Phage recombinases and their applications." Adv. Virus Res. 2012; 83:367-414.
Zhang et al., "Conditional gene manipulation: Creating a new biological era." J. Zhejiang Univ. Sci. B. 2012; 13(7):511-24.
Karpenshif and Bernstein, "From yeast to mammals: recent advances in genetic control of homologous recombination." DNA Repair (Amst). 2012; 1; 11(10):781-8.
Groth et al., "Phage integrases: biology and applications." J. Mol. Biol. 2004; 335, 667-678.
Gordley et al., "Synthesis of programmable integrases." Proc. Natl. Acad. Sci. USA. 2009; 106, 5053-5058.
Moss, W. N. et al., RNA Biol. 2011, 8(5), 714-718.

PASTE literature
ACTB (cytoskeletal)
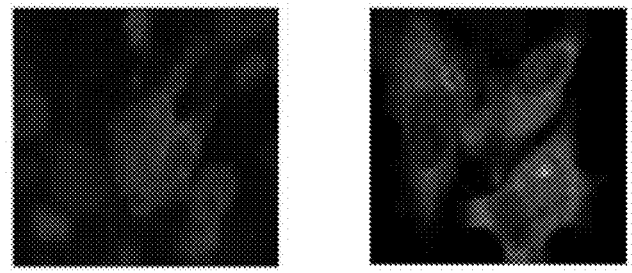
SUPT16H (nucleus)
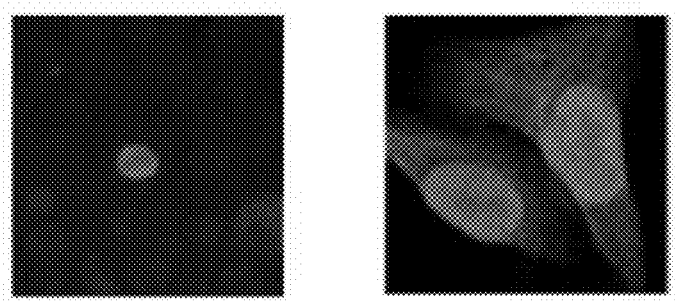
FIG. 28A PASTE  literature
NOLC1 (fibrillar center)
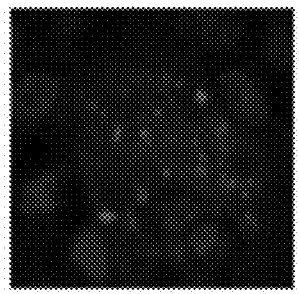 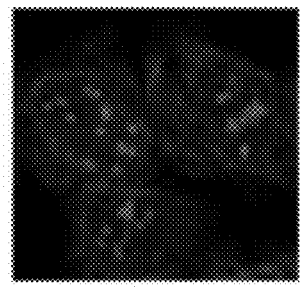
SRRM2 (nuclear speckles)
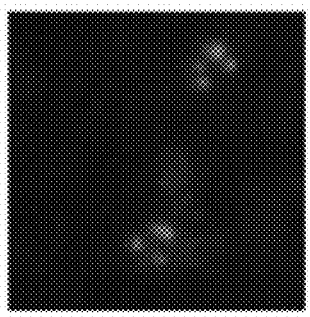 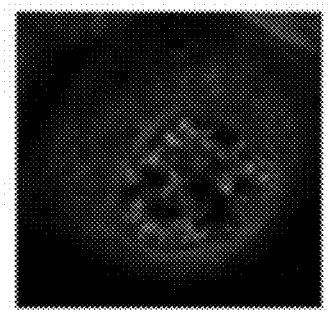
FIG. 28B PASTE literature
LMNB1 (nuclear membrane)
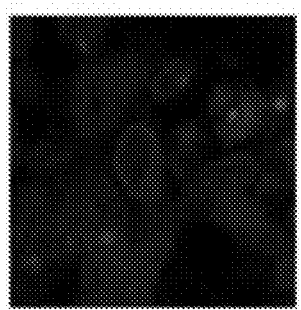 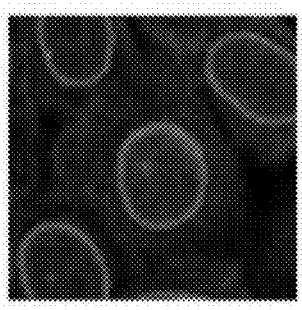
DEPDC4 (aggresome)
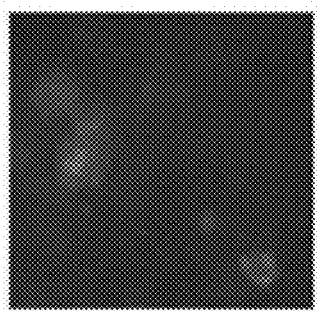 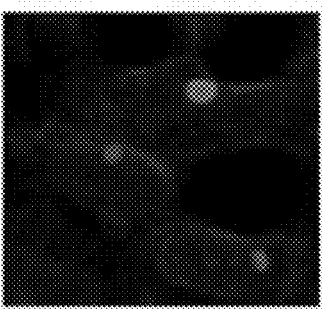
FIG. 28C

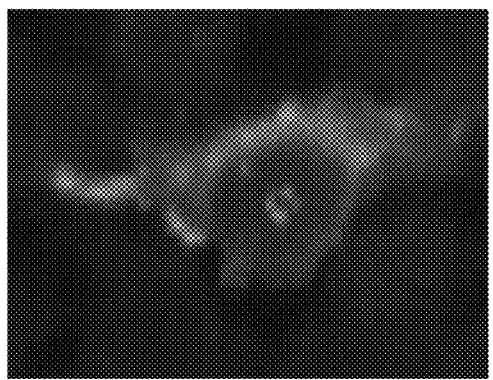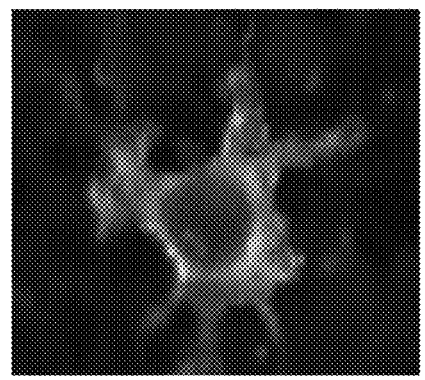
FIG. 28F

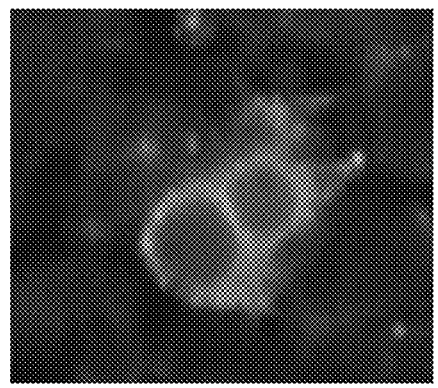 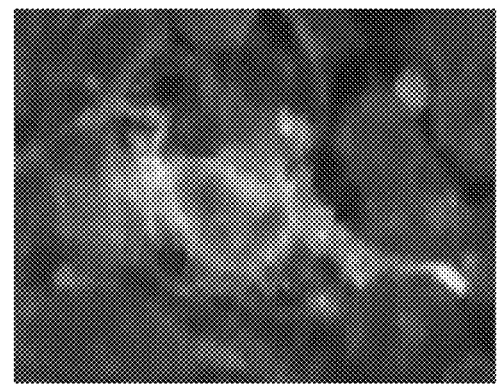
FIG. 28G

PASTE pegRNA Design
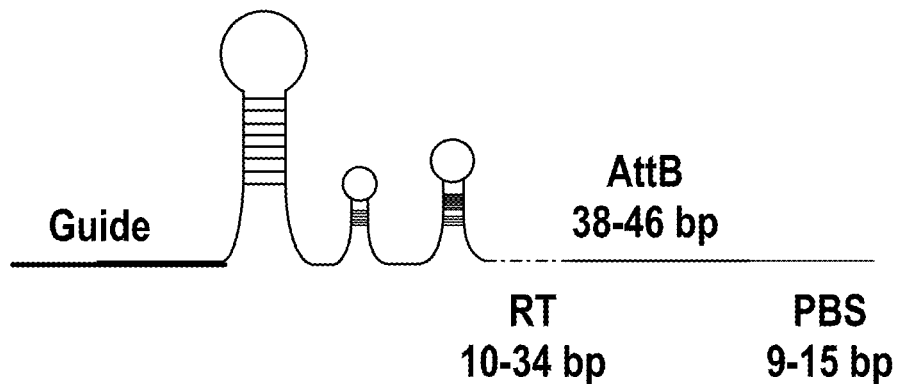
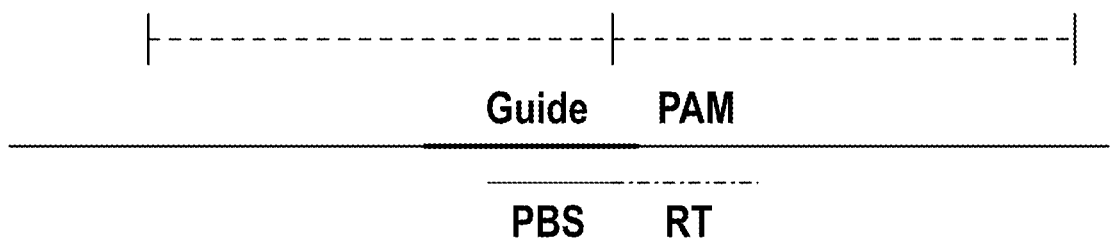
Target Considerations
FIG. 31A

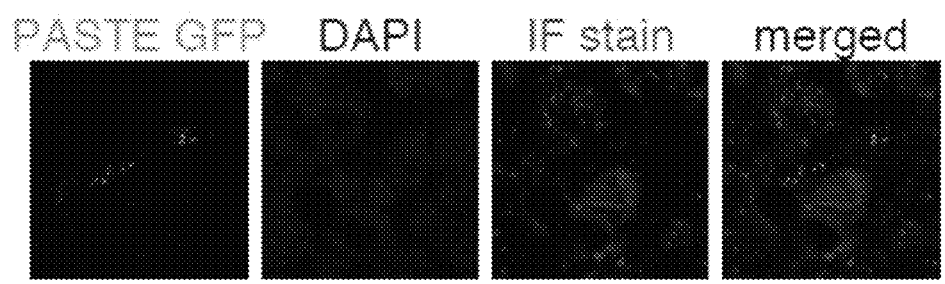
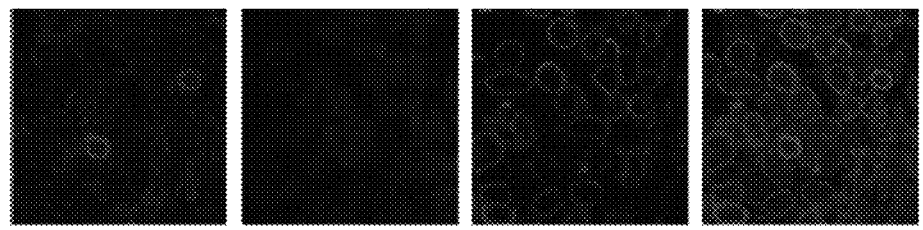
FIG. 34E

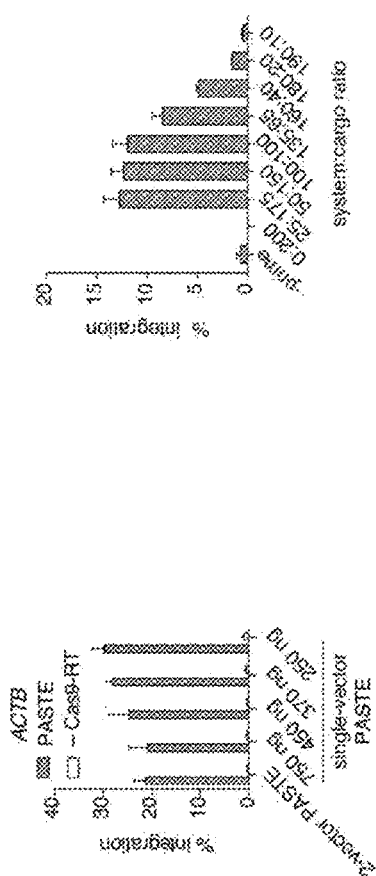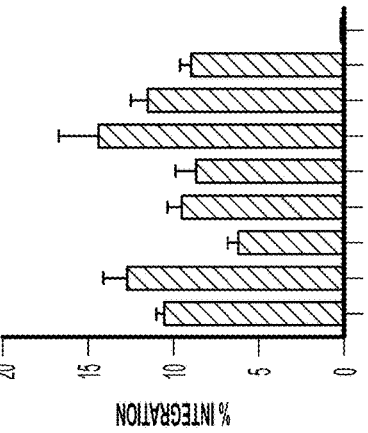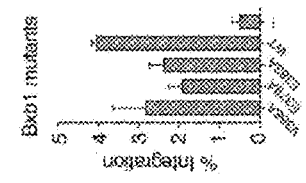
FIG. 49A
FIG. 49B
FIG. 49C
FIG. 49D
FIG. 49E
FIG. 49F

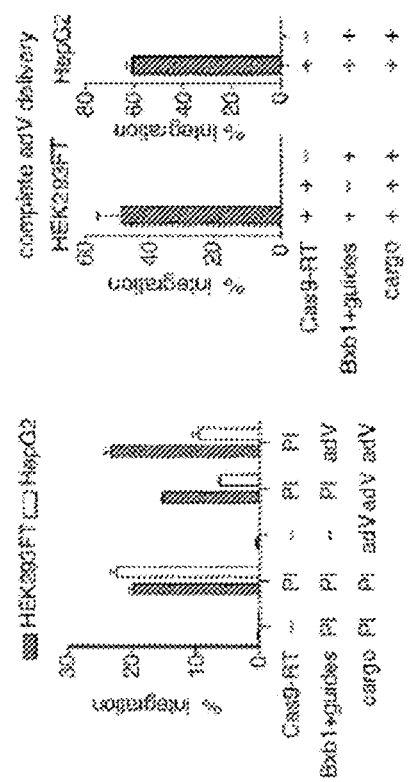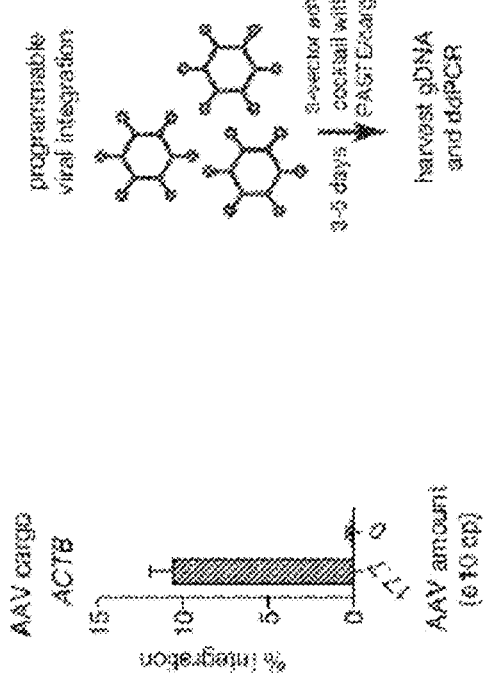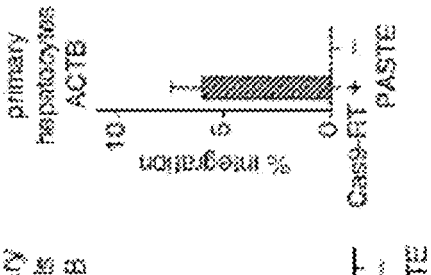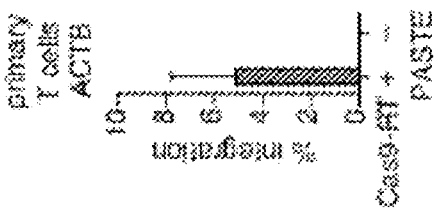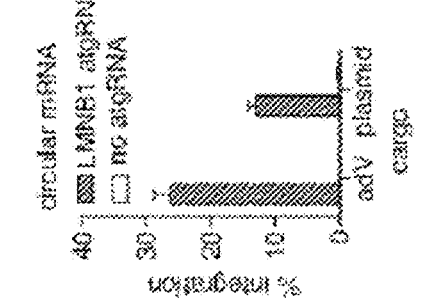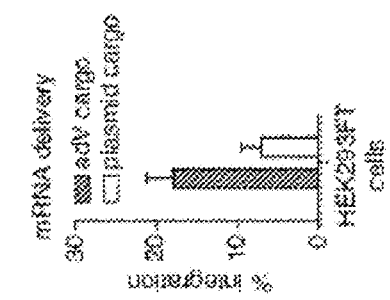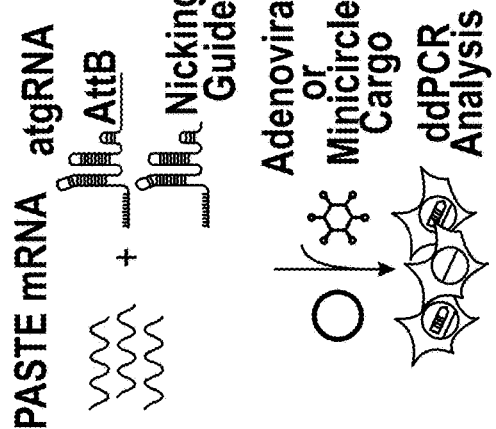

SYSTEMS, METHODS, AND COMPOSITIONS FOR SITE-SPECIFIC GENETIC ENGINEERING USING PROGRAMMABLE ADDITION VIA SITE-SPECIFIC TARGETING ELEMENTS (PASTE)

CROSS REFERENCE TO RELATED APPLICATIONS

This application is a continuation of U.S. application Ser. No. 18/066,223, filed Dec. 14, 2022, which is a continuation of U.S. application Ser. No. 17/649,308, filed Jan. 28, 2022, which is a continuation of U.S. application Ser. No. 17/451,734, filed Oct. 21, 2021, which claims the benefit of U.S. Provisional Patent Application Ser. No. 63/222,550, filed Jul. 16, 2021 and U.S. Provisional Patent Application Ser. No. 63/094,803, filed Oct. 21, 2020. The entire contents of the above-referenced patent applications are incorporated by reference in their entirety herein.

SEQUENCE LISTING

The instant application contains a Sequence Listing which has been submitted electronically in XML format and is hereby incorporated by reference in its entirety. Said XML file, created on Dec. 14, 2022, is named 737607_083474_016CON2_SL_ST26v2.xml and is 775,000 bytes in size.

FIELD OF DISCLOSURE

The subject matter disclosed herein is generally directed to systems, methods, and compositions for site-specific genetic engineering using Programmable Addition via Site-Specific Targeting Elements (PASTE) for the treatment of diseases and diagnostics.

BACKGROUND

Editing genomes using the RNA-guided DNA targeting principle of CRISPR-Cas (Clustered Regularly Interspaced Short Palindromic Repeats-CRISPR associated proteins) immunity has been widely exploited and has become a powerful genome editing means for a wide variety of applications. The main advantage of CRISPR-Cas system lies in the minimal requirement for programmable DNA interference: an endonuclease, such as a Cas9, Cas12, or any programmable nucleases, guided by a customizable dual-RNA structure. Cas9 is a multi-domain enzyme that uses an HNH nuclease domain to cleave the target strand. The CRISPR/Cas9 protein-RNA complex is localized on the target by a guide RNA (guide RNA), then cleaved to generate a DNA double strand break (dsDNA break, DSB). After cleavage, DNA repair mechanisms are activated to repair the cleaved strand. Repair mechanisms are generally from one of two types: non-homologous end joining (NHEJ) or homologous recombination (HR). In general, NHEJ dominates the repair, and, being error prone, generates random indels (insertions or deletions) causing frame shift mutations, among others. In contrast, HR has a more precise repairing capability and is potentially capable of incorporating the exact substitution or insertion. To enhance HR, several techniques have been tried, for example: combination of fusion proteins of Cas9 nuclease with homology-directed repair (HDR) effectors to enforce their localization at DSBs, introducing an overlapping homology arm, or suppression of NHEJ. Most of these techniques rely on the host DNA repair systems.

Recently, new guided editors have been developed, such as guided prime editors (PE) PE1, PE2, and PE3, e.g., Liu, D. et al., Nature 2019, 576, 149-157. These PEs are reverse transcriptase (RT) fused with Cas 9 H 840A nickase (Cas9n (H840A)), and the genome editing is achieved using a prime-editing guide RNA (pegRNA). Despite these developments, programmable gene integration is still generally dependent on cellular pathways or repair processes.

Therefore, there is a need for more effective tools for gene editing and delivery.

SUMMARY

The present disclosure provides a method of site-specific integration of a nucleic acid into a cell genome. The method comprises incorporating an integration site at a desired location in the cell genome by introducing into the cell a DNA binding nuclease linked to a reverse transcriptase domain, wherein the DNA binding nuclease comprises a nickase activity; and a guide RNA (gRNA) comprising a primer binding sequence linked to an integration sequence, wherein the gRNA interacts with the DNA binding nuclease and targets the desired location in the cell genome, wherein the DNA binding nuclease nicks a strand of the cell genome and the reverse transcriptase domain incorporates the integration sequence of the gRNA into the nicked site, thereby providing the integration site at the desired location of the cell genome. The method further comprises integrating the nucleic acid into the cell genome by introducing into the cell a DNA or RNA strand comprising the nucleic acid linked to a sequence that is complementary or associated to the integration site, and an integration enzyme, wherein the integration enzyme incorporates the nucleic acid into the cell genome at the integration site by integration, recombination, or reverse transcription of the sequence that is complementary or associated to the integration site, thereby introducing the nucleic acid into the desired location of the cell genome of the cell.

In some embodiments, the gRNA can be hybridized to a complementary strand of the cell genome to the genomic strand that is nicked by the DNA binding nuclease.

In some embodiments, the integration enzyme can be introduced as a peptide or a nucleic acid encoding the same.

In some embodiments, the DNA binding nuclease can be introduced as a peptide or a nucleic acid encoding the same.

In some embodiments, the DNA or RNA strand comprising the nucleic acid can be introduced into the cell as a minicircle, a plasmid, mRNA or a linear DNA.

In some embodiments, the DNA or RNA strand comprising the nucleic acid can be between 1000 bp and 10,000 bp.

In some embodiments, the DNA or RNA strand comprising the nucleic acid can be more than 10,000 bp.

In some embodiments, the DNA or RNA strand comprising the nucleic acid can be less than 1000 bp.

In some embodiments, the DNA comprising the nucleic acid can be introduced into the cell as a minicircle.

In some embodiment, the minicircle cannot comprise sequences of a bacterial origin.

In some embodiments, the DNA binding nuclease can be linked to a reverse transcriptase domain and the integration enzyme can be linked via a linker. The linker can be cleavable. The linker can be non-cleavable. The linker can be replaced by two associating binding domains of the DNA binding nuclease linked to a reverse transcriptase.

In some embodiments, the integration enzyme can be selected from the group consisting of Cre, Dre, Vika, Bxb1, φC31, RDF, FLP, φBT1, R1, R2, R3, R4, R5, TP901-1, A118, φFC1, φC1, MR11, TG1, φ370.1, Wβ, BL3, SPBc, K38, Peaches, Veracruz, Rebeuca, Theia, Benedict, KSSJEB, PattyP, Doom, Scowl, Lockley, Switzer, Bob3, Troube, Abrogate, Anglerfish, Sarfire, SkiPole, Conceptll, Museum, Severus, Airmid, Benedict, Hinder, ICleared, Sheen, Mundrea, BxZ2, φRV, retrotransposases encoded by R2, L1, Tol2 Tc1, Tc3, Mariner (Himar 1), Mariner (mos 1), and Minos, and any mutants thereof.

In some embodiments, the integration enzyme can be Bxb1 or a mutant thereof.

In some embodiments, the integration site can be selected from an attB site, an attP site, an attL site, an attR site, a lox71 site a Vox site, or a FRT site.

In some embodiments, the DNA binding nuclease comprising a nickase activity can be selected from Cas9-D10A, Cas9-H840A, and Cas12a/b nickase.

In some embodiments, the reverse transcriptase domain can be selected from the group consisting of Moloney Murine Leukemia Virus (M-MLV) reverse transcriptase domain, transcription xenopolymerase (RTX), avian myeloblastosis virus reverse transcriptase (AMV-RT), and Eubacterium rectale maturase RT (MarathonRT).

In some embodiments, the reverse transcriptase domain can comprise a mutation relative to the wild-type sequence.

In some embodiments, the M-MLV reverse transcriptase domain can comprise one or more mutations selected from the group consisting of D200N, T306K, W313F, T330P and L603W.

In some embodiments, the method can further comprise introducing a second nicking guide RNA (ngRNA). The ngRNA can direct nicking at 90 bases downstream of the gRNA nick on a complementary strand.

In some embodiments, the gRNA, the nucleic acid encoding the DNA binding nuclease, the reverse transcriptase, the DNA comprising nucleic acid linked to a complementary integration site, the integration enzyme, and optionally the ngRNA can be introduced into a cell in a single reaction.

In some embodiments, the gRNA, the nucleic acid encoding the DNA binding nuclease, the reverse transcriptase, the DNA comprising nucleic acid linked to a complementary integration site, the integration enzyme, and optionally the ngRNA can be introduced using a virus, a RNP, an mRNA, a lipid, or a polymeric nanoparticle.

In some embodiments, the nucleic acid can be a reporter gene. The reporter gene can be a fluorescent protein.

In some embodiments, the cell can be a dividing cell.

In some embodiments, the cell can be a non-dividing cell.

In some embodiments, the desired location in the cell genome can be the locus of a mutated gene.

In some embodiments, the nucleic acid can be a degradation tag for programmable knockdown of proteins in the presence of small molecules.

In some embodiments, the cell can be a mammalian cell, a bacterial cell or a plant cell.

In some embodiments, nucleic acid can be a T-cell receptor (TCR), a chimeric antigen receptor (CAR), an interleukin, a cytokine, or an immune checkpoint gene for integration into a T-cell or natural killer (NK) cell. The TCR, the CAR, the interleukin, the cytokine, or the immune checkpoint gene can be incorporated into the target site of the T-cell or NK cell genome using a minicircle DNA.

In some embodiments, the nucleic acid can be a beta hemoglobin (HBB) gene and the cell can be a hematopoietic stem cell (HSC). The HBB gene can be incorporated into the target site in the HSC genome using a minicircle DNA. The nucleic acid can be a gene responsible for beta thalassemia or sickle cell anemia.

In some embodiments, the nucleic acid can be a metabolic gene. The metabolic gene can be involved in alpha-1 antitrypsin deficiency or ornithine transcarbamylase (OTC) deficiency. The metabolic gene can be a gene involved in inherited diseases.

In some embodiments, the nucleic acid can be a gene involved in an inherited disease or an inherited syndrome. The inherited disease can be cystic fibrosis, familial hypercholesterolemia, adenosine deaminase (ADA) deficiency, X-linked SCID (X-SCID), Wiskott-Aldrich syndrome (WAS), hemochromatosis, Tay-Sachs, fragile X syndrome, Huntington's disease, Marfan syndrome, phenylketonuria, or muscular dystrophy.

The present disclosure provides a vector comprising a nucleic acid encoding a DNA binding nuclease comprising a nickase activity C-terminally linked to a reverse transcriptase linked to an integration enzyme via a linker.

In some embodiments, the linker can be cleavable.

In some embodiments, the linker can be non-cleavable.

In some embodiments, the linker can comprise two associating binding domains of the DNA binding nuclease linked to a reverse transcriptase.

In some embodiments, the integration enzyme can comprise a conditional activation domain or conditional expression domain.

In some embodiments, the integration enzyme can be fused to an estrogen receptor.

In some embodiments, the DNA binding nuclease comprising a nickase activity can be selected from the group consisting of Cas9-D10A, Cas9-H840A, and Cas12a/b.

In some embodiments, the reverse transcriptase can be a M-MLV reverse transcriptase, a AMV-RT, MarathonRT, or a RTX. The reverse transcriptase can be a modified M-MLV reverse transcriptase relative to the wildtype M-MLV reverse transcriptase. The M-MLV reverse transcriptase domain can comprise one or more of the mutations selected from the group consisting of D200N, T306K, W313F, T330P and L603W.

In some embodiments, the integration enzyme can be selected from the group consisting of Cre, Dre, Vika, Bxb1, φC31, RDF, FLP, φBT1, R1, R2, R3, R4, R5, TP901-1, A118, φFC1, φC1, MR11, TG1, φ370.1, Wβ, BL3, SPBc, K38, Peaches, Veracruz, Rebeuca, Theia, KSSJEB, PattyP, Doom, Scowl, Lockley, Switzer, Bob3, Troube, Abrogate, Anglerfish, Sarfire, SkiPole, Conceptll, Museum, Severus, Airmid, Benedict, Hinder, ICleared, Sheen, Mundrea, BxZ2, φRV, retrotransposases encoded by R2, L1, Tol2 Tc1, Tc3, Mariner (Himar 1), Mariner (mos 1), and Minos, and any mutants thereof.

In some embodiments, the recombinase or integrase can be Bxb1 or a mutant thereof.

The present disclosure provides a cell comprising a vector comprising a nucleic acid encoding a DNA binding nuclease comprising a nickase activity C-terminally linked to a reverse transcriptase linked to an integration enzyme via a linker. The cell further comprises a gRNA comprising a primer binding sequence, an integration sequence, and a guide sequence, wherein the gRNA can interact with the encoded nuclease comprising a nickase activity. The cell further comprising a DNA minicircle comprising a nucleic acid and a sequence recognized by the encoded integrase, recombinase, or reverse transcriptase. The cell further comprising a nicking guide RNA (ngRNA) capable of binding the encoded nuclease comprising a nickase activity, and wherein the ngRNA targets a sequence away from the gRNA.

In some embodiments, the minicircle cannot comprise a sequence of bacterial origin.

In some embodiments, the integration enzyme can be selected from the group consisting of Cre, Dre, Vika, Bxb1, φC31, RDF, FLP, φBT1, R1, R2, R3, R4, R5, TP901-1, A118, φFC1, φC1, MR11, TG1, φ370.1, Wβ, BL3, SPBc, K38, Peaches, Veracruz, Rebeuca, Theia, KSSJEB, PattyP, Doom, Scowl, Lockley, Switzer, Bob3, Troube, Abrogate, Anglerfish, Sarfire, SkiPole, Conceptll, Museum, Severus, Airmid, Benedict, Hinder, ICleared, Sheen, Mundrea, BxZ2, φRV, retrotransposases encoded by R2, L1, Tol2 Tc1, Tc3, Mariner (Himar 1), Mariner (mos 1), and Minos, and any mutants thereof.

In some embodiments, the integration enzyme can be Bxb1 or a mutant thereof.

In some embodiments, the DNA binding nuclease comprising a nickase activity can be selected from the group consisting of Cas9-D10A, Cas9-H840A and Cas12a.

In some embodiments, the reverse transcriptase can be a M-MLV reverse transcriptase. The reverse transcriptase can be a modified M-MLV reverse transcriptase. The amino acid sequence of the M-MLV reverse transcriptase can comprise one or more mutations selected from the group consisting of D200N, T306K, W313F, T330P, and L603W.

In some embodiments, the cell can further comprise introducing ngRNA to the cell. The ngRNA can be a +90 ngRNA. The +90 ngRNA can direct nicking at 90 bases downstream of the gRNA nick on a complementary strand.

The present disclosure provides a polypeptide comprising a DNA binding nuclease comprising a nickase activity C-terminally linked to a reverse transcriptase linked to an integration enzyme via a linker.

In some embodiments, the linker can be cleavable.

In some embodiments, the linker can be non-cleavable.

In some embodiments, the integration enzyme can be fused to an estrogen receptor.

In some embodiments, the DNA binding nuclease comprising a nickase activity can be selected from the group consisting of Cas9-D10A, Cas9-H840A, and Cas12a/b.

In some embodiments, the reverse transcriptase can be a M-MLV reverse transcriptase, a AMV-RT, a MarathonRT, or a XRT. The reverse transcriptase can be a modified M-MLV relative to a wild-type M-MLV reverse transcriptase. The M-MLV reverse transcriptase domain can comprise one or more of mutations selected from the group consisting of D200N, T306K, W313F, T330P, and L603W.

In some embodiments, the integration enzyme can be selected from group consisting of Cre, Dre, Vika, Bxb1, φC31, RDF, FLP, φBT1, R1, R2, R3, R4, R5, TP901-1, A118, φFC1, φC1, MR11, TG1, φ370.1, Wβ, BL3, SPBc, K38, Peaches, Veracruz, Rebeuca, Theia, KSSJEB, PattyP, Doom, Scowl, Lockley, Switzer, Bob3, Troube, Abrogate, Anglerfish, Sarfire, SkiPole, Conceptll, Museum, Severus, Airmid, Benedict, Hinder, ICleared, Sheen, Mundrea, BxZ2, φRV, retrotransposases encoded by R2, L1, Tol2 Tc1, Tc3, Mariner (Himar 1), Mariner (mos 1), and Minos, and any mutants thereof.

In some embodiments, the integration enzyme can be Bxb1 or a mutant thereof.

The present disclosure provides a gRNA that specifically binds to a DNA binding nuclease comprising nickase activity, the gRNA comprising a primer binding site, which hybridizes to a nicked DNA strand, a recognition site for an integration enzyme, and a target recognition sequence recognizing a target site in a cell genome and hybridizing to a genomic strand complementary to the strand that is nicked by the DNA binding nuclease.

In some embodiments, the DNA binding nuclease comprising a nickase activity can be selected from the group consisting of Cas9-D10A, Cas9-H840A, and Cas12a/b.

In some embodiments, the primer binding site can hybridize to the 3' end of the nicked DNA strand.

In some embodiments, the recognition site for the integration enzyme can be selected from an attB site, an attP site, an attL site, an attR site, a lox71 site, and a FRT site.

In some embodiments, the recognition site for the integration enzyme can be a Bxb1 site.

The present disclosure provides a method of site-specific integration of two or more nucleic acids into a cell genome. The method comprises incorporating two integration sites at desired locations in the cell genome by introducing into the cell a DNA binding nuclease linked to a reverse transcriptase domain, wherein the DNA binding nuclease comprises a nickase activity, and two guide RNAs (gRNAs), each comprising, a primer binding sequence, linked to a unique integration sequence, wherein the gRNA interacts with the DNA binding nuclease and targets the desired locations in the cell genome, wherein the DNA binding nuclease nicks a strand of the cell genome and the reverse transcriptase domain incorporates each of the integration sequence of the gRNA into the nicked site, thereby providing the integration site at the desired locations of the cell genome. The method further comprises integrating the nucleic acid by introducing into the cell two or more DNA or RNA comprising the nucleic acids, wherein each DNA is flanked by orthogonal integration sites, and an integration enzyme, wherein the integration enzyme incorporates the nucleic acids into the cell genome at the integration sites by integrase, recombinase, or reverse transcriptase of the sequence that is complementary or associated to the integration site, thereby introducing the nucleic acids into the desired locations of the cell genome of the cell.

In some embodiments, each of the two different integration sites inserted into the cell genome can be attB sequences comprising different palindromic or non-palindromic central dinucleotide.

In some embodiments, each of the two different integration sites inserted into the cell genome can be attP sequences comprising different palindromic or non-palindromic central dinucleotide.

In some embodiments, the integration enzyme can enable each of the two or more DNA or RNA comprising the nucleic acids to directionally enable integration of the nucleic acids into a genome via recombination of a pair of orthogonal attB site sequence and an attP site sequence.

In some embodiments, the integration enzyme can be selected from the group consisting of Cre, Dre, Vika, Bxb1, φC31, RDF, FLP, φBT1, TP901-1, A118, φFC1, φC1, MR11, TG1, φ370.1, Wβ, BL3, SPBc, K38, Peaches, Veracruz, Rebeuca, Theia, KSSJEB, PattyP, Doom, Scowl, Lockley, Switzer, Bob3, Troube, Abrogate, Anglerfish, Sarfire, SkiPole, Conceptll, Museum, Severus, Airmid, Benedict, Hinder, ICleared, Sheen, Mundrea, BxZ2, φRV, retrotransposases encoded by R1, R2, R3, R4, R5, L1, Tol2 Tc1, Tc3, Mariner (Himar 1), Mariner (mos 1), and Minos, and any mutants thereof.

In some embodiments, the integration enzyme can be Bxb1 or a mutant thereof.

In some embodiments, the DNA comprising genes can be genes involved in a cell maintenance pathway, cell-division, or a signal transduction pathway.

In some embodiments, the reverse transcriptase domain can comprise Moloney Murine Leukemia Virus (M-MLV) reverse transcriptase domain, transcription xenopolymerase (RTX), avian myeloblastosis virus reverse transcriptase (AMV-RT), or Eubacterium rectale maturase RT (MarathonRT).

In some embodiments, the DNA binding nuclease comprising a nickase activity can be selected from the group consisting of Cas9-D10A, Cas9-H840A, and Cas12a/b.

In some embodiments, the pair of an attB site sequence and an attP site sequence can be selected from the group consisting of SEQ ID NO: 5 and SEQ ID NO: 6, SEQ ID NO: 7 and SEQ ID NO: 8, SEQ ID NO: 9 and SEQ ID NO: 10, SEQ ID NO: 11 and SEQ ID NO: 12, SEQ ID NO: 13 and SEQ ID NO: 14, SEQ ID NO: 15 and SEQ ID NO: 16, SEQ ID NO: 17 and SEQ ID NO: 18, SEQ ID NO: 19 and SEQ ID NO: 20, SEQ ID NO: 21 and SEQ ID NO: 22, SEQ ID NO: 23 and SEQ ID NO: 24, SEQ ID NO: 25 and SEQ ID NO: 26, SEQ ID NO: 27 and SEQ ID NO: 28, SEQ ID NO: 29 and SEQ ID NO: 30, SEQ ID NO: 31 and SEQ ID NO: 32, SEQ ID NO: 33 and SEQ ID NO: 34 and SEQ ID NO: 35 and SEQ ID NO: 36.

The present disclosure provides a cell comprising a vector comprising a nucleic acid encoding a DNA binding nuclease comprising a nickase activity, wherein the DNA binding nuclease is C-terminally linked to a reverse transcriptase, wherein the reverse transcriptase is linked to a recombinase or integrase via a linker. The cell further comprises two guide RNAs (gRNAs) comprising a primer binding sequence, an integration sequence and a guide sequence, wherein the gRNA can interact with the encoded DNA binding nuclease comprising a nickase activity. The cell further comprises two or more DNA or RNA strands comprising a nucleic acid and a pair of flanking attB site sequence and an attP site sequence recognized by the encoded integrase or recombinase. The cell optionally further comprises a nicking guide RNA (ngRNA) capable of binding the encoded nuclease comprising a nickase activity, and wherein the ngRNA targets a sequence away from the gRNA.

The present disclosure provides a cell comprising a modified genome, wherein the modification comprises incorporation of two orthogonal integration sites within the cell genome by introducing into the cell a: vector comprising a nucleic acid encoding a DNA binding nuclease comprising a nickase activity, wherein the DNA binding nuclease is C-terminally linked to a reverse transcriptase; two guide RNAs (gRNAs), each comprising a primer binding sequence, a genomic integration sequence, and a guide sequence, wherein the gRNA can interact with the encoded nuclease comprising a nickase activity; and optionally a nicking guide RNA (ngRNA) capable of binding the encoded nuclease comprising a nickase activity, and wherein the ngRNA targets a sequence away from the gRNA.

The present disclosure provides a method of integrating two or more nucleic acids into the cell genome of cell of claim 90, the method comprising introducing into the cell: two or more DNA, each comprising a nucleic acid and a pair of flanking orthogonal integration site sequences; an integration enzyme that can recognize the integration site sequence enabling directional linking of the two or more DNA comprising nucleic acid; and enabling incorporation of the nucleic acids into the cell genome by integrating the 5' orthogonal integration sequence of the first DNA with the first genomic integration sequence and 3' orthogonal integration sequence of the last DNA with the last genomic integration sequence, thereby incorporating the two or more nucleic acids into the cell genome.

The present disclosure provides a cell comprising a modified genome, wherein the modification comprises incorporation of two orthogonal integration sites within the cell genome by introducing into the cell: a vector comprising a nucleic acid encoding a DNA binding nuclease comprising a nickase activity, wherein the DNA binding nuclease is C-terminally linked to a reverse transcriptase; two guide RNAs (gRNAs), each comprising a primer binding sequence, a genomic integration sequence, and a guide sequence, wherein the gRNA can interact with the encoded nuclease comprising a nickase activity; and optionally a nicking guide RNA (ngRNA) capable of binding the encoded nuclease comprising a nickase activity, and wherein the ngRNA targets a sequence away from the gRNA; two or more DNA or RNA comprising the nucleic acids, wherein each DNA is flanked by orthogonal integration sites; and an integration enzyme, wherein the integration enzyme incorporates the nucleic acids into the cell genome at the integration sites.

BRIEF DESCRIPTION OF THE DRAWINGS

Aspects, features, benefits and advantages of the embodiments described herein will be apparent with regard to the following description, appended claims, and accompanying drawings where:

FIG. 28A shows fluorescent images of the GFP tagging of ACTB and SUPT16H genes with PASTE according to embodiments of the present teachings;

FIG. 28B shows fluorescent images of the GFP tagging of NOLC1 and SRRM2 genes with PASTE according to embodiments of the present teachings;

FIG. 28C shows fluorescent images of the GFP tagging of LMNB1 and DEPDC4 genes with PASTE according to embodiments of the present teachings;

FIG. 28F shows fluorescent images of two single cells with multiplexed gene tagging of ACTB (EGFP) and NOLC1 (mCherry) using PASTE according to embodiments of the present teachings;

FIG. 28G shows fluorescent images two single cells with multiplexed gene tagging of ACTB (EGFP) and LMNB1 (mCherry) using PASTE according to embodiments of the present teachings;

FIG. 29E discloses SEQ ID NOS 428-431, respectively, in order of appearance;

FIG. 31A shows a schematic of various parameters that affect PASTE integration of ~1 kb GFP insert, wherein on the pegRNA, the PBS, RT, and attB lengths can alter the efficiency of attB insertion, and nicking guide selection also affects overall gene integration efficiency according to embodiments of the present teachings;

FIG. 34E shows the endogenous protein tagging with GFP via PASTE by in-frame endogenous gene tagging at the NOLC1 loci and LMNB1 loci according to embodiments of the present teachings;

FIG. 40C shows the validation of ddPCR assays for detecting editing at predicted PASTE ACTB Cas9 guide off-target sites using synthetic amplicons according to embodiments of the present teachings;

FIG. 40D shows the validation of ddPCR assays for detecting editing at predicted HITI ACTB Cas9 guide off-target sites using synthetic amplicons according to embodiments of the present teachings;

FIG. 41A shows a number of significant differentially regulated genes in HEK293FT cells expressing Bxb1 integrase, PASTE targeting ACTB integration of EGFP, or Prime editing targeting ACTB for EGFP insertion without Bxb1 expression according to embodiments of the present teachings;

Figure 41A:
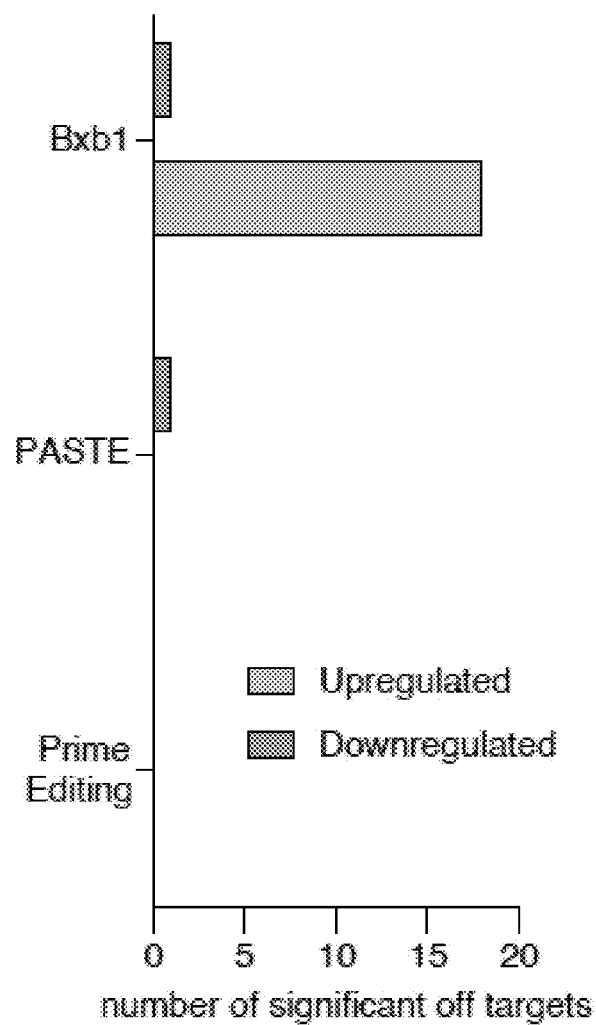
Figure 41B:
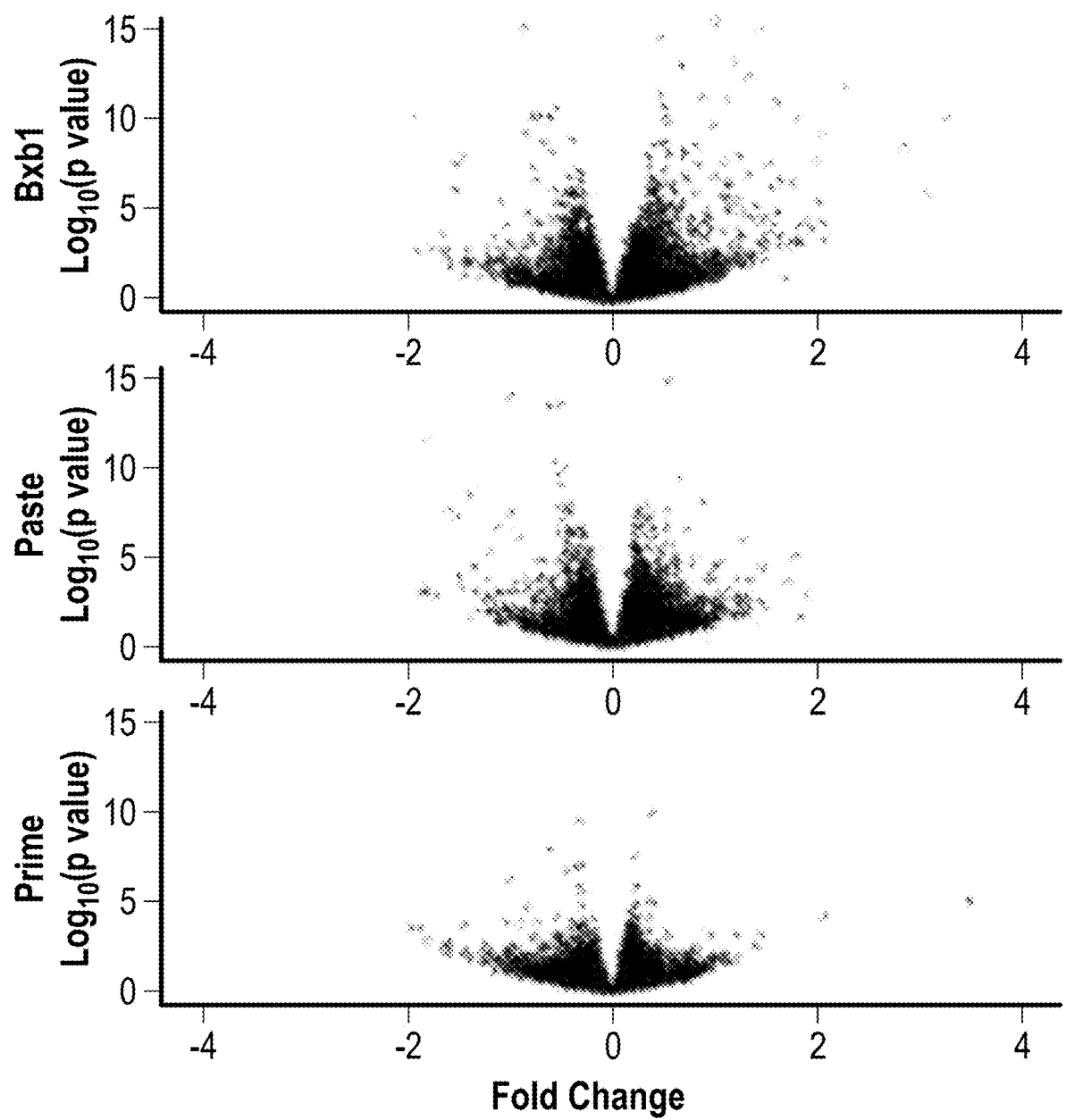
Figure 41C:
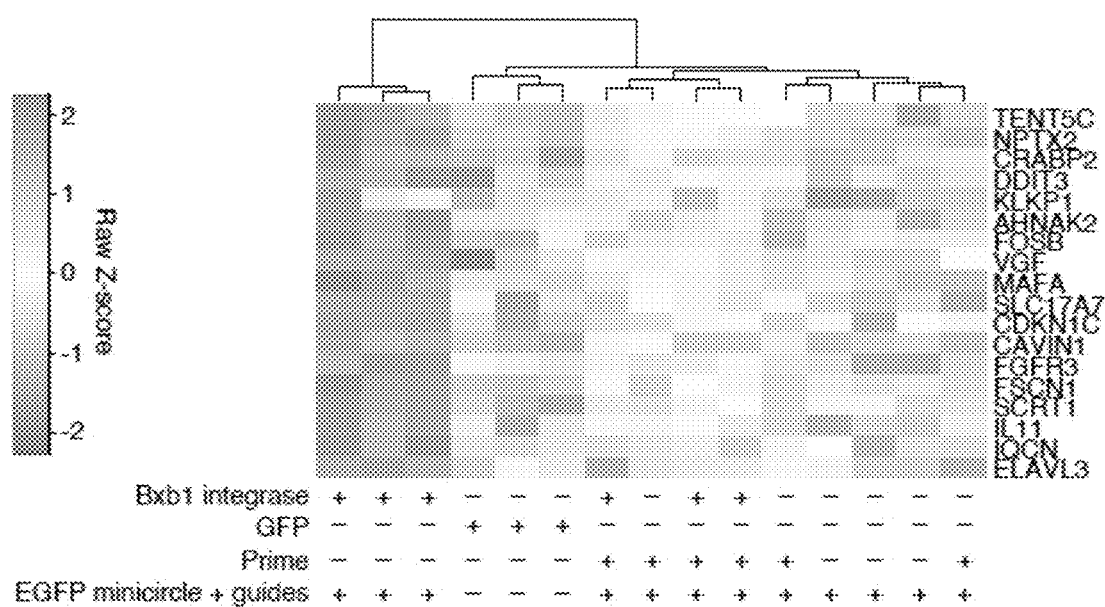
Figure 42A:
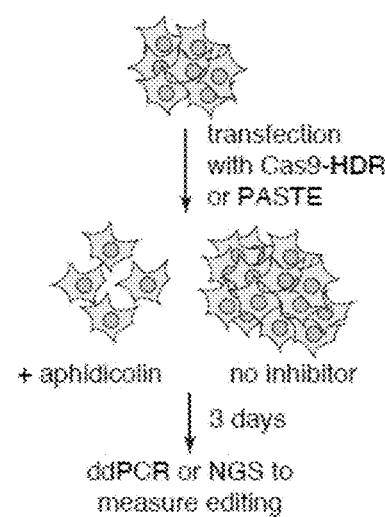
Figure 42B:
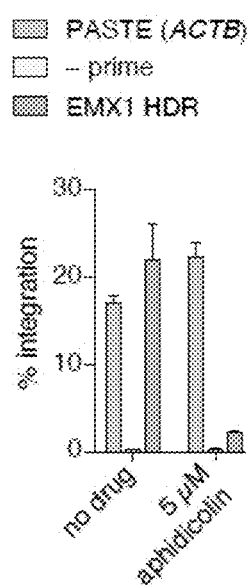
Figure 42C:
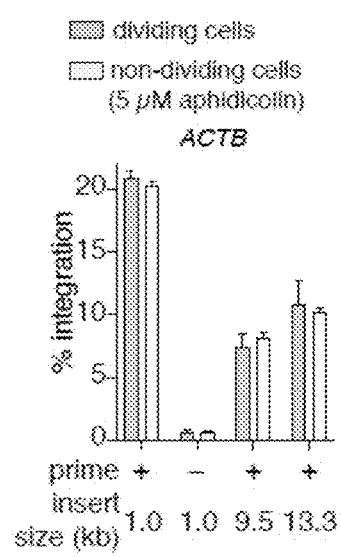
Figure 42D:
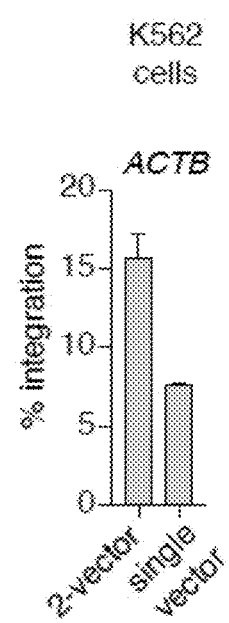
Figure 42E:
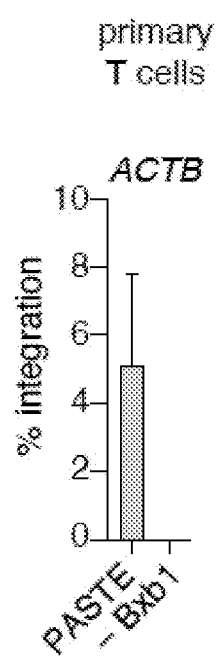
Figure 42F:
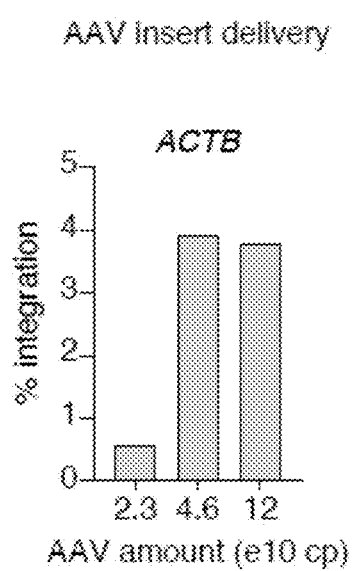
Figure 42G:
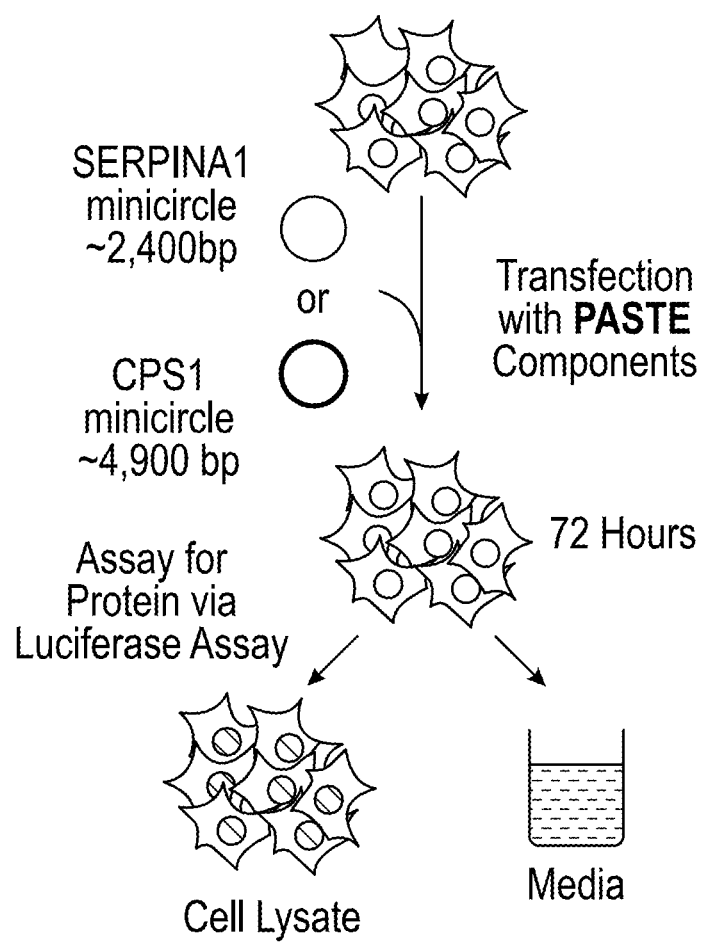
Figure 42H:
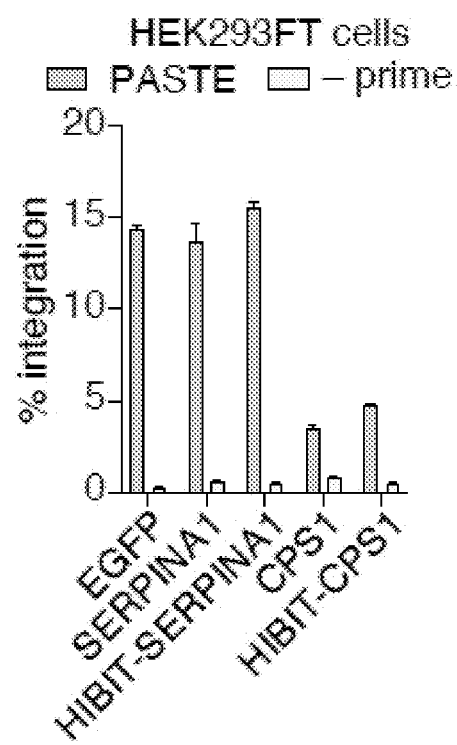
Figure 42I:
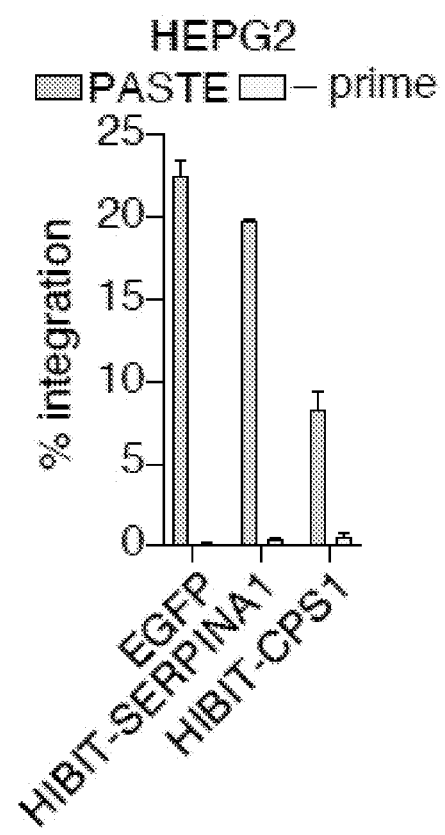
Figure 42J:
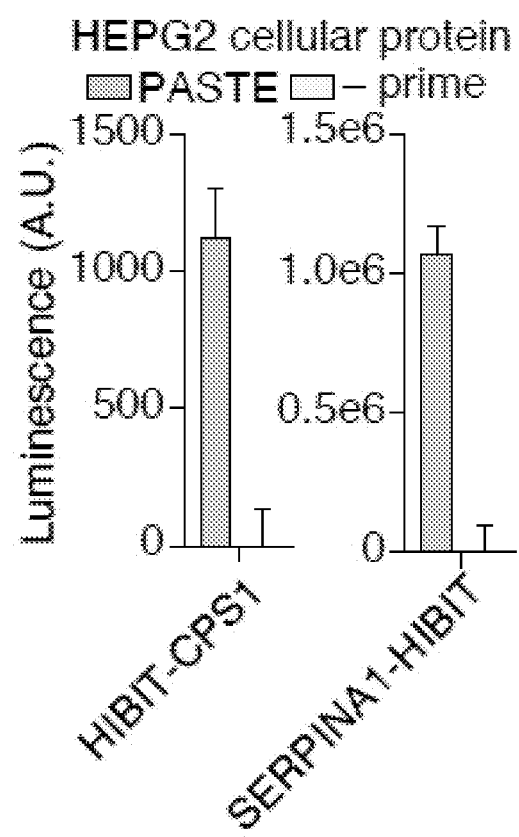
Figure 42K:
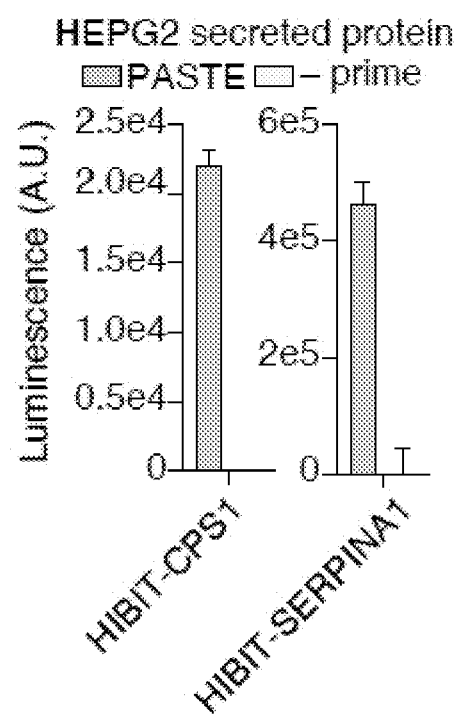
Figure 43A:
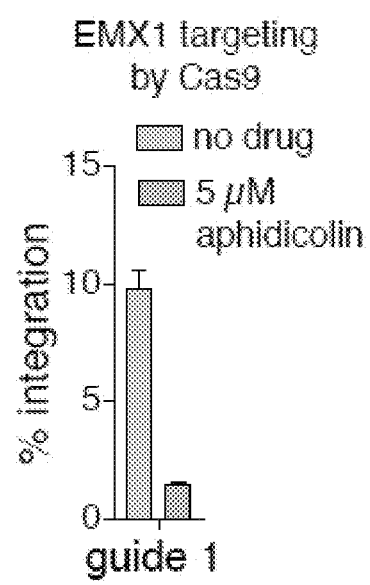
Figure 43B:
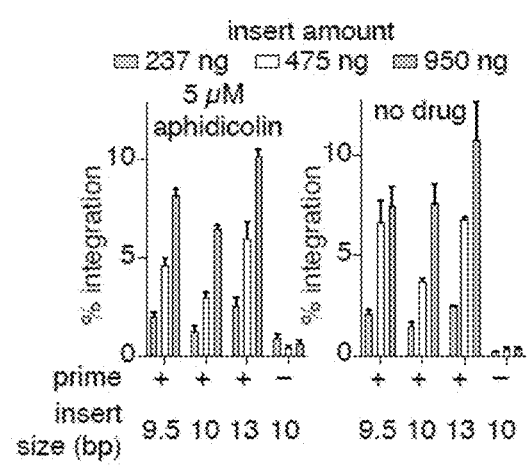
Figure 43C:
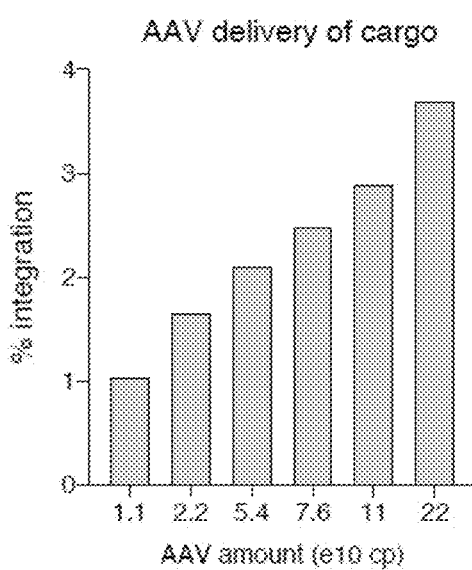
Figure 44A:
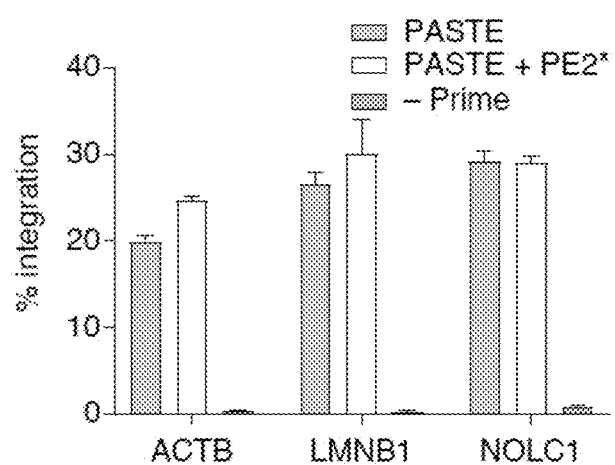
Figure 44B:
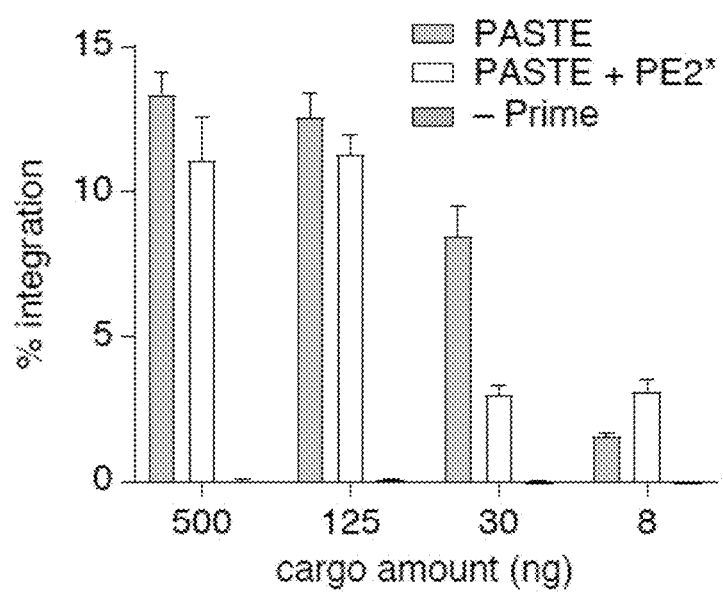
Figure 45:
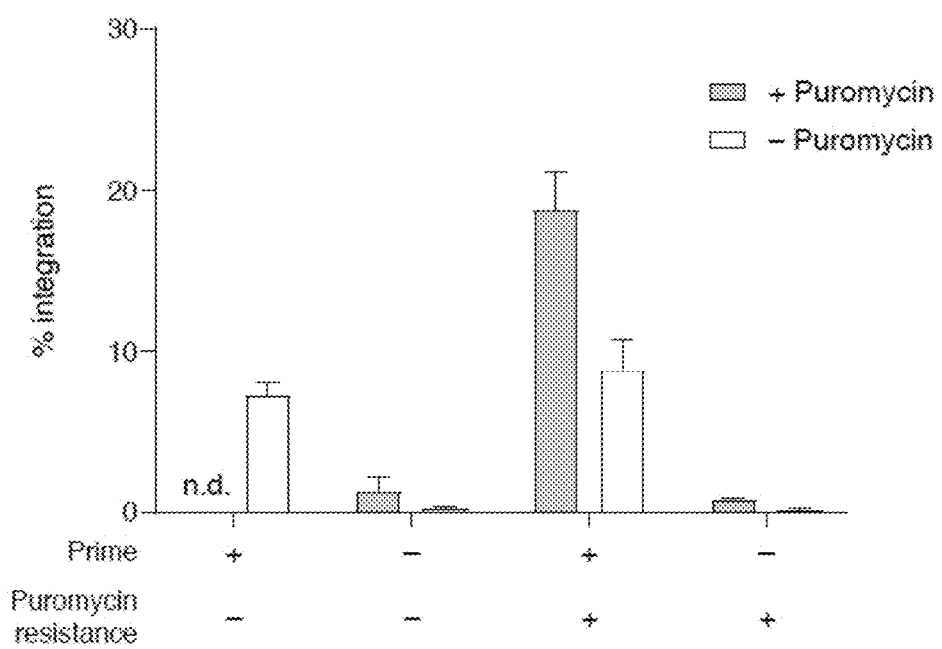
Figure 46A:
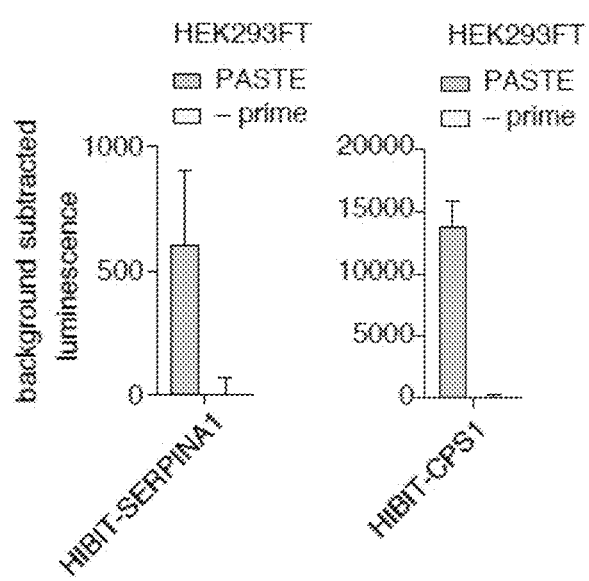
Figure 46B:
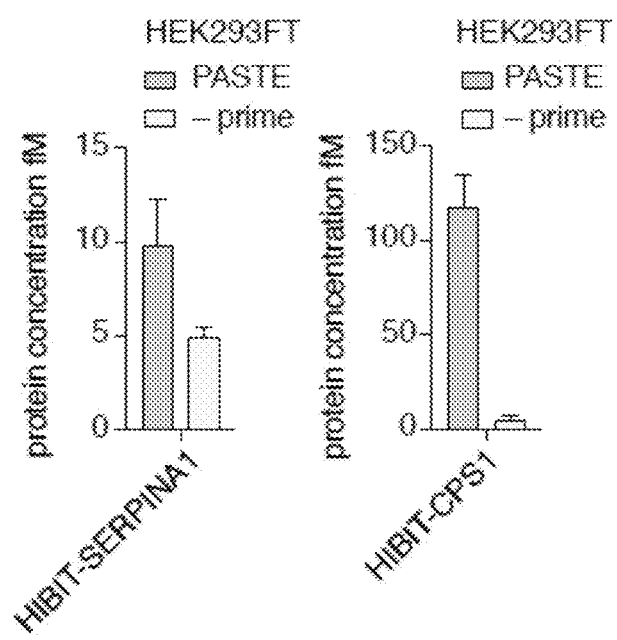
Figure 47A:
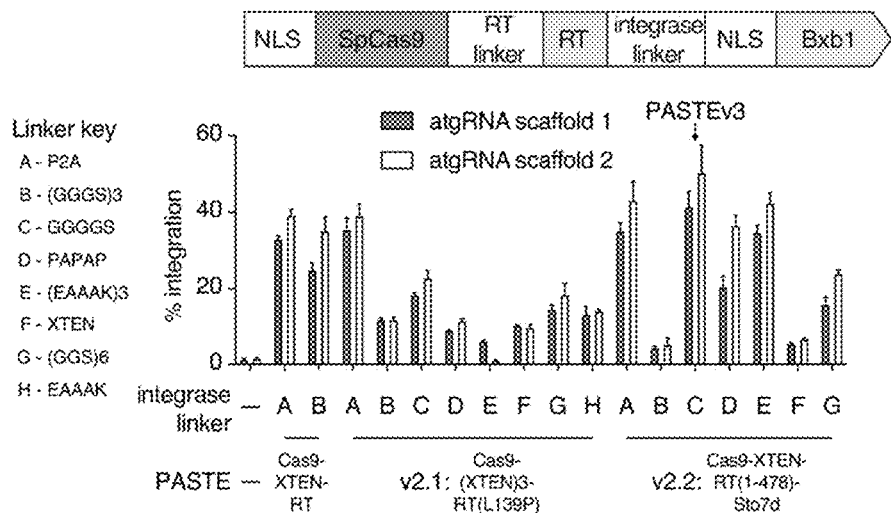
Figure 47B:
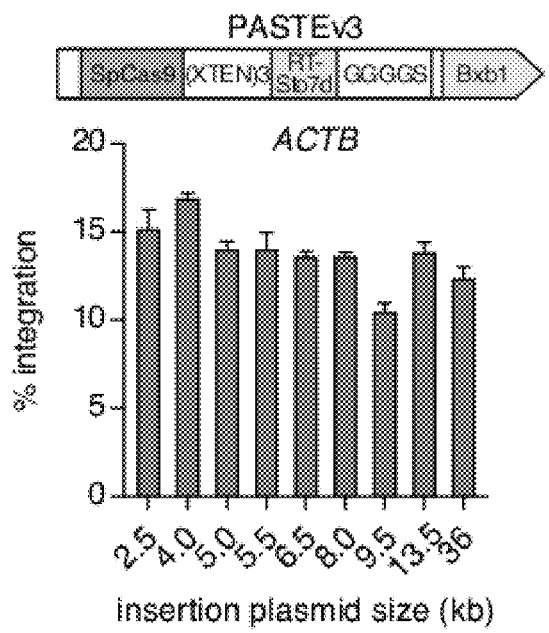
Figure 48A:
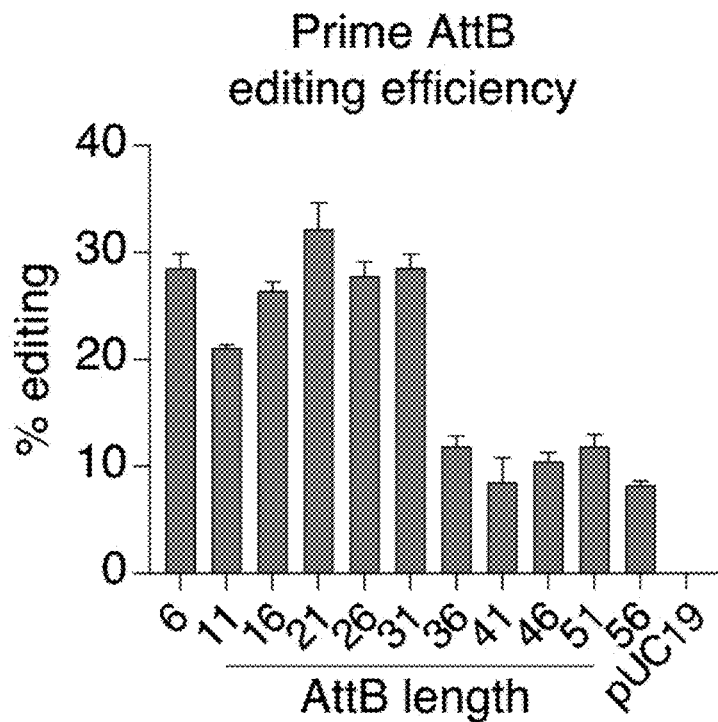
Figure 48B:
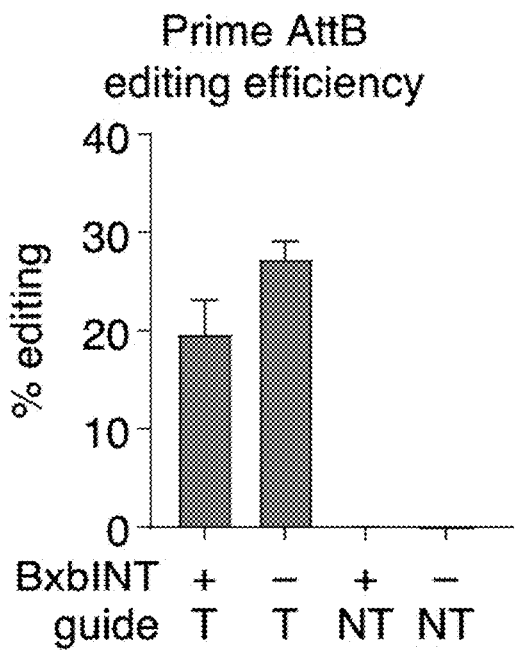
Figure 48C:
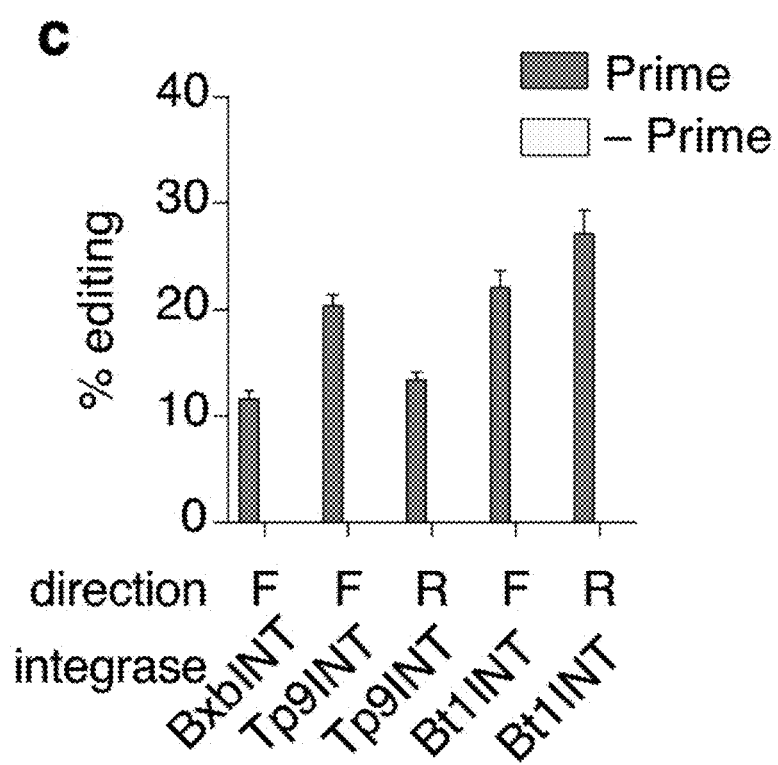
Figure 48D:
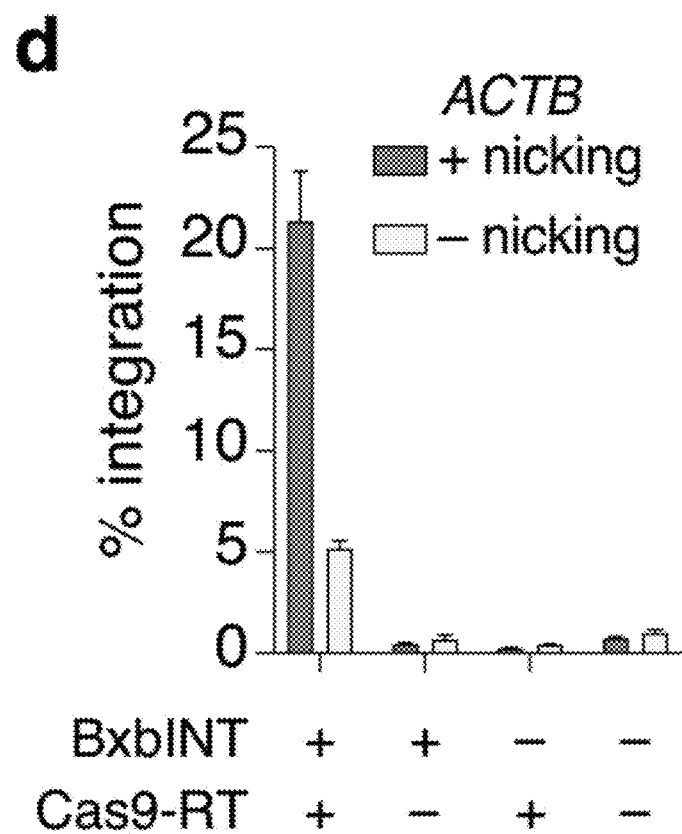

FIG. 41B shows Volcano plots depicting the fold expression change of sequenced mRNAs versus significance (p-value), wherein each dot represents a unique mRNA transcript and significant transcripts are shaded according to either upregulation (red) or downregulation (blue), and wherein fold expression change is measured against ACTB-targeting guide-only expression (including cargo) according to embodiments of the present teachings;

FIG. 41C shows top significantly upregulated and downregulated genes for Bxb1-only conditions, wherein genes are shown with their corresponding Z-scores of counts per million (cpm) for Bxb1 only expression, GFP-only expression, PASTE targeting ACTB for EGFP insertion, Prime targeting ACTB for EGFP expression without Bxb1, and guide/cargo only according to embodiments of the present teachings;

FIG. 42A shows a schematic of PASTE performance in the presence of cell cycle inhibition, wherein cells are transfected with plasmids for insertion with PASTE or Cas9-induced HDR and treated with aphidicolin to arrest cell division, and wherein the efficiency of PASTE and HDR are read out with ddPCR or amplicon sequencing respectively according to embodiments of the present teachings;

FIG. 42B shows the editing efficiency of single mutations by HDR at EMX1 locus with two Cas9 guides in the presence or absence of cell division read out with amplicon sequencing according to embodiments of the present teachings;

FIG. 42C shows the integration efficiency of various sized GFP inserts up to 13.3 kb at the ACTB locus with PASTE in the presence or absence of cell division according to embodiments of the present teachings;

FIG. 42D shows the PASTE editing efficiency with two vector (PE2 and Bxb1) and single vector (PE2-P2A-Bxb1) designs in K562 cells according to embodiments of the present teachings;

FIG. 42E shows the PASTE editing efficiency with single vector (PE2-P2A-Bxb1) designs in primary human T cells according to embodiments of the present teachings;

FIG. 42F shows the integration efficiency of therapeutically relevant genes at the ACTB locus according to embodiments of the present teachings;

FIG. 42G shows a schematic of protein production assay for PASTE-integrated transgene, wherein SERPINA1 and CPS1 transgenes are tagged with HIBIT luciferase for readout with both ddPCR and luminescence according to embodiments of the present teachings;

FIG. 42H shows the integration efficiency of SERPINA1 and CPS1 transgenes in HEK293FT cells at the ACTB locus according to embodiments of the present teachings;

FIG. 42I shows the integration efficiency of SERPINA1 and CPS1 transgenes in HepG2 cells at the ACTB locus according to embodiments of the present teachings;

FIG. 42J shows the intracellular levels of SERPINA1-HIBIT and CPS1-HIBIT in HepG2 cells according to embodiments of the present teachings;

FIG. 42K shows the secreted levels of SERPINA1-HIBIT and CPS1-HIBIT in HepG2 cells according to embodiments of the present teachings;

FIG. 43A shows the HDR mediated editing of the EMX1 locus that is significantly diminished in non-dividing HEK293FT cells blocked by 5 μM aphidicolin treatment according to embodiments of the present teachings;

FIG. 43B shows the effect of insert minicircle DNA amount on PASTE-mediated insertion at the ACTB locus in dividing and nondividing HEK293FT cells blocked by 5 μM aphidicolin treatment according to embodiments of the present teachings;

FIG. 43C shows the PASTE integration of GFP at the ACTB locus with the GFP template delivered via AAV, showing dose dependence of integration efficiency according to embodiments of the present teachings;

FIG. 44A shows the PASTE integration activity at three endogenous loci comparing the normal PASTE SV40 NLS to a c-Myc NLS/variable bi-partite SV40 NLS design according to embodiments of the present teachings;

FIG. 44B shows the PASTE integration activity at the ACTB locus with different GFP minicircle template amounts comparing the normal PASTE SV40 NLS to a c-Myc NLS/variable bi-partite SV40 NLS design according to embodiments of the present teachings;

FIG. 45 shows the improvement of the PASTE editing activity using a puromycin growth selection marker according to embodiments of the present teachings;

FIG. 46A shows the integration of SERPINA1 and CPS1 genes that are HIBIT tagged as measured by a protein expression luciferase assay according to embodiments of the present teachings;

FIG. 46B shows the integration of SERPINA1 and CPS1 genes that are HIBIT tagged as measured by a protein expression luciferase assay normalized to a standardized HIBIT ladder, enabling accurate quantification of protein levels according to embodiments of the present teachings;

FIG. 47A shows optimization of PASTE constructs with a panel of linkers and reverse transcriptase (RT) modifications for EGFP integration at the ACTB locus, according to embodiments of the present teachings;

FIG. 47B shows the effect of cargo size on PASTE insertion efficiency at the endogenous ACTB target. Cargos were transfected with fixed molar amounts, according to embodiments of the present teachings;

FIG. 48A shows prime editing efficiency for the insertion of different length BxbINT AttB sites at ACTB, according to embodiments of the present teachings;

FIG. 48B shows prime editing efficiency for the insertion of a BxbINT AttB site at ACTB with targeting and non-targeting guides, according to embodiments of the present teachings;

FIG. 48C shows prime editing efficiency for the insertion of different integrases' (Bxb1, Tp9, and Bt1) AttB sites at ACTB. Both orientations of landing sites are profiled (F, forward; R, reverse), according to embodiments of the present teachings;

FIG. 48D shows PASTE editing efficiency for the insertion of EGFP at ACTB with and without a nicking guide, according to embodiments of the present teachings; and FIG. 49A shows optimization of PASTE editing by dosage titration and protein optimization. PASTE integration efficiency of EGFP at ACTB measured with different doses of a single-vector delivery of components.

FIG. 49B PASTE integration efficiency of EGFP at ACTB measured with different ratios of a single-vector delivery of components to the EGFP template vector.

FIG. 49C PASTE integration efficiency of EGFP at ACTB with different RT domain fusions.

FIG. 49D PASTE integration efficiency of EGFP at ACTB with different RT domain fusions and linkers.

FIG. 49E PASTE integration efficiency of EGFP at ACTB with mutant RT domains.

FIG. 49F PASTE integration efficiency of EGFP at ACTB with mutated BxbINT domains.

FIG. 50A Insertion templates delivered via AAV transduction. PASTE editing machinery was delivered via transfection, and templates were co-delivered via AAV dosing at levels indicated.

FIG. 50B Schematic of AdV delivery of the complete PASTE system with three viral vectors.

FIG. 50C Integration efficiency of AdV delivery of integrase, guides, and cargo in HEK293FT and HepG2 cells. BxbINT and guide RNAs or cargo were delivered either via plasmid transfection (P1), AdV transduction (AdV), or omitted (-). SpCas9-RT was only delivered as plasmid or omitted.

FIG. 50D AdV delivery of all PASTE components in HEK293FT and HepG2 cells.

FIG. 50E Schematic of mRNA and synthetic guide delivery of PASTE components.

FIG. 50F Delivery of PASTE system components with mRNA and synthetic guides, paired with either AdV or plasmid cargo.

FIG. 50G Delivery of circular mRNA with synthetic guides and either AdV or plasmid cargo.

FIG. 50H PASTE editing efficiency with single vector designs in primary human T cells.

FIG. 50I PASTE editing efficiency with single vector designs in primary human hepatocytes.

Figure 51A:
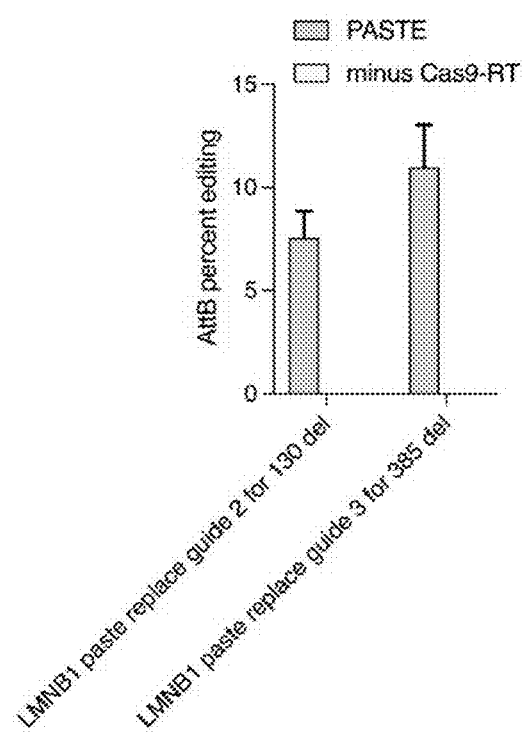

FIG. 51A PASTE editing efficiency at the LMNB1 locus with 130 bp and 385 bp deletions of the first exon of LMNB1 with combined insertion of an attB sequence.

Figure 51B:
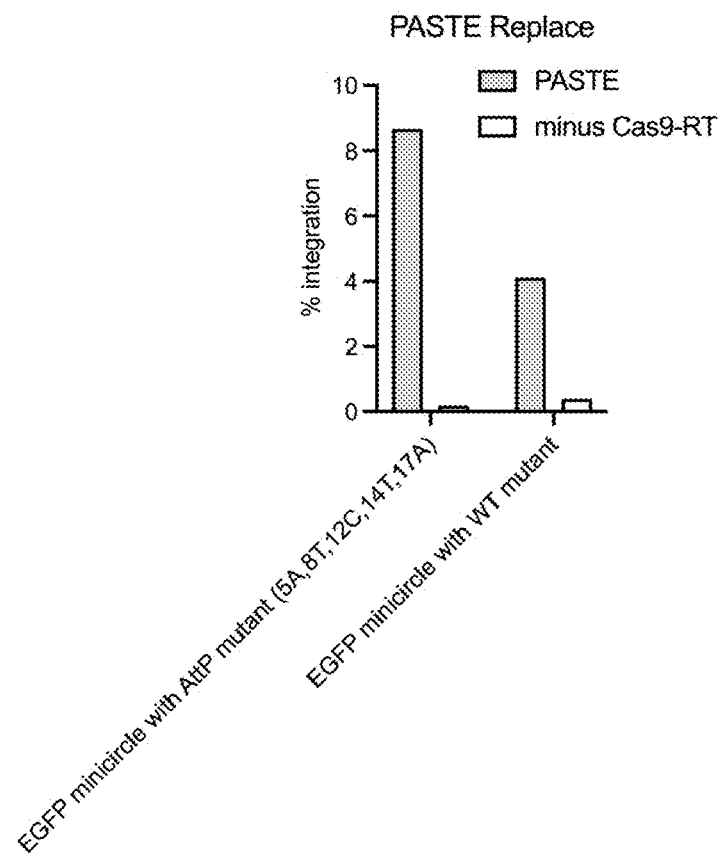

FIG. 51B PASTE editing efficiency with a 130 bp deletion of the first exon of LMNB1 with a combined insertion of a 967 bp cargo using the PASTE system.

DETAILED DESCRIPTION

It will be appreciated that for clarity, the following discussion will describe various aspects of embodiments of the applicant's teachings. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present disclosure. Thus, appearances of the phrases "in one embodiment," "in an embodiment," or "an example embodiment" in various places throughout this specification are not necessarily all referring to the same embodiment, but may. Furthermore, the particular feature, structures or characteristics may be combined in any suitable manner, as would be apparent to a person skilled in the art from this disclosure, in one or more embodiments.

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2nd edition (1989) (Sambrook, Fritsch, and Maniatis); Molecular Cloning: A Laboratory Manual, 4th edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2nd edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2nd edition (2011).

As used herein, the singular forms "a", "an," and "the" include both singular and plural referents unless the context clearly dictates otherwise. Thus, for example, reference to "a cell" includes a plurality of such cells.

As used herein, the term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

As used herein, the term "about" or "approximately" refers to a measurable value such as a parameter, an amount, a temporal duration, and the like, are meant to encompass variations of and from the specified value, such as variations of +/−10% or less, +/−5% or less, +/−1% or less, +/−0.5% or less, and +/−0.1% or less of and from the specified value, insofar such variations are appropriate to perform in the disclosure. It is to be understood that the value to which the modifier "about" or "approximately" refers is itself also specifically, and preferably, disclosed.

It is noted that all publications and references cited herein are expressly incorporated herein by reference in their entirety. The publications discussed herein are provided solely for their disclosure prior to the filing date of the present application. Nothing herein is to be construed as an admission that the present disclosure is not entitled to antedate such publication. Further, the dates of publication provided may be different from the actual publication dates which may need to be independently confirmed.

Overview

Figure 1:
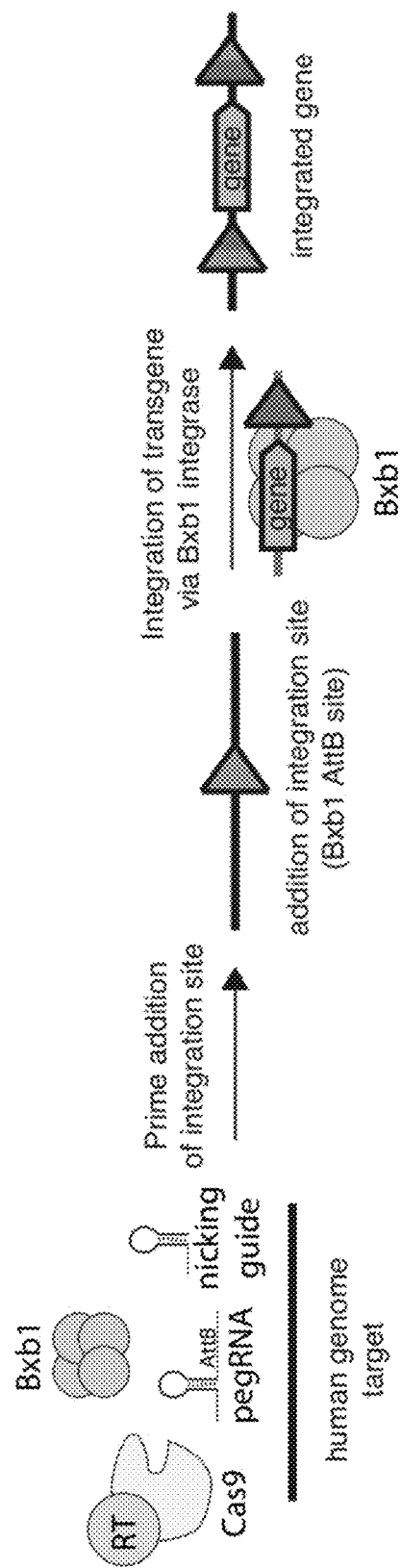
FIG. 1 shows a schematic diagram of a concept of Programmable Addition via Site-Specific Targeting Elements (PASTE) according to embodiments of the present teachings.

The embodiments disclosed herein provide non-naturally occurring or engineered systems, methods, and compositions for site-specific genetic engineering using Programmable Addition via Site-Specific Targeting Elements (PASTE). A schematic diagram illustrating the concept of PASTE is shown in FIG. 1. As discussed in more details below, PASTE comprises the addition of an integration site into a target genome followed by the insertion of one or more genes of interest or one or more nucleic acid sequences of interest at the site. This process can be done as one or more reactions in a cell. The addition of the integration site into the target genome is done using gene editing technologies that include for example, without limitation, prime editing, recombinant adeno-associated virus (rAAV)-mediated nucleic acid integration, transcription activator-like effector nucleases (TALENS), and zinc finger nucleases (ZFNs). The integration of the transgene at the integration site is done using integrase technologies that include for example, without limitation, integrases, recombinases and reverse transcriptases. The necessary components for the site-specific genetic engineering disclosed herein comprise at least one or more nucleases, one or more gRNA, one or more integration enzymes, and one or more sequences that are complementary or associated to the integration site and linked to the one or more genes of interest or one or more nucleic acid sequences of interest to be inserted into the cell genome.

An advantage of the non-naturally occurring or engineered systems, methods, and compositions for site-specific genetic engineering disclosed herein is programmable insertion of large elements without reliance on DNA damage responses.

Another advantage of the non-naturally occurring or engineered systems, methods, and compositions for site-specific genetic engineering disclosed herein is facile multiplexing, enabling programmable insertion at multiple sites.

Another advantage of the non-naturally occurring or engineered systems, methods, and compositions for site-specific genetic engineering disclosed herein is scalable production and delivery through minicircle templates.

Prime Editing

The present disclosure provides non-naturally occurring or engineered systems, methods, and compositions for site-specific genetic engineering using gene editing technologies, such as prime editing, to add an integration site into a target genome. Prime editing will be discussed in more details below.

Figure 2:
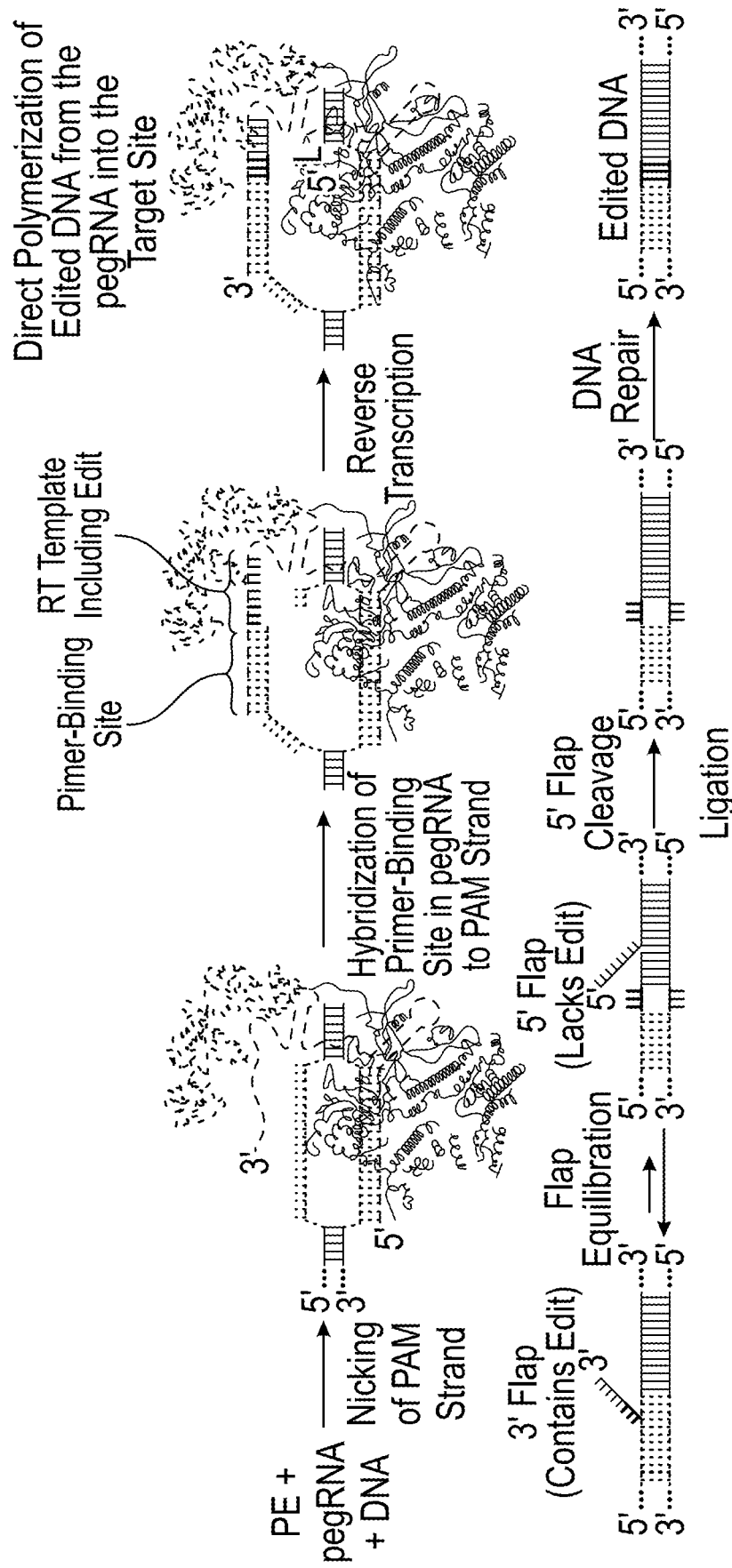
FIG. 2 shows a schematic diagram of a prime editing process according to embodiments of the present teachings.

Prime editing is a versatile and precise genome editing method that directly writes new genetic information into a specified DNA site. A schematic diagram illustrating the concept of prime editing is shown in FIG. 2. See, Anzalone, A. V., et al. "Search-and-replace genome editing without double-strand breaks or donor DNA," Nature 576, 149-157 (2019). Prime editing uses a catalytically-impaired Cas9 endonuclease that is fused to an engineered reverse transcriptase (RT) and programmed with a prime-editing guide RNA (pegRNA). The skilled person in the art would appreciate that the pegRNA both specifies the target site and encodes the desired edit. The catalytically-impaired Cas9 endonuclease also comprises a Cas9 nickase that is fused to the reverse transcriptase. During genetic editing, the Cas9 nickase part of the protein is guided to the DNA target site by the pegRNA. The reverse transcriptase domain then uses the pegRNA to template reverse transcription of the desired edit, directly polymerizing DNA onto the nicked target DNA strand. The edited DNA strand replaces the original DNA strand, creating a heteroduplex containing one edited strand and one unedited strand. Afterward, the prime editor (PE) guides resolution of the heteroduplex to favor copying the edit onto the unedited strand, completing the process.

The prime editors refer to a Moloney Murine Leukemia Virus (M-MLV) reverse transcriptase (RT) fused to a Cas9 H840A nickase. Fusing the RT to the C-terminus of the Cas9 nickase may result in higher editing efficiency. Such a complex is called PE1. The Cas9(H840A) can also be linked to a non-M-MLV reverse transcriptase such as a AMV-RT or XRT (Cas9(H840A)-AMV-RT or XRT). In some embodiments, Cas 9(H840A) can be replaced with Cas12a/b or Cas9(D10A). A Cas9 (wild type), Cas9(H840A), Cas9 (D10A) or Cas 12a/b nickase fused to a pentamutant of M-MLV RT (D200N/L603W/T330P/T306K/20 W313F), having up to about 45-fold higher efficiency is called PE2. In some embodiments, the M-MLV RT comprise one or more of the mutations: Y8H, P51L, S56A, S67R, E69K, V129P, L139P, T197A, H204R, V223H, T246E, N249D, E286R, Q291I, E302K, E302R, F309N, M320L, P330E, L435G, L435R, N454K, D524A, D524G, D524N, E562Q, D583N, H594Q, E607K, D653N, and L671P. In some embodiments, the reverse transcriptase can also be a wild-type or modified transcription xenopolymerase (RTX), avian myeloblastosis virus reverse transcriptase (AMV-RT), Feline Immunodeficiency Virus reverse transcriptase (FIV-RT), FeLV-RT (Feline leukemia virus reverse transcriptase), HIV-RT (Human Immunodeficiency Virus reverse transcriptase), or Eubacterium rectale maturase RT (MarathonRT). PE3 involves nicking the non-edited strand, potentially causing the cell to remake that strand using the edited strand as the template to induce HR. The nicking of the non-edited strand can involve the use of a nicking guide RNA (ngRNA).

Nicking the non-edited strand can increase editing efficiency. For example, nicking the non-edited strand can increase editing efficiency by about 1.1 fold, about 1.3 fold, about 1.5 fold, about 1.7 fold, about 1.9 fold, about 2.1 fold, about 2.3 fold, about 2.5 fold, about 2.7 fold, about 2.9 fold, about 3.1 fold, about 3.3 fold, about 3.5 fold, about 3.7 fold, about 3.9 fold, 4.1 fold, about 4.3 fold, about 4.5 fold, about 4.7 fold, about 4.9 fold, or any range that is formed from any two of those values as endpoints.

Although the optimal nicking position varies depending on the genomic site, nicks positioned 3' of the edit about 40-90 bp from the pegRNA-induced nick can generally increase editing efficiency without excess indel formation. The prime editing practice allows starting with non-edited strand nicks about 50 bp from the pegRNA-mediated nick, and testing alternative nick locations if indel frequencies exceed acceptable levels.

As used herein, the term "guide RNA" (gRNA) and the like refer to a RNA that guide the insertion or deletion of one or more genes of interest or one or more nucleic acid sequences of interest into a target genome. The gRNA can also refer to a prime editing guide RNA (pegRNA), a nicking guide RNA (ngRNA), and a single guide RNA (sgRNA). In some embodiments, the term "gRNA molecule" refers to a nucleic acid encoding a gRNA. In some embodiments, the gRNA molecule is naturally occurring. In some embodiments, a gRNA molecule is non-naturally occurring. In some embodiments, a gRNA molecule is a synthetic gRNA molecule. A gRNA can target a nuclease or a nickase such as Cas9, Cas 12a/b, Cas9 (H840A) or Cas9 (D10A) molecule to a target nucleic acid or sequence in a genome. In some embodiments, the gRNA can bind to a DNA nickase bound to a reverse transcriptase domain. A "modified gRNA," as used herein, refers to a gRNA molecule that has an improved half-life after being introduced into a cell as compared to a non-modified gRNA molecule after being introduced into a cell. In some embodiments, the guide RNA can facilitate the addition of the insertion site sequence for recognition by integrases, transposases, or recombinases.

Figure 24A:
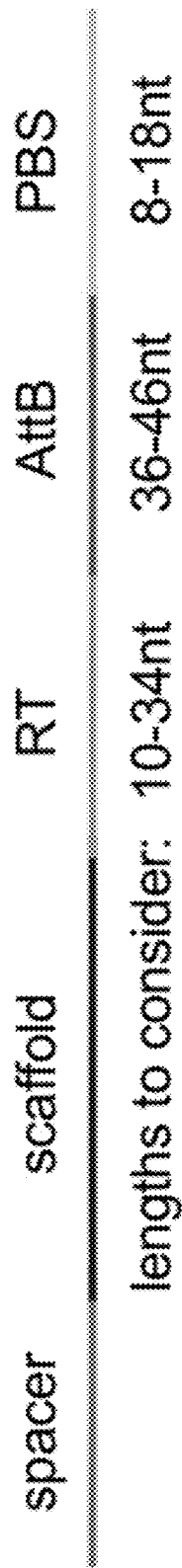
FIG. 24A shows a schematic of the design parameters for the pegRNA according to embodiments of the present teachings.

As used herein, the term "prime-editing guide RNA" (pegRNA) and the like refer to an extended single guide RNA (sgRNA) comprising a primer binding site (PBS), a reverse transcriptase (RT) template sequence, and an integration site sequence that can be recognized by recombinases, integrases, or transposases. Exemplary design parameters for pegRNA are shown in FIG. 24A. For example, the PBS can have a length of at least about 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, 30 nt, or more nt. For example, the PBS can have a length of about 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, 30 nt, or any range that is formed from any two of those values as endpoints. For example, the RT template sequence can have a length of at least about 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, 30 nt, 31 nt, 32 nt, 33 nt, 34 nt, 35 nt, 36 nt, 37 nt, 38 nt, 39 nt, 40 nt, 41 nt, 42 nt, 43 nt, 44 nt, 45 nt, 46 nt, 47 nt, 48 nt, 49 nt, 50 nt, or more nt. For example, the RT template sequence can have a length of about 4 nt, 5 nt, 6 nt, 7 nt, 8 nt, 9 nt, 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, 30 nt, 31 nt, 32 nt, 33 nt, 34 nt, 35 nt, 36 nt, 37 nt, 38 nt, 39 nt, 40 nt, 41 nt, 42 nt, 43 nt, 44 nt, 45 nt, 46 nt, 47 nt, 48 nt, 49 nt, 50 nt, or any range that is formed from any two of those values as endpoints.

During genome editing, the primer binding site allows the 3' end of the nicked DNA strand to hybridize to the pegRNA, while the RT template serves as a template for the synthesis of edited genetic information. The pegRNA is capable for instance, without limitation, of (i) identifying the target nucleotide sequence to be edited and (ii) encoding new genetic information that replaces the targeted sequence. In some embodiments, the pegRNA is capable of (i) identifying the target nucleotide sequence to be edited and (ii) encoding an integration site that replaces the targeted sequence.

Figure 24B:
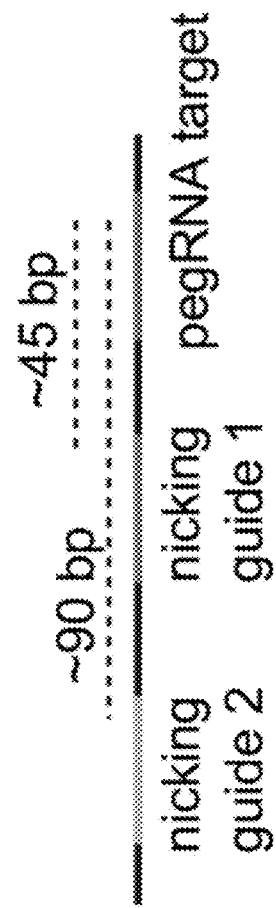
FIG. 24B shows a schematic of the design parameters for nicking guide RNA according to embodiments of the present teachings.

As used herein, the term "nicking guide RNA" (ngRNA) and the like refer to an RNA sequence that can nick a strand such as an edited strand and a non-edited strand. Exemplary design parameters for ngRNA are shown in FIG. 24B. The ngRNA can induce nicks at about 1 or more nt away from the site of the gRNA-induced nick. For example, the ngRNA can nick at least at about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, or more nt away from the site of the gRNA induced nick. In some embodiments, the ngRNA comprises SEQ ID NO: 75 with guide sequence SEQ ID NO: 74. As used herein, the terms "reverse transcriptase" and "reverse transcriptase domain" refer to an enzyme or an enzymatically active domain that can reverse a RNA transcribe into a complementary DNA. The reverse transcriptase or reverse transcriptase domain is a RNA dependent DNA polymerase. Such reverse transcriptase domains encompass, but are not limited, to a M-MLV reverse transcriptase, or a modified reverse transcriptase such as, without limitation, Superscript® reverse transcriptase (Invitrogen; Carlsbad, California), Superscript® VILO™ cDNA synthesis (Invitrogen; Carlsbad, California), RTX, AMV-RT, and Quantiscript Reverse Transcriptase (Qiagen, Hilden, Germany).

The pegRNA-PE complex disclosed herein recognizes the target site in the genome and the Cas9 for example nicks a protospacer adjacent motif (PAM) strand. The primer binding site (PBS) in the pegRNA hybridizes to the PAM strand. The RT template operably linked to the PBS, containing the edit sequence, directs the reverse transcription of the RT template to DNA into the target site. Equilibration between the edited 3' flap and the unedited 5' flap, cellular 5' flap cleavage and ligation, and DNA repair results in stably edited DNA. To optimize base editing, a Cas9 nickase can be used to nick the non-edited strand, thereby directing DNA repair to that strand, using the edited strand as a template.

Integrase Technologies

The present disclosure provides non-naturally occurring or engineered systems, methods, and compositions for site-specific genetic engineering using integrase technologies. Integrase technologies will be discussed in more details below.

The integrase technologies used herein comprise proteins or nucleic acids encoding the proteins that direct integration of a gene of interest or nucleic acid sequence of interest into an integration site via a nuclease such as a prime editing nuclease. The protein directing the integration can be an enzyme such as integration enzyme. The integration enzyme can be an integrase that incorporates the genome or nucleic acid of interest into the cell genome at the integration site by integration. The integration enzyme can be a recombinase that incorporates the genome or nucleic acid of interest into the cell genome at the integration site by recombination. The integration enzyme can be a reverse transcriptase that incorporates the genome or nucleic acid of interest into the cell genome at the integration site by reverse transcription. The integration enzyme can be a retrotransposase that incorporates the genome or nucleic acid of interest into the cell genome at the integration site by retrotransposition.

As used herein, the term "integration enzyme" refers to an enzyme or protein used to integrate a gene of interest or nucleic acid sequence of interest into a desired location or at the integration site, in the genome of a cell, in a single reaction or multiple reactions. Example of integration enzymes include for example, without limitation, Cre, Dre, Vika, Bxb1, φC31, RDF, FLP, φBT1, R1, R2, R3, R4, R5, TP901-1, A118, φFC1, φC1, MR11, TG1, φ370.1, Wβ, BL3, SPBc, K38, Peaches, Veracruz, Rebeuca, Theia, Benedict, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, φRV, and retrotransposases encoded by R2, L1, Tol2 Tc1, Tc3, Mariner (Himar 1), Mariner (mos 1), and Minos. In some embodiments, the term "integration enzyme" refers to a nucleic acid (DNA or RNA) encoding the above-mentioned enzymes. In some embodiments, the Cre ecombinase is expressed from a Cre recombinase expression plasmid (SEQ ID NO: 71).

Mammalian expression plasmids can be found in Table 1 below.

TABLE 1

| Name | Full Description | SEQ ID NOS: |
| --- | --- | --- |
| PE2-Bxb1 Single Vector | pCMV-PE2-P2A-Bxb1 | (SEQ ID NO: 381) |
| PE2 prime editor | pCMV-PE2/ Addgene #132775 | (SEQ ID NO: 382) |
| PE2*-Bxb1 Single Vector | New NLS pCMV-PE2-P2A-Bxb1 | (SEQ ID NO: 383) |
| PASTEv3 | pCMV-SpCas9-XTEN-RT(1-478)- | (SEQ ID NO: 384) |

TABLE 1-continued

| Name | Full Description | SEQ ID NOS: |
|---|---|---|
| ACTB pegRNA | Sto7d-GGGGS-BxbINT ACTB N-term PBS 13 RT 29 attB 46 pegRNA | (SEQ ID NO: 385) |
| ACTB Nicking +48 | ACTB N-term Nicking guide 1 +48 guide | (SEQ ID NO: 386) |
| Bxb1 integrase | pCAG-NLS-HA-Bxb1integrase/ Addgene #51271 | (SEQ ID NO: 387) |
| TP901-1 Integrase | TP901-1 Integrase | (SEQ ID NO: 388) |
| PhiBT Integrase | PhiBT Integrase | (SEQ ID NO: 389) |
| HDR sgRNA guide | Minicircle U6-sgRNA EFS-SpCas9 | (SEQ ID NO: 390) |
| HDR EGFP cargo | Cas9 HDR template site with EGFP | (SEQ ID NO: 391) |
| AAV helper plasmid | PDF6 AAV helper plasmid | (SEQ ID NO: 392) |
| AAV EGFP donor | GFP AAV donor plasmid | (SEQ ID NO: 393) |
| AAV2/8 | AAV2/8 capsid protein | (SEQ ID NO: 394) |

Minicircle cargo gene maps can be found in Table 2 below.

TABLE 2

| Name | Full Description | SEQ ID NOS: |
|---|---|---|
| Cargo EGFP | Parent minicircle plasmid-Cargo EGFP with attP Bxb1 site | (SEQ ID NO: 76) |
| Cargo EGFP post cleavage | Cargo EGFP with attP Bxb1 site-post minicircle cleavage | (SEQ ID NO: 395) |
| Cargo EGFP for fusion | Parent minicircle plasmid-Cargo EGFP with attP Bxb1 site for fusion | (SEQ ID NO: 396) |
| mCherry Cargo post cleavage | Cargo mCherry with attP Bxb1 site-post minicircle cleavage | (SEQ ID NO: 397) |
| YFP Cargo post cleavage | Cargo YFP with attP Bxb1 site-post minicircle cleavage | (SEQ ID NO: 398) |
| SERPINA1 Cargo post cleavage | Cargo SERPINA1 with attP Bxb1 site-post minicircle cleavage | (SEQ ID NO: 399) |
| CPS1 Cargo post cleavage | Cargo CPS1 with attP Bxb1 site-post minicircle cleavage | (SEQ ID NO: 400) |
| CFTR Cargo | Parent minicircle plasmid-Cargo CFTR with attP Bxb1 site | (SEQ ID NO: 401) |
| NYESO TCR Cargo post cleavage | Cargo NYESO TCR with attP Bxb1 site-post minicircle cleavage | (SEQ ID NO: 402) |

In some embodiments, the serine integrase φC31 from φC31 phage is use as integration enzyme. The integrase φC31 in combination with a pegRNA can be used to insert the pseudo attP integration site (SEQ ID NO: 78). A DNA minicircle containing a gene or nucleic acid of interest and attB (SEQ ID NO: 3) site can be used to integrate the gene or nucleic acid of interest into the genome of a cell. This integration can be aided by a co-transfection of an expression vector having the φC31 integrase.

As used herein, the term "integrase" refers to a bacteriophage derived integrase, including wild-type integrase and any of a variety of mutant or modified integrases. As used herein, the term "integrase complex" may refer to a complex comprising integrase and integration host factor (IF). As used herein, the term "integrase complex" and the like may also refer to a complex comprising an integrase, an integration host factor, and a bacteriophage X-derived excisionase (Xis).

As used herein, the term "recombinase" and the like refer to a site-specific enzyme that mediates the recombination of DNA between recombinase recognition sequences, which results in the excision, integration, inversion, or exchange (e.g., translocation) of DNA fragments between the recombinase recognition sequences. Recombinases can be classified into two distinct families: serine recombinases (e.g., resolvases and invertases) and tyrosine recombinases (e.g., integrases). Examples of serine recombinases include, without limitation, Hin, Gin, Tn3, β-six, CinH, ParA, γδ, Bxb1, φC31, TP901, TG1, φBT1, R1, R2, R3, R4, R5, φRV1, φFC1, MR11, A118, U153, and gp29. Examples of serine recombinases also include, without limitation, recombinases Peaches, Veracruz, Rebeuca, Theia, Benedict, KSSJEB, PattyP, Doom, Scowl, Lockley, Switzer, Bob3, Troube, Abrogate, Anglerfish, Sarfire, SkiPole, Conceptll, Museum, Severus, Airmid, Benedict, Hinder, ICleared, Sheen, Mundrea, and BxZ2 from Mycobacterial phages. Examples of tyrosine recombinases include, without limitation, Cre, FLP, R, Lambda, HK101, HK022, and pSAM2. The serine and tyrosine recombinase names stem from the conserved nucleophilic amino acid residue that the recombinase uses to attack the DNA and which becomes covalently linked to the DNA during strand exchange.

Recombinases have numerous applications, including the creation of gene knockouts/knock-ins and gene therapy applications. See, e.g., Brown et al., "Serine recombinases as tools for genome engineering."*Methods,* 2011; 53(4):372-9; Hirano et al., "Site-specific recombinases as tools for heterologous gene integration." Appl. Microbiol. Biotechnol. 2011; 92(2):227-39; Chavez and Calos, "Therapeutic applications of the ΦC31 integrase system." *Curr. Gene Ther.* 2011; 11(5):375-81; Turan and Bode, "Site-specific recombinases: from tag-and-target- to tag-and-exchange-based genomic modifications." *FASEB J.* 2011; 25(12): 4088-107; Venken and Bellen, "Genome-wide manipulations of Drosophila melanogaster with transposons, Flp recombinase, and ΦC31 integrase."*Methods Mol. Biol.* 2012; 859:203-28; Murphy, "Phage recombinases and their applications."*Adv. Virus Res.* 2012; 83:367-414; Zhang et al., "Conditional gene manipulation: Creating a new biological era." J. Zhejiang Univ. Sci. B. 2012; 13(7):511-24; Karpenshif and Bernstein, "From yeast to mammals: recent advances in genetic control of homologous recombination." DNA Repair (Amst). 2012; 1; 11(10):781-8; the entire contents of each are hereby incorporated by reference in their entirety.

The recombinases provided herein are not meant to be exclusive examples of recombinases that can be used in embodiments of the disclosure. The methods and compositions of the disclosure can be expanded by mining databases for new orthogonal recombinases or designing synthetic recombinases with defined DNA specificities (See, e.g., Groth et al., "Phage integrases: biology and applications." *J. Mol. Biol.* 2004; 335, 667-678; Gordley et al., "Synthesis of programmable integrases." *Proc. Natl. Acad. Sci. USA.*

2009; 106, 5053-5058; the entire contents of each are hereby incorporated by reference in their entirety).

Other examples of recombinases that are useful in the systems, methods, and compositions described herein are known to those of skill in the art, and any new recombinase that is discovered or generated is expected to be able to be used in the different embodiments of the disclosure.

As used herein, the term "retrotransposase" and the like refer to an enzyme, or combination of one or more enzymes, wherein at least one enzyme has a reverse transcriptase domain. Retrotransposases are capable of inserting long sequences (e.g., over 3000 nucleotides) of heterologous nucleic acid into a genome. Examples of retrotransposases include for example, without limitation, retrotransposases encoded by elements such as R2, L1, Tol2 Tc1, Tc3, Mariner (Himar 1), Mariner (mos 1), Minos, and any mutants thereof.

In some embodiments, the one or more genes of interest or one or more nucleic acid sequences of interest are inserted into a desired location in a genome using a RNA fragment, such as a retrotransposon, encoding the nucleic acid linked to a complementary or associated integration site. The insertion of the nucleic acid of interest into a location in the desired location in the genome using a retrotransposon is aided by a retrotransposase.

The gene and nucleic acid sequence of interest disclosed herein can be any gene and nucleic acid sequence that are known in the art. The gene and nucleic acid sequence of interest can be for therapeutic and/or diagnostic uses. Examples of genes of interest include, without limitation, GBA, BTK, ADA, CNGB3, CNGA3, ATF6, GNAT2, ABCA1, ABCA7, APOE, CETP, LIPC, MMP9, PLTP, VTN, ABCA4, MFSD8, TLR3, TLR4, ERCC6, HMCN1, HTRA1, MCDR4, MCDR5, ARMS2, C2, C3, CFB, CFH, JAG1, NOTCH2, CACNA1F, SERPINA1, TTR, GSN, B2M, APOA2, APOA1, OSMR, ELP4, PAX6, ARG, ASL, PITX2, FOXC1, BBS1, BBS10, BBS2, BBS9, MKKS, MKS1, BBS4, BBS7, TTC8, ARL6, BBS5, BBS12, TRIM32, CEP290, ADIPOR1, BBIP1, CEP19, IFT27, LZTFL1, DMD, BEST1, HBB, CYP4V2, AMACR, CYP7B1, HSD3B7, AKR1D1, OPN1SW, NR2F1, RLBP1, RGS9, RGS9BP, PROM1, PRPH2, GUCY2D, CACD, CHM, ALAD, ASS1, SLC25A13, OTC, ACADVL, ETFDH, TMEM67, CC2D2A, RPGRIP1L, KCNV2, CRX, GUCA1A, CERKL, CDHR1, PDE6C, TTLL5, RPGR, CEP78, C21orf2, C80RF37, RPGRIP1, ADAM9, POC1B, PITPNM3, RAB28, CACNA2D4, AIPL1, UNC119, PDE6H, OPN1LW, RIMS1, CNNM4, IFT81, RAX2, RDH5, SEMA4A, CORD17, PDE6B, GRK1, SAG, RHO, CABP4, GNB3, SLC24A1, GNAT1, GRM6, TRPM1, LRIT3, TGFBI, TACSTD2, KRT12, OVOL2, CPS1, UGT1A1, UGT1A9, UGT1A8, UGT1A7, UGT1A6, UGT1A5, UGT1A4, CFTR, DLD, EFEMP1, ABCC2, ZNF408, LRP5, FZD4, TSPAN12, EVR3, APOB, SLC2A2, LOC106627981, GBA1, NR2E3, OAT, SLC40A1, F8, F9, UROD, CPOX, HFE, JH, LDLR, EPHX1, TJP2, BAAT, NBAS, LARS1, HAMP, HJV, RS1, ADAMTS18, LRAT, RPE65, LCA5, MERTK, GDF6, RD3, CCT2, CLUAP1, DTHD1, NMNAT1, SPATA7, IFT140, IMPDH1, OTX2, RDH12, TULP1, CRB1, MT-ND4, MT-ND1, MT-ND6, BCKDHA, BCKDHB, DBT, MMAB, ARSB, GUSB, NAGS, NPC1, NPC2, NDP, OPA1, OPA3, OPA4, OPA5, RTN4IP1, TMEM126A, OPA6, OPA8, ACO2, PAH, PRKCSH, SEC63, GAA, UROS, PPOX, HPX, HMOX1, HMBS, MIR223, CYP1B1, LTBP2, AGXT, ATP8B1, ABCB11, ABCB4, FECH, ALAS2, PRPF31, RP1, EYS, TOPORS, USH2A, CNGA1, C2ORF71, RP2, KLHL7, ORF1, RP6, RP24, RP34, ROM1, ADGRA3, AGBL5, AHR, ARHGEF18, CA4, CLCC1, DHDDS, EMC1, FAM161A, HGSNAT, HK1, IDH3B, KIAA1549, KIZ, MAK, NEURODI, NRL, PDE6A, PDE6G, PRCD, PRPF3, PRPF4, PRPF6, PRPF8, RBP3, REEP6, SAMD11, SLC7A14, SNRNP200, SPP2, ZNF513, NEK2, NEK4, NXNL1, OFD1, RP1L1, RP22, RP29, RP32, RP63, RP9, RGR, POMGNT1, DHX38, ARL3, COL2A1, SLCO1B1, SLCO1B3, KCNJ13, TIMP3, ELOVL4, TFR2, FAH, HPD, MYO7A, CDH23, PCDH15, DFNB31, GPR98, USH1C, USH1G, CIB2, CLRN1, HARS, ABHD12, ADGRV1, ARSG, CEP250, IMPG1, IMPG2, VCAN, G6PC1, ATP7B and any derivatives thereof.

As used here, the terms "retrotransposons," "jumping genes," "jumping nucleic acids," and the like refer to cellular movable genetic elements dependent on reverse transcription. The retrotransposons are of non-replication competent cellular origin, and are capable of carrying a foreign nucleic acid sequence. The retrotransposons can act as parasites of retroviruses, retaining certain classical hallmarks, such as long terminal repeats (LTR), retroviral primer binding sites, and the like. However, the naturally occurring retrotransposons usually do not contain functional retroviral structure genes, which would normally be capable of recombining to yield replication competent viruses. Some retrotransposons are examples of so-called "selfish DNA", or genetic information, which encodes nothing except the ability to replicate itself. The retrotransposon may do so by utilizing the occasional presence of a retrovirus or a retrotransposase within the host cell, efficiently packaging itself within the viral particle, which transports it to the new host genome, where it is expressed again as RNA. The information encoded within that RNA is potentially transported with the jumping gene. A retrotransposon can be a DNA transposon or a retrotransposon, including a LTR retrotransposon or a non-LTR retrotransposon.

Non-long terminal repeat (LTR) retrotransposons are a type of mobile genetic elements that are widespread in eukaryotic genomes. They include two classes: the apurinic/apyrimidinic endonuclease (APE)-type and the restriction enzyme-like endonuclease (RLE)-type. The APE class retrotransposons are comprised of two functional domains: an endonuclease/DNA binding domain, and a reverse transcriptase domain. The RLE class are comprised of three functional domains: a DNA binding domain, a reverse transcription domain, and an endonuclease domain. The reverse transcriptase domain of non-LTR retrotransposon functions by binding an RNA sequence template and reverse transcribing it into the host genome's target DNA. The RNA sequence template has a 3' untranslated region which is specifically bound to the transposase, and a variable 5' region generally having Open Reading Frame(s) ("ORF") encoding transposase proteins. The RNA sequence template may also comprise a 5' untranslated region which specifically binds the retrotransposase. In some embodiments, a non-LTR transposons can include a LINE retrotransposon, such as L1, and a SINE retrotransposon, such as an Alu sequence. Other examples include for example, without limitation, R1, R2, R3, R4, and R5 retro-transposons (Moss, W. N. et al., RNA Biol. 2011, 8(5), 714-718; and Burke, W. D. et al., Molecular Biology and Evolution 2003, 20(8), 1260-1270). The transposon can be autonomous or non-autonomous.

LTR retrotransposons, which include retroviruses, make up a significant fraction of the typical mammalian genome, comprising about 8% of the human genome and 10% of the mouse genome. Lander et al., 2001, *Nature* 409, 860-921;

Waterson et al., 2002, *Nature* 420, 520-562. LTR elements include retrotransposons, endogenous retroviruses (ERVs), and repeat elements with HERV origins, such as SINE-R. LTR retrotransposons include two LTR sequences that flank a region encoding two enzymes: integrase and retrotransposase.

ERVs include human endogenous retroviruses (HERVs), the remnants of ancient germ-cell infections. While most HERV proviruses have undergone extensive deletions and mutations, some have retained ORFS coding for functional proteins, including the glycosylated env protein. The env gene confers the potential for LTR elements to spread between cells and individuals. Indeed, all three open reading frames (pol, gag, and env) have been identified in humans, and evidence suggests that ERVs are active in the germline. See, e.g., Wang et al., 2010, *Genome Res.* 20, 19-27. Moreover, a few families, including the HERV-K (HML-2) group, have been shown to form viral particles, and an apparently intact provirus has recently been discovered in a small fraction of the human population. See, e.g., Bannert and Kurth, 2006, Proc. Natl. Acad. USA 101, 14572-14579.

LTR retrotransposons insert into new sites in the genome using the same steps of DNA cleavage and DNA strand-transfer observed in DNA transposons. In contrast to DNA transposons, however, recombination of LTR retrotransposons involves an RNA intermediate. LTR retrotransposons make up about 8% of the human genome. See, e.g., Lander et al., 2001, *Nature* 409, 860-921; Hua-Van et al., 2011, Biol. Dir. 6, 19.

Integration Site

The present disclosure provides non-naturally occurring or engineered systems, methods, and compositions for site-specific genetic engineering via the addition of an integration site into a target genome. The integration site will be discussed in more details below.

As used herein, the term "integration site" refers to the site within the target genome where one or more genes of interest or one or more nucleic acid sequences of interest are inserted. Examples of integration sites include for example, without limitation, a lox71 site (SEQ ID NO: 1), attB sites (SEQ ID NO: 3 and SEQ ID NO: 43), attP sites (SEQ ID NO: 4 and SEQ ID NO: 44), an attL site (SEQ ID NO: 67), an attR site (SEQ ID NO: 68), a Vox site (SEQ ID NO: 69), a FRT site (SEQ ID NO: 70), or a pseudo attP site (SEQ ID NO: 78). The integration site can be inserted into the genome or a fragment thereof of a cell using a nuclease, a gRNA, and/or an integration enzyme. The integration site can be inserted into the genome of a cell using a prime editor such as, without limitation, PE1, PE2, and PE3, wherein the integration site is carried on a pegRNA. The pegRNA can target any site that is known in the art. Examples of cites targeted by the pegRNA include, without limitation, ACTB, SUPT16H, SRRM2, NOLC1, DEPDC4, NES, LMNB1, AAVS1 locus, CC10, CFTR, SERPINA1, ABCA4, and any derivatives thereof. The complementary integration site may be operably linked to a gene of interest or nucleic acid sequence of interest in an exogenous DNA or RNA. In some embodiments, one integration site is added to a target genome. In some embodiments, more than one integration sites are added to a target genome.

To insert multiple genes or nucleic acids of interest, two or more integration sites are added to a desired location. Multiple DNA comprising nucleic acid sequences of interest are flanked orthogonal to the integration sequences, such as, without limitation, attB and attP. An integration site is "orthogonal" when it does not significantly recognize the recognition site or nucleotide sequence of a recombinase. Thus, one attB site of a recombinase can be orthogonal to an attB site of a different recombinase. In addition, one pair of attB and attP sites of a recombinase can be orthogonal to another pair of attB and attP sites recognized by the same recombinase. A pair of recombinases are considered orthogonal to each other, as defined herein, when there is recognition of each other's attB or attP site sequences.

The lack of recognition of integration sites or pairs of sites by the same recombinase or a different recombinase can be less than about 30%. In some embodiments, the lack of recognition of integration sites or pairs of sites by the same recombinase or a different recombinase can be less than about 30%, less than about 28%, less than about 26%, less than about 24%, less than about 22%, less than about 20%, less than about 18%, less than about 16%, less than about 14%, less than about 12%, less than about 10%, less than about 8%, less than about 6%, less than about 4%, less than about 2%, about 1%, or any range that is formed from any two of those values as endpoints. The crosstalk can be less than about 30%. In some embodiments, the crosstalk is less than about 30%, less than about 28%, less than about 26%, less than about 24%, less than about 22%, less than about 20%, less than about 18%, less than about 16%, less than about 14%, less than about 12%, less than about 10%, less than about 8%, less than about 6%, less than about 4%, less than about 2%, less than about 1%, or any range that is formed from any two of those values as endpoints.

In some embodiments, the attB and/or attP site sequences comprise a central dinucleotide sequence. It has been shown that, for example, the central dinucleotide can be changed to GA from GT and that only GA containing attB/attP sites interact and will not cross react with GT containing sequences. In some embodiments, the central dinucleotide is selected from the group consisting of AG, AC, TG, TC, CA, CT, GA, AA, TT, CC, GG, AT, TA, GC, CG and GT.

As used herein, the term "pair of an attB and attP site sequences" and the like refer to attB and attP site sequences that share the same central dinucleotide and can recombine. This means that in the presence of one serine integrase as many as six pairs of these orthogonal alt sites can recombine (attPTT will specifically recombine with attBTT, attPTC will specifically recombine with attBTC, and so on).

In some embodiments, the central dinucleotide is nonpalindromic. In some embodiments, the central dinucleotide is palindromic. In some embodiments, a pair of an attB site sequence and an attP site sequence are used in different DNA encoding genes of interest or nucleic acid sequences of interest for inducing directional integration of two or more different nucleic acids.

The Table 3 below shows examples of pairs of attB site sequence and attP site sequence with different central dinucleotide (CD).

Paste

The present disclosure provides non-naturally occurring or engineered systems, methods, and compositions for site-specific genetic engineering using PASTE. PASTE will be discussed in more details below.

The site-specific genetic engineering disclosed herein is for the insertion of one or more genes of interest or one or more nucleic acid sequences of interest into a genome of a cell. In some embodiments, the gene of interest is a mutated gene implicated in a genetic disease such as, without limitation, a metabolic disease, cystic fibrosis, muscular dystrophy, hemochromatosis, Tay-Sachs, Huntington disease, Congenital Deafness, Sickle cell anemia, Familial hypercholesterolemia, adenosine deaminase (ADA) deficiency, X-linked SCID (X-SCID), and Wiskott-Aldrich syndrome (WAS). In some embodiments, the gene of interest or nucleic acid sequence of interest can be a reporter gene upstream or downstream of a gene for genetic analyses such as, without limitation, for determining the expression of a gene. In some embodiments, the reporter gene is a GFP template (SEQ ID NO: 76) or a Gaussia Luciferase (G-Luciferase) template (SEQ ID NO: 77) In some embodiments, the gene of interest or nucleic acid sequence of interest can be used in plant genetics to insert genes to enhance drought tolerance, weather hardiness, and increased yield and herbicide resistance in plants. In some embodiments, the gene of interest or nucleic acid sequence of interest can be used for site-specific insertion of a protein (e.g., a lysosomal enzyme), a blood factor (e.g., Factor I, II, V, VII, X, XI, XII or XIII), a membrane protein, an exon, an intracellular protein (e.g., a cytoplasmic protein, a nuclear protein, an organellar protein such as a mitochondrial protein or lysosomal protein), an extracellular protein, a structural protein, a signaling protein, a regulatory protein, a transport protein, a sensory protein, a motor protein, a defense protein, or a storage protein, an anti-inflammatory signaling molecules into cells for treatment of immune diseases, including but not limited to arthritis, psoriasis, lupus, coeliac disease, glomerulonephritis, hepatitis, and inflammatory bowel disease.

The size of the inserted gene or nucleic acid can vary from about 1 bp to about 50,000 bp. In some embodiments, the size of the inserted gene or nucleic acid can be about 1 bp, 10 bp, 50 bp, 100 bp, 150 bp, 200 bp, 250 bp, 300 bp, 350 bp, 400 bp, 600 bp, 800 bp, 1000 bp, 1200 bp, 1400 bp, 1600 bp, 1800 bp, 2000 bp, 2200 bp, 2400 bp, 2600 bp, 2800 bp, 3000 bp, 3200 bp, 3400 bp, 3600 bp, 3800 bp, 4000 bp, 4200 bp, 4400 bp, 4600 bp, 4800 bp, 5000 bp, 5200 bp, 5400 bp, 5600 bp, 5800 bp, 6000 bp, 6200 bp, 6400 bp, 6600 bp, 6800 bp, 7000 bp, 7200 bp, 7400 bp, 7600 bp, 7800 bp, 8000 bp, 8200 bp, 8400 bp, 8600 bp, 8800 bp, 9000 bp, 9200 bp, 9400 bp, 9600 bp, 9800 bp, 10,000 bp, 10,200 bp, 10,400 bp, 10,600 bp, 10,800 bp, 11,000 bp, 11,200 bp, 11,400 bp, 11,600 bp, 11,800 bp, 12,000 bp, 14,000 bp, 16,000 bp, 18,000 bp, 20,000 bp, 30,000 bp, 40,000 bp, 50,000 bp, or any range that is formed from any two of those values as endpoints.

In some embodiments, the site-specific engineering using the gene of interest or nucleic acid sequence of interest disclosed herein is for the engineering of T cells and NKs for tumor targeting or allogeneic generation. These can involve the use of receptor or CAR for tumor specificity, anti-PD1 antibody, cytokines like IFN-gamma, TNF-alpha, IL-15, IL-12, IL-18, IL-21, and IL-10, and immune escape genes.

In the present disclosure, the site-specific insertion of the gene of interest or nucleic acid of interest is performed through Programmable Addition via Site-Specific Targeting Elements (PASTE). Components for inserting a gene of interest or a nucleic acid of interest using PASTE are for example, without limitation, a nuclease, a gRNA adding the integration site, a DNA or RNA strand comprising the gene or nucleic acid linked to a sequence that is complementary or associated to the integration site, and an integration enzyme. Components for inserting a gene of interest or a nucleic acid of interest using PASTE are for example, without limitation, a prime editor expression, pegRNA adding the integration site, nicking guide RNA, integration enzyme (Cre or serine recombinase), transgene vector comprising the gene of interest or nucleic acid sequence of interest with gene and integration signal. The nuclease and prime editor integrate the integration site into the genome. The integration enzyme integrates the gene of interest into the integration site. In some embodiments, the transgene vector comprising the gene or nucleic acid sequence of interest with gene and integration signal is a DNA minicircle devoid of bacterial DNA sequences. In some embodiments, the transgenic vector is a eukaryotic or prokaryotic vector.

As used herein, the term "vector" or "transgene vector" refers to a recombinant DNA molecule containing a desired coding sequence and appropriate nucleic acid sequences necessary for the expression of the operably linked coding sequence in a host organism. Nucleic acid sequences necessary for expression in prokaryotes usually include for example, without limitation, a promoter, an operator (optional), a ribosome binding site, and/or other sequences. Eukaryotic cells are generally known to utilize promoters (constitutive, inducible or tissue specific), enhancers, and termination and polyadenylation signals, although some elements may be deleted and other elements added without sacrificing the necessary expression. The transgenic vector may encode the PE and the integration enzyme, linked to each other via a linker. The linker can be a cleavable linker. For example, transgenic vector encoding the PE and the integration enzyme, linked to each other via a linker is pCMV PE2 P2A Cre comprises SEQ ID NO: 73. In some embodiments, the linker can be a non-cleavable linker. In some embodiments the nuclease, prime editor, and/or integration enzyme can be encoded in different vectors.

Figure 12:
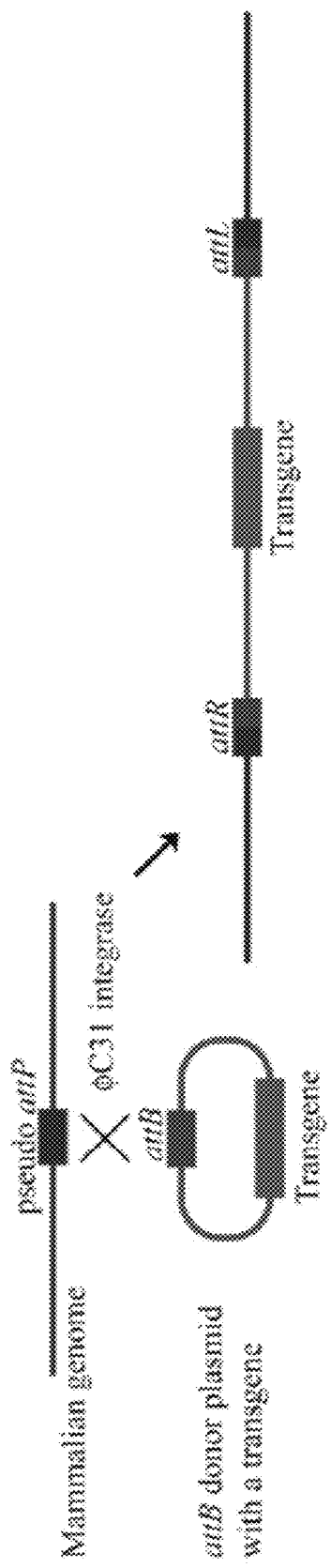
FIG. 12 shows a schematic diagram of the using φC31 as the integration enzyme, according to embodiments of the present teachings.
Figure 13:
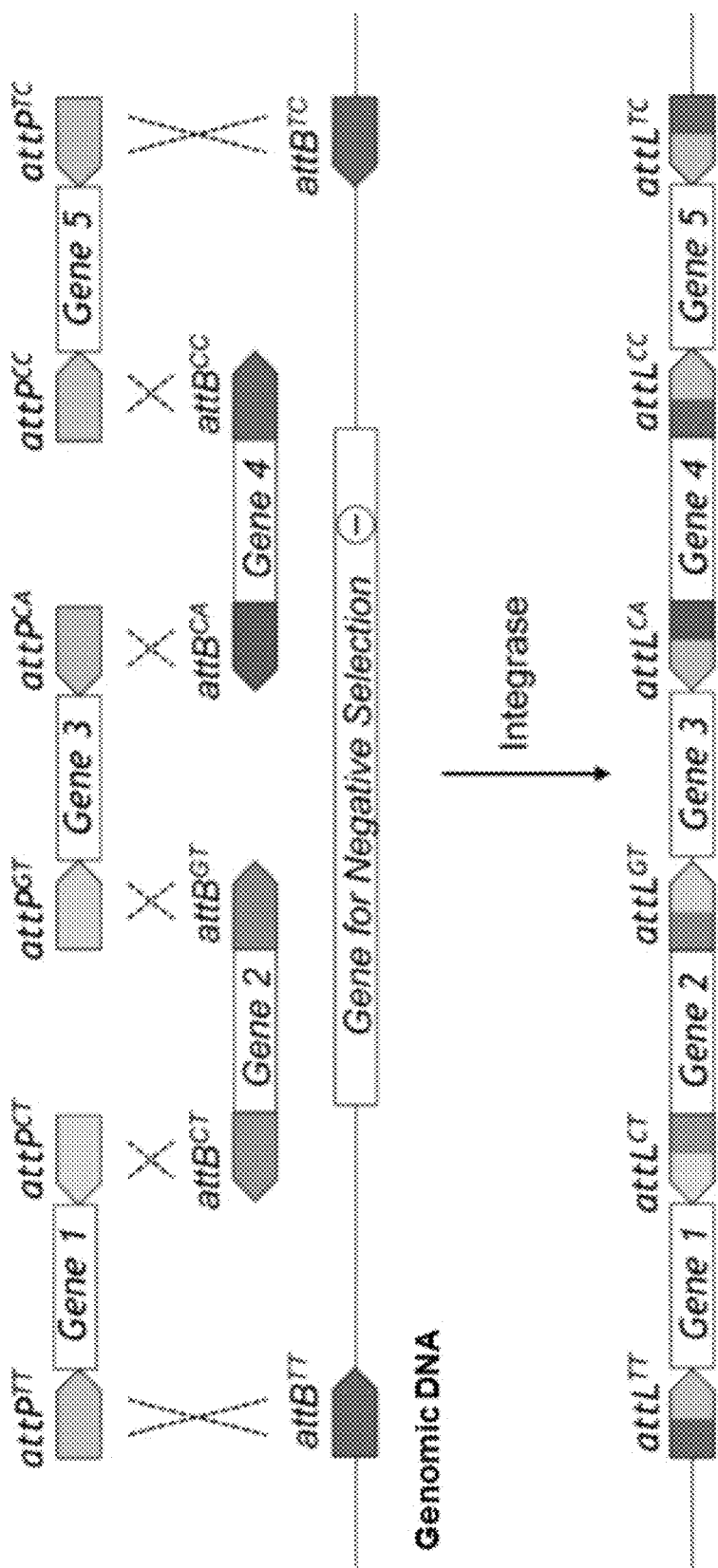
FIG. 13 shows a schematic diagram of multiplexing involving inserting multiple genes of interest in multiple loci using unique guide RNAs that incorporated exterior flanking attB sites according to embodiments of the present teachings.

A method of inserting multiple genes or nucleic acid sequences of interest into a single site according to embodiments of the present disclosure is illustrated in FIG. 12. In some embodiments, multiplexing involves inserting multiple genes of interest in multiple loci using unique pegRNA as illustrated in FIG. 13 (Merrick, C. A. et al., ACS Synth. Biol. 2018, 7, 299-310). The insertion of multiple genes of interest or nucleic acids of interest into a cell genome, referred herein as "multiplexing," is facilitated by incorporation of the complementary 5' integration site to the 5' end of the DNA or RNA comprising the first nucleic acid and 3' integration site to the 3' end of the DNA or RNA comprising the last nucleic acid. In some embodiments, the number of genome of interest or amino acid sequences of interest that are inserted into a cell genome using multiplexing can be about 1, 2, 3, 4, 5, 6, 7, 8, 9 10, 11, 12, 13, 14, 15, 16, 17, 18, 19, 20, 21, 22, 23, 24, 25, or any range that is formed from any two of those values as endpoints.

In some embodiments, multiplexing allows integration of for example, signaling cascade, over-expression of a protein of interest with its cofactor, insertion of multiple genes mutated in a neoplastic condition, or insertion of multiple CARs for treatment of cancer.

In some embodiments, the integration sites may be inserted into the genome using non-prime editing methods such as rAAV mediated nucleic acid integration, TALENS and ZFNs. A number of unique properties make AAV a promising vector for human gene therapy (Muzyczka, CURRENT TOPICS IN MICROBIOLOGY AND IMMUNOLOGY, 158:97-129 (1992)). Unlike other viral vectors, AAVs have not been shown to be associated with any known human disease and are generally not considered pathogenic. Wild type AAV is capable of integrating into host chromosomes in a site-specific manner M. Kotin et al., PROC. NATL. ACAD. SCI, USA, 87:2211-2215 (1990); R. J. Samulski, EMBO 10(12):3941-3950 (1991)). Instead of creating a double-stranded DNA break, AAV stimulates endogenous homologous recombination to achieve the DNA modification. Further, transcription activator-like effector nucleases (TALENs) and Zinc-finger nucleases (ZFNs) for genome editing and introducing targeted DSBs. The specificity of TALENs arises from two polymorphic amino acids, the so-called repeat variable diresidues (RVDs) located at positions 12 and 13 of a repeated unit. TALENS are linked to FokI nucleases, which cleaves the DNA at the desired locations. ZFNs are artificial restriction enzymes for custom site-specific genome editing. Zinc fingers themselves are transcription factors, where each finger recognizes 3-4 bases. By mixing and matching these finger modules, researchers can customize which sequence to target.

As used herein, the terms "administration," "introducing," or "delivery" into a cell, a tissue, or an organ of a plasmid, nucleic acids, or proteins for modification of the host genome refers to the transport for such administration, introduction, or delivery that can occur in vivo, in vitro, or ex vivo. Plasmids, DNA, or RNA for genetic modification can be introduced into cells by transfection, which is typically accomplished by chemical means (e.g., calcium phosphate transfection, polyethyleneimine (PEI) Or lipofection), physical means (electroporation or microinjection), infection (this typically means the introduction of an infectious agent such as a virus (e.g., a baculovirus expressing the AAV Rep gene)), transduction (in microbiology, this refers to the stable infection of cells by viruses, or the transfer of genetic material from one microorganism to another by viral factors (e.g., bacteriophages)). Vectors for the expression of a recombinant polypeptide, protein or oligonucleotide may be obtained by physical means (e.g., calcium phosphate transfection, electroporation, microinjection, or lipofection) in a cell, a tissue, an organ or a subject. The vector can be delivered by preparing the vector in a pharmaceutically acceptable carrier for the in vitro, ex vivo, or in vivo delivery to the carrier.

As used herein, the term "transfection" refers to the uptake of an exogenous nucleic acid molecule by a cell. A cell is "transfected" when an exogenous nucleic acid has been introduced into the cell membrane. The transfection can be a single transfection, co-transfection, or multiple transfection. Numerous transfection techniques are generally known in the art. See, for example, Graham et al. (1973) Virology, 52: 456. Such techniques can be used to introduce one or more exogenous nucleic acid molecules into a suitable host cell.

In some embodiments, the exogenous nucleic acid molecule and/or other components for gene editing are combined and delivered in a single transfection. In other embodiments, the exogenous nucleic acid molecule and/or other components for gene editing are not combined and delivered in a single transfection. In some embodiments, exogenous nucleic acid molecule and/or other components for gene editing are combined and delivered in a single transfection to comprise for example, without limitation, a prime editing vector, a landing site such as a landing site containing pegRNA, a nicking guide such as a nicking guide for stimulating prime editing, an expression vector such as an expression vector for a corresponding integrase or recombinase, a minicircle DNA cargo such as a minicircle DNA cargo encoding for green fluorescent protein (GFP), any derivatives thereof, and any combinations thereof. In some embodiments, the gene of interest or amino acid sequence of interest can be introduced using liposomes. In some embodiments, the gene of interest or amino acid sequence of interest can be delivered using suitable vectors for instance, without limitation, plasmids and viral vectors. Examples of viral vectors include, without limitation, adeno-associated viruses (AAV), lentiviruses, adenoviruses, other viral vectors, derivatives thereof, or combinations thereof. The proteins and one or more guide RNAs can be packaged into one or more vectors, e.g., plasmids or viral vectors. In some embodiments, the delivery is via nanoparticles or exosomes. For example, exosomes can be particularly useful in delivery RNA.

In some embodiments, the prime editing inserts the landing site with efficiencies of at least about 1%, at least about 5%, at least about 10%, at least about 15%, at least about, at least about 20%, at least about 25%, at least about 30%, at least about 35%, at least about 40%, at least about 45%, or at least about 50%. In some embodiments, the prime editing inserts the landing site(s) with efficiencies of about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, or any range that is formed from any two of those values as endpoints.

Sequences

Sequences of enzymes, guides, integration sites, and plasmids can be found in Table 4 below.

TABLE 4

| SEQ ID NO/ DESCRIPTION/ SOURCE | SEQUENCE |
| --- | --- |
| SEQ ID NO: 1 Lox71 (Artificial sequence) | ATAACTTCGTATAATGTATGCTATACGAACGGTA |
| SEQ ID NO: 2 Lox66 (Artificial sequence) | TACCGTTCGTATAATGTATGCTATACGAAGTTAT |
| SEQ ID NO: 3 attB (Artificial sequence) | GGCCGGCTTGTCGACGACGGCGGTCTCCGTCGTCAGGATCATCCGG |
| SEQ ID NO: 4 attP (Artificial Sequence) | CCGGATGATCCTGACGACGGAGACCGCCGTCGTCGACAAGCCGGCC |

TABLE 4-continued

| SEQ ID NO/<br>DESCRIPTION/<br>SOURCE | SEQUENCE |
| --- | --- |
| SEQ ID NO: 5<br>attB-TT<br>(Artificial Sequence) | GGCTTGTCGACGACGGCGTTCTCCGTCGTCAGGATCAT |
| SEQ ID NO: 6<br>attP-TT<br>(Artificial Sequence) | GTGGTTTGTCTGGTCAACCACCGCGTTCTCAGTGGTGTACGGTACA<br>AACCCA |
| SEQ ID NO: 7<br>attB-AA<br>(Artificial Sequence) | GGCTTGTCGACGACGGCGAACTCCGTCGTCAGGATCAT |
| SEQ ID NO: 8<br>attP-AA<br>(Artificial Sequence) | GTGGTTTGTCTGGTCAACCACCGCGAACTCAGTGGTGTACGGTAC<br>AAACCCA |
| SEQ ID NO: 9<br>attB-CC<br>(Artificial Sequence) | GGCTTGTCGACGACGGCGCCCTCCGTCGTCAGGATCAT |
| SEQ ID NO: 10<br>attP-CC<br>(Artificial Sequence) | GTGGTTTGTCTGGTCAACCACCGCGCCCTCAGTGGTGTACGGTACA<br>AACCCA |
| SEQ ID NO: 11<br>attB-GG<br>(Artificial Sequence) | GGCTTGTCGACGACGGCGGGCTCCGTCGTCAGGATCAT |
| SEQ ID NO: 12<br>attP-GG<br>(Artificial Sequence) | GTGGTTTGTCTGGTCAACCACCGCGGGCTCAGTGGTGTACGGTAC<br>AAACCCA |
| SEQ ID NO: 13<br>attB-TG<br>(Artificial Sequence) | GGCTTGTCGACGACGGCGTGCTCCGTCGTCAGGATCAT |
| SEQ ID NO: 14<br>attP-TG<br>(Artificial Sequence) | GTGGTTTGTCTGGTCAACCACCGCGTGCTCAGTGGTGTACGGTACA<br>AACCCA |
| SEQ ID NO: 15<br>attB-GT<br>(Artificial Sequence) | GGCTTGTCGACGACGGCGGTCTCCGTCGTCAGGATCAT |
| SEQ ID NO: 16<br>attP-GT<br>(Artificial Sequence) | GTGGTTTGTCTGGTCAACCACCGCGGTCTCAGTGGTGTACGGTACA<br>AACCCA |
| SEQ ID NO: 17<br>attB-CT<br>(Artificial Sequence) | GGCTTGTCGACGACGGCGCTCTCCGTCGTCAGGATCAT |
| SEQ ID NO: 18<br>attP-CT<br>(Artificial Sequence) | GTGGTTTGTCTGGTCAACCACCGCGCTCTCAGTGGTGTACGGTACA<br>AACCCA |
| SEQ ID NO: 19<br>attB-CA<br>(Artificial Sequence) | GGCTTGTCGACGACGGCGCACTCCGTCGTCAGGATCAT |
| SEQ ID NO: 20<br>attP-CA<br>(Artificial Sequence) | GTGGTTTGTCTGGTCAACCACCGCGCACTCAGTGGTGTACGGTACA<br>AACCCA |
| SEQ ID NO: 21<br>attB-TC<br>(Artificial Sequence) | GGCTTGTCGACGACGGCGTCCTCCGTCGTCAGGATCAT |
| SEQ ID NO: 22<br>attP-TC<br>(Artificial Sequence) | GTGGTTTGTCTGGTCAACCACCGCGTCCTCAGTGGTGTACGGTACA<br>AACCCA |
| SEQ ID NO: 23<br>attB-GA<br>(Artificial Sequence) | GGCTTGTCGACGACGGCGGACTCCGTCGTCAGGATCAT |

TABLE 4-continued

| SEQ ID NO/<br>DESCRIPTION/<br>SOURCE | SEQUENCE |
| --- | --- |
| SEQ ID NO: 24<br>attP-GA<br>(Artificial Sequence) | GTGGTTTGTCTGGTCAACCACCGCGGACTCAGTGGTGTACGGTAC<br>AAACCCA |
| SEQ ID NO: 25<br>attB-AG<br>(Artificial Sequence) | GGCTTGTCGACGACGGCGAGCTCCGTCGTCAGGATCAT |
| SEQ ID NO: 26<br>attP-AG<br>(Artificial Sequence) | GTGGTTTGTCTGGTCAACCACCGCGAGCTCAGTGGTGTACGGTAC<br>AAACCCA |
| SEQ ID NO: 27<br>attB-AC<br>(Artificial Sequence) | GGCTTGTCGACGACGGCGACCTCCGTCGTCAGGATCAT |
| SEQ ID NO: 28<br>attP-AC<br>(Artificial Sequence) | GTGGTTTGTCTGGTCAACCACCGCGACCTCAGTGGTGTACGGTACA<br>AACCCA |
| SEQ ID NO: 29<br>attB-AT<br>(Artificial Sequence) | GGCTTGTCGACGACGGCGATCTCCGTCGTCAGGATCAT |
| SEQ ID NO: 30<br>attP-AT<br>(Artificial Sequence) | GTGGTTTGTCTGGTCAACCACCGCGATCTCAGTGGTGTACGGTACA<br>AACCCA |
| SEQ ID NO: 31<br>attB-GC<br>(Artificial Sequence | GGCTTGTCGACGACGGCGGCCTCCGTCGTCAGGATCAT |
| SEQ ID NO: 32<br>attP-GC<br>(Artificial Sequence) | GTGGTTTGTCTGGTCAACCACCGCGGCCTCAGTGGTGTACGGTACA<br>AACCCA |
| SEQ ID NO: 33<br>attB-CG<br>(Artificial Sequence) | GGCTTGTCGACGACGGCGCGCTCCGTCGTCAGGATCAT |
| SEQ ID NO: 34<br>attP-CG<br>(Artificial Sequence) | GTGGTTTGTCTGGTCAACCACCGCGCGCTCAGTGGTGTACGGTACA<br>AACCCA |
| SEQ ID NO: 35<br>attB-TA<br>(Artificial Sequence) | GGCTTGTCGACGACGGCGTACTCCGTCGTCAGGATCAT |
| SEQ ID NO: 36<br>attP-TA<br>(Artificial Sequence) | GTGGTTTGTCTGGTCAACCACCGCGTACTCAGTGGTGTACGGTACA<br>AACCCA |
| SEQ ID NO: 37<br>C31-attB<br>(Artificial Sequence) | TGCGGGTGCCAGGGCGTGCCCTTGGGCTCCCCGGGCGCGTACTCC |
| SEQ ID NO: 38<br>C31-attP<br>(Artificial Sequence) | GTGCCCCAACTGGGGTAACCTTTGAGTTCTCTCAGTTGGGGG |
| SEQ ID NO: 39<br>R4-attB<br>(Artificial Sequence) | GCGCCCAAGTTGCCCATGACCATGCCGAAGCAGTGGTAGAAGGGC<br>ACCGGCAGACAC |
| SEQ ID NO: 40<br>R4-attP<br>(Artificial Sequence) | AGGCATGTTCCCCAAAGCGATACCACTTGAAGCAGTGGTACTGCT<br>TGTGGGTACACTCTGCGGGTGATGA |
| SEQ ID NO: 41<br>BT1-attB<br>(Artificial Sequence) | GTCCTTGACCAGGTTTTTGACGAAAGTGATCCAGATGATCCAGCTC<br>CACACCCCGAACGC |
| SEQ ID NO: 42<br>BT1-attP<br>(Artificial Sequence) | GGTGCTGGGTTGTTGTCTCTGGACAGTGATCCATGGGAAACTACTC<br>AGCACCACCAATGTTCC |

TABLE 4-continued

| SEQ ID NO/<br>DESCRIPTION/<br>SOURCE | SEQUENCE |
| --- | --- |
| SEQ ID NO: 43<br>Bxb-attB<br>(Artificial Sequence) | TCGGCCGGCTTGTCGACGACGGCGGTCTCCGTCGTCAGGATCATCC<br>GGGC |
| SEQ ID NO: 44<br>Bxb-attP<br>(Artificial Sequence) | GTCGTGGTTTGTCTGGTCAACCACCGCGGTCTCAGTGGTGTACGGT<br>ACAAACCCCGAC |
| SEQ ID NO: 45<br>TG1-attB<br>(Artificial Sequence) | GATCAGCTCCGCGGGCAAGACCTTCTCCTTCACGGGGTGGAAGGT<br>C |
| SEQ ID NO: 46<br>TG1-attP<br>(Artificial Sequence) | TCAACCCCGTTCCAGCCCAACAGTGTTAGTCTTTGCTCTTACCCAG<br>TTGGGCGGGATAGCCTGCCCG |
| SEQ ID NO: 47<br>C1-attB<br>(Artificial Sequence) | AACGATTTTCAAAGGATCACTGAATCAAAAGTATTGCTCATCCAC<br>GCGAAATTTTTC |
| SEQ ID NO: 48<br>C1-attP<br>(Artificial Sequence) | AATATTTTAGGTATATGATTTTGTTTATTAGTGTAAATAACACTAT<br>GTACCTAAAAT |
| SEQ ID NO: 49<br>C370-attB<br>(Artificial Sequence) | TGTAAAGGAGACTGATAATGGCATGTACAACTATACTCGTCGGTA<br>AAAAGGCA |
| SEQ ID NO: 50<br>C370-attP<br>(Artificial Sequence) | TAAAAAAATACAGCGTTTTTCATGTACAACTATACTAGTTGTAGTG<br>CCTAAA |
| SEQ ID NO: 51<br>K38-attB<br>(Artificial Sequence) | GAGCGCCGGATCAGGGAGTGGACGGCCTGGGAGCGCTACACGCT<br>GTGGCTGCGGTC |
| SEQ ID NO: 52<br>K38-attP<br>(Artificial Sequence) | CCCTAATACGCAAGTCGATAACTCTCCTGGGAGCGTTGACAACTT<br>GCGCACCCTGA |
| SEQ ID NO: 53<br>RB-attB<br>(Artificial Sequence) | TCTCGTGGTGGTGGAAGGTGTTGGTGCGGGGTTGGCCGTGGTCGA<br>GGTGGGGTGGTGGTAGCCATTCG |
| SEQ ID NO: 54<br>RV-attP<br>(Artificial Sequence) | GCACAGGTGTAGTGTATCTCACAGGTCCACGGTTGGCCGTGGACT<br>GCTGAAGAACATTCCACGCCAGGA |
| SEQ ID NO: 55<br>SPBC-attB<br>(Artificial Sequence) | AGTGCAGCATGTCATTAATATCAGTACAGATAAAGCTGTATCTCCT<br>GTGAACACAATGGGTGCCA |
| SEQ ID NO: 56<br>SPBC-attP<br>(Artificial Sequence) | AAAGTAGTAAGTATCTTAAAAAACAGATAAAGCTGTATATTAAGA<br>TACTTACTAC |
| SEQ ID NO: 57<br>TP901-attB<br>(Artificial Sequence) | TGATAATTGCCAACACAATTAACATCTCAATCAAGGTAAATGCTTT<br>TTCGTTTT |
| SEQ ID NO: 58<br>TP901-attP<br>(Artificial Sequence) | AATTGCGAGTTTTTATTTCGTTTATTTCAATTAAGGTAACTAAAAA<br>ACTCCTTT |
| SEQ ID NO: 59<br>Wβ-attB<br>(Artificial Sequence) | AAGGTAGCGTCAACGATAGGTGTAACTGTCGTGTTTGTAACGGTA<br>CTTCCAACAGCTGGCGTTTCAGT |
| SEQ ID NO: 60<br>Wβ-attP<br>(Artificial Sequence) | TAGTTTTAAAGTTGGTTATTAGTTACTGTGATATTTATCACGGTAC<br>CCAATAACCAATGAATATTTGA |
| SEQ ID NO: 61<br>A118-attB<br>(Artificial Sequence) | TGTAACTTTTTCGGATCAAGCTATGAAGGACGCAAAGAGGGAACT<br>AAACACTTAATT |

TABLE 4-continued

| SEQ ID NO/ DESCRIPTION/ SOURCE | SEQUENCE |
|---|---|
| SEQ ID NO: 62 A118-attP (Artificial Sequence) | TTGTTTAGTTCCTCGTTTTCTCTCGTTGGAAGAAGAAGAAACGAGA AACTAAAATTA |
| SEQ ID NO: 63 BL3-attB (Artificial Sequence) | CAACCTGTTGACATGTTTCCACAGACAACTCACGTGGAGGTAGTC ACGGCTTTTACGTTAGTT |
| SEQ ID NO: 64 BL3-attP (Artificial Sequence) | GAGAATACTGTTGAACAATGAAAAACTAGGCATGTAGAAGTTGTT TGTGCACTAACTTTAA |
| SEQ ID NO: 65 MR11-attB (Artificial Sequence) | ACAGGTCAACACATCGCAGTTATCGAACAATCTTCGAAAATGTAT GGAGGCACTTGTATCAATATAGGATGTATACCTTCGAAGACACTT GTACATGATGGATTAGAAGGCAAATCCTTT |
| SEQ ID NO: 66 MR11-attP (Artificial Sequence) | CAAAATAAAAAACATTGATTTTTATTAACTTCTTTTGTGCGGAACT ACGAACAGTTCATTAATACGAAGTGTACAAACTTCCATACAAAAA TAACCACGACAATTAAGACGTGGTTTCTA |
| SEQ ID NO: 67 attL (Artificial Sequence) | ATTATTTCTCACCCTGA |
| SEQ ID NO: 68 attR (Artificial Sequence) | ATCATCTCCCACCCGGA |
| SEQ ID NO: 69 Vox (Artificial Sequence) | AATAGGTCTG AGAACGCCCA TTCTCAGACG TATT |
| SEQ ID NO: 70 FRT (Artificial Sequence) | GAAGTTCCTATAC TTTCTAGA GAATAGGAACTTC |
| SEQ ID NO: 71 Cre recombinase expression plasmid (Artificial Sequence) | GGTCGACATTGATTATTGACTAGTTATTAATAGTAATCAATTACGG GGTCATTAGTTCATAGCCCATATATGGAGTTCCGCGTTACATAACT TACGGTAAATGGCCCGCCTGGCTGACCGCCCAACGACCCCCGCCC ATTGACGTCAATAATGACGTATGTTCCCATAGTAACGCCAATAGG GACTTTCCATTGACGTCAATGGGTGGAGTATTTACGGTAAACTGCC CACTTGGCAGTACATCAAGTGTATCATATGCCAAGTACGCCCCCTA TTGACGTCAATGACGGTAAATGGCCCGCCTGGCATTATGCCCAGT ACATGACCTTATGGGACTTTCCTACTTGGCAGTACATCTACGTATT AGTCATCGCTATTACCATGGTCGAGGTGAGCCCCACGTTCTGCTTC ACTCTCCCCATCTCCCCCCCCTCCCCACCCCCAATTTTGTATTTATT TATTTTTTAATTATTTTGTGCAGCGATGGGGGCGGGGGGGGGGGG GGCGCGCGCCAGGCGGGGGGGGGGGGGGGGGGGGGGGGGG GGGGGGCGGGGGGGGGGGGCGGCAGCCAATCAGAGCGGCGCGC TCCGAAAGTTTCCTTTTATGGCGAGGCGGCGGCGGCGGCGGCCCT ATAAAAAGCGAAGCGCGCGGCGGGCGGGAGTCGCTGCGCGCTGC CTTCGCCCCGTGCCCCGCTCCGCCGCCGCCTCGCGCCGCCCGCCCC GGCTCTGACTGACCGCGTTACTCCCACAGGTGAGCGGGCGGGACG GCCCTTCTCCTCCGGGCTGTAATTAGCGCTTGGTTTAATGACGGCT TGTTTCTTTTCTGTGGCTGCGTGAAAGCCTTGAGGGGCTCCGGGAG GGCCCTTTGTGCGGGGGGAGCGGCTCGGGGGGTGCGTGCGTGTGT GTGTGCGTGGGGAGCGCCGCGTGCGGCTCCGCGCTGCCCGGCGGC TGTGAGCGCTGCGGGCGCGGCGCGGGGCTTTGTGCGCTCCGCAGT GTGCGCGAGGGGAGCGCGGCCGGGGGCGGTGCCCCGCGGTGCGG GGGGGGCTGCGAGGGGAACAAAGGCTGCGTGCGGGGTGTGTGCG TGGGGGGGTGAGCAGGGGGTGTGGGCGCGTCGGTCGGGCTGCAA CCCCCCCTGCACCCCCCTCCCCGAGTTGCTGAGCACGGCCCGGCTT CGGGTGCGGGGCTCCGTACGGGGCGTGGCGCGGGGCTCGCCGTGC CGGGCGGGGGTGGCGGCAGGTGGGGGTGCCGGCGGGGCGGGG CCGCCTCGGGCCGGGAGGGCTCGGGGAGGGGCGCGGCGGCCC CCGGAGCGCCGGCGGCTGTCGAGGCGCGGCGAGCCGCAGCCATTG CCTTTTATGGTAATCGTGCGAGAGGGCGCAGGGACTTCCTTTGTCC CAAATCTGTGCGGAGCCGAAATCTGGGAGGCGCCGCCGCACCCCC TCTAGCGGGCGCGGGCGAAGCGGTGCGGCGCCGGCAGGAAGGA AATGGGCGGGAGGGCCTTCGTGCGTCGCCGCGCCGCCGTCCCCT TCTCCCTCTCCAGCCTCGGGGCTGTCCGCGGGGGACGGCTGCCTT CGGGGGGACGGGGCAGGGCGGGGTTCGGCTTCTGGCGTGTGACC GGCGGCTCTAGAGCCTCTGCTAACCATGTTCATGCCTTCTTCTTTTT CCTACAGCTCCTGGGCAACGTGCTGGTTATTGTGCTGTCTCATCAT TTTGGCAAAGAATTCTGAGCCGCCACCATGGCCAATTTACTGACC |

TABLE 4-continued

| SEQ ID NO/<br>DESCRIPTION/<br>SOURCE | SEQUENCE |
|---|---|
| | GTACACCAAAATTTGCCTGCATTACCGGTCGATGCAACGAGTGAT |
| | GAGGTTCGCAAGAACCTGATGGACATGTTCAGGGATCGCCAGGCG |
| | TTTTCTGAGCATACCTGGAAAATGCTTCTGTCCGTTTGCCGGTCGT |
| | GGGCGGCATGGTGCAAGTTGAATAACCGGAAATGGTTTCCCGCAG |
| | AACCTGAAGATGTTCGCGATTATCTTCTATATCTTCAGGCGCGCGG |
| | TCTGGCAGTAAAAACTATCCAGCAACATTTGGGCCAGCTAAACAT |
| | GCTTCATCGTCGGTCCGGGCTGCCACGACCAAGTGACAGCAATGC |
| | TGTTTCACTGGTTATGCGGCGGATCCGAAAAGAAAACGTTGATGC |
| | CGGTGAACGTGCAAAACAGGCTCTAGCGTTCGAACGCACTGATTT |
| | CGACCAGGTTCGTTCACTCATGGAAAATAGCGATCGCTGCCAGGA |
| | TATACGTAATCTGGCATTTCTGGGGATTGCTTATAACACCCTGTTA |
| | CGTATAGCCGAAATTGCCAGGATCAGGGTTAAAGATATCTCACGT |
| | ACTGACGGTGGGAGAATGTTAATCCATATTGGCAGAACGAAAACG |
| | CTGGTTAGCACCGCAGGTGTAGAGAAGGCACTTAGCCTGGGGGTA |
| | ACTAAACTGGTCGAGCGATGGATTTCCGTCTCTGGTGTAGCTGATG |
| | ATCCGAATAACTACCTGTTTTGCCGGGTCAGAAAAATGGTGTTG |
| | CCGCGCCATCTGCCACCAGCCAGCTATCAACTCGCGCCCTGGAAG |
| | GGATTTTTGAAGCAACTCATCGATTGATTTACGGCGCTAAGGATG |
| | ACTCTGGTCAGAGATACCTGGCCTGGTCTGGACACAGTGCCCGTG |
| | TCGGAGCCGCGCGAGATATGGCCCGCGCTGGAGTTTCAATACCGG |
| | AGATCATGCAAGCTGGTGGCTGGACCAATGTAAATATTGTCATGA |
| | ACTATATCCGTAACCTGGATAGTGAAACAGGGGCAATGGTGCGCC |
| | TGCTGGAAGATGGCGATGGACCGGTGGAACAAAAACTTATTTCTG |
| | AAGAAGATCTGTGATAGCGGCCGCACTCCTCAGGTGCAGGCTGCC |
| | TATCAGAAGGTGGTGGCTGGTGTGGCCAATGCCCTGGCTCACAAA |
| | TACCACTGAGATCTTTTTCCCTCTGCCAAAAATTATGGGGACATCA |
| | TGAAGCCCCTTGAGCATCTGACTTCTGGCTAATAAAGGAAATTTAT |
| | TTTCATTGCAATAGTGTGTTGGAATTTTTTGTGTCTCTCACTCGGAA |
| | GGACATATGGGAGGGCAAATCATTTAAAACATCAGAATGAGTATT |
| | TGGTTTAGAGTTTGGCAACATATGCCCATATGCTGGCTGCCATGAA |
| | CAAAGGTTGGCTATAAAGAGGTCATCAGTATATGAAACAGCCCCC |
| | TGCTGTCCATTCCTTATTCCATAGAAAAGCCTTGACTTGAGGTTAG |
| | ATTTTTTTTATATTTTGTTTTGTGTTATTTTTTCTTTAACATCCCTA |
| | AAATTTTCCTTACATGTTTTACTAGCCAGATTTTTCCTCCTCTCCTG |
| | ACTACTCCCAGTCATAGCTGTCCCTCTTCTCTTATGGAGATCCCTC |
| | GACCTGCAGCCCAAGCTTGGCGTAATCATGGTCATAGCTGTTTCCT |
| | GTGTGAAATTGTTATCCGCTCACAATTCCACACAACATACGAGCC |
| | GGAAGCATAAAGTGTAAAGCCTGGGGTGCCTAATGAGTGAGCTAA |
| | CTCACATTAATTGCGTTGCGCTCACTGCCCGCTTTCCAGTCGGGAA |
| | ACCTGTCGTGCCAGCGGATCCGCATCTCAATTAGTCAGCAACCAT |
| | AGTCCCGCCCCTAACTCCGCCCATCCCGCCCCTAACTCCGCCCAGT |
| | TCCGCCCATTCTCCGCCCCATGGCTGACTAATTTTTTTATTTATGC |
| | AGAGGCCGAGGCCGCCTCGGCCTCTGAGCTATTCCAGAAGTAGTG |
| | AGGAGGCTTTTTTGGAGGCCTAGGCTTTTGCAAAAAGCTAACTTGT |
| | TTATTGCAGCTTATAATGGTTACAAATAAAGCAATAGCATCACAA |
| | ATTTCACAAATAAAGCATTTTTTTCACTGCATTCTAGTTGTGGTTTG |
| | TCCAAACTCATCAATGTATCTTATCATGTCTGGATCCGCTGCATTA |
| | ATGAATCGGCCAACGCGCGGGGAGAGGCGGTTTGCGTATTGGGCG |
| | CTCTTCCGCTTCCTCGCTCACTGACTCGCTGCGCTCGGTCGTTCGG |
| | CTGCGGCGAGCGGTATCAGCTCACTCAAAGGCGGTAATACGGTTA |
| | TCCACAGAATCAGGGGATAACGCAGGAAAGAACATGTGAGCAAA |
| | AGGCCAGCAAAAGGCCAGGAACCGTAAAAAGGCCGCGTTGCTGG |
| | CGTTTTTCCATAGGCTCCGCCCCCCTGACGAGCATCACAAAAATCG |
| | ACGCTCAAGTCAGAGGTGGCGAAACCCGACAGGACTATAAAGAT |
| | ACCAGGCGTTTCCCCCTGGAAGCTCCCTCGTGCGCTCTCCTGTTCC |
| | GACCCTGCCGCTTACCGGATACCTGTCCGCCTTTCTCCCTTCGGGA |
| | AGCGTGGCGCTTTCTCATAGCTCACGCTGTAGGTATCTCAGTTCGG |
| | TGTAGGTCGTTCGCTCCAAGCTGGGCTGTGTGCACGAACCCCCCGT |
| | TCAGCCCGACCGCTGCGCCTTATCCGGTAACTATCGTCTTGAGTCC |
| | AACCCGGTAAGACACGACTTATCGCCACTGGCAGCAGCCACTGGT |
| | AACAGGATTAGCAGAGCGAGGTATGTAGGCGGTGCTACAGAGTTC |
| | TTGAAGTGGTGGCCTAACTACGGCTACACTAGAAGAACAGTATTT |
| | GGTATCTGCGCTCTGCTGAAGCCAGTTACCTTCGGAAAAAGAGTT |
| | GGTAGCTCTTGATCCGGCAAACAAACCACCGCTGGTAGCGGTGGT |
| | TTTTTTGTTTGCAAGCAGCAGATTACGCGCAGAAAAAAAGGATCT |
| | CAAGAAGATCCTTTGATCTTTTCTACGGGGTCTGACGCTCAGTGGA |
| | ACGAAAACTCACGTTAAGGGATTTTGGTCATGAGATTATCAAAAA |
| | GGATCTTCACCTAGATCCTTTTAAATTAAAAATGAAGTTTTAAATC |
| | AATCTAAAGTATATATGAGTAAACTTGGTCTGACAGTTACCAATG |
| | CTTAATCAGTGAGGCACCTATCTCAGCGATCTGTCTATTTCGTTCA |
| | TCCATAGTTGCCTGACTCCCCGTCGTGTAGATAACTACGATACGGG |
| | AGGGCTTACCATCTGGCCCCAGTGCTGCAATGATACCGCGAGACC |
| | CACGCTCACCGGCTCCAGATTTATCAGCAATAAACCAGCCAGCCG |
| | GAAGGGCCGAGCGCAGAAGTGGTCCTGCAACTTTATCCGCCTCCA |
| | TCCAGTCTATTAATTGTTGCCGGGAAGCTAGAGTAAGTAGTTCGCC |
| | AGTTAATAGTTTGCGCAACGTTGTTGCCATTGCTACAGGCATCGTG |

TABLE 4-continued

| SEQ ID NO/<br>DESCRIPTION/<br>SOURCE | SEQUENCE |
|---|---|
| | GTGTCACGCTCGTCGTTTGGTATGGCTTCATTCAGCTCCGGTTCCC<br>AACGATCAAGGCGAGTTACATGATCCCCCATGTTGTGCAAAAAAG<br>CGGTTAGCTCCTTCGGTCCTCCGATCGTTGTCAGAAGTAAGTTGGC<br>CGCAGTGTTATCACTCATGGTTATGGCAGCACTGCATAATTCTCTT<br>ACTGTCATGCCATCCGTAAGATGCTTTTCTGTGACTGGTGAGTACT<br>CAACCAAGTCATTCTGAGAATAGTGTATGCGGCGACCGAGTTGCT<br>CTTGCCCGGCGTCAATACGGGATAATACCGCGCCACATAGCAGAA<br>CTTTAAAAGTGCTCATCATTGGAAAACGTTCTTCGGGGCGAAAAC<br>TCTCAAGGATCTTACCGCTGTTGAGATCCAGTTCGATGTAACCCAC<br>TCGTGCACCCAACTGATCTTCAGCATCTTTTACTTTCACCAGCGTTT<br>CTGGGTGAGCAAAAACAGGAAGGCAAATGCCGCAAAAAAGGGA<br>ATAAGGGCGACACGGAAATGTTGAATACTCATACTCTTCCTTTTTC<br>AATATTATTGAAGCATTTATCAGGGTTATTGTCTCATGAGCGGATA<br>CATATTTGAATGTATTTAGAAAAATAAACAAATAGGGGTTCCGCG<br>CACATTTCCCCGAAAAGTGCCACCTG |
| SEQ ID NO: 72<br>GFP-Lox66 Cre<br>expression plasmid<br>(Artificial Sequence) | AGCTCTGATCAAGAGACAGGATGAGGATCGTTTCGCATGATTGAA<br>CAAGATGGATTGCACGCAGGTTCTCCGGCCGCTTGGGTGGAGAGG<br>CTATTCGGCTATGACTGGGCACAACAGACAATCGGCTGCTCTGAT<br>GCCGCCGTGTTCCGGCTGTCAGCGCAGGGGCGCCCGGTTCTTTTTG<br>TCAAGACCGACCTGTCCGGTGCCCTGAATGAACTGCAAGACGAGG<br>CAGCGCGGCTATCGTGGCTGGCCACGACGGGCGTTCCTTGCGCAG<br>CTGTGCTCGACGTTGTCACTGAAGCGGGAAGGGACTGGCTGCTAT<br>TGGGCGAAGTGCCGGGGCAGGATCTCCATGTCATCTACACCTTGC<br>TCCTGCCGAGAAAGTATCCATCATGGCTGATGCAATGCGGCGGCT<br>GCATACGCTTGATCCGGCTACCTGCCCATTCGACCACCAAGCGAA<br>ACATCGCATCGAGCGAGCACGTACTCGGATGGAAGCCGGTCTTGT<br>CGATCAGGATGATCTGGACGAAGAGCATCAGGGGCTCGCGCCAGC<br>CGAACTGTTCGCCAGGCTCAAGGCGAGCATGCCCGACGGCGAGGA<br>TCTCGTCGTGACCCATGGCGATGCCTGCTTGCCGAATATCATGGTG<br>GAAAATGGCCGCTTTTCTGGATTCATCGACTGTGGCCGGCTGGGTG<br>TGGCGGACCGCTATCAGGACATAGCGTTGGCTACCCGTGATATTG<br>CTGAAGAGCTTGGCGGCGAATGGGCTGACCGCTTCCTCGTGCTTTA<br>CGGTATCGCCGCTCCCGATTCGCAGCGCATCGCCTTCTATCGCCTT<br>CTTGACGAGTTCTTCTGAATTATTAACTCGAGATCCACTAGAGTGT<br>GGCGGCCGCATTCTTATAATCAGCATCATGATGTGGTACCACATCA<br>TGATGCTGATTACCCCCAACTGAGAGAACTCAAAGGTTACCCCAG<br>TTGGGGCGGGCCCACAAATAAAGCAATAGCATCACAAATTTCACA<br>AATAAAGCATTTTTTTCACTGCATTCTAGTTGTGGTTTGTCCAAAC<br>TCATCGAGCTCGAGATCTGGCGAAGGCGATGGGGGTCTTGAAGGC<br>GTGCTGGTACTCCACGATGCCCAGCTCGGTGTTGCTGTGCAGCTCC<br>TCCACGCGGCGGAAGGCGAACATGGGGCCCCCGTTCTGCAGGATG<br>CTGGGGTGGATGGCGCTCTTGAAGTGCATGTGGCTGTCCACCACG<br>AAGCTGTAGTAGCCGCCGTCGCGCAGGCTGAAGGTGCGGGCGAAG<br>CTGCCCACCAGCACGTTATCGCCCATGGGGTGCAGGTGCTCCACG<br>GTGGCGTTGCTGCGGATGATCTTGTCGGTGAAGATCACGCTGTCCT<br>CGGGGAAGCCGGTGCCCACCACCTTGAAGTCGCCGATCACGCGGC<br>CGGCCTCGTAGCGGTAGCTGAAGCTCACGTGCAGCACGCCGCCGT<br>CCTCGTACTTCTCGATGCGGGTGTTGGTGTAGCCGCCGTTGTTGAT<br>GGCGTGCAGGAAGGGGTTCTCGTAGCCGCTGGGGTAGGTGCCGAA<br>GTGGTAGAAGCCGTAGCCCATCACGTGGCTCAGCAGGTAGGGGCT<br>GAAGGTCAGGGCGCCTTTGGTGCTCTTCATCTTGTTGGTCATGCGG<br>CCCTGCTCGGGGGTGCCCTCTCCGCCGCCCACCAGCTCGAACTCCA<br>CGCCGTTCAGGGTGCCGGTGATGCGGCACTCGATCTTCATGGCGG<br>GCATGGTGGCGACCGGTAGCGCTAGCGGCTTCGGATAACTTCGTA<br>TAGCATACATTATACGAACGGTAAGCGCTACCGCCGGCATACCCA<br>AGTGAAGTTGCTCGCAGCTTATAGTCGCGCCCGGGGAGCCCAAGG<br>GCACGCCCTGGCACCGCGGCCGCTGAGTCTCGACCATCATCATCA<br>TCATCATTGAGTTTATCTGGGATAACAGGGTAATGTCATCTAGGGA<br>TAACAGGGTATGTCATCTGGGATAACAGGGTAATGTATCTAGGGA<br>TAACAGGGTAATGTCATCTGGGATAACAGGGTAATGTCATCTAGG<br>GATAACAGGGTATGTCATCTGGGATAACAGGGTAATGTATCTAGG<br>GATAACAGGGTAATGTCATCTGGGATAACAGGGTAATGTCATCTA<br>GGGATAACAGGGTATGTCATCTGGGATAACAGGGTAATGTATCTA<br>GGGATAACAGGGTAATGTCATCTGGGATAACAGGGTAATGTCATC<br>TAGGGATAACAGGGTATGTCATCTGGGATAACAGGGTAATGTATC<br>TAGGGATAACAGGGTAATGTCATCTGGGATAACAGGGTAATGTCA<br>TCTAGGGATAACAGGGTATGTCATCTGGGATAACAGGGTAATGTA<br>TCTAGGGATAACAGGGTAATGTCATCTGGGATAACAGGGTAATGT<br>CATCTAGGGATAACAGGGTATGTCATCTGGGATAACAGGGTAATG<br>TATCTAGGGATAACAGGGTAATGTCATCTGGGATAACAGGGTAAT<br>GTCATCTAGGGATAACAGGGTAAATGTCATCTAGGGATAACAGGG<br>TAATGTCATCTAGGGATAACAGGGTAATGTCATCTGGGATAACAG<br>GGTAATGTCATCTAGGGATAACAGGGTAATGTATCGCCAGCGTCG<br>CACAGCATGTTTGCTTGTCGCCGTCGCGTCTGTCACATCTTTTCCG<br>CCAGCAGTTAGGGATTAGCGTCTTAAGCTGGCGCGAGGACCAACG |

TABLE 4-continued

| SEQ ID NO/<br>DESCRIPTION/<br>SOURCE | SEQUENCE |
|---|---|
| | TATCAGCCAGGCGAAGCTGCTTTTGAGCACCACCCGGATGCCTAT<br>CGCCACCGTCGGTCGCAATGTTGGTTTTGACGATCAACTCTATTTC<br>TCGCGGGTATTTAAAAAATGCACCGGGGCCAGCCCGAGCGAGTTC<br>CGTGCCGGTTGTGAAGAAAAAGTGAATGATGTAGCCGTCAAGTTG<br>TCATAATTGGTAACGAATCAGACAATTGACGGCTTGACGGAGTAG<br>CATAGGGTTTGCAGAATCCCTGCTTCGTCCATTTGACAGGCACATT<br>ATGCATGCCGCTTCGCCTTCGCGCGCGAATTGATCTGCTGCCTCGC<br>GCGTTTCGGTGATGACGGTGAAAACCTCTGACACATGCAGCTCCC<br>GGAGACGGTCACAGCTTGTCTGTAAGCGGATGCCGGGAGCAGACA<br>AGCCCGTCAGGGCGCGTCAGCGGGTGTTGGCGGGTGTCGGGGCGC<br>AGCCATGACCCAGTCACGTAGCGATAGCGGAGTGTATACTGGCTT<br>AACTATGCGGCATCAGAGCAGATTGTACTGAGAGTGCACCATATG<br>CGGTGTGAAATACCGCACAGATGCGTAAGGAGAAAATACCGCATC<br>AGGCGCTCTTCCGCTTCCTCGCTCACTGACTCGCTGCGCTCGGTCG<br>TTCGGCTGCGGCGAGCGGTATCAGCTCACTCAAAGGCGGTAATAC<br>GGTTATCCACAGAATCAGGGGATAACGCAGGAAAGAACATGTGA<br>GCAAAAGGCCAGCAAAAGGCCAGGAACCGTAAAAAGGCCGCGTT<br>GCTGGCGTTTTTCCATAGGCTCCGCCCCCTGACGAGCATCACAAA<br>AATCGACGCTCAAGTCAGAGGTGGCGAAACCCGACAGGACTATAA<br>AGATACCAGGCGTTTCCCCCTGGAAGCTCCCTCGTGCGCTCTCCTG<br>TTCCGACCCTGCCGCTTACCGGATACCTGTCCGCCTTTCTCCCTTCG<br>GGAAGCGTGGCGCTTTCTCATAGCTCACGCTGTAGGTATCTCAGTT<br>CGGTGTAGGTCGTTCGCTCCAAGCTGGGCTGTGTGCACGAACCCC<br>CCGTTCAGCCCGACCGCTGCGCCTTATCCGGTAACTATCGTCTTGA<br>GTCCAACCCGGTAAGACACGACTTATCGCCACTGGCAGCAGCCAC<br>TGGTAACAGGATTAGCAGAGCGAGGTATGTAGGCGGTGCTACAGA<br>GTTCTTGAAGTGGTGGCCTAACTACGGCTACACTAGAAGGACAGT<br>ATTTGGTATCTGCGCTCTGCTGAAGCCAGTTACCTTCGGAAAAAGA<br>GTTGGTAGCTCTTGATCCGGCAAACAAACCACCGCTGGTAGCGGT<br>GGTTTTTTTGTTTGCAAGCAGCAGATTACGCGCAGAAAAAAAGGA<br>TCTCAAGAAGATCCTTTGATCTTTTCTACGGGGTCTGACGCTCAGT<br>GGAACGAAAACTCACGTTAAGGGATTTTGGTCATGAGCGGATACA<br>TATTTGAATGTATTTAGAAAAATAAACAAAAGAGTTTGTAGAAAC<br>GCAAAAAGGCCATCCGTCAGGATGGCCTTCTGCTTAATTTGATGCC<br>TGGCAGTTTATGGCGGGCGTCCTGCCCGCCACCCTCCGGGCCGTTG<br>CTTCGCAACGTTCAAATCCGCTCCCGGCGGATTTGTCCTACTCAGG<br>AGAGCGTTCACCGACAAACAACAGATAAAACGAAAGGCCCAGTC<br>TTTCGACTGAGCCTTTCGTTTTATTTGATGCCTGGCAGTTCCCTACT<br>CTCGCATGGGGAGACCCCACACTACCATCGGCGCTACGGCGTTTC<br>ACTTCTGAGTTCGGCATGGGGTCAGGTGGGACCACCGCGCTACTG<br>CCGCCAGGCAAATTCTGTTTTATCAGACCGCTTCTGCGTTCTGATT<br>TAATCTGTATCAGGCTGAAAATCTTCTCTCATCCGCCAAAACAGCC<br>AAGCTGGAGACCGTTTGGCCCCCCTCGAGCACGTAGAAAAGCCAGT<br>CCGCAGAAACGGTGCTGACCCCGGATGAATGTCAGCTACTGGGCT<br>ATCTGGACAAGGGAAAACGCAAGCGCAAAGAGAAAGCAGGTAGC<br>TTGCAGTGGGCTTACATGGCGATAGCTAGACTGGGCGGTTTTATG<br>GACAGCAAGCGAACCGGAATTGCCAGCTGGGGCGCCCTCTGGTAA<br>GGTTGGGAAGCCCTGCAAAGTAAACTGGATGGCTTTCTCGCCGCC<br>AAGGATCTGATGGCGCAGGGGATCA |
| SEQ ID NO: 73<br>pCMV PE2 P2A Cre<br>plasmid<br>(Artificial Sequence) | ACGCGTTGACATTGATTATTGACTAGTTATTAATAGTAATCAATTA<br>CGGGGTCATTAGTTCATAGCCCATATATGGAGTTCCGCGTTACATA<br>ACTTACGGTAAATGGCCCGCCTGGCTGACCGCCCAACGACCCCCG<br>CCCATTGACGTCAATAATGACGTATGTTCCCATAGTAACGCCAATA<br>GGGACTTTCCATTGACGTCAATGGGTGGAGTATTTACGGTAAACT<br>GCCCACTTGGCAGTACATCAAGTGTATCATATGCCAAGTACGCCC<br>CCTATTGACGTCAATGACGGTAAATGGCCCGCCTGGCATTATGCCC<br>AGTACATGACCTTATGGGACTTTCCTACTTGGCAGTACATCTACGT<br>ATTAGTCATCGCTATTACCATGGTGATGCGGTTTTGGCAGTACATC<br>AATGGGCGTGGATAGCGGTTTGACTCACGGGGATTTCCAAGTCTC<br>CACCCCATTGACGTCAATGGGAGTTTGTTTTGGCACCAAAATCAAC<br>GGGACTTTCCAAAATGTCGTAACAACTCCGCCCCATTGACGCAAA<br>TGGGCGGTAGGCGTGTACGGTGGGAGGTCTATATAAGCAGAGCTG<br>GTTTAGTGAACCGTCAGATCCGCTAGAGATCCGCGGCCGCTAATA<br>CGACTCACTATAGGGAGAGCCGCCACCATGAAACGGACAGCCGAC<br>GGAAGCGAGTTCGAGTCACCAAAGAAGAAGCGGAAAGTCGACAA<br>GAAGTACAGCATCGGCCTGGACATCGGCACCAACTCTGTGGGCTG<br>GGCCGTGATCACCGACGAGTACAAGGTGCCCAGCAAGAAATTCAA<br>GGTGCTGGGCAACACCGACCGGCACAGCATCAAGAAGAACCTGAT<br>CGGAGCCCTGCTGTTCGACAGCGGCGAAACAGCCGAGGCCACCCG<br>GCTGAAGAGAACCGCCAGAAGAAGATACACCAGACGGAAGAACC<br>GGATCTGCTATCTGCAAGAGATCTTCAGCAACGAGATGGCCAAGG<br>TGGACGACAGCTTCTTCCACAGACTGGAAGAGTCCTTCCTGGTGG<br>AAGAGGATAAGAAGCACGAGCGGCACCCCATCTTCGGCAACATCG<br>TGGACGAGGTGGCCTACCACGAGAAGTACCCCACCATCTACCACC<br>TGAGAAAGAAACTGGTGGACAGCACCGACAAGGCCGACCTGCGG |

TABLE 4-continued

| SEQ ID NO/<br>DESCRIPTION/<br>SOURCE | SEQUENCE |
|---|---|
| | CTGATCTATCTGGCCCTGGCCCACATGATCAAGTTCCGGGGCCACT |
| | TCCTGATCGAGGGCGACCTGAACCCCGACAACAGCGACGTGGACA |
| | AGCTGTTCATCCAGCTGGTGCAGACCTACAACCAGCTGTTCGAGG |
| | AAAACCCCATCAACGCCAGCGGCGTGGACGCCAAGGCCATCCTGT |
| | CTGCCAGACTGAGCAAGAGCAGACGGCTGGAAAATCTGATCGCCC |
| | AGCTGCCCGGCGAGAAGAAGAATGGCCTGTTCGGAAACCTGATTG |
| | CCCTGAGCCTGGGCCTGACCCCCAACTTCAAGAGCAACTTCGACC |
| | TGGCCGAGGATGCCAAACTGCCAGCTGAGCAAGGACACCTACGACG |
| | ACGACCTGGACAACCTGCTGGCCCAGATCGGCGACCAGTACGCCG |
| | ACCTGTTTCTGGCCGCCAAGAACCTGTCCGACGCCATCCTGCTGAG |
| | CGACATCCTGAGAGTGAACACCGAGATCACCAAGGCCCCCCTGAG |
| | CGCCTCTATGATCAAGAGATACGACGAGCACCACCAGGACCTGAC |
| | CCTGCTGAAAGCTCTCGTGCGGCAGCAGCTGCCTGAGAAGTACAA |
| | AGAGATTTTCTTCGACCAGAGCAAGAACGGCTACGCCGGCTACAT |
| | TGACGGCGGAGCCAGCCAGGAAGAGTTCTACAAGTTCATCAAGCC |
| | CATCCTGGAAAAGATGGACGGCACCGAGGAACTGCTCGTGAAGCT |
| | GAACAGAGAGGACCTGCTGCGGAAGCAGCGGACCTTCGACAACG |
| | GCAGCATCCCCCACCAGATCCACCTGGGAGAGCTGCACGCCATTC |
| | TGCGGCGGCAGGAAGATTTTTACCCATTCCTGAAGGACAACCGGG |
| | AAAAGATCGAGAAGATCCTGACCTTCCGCATCCCCTACTACGTGG |
| | GCCCTCTGGCCAGGGGAAACAGCAGATTCGCCTGGATGACCAGAA |
| | AGAGCGAGGAAACCATCACCCCCTGGAACTTCGAGGAAGTGGTGG |
| | ACAAGGGCGCTTCCGCCCAGAGCTTCATCGAGCGGATGACCAACT |
| | TCGATAAGAACCTGCCCAACGAGAAGGTGCTGCCCAAGCACAGCC |
| | TGCTGTACGAGTACTTCACCGTGTATAACGAGCTGACCAAAGTGA |
| | AATACGTGACCGAGGGAATGAGAAAGCCCGCCTTCCTGAGCGGCG |
| | AGCAGAAAAAGGCCATCGTGGACCTGCTGTTCAAGACCAACCGGA |
| | AAGTGACCGTGAAGCAGCTGAAAGAGGACTACTTCAAGAAAATC |
| | GAGTGCTTCGACTCCGTGGAAATCTCCGGCGTGGAAGATCGGTTC |
| | AACGCCTCCCTGGGCACATACCACGATCTGCTGAAAATTATCAAG |
| | GACAAGGACTTCCTGGACAATGAGGAAAACGAGGACATTCTGGA |
| | AGATATCGTGCTGACCCTGACACTGTTTGAGGACAGAGAGATGAT |
| | CGAGGAACGGCTGAAAACCTATGCCCACCTGTTCGACGACAAAGT |
| | GATGAAGCAGCTGAAGCGGCGGAGATACACCGGCTGGGGCAGGC |
| | TGAGCCGGAAGCTGATCAACGGCATCCGGGACAAGCAGTCCGGCA |
| | AGACAATCCTGGATTTCCTGAAGTCCGACGGCTTCGCCAACAGAA |
| | ACTTCATGCAGCTGATCCACGACGACAGCCTGACCTTTAAAGAGG |
| | ACATCCAGAAAGCCCAGGTGTCCGGCCAGGGCGATAGCCTGCACG |
| | AGCACATTGCCAATCTGGCCGGCAGCCCCGCCATTAAGAAGGGCA |
| | TCCTGCAGACAGTGAAGGTGGTGGACGAGCTCGTGAAAGTGATGG |
| | GCCGGCACAAGCCCGAGAACATCGTGATCGAAATGGCCAGAGAG |
| | AACCAGACCACCCAGAAGGGACAGAAGAACAGCCGCGAGAGAAT |
| | GAAGCGGATCGAAGAGGGCATCAAAGAGCTGGGCAGCCAGATCC |
| | TGAAAGAACACCCCGTGGAAAACACCCAGCTGCAGAACGAGAAG |
| | CTGTACCTGTACTACCTGCAGAATGGGCGGGATATGTACGTGGAC |
| | CAGGAACTGGACATCAACCGGCTGTCCGACTACGATGTGGACGCT |
| | ATCGTGCCTCAGAGCTTTCTGAAGGACGACTCCATCGACAACAAG |
| | GTGCTGACCAGAAGCGACAAGAACCGGGGCAAGAGCGACAACGT |
| | GCCCTCCGAAGAGGTCGTGAAGAAGATGAAGAACTACTGGCGGC |
| | AGCTGCTGAACGCCAAGCTGATTACCCAGAGAAAGTTCGACAATC |
| | TGACCAAGGCCGAGAGAGGCGGCCTGAGCGAACTGGATAAGGCC |
| | GGCTTCATCAAGAGACAGCTGGTGGAAACCCGGCAGATCACAAAG |
| | CACGTGGCACAGATCCTGGACTCCCGGATGAACACTAAGTACGAC |
| | GAGAATGACAAGCTGATCCGGGAAGTGAAAGTGATCACCCTGAA |
| | GTCCAAGCTGGTGTCCGATTTCCGGAAGGATTTCCAGTTTTACAAA |
| | GTGCGCGAGATCAACAACTACCACCACGCCCACGACGCCTACCTG |
| | AACGCCGTCGTGGGAACCGCCCTGATCAAAAAGTACCCTAAGCTG |
| | GAAAGCGAGTTCGTGTACGGCGACTACAAGGTGTACGACGTGCGG |
| | AAGATGATCGCCAAGAGCGAGCAGGAAATCGGCAAGGCTACCGC |
| | CAAGTACTTCTTCTACAGCAACATCATGAACTTTTTCAAGACCGAG |
| | ATTACCCTGGCCAACGGCGAGATCCGGAAGCGGCCTCTGATCGAG |
| | ACAAACGGCGAAACCGGGGAGATCGTGTGGGATAAGGGCCGGGA |
| | TTTTGCCACCGTGCGGAAAGTGCTGAGCATGCCCCAAGTGAATAT |
| | CGTGAAAAAGACCGAGGTGCAGACAGGCGGCTTCAGCAAAGAGT |
| | CTATCCTGCCCAAGAGGAACAGCGATAAGCTGATCGCCAGAAAGA |
| | AGGACTGGGACCCTAAGAAGTACGGCGGCTTCGACAGCCCCACCG |
| | TGGCCTATTCTGTGCTGGTGGTGGCCAAAGTGGAAAAGGGCAAGT |
| | CCAAGAAACTGAAGAGTGTGAAAGAGCTGCTGGGGATCACCATCA |
| | TGGAAAAGAAGCAGCTTCGAGAAGAATCCCATCGACTTTCTGGAAG |
| | CCAAGGGCTACAAAGAAGTGAAAAAGGACCTGATCATCAAGCTG |
| | CCTAAGTACTCCCTGTTCGAGCTGGAAAACGGCCGGAAGAGAATG |
| | CTGGCCTCTGCCGGCGAACTGCAGAAGGGAAACGAACTGGCCCTG |
| | CCCTCCAAATATGTGAACTTCCTGTACCTGGCCAGCCACTATGAGA |
| | AGCTGAAGGGCTCCCCCGAGGATAATGAGCAGAAACAGCTGTTTG |
| | TGGAACAGCACAAGCACTACCTGGACGAGATCATCGAGCAGATCA |
| | GCGAGTTCTCCAAGAGAGTGATCCTGGCCGACGCTAATCTGGACA |

TABLE 4-continued

| SEQ ID NO/<br>DESCRIPTION/<br>SOURCE | SEQUENCE |
|---|---|
| | AAGTGCTGTCCGCCTACAACAAGCACCGGGATAAGCCCATCAGAG |
| | AGCAGGCCGAGAATATCATCCACCTGTTTACCCTGACCAATCTGG |
| | GAGCCCCTGCCGCCTTCAAGTACTTTGACACCACCATCGACCGGA |
| | AGAGGTACACCAGCACCAAAGAGGTGCTGGACGCCACCCTGATCC |
| | ACCAGAGCATCACCGGCCTGTACGAGACACGGATCGACCTGTCTC |
| | AGCTGGGAGGTGACTCTGGAGGATCTAGCGGAGGATCCTCTGGCA |
| | GCGAGACACCAGGAACAAGCGAGTCAGCAACACCAGAGAGCAGT |
| | GGCGGCAGCAGCGGCGGCAGCAGCACCCTAAATATAGAAGATGA |
| | GTATCGGCTACATGAGACCTCAAAAGAGCCAGATGTTTCTCTAGG |
| | GTCCACATGGCTGTCTGATTTTCCTCAGGCCTGGGCGGAAACCGG |
| | GGGCATGGGACTGGCAGTTCGCCAAGCTCCTCTGATCATACCTCTG |
| | AAAGCAACCTCTACCCCCGTGTCCATAAAACAATACCCCATGTCA |
| | CAAGAAGCCAGACTGGGGATCAAGCCCCACATACAGAGACTGTTG |
| | GACCAGGGAATACTGGTACCCTGCCAGTCCCCCTGGAACACGCCC |
| | CTGCTACCCGTTAAGAAACCAGGGACTAATGATTATAGGCCTGTC |
| | CAGGATCTGAGAGAAGTCAACAAGCGGGTGGAAGACATCCACCC |
| | CACCGTGCCCAACCCTTACAACCTCTTGAGCGGGCTCCCACCGTCC |
| | CACCAGTGGTACACTGTGCTTGATTTAAAGGATGCCTTTTTCTGCC |
| | TGAGACTCCACCCCACCAGTCAGCCTCTCTTCGCCTTTGAGTGGAG |
| | AGATCCAGAGATGGGAATCTCAGGACAATTGACCTGGACCAGACT |
| | CCCACAGGGTTTCAAAAACAGTCCCACCCTGTTTAATGAGGCACT |
| | GCACAGAGACCTAGCAGACTTCCGGATCCAGCACCCAGACTTGAT |
| | CCTGCTACAGTACGTGGATGACTTACTGCTGGCCGCCACTTCTGAG |
| | CTAGACTGCCAACAAGGTACTCGGGCCCTGTTACAAACCCTAGGG |
| | AACCTCGGGTATCGGGCCTCGGCCAAGAAAGCCCAAATTTGCCAG |
| | AAACAGGTCAAGTATCTGGGGTATCTTCTAAAAGAGGGTCAGAGA |
| | TGGCTGACTGAGGCCAGAAAAGAGACTGTGATGGGGCAGCCTACT |
| | CCGAAGACCCCTCGACAACTAAGGGAGTTCCTAGGGAAGGCAGGC |
| | TTCTGTCGCCTCTTCATCCCTGGGTTTGCAGAAATGGCAGCCCCCC |
| | TGTACCCTCTCACCAAACCGGGGACTCTGTTTAATTGGGGCCCAGA |
| | CCAACAAAAGGCCTATCAAGAAATCAAGCAAGCTCTTCTAACTGC |
| | CCCAGCCCTGGGGTTGCCAGATTTGACTAAGCCCTTTGAACTCTTT |
| | GTCGACGAGAAGCAGGGCTACGCCAAAGGTGTCCTAACGCAAAA |
| | ACTGGGACCTTGGCGTCGGCCGGTGGCCTACCTGTCCAAAAAGCT |
| | AGACCCAGTAGCAGCTGGGTGGCCCCCTTGCCTACGGATGGTAGC |
| | AGCCATTGCCGTACTGACAAAGGATGCAGGCAAGCTAACCATGGG |
| | ACAGCCACTAGTCATTCTGGCCCCCCATGCAGTAGAGGCACTAGT |
| | CAAACAACCCCCGACCGCTGGCTTTCCAACGCCCGGATGACTCA |
| | CTATCAGGCCTTGCTTTTGGACACGGACCGGGTCCAGTTCGGACCG |
| | GTGGTAGCCCTGAACCCGGCTACGCTGCTCCCACTGCCTGAGGAA |
| | GGGCTGCAACACAACTGCCTTGATATCCTGGCCGAAGCCCACGGA |
| | ACCCGACCCGACCTAACGGACCAGCCGCTCCCAGACGCCGACCAC |
| | ACCTGGTACACGGATGGAAGCAGTCTCTTACAAGAGGGACAGCGT |
| | AAGGCGGGAGCTGCGGTGACCACCGAGACCGAGGTAATCTGGGCT |
| | AAAGCCCTGCCAGCCGGGACATCCGCTCAGCGGGCTGAACTGATA |
| | GCACTCACCCAGGCCCTAAAGATGGCAGAAGGTAAGAAGCTAAAT |
| | GTTTATACTGATAGCCGTTATGCTTTTGCTACTGCCCATATCCATG |
| | GAGAAATATACAGAAGGCGTGGGTGGCTCACATCAGAAGGCAAA |
| | GAGATCAAAAATAAAGACGAGATCTTGGCCCTACTAAAAGCCCTC |
| | TTTCTGCCCAAAAGACTTAGCATAATCCATTGTCCAGGACATCAAA |
| | AGGGACACAGCGCCGAGGCTAGAGGCAACCGGATGGCTGACCAA |
| | GCGGCCCGAAAGGCAGCCATCACAGAGACTCCAGACACCTCTACC |
| | CTCCTCATAGAAAATTCATCACCCTCTGGCGGCTCAAAAAGAACC |
| | GCCGACGGCAGCGAATTCGAGCCCAAGAAGAAGAGGAAAGTCGG |
| | AAGCGGAGCTACTAACTTCAGCCTGCTGAAGCAGGCTGGCGACGT |
| | GGAGGAGAACCCTGGACCTAATTTACTGACCGTACACCAAAATTT |
| | GCCTGCATTACCGGTCGATGCAACAGTGATGAGGTTCGCAAGAA |
| | CCTGATGGACATGTTCAGGGATCGCCAGGCGTTTTCTGAGCATACC |
| | TGGAAAATGCTTCTGTCCGTTTGCCGGTCGTGGGCGGCATGGTGCA |
| | AGTTGAATAACCGGAAATGGTTTCCCGCAGAACCTGAAGATGTTC |
| | GCGATTATCTTCTATATCTTCAGGCGCGCGGTCTGGCAGTAAAAAC |
| | TATCCAGCAACATTTGGGCCAGCTAAACATGCTTCATCGTCGGTCC |
| | GGGCTGCCACGACCAAGTGACAGCAATGCTGTTTCACTGGTTATG |
| | CGGCGGATCCGAAAAGAAAACGTTGATGCCGGTGAACGTGCAAA |
| | ACAGGCTCTAGCGTTCGAACGCACTGATTTCGACCAGGTTCGTTCA |
| | CTCATGGAAAATAGCGATCGCTGCCAGGATATACGTAATCTGGCA |
| | TTTCTGGGGATTGCTTATAACACCCTGTTACGTATAGCCGAAATTG |
| | CCAGGATCAGGGTTAAAGATATCTCACGTACTGACGGTGGGAGAA |
| | TGTTAATCCATATTGGCAGAACGAAAACGCTGGTTAGCACCGCAG |
| | GTGTAGAGAAGGCACTTAGCCTGGGGGTAACTAAACTGGTCGAGC |
| | GATGGATTTCCGTCTCTGGTGTAGCTGATGATCCGAATAACTACCT |
| | GTTTTGCCGGGTCAGAAAAAATGGTGTTGCCGCGCCATCTGCCAC |
| | CAGCCAGCTATCAACTCGCGCCCTGGAAGGGATTTTTGAAGCAAC |
| | TCATCGATTGATTTACGGCGCTAAGGATGACTCTGGTCAGAGATA |
| | CCTGGCCTGGTCTGGACACAGTGCCCGTGTCGGAGCCGCGCGAGA |
| | TATGGCCCGCGCTGGAGTTTCAATACCGGAGATCATGCAAGCTGG |

TABLE 4-continued

| SEQ ID NO/<br>DESCRIPTION/<br>SOURCE | SEQUENCE |
|---|---|
| | TGGCTGGACCAATGTAAATATTGTCATGAACTATATCCGTAACCTG<br>GATAGTGAAACAGGGGCAATGGTGCGCCTGCTGGAAGATGGCGAT<br>TAATTTAAACCCGCTGATCAGCCTCGACTGTGCCTTCTAGTTGCCA<br>GCCATCTGTTGTTTGCCCCTCCCCCGTGCCTTCCTTGACCCTGGAA<br>GGTGCCACTCCCACTGTCCTTTCCTAATAAAATGAGAAAATTGCAT<br>CGCATTGTCTGAGTAGGTGTCATTCTATTCTGGGGGGTGGGGTGGG<br>GCAGGACAGCAAGGGGAGGATTGGGAAGACAATAGCAGGCATG<br>CTGGGGATGCGGTGGGCTCTATGGCTTCTGAGGCGGAAAGAACCA<br>GCTGGGGCTCGATACCGTCGACCTCTAGCTAGAGCTTGGCGTAAT<br>CATGGTCATAGCTGTTTCCTGTGTGAAATTGTTATCCGCTCACAAT<br>TCCACACAACATACGAGCCGGAAGCATAAAGTGTAAAGCCTAGGG<br>TGCCTAATGAGTGAGCTAACTCACATTAATTGCGTTGCGCTCACTG<br>CCCGCTTTCCAGTCGGGAAACCTGTCGTGCCAGCTGCATTAATGAA<br>TCGGCCAACGCGCGGGGAGAGGCGGTTTGCGTATTGGGCGCTCTT<br>CCGCTTCCTCGCTCACTGACTCGCTGCGCTCGGTCGTTCGGCTGCG<br>GCGAGCGGTATCAGCTCACTCAAAGGCGGTAATACGGTTATCCAC<br>AGAATCAGGGGATAACGCAGGAAAGAACATGTGAGCAAAAGGCC<br>AGCAAAAGGCCAGGAACCGTAAAAAGGCCGCGTTGCTGGCGTTTT<br>TCCATAGGCTCCGCCCCCTGACGAGCATCACAAAAATCGACGCT<br>CAAGTCAGAGGTGGCGAAACCCGACAGGACTATAAAGATACCAG<br>GCGTTTCCCCCTGGAAGCTCCCTCGTGCGCTCTCCTGTTCCGACCC<br>TGCCGCTTACCGGATACCTGTCCGCCTTTCTCCCTTCGGGAAGCGT<br>GGCGCTTTCTCATAGCTCACGCTGTAGGTATCTCAGTTCGGTGTAG<br>GTCGTTCGCTCCAAGCTGGGCTGTGTGCACGAACCCCCCGTTCAGC<br>CCGACCGCTGCGCCTTATCCGGTAACTATCGTCTTGAGTCCAACCC<br>GGTAAGACACGACTTATCGCCACTGGCAGCAGCCACTGGTAACAG<br>GATTAGCAGAGCGAGGTATGTAGGCGGTGCTACAGAGTTCTTGAA<br>GTGGTGGCCTAACTACGGCTACACTAGAAGAACAGTATTTGGTAT<br>CTGCGCTCTGCTGAAGCCAGTTACCTTCGGAAAAAGAGTTGGTAG<br>CTCTTGATCCGGCAAACAAACCACCGCTGGTAGCGGTGGTTTTTTT<br>GTTTGCAAGCAGCAGATTACGCGCAGAAAAAAAGGATCTCAAGA<br>AGATCCTTTGATCTTTTCTACGGGGTCTGACGCTCAGTGGAACGAA<br>AACTCACGTTAAGGGATTTTGGTCATGAGATTATCAAAAAGGATC<br>TTCACCTAGATCCTTTTAAATTAAAAATGAAGTTTTAAATCAATCT<br>AAAGTATATATGAGTAAACTTGGTCTGACAGTTACCAATGCTTAAT<br>CAGTGAGGCACCTATCTCAGCGATCTGTCTATTTCGTTCATCCATA<br>GTTGCCTGACTCCCCGTCGTGTAGATAACTACGATACGGGAGGGC<br>TTACCATCTGGCCCCAGTGCTGCAATGATACCGCGAGACCCACGC<br>TCACCGGCTCCAGATTTATCAGCAATAAACCAGCCAGCCGGAAGG<br>GCCGAGCGCAGAAGTGGTCCTGCAACTTTATCCGCCTCCATCCAGT<br>CTATTAATTGTTGCCGGGAAGCTAGAGTAAGTAGTTCGCCAGTTA<br>ATAGTTTGCGCAACGTTGTTGCCATTGCTACAGGCATCGTGGTGTC<br>ACGCTCGTCGTTTGGTATGGCTTCATTCAGCTCCGGTTCCCAACGA<br>TCAAGGCGAGTTACATGATCCCCCATGTTGTGCAAAAAAGCGGTT<br>AGCTCCTTCGGTCCTCCGATCGTTGTCAGAAGTAAGTTGGCCGCAG<br>TGTTATCACTCATGGTTATGGCAGCACTGCATAATTCTCTTACTGT<br>CATGCCATCCGTAAGATGCTTTTCTGTGACTGGTGAGTACTCAACC<br>AAGTCATTCTGAGAATAGTGTATGCGGCGACCGAGTTGCTCTTGCC<br>CGGCGTCAATACGGGATAATACCGCGCCACATAGCAGAACTTTAA<br>AAGTGCTCATCATTGGAAAACGTTCTTCGGGGCGAAAACTCTCAA<br>GGATCTTACCGCTGTTGAGATCCAGTTCGATGTAACCCACTCGTGC<br>ACCCAACTGATCTTCAGCATCTTTTACTTTCACCAGCGTTTCTGGG<br>TGAGCAAAAACAGGAAGGCAAAATGCCGCAAAAAAGGGAATAAG<br>GGCGACACGGAAATGTTGAATACTCATACTCTTCCTTTTTCAATAT<br>TATTGAAGCATTTATCAGGGTTATTGTCTCATGAGCGGATACATAT<br>TTGAATGTATTTAGAAAAATAAACAAATAGGGGTTCCGCGCACAT<br>TTCCCCGAAAAGTGCCACCTGACGTCGACGGATCGGGAGATCGAT<br>CTCCCGATCCCCTAGGGTCGACTCTCAGTACAATCTGCTCTGATGC<br>CGCATAGTTAAGCCAGTATCTGCTCCCTGCTTGTGTGTTGGAGGTC<br>GCTGAGTAGTGCGCGAGCAAAATTTAAGCTACAACAAGGCAAGGC<br>TTGACCGACAATTGCATGAAGAATCTGCTTAGGGTTAGGCGTTTTG<br>CGCTGCTTCGCGATGTACGGGCCAGATAT |
| SEQ ID NO: 74<br>+90 ngRNA guide<br>sequence<br>(Artificial Sequence) | GTCAACCAGTATCCCGGTGC |
| SEQ ID NO: 75<br>+90 ngRNA<br>(Artificial Sequence) | GTCAACCAGTATCCCGGTGCGTTTTAGAGCTAGAAATAGCAAGTT<br>AAAATAAGGCTAGTCCGTTATCAACTTGAAAAAGTGGCACCGAGT<br>CGGTGC |
| SEQ ID NO: 76<br>GFP minicircle<br>template (before<br>cleavage into a | TGATCCCCTGCGCCATCAGATCCTTGGCGGCGAGAAAGCCATCCA<br>GTTTACTTTGCAGGGCTTCCCAACCTTACCAGAGGGCGCCCCAGCT<br>GGCAATTCCGGTTCGCTTGCTGTCCATAAAACCGCCCAGTCTAGCT<br>ATCGCCATGTAAGCCCACTGCAAGCTACCTGCTTTCTCTTTGCGCT |

TABLE 4-continued

| SEQ ID NO/<br>DESCRIPTION/<br>SOURCE | SEQUENCE |
|---|---|
| minicircle)<br>(Artificial Sequence) | TGCGTTTTCCCTTGTCCAGATAGCCCAGTAGCTGACATTCATCCGG<br>GGTCAGCACCGTTTCTGCGGACTGGCTTTCTACGTGCTCGAGGGGG<br>GCCAAACGGTCTCCAGCTTGGCTGTTTTGGCGGATGAGAGAAGAT<br>TTTCAGCCTGATACAGATTAAATCAGAACGCAGAAGCGGTCTGAT<br>AAAACAGAATTTGCCTGGCGGCAGTAGCGCGGTGGTCCCACCTGA<br>CCCCATGCCGAACTCAGAAGTGAAACGCCGTAGCGCCGATGGTAG<br>TGTGGGGTCTCCCCATGCGAGAGTAGGGAACTGCCAGGCATCAAA<br>TAAAACGAAAGGCTCAGTCGAAAGACTGGGCCTTTCGTTTTATCT<br>GTTGTTTGTCGGTGAACGCTCTCCTGAGTAGGACAAATCCGCCGG<br>GAGCGGATTTGAACGTTGCGAAGCAACGGCCCGGAGGGTGGCGG<br>GCAGGACGCCCGCCATAAACTGCCAGGCATCAAATTAAGCAGAAG<br>GCCATCCTGACGGATGGCCTTTTTGCGTTTCTACAAACTCTTTTGTT<br>TATTTTTCTAAATACATTCAAATATGTATCCGCTCATGACCAAAAT<br>CCCTTAACGTGAGTTTTCGTTCCACTGAGCGTCAGACCCCGTAGAA<br>AAGATCAAAGGATCTTCTTGAGATCCTTTTTTTCTGCGCGTAATCT<br>GCTGCTTGCAAACAAAAAAACCACCGCTACCAGCGGTGGTTTGTT<br>TGCCGGATCAAGAGCTACCAACTCTTTTTCCGAAGGTAACTGGCTT<br>CAGCAGAGCGCAGATACCAAATACTGTCCTTCTAGTGTAGCCGTA<br>GTTAGGCCACCACTTCAAGAACTCTGTAGCACCGCCTACATACCTC<br>GCTCTGCTAATCCTGTTACCAGTGGCTGCTGCCAGTGGCGATAAGT<br>CGTGTCTTACCGGGTTGGACTCAAGACGATAGTTACCGGATAAGG<br>CGCAGCGGTCGGGCTGAACGGGGGGTTCGTGCACACAGCCCAGCT<br>TGGAGCGAACGACCTACACCGAACTGAGATACCTACAGCGTGAGC<br>TATGAGAAAGCGCCACGCTTCCCGAAGGGAGAAAGGCGGACAGG<br>TATCCGGTAAGCGGCAGGGTCGGAACAGGAGAGCGCACGAGGGA<br>GCTTCCAGGGGGAAACGCCTGGTATCTTTATAGTCCTGTCGGGTTT<br>CGCCACCTCTGACTTGAGCGTCGATTTTTGTGATGCTCGTCAGGGG<br>GGCGGAGCCTATGGAAAAACGCCAGCAACGCGGCCTTTTTACGGT<br>TCCTGGCCTTTTGCTGGCCTTTTGCTCACATGTTCTTTCCTGCGTTA<br>TCCCCTGATTCTGTGGATAACCGTATTACCGCCTTTGAGTGAGCTG<br>ATACCGCTCGCCGCAGCCGAACGACCGAGCGCAGCGAGTCAGTGA<br>GCGAGGAAGCGGAAGAGCGCCTGATGCGGTATTTTCTCCTTACGC<br>ATCTGTGCGGTATTTCACACCGCATATGGTGCACTCTCAGTACAAT<br>CTGCTCTGATGCCGCATAGTTAAGCCAGTATACACTCCGCTATCGC<br>TACGTGACTGGGTCATGGCTGCGCCCCGACACCCGCCAACACCCG<br>CTGACGCGCCCTGACGGGCTTGTCTGCTCCCGGCATCCGCTTACAG<br>ACAAGCTGTGACCGTCTCCGGGAGCTGCATGTGTCAGAGGTTTTC<br>ACCGTCATCACCGAAACGCGCGAGGCAGCAGATCAATTCGCGCGC<br>GAAGGCGAAGCGGCATGCATAATGTGCCTGTCAAATGGACGAAGC<br>AGGGATTCTGCAAACCCTATGCTACTCCGTCAAGCCGTCAATTGTC<br>TGATTCGTTACCAATTATGACAACTTGACGGCTACATCATTCACTT<br>TTTCTTCACAACCGGCACGGAACTCGCTCGGGCTGGCCCCGGTGC<br>ATTTTTTAAATACCCGCGAGAAATAGAGTTGATCGTCAAAACCAA<br>CATTGCGACCGACGGTGGCGATAGGCATCCGGGTGGTGCTCAAAA<br>GCAGCTTCGCCTGGCTGATACGTTGGTCCTCGCGCCAGCTTAAGAC<br>GCTAATCCCTAACTGCTGGCGGAAAAGATGTGACAGACGCGACGG<br>CGACAAGCAAACATGCTGTGCGACGCTGGCGATACATTACCCTGT<br>TATCCCTAGATGACATTACCCTGTTATCCCAGATGACATTACCCTG<br>TTATCCCTAGATGACATTACCCTGTTATCCCTAGATGACATTTACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATAAACTCAA<br>TGATGATGATGATGGTCGAGACTCAGCGGCCGCGGTGCCAGG<br>GCGTGCCCTTGGGCTCCCCGGGCGCGACTATAAGCTGCGAGCAAC<br>TTCACTTGGGTATGCCGGCGGTAGCGCTTACCGTTCGTATAATGTA<br>TGCTATACGAAGTTATCCGAAGCCGCTAGCGGTGGTTTGTCTGGTC<br>AACCACCGCGGTCTCAGTGGTGTACGGTACAAACCCAGCTACCGG<br>TCGCCACCATGCCCGCCATGAAGATCGAGTGCCGCATCACCGGCA<br>CCCTGAACGGCGTGGAGTTCGAGCTGGTGGGCGCGGAGAGGGC<br>ACCCCCGAGCAGGGCCGCATGACCAACAAGATGAAGAGCACCAA<br>AGGCGCCCTGACCTTCAGCCCCTACCTGCTGAGCCACGTGATGGG<br>CTACGGCTTCTACCACTTCGGCACCTACCCCAGCGGCTACGAGAA<br>CCCCTTCCTGCACGCCATCAACAACGGCGGCTACACCAACACCCG<br>CATCGAGAAGTACGAGGACGGCGGCGTGCTGCACGTGAGCTTCAG<br>CTACCGCTACGAGGCCGGCCGCGTGATCGGCGACTTCAAGGTGGT<br>GGGCACCGGCTTCCCCGAGGACAGCGTGATCTTCACCGACAAGAT |

TABLE 4-continued

| SEQ ID NO/ DESCRIPTION/ SOURCE | SEQUENCE |
| --- | --- |
| | CATCCGCAGCAACGCCACCGTGGAGCACCTGCACCCCATGGGCGA<br>TAACGTGCTGGTGGGCAGCTTCGCCCGCACCTTCAGCCTGCGCGA<br>CGGCGGCTACTACAGCTTCGTGGTGGACAGCCACATGCACTTCAA<br>GAGCGCCATCCACCCCAGCATCCTGCAGAACGGGGGCCCCATGTT<br>CGCCTTCCGCCGCGTGGAGGAGCTGCACAGCAACACCGAGCTGGG<br>CATCGTGGAGTACCAGCACGCCTTCAAGACCCCCATCGCCTTCGCC<br>AGATCTCGAGCTCGATGAGTTTGGACAAACCACAACTAGAATGCA<br>GTGAAAAAAATGCTTTATTTGTGAAATTTGTGATGCTATTGCTTTA<br>TTTGTGGGCCCGCCCCAACTGGGGTAACCTTTGAGTTCTCTCAGTT<br>GGGGGGTAATCAGCATCATGATGTGGTACCACATCATGATGCTGAT<br>TATAAGAATGCGGCCGCCACACTCTAGTGGATCTCGAGTTAATAA<br>TTCAGAAGAACTCGTCAAGAAGGCGATAGAAGGCGATGCGCTGCG<br>AATCGGGAGCGGCGATACCGTAAAGCACGAGGAAGCGGTCAGCC<br>CATTCGCCGCCAAGCTCTTCAGCAATATCACGGGTAGCCAACGCT<br>ATGTCCTGATAGCGGTCCGCCACACCCAGCCGGCCACAGTCGATG<br>AATCCAGAAAAGCGGCCATTTTCCACCATGATATTCGGCAAGCAG<br>GCATCGCCATGGGTCACGACGAGATCCTCGCCGTCGGGCATGCTC<br>GCCTTGAGCCTGGCGAACAGTTCGGCTGGCGCGAGCCCCTGATGC<br>TCTTCGTCCAGATCATCCTGATCGACAAGACCGGCTTCCATCCGAG<br>TACGTGCTCGCTCGATGCGATGTTTCGCTTGGTGGTCGAATGGGCA<br>GGTAGCCGGATCAAGCGTATGCAGCCGCCGCATTGCATCAGCCAT<br>GATGGATACTTTCTCGGCAGGAGCAAGGTGTAGATGACATGGAGA<br>TCCTGCCCCGGCACTTCGCCCAATAGCAGCCAGTCCCTTCCCGCTT<br>CAGTGACAACGTCGAGCACAGCTGCGCAAGGAACGCCCGTCGTGG<br>CCAGCCACGATAGCCGCGCTGCCTCGTCTTGCAGTTCATTCAGGGC<br>ACCGGACAGGTCGGTCTTGACAAAAAGAACCGGGCGCCCCTGCGC<br>TGACAGCCGGAACACGGCGGCATCAGAGCAGCCGATTGTCTGTTG<br>TGCCCAGTCATAGCCGAATAGCCTCTCCACCCAAGCGGCCGGAGA<br>ACCTGCGTGCAATCCATCTTGTTCAATCATGCGAAACGATCCTCAT<br>CCTGTCTCTTGATCAGAGCT |
| SEQ ID NO: 77<br>Gaussia Luciferase<br>minicircle template<br>(Artificial Sequence) | TGATCCCCTGCGCCATCAGATCCTTGGCGGCGAGAAAGCCATCCA<br>GTTTACTTTGCAGGGCTTCCCAACCTTACCAGAGGGCGCCCCAGCT<br>GGCAATTCCGGTTCGCTTGCTGTCCATAAAACCGCCCAGTCTAGCT<br>ATCGCCATGTAAGCCCACTGCAAGCTACCTGCTTTCTCTTTGCGCT<br>TGCGTTTTCCCTTGTCCAGATAGCCCAGTAGCTGACATTCATCCGG<br>GGTCAGCACCGTTTCTGCGGACTGGCTTTCTACGTGCTCGAGGGGG<br>GCCAAACGGTCTCCAGCTTGGCTGTTTTGGCGGATGAGAGAAGAT<br>TTTCAGCCTGATACAGATTAAATCAGAACGCAGAAGCGGTCTGAT<br>AAAACAGAATTTGCCTGGCGGCAGTAGCGCGGTGGTCCCACCTGA<br>CCCCATGCCGAACTCAGAAGTGAAACGCCGTAGCGCCGATGGTAG<br>TGTGGGGTCTCCCCATGCGAGAGTAGGGAACTGCCAGGCATCAAA<br>TAAAACGAAAGGCTCAGTCGAAAGACTGGGCCTTTCGTTTTATCT<br>GTTGTTTGTCGGTGAACGCTCTCCTGAGTAGGACAAATCCGCCGG<br>GAGCGGATTTGAACGTTGCGAAGCAACGGCCCGGAGGGTGGCGG<br>GCAGGACGCCCGCCATAAACTGCCAGGCATCAAATTAAGCAGAAG<br>GCCATCCTGACGGATGGCCTTTTTGCGTTTCTACAAACTCTTTTGTT<br>TATTTTTCTAAATACATTCAAATATGTATCCGCTCATGACCAAAAT<br>CCCTTAACGTGAGTTTTCGTTCCACTGAGCGTCAGACCCCGTAGAA<br>AAGATCAAAGGATCTTCTTGAGATCCTTTTTTTCTGCGCGTAATCT<br>GCTGCTTGCAAACAAAAAAACCACCGCTACCAGCGGTGGTTTGTT<br>TGCCGGATCAAGAGCTACCAACTCTTTTTCCGAAGGTAACTGGCTT<br>CAGCAGAGCGCAGATACCAAATACTGTCCTTCTAGTGTAGCCGTA<br>GTTAGGCCACCACTTCAAGAACTCTGTAGCACCGCCTACATACCTC<br>GCTCTGCTAATCCTGTTACCAGTGGCTGCTGCCAGTGGCGATAAGT<br>CGTGTCTTACCGGGTTGGACTCAAGACGATAGTTACCGGATAAGG<br>CGCAGCGGTCGGGCTGAACGGGGGGTTCGTGCACACAGCCCAGCT<br>TGGAGCGAACGACCTACACCGAACTGAGATACCTACAGCGTGAGC<br>TATGAGAAAGCGCCACGCTTCCCGAAGGGAGAAAGGCGGACAGG<br>TATCCGGTAAGCGGCAGGGTCGGAACAGGAGAGCGCACGAGGGA<br>GCTTCCAGGGGGAAACGCCTGGTATCTTTATAGTCCTGTCGGGTTT<br>CGCCACCTCTGACTTGAGCGTCGATTTTTGTGATGCTCGTCAGGGG<br>GGCGGAGCCTATGGAAAAACGCCAGCAACGCGGCCTTTTTACGGT<br>TCCTGGCCTTTTGCTGGCCTTTTGCTCACATGTTCTTTCCTGCGTTA<br>TCCCCTGATTCTGTGGATAACCGTATTACCGCCTTTGAGTGAGCTG<br>ATACCGCTCGCCGCAGCCGAACGACCGAGCGCAGCGAGTCAGTGA<br>GCGAGGAAGCGGAAGAGCGCCTGATGCGGTATTTTCTCCTTACGC<br>ATCTGTGCGGTATTTCACACCGCATATGGTGCACTCTCAGTACAAT<br>CTGCTCTGATGCCGCATAGTTAAGCCAGTATACACTCCGCTATCGC<br>TACGTGACTGGGTCATGGCTGCGCCCCGACACCCGCCAACACCCG<br>CTGACGCGCCCTGACGGGCTTGTCTGCTCCCGGCATCCGCTTACAG<br>ACAAGCTGTGACCGTCTCCGGGAGCTGCATGTGTCAGAGGTTTTC<br>ACCGTCATCACCGAAACGCGCGAGGCAGCAGATCAATTCGCGCGC<br>GAAGGCGAAGCGGCATGCATAATGTGCCTGTCAAATGGACGAAGC<br>AGGGATTCTGCAAACCCTATGCTACTCCGTCAAGCCGTCAATTGTC<br>TGATTCGTTACCAATTATGACAACTTGACGGCTACATCATTCACTT |

TABLE 4-continued

| SEQ ID NO/<br>DESCRIPTION/<br>SOURCE | SEQUENCE |
|---|---|
| | TTTCTTCACAACCGGCACGGAACTCGCTCGGGCTGGCCCCGGTGC<br>ATTTTTTAAATACCCGCGAGAAATAGAGTTGATCGTCAAAACCAA<br>CATTGCGACCGACGGTGGCGATAGGCATCCGGGTGGTGCTCAAAA<br>GCAGCTTCGCCTGGCTGATACGTTGGTCCTCGCGCCAGCTTAAGAC<br>GCTAATCCCTAACTGCTGGCGGAAAAGATGTGACAGACGCGACGG<br>CGACAAGCAAACATGCTGTGCGACGCTGGCGATACATTACCCTGT<br>TATCCCTAGATGACATTACCCTGTTATCCCAGATGACATTACCCTG<br>TTATCCCTAGATGACATTACCCTGTTATCCCTAGATGACATTTACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATGACATTAC<br>CCTGTTATCCCTAGATACATTACCCTGTTATCCCAGATGACATACC<br>CTGTTATCCCTAGATGACATTACCCTGTTATCCCAGATAAACTCAA<br>TGATGATGATGATGATGGTCGAGACTCAGCGGCCGCGGTGCCAGG<br>GCGTGCCCTTGGGCTCCCCGGGCGCGACTATAAGCTGCGAGCAAC<br>TTCACTTGGGTATGCCGGCGGTAGCGCTTACCGTTCGTATAATGTA<br>TGCTATACGAAGTTATCCGAAGCCGCTAGCGGTGGTTTGTCTGGTC<br>AACCACCGCGGTCTCAGTGGTGTACGGTACAAACCCACTACCGGT<br>CGCCACCATGGGAGTCAAAGTTCTGTTTGCCCTGATCTGCATCGCT<br>GTGGCCGAGGCCAAGCCCACCGAGAACAACGAAGACTTCAACATC<br>GTGGCCGTGGCCAGCAACTTCGCGACCACGGATCTCGATGCTGAC<br>CGCGGGAAGTTGCCCGGCAAGAAGCTGCCGCTGGAGGTGCTCAAA<br>GAGATGGAAGCCAATGCCCGGAAAGCTGGCTGCACCAGGGGCTGT<br>CTGATCTGCCTGTCCCACATCAAGTGCACGCCCAAGATGAAGAAG<br>TTCATCCCAGGACGCTGCCACACCTACGAAGGCGACAAAGAGTCC<br>GCACAGGGCGGCATAGGCGAGGCGATCGTCGACATTCCTGAGATT<br>CCTGGGTTCAAGGACTTGGAGCCCATGGAGCAGTTCATCGCACAG<br>GTCGATCTGTGTGTGGACTGCACAACTGGCTGCCTCAAAGGGCTT<br>GCCAACGTGCAGTGTTCTGACCTGCTCAAGAAGTGGCTGCCGCAA<br>CGCTGTGCGACCTTTGCCAGCAAGATCCAGGGCCAGGTGGACAAG<br>ATCAAGGGGGCCGGTGGTGACTAAGCGGAGCTCGATGAGTTTGGA<br>CAAACCACAACTAGAATGCAGTGAAAAAAATGCTTTATTTGTGAA<br>ATTTGTGATGCTATTGCTTTATTTGTGGGCCCGCCCCAACTGGGGT<br>AACCTTTGAGTTCTCTCAGTTGGGGGTAATCAGCATCATGATGTGG<br>TACCACATCATGATGCTGATTATAAGAATGCGGCCGCCACACTCT<br>AGTGGATCTCGAGTTAATAATTCAGAAGAACTCGTCAAGAAGGCG<br>ATAGAAGGCGATGCGCTGCGAATCGGGAGCGGCGATACCGTAAA<br>GCACGAGGAAGCGGTCAGCCCATTCGCCGCCAAGCTCTTCAGCAA<br>TATCACGGGTAGCCAACGCTATGTCCTGATAGCGGTCCGCCACAC<br>CCAGCCGGCCACAGTCGATGAATCCAGAAAAGCGGCCATTTTCCA<br>CCATGATATTCGGCAAGCAGGCATCGCCATGGGTCACGACGAGAT<br>CCTCGCCGTCGGGCATGCTCGCCTTGAGCCTGGCGAACAGTTCGG<br>CTGGCGCGAGCCCCTGATGCTCTTCGTCCAGATCATCCTGATCGAC<br>AAGACCGGCTTCCATCCGAGTACGTGCTCGCTCGATGCGATGTTTC<br>GCTTGGTGGTCGAATGGGCAGGTAGCCGGATCAAGCGTATGCAGC<br>CGCCGCATTGCATCAGCCATGATGGATACTTTCTCGGCAGGAGCA<br>AGGTGTAGATGACATGGAGATCCTGCCCCGGCACTTCGCCCAATA<br>GCAGCCAGTCCCTTCCCGCTTCAGTGACAACGTCGAGCACAGCTG<br>CGCAAGGAACGCCCGTCGTGGCCAGCCACGATAGCCGCGCTGCCT<br>CGTCTTGCAGTTCATTCAGGGCACCGGACAGGTCGGTCTTGACAA<br>AAAGAACCGGGCGCCCCTGCGCTGACAGCCGGAACACGGCGGCA<br>TCAGAGCAGCCGATTGTCTGTTGTGCCCAGTCATAGCCGAATAGC<br>CTCTCCACCCAAGCGGCCGGAGAACCTGCGTGCAATCCATCTTGTT<br>CAATCATGCGAAACGATCCTCATCCTGTCTCTTGATCAGAGCT |
| SEQ ID NO: 78<br>pseudo attP site<br>(Artificial sequence) | CCCCAACTGGGGTAACCTTTGAGTTCTCTCAGTTGGGG |
| SEQ ID NO: 79<br>Albumin-pegRNA-<br>SERPIN<br>(Artificial Sequence) | GACTGAAACTTCACAGAATAGTTTTAGAGCTAGAAATAGCAAGTT<br>AAAATAAGGCTAGTCCGTTATCAACTTGAAAAAGTGGCACCGAGT<br>CGGTGCTTGGGATAGTTATGAATTCAATCTTCAACCCTATCCGGAT<br>GATCCTGACGACGGAGACCGCCGTCGTCGACAAGCCGGCCTCTGT<br>GAAGTTTCAGTCA |
| SEQ ID NO: 80<br>Albumin-pegRNA-<br>CPS1 | GACTGAAACTTCACAGAATAGTTTTAGAGCTAGAAATAGCAAGTT<br>AAAATAAGGCTAGTCCGTTATCAACTTGAAAAAGTGGCACCGAGT<br>CGGTGCTTGGGATAGTTATGAATTCAATCTTCAACCCTATCCGGAT |

TABLE 4-continued

| SEQ ID NO/ DESCRIPTION/ SOURCE | SEQUENCE |
| --- | --- |
| (Artificial Sequence) | GATCCTGACGACGGAGACCGCCGTCGTCGACAAGCCGGCCTCTGT GAAGTTTC |
| SEQ ID NO: 81<br>34 bp lox71 pegRNA<br>(Artificial Sequence) | GGCCCAGACTGAGCACGTGAGTTTTAGAGCTAGAAATAGCAAGTT AAAATAAGGCTAGTCCGTTATCAACTTGAAAAAGTGGCACCGAGT CGGTGCTGGAGGAAGCAGGGCTTCCTTTCCTCTGCCATCATACCGT TCGTATAGCATACATTATACGAAGTTATCGTGCTCAGTCTG |
| SEQ ID NO: 82<br>34 bp lox66 pegRNA<br>(Artificial Sequence) | GGCCCAGACTGAGCACGTGAGTTTTAGAGCTAGAAATAGCAAGTT AAAATAAGGCTAGTCCGTTATCAACTTGAAAAAGTGGCACCGAGT CGGTGCTGGAGGAAGCAGGGCTTCCTTTCCTCTGCCATCAATAACT TCGTATAGCATACATTATACGAACGGTACGTGCTCAGTCTG |
| SEQ ID NO: 83<br>gRNA<br>(Artificial Sequence) | GGCCCAGACTGAGCACGTGA |
| SEQ ID NO: 84<br>ACTB N-term PBS 13 RT 29 attB 46 (original length) pegRNA<br>(Artificial Sequence) | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCGACGAGCGCGGCGATATCATCATCCATGGCCGGATGATCC TGACGACGGAGACCGCCGTCGTCGACAAGCCGGCCTGAGCTGCGA GAA |
| SEQ ID NO: 85<br>ACTB N-term PBS_13_RT_29_with TP901-1 minimal attB f pegRNA<br>(Artificial Sequence) | GCTATTCTCGCAGCTCACCAGTTTTAGAGCTAGAAATAGCAAGTT AAAATAAGGCTAGTCCGTTATCAACTTGAAAAAGTGGCACCGAG TCGGTGCGAGTCGGTGCGACGAGCGCGGCGATATCATCATCCAT GGCACAATTAACATCTCAATCAAGGTAAATGCTTGAGCTGCGAG AA |
| SEQ ID NO: 86<br>ACTB N-term PBS_13_RT_29_with TP901-1 minimal attB rc pegRNA<br>(Artificial Sequence) | GCTATTCTCGCAGCTCACCAGTTTTAGAGCTAGAAATAGCAAGTT AAAATAAGGCTAGTCCGTTATCAACTTGAAAAAGTGGCACCGAG TCGGTGCGAGTCGGTGCGACGAGCGCGGCGATATCATCATCCAT GGAGCATTTACCTTGATTGAGATGTTAATTGTGTGAGCTGCGAGA A |
| SEQ ID NO: 87<br>ACTB N-term PBS_13_RT_29_with PhiBT1 minimal attB f pegRNA<br>(Artificial Sequence) | GCTATTCTCGCAGCTCACCAGTTTTAGAGCTAGAAATAGCAAGTT AAAATAAGGCTAGTCCGTTATCAACTTGAAAAAGTGGCACCGAG TCGGTGCGAGTCGGTGCGACGAGCGCGGCGATATCATCATCCAT GGCAGGTTTTTGACGAAAGTGATCCAGATGATCCAGTGAGCTGC GAGAA |
| SEQ ID NO: 88<br>ACTB N-term PBS_13_RT_29_with PhiBT1 minimal attB rc pegRNA<br>(Artificial Sequence) | GCTATTCTCGCAGCTCACCAGTTTTAGAGCTAGAAATAGCAAGTT AAAATAAGGCTAGTCCGTTATCAACTTGAAAAAGTGGCACCGAG TCGGTGCGAGTCGGTGCGACGAGCGCGGCGATATCATCATCCAT GGCTGGATCATCTGGATCACTTTCGTCAAAAACCTGTGAGCTGCG AGAA |
| SEQ ID NO: 89<br>ACTB N-term Nicking guide 1 +48 guide<br>(Artificial Sequence) | GAAGCCGGCCTTGCACATGCGTTTTAGAGCTAGAAATAGCAAGT TAAAATAAGGCTAGTCCGTTATCAACTTGAAAAAGTGGCACCGA GTCGGTGC |
| SEQ ID NO: 90<br>ACTB N-term PBS_18_RT_16_with_ Lox71_Cre pegRNA<br>(Artificial Sequence) | GAAGCCGGCCTTGCACATGCGTTTTAGAGCTAGAAATAGCAAGT TAAAATAAGGCTAGTCCGTTATCAACTTGAAAAAGTGGCACCGA GTCGGTGCATATCATCATCCATGGTACCGTTCGTATAGCATACAT TATACGAAGTTATTGAGCTGCGAGAATAGCC |
| SEQ ID NO: 91<br>ACTB N-term PBS_13_RT_29_with_ Lox71_Cre pegRNA<br>(Artificial Sequence) | GAAGCCGGCCTTGCACATGCGTTTTAGAGCTAGAAATAGCAAGT TAAAATAAGGCTAGTCCGTTATCAACTTGAAAAAGTGGCACCGA GTCGGTGCGACGAGCGCGGCGATATCATCATCCATGGTACCGTT CGTATAGCATACATTATACGAAGTTATTGAGCTGCGAGAA |
| SEQ ID NO: 92<br>ACTB N-term PBS 13 RT 34 pegRNA | GCTATTCTCGCAGCTCACCAGTTTTAGAGCTAGAAATAGCAAGTTA AAATAAGGCTAGTCCGTTATCAACTTGAAAAAGTGGCACCGAGTC GGTGCTCGACGACGAGCGCGGCGATATCATCATCCATGGCCGGAT |

TABLE 4-continued

| SEQ ID NO/ DESCRIPTION/ SOURCE | SEQUENCE |
| --- | --- |
| (Artificial Sequence) | GATCCTGACGACGGAGACCGCCGTCGTCGACAAGCCGGCCTGAGC<br>TGCGAGAA |
| SEQ ID NO: 93<br>ACTB N-term PBS<br>13 RT 26 pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGAGCGCGGCGATATCATCATCCATGGCCGGATGATCCTGA<br>CGACGGAGACCGCCGTCGTCGACAAGCCGGCCTGAGCTGCGAGAA |
| SEQ ID NO: 94<br>ACTB N-term PBS<br>13 RT 23 pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCCGCGGCGATATCATCATCCATGGCCGGATGATCCTGACGAC<br>GGAGACCGCCGTCGTCGACAAGCCGGCCTGAGCTGCGAGAA |
| SEQ ID NO: 95<br>ACTB N-term PBS<br>13 RT 20 pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGGCGATATCATCATCCATGGCCGGATGATCCTGACGACGG<br>AGACCGCCGTCGTCGACAAGCCGGCCTGAGCTGCGAGAA |
| SEQ ID NO: 96<br>ACTB N-term PBS<br>13 RT 16 pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCATATCATCATCCATGGCCGGATGATCCTGACGACGGAGAC<br>CGCCGTCGTCGACAAGCCGGCCTGAGCTGCGAGAA |
| SEQ ID NO: 97<br>ACTB N-term PBS<br>18 RT 34 pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCTCGACGACGAGCGCGGCGATATCATCATCCATGGCGGAT<br>GATCCTGACGACGGAGACCGCCGTCGTCGACAAGCCGGCCTGAGC<br>TGCGAGAATAGCC |
| SEQ ID NO: 98<br>ACTB N-term PBS<br>18 RT 29 pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGCCGGATGATCC<br>TGACGACGGAGACCGCCGTCGTCGACAAGCCGGCCTGAGCTGCGA<br>GAATAGCC |
| SEQ ID NO: 99<br>ACTB N-term PBS<br>18 RT 16 pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCATATCATCATCCATGGCCGGATGATCCTGACGACGGAGAC<br>CGCCGTCGTCGACAAGCCGGCCTGAGCTGCGAGAATAGCC |
| SEQ ID NO: 100<br>LMNB1 N-term PBS<br>13 RT 39 pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGA<br>TCGGTGCCTGCCCATCCGCGGCGGCACGGGGGTCGCAGTCGCCA<br>TGCCGGATGATCCTGACGACGGAGACCGCCGTCGTCGACAAGCC<br>GGCCCGGGCGGCGGAGA |
| SEQ ID NO: 101<br>LMNB1 N-term PBS<br>13 RT 34 pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCCATCCGCGGCGGCACGGGGGTCGCAGTCGCCATGCCG<br>GATGATCCTGACGACGGAGACCGCCGTCGTCGACAAGCCGGCCC<br>GGGCGGCGGAGA |
| SEQ ID NO: 102<br>LMNB1 N-term PBS<br>13 RT 29 pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCGCGGCGGCACGGGGGTCGCAGTCGCCATGCCGGATGA<br>TCCTGACGACGGAGACCGCCGTCGTCGACAAGCCGGCCCGGGCG<br>GCGGAGA |
| SEQ ID NO: 103<br>LMNB1 N-term PBS<br>13 RT 24 pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCGGCACGGGGGTCGCAGTCGCCATGCCGGATGATCCTG<br>ACGACGGAGACCGCCGTCGTCGACAAGCCGGCCCGGGCGGCGGA<br>GA |
| SEQ ID NO: 104<br>LMNB1 N-term PBS<br>13 RT 19 pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCGGGGGTCGCAGTCGCCATGCCGGATGATCCTGACGAC<br>GGAGACCGCCGTCGTCGACAAGCCGGCCCGGGCGGCGGAGA |
| SEQ ID NO: 105<br>LMNB1 N-term PBS<br>18 RT 39 pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCCTGCCCATCCGCGGCGGCACGGGGGTCGCAGTCGCCA<br>TGCCGGATGATCCTGACGACGGAGACCGCCGTCGTCGACAAGCC<br>GGCCCGGGCGGCGGAGACAGCG |

TABLE 4-continued

| SEQ ID NO/<br>DESCRIPTION/<br>SOURCE | SEQUENCE |
|---|---|
| SEQ ID NO: 106<br>LMNB1 N-term PBS<br>18 RT 34 pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCCATCCGCGGCGGCACGGGGGTCGCAGTCGCCATGCCG<br>GATGATCCTGACGACGGAGACCGCCGTCGTCGACAAGCCGGCCC<br>GGGCGGCGGAGACAGCG |
| SEQ ID NO: 107<br>LMNB1 N-term PBS<br>18 RT 29 pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAGT<br>CGGTGCGCGGCGGCACGGGGGTCGCAGTCGCCATGCCGGATGATC<br>CTGACGACGGAGACCGCCGTCGTCGACAAGCCGGCCCGGGCGGCG<br>GAGACAGCG |
| SEQ ID NO: 108<br>LMNB1 N-term PBS<br>18 RT 24 pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCGGCACGGGGGTCGCAGTCGCCATGCCGGATGATCCTG<br>ACGACGGAGACCGCCGTCGTCGACAAGCCGGCCCGGGCGGCGGA<br>GACAGCG |
| SEQ ID NO: 109<br>LMNB1 N-term PBS<br>18 RT 19 pegRNA<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAG<br>TCGGTGCGGGGGTCGCAGTCGCCATGCCGGATGATCCTGACGAC<br>GGAGACCGCCGTCGTCGACAAGCCGGCCCGGGCGGCGGAGACAG<br>CG |
| SEQ ID NO: 110<br>LMNB1 N-term<br>Nicking guide 1 +46<br>(Artificial Sequence) | GCGTGGTGGGGCCGCCAGCGGTTTTAGAGCTAGAAATAGCAAGT<br>TAAAATAAGGCTAGTCCGTTATCAACTTGAAAAAGTGGCACCGA<br>GTCGGTGC |
| SEQ ID NO: 111<br>ACTB N-term PBS<br>13 RT 29 attB 42<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGGGATGATCCTG<br>ACGACGGAGACCGCCGTCGTCGACAAGCCGGTGAGCTGCGAGAA |
| SEQ ID NO: 112<br>ACTB N-term PBS<br>13 RT 29 attB 40<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGGATGATCCTGA<br>CGACGGAGACCGCCGTCGTCGACAAGCCGTGAGCTGCGAGAA |
| SEQ ID NO: 113<br>ACTB N-term PBS<br>13 RT 29 attB 38<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGATGATCCTGAC<br>GACGGAGACCGCCGTCGTCGACAAGCCTGAGCTGCGAGAA |
| SEQ ID NO: 114<br>ACTB N-term PBS<br>13 RT 29 attB 36<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGTGATCCTGACG<br>ACGGAGACCGCCGTCGTCGACAAGCTGAGCTGCGAGAA |
| SEQ ID NO: 115<br>LMNB1 N-term PBS<br>13 RT 29 attB 44<br>pegRNA v2<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAGT<br>CGGTGCGCGGCGGCACGGGGGTCGCAGTCGCCATGCGGATGATCC<br>TGACGACGGAGACCGCCGTCGTCGACAAGCCGGCCGGGCGGCGG<br>AGA |
| SEQ ID NO: 116<br>LMNB1 N-term PBS<br>13 RT 29 attB 42<br>pegRNA v2<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAGT<br>CGGTGCGCGGCGGCACGGGGGTCGCAGTCGCCATGGGATGATCCT<br>GACGACGGAGACCGCCGTCGTCGACAAGCCGGCGGGCGGCGGAG<br>A |
| SEQ ID NO: 117<br>LMNB1 N-term PBS<br>13 RT 29 attB 40<br>pegRNA v2<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAGT<br>CGGTGCGCGGCGGCACGGGGGTCGCAGTCGCCATGGATGATCCTG<br>ACGACGGAGACCGCCGTCGTCGACAAGCCGCGGGCGGCGGAGA |
| SEQ ID NO: 118<br>LMNB1 N-term PBS<br>13 RT 29 attB 38 | GCTGTCTCCGCCGCCCGCCAGTTTTAGAGCTAGAAATAGCAAGTT<br>AAAATAAGGCTAGTCCGTTATCAACTTGAAAAAGTGGCACCGAGT<br>CGGTGCGCGGCGGCACGGGGGTCGCAGTCGCCATGATGATCCTGA |

TABLE 4-continued

| SEQ ID NO/<br>DESCRIPTION/<br>SOURCE | SEQUENCE |
|---|---|
| pegRNA v2<br>(Artificial Sequence) | CGACGGAGACCGCCGTCGTCGACAAGCCCGGGCGGCGGAGA |
| SEQ ID NO: 119<br>NOLC1 N-term PBS<br>18 RT 29 attB 46<br>pegRNA<br>(Artificial Sequence) | GCGTATTGCCTGGAGGATGGGTTTTAGAGCTAGAAATAGCAAGT<br>TAAAATAAGGCTAGTCCGTTATCAACTTGAAAAAGTGGCACCGA<br>GTCGGTGCGAACCACGCGGCGAATGCCGGCGTCCGCCCCGGATG<br>ATCCTGACGACGGAGACCGCCGTCGTCGACAAGCCGGCCTCCTC<br>CAGGCAATACGCG |
| SEQ ID NO: 120<br>NOLC1 N-term PBS<br>13 RT 29 attB 46<br>pegRNA<br>(Artificial Sequence) | GCGTATTGCCTGGAGGATGGGTTTTAGAGCTAGAAATAGCAAGTT<br>AAAATAAGGCTAGTCCGTTATCAACTTGAAAAAGTGGCACCGAGT<br>CGGTGCGAACCACGCGGCGAATGCCGGCGTCCGCCCCGGATGATC<br>CTGACGACGGAGACCGCCGTCGTCGACAAGCCGGCCTCCTCCAGG<br>CAAT |
| SEQ ID NO: 121<br>NOLC1 N-term PBS<br>13 RT 29 attB 44<br>pegRNA<br>(Artificial Sequence) | GCGTATTGCCTGGAGGATGGGTTTTAGAGCTAGAAATAGCAAGT<br>TAAAATAAGGCTAGTCCGTTATCAACTTGAAAAAGTGGCACCGA<br>GTCGGTGCGAACCACGCGGCGAATGCCGGCGTCCGCCCGGATGA<br>TCCTGACGACGGAGACCGCCGTCGTCGACAAGCCGGCTCCTCCA<br>GGCAAT |
| SEQ ID NO: 122<br>NOLC1 N-term PBS<br>13 RT 29 attB 42<br>pegRNA<br>(Artificial Sequence) | GCGTATTGCCTGGAGGATGGGTTTTAGAGCTAGAAATAGCAAGT<br>TAAAATAAGGCTAGTCCGTTATCAACTTGAAAAAGTGGCACCGA<br>GTCGGTGCGAACCACGCGGCGAATGCCGGCGTCCGCCGGATGAT<br>CCTGACGACGGAGACCGCCGTCGTCGACAAGCCGGTCCTCCAGG<br>CAAT |
| SEQ ID NO: 123<br>NOLC1 N-term PBS<br>13 RT 29 attB 40<br>pegRNA<br>(Artificial Sequence) | GCGTATTGCCTGGAGGATGGGTTTTAGAGCTAGAAATAGCAAGT<br>TAAAATAAGGCTAGTCCGTTATCAACTTGAAAAAGTGGCACCGA<br>GTCGGTGCGAACCACGCGGCGAATGCCGGCGTCCGCCGATGATC<br>CTGACGACGGAGACCGCCGTCGTCGACAAGCCGTCCTCCAGGCA<br>AT |
| SEQ ID NO: 124<br>NOLC1 N-term PBS<br>13 RT 29 attB 38<br>pegRNA<br>(Artificial Sequence) | GCGTATTGCCTGGAGGATGGGTTTTAGAGCTAGAAATAGCAAGTT<br>AAAATAAGGCTAGTCCGTTATCAACTTGAAAAAGTGGCACCGAG<br>TCGGTGCGAACCACGCGGCGAATGCCGGCGTCCGCCATGATCCT<br>GACGACGGAGACCGCCGTCGTCGACAAGCCTCCTCCAGGCAAT |
| SEQ ID NO: 125<br>NOLC1 nicking<br>guide-43<br>(Artificial Sequence) | GAGCCGAGCACGAGGGGATACGTTTTAGAGCTAGAAATAGCAAGT<br>TAAAATAAGGCTAGTCCGTTATCAACTTGAAAAAGTGGCACCGAG<br>TCGGTGC |
| SEQ ID NO: 126<br>ACTB N-term PBS<br>13 RT 20 attB 38<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGGCGATATCATCATCCATGGATGATCCTGACGACGGAGAC<br>CGCCGTCGTCGACAAGCCTGAGCTGCGAGAA |
| SEQ ID NO: 127<br>ACTB N-term PBS<br>13 RT 15 attB 38<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCTATCATCATCCATGGATGATCCTGACGACGGAGACCGCCG<br>TCGTCGACAAGCCTGAGCTGCGAGAA |
| SEQ ID NO: 128<br>ACTB N-term PBS<br>13 RT 10 attB 38<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCTCATCCATGGATGATCCTGACGACGGAGACCGCCGTCGTC<br>GACAAGCCTGAGCTGCGAGAA |
| SEQ ID NO: 129<br>ACTB N-term PBS 9<br>RT 20 attB 38<br>pegRNA<br>(Artificial Sequence) | GCTATTCTCGCAGCTCACCAGTTTTAGAGCTAGAAATAGCAAGTT<br>AAAATAAGGCTAGTCCGTTATCAACTTGAAAAAGTGGCACCGAG<br>TCGGTGCGGCGATATCATCATCCATGGATGATCCTGACGACGGAG<br>ACCGCCGTCGTCGACAAGCCTGAGCTGCG |
| SEQ ID NO: 130<br>ACTB N-term PBS 9<br>RT 15 attB 38<br>pegRNA<br>(Artificial Sequence) | GCTATTCTCGCAGCTCACCAGTTTTAGAGCTAGAAATAGCAAGTT<br>AAAATAAGGCTAGTCCGTTATCAACTTGAAAAAGTGGCACCGAGTC<br>GGTGCTATCATCATCCATGGATGATCCTGACGACGGAGACCGCCG<br>TCGTCGACAAGCCTGAGCTGCG |
| SEQ ID NO: 131<br>ACTB N-term PBS 9 | GCTATTCTCGCAGCTCACCAGTTTTAGAGCTAGAAATAGCAAGTTA<br>AAATAAGGCTAGTCCGTTATCAACTTGAAAAAGTGGCACCGAGTC |

TABLE 4-continued

| SEQ ID NO/ DESCRIPTION/ SOURCE | SEQUENCE |
|---|---|
| RT 10 attB 38 pegRNA (Artificial Sequence) | GGTGCTCATCCATGGATGATCCTGACGACGGAGACCGCCGTCGTC GACAAGCCTGAGCTGCG |
| SEQ ID NO: 132 LMNB1 N-term PBS 13 RT 20 attB 38 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCCGGGGGTCGCAGTCGCCATGATGATCCTGACGACGGA GACCGCCGTCGTCGACAAGCCCGGGCGGCGGAGA |
| SEQ ID NO: 133 LMNB1 N-term PBS 13 RT 15 attB 38 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCGTCGCAGTCGCCATGATGATCCTGACGACGGAGACCG CCGTCGTCGACAAGCCCGGGCGGCGGAGA |
| SEQ ID NO: 134 LMNB1 N-term PBS 13 RT 10 attB 38 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCAGTCGCCATGATGATCCTGACGACGGAGACCGCCGTC GTCGACAAGCCCGGGCGGCGGAGA |
| SEQ ID NO: 135 LMNB1 N-term PBS 9 RT 20 attB 38 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAGT CGGTGCCGGGGGTCGCAGTCGCCATGATGATCCTGACGACGGAGA CCGCCGTCGTCGACAAGCCCGGGCGGCG |
| SEQ ID NO: 136 LMNB1 N-term PBS 9 RT 15 attB 38 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAG TCGGTGCGTCGCAGTCGCCATGATGATCCTGACGACGGAGACCG CCGTCGTCGACAAGCCCGGGCGGCG |
| SEQ ID NO: 137 LMNB1 N-term PBS 9 RT 10 attB 38 pegRNA (Artificial Sequence) | GCTGTCTCCGCCGCCCGCCAGTTTTAGAGCTAGAAATAGCAAGTT AAAATAAGGCTAGTCCGTTATCAACTTGAAAAAGTGGCACCGAGT CGGTGCAGTCGCCATGATGATCCTGACGACGGAGACCGCCGTCGT CGACAAGCCCGGGCGGCG |
| SEQ ID NO: 138 SUPT16H N-term PBS 13 RT 24 Bxb1- GT_Initial length (Artificial Sequence) | GAGAAGCGGCGTCCGGGGCTAGTTTTAGAGCTAGAAATAGCAAGT TAAAATAAGGCTAGTCCGTTATCAACTTGAAAAAGTGGCACCGAG TCGGTGCTCTTTGTCCAGAGTCACAGCCATACCGGATGATCCTGAC GACGGAGACCGCCGTCGTCGACAAGCCGGCCCCCCGGACGCCGC |
| SEQ ID NO: 139 SRRM2 N-term PBS 13 RT 24 Bxb1 Initial length (Artificial Sequence) | GGGCACGGGGCCATGTACAAGTTTTAGAGCTAGAAATAGCAAGT TAAAATAAGGCTAGTCCGTTATCAACTTGAAAAAGTGGCACCGA GTCGGTGCGGCGTCGGCAGCCCGATCCCGTTGCCGGATGATCCT GACGACGGAGACCGCCGTCGTCGACAAGCCGGCCTACATGGCCC CGT |
| SEQ ID NO: 140 DEPDC4 N-term PBS 18 RT 24 Bxb1 Initial length (Artificial Sequence) | GTGTCAGGTGGGGGGGCTAGTTTTAGAGCTAGAAATAGCAAG TTAAAATAAGGCTAGTCCGTTATCAACTTGAAAAAGTGGCACCG AGTCGGTGCGCTGGCTCCTCCCCTGGCACCATACCGGATGATCCT GACGACGGAGACCGCCGTCGTCGACAAGCCGGCCCCCCGCCCCA CCTGACAC |
| SEQ ID NO: 141 NES N-term PBS 13 RT 29 Bxb1 Initial length (Artificial Sequence) | GAGTGGGTCAGACGAGCAGGAGTTTTAGAGCTAGAAATAGCAAGT TAAAATAAGGCTAGTCCGTTATCAACTTGAAAAAGTGGCACCGAG TCGGTGCGATGGAGGGCTGCATGGGGAGGAGTCGCCGGATGATC CTGACGACGGAGACCGCCGTCGTCGACAAGCCGGCCTGCTCGTCT GACC |
| SEQ ID NO: 142 SUPT16H nicking guide-53 (Artificial Sequence) | GCAGCCACCCGCTCTCGGCCCGTTTTAGAGCTAGAAATAGCAAG TTAAAATAAGGCTAGTCCGTTATCAACTTGAAAAAGTGGCACCG AGTCGGTGC |
| SEQ ID NO: 143 SRRM2 N-term nicking guide 1 +87 (Artificial Sequence) | GTGTAGTCAGGCCGCTCACCCGTTTTAGAGCTAGAAATAGCAAG TTAAAATAAGGCTAGTCCGTTATCAACTTGAAAAAGTGGCACCG AGTCGGTGC |
| SEQ ID NO: 144 DEPDC4 N-term | GCTGACAAGTCTACGGAACCTGTTTTAGAGCTAGAAATAGCAAG TTAAAATAAGGCTAGTCCGTTATCAACTTGAAAAAGTGGCACCG |

TABLE 4-continued

| SEQ ID NO/<br>DESCRIPTION/<br>SOURCE | SEQUENCE |
|---|---|
| Nicking guide 1 +59<br>(Artificial Sequence) | AGTCGGTGC |
| SEQ ID NO: 145<br>NES N-term Nicking<br>guide 2 +79<br>(Artificial Sequence) | GCTCCTCCAGCGCCTTGACCGTTTTAGAGCTAGAAATAGCAAGTTA<br>AAATAAGGCTAGTCCGTTATCAACTTGAAAAAGTGGCACCGAGTC<br>GGTGC |
| SEQ ID NO: 146<br>HITI_ACTB_guide<br>(Artificial Sequence) | GCTATTCTCGCAGCTCACCA |
| SEQ ID NO: 147<br>HITI_SUPTH16_guide<br>(Artificial Sequence) | AGAAGCGGCGTCCGGGGCTA |
| SEQ ID NO: 148<br>HITI_SRRM2_guide<br>(Artificial Sequence) | GGGCACGGGGCCATGTACAA |
| SEQ ID NO: 149<br>HITI_NOLC1_guide<br>(Artificial Sequence) | GCGTATTGCCTGGAGGATGG |
| SEQ ID NO: 150<br>HITI_DEPDC4_guide<br>(Artificial Sequence) | TGTCAGGTGGGGCGGGGCTA |
| SEQ ID NO: 151<br>HITI_NES_guide<br>(Artificial Sequence) | AGTGGGTCAGACGAGCAGGA |
| SEQ ID NO: 152<br>HITI_LMNB1_guide<br>(Artificial Sequence) | GCTGTCTCCGCCGCCCGCCA |
| SEQ ID NO: 153<br>HDR Cas9 ACTB<br>guide<br>(Artificial Sequence) | GCTATTCTCGCAGCTCACCAGTTTTAGAGCTAGAAATAGCAAGTT<br>AAAATAAGGCTAGTCCGTTATCAACTTGAAAAAGTGGCACCGAG<br>TCGGTGC |
| SEQ ID NO: 154<br>ACTB N-term PBS<br>13 RT 29 attB<br>original length<br>pegRNAs for<br>dinucleotides<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGCCGGATGATCC<br>TGACGACGGAGXXCGCCGTCGTCGACAAGCCGGCCTGAGCTGCGA<br>GAA<br>XX: CG, GC, AT, TA, GG, TT, GA, AG, CC, TC,<br>CT, AA, TG, GT, CA, or AC |
| SEQ ID NO: 155<br>ACTB N-term PBS<br>13 RT 29 pegRNA<br>with attB 46 GT for<br>fusion<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGCCGGATGATCCT<br>GACGACGGAGACCGCCGTCGTCGACAAGCCGGCCTGAGCTGCGAG<br>AA |
| SEQ ID NO: 156<br>ACTB N-term PBS<br>13 RT 29 pegRNA<br>with attB 46 CT for<br>multiplexing<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGCCGGATGATCCT<br>GACGACGGAGAGCGCCGTCGTCGACAAGCCGGCCTGAGCTGCGA<br>GAA |
| SEQ ID NO: 157<br>NOLC1 N-term PBS<br>18 RT 29 pegRNA<br>with attB 46 GA for<br>multiplexing<br>(Artificial Sequence) | GCGTATTGCCTGGAGGATGGGTTTTAGAGCTAGAAATAGCAAGTT<br>AAAATAAGGCTAGTCCGTTATCAACTTGAAAAAGTGGCACCGAGT<br>CGGTGCGAACCACGCGGCGAATGCCGGCGTCCGCCCCGGATGATC<br>CTGACGACGGAGTCCGCCGTCGTCGACAAGCCGGCCTCCTCCAGG<br>CAATACGCG |
| SEQ ID NO: 158<br>LMNB1 N-term PBS<br>18 RT 29 pegRNA<br>with attB 46 AG for<br>multiplexing<br>(Artificial Sequence) | GCTGTCTCCGCCGCCCGCCAGTTTTAGAGCTAGAAATAGCAAGTT<br>AAAATAAGGCTAGTCCGTTATCAACTTGAAAAAGTGGCACCGAGT<br>CGGTGCGCGGCGGCACGGGGGTCGCAGTCGCCATGCCGGATGATC<br>CTGACGACGGAGCTCGCCGTCGTCGACAAGCCGGCCCGGGCGGCG<br>GAGACAGCG |

TABLE 4-continued

| SEQ ID NO/<br>DESCRIPTION/<br>SOURCE | SEQUENCE |
|---|---|
| SEQ ID NO: 159<br>EMX1 Cas9 guide 1<br>(Artificial Sequence) | GTCACCTCCAATGACTAGGG |
| SEQ ID NO: 160<br>EMX1 Cas9 guide 2<br>(Artificial Sequence) | GGGCAACCACAAACCCACGA |
| SEQ ID NO: 161<br>ACTB N-term PBS<br>13 RT 29 attB 56 GA<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGCTATGCCGGAT<br>GATCCTGACGACGGAGTCCGCCGTCGTCGACAAGCCGGCCCTAGC<br>TGAGCTGCGAGAA |
| SEQ ID NO: 162<br>ACTB N-term PBS<br>13 RT 29 attB 51 GA<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGTGCCGGATGAT<br>CCTGACGACGGAGTCCGCCGTCGTCGACAAGCCGGCCCTATGAGC<br>TGCGAGAA |
| SEQ ID NO: 163<br>ACTB N-term PBS<br>13 RT 29 attB 46 GA<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGCCGGATGATCC<br>TGACGACGGAGTCCGCCGTCGTCGACAAGCCGGCCTGAGCTGCGA<br>GAA |
| SEQ ID NO: 164<br>ACTB N-term PBS<br>13 RT 29 attB 41 GA<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGGATGATCCTG<br>ACGACGGAGTCCGCCGTCGTCGACAAGCCGTGAGCTGCGAGAA |
| SEQ ID NO: 165<br>ACTB N-term PBS<br>13 RT 29 attB 36 GA<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGTGATCCTGACG<br>ACGGAGTCCGCCGTCGTCGACAAGCTGAGCTGCGAGAA |
| SEQ ID NO: 166<br>ACTB N-term PBS<br>13 RT 29 attB 31 GA<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGATCCTGACGAC<br>GGAGTCCGCCGTCGTCGACATGAGCTGCGAGAA |
| SEQ ID NO: 167<br>ACTB N-term PBS<br>13 RT 29 attB 26 GA<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGCCTGACGACGG<br>AGTCCGCCGTCGTCGTGAGCTGCGAGAA |
| SEQ ID NO: 168<br>ACTB N-term PBS<br>13 RT 29 attB 21 GA<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGTGACGACGGAG<br>TCCGCCGTCGTGAGCTGCGAGAA |
| SEQ ID NO: 169<br>ACTB N-term PBS<br>13 RT 29 attB 16 GA<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGACGACGGAGTC<br>CGCCGTGAGCTGCGAGAA |
| SEQ ID NO: 170<br>ACTB N-term PBS<br>13 RT 29 attB 11 GA<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGGACGGAGTCCG<br>TGAGCTGCGAGAA |
| SEQ ID NO: 171<br>ACTB N-term PBS<br>13 RT 29 attB 6 GA<br>pegRNA<br>(Artificial Sequence) | GCTATTCTCGCAGCTCACCAGTTTTAGAGCTAGAAATAGCAAGTTA<br>AAATAAGGCTAGTCCGTTATCAACTTGAAAAAGTGGCACCGAGTC<br>GGTGCGACGAGCGCGGCGATATCATCATCCATGGCGGAGTTGAGC<br>TGCGAGAA |

TABLE 4-continued

| SEQ ID NO/ DESCRIPTION/ SOURCE | SEQUENCE |
|---|---|
| SEQ ID NO: 172 ACTB N-term PBS_18_RT_34_with_ L ox71_Cre pegRNA (Artificial Sequence) | GAAGCCGGCCTTGCACATGCGTTTTAGAGCTAGAAATAGCAAGTT AAAATAAGGCTAGTCCGTTATCAACTTGAAAAAGTGGCACCGAGT CGGTGCTCGACGACGAGCGCGGCGATATCATCATCCATGGTACCG TTCGTATAGCATACATTATACGAAGTTATTGAGCTGCGAGAATAG CC |
| SEQ ID NO: 173 ACTB N-term PBS_18_RT_29_with_ L ox71_Cre pegRNA (Artificial Sequence) | GAAGCCGGCCTTGCACATGCGTTTTAGAGCTAGAAATAGCAAGTT AAAATAAGGCTAGTCCGTTATCAACTTGAAAAAGTGGCACCGAGT CGGTGCGACGAGCGCGGCGATATCATCATCCATGGTACCGTTCGT ATAGCATACATTATACGAAGTTATTGAGCTGCGAGAATAGCC |
| SEQ ID NO: 174 ACTB N-term PBS_13_RT_34_with_ L ox71_Cre pegRNA (Artificial Sequence) | GAAGCCGGCCTTGCACATGCGTTTTAGAGCTAGAAATAGCAAGTT AAAATAAGGCTAGTCCGTTATCAACTTGAAAAAGTGGCACCGAGT CGGTGCTCGACGACGAGCGCGGCGATATCATCATCCATGGTACCG TTCGTATAGCATACATTATACGAAGTTATTGAGCTGCGAGAA |
| SEQ ID NO: 175 ACTB N-term PBS_13_RT_16_with_ L ox71_Cre pegRNA (Artificial Sequence) | GAAGCCGGCCTTGCACATGCGTTTTAGAGCTAGAAATAGCAAGTT AAAATAAGGCTAGTCCGTTATCAACTTGAAAAAGTGGCACCGAGT CGGTGCATATCATCATCCATGGTACCGTTCGTATAGCATACATTAT ACGAAGTTATTGAGCTGCGAGAA |
| SEQ ID NO: 176 ACTB N-term Nicking guide 2 +93 guide (Artificial Sequence) | CCCCACGATGGAGGGGAAGAGTTTTAGAGCTAGAAATAGCAAGTT AAAATAAGGCTAGTCCGTTATCAACTTGAAAAAGTGGCACCGAGT CGGTGC |
| SEQ ID NO: 177 LMNB1 N-term Nicking guide 2 +87 guide (Artificial Sequence) | CCTTCTCCTGGAGCCGCGACGTTTTAGAGCTAGAAATAGCAAGTT AAAATAAGGCTAGTCCGTTATCAACTTGAAAAAGTGGCACCGAGT CGGTGC |

Sequences of insertion sites can be found in Table 4 below.

TABLE 4

| DESCRIPTION/ SOURCE | FORWARD SEQUENCE (5'-3') | | REVERSE SEQUENCE (5'-3') | |
|---|---|---|---|---|
| | SEQ ID NO | Sequence | SEQ ID NO | Sequence |
| Bxb1_attP_GT_ original _site (Artificial Sequence) | 178 | GTGGTTTGTCTGGTC AACCACCGCGGTCT CAGTGGTGTACGGT ACAAACCCA | 179 | TGGGTTTGTACCGTA CACCACTGAGACCG CGGTGGTTGACCAG ACAAACCAC |
| Bxb1_attP_CG_ site (Artificial Sequence) | 180 | GTGGTTTGTCTGGTC AACCACCGCGCGCT CAGTGGTGTACGGT ACAAACCCA | 181 | TGGGTTTGTACCGTA CACCACTGAGCGCG CGGTGGTTGACCAG ACAAACCAC |
| Bxb1_attP_GC_ site (Artificial Sequence) | 182 | GTGGTTTGTCTGGTC AACCACCGCGGCCT CAGTGGTGTACGGT ACAAACCCA | 183 | TGGGTTTGTACCGTA CACCACTGAGGCCG CGGTGGTTGACCAG ACAAACCAC |
| Bxb1_attP_AT_ site (Artificial Sequence) | 184 | GTGGTTTGTCTGGTC AACCACCGCGATCT CAGTGGTGTACGGT ACAAACCCA | 185 | TGGGTTTGTACCGTA CACCACTGAGATCG CGGTGGTTGACCAG ACAAACCAC |
| Bxb1_attP_TA_ site | 186 | GTGGTTTGTCTGGTC AACCACCGCGTACT | 187 | TGGGTTTGTACCGTA CACCACTGAGTACG |

TABLE 4-continued

| DESCRIPTION/ SOURCE | FORWARD SEQUENCE (5'-3') | | REVERSE SEQUENCE (5'-3') | |
|---|---|---|---|---|
| | SEQ ID NO | Sequence | SEQ ID NO | Sequence |
| (Artificial Sequence) | | CAGTGGTGTACGGT ACAAACCCA | | CGGTGGTTGACCAG ACAAACCAC |
| Bxb1_attP_GG_ site (Artificial Sequence) | 188 | GTGGTTTGTCTGGTC AACCACCGCGGGCT CAGTGGTGTACGGT ACAAACCCA | 189 | TGGGTTTGTACCGTA CACCACTGAGCCCG CGGTGGTTGACCAG ACAAACCAC |
| Bxb1_attP_TT_ site (Artificial Sequence) | 190 | GTGGTTTGTCTGGTC AACCACCGCGTTCTC AGTGGTGTACGGTA CAAACCCA | 191 | TGGGTTTGTACCGTA CACCACTGAGAACG CGGTGGTTGACCAG ACAAACCAC |
| Bxb1_attP_GA_ site (Artificial Sequence) | 192 | GTGGTTTGTCTGGTC AACCACCGCGGACT CAGTGGTGTACGGT ACAAACCCA | 193 | TGGGTTTGTACCGTA CACCACTGAGTCCG CGGTGGTTGACCAG ACAAACCAC |
| Bxb1_attP_AG_ site (Artificial Sequence) | 194 | GTGGTTTGTCTGGTC AACCACCGCGAGCT CAGTGGTGTACGGT ACAAACCCA | 195 | TGGGTTTGTACCGTA CACCACTGAGCTCG CGGTGGTTGACCAG ACAAACCAC |
| Bxb1_attP_CC_ site (Artificial Sequence) | 196 | GTGGTTTGTCTGGTC AACCACCGCGCCCT CAGTGGTGTACGGT ACAAACCCA | 197 | TGGGTTTGTACCGTA CACCACTGAGGGCG CGGTGGTTGACCAG ACAAACCAC |
| Bxb1_attP_TC_ site (Artificial Sequence) | 198 | GTGGTTTGTCTGGTC AACCACCGCGTCCTC AGTGGTGTACGGTA CAAACCCA | 199 | TGGGTTTGTACCGTA CACCACTGAGGACG CGGTGGTTGACCAG ACAAACCAC |
| Bxb1_attP_CT_ site (Artificial Sequence) | 200 | GTGGTTTGTCTGGTC AACCACCGCGCTCTC AGTGGTGTACGGTA CAAACCCA | 201 | TGGGTTTGTACCGTA CACCACTGAGAGCG CGGTGGTTGACCAG ACAAACCAC |
| Bxb1_attP_AA_ site (Artificial Sequence) | 202 | GTGGTTTGTCTGGTC AACCACCGCGAACT CAGTGGTGTACGGT ACAAACCCA | 203 | TGGGTTTGTACCGTA CACCACTGAGTTCGC GGTGGTTGACCAGA CAAACCAC |
| Bxb1_attP_CA_ site (Artificial Sequence) | 204 | GTGGTTTGTCTGGTC AACCACCGCGCACT CAGTGGTGTACGGT ACAAACCCA | 205 | TGGGTTTGTACCGTA CACCACTGAGTGCG CGGTGGTTGACCAG ACAAACCAC |
| Bxb1_attP_AC_ site (Artificial Sequence) | 206 | GTGGTTTGTCTGGTC AACCACCGCGACCT CAGTGGTGTACGGT ACAAACCCA | 207 | TGGGTTTGTACCGTA CACCACTGAGGTCG CGGTGGTTGACCAG ACAAACCAC |
| Bxb1_attP_TG_ site (Artificial Sequence) | 208 | GTGGTTTGTCTGGTC AACCACCGCGTGCT CAGTGGTGTACGGT ACAAACCCA | 209 | TGGGTTTGTACCGTA CACCACTGAGCACG CGGTGGTTGACCAG ACAAACCAC |
| Bxb1_attB_46_ GT_ original site (Artificial Sequence) | 210 | GGCCGGCTTGTCGA CGACGGCGGTCTCC GTCGTCAGGATCATC CGG | 211 | CCGGATGATCCTGA CGACGGAGACCGCC GTCGTCGACAAGCC GGCC |
| Bxb1_attB_46_ AA_site (Artificial Sequence) | 212 | GGCCGGCTTGTCGA CGACGGCGAACTCC GTCGTCAGGATCATC CGG | 213 | CCGGATGATCCTGA CGACGGAGTTCGCC GTCGTCGACAAGCC GGCC |
| Bxb1_attB_46_ GA_site (Artificial Sequence) | 214 | GGCCGGCTTGTCGA CGACGGCGGACTCC GTCGTCAGGATCATC CGG | 215 | CCGGATGATCCTGA CGACGGAGTCCGCC GTCGTCGACAAGCC GGCC |

TABLE 4-continued

| DESCRIPTION/ SOURCE | FORWARD SEQUENCE (5'-3') | | REVERSE SEQUENCE (5'-3') | |
|---|---|---|---|---|
| | SEQ ID NO | Sequence | SEQ ID NO | Sequence |
| Bxb1_attB_46_ CA_site (Artificial Sequence) | 216 | GGCCGGCTTGTCGA CGACGGCGCACTCC GTCGTCAGGATCATC CGG | 217 | CCGGATGATCCTGA CGACGGAGTGCGCC GTCGTCGACAAGCC GGCC |
| Bxb1_attB_46_ TA_site (Artificial Sequence) | 218 | GGCCGGCTTGTCGA CGACGGCGTACTCC GTCGTCAGGATCATC CGG | 219 | CCGGATGATCCTGA CGACGGAGTACGCC GTCGTCGACAAGCC GGCC |
| Bxb1_attB_46_ AG_site (Artificial Sequence) | 220 | GGCCGGCTTGTCGA CGACGGCGAGCTCC GTCGTCAGGATCATC CGG | 221 | CCGGATGATCCTGA CGACGGAGCTCGCC GTCGTCGACAAGCC GGCC |
| Bxb1_attB_46_ GG_site (Artificial Sequence) | 222 | GGCCGGCTTGTCGA CGACGGCGGGCTCC GTCGTCAGGATCATC CGG | 223 | CCGGATGATCCTGA CGACGGAGCCCGCC GTCGTCGACAAGCC GGCC |
| Bxb1_attB_46_ CG_site (Artificial Sequence) | 224 | GGCCGGCTTGTCGA CGACGGCGCGCTCC GTCGTCAGGATCATC CGG | 225 | CCGGATGATCCTGA CGACGGAGCGCGCC GTCGTCGACAAGCC GGCC |
| Bxb1_attB_46_ TG_site (Artificial Sequence) | 226 | GGCCGGCTTGTCGA CGACGGCGTGCTCC GTCGTCAGGATCATC CGG | 227 | CCGGATGATCCTGA CGACGGAGCACGCC GTCGTCGACAAGCC GGCC |
| Bxb1_attB_46_ AC_site (Artificial Sequence) | 228 | GGCCGGCTTGTCGA CGACGGCGACCTCC GTCGTCAGGATCATC CGG | 229 | CCGGATGATCCTGA CGACGGAGGTCGCC GTCGTCGACAAGCC GGCC |
| Bxb1_attB_46_ GC_site (Artificial Sequence) | 230 | GGCCGGCTTGTCGA CGACGGCGGCCTCC GTCGTCAGGATCATC CGG | 231 | CCGGATGATCCTGA CGACGGAGGCCGCC GTCGTCGACAAGCC GGCC |
| Bxb1_attB_46_ CC_site (Artificial Sequence) | 232 | GGCCGGCTTGTCGA CGACGGCGCCCTCC GTCGTCAGGATCATC CGG | 233 | CCGGATGATCCTGA CGACGGAGGGCGCC GTCGTCGACAAGCC GGCC |
| Bxb1_attB_46_ TC_site (Artificial Sequence) | 234 | GGCCGGCTTGTCGA CGACGGCGTCCTCC GTCGTCAGGATCATC CGG | 235 | CCGGATGATCCTGA CGACGGAGGACGCC GTCGTCGACAAGCC GGCC |
| Bxb1_attB_46_ AT_site (Artificial Sequence) | 236 | GGCCGGCTTGTCGA CGACGGCGATCTCC GTCGTCAGGATCATC CGG | 237 | CCGGATGATCCTGA CGACGGAGATCGCC GTCGTCGACAAGCC GGCC |
| Bxb1_attB_46_ CT_site (Artificial Sequence) | 238 | GGCCGGCTTGTCGA CGACGGCGCTCTCC GTCGTCAGGATCATC CGG | 239 | CCGGATGATCCTGA CGACGGAGAGCGCC GTCGTCGACAAGCC GGCC |
| Bxb1_attB_46_ TT_site (Artificial Sequence) | 240 | GGCCGGCTTGTCGA CGACGGCGTTCTCCG TCGTCAGGATCATCC GG | 241 | CCGGATGATCCTGA CGACGGAGAACGCC GTCGTCGACAAGCC GGCC |
| Bxb1_attB_38_ GT_site (Artificial Sequence) | 242 | GGCTTGTCGACGAC GGCGGTCTCCGTCGT CAGGATCAT | 243 | ATGATCCTGACGAC GGAGACCGCCGTCG TCGACAAGCC |
| Bxb1_attB_38_ AA_site (Artificial Sequence) | 244 | GGCTTGTCGACGAC GGCGAACTCCGTCG TCAGGATCAT | 245 | ATGATCCTGACGAC GGAGTTCGCCGTCGT CGACAAGCC |

TABLE 4-continued

| DESCRIPTION/ SOURCE | FORWARD SEQUENCE (5'-3') | | REVERSE SEQUENCE (5'-3') | |
|---|---|---|---|---|
| | SEQ ID NO | Sequence | SEQ ID NO | Sequence |
| Bxb1_attB_38_ GA_site (Artificial Sequence) | 246 | GGCTTGTCGACGAC GGCGGACTCCGTCG TCAGGATCAT | 247 | ATGATCCTGACGAC GGAGTCCGCCGTCG TCGACAAGCC |
| Bxb1_attB_38_ CA_site (Artificial Sequence) | 248 | GGCTTGTCGACGAC GGCGCACTCCGTCGT CAGGATCAT | 249 | ATGATCCTGACGAC GGAGTGCGCCGTCG TCGACAAGCC |
| Bxb1_attB_38_ TA_site (Artificial Sequence) | 250 | GGCTTGTCGACGAC GGCGTACTCCGTCGT CAGGATCAT | 251 | ATGATCCTGACGAC GGAGTACGCCGTCG TCGACAAGCC |
| Bxb1_attB_38_ AG_site (Artificial Sequence) | 252 | GGCTTGTCGACGAC GGCGAGCTCCGTCG TCAGGATCAT | 253 | ATGATCCTGACGAC GGAGCTCGCCGTCG TCGACAAGCC |
| Bxb1_attB_38_ GG_site (Artificial Sequence) | 254 | GGCTTGTCGACGAC GGCGGGCTCCGTCG TCAGGATCAT | 255 | ATGATCCTGACGAC GGAGCCCGCCGTCG TCGACAAGCC |
| Bxb1_attB_38_ CG_site (Artificial Sequence) | 256 | GGCTTGTCGACGAC GGCGCGCTCCGTCGT CAGGATCAT | 257 | ATGATCCTGACGAC GGAGCGCGCCGTCG TCGACAAGCC |
| Bxb1_attB_38_ TG_site (Artificial Sequence) | 258 | GGCTTGTCGACGAC GGCGTGCTCCGTCGT CAGGATCAT | 259 | ATGATCCTGACGAC GGAGCACGCCGTCG TCGACAAGCC |
| Bxb1_attB_38_ AC_site (Artificial Sequence) | 260 | GGCTTGTCGACGAC GGCGACCTCCGTCGT CAGGATCAT | 261 | ATGATCCTGACGAC GGAGGTCGCCGTCG TCGACAAGCC |
| Bxb1_attB_38_ GC_site (Artificial Sequence) | 262 | GGCTTGTCGACGAC GGCGGCCTCCGTCGT CAGGATCAT | 263 | ATGATCCTGACGAC GGAGGCCGCCGTCG TCGACAAGCC |
| Bxb1_attB_38_ CC_site (Artificial Sequence) | 264 | GGCTTGTCGACGAC GGCGCCCTCCGTCGT CAGGATCAT | 265 | ATGATCCTGACGAC GGAGGGCGCCGTCG TCGACAAGCC |
| Bxb1_attB_38_ TC_site (Artificial Sequence) | 266 | GGCTTGTCGACGAC GGCGTCCTCCGTCGT CAGGATCAT | 267 | ATGATCCTGACGAC GGAGGACGCCGTCG TCGACAAGCC |
| Bxb1_attB_38_ AT_site (Artificial Sequence) | 268 | GGCTTGTCGACGAC GGCGATCTCCGTCGT CAGGATCAT | 269 | ATGATCCTGACGAC GGAGATCGCCGTCG TCGACAAGCC |
| Bxb1_attB_38_ CT_site (Artificial Sequence) | 270 | GGCTTGTCGACGAC GGCGCTCTCCGTCGT CAGGATCAT | 271 | ATGATCCTGACGAC GGAGAGCGCCGTCG TCGACAAGCC |
| Bxb1_attB_38_ TT_site (Artificial Sequence) | 272 | GGCTTGTCGACGAC GGCGTTCTCCGTCGT CAGGATCAT | 273 | ATGATCCTGACGAC GGAGAACGCCGTCG TCGACAAGCC |
| Cre Lox 66 site (Artificial Sequence) | 274 | TACCGTTCGTATAAT GTATGCTATACGAA GTTAT | 275 | ATAACTTCGTATAGC ATACATTATACGAA CGGTA |

TABLE 4-continued

| DESCRIPTION/ SOURCE | SEQ ID NO | FORWARD SEQUENCE (5'-3') Sequence | SEQ ID NO | REVERSE SEQUENCE (5'-3') Sequence |
|---|---|---|---|---|
| Cre Lox 71 site (Artificial Sequence) | 276 | ATAACTTCGTATAAT GTATGCTATACGAA CGGTA | 277 | TACCGTTCGTATAGC ATACATTATACGAA GTTAT |
| TP901-1 minimal attB site (Artificial Sequence) | 278 | TTTACCTTGATTGAG ATGTTAATTGTG | 279 | CACAATTAACATCTC AATCAAGGTAAA |
| TP901-1 minimal attP site (Artificial Sequence) | 280 | GCGAGTTTTTATTTC GTTTATTTCAATTAA GGTAACTAAAAAAC TCCTTT | 281 | AAAGGAGTTTTTTAG TTACCTTAATTGAAA TAAACGAAATAAAA ACTCGC |
| PhiBT1 minimal attB site (Artificial Sequence) | 282 | CTGGATCATCTGGAT CACTTTCGTCAAAAA CCTG | 283 | CAGGTTTTTGACGAA AGTGATCCAGATGA TCCAG |
| PhiBT1 minimal attP site (Artificial Sequence) | 284 | TTCGGGTGCTGGGTT GTTGTCTCTGGACAG TGATCCATGGGAAA CTACTCAGCACCA | 285 | TGGTGCTGAGTAGTT TCCCATGGATCACTG TCCAGAGACAACAA CCCAGCACCCGAA |

Sequences of Bxb1 and RT mutants can be found in Table 6 below.

TABLE 6

| SEQ ID NO/ DESCRIPTION/ SOURCE | FORWARD SEQUENCE (5'-3') |
|---|---|
| SEQ ID NO: 286 Bxb1_mut_V368A (Artificial Sequence) | AAAAGTGTGGGCTGCAGGATCTGA |
| SEQ ID NO: 287 Bxb1_mut_E379A (Artificial Sequence) | GGAGCTGGCAGCTGTCAATGCC |
| SEQ ID NO: 288 Bxb1_mut_E383A (Artificial Sequence) | AGTCAATGCCGCTCTCGTGGA |
| SEQ ID NO: 403 RT_mut_L139P (Artificial Sequence) | TTGAGCGGGCCCCCACCGT |
| SEQ ID NO: 289 RT_mut_E562Q (Artificial Sequence) | CAGCGGGCTCAGCTGATAGCA |
| SEQ ID NO: 290 RT mut D653N (Artificial Sequence) | CGGATGGCTAACCAAGCGGCC |
| SEQ ID NO: 404 RT(1-478)_Sto7d fusion | atgactcactatcaggccttgcttttgg acacggaccgggtccagttcggaccggt ggtagccctgaacccggctacgctgctc ccactgcctgaggaagggctgcaacaca actgccttgatGGGACAGGTGGCGGTGG TGTCACCGTCAAGTTCAAGTACAAGGGT GAGGAACTTGAAGTTGATATTAGCAAAA TCAAGAAGGTTTGGCGCGTTGGTAAAAT GATATCTTTTACTTATGACGACAACGGC AAGACAGGTAGAGGGGCAGTGTCTGAGA AAGACGCCCCAAGGAGCTGTTGCAAAT GTTGGAAAAGTCTGGGAAAAAGtctggc ggctcaaaaagaaccgccgacggcagcg aattcgagcccaagaagaagaggaaagt c |

Sequences of primers, probes and restriction enzymes used in ddPCR readout can be found in Table 7 below.

TABLE 7

| Locus | Cargo | SEQ ID NO: Forward Primer | SEQ ID NO: Reverse Primer | Probe | SEQ ID NO: Restriction Enzymes |
|---|---|---|---|---|---|
| ACTB | GFP (pDY0186) | 291 CCCG GCTTC CTTTG TCC | 292 GAAC TCCAC GCCG TTCA | /56- FAM/C C GGC TTGT/ ZEN/ | 405 Eco91I, HindIII |

TABLE 7-continued

| Locus | Cargo | SEQ ID NO: Forward Primer | SEQ ID NO: | Reverse Primer | Probe | SEQ ID NO: | Restriction Enzymes |
|---|---|---|---|---|---|---|---|
| | | | | | C GAC GAC GGCG/ 3IAB kFQ/ | | |
| ACTB | TP90-1 GFP (pDY0333) | 293 CCCG GCTTC CTTTG TCC | 294 | AACC ACAA CTAG AATG CAGT GA | /56-FAM/T G CTA TTGC/ ZEN/ T TTA TTT GTG GGC CCG/ 3IABk FQ/ | 406 | None |
| ACTB | TP90-1 rc GFP (pDY0334) | 295 CCCG GCTTC CTTTG TCC | 296 | GAAC TCCAC GCCG TTCA | /56-FAM/ CC ATG AAGA/ ZEN/ TCGA GTG CCG CAT CA/3I ABKF Q/ | 407 | None |
| ACTB | PhiBT1 GFP (pDY0367) | 297 CCCG GCTTC CTTTG TCC | 298 | AACC ACAA CTAG AATG CAGT GA | /56-FAM/T G CTA TTG C/ZEN/ T TTA TTT GTG GGC CCG/ 3IABk FQ/ | 406 | None |
| ACTB | PhiBT1 rc GFP (pDY0368) | 299 CCCG GCTTC CTTTG TCC | 300 | GAAC TCCAC GCCG TTCA | /56-FAM/ CC ATG AAG A/ZE N/T CGA GTG CCG CAT CA/3I ABKF Q/ | 407 | None |
| LMNB1 | GFP (pDY0186) | 301 TCCTT ATCA CGGT CCCG CTCG | 302 | GAAC TCCAC GCCG TTCA | /56-FAM/ CC ATG AAG A/ZE N/T CGA GTG CCG CAT CA/3I ABKF Q/ | 407 | Eco91I, HindIII |

TABLE 7-continued

| Locus | Cargo | SEQ ID NO: Forward Primer | SEQ ID NO: | Reverse Primer | Probe | SEQ ID NO: | Restriction Enzymes |
|---|---|---|---|---|---|---|---|
| NOLC1 | GFP (pDY0186) | 303 CGTCGACAACGGTAGTG | 304 | GAACTCCACGCCGTTCA | /56-FAM/CC ATG AAG A/ZEN/T CGA GTG CCG CAT CA/3IABKFQ/ | 407 | Eco91I, HindIII |
| SUPT16H | GFP (pDY0186) | 305 TCGCGTGATTCTCGGAAC | 306 | GAACTCCACGCCGTTCA | /56.FAM/C C ATG AAG A/ZEN/T CGA GTG CCG CAT CA/3IABkFQ/ | 407 | Eco91I, HindIII |
| SRRM2 | GFP (pDY0186) | 307 GGGCGGTAAGTG GTTAGTTT | 308 | GAACTCCACGCCGTTCA | /56-FAM/CC ATG AAG A/ZEN/T CGA GTG CCG CAT CA/3IABKFQ/ | 407 | Eco91I, HindIII |
| DEPDC4 | GFP (pDY0186) | 309 AAGAGGCGGAGCCAGTA | 310 | GAACTCCACGCCGTTCA | /56-FAM/CC ATG AAG A/ZEN/T CGA GTG CCG CAT CA/3IABKFQ/ | 407 | Eco91I, HindIII |
| NES | GFP (pDY0186) | 311 CTCCCTTCTCCCGGTGCCC | 312 | GAACTCCACGCCGTTCA | /56-FAM/C C GGC TTG T/ZEN/C GAC GAC GGC G/3IABkFQ/ | 405 | Eco91I, HindIII |
| ACTB | ACTB HITI template GFP (pDY0219) | 313 CCCGGCTTCCTTTGTCC | 314 | GAACTCCACGCCGTTCA | /56-FAM/CC ATG AAG A/ZEN/T CGA GTG CCG | 407 | Eco91I |

TABLE 7-continued

| Locus | Cargo | SEQ ID NO: Forward Primer | SEQ ID NO: Reverse Primer | Probe | SEQ ID NO: Restriction Enzymes |
|---|---|---|---|---|---|
| | | | | CAT CA/3I ABKF Q | |
| SRRM2 | SRRM2 HITI template GFP (aRY0182_A2) | 315 GGGC GGTA AGTG GTTA GTTT | 316 GAAC TCCAC GCCG TTCA | /56-FAM/ CC ATG AAG A/ZE N/T CGA GTG CCG CAT CA/3I ABKF Q/ | 407 Eco91I |
| NOLC1 | NOLC1 HITI template GFP (aRY0182_A3) | 317 CGTC GACA ACGG TAGT G | 318 GAAC TCCAC GCCG TTCA | /56-FAM/ CC ATG AAG A/ZE N/T CGA GTG CCG CAT CA/3I ABKF Q/ | 407 Eco91I |
| DEPDC4 | DEPDC4 HITI template GFP (aRY0182_A5) | 319 AAGA GGCG GAGC CAGT A | 320 GAAC TCCAC GCCG TTCA | /56-FAM/ CC ATG AAG A/ZE N/T CGA GTG CCG CAT CA/3I ABKF Q/ | 407 Eco91I |
| NES | NES HITI template GFP (aRY0182_A7) | 321 CTCCC TTCTC CCGG TGCCC | 322 GAAC TCCAC GCCG TTCA | /56 FAM/ CC ATG AAG A/ZE N/T CGA GTG CCG CAT CA/3I ABkF Q/ | 407 Eco91I |
| LMNB1 | LMNB1 HITI template GFP (aRY0182_A4) | 323 TCCTT ATCA CGGT CCCG CTCG | 324 GAAC TCCAC GCCG TTCA | /56-FAM/ CC ATG AAG A/ZE N/T CGA GTG CCG CAT | 407 Eco91I |

TABLE 7-continued

| Locus | Cargo | SEQ ID NO: Forward Primer | SEQ ID NO: | Reverse Primer | Probe | SEQ ID NO: | Restriction Enzymes |
|---|---|---|---|---|---|---|---|
| | | | | | CA/3I ABKFQ/ | | |
| ACTB | SERPINA (pDY0298) | 325 CCCGGCTTCCTTTGTCC | 326 | GGCCTGCCAGCAGGAGGA | /56-FAM/CCGGCTTGT/ZEN/CGACGACGGCG/3IABKFQ/ | 405 | EcoRI, XhoI, HindIII |
| ACTB | CPS1 (pDY299) | 327 CCCGGCTTCCTTTGTCC | 328 | GGTGTGCAGTCACATTGGTAAAGCC | /56-FAM/ACAGCTTTC/ZEN/AAAGTGGTGAGGACACT/3IABkFQ/ | 408 | XhoI, HindIII |
| ACTB | CFTR (pDY0373) | 329 CCCGGCTTCCTTTGTCC | 330 | GATGGGTCTAGTCCAGCTAAAG | /56-FAM/TACGGTACA/ZEN/AACCCACCCGAGAGA/3IABKFQ/ | 409 | Eco91I, HindIII |
| ACTB | NYESOTRAC (pDY0318) | 331 CCCGGCTTCCTTTGTCC | 332 | GAGAGACAAGGCTGCACA | /56-FAM/TACGGTACA/ZEN/AACCCACCCGAGAGA/3IABKFQ/ | 409 | Eco47III, HindIII |
| NC_000003 | GFP (pDY0186) | 333 CCAGGTGAGAGTCAGGGTAGTGTTCA | 334 | GAACTCCACGCCGTTCA | /56-FAM/CCGGCTTGT/ZEN/CGACGACGGCG/3IABkFQ/ | 405 | Eco91I, HindIII |

TABLE 7-continued

| Locus | Cargo | SEQ ID NO: Forward Primer | SEQ ID NO: | Reverse Primer | Probe | SEQ ID NO: | Restriction Enzymes |
|---|---|---|---|---|---|---|---|
| NC_0000 02 | GFP (pDY0186) | 335 AGGGACCTTTGCCTGTGTGAGTC | 336 | GAACTCCACGCCGTTCA | /56-FAM/CCGGCTTGT/ZEN/CGACGACGGCG/3IABKFQ/ | 405 | Eco91I, HindIII |
| NC_0000 09 | GFP (pDY0186) | 337 TCAGCTCTGTGCTGAGGCGAA | 338 | GAACTCCACGCCGTTCA | /56-FAM/CCGGCTTGT/ZEN/CGACGACGGCG/3IABKFQ/ | 405 | Eco91I, HindIII |
| chr6: 149045959 | GFP (pDY0186) | 339 AAGCCATCTCCCAGAATATCTGCTTAGAAATG | 340 | GAACTCCACGCCGTTCA | /56-FAM/CCGGCTTGT/ZEN/CGACGACGGCG/3IABKFQ/ | 405 | Eco91I, HindIII |
| chr16: 18607730 | GFP (pDY0186) | 341 GAGAGGAGCAACAGTGAGCATGATG | 342 | GAACTCCACGCCGTTCA | /56-FAM/CCGGCTTGT/ZEN/CGACGACGGCG/3IABKFQ/ | 405 | Eco91I, HindIII |
| chr6: 149045959 | ACTB HITI template GFP (pDY0219) | 343 AAGCCATCTCCCAGAATATCTGCTTAGAAATG | 344 | GAACTCCACGCCGTTCA | /56-FAM/CCGGCTTGT/ZEN/CGACGACGGCG/3IABKFQ/ | 405 | Eco91I |
| chr16: 18607730 | ACTB HITI template GFP (pDY0219) | 345 GAGAGGAGCAACAGTGAGCA | 346 | GAACTCCACGCCGTTCA | /56-FAM/CCGGCTTG | 405 | Eco91I |

TABLE 7-continued

| Locus | Cargo | SEQ ID NO: Forward Primer | SEQ ID NO: | Reverse Primer | Probe | SEQ ID NO: | Restriction Enzymes |
|---|---|---|---|---|---|---|---|
| | | TGATG | | | /56-FAM/CC GAC GAC GGC G/3I ABKFQ/ | | |
| ACTB | CAG_Kozak_bGH_therapeutic genes generic minicircle | 347 CCCGGCTTCCTTTGTCC | 348 | GGCTATGAACTAATGACCCCGT | /56-FAM/CC GGC TTG T/ZEN/C GAC GAC GGC G/3I ABKFQ/ | 405 | Eco91I, HindIII |
| ACTB | Hibit-SERPINA (pDY0405) | 349 CCCGGCTTCCTTTGTCC | 350 | GGCCTGCCAGCAGGAGGA | /56-FAM/CC GGC TTG T/ZEN/C GAC GAC GGC G/3I ABKFQ/ | 405 | EcoRI, XhoI, HindIII |
| ACTB | Hibit-CPS1 (pDY406) | 351 CCCGGCTTCCTTTGTCC | 352 | GGTGTGCAGTCACATTGGTAAAGCC | /56-FAM/AC AGC TTT C/ZEN/A AAG TGG TGA GGA CAC T/3IA BkFQ/ | 408 | XhoI, HindIII |

Sequences of primers used for NGS readout can be found in Table 8 below.

TABLE 8

| SEQ ID NO / DESCRIPTION / SOURCE | ID | SEQUENCE (5'-3') |
|---|---|---|
| SEQ ID NO: 353 N-term ACTB Tn5 readout F 1 (Artificial Sequence) | PD0966 | ACACTCTTTCCCTACACGACGCTCTTCCGATCTCCGACCTCGGC TCACAGCG |
| SEQ ID NO: 354 N-term ACTB Tn5 readout F 2 (Artificial Sequence) | PD0967 | ACACTCTTTCCCTACACGACGCTCTTCCGATCTACCGACCTCGG CTCACAGCG |
| SEQ ID NO: 355 N-term ACTB Tn5 | PD0968 | ACACTCTTTCCCTACACGACGCTCTTCCGATCTGACCGACCTCG GCTCACAGCG |

TABLE 8-continued

| SEQ ID NO / DESCRIPTION / SOURCE | ID | SEQUENCE (5'-3') |
|---|---|---|
| readout F 3 (Artificial Sequence) | | |
| SEQ ID NO: 356 N-term ACTB Tn5 readout F 4 (Artificial Sequence) | PD0969 | ACACTCTTTCCCTACACGACGCTCTTCCGATCTTGACC GACCTC GGCTCACAGCG |
| SEQ ID NO: 357 N-term ACTB Tn5 readout F 5 (Artificial Sequence) | PD0970 | ACACTCTTTCCCTACACGACGCTCTTCCGATCTCTGAC CGACCT CGGCTCACAGCG |
| SEQ ID NO: 358 N-term ACTB Tn5 readout F 6 (Artificial Sequence) | PD0971 | ACACTCTTTCCCTACACGACGCTCTTCCGATCTACTGA CCGACC TCGGCTCACAGCG |
| SEQ ID NO: 359 N-term ACTB Tn5 readout F 7 (Artificial Sequence) | PD0972 | ACACTCTTTCCCTACACGACGCTCTTCCGATCTTACTG ACCGAC CTCGGCTCACAGCG |
| SEQ ID NO: 360 N-term ACTB Tn5 readout F 8 (Artificial Sequence) | PD0973 | ACACTCTTTCCCTACACGACGCTCTTCCGATCTGTACT GACCGA CCTCGGCTCACAGCG |
| SEQ ID NO: 361 ACTB N-term NGS R for Cas14 indels (Artificial Sequence) | FP0952 | GTGACTGGAGTTCAGACGTGTGCTCTTCCGATCTCCAC CCAGCC AGCTCCC |
| SEQ ID NO: 362 NGS EMX1 Forward 1 (Artificial Sequence) | PD0313 | ACACTCTTTCCCTACACGACGCTCTTCCGATCTCCGGT GGCGCAT TGCCAC |
| SEQ ID NO: 363 NGS EMX1 Forward 2 (Artificial Sequence) | PD0314 | ACACTCTTTCCCTACACGACGCTCTTCCGATCTACCGG TGGCGCA TTGCCAC |
| SEQ ID NO: 364 NGS EMX1 Forward 3 (Artificial Sequence) | PD0315 | ACACTCTTTCCCTACACGACGCTCTTCCGATCTGACCG GTGGCGC ATTGCCAC |
| SEQ ID NO: 365 NGS EMX1 Forward 4 (Artificial Sequence) | PD0316 | ACACTCTTTCCCTACACGACGCTCTTCCGATCTTGACC GGTGGCG CATTGCCAC |
| SEQ ID NO: 366 NGS EMX1 Forward 5 (Artificial Sequence) | PD0317 | ACACTCTTTCCCTACACGACGCTCTTCCGATCTCTGAC CGGTGGC GCATTGCCAC |
| SEQ ID NO: 367 NGS EMX1 Forward 6 (Artificial Sequence) | PD0318 | ACACTCTTTCCCTACACGACGCTCTTCCGATCTACTGA CCGGTGG CGCATTGCCAC |
| SEQ ID NO: 368 NGS EMX1 Forward 7 (Artificial Sequence) | PD0319 | ACACTCTTTCCCTACACGACGCTCTTCCGATCTTACTG ACCGGTG GCGCATTGCCAC |
| SEQ ID NO: 369 NGS EMX1 Forward 8 (Artificial Sequence) | PD0320 | ACACTCTTTCCCTACACGACGCTCTTCCGATCTGTACT GACCGGT GGCGCATTGCCAC |

TABLE 8-continued

| SEQ ID NO / DESCRIPTION / SOURCE | ID | SEQUENCE (5'-3') |
|---|---|---|
| SEQ ID NO: 370 NGS EMX1 Reverse (Artificial Sequence) | PD0321 | GTGACTGGAGTTCAGACGTGTGCTCTTCCGATCTCAGA GTCCAGC TTGGGCCCA |

Sequences of off-target sites can be found in Table 9 below.

TABLE 9

| SEQ ID NO/ DESCRIPTION/ SOURCE | SEQUENCE (5'-3') |
|---|---|
| SEQ ID NO: 371 Cas9_chr6:149045959 (Artificial Sequence) | GATATTTTCCCAGCTCACCA |
| SEQ ID NO: 372 Cas9_chr16:18607730 (Artificial Sequence) | TCTATTCTCCCAGCTCCCCA |
| SEQ ID NO: 373 Bxb1_NC_000002 (Artificial Sequence) | AGCGGCTTCTGTCTCTGTGA GTGAGCTGGCGGTCTCCGTC |
| SEQ ID NO: 374 Bxb1_NC_000003 (Artificial Sequence) | GACTAGCCCACGCTCCGGTT CTGAGCCGCGACGGCGGTCT CCG |
| SEQ ID NO: 375 Bxb1_NC_000009 (Artificial Sequence) | CCCAGGGTCCCATGCGCTCC CCGGCCCTGACGGCGGTCTC C |

Linker sequences in Table 10 below.

TABLE 10

| Description | Sequence (5'-3') | Amino acid sequence |
|---|---|---|
| A-P2A | GGAAGCGGAGCTACTAACTTCAGCCT GCTGAAGCAGGCTGGCGACGTGGAGG AGAACCCTGGACCT (SEQ ID NO: 410) | GSGATNFSLLKQAGDVEENPGP (SEQ ID NO: 418) |
| B-(GGGS)3 | GGGGGAGGAGGTTCTGGAGGCGGAGG CTCCGGAGGCGGAGGGTCA (SEQ ID NO: 411) | GGGGSGGGSGGGS (SEQ ID NO: 419) |
| C-GGGGS | GGAGGTGGCGGGAGC (SEQ ID NO: 412) | GGGGS (SEQ ID NO: 420) |
| D-PAPAP | CCCGCACCAGCGCCT (SEQ ID NO: 413) | PAPAP (SEQ ID NO: 421) |
| E-(EAAAK)3 | GAGGCAGCTGCCAAGGAAGCCGCT GCCAAGGAGGCGGCCGCAAAG (SEQ ID NO: 414) | EAAAKEAAAKEAAAK (SEQ ID NO: 422) |
| F-XTEN | AGTGGGAGCGAGACCCCTGGGACT AGCGAGTCAGCTACACCCGAAAGC (SEQ ID NO: 415) | SGSETPGTSESATPES (SEQ ID NO: 423) |
| G-(GGS)6 | GGGGGGTCAGGTGGATCCGGCGG AAGTGGCGGATCCGGTGGATCTGG CGGCAGT (SEQ ID NO: 416) | GGSGGSGGSGGSGGSGGS (SEQ ID NO 424) |
| H-EAAAK | GAAGCTGCTGCTAAG (SEQ ID NO: 417) | EAAAK (SEQ ID NO: 425) |

Exemplary fusion sequences in Table 11 below.

| Description | Sequence |
|---|---|
| SpCas9-XTEN-RT(1-478)-Sto7d- | MKRTADGSEFESPKKKRKVDKKYSIGLDIGTNSVGWAVITDEYKVPS KKFKVLGNTDRHSIKKNLIGALLFDSGETAEATRLKRTARRRYTRR |

| Description | Sequence |
|---|---|
| GGGGS-BxbINT Amino acid SEQ ID NO: 376 | KNRICYLQEIFSNEMAKVDDSFFHRLEESFLVEEDKKHERHPIFGNI VDEVAYHEKYPTIYHLRKKLVDSTDKADLRLIYLALAHMIKFRGHF LIEGDLNPDNSDVDKLFIQLVQTYNQLFEENPINASGVDAKAILSAR LSKSRRLENLIAQLPGEKKNGLFGNLIALSLGLTPNFKSNFDLAEDA KLQLSKDTYDDDLDNLLAQIGDOYADLFLAAKNLSDAILLSDILRVN TEITKAPLSASMIKRYDEHHODLTLLKALVROOLPEKYKEIFFDOS KNGYAGYIDGGASQEEFYKFIKPILEKMDGTEELLVKLNREDLLRK QRTFDNGSIPHQIHLGELHAILRRQEDFYPFLKDNREKIEKILTFRIP YYVGPLARGNSRFAWMTRKSEETITPWNFEEVVDKGASAQSFIER MTNFDKNLPNEKVLPKHSLLYEYFTVYNELTKVKYVTEGMRKPAF LSGEQKKAIVDLLFKTNRKVTVKOLKEDYFKKIECFDSVEISGVED RFNASLGTYHDLLKIIKDKDFLDNEENEDILEDIVLTLTLFEDREMIE ERLKTYAHLFDDKVMKOLKRRRYTGWGRLSRKLINGIRDKQSGK TILDFLKSDGFANRNFMQLIHDDSLTFKEDIQKAQVSGOGDSLHEHI ANLAGSPAIKKGILQTVKVVDELVKVMGRHKPENIVIEMARENQTT QKGQKNSRERMKRIEEGIKELGSQILKEHPVENTQLQNEKLYLYYL QNGRDMYVDQELDINRLSDYDVDAIVPQSFLKDDSIDNKVLTRSDK NRGKSDNVPSEEVVKKMKNYWRQLLNAKLITQRKFDNLTKAERG GLSELDKAGFIKROLVETROITKHVAQILDSRMNTKYDENDKLIRE VKVITLKSKLVSDFRKDFQFYKVREINNYHHAHDAYLNAVVGTALI KKYPKLESEFVYGDYKVYDVRKMIAKSEQEIGKATAKYFFYSNIMN FFKTEITLANGEIRKRPLIETNGETGEIVWDKGRDFATVRKVLSMP QVNIVKKTEVQTGGFSKESILPKRNSDKLIARKKDWDPKKYGGFDS PTVAYSVLVVAKVEKGKSKKLKSVKELLGITIMERSSFEKNPIDFLE AKGYKEVKKDLIIKLPKYSLFELENGRKRMLASAGELQKGNELAL PSKYVNFLYLASHYEKLKGSPEDNEQKOLFVEQHKHYLDEIIEQISE FSKRVILADANLDKVLSAYNKHRDKPIREQAENIIHLFTLTNLGAPA AFKYFDTTIDRKRYTSTKEVLDATLIHQSITGLYETRIDLSQLGGDS GGSSGGSGSETPGTSESATPESSGSETPGTSESATPESSGSETPGTS-ESAT PESSGGSSGGSSTLNIEDEYRLHETSKEPDVSLGSTWLSDFPQAWAET GGMGLAVRQAPLIIPLKATSTPVSIKQYPMSQEARLGIKPHIQRLLD QGILVPCQSPWNTPLLPVKKPGTNDYRPVODLREVNKRVEDIHPTV PNPYNLLSGPPPSHQWYTVLDLKDAFFCLRLHPTSQPLFAFEWRDP EMGISGOLTWTRLPQGFKNSPTLFNEALHRDLADFRIQHPDLILLQ YVDDLLLAATSELDCQQGTRALLOTLGNLGYRASAKKAQICQKOV KYLGYLLKEGORWLTEARKETVMGQPTPKTPROLREFLGKAGFC RLFIPGFAEMAAPLYPLTKPGTLFNWGPDQQKAYQEIKQALLTAPA LGLPDLTKPFELFVDEKQGYAKGVLTQKLGPWRRPVAYLSKKLDP VAAGWPPCLRMVAAIAVLTKDAGKLTMGQPLVILAPHAVEALVK QPPDRWLSNARMTHYQALLLDTDRVQFGPVVALNPATLLPLPEEG LOHNCLDGTGGGVTVKFKYKGEELEVDISKIKKVWRVGKMISFT YDDNGKTGRGAVSEKDAPKELLQMLEKSGKKSGGSKRTADGSEFE PKKKRKVGGGSPKKKRKVYPYDVPDYAGSRALVVIRLSRVTDATTS PERQLESCQQLCAQRGWDVVGVAEDLDVSGAVDPFDRKRRPNLAR WLAFEEQPFDVIVAYRVDRLTRSIRHLQQLVHWAEDHKKLVVSAT EAHFDTTTPFAAVVIALMGTVAQMELEAIKERNRSAAHFNIRAGKY RGSLPPWGYLPTRVDGEWRLVPDPVQRERILEVYHRVVDNHEPLH LVAHDLNRRGVLSPKDYFAQLQGREPQGREWSATALKRSMISEAM LGYATLNGKTVRDDDGAPLVRAEPILTREQLEALRAELVKTSRAKP AVSTPSLLLRVLFCAVCGEPAYKFAGGGRKHPRYRCRSMGFPKHC GNGTVAMAEWDAFCEEQVLDLLGDAERLEKVWVAGSDSAVELAE VNAELVDLTSLIGSPAYRAGSPQREALDARIAALAARQEELEGLEAR PSGWEWRETGQRFGDWWREQDTAAKNTWLRSMNVRLTFDVRGG LTRTIDFGDLQEYEQHLRLGSVVERLHTGMS |
| SpCas9-XTEN-RT(1-478)-Sto7d-GGGGS-BxbINT Nucleic acid SEQ ID NO: 377 | ATGAAACGGACAGCCGACGGAAGCGAGTTCGAGTCACCAAAGAAG AAGCGGAAAGTCGACAAGAAGTACAGCATCGGCCTGGACATCGGCA CCAACTCTGTGGGCTGGGCCGTGATCACCGACGAGTACAAGGTGCC CAGCAAGAAATTCAAGGTGCTGGGCAACACCGACCGGCACAGCATC AAGAAGAACCTGATCGGAGCCCTGCTGTTCGACAGCGGCGAAACAG CCGAGGCCACCCGGCTGAAGAGAACCGCCAGAAGAAGATACACCA GACGGAAGAACCGGATCTGCTATCTGCAAGAGATCTTCAGCAACGA GATGGCCAAGGTGGACGACAGCTTCTTCCACAGACTGGAAGAGTCC TTCCTGGTGGAAGAGGATAAGAAGCACGAGCGGCACCCCATCTTCG GCAACATCGTGGACGAGGTGGCCTACCACGAGAAGTACCCCACCAT CTACCACCTGAGAAAGAAACTGGTGGACAGCACCGACAAGGCCGAC CTGCGGCTGATCTATCTGGCCCTGGCCCACATGATCAAGTTCCGGGG CCACTTCCTGATCGAGGGCGACCTGAACCCCGACAACAGCGACGTG GACAAGCTGTTCATCCAGCTGGTGCAGACCTACAACCAGCTGTTCGA GGAAAACCCCATCAACGCCAGCGGCGTGGACGCCAAGGCCATCCTG TCTGCCAGACTGAGCAAGAGCAGACGGCTGGAAAATCTGATCGCCC AGCTGCCCGGCGAGAAGAAGAATGGCCTGTTCGGAAACCTGATTGC CCTGAGCCTGGGCCTGACCCCCAACTTCAAGAGCAACTTCGACCTGG CCGAGGATGCCAAACTGCAGCTGAGCAAGGACACCTACGACGACGA CCTGGACAACCTGCTGGCCCAGATCGGCGACCAGTACGCCGACCTG TTTCTGGCCGCCAAGAACCTGTCCGACGCCATCCTGCTGAGCGACAT CCTGAGAGTGAACACCGAGATCACCAAGGCCCCCCTGAGCGCCTCT |

| Description | Sequence |
|---|---|
| | ATGATCAAGAGATACGACGAGCACCACCAGGACCTGACCCTGCTGA |
| | AAGCTCTCGTGCGGCAGCAGCTGCCTGAGAAGTACAAAGAGATTTT |
| | CTTCGACCAGAGCAAGAACGGCTACGCCGGCTACATTGACGGCGGA |
| | GCCAGCCAGGAAGAGTTCTACAAGTTCATCAAGCCCATCCTGGAAA |
| | AGATGGACGGCACCGAGGAACTGCTCGTGAAGCTGAACAGAGAGG |
| | ACCTGCTGCGGAAGCAGCGGACCTTCGACAACGGCAGCATCCCCCA |
| | CCAGATCCACCTGGGAGAGCTGCACGCCATTCTGCGGCGGCAGGAA |
| | GATTTTTACCCATTCCTGAAGGACAACCGGGAAAAGATCGAGAAGA |
| | TCCTGACCTTCCGCATCCCCTACTACGTGGGCCCTCTGGCCAGGGA |
| | AACAGCAGATTCGCCTGGATGACCAGAAAGAGCGAGGAAACCATCA |
| | CCCCCTGGAACTTCGAGGAAGTGGTGGACAAGGGCGCTTCCGCCCA |
| | GAGCTTCATCGAGCGGATGACCAACTTCGATAAGAACCTGCCCAAC |
| | GAGAAGGTGCTGCCCAAGCACAGCCTGCTGTACGAGTACTTCACCG |
| | TGTATAACGAGCTGACCAAAGTGAAATACGTGACCGAGGGAATGAG |
| | AAAGCCCGCCTTCCTGAGCGGCGAGCAGAAAAAGGCCATCGTGGAC |
| | CTGCTGTTCAAGACCAACCGGAAAGTGACCGTGAAGCAGCTGAAAG |
| | AGGACTACTTCAAGAAAATCGAGTGCTTCGACTCCGTGGAAATCTCC |
| | GGCGTGGAAGATCGGTTCAACGCCTCCCTGGGCACATACCACGATC |
| | TGCTGAAAATTATCAAGGACAAGGACTTCCTGGACAATGAGGAAAA |
| | CGAGGACATTCTGGAAGATATCGTGCTGACCCTGACACTGTTTGAGG |
| | ACAGAGAGATGATCGAGGAACGGCTGAAAACCTATGCCCACCTGTT |
| | CGACGACAAAGTGATGAAGCAGCTGAAGCGGCGGAGATACACCGG |
| | CTGGGGCAGGCTGAGCCGGAAGCTGATCAACGGCATCCGGGACAAG |
| | CAGTCCGGCAAGACAATCCTGGATTTCCTGAAGTCCGACGGCTTCGC |
| | CAACAGAAACTTCATGCAGCTGATCCACGACGACAGCCTGACCTTT |
| | AAAGAGGACATCCAGAAAGCCCAGGTGTCCGGCCAGGGCGATAGCC |
| | TGCACGAGCACATTGCCAATCTGGCCGGCAGCCCCGCCATTAAGAA |
| | GGGCATCCTGCAGACAGTGAAGGTGGTGGACGAGCTCGTGAAAGTG |
| | ATGGGCCGGCACAAGCCCGAGAACATCGTGATCGAAATGGCCAGAG |
| | AGAACCAGACCACCCAGAAGGGACAGAAGAACAGCCGCGAGAGAA |
| | TGAAGCGGATCGAAGAGGGCATCAAAGAGCTGGGCAGCCAGATCCT |
| | GAAAGAACACCCCGTGGAAAACACCCAGCTGCAGAACGAGAAGCT |
| | GTACCTGTACTACCTGCAGAATGGGCGGGATATGTACGTGGACCAG |
| | GAACTGGACATCAACCGGCTGTCCGACTACGATGTGGACGCTATCG |
| | TGCCTCAGAGCTTTCTGAAGGACGACTCCATCGACAACAAGGTGCT |
| | GACCAGAAGCGACAAGAACCGGGGCAAGAGCGACAACGTGCCCTC |
| | CGAAGAGGTCGTGAAGAAGATGAAGAACTACTGGCGGCAGCTGCTG |
| | AACGCCAAGCTGATTACCCAGAGAAAGTTCGACAATCTGACCAAGG |
| | CCGAGAGAGGCGGCCTGAGCGAACTGGATAAGGCCGGCTTCATCAA |
| | GAGACAGCTGGTGGAAACCCGGCAGATCACAAAGCACGTGGCACA |
| | GATCCTGGACTCCCGGATGAACACTAAGTACGACGAGAATGACAAG |
| | CTGATCCGGGAAGTGAAAGTGATCACCCTGAAGTCCAAGCTGGTGT |
| | CCGATTTCCGGAAGGATTTCCAGTTTTACAAAGTGCGCGAGATCAAC |
| | AACTACCACCACGCCCACGACGCCTACCTGAACGCCGTCGTGGGAA |
| | CCGCCCTGATCAAAAAGTACCCTAAGCTGGAAAGCGAGTTCGTGTA |
| | CGGCGACTACAAGGTGTACGACGTGCGGAAGATGATCGCCAAGAGC |
| | GAGCAGGAAATCGGCAAGGCTACCGCCAAGTACTTCTTCTACAGCA |
| | ACATCATGAACTTTTTCAAGACCGAGATTACCCTGGCCAACGGCGA |
| | GATCCGGAAGCGGCCTCTGATCGAGACAAACGGCGAAACCGGGGA |
| | GATCGTGTGGGATAAGGGCCGGGATTTTGCCACCGTGCGGAAAGTG |
| | CTGAGCATGCCCCAAGTGAATATCGTGAAAAAGACCGAGGTGCAGA |
| | CAGGCGGCTTCAGCAAAGAGTCTATCCTGCCCAAGAGGAACAGCGA |
| | TAAGCTGATCGCCAGAAAGAAGGACTGGGACCCTAAGAAGTACGGC |
| | GGCTTCGACAGCCCCACCGTGGCCTATTCTGTGCTGGTGGTGGCCAA |
| | AGTGGAAAAGGGCAAGTCCAAGAAACTGAAGAGTGTGAAAGAGCT |
| | GCTGGGGATCACCATCATGGAAAGAAGCAGCTTCGAGAAGAATCCC |
| | ATCGACTTTCTGGAAGCCAAGGGCTACAAAGAAGTGAAAAAGGACC |
| | TGATCATCAAGCTGCCTAAGTACTCCCTGTTCGAGCTGGAAAACGGC |
| | CGGAAGAGAATGCTGGCCTCTGCCGGCGAACTGCAGAAGGGAAACG |
| | AACTGGCCCTGCCCTCCAAATATGTGAACTTCCTGTACCTGGCCAGC |
| | CACTATGAGAAGCTGAAGGGCTCCCCCGAGGATAATGAGCAGAAAC |
| | AGCTGTTTGTGGAACAGCACAAGCACTACCTGGACGAGATCATCGA |
| | GCAGATCAGCGAGTTCTCCAAGAGAGTGATCCTGGCCGACGCTAAT |
| | CTGGACAAAGTGCTGTCCGCCTACAACAAGCACCGGGATAAGCCCA |
| | TCAGAGAGCAGGCCGAGAATATCATCCACCTGTTTACCCTGACCAAT |
| | CTGGGAGCCCCTGCCGCCTTCAAGTACTTTGACACCACCATCGACCG |
| | GAAGAGGTACACCAGCACCAAAGAGGTGCTGGACGCCACCCTGATC |
| | CACCAGAGCATCACCGGCCTGTACGAGACACGGATCGACCTGTCTC |
| | AGCTGGGAGGTGACTCTGGAGGATCTAGCGGAGGATCCTCTGGCAG |
| | CGAGACACCAGGAACAAGCGAGTCAGCAACACCAGAGAGCTCTGGT |
| | AGCGAGACACCCGGTACCAGTGAAAGCGCCACGCCAGAAAGCAGT |
| | GGGAGTGAGACTCCGGGTACATCTGAATCAGCGACACCGGAATCAA |
| | GTGGCGGCAGCAGCGGCGGCAGCAGCACCCTAAATATAGAAGATGA |
| | GTATCGGCTACATGAGACCTCAAAAGAGCCAGATGTTTCTCTAGGGT |
| | CCACATGGCTGTCTGATTTTCCTCAGGCCTGGGCGAAACCGGGGC |
| | ATGGGACTGGCAGTTCGCCAAGCTCCTCTGATCATACCTCTGAAAGC |
| | AACCTCTACCCCCGTGTCCATAAAACAATACCCCATGTCACAAGAA |

| Description | Sequence |
|---|---|
| | GCCAGACTGGGGATCAAGCCCCACATACAGAGACTGTTGGACCAGG |
| | GAATACTGGTACCCTGCCAGTCCCCTGGAACACGCCCCTGCTACCC |
| | GTTAAGAAACCAGGGACTAATGATTATAGGCCTGTCCAGGATCTGA |
| | GAGAAGTCAACAAGCGGGTGGAAGACATCCACCCCACCGTGCCCAA |
| | CCCTTACAACCTCTTGAGCGGGCCCCACCGTCCCACCAGTGGTACA |
| | CTGTGCTTGATTTAAAGGATGCCTTTTTCTGCCTGAGACTCCACCCC |
| | ACCAGTCAGCCTCTCTTCGCCTTTGAGTGGAGAGATCCAGAGATGGG |
| | AATCTCAGGACAATTGACCTGGACCAGACTCCCACAGGGTTTCAAA |
| | AACAGTCCCACCCTGTTTAATGAGGCACTGCACAGAGACCTAGCAG |
| | ACTTCCGGATCCAGCACCCAGACTTGATCCTGCTACAGTACGTGGAT |
| | GACTTACTGCTGGCCGCCACTTCTGAGCTAGACTGCCAACAAGGTAC |
| | TCGGGCCCTGTTACAAACCCTAGGGAACCTCGGGTATCGGGCCTCG |
| | GCCAAGAAAGCCCAAATTTGCCAGAAACAGGTCAAGTATCTGGGGT |
| | ATCTTCTAAAAGAGGGTCAGAGATGGCTGACTGAGGCCAGAAAAGA |
| | GACTGTGATGGGGCAGCCTACTCCGAAGACCCCTCGACAACTAAGG |
| | GAGTTCCTAGGGAAGGCAGGCTTCTGTCGCCTCTTCATCCCTGGGTT |
| | TGCAGAAATGGCAGCCCCCCTGTACCCTCTCACCAAACCGGGGACT |
| | CTGTTTAATTGGGGCCCAGACCAACAAAAGGCCTATCAAGAAATCA |
| | AGCAAGCTCTTCTAACTGCCCCAGCCCTGGGGTTGCCAGATTTGACT |
| | AAGCCCTTTGAACTCTTTGTCGACGAGAAGCAGGGCTACGCCAAAG |
| | GTGTCCTAACGCAAAAACTGGGACCTTGGCGTCGGCCGGTGGCCTA |
| | CCTGTCCAAAAAGCTAGACCCAGTAGCAGCTGGGTGGCCCCCTTGC |
| | CTACGGATGGTAGCAGCCATTGCCGTACTGACAAAGGATGCAGGCA |
| | AGCTAACCATGGGACAGCCACTAGTCATTCTGGCCCCCCATGCAGTA |
| | GAGGCACTAGTCAAACAACCCCCCGACCGCTGGCTTTCCAACGCCC |
| | GGATGACTCACTATCAGGCCTTGCTTTTGGACACGGACCGGGTCCAG |
| | TTCGGACCGGTGGTAGCCCTGAACCCGGCTACGCTGCTCCCACTGCC |
| | TGAGGAAGGGCTGCAACACAACTGCCTTGATGGGACAGGTGGCGGT |
| | GGTGTCACCGTCAAGTTCAAGTACAAGGGTGAGGAACTTGAAGTTG |
| | ATATTAGCAAAATCAAGAAGGTTTGGCGCGTTGGTAAAATGATATC |
| | TTTTACTTATGACGACAACGGCAAGACAGGTAGAGGGGCAGTGTCT |
| | GAGAAAGACGCCCCCAAGGAGCTGTTGCAAATGTTGGAAAAGTCTG |
| | GGAAAAAGTCTGGCGGCTCAAAAAGAACCGCCGACGGCAGCGAATT |
| | CGAGCCCAAGAAGAAGAGGAAAGTCGGAGGTGGCGGGAGCCCAAA |
| | AAAGAAAAGAAAAGTGTATCCCTATGATGTCCCCGATTATGCCGGT |
| | TCAAGAGCCCTGGTCGTGATTAGACTGAGCCGAGTGACAGACGCCA |
| | CCACAAGTCCCGAGAGACAGCTGGAATCATGCCAGCAGCTCTGTGC |
| | TCAGCGGGGTTGGGATGTGGTCGGCGTGGCAGAGGATCTGGACGTG |
| | AGCGGGGCCGTCGATCCATTCGACAGAAAGAGGAGGCCCAACCTGG |
| | CAAGATGGCTCGCTTTCGAGGAACAGCCCTTTGATGTGATCGTCGCC |
| | TACAGAGTGGACCGGCTGACCCGCTCAATTCGACATCTCCAGCAGCT |
| | GGTGCATTGGGCTGAGGACCACAAGAAACTGGTGGTCAGCGCAACA |
| | GAAGCCCACTTCGATACTACCACACCTTTTGCCGCTGTGGTCATCGC |
| | ACTGATGGGCACTGTGGCCCAGATGGAGCTCGAAGCTATCAAGGAG |
| | CGAAACAGGAGCGCAGCCCATTTCAATATTAGGGCCGGTAAATACA |
| | GAGGCTCCCTGCCCCCTTGGGGATATCTCCCTACCAGGGTGGATGGG |
| | GAGTGGAGACTGGTGCCAGACCCCGTCAGAGAGAGCGGATTCTGG |
| | AAGTGTACCACAGAGTGGTCGATAACCACGAACCACTCCATCTGGT |
| | GGCACACGACCTGAATAGACGCGGCGTGCTCTCTCCAAAGGATTAT |
| | TTTGCTCAGCTGCAGGGAAGAGAGCCACAGGGAAGAGAATGGAGTG |
| | CTACTGCACTGAAGAGATCTATGATCAGTGAGGCTATGCTGGGTTAC |
| | GCAACACTCAATGGCAAAACTGTCCGGGACGATGACGGAGCCCCTC |
| | TGGTGAGGGCTGAGCCTATTCTCACCAGAGAGCAGCTCGAAGCTCT |
| | GCGGGCAGAACTGGTCAAGACTAGTCGCGCCAAACCTGCCGTGAGC |
| | ACCCCAAGCCTGCTCCTGAGGGTGCTGTTCTGCGCCGTCTGTGGAGA |
| | GCCAGCATACAAGTTTGCCGGCGGAGGGCGCAAACATCCCCGCTAT |
| | CGATGCAGGAGCATGGGGTTCCCTAAGCACTGTGGAAACGGGACAG |
| | TGGCCATGGCTGAGTGGGACGCCTTTTGCGAGGAACAGGTGCTGGA |
| | TCTCCTGGGTGACGCTGAGCGGCTGGAAAAAGTGTGGGTGGCAGGA |
| | TCTGACTCCGCTGTGGAGCTGGCAGAAGTCAATGCCGAGCTCGTGG |
| | ATCTGACTTCCCTCATCGGATCTCCTGCATATAGAGCTGGGTCCCCA |
| | CAGAGAGAAGCTCTGGACGCACGAATTGCTGCACTCGCTGCTAGAC |
| | AGGAGGAACTGGAGGGCCTGGAGGCCAGGCCCTCTGGATGGGAGTG |
| | GCGAGAAACCGGACAGAGGTTTGGGGATTGGTGGAGGGAGCAGGA |
| | CACCGCAGCCAAGAACACATGGCTGAGATCCATGAATGTCCGGCTC |
| | ACATTCGACGTGCGCGGTGGCCTGACTCGAACCATCGATTTTGGCGA |
| | CCTGCAGGAGTATGAACAGCACCTGAGACTGGGGTCCGTGGTCGAA |
| | AGACTGCACACTGGGATGTCC |
| SpCas9 Amino acid SEQ ID NO: 378 | DKKYSIGLDIGTNSVGWAVITDEYKVPSKKFKVLGNTDRHSIKKNLIGA LLFDSGETAEATRLKRTARRRYTRRKNRICYLQEIFSNEMAKVDDSFFH RLEESFLVEEDKKHERHPIFGNIVDEVAYHEKYPTIYHLRKKLVDSTDK ADLRLIYLALAHMIKFRGHFLIEGDLNPDNSDVDKLFIQLVQTYNQLFE ENPINASGVDAKAILSARLSKSRRLENLIAQLPGEKKNGLFGNLIALSLG LTPNFKSNFDLAEDAKLQLSKDTYDDDLDNLLAQIGDQYADLFLAAKN LSDAILLSDILRVNTEITKAPLSASMIKRYDEHHQDLTLLKALVRQQLPE KYKEIFFDQSKNGYAGYIDGGASQEEFYKFIKPILEKMDGTEELLVKLN |

| Description | Sequence |
|---|---|
| | REDLLRKQRTFDNGSIPHQIHLGELHAILRRQEDFYPFLKDNREKIEKILT<br>FRIPYYVGPLARGNSRFAWMTRKSEETITPWNFEEVVDKGASAQSFIER<br>MTNFDKNLPNEKVLPKHSLLYEYFTVYNELTKVKYVTEGMRKPAFLSG<br>EQKKAIVDLLFKTNRKVTVKQLKEDYFKKIECFDSVEISGVEDRFNASL<br>GTYHDLLKIIKDKDFLDNEENEDILEDIVLTLTLFEDREMIEERLKTYAH<br>LFDDKVMKQLKRRRYTGWGRLSRKLINGIRDKQSGKTILDFLKSDGFA<br>NRNFMQLIHDDSLTFKEDIQKAQVSGQGDSLHEHIANLAGSPAIKKGIL<br>QTVKVVDELVKVMGRHKPENIVIEMARENQTTQKGQKNSRERMKRIE<br>EGIKELGSQILKEHPVENTQLQNEKLYLYYLQNGRDMYVDQELDINRL<br>SDYDVDAIVPQSFLKDDSIDNKVLTRSDKNRGKSDNVPSEEVVKKMKN<br>YWRQLLNAKLITQRKFDNLTKAERGGLSELDKAGFIKRQLVETRQITK<br>HVAQILDSRMNTKYDENDKLIREVKVITLKSKLVSDFRKDFQFYKVREI<br>NNYHHAHDAYLNAVVGTALIKKYPKLESEFVYGDYKVYDVRKMIAKS<br>EQEIGKATAKYFFYSNIMNFFKTEITLANGEIRKRPLIETNGETGEIVWD<br>KGRDFATVRKVLSMPQVNIVKKTEVQTGGFSKESILPKRNSDKLIARKK<br>DWDPKKYGGFDSPTVAYSVLVVAKVEKGKSKKLKSVKELLGITIMERS<br>SFEKNPIDFLEAKGYKEVKKDLIIKLPKYSLFELENGRKRMLASAGELQ<br>KGNELALPSKYVNFLYLASHYEKLKGSPEDNEQKQLFVEQHKHYLDEII<br>EQISEFSKRVILADANLDKVLSAYNKHRDKPIREQAENIIHLFTLTNLGA<br>PAAFKYFDTTIDRKRYTSTKEVLDATLIHQSITGLYETRIDLSQLGGD |
| RT(1-478)-Sto7d<br>Amino acid<br>SEQ ID NO: 379 | LNIEDEYRLHETSKEPDVSLGSTWLSDFPQAWAETGGMGLAVRQAPLII<br>PLKATSTPVSIKQYPMSQEARLGIKPHIQRLLDQGILVPCQSPWNTPLLP<br>VKKPGTNDYRPVQDLREVNKRVEDIHPTVPNPYNLLSGPPPSHQWYTV<br>LDLKDAFFCLRLHPTSQPLFAFEWRDPEMGISGQLTWTRLPQGFKNSPT<br>LFNEALHRDLADFRIQHPDLILLQYVDDLLLAATSELDCQQGTRALLQT<br>LGNLGYRASAKKAQICQKQVKYLGYLLKEGQRWLTEARKETVMGQPT<br>PKTPRQLREFLGKAGFCRLFIPGFAEMAAPLYPLTKPGTLFNWGPDQQK<br>AYQEIKQALLTAPALGLPDLTKPFELFVDEKQGYAKGVLTQKLGPWRR<br>PVAYLSKKLDPVAAGWPPCLRMVAAIAVLTKDAGKLTMGQPLVILAP<br>HAVEALVKQPPDRWLSNARMTHYQALLLDTDRVQFGPVVALNPATLL<br>PLPEEGLQHNCLDGTGGGVTVKFKYKGEELEVDISKIKKVWRVGKMI<br>SFTYDDNGKTGRGAVSEKDAPKELLQMLEKSGKKSGGSKRTADGS |
| BxbINT<br>Amino acid<br>SEQ ID NO: 380 | SRALVVIRLSRVTDATTSPERQLESCQQLCAQRGWDVVGVAEDLDVSG<br>AVDPFDRKRRPNLARWLAFEEQPFDVIVAYRVDRLTRSIRHLQQLVHW<br>AEDHKKLVVSATEAHFDTTTPFAAVVIALMGTVAQMELEAIKERNRSA<br>AHFNIRAGKYRGSLPPWGYLPTRVDGEWRLVPDPVQRERILEVYHRVV<br>DNHEPLHLVAHDLNRRGVLSPKDYFAQLQGREPQGREWSATALKRSM<br>ISEAMLGYATLNGKTVRDDDGAPLVRAEPILTREQLEALRAELVKTSRA<br>KPAVSTPSLLLRVLFCAVCGEPAYKFAGGGRKHPRYRCRSMGFPKHCG<br>NGTVAMAEWDAFCEEQVLDLLGDAERLEKVWVAGSDSAVELAEVNA<br>ELVDLTSLIGSPAYRAGSPQREALDARIAALAARQEELEGLEARPSGWE<br>WRETGQRFGDWWREQDTAAKNTWLRSMNVRLTFDVRGGLTRTIDFG<br>DLQEYEQHLRLGSVVERLHTGMS |

EXAMPLES

While several experimental Examples are contemplated, these Examples are intended to be non-limiting.

Example 1

CRE Integration Efficiency

Figure 3:
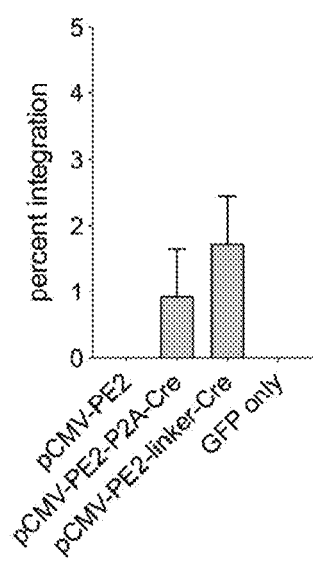
FIG. 3 shows the percent integration of green fluorescent protein (GFP) in the lentiviral integrated lox71 site in HEK293FT cell line in the presence of various plasmids according to embodiments of the present teachings.

The efficiency of the CRE integration was tested. In order to test the efficacy of PASTE with GFP using lox71/lox66/Cre recombinase system, a clonal HEK293FT cell line with lox71 sequence (SEQ ID NO: 1) integrated into the genome using lentivirus was developed. The integration of GFP was tested by transfection of modified HEK293FT cell line with: (1) plus/minus SEQ ID NO: 71 comprising a Cre recombinase expression plasmid, and (2) SEQ ID NO: 72 comprising a GFP template and a lox 66 Cre site of SEQ ID NO: 2. After 72 hours, the percent integration of GFP into the lox71 site was probed. FIG. 3 shows the percent integration of GFP in the lentiviral integrated lox71 site in HEK293FT cell line in the presence of various plasmids. It was observed that pCMV PE2 P2A Cre (SEQ ID NO: 73), a mammalian expression vector with prime editing complex and Cre recombinase linked to PE2 via a cleavable linker or a non-cleavable linker, shows integration of GFP.

Example 2

Figure 4:
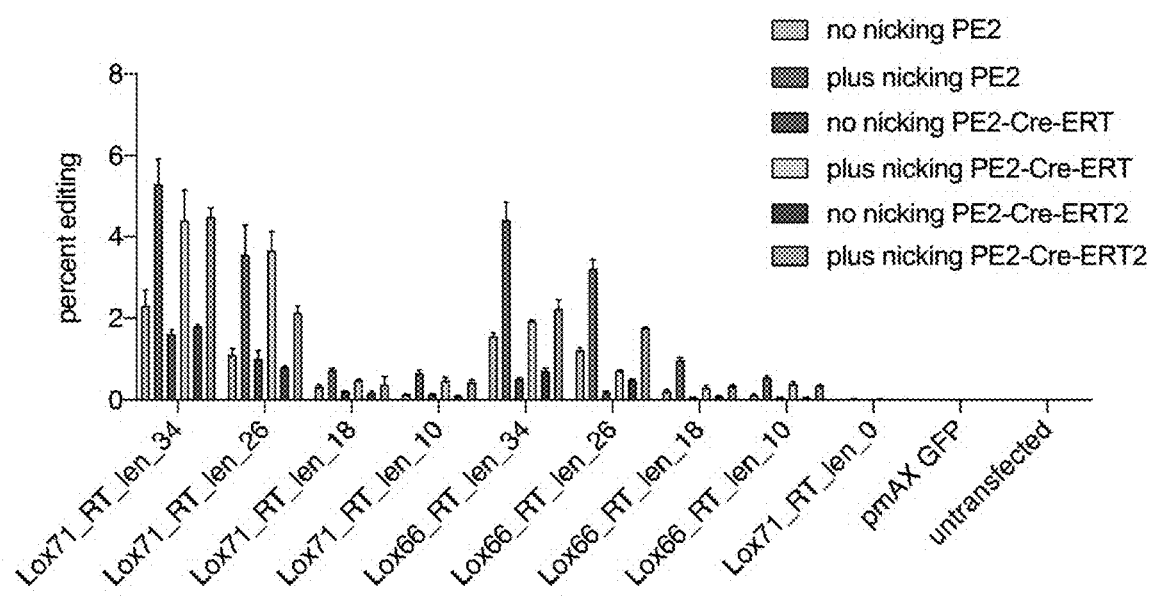
FIG. 4 shows the percent editing of the HEK293FT genome for incorporation of various lengths of lox71 or lox66 according to embodiments of the present teachings.

Programmable Addition Via Site-Specific Targeting Elements (PASTE) with Cre Recombinase—Addition of Lox Site The lox71 (SEQ ID NO: 1) or lox66 (SEQ ID NO: 2) sequence was inserted into the HEK293FT cell genome using prime editing to test integration of GFP into the HEK293FT genome. In order to insert lox71 or lox66 sequence into HEK293FT cell genome, a pegRNA with PBS length of 13 base pairs operably linked to RT region of varying lengths was used. The following plasmids were used in the transfection of HEK293FT cells. The cells were transfected with (1) prime editing construct (PE2) or PE2 with conditional Cre expression, (2) Lox71 or Lox66 pegRNA targeting the HEK3 locus, and (3) plus/minus+90 HEK3 nicking second guide RNA targeting the HEK3 locus (+90 ngRNA). After 72 hours, the percent editing of the HEK293FT genome at the HEK3 locus was probed for incorporation of various lengths of lox71 or lox66 (see FIG. 4). It was observed that 34 base pair lox71 (HEK3 locus guide, SEQ ID NO: 83; and Lox71 pegRNA with RT 34 and PBS 13, SEQ ID NO: 81) with +90 ngRNA (SEQ ID NO: 75) and 34 base pair lox66 (HEK3 locus guide, SEQ ID NO: 83; and Lox66 pegRNA with RT 34 and PBS 13, SEQ ID NO: 82) with +90 ngRNA (SEQ ID NO: 75) had the highest percent editing.

Example 3

PASTE with Cre Recombinase—Integration of Gene

Figure 5A:
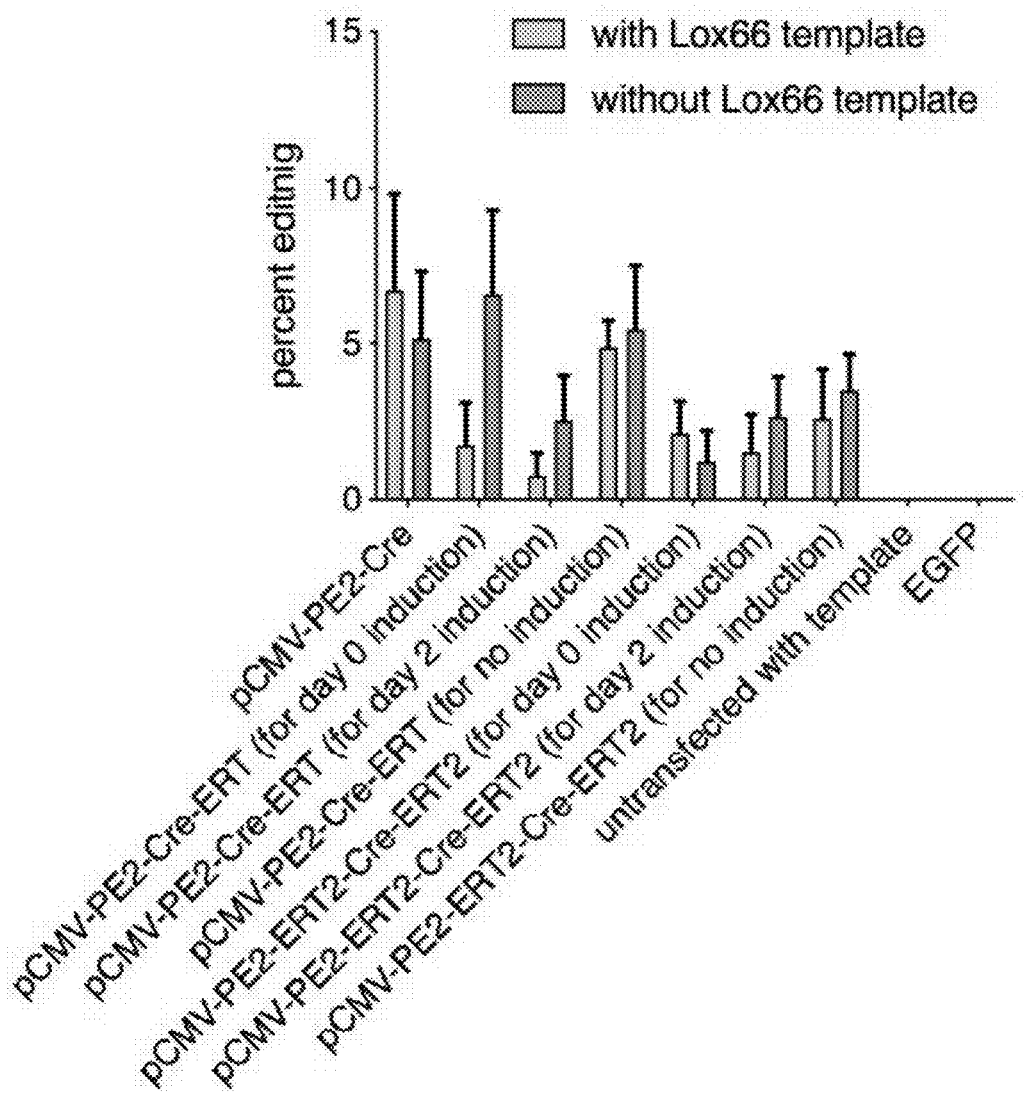
FIG. 5A shows the percent editing of lox71 site with different PE/Cre vectors according to embodiments of the present teachings.
Figure 5B:
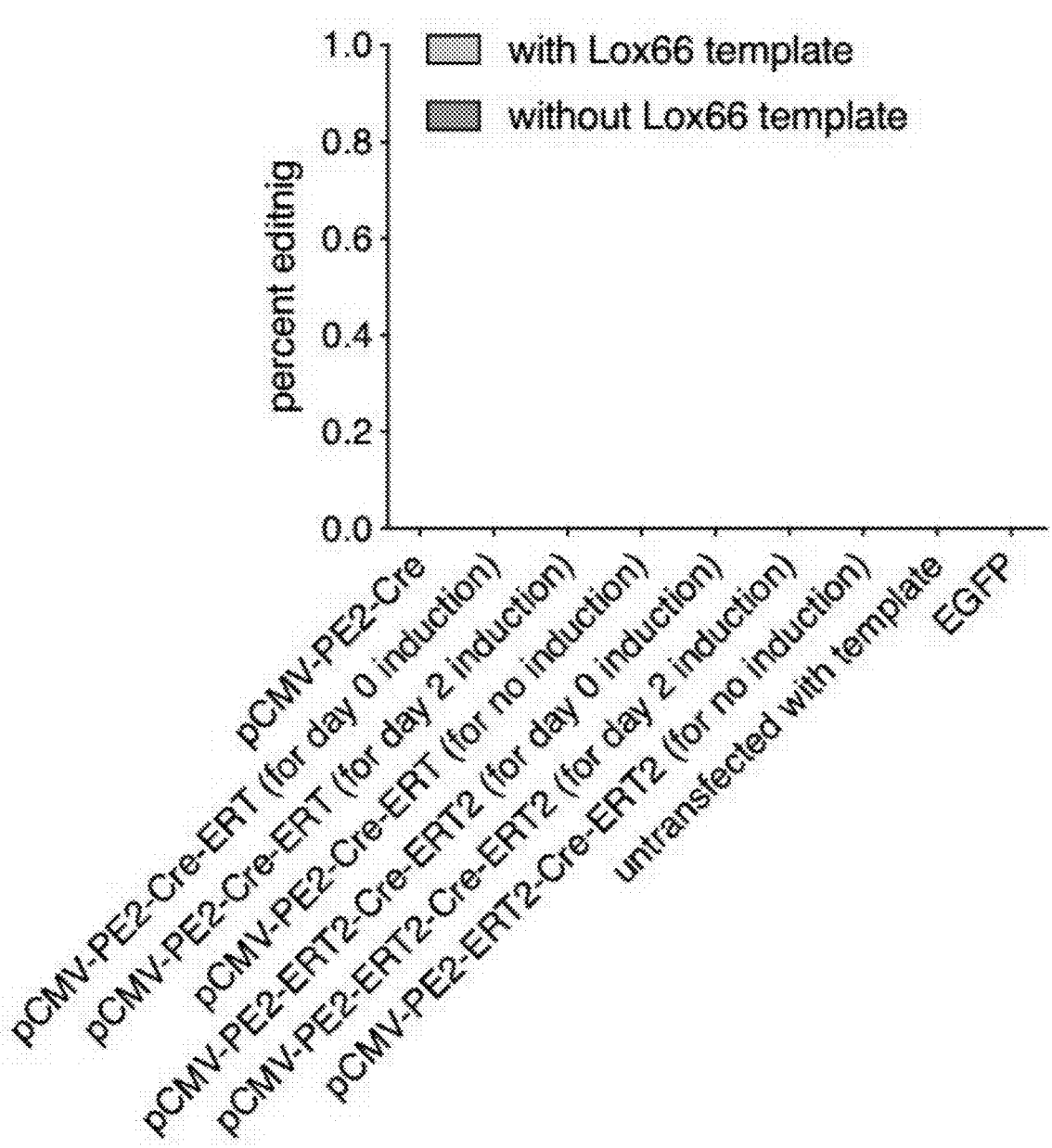
FIG. 5B shows the percent integration of GFP at the lox71 site in HEK293FT cell genome according to embodiments of the present teachings.

The lox71 or lox66 pegRNAs having PBS length of 13 base pairs and insert length of 34 base pairs were used to probe integration of GFP in the HEK293F genome. The PE and Cre were delivered in an inducible expression vectors and induced at day 2. The HEK293FT cells were transfected with the following plasmids: (1) prime editing construct (PE2 or PE2 with conditional Cre expression); (2) Lox71 pegRNA; (3) plus/minus+90 HEK3 nicking guide RNA; and (4) EGFP template with Lox66 site. After 72 hours, the percent editing of lox71 site and percent integration of GFP was probed with or without lox66 site in the presence of various PE/Cre constructs. FIG. 5A summarizes the percent editing of lox71 site with different PE/Cre vectors. FIG. 5B summarizes the percent integration of GFP at the lox71 site in HEK293FT cell genome. It was observed that although the lox71 site was edited in the presence of inducible or non-inducible PE/Cre expression system, there was no GFP integration.

Example 4

Bxb1 Integration Data Lenti Reporter

Figure 6:
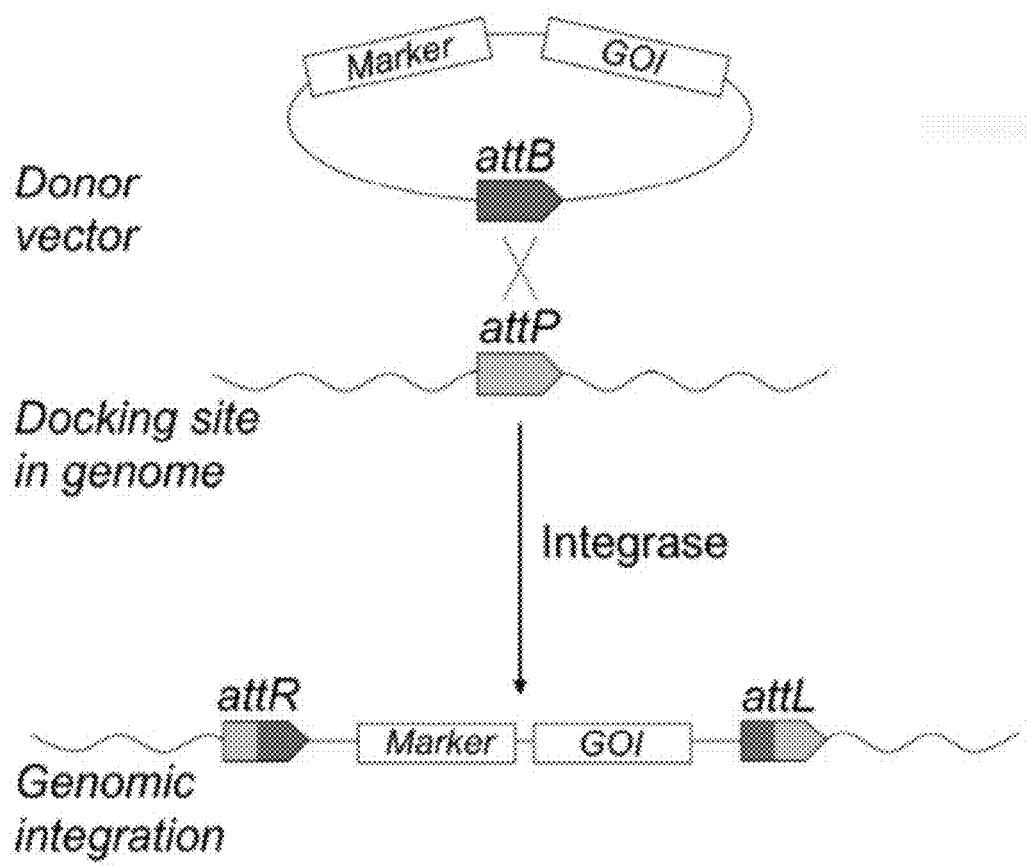
FIG. 6 shows a schematic representation of using Bxb1 to integrate a nucleic acid into the genome according to embodiments of the present teachings.

The integration system was switched to an integrase system that could result in an integration of target genes into a genome with higher efficiency. Serine integrase Bxb1 has been shown to be more active than Cre recombinase and highly efficient in bacteria and mammalian cells for irreversible integration of target genes. FIG. 6 shows a schematic of PASTE methodology using Bxb1 (Merrick, C. A. et al., ACSSynth. Biol. 2018, 7, 299-310).

Figure 7:
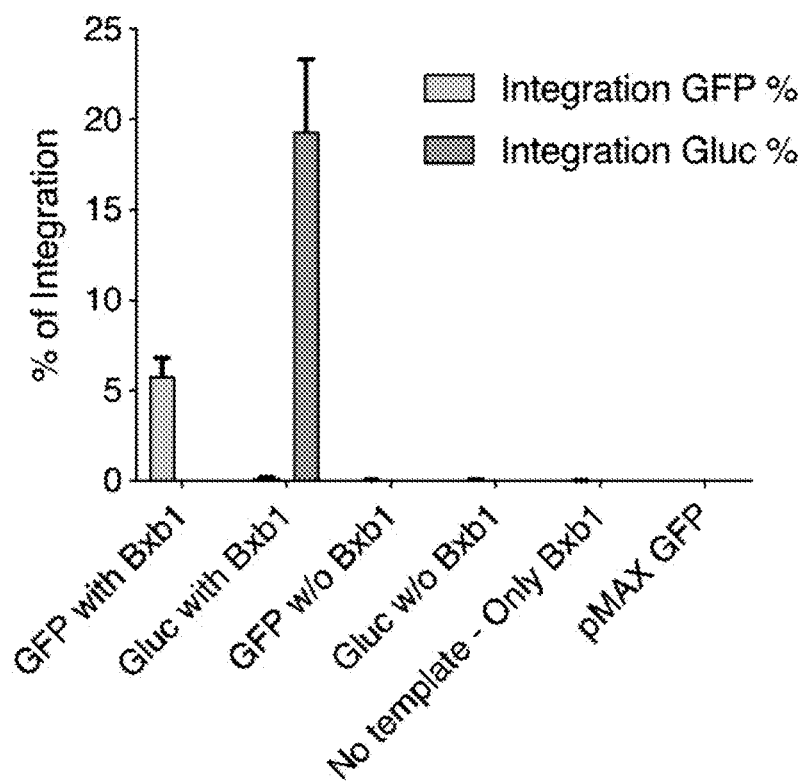
FIG. 7 shows the percent integration of GFP or Gluc into the attB locus using Bxb1 Programmable Addition via Site-Specific Targeting Elements (PASTE) according to embodiments of the present teachings.

To probe the efficiency of the Bxb1 integration system, a clonal HEK293FT cell line with attB Bxb1 site (SEQ ID NO: 3) integrated using lentivirus was developed. The modified HEK293FT cell line was then transferred with the following plasmids: (1) plus/minus Bxb1 expression plasmid and (2) plus/minus GFP (SEQ ID NO: 76) or G-Luc (SEQ ID NO: 77) minicircle template with attP Bxb1 site. After 72 hours, the integration of GFP or Gluc into the attB site in the HEK293FT genome was probed. The percent integrations of GFP or Gluc into the attB locus are shown in FIG. 7. It was observed that GFP and Gluc showed efficient integration into the attB site in HEK293FT cells.

Example 5

Addition of Bxb1 Site to Human Genome Using PRIME

Figure 8:
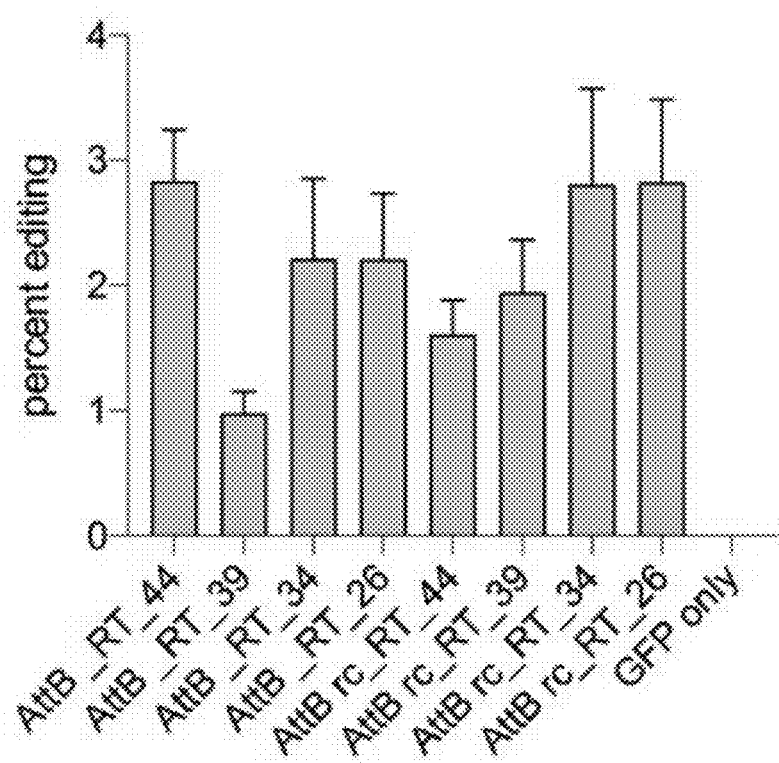
FIG. 8 shows the percent editing of various HEK3 targeting pegRNA Programmable Addition via Site-Specific Targeting Elements (PASTE) according to embodiments of the present teachings.
Figure 9A:
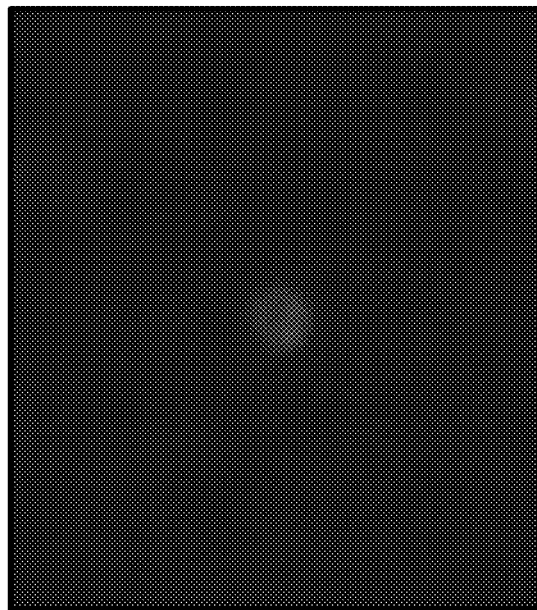
FIG. 9A shows a fluorescent image of cells wherein the SUPT16H marker is tagged with EGFP using PASTE according to embodiments of the present teachings.
Figure 9B:
FIG. 9B shows a fluorescent image of cells wherein the SRRM2 marker is tagged with EGFP using Programmable Addition via Site-Specific Targeting Elements (PASTE) according to embodiments of the present teachings.
Figure 9C:
FIG. 9C shows a fluorescent image of cells wherein the LAMNB1 marker is tagged with EGFP using Programmable Addition via Site-Specific Targeting Elements (PASTE) according to embodiments of the present teachings.
Figure 9D:
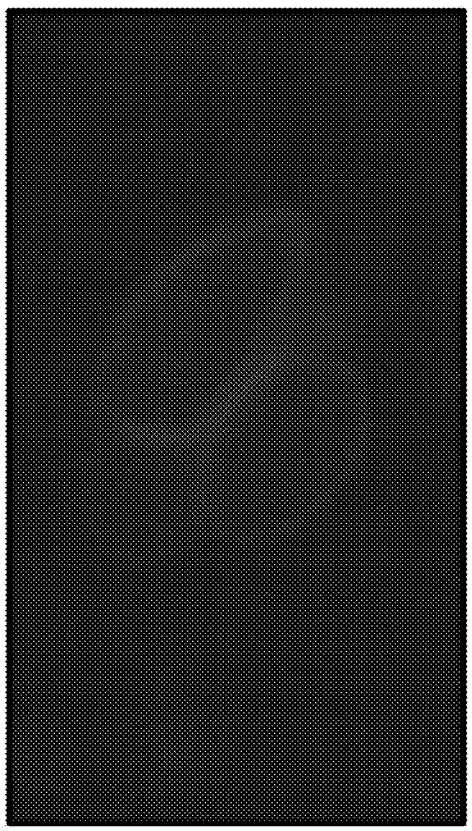
FIG. 9D shows a fluorescent image of cells wherein the NOLC1 marker is tagged with EGFP using Programmable Addition via Site-Specific Targeting Elements (PASTE) according to embodiments of the present teachings.
Figure 9E:
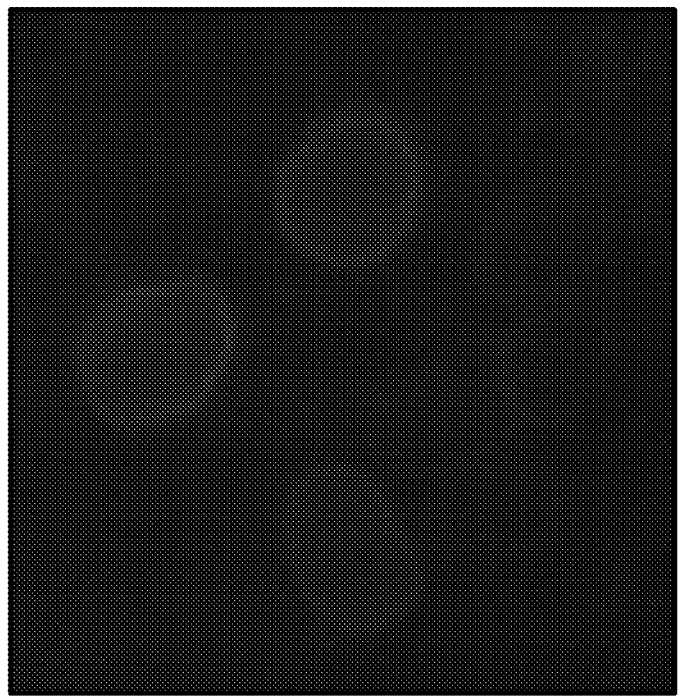
FIG. 9E shows a fluorescent image of cells wherein the NOLC1 marker is tagged with EGFP using Programmable Addition via Site-Specific Targeting Elements (PASTE) according to embodiments of the present teachings.
Figure 9F:
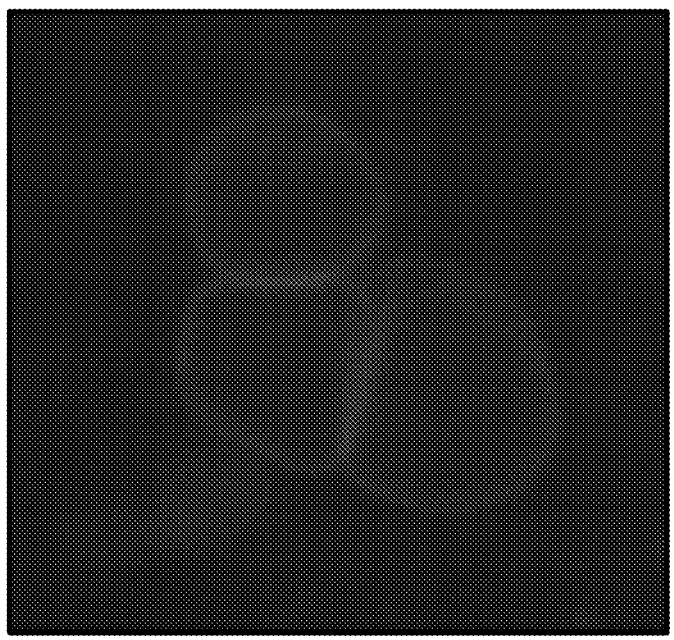
FIG. 9F shows a fluorescent image of cells wherein the NOLC1 marker is tagged with EGFP using Programmable Addition via Site-Specific Targeting Elements (PASTE) according to embodiments of the present teachings.
Figure 9G:
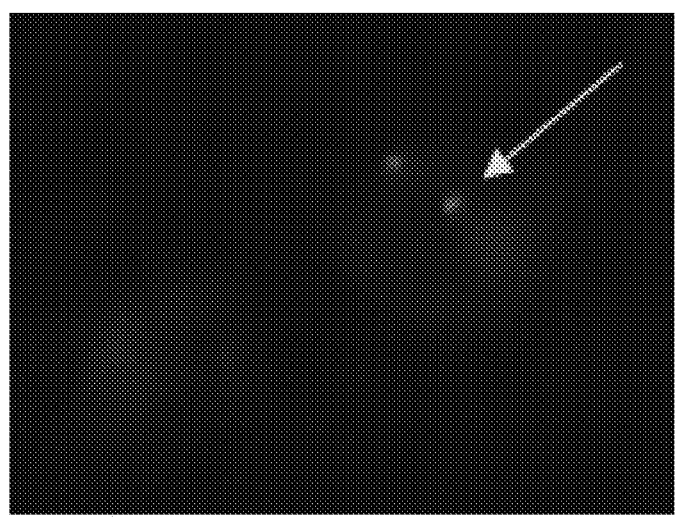
FIG. 9G shows a fluorescent image of cells wherein the DEPDC4 marker is tagged with EGFP using Programmable Addition via Site-Specific Targeting Elements (PASTE) according to embodiments of the present teachings.

The maximum length of attB that can be integrated into a HEK293FT cell line with the best efficiency was probed. To probe the best length of attB (SEQ ID NO: 3) or its reverse complement attP (SEQ ID NO: 4) for prime editing, pegRNAs having PBS length of 13 nt with varying RT homology length were used. The following plasmids were transfected in HEK293FT: (1) prime expression plasmid; (2) HEK3 targeting pegRNA design; and (3) HEK3 +90 nicking guide. After 72 hours, the percent integration of each of the attB construct was probed. FIG. 8 shows the percent editing in each HEK3 targeting pegRNA. It was observed that attB with 44, 34 and 26 base pairs and attB reverse complement with 34 and 26 base pairs showed the highest percent editing.

Integration PASTE was then tested with tagging cell-organelle marker proteins with GFP in HEK29FT cells. PASTE was used to tag SUPT16H, SRRM2, LAMNB1, NOLC1 and DEPDC4 with GFP in different cell-culture wells and to test the usefulness of PASTE in tracking protein localization within the cells using microscopy. FIGS. 9A-9G shows the fluorescent microscopy results for each of the organelles. SUPT16H-GFP was observed to be enriched in the nucleus, SRRM2-GFP was observed to be enriched in the nuclear speckles, LAMNB1-GFP was observed to be enriched in the nuclear membrane, NOLC1-GFP was observed to be enriched in the fibrillar center, and DEPDC4-GFP was observed to be enriched in the aggresome.

Figure 10A:
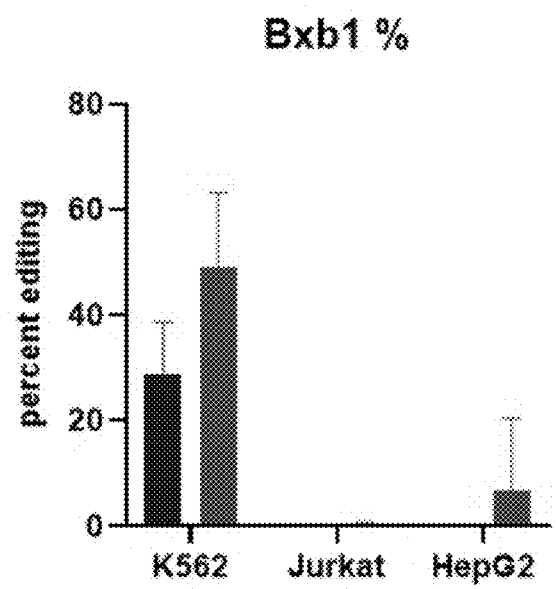
FIG. 10A shows comparisons of lipofectamine aided transfection in blue with electroporation aided transfection in red for the addition of the Bxb1 attB site at the ACTB N-terminal site in the genome using PASTE according to embodiments of the present teachings.
Figure 10B:
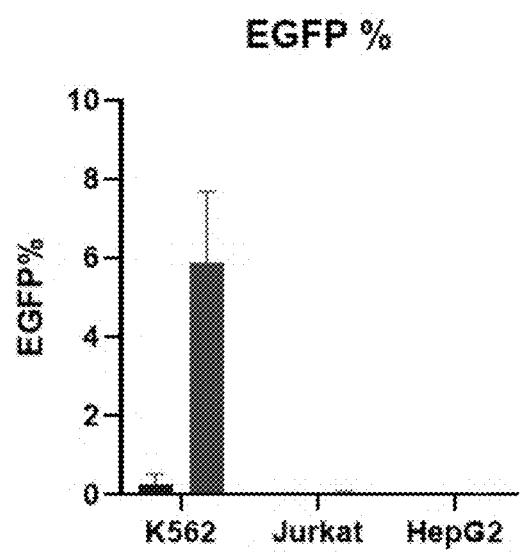
FIG. 10B shows comparisons of lipofectamine aided transfection in blue with electroporation aided transfection in red for EGFP integration at the ACTB N-terminal site in the genome using PASTE according to embodiments of the present teachings.

The transfection of the plasmids can be achieved using electroporation as illustrated in FIGS. 10A-10B.

Example 6

Programmable Integration of Genes with PASTE

The efficiency of gene integration of Gluc or EGFP with PASTE was tested. To enable gene integration with PASTE, the following HEK3 targeting pegRNAs were used: (1) 44 pegRNA: PBS of 13 nt and RT homology of 44 nt; (2) 34 pegRNA: PBS of 13 nt and RT homology of 34 nt; and (3) 26 pegRNA: PBS of 13 nt and RT homology of 26 nt.

Figure 11:
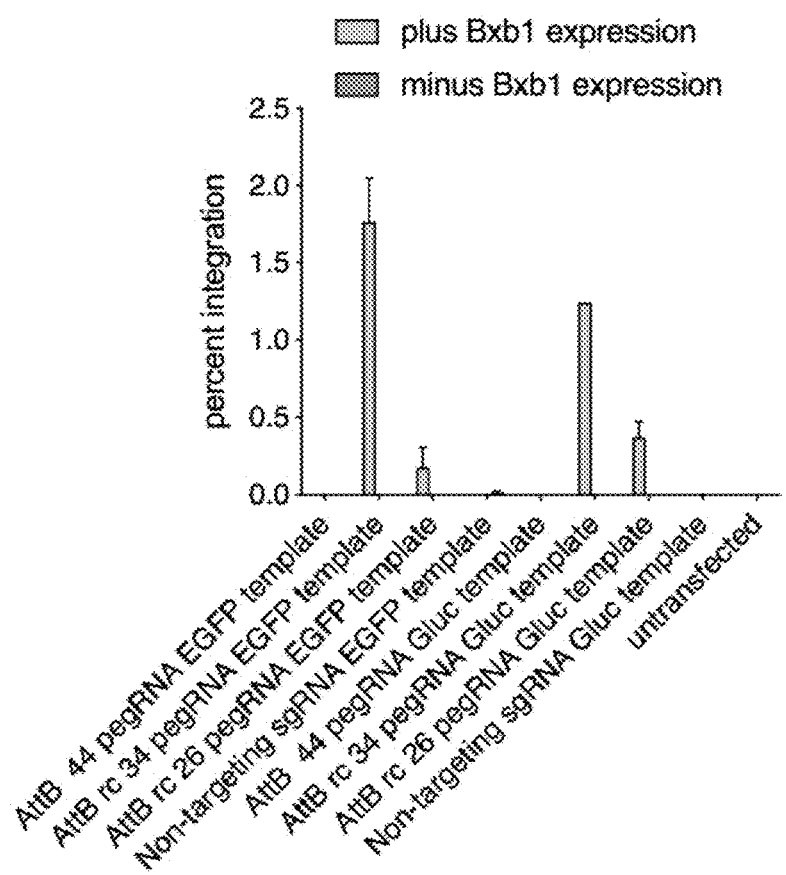
FIG. 11 shows a diagram of the integration of EGFP and Gluc with various HEK3 targeting pegRNAs according to embodiments of the present teachings.

A HEK293 cell line was transfected with following plasmids HEK293FT: (1) Prime expression plasmid; (2) Bxb1 expression plasmid; (3) HEK3 targeting pegRNA design; (4) HEK3 +90 nicking guide; and (5) EGFP or Gluc minicircle. After 72 hours, the percent integration of Gluc or EGFP was observed. FIG. 11 shows integration of EGFP and Gluc with each of the tested HEK3 targeting pegRNAs. It was observed that EGFP and Gluc were efficiently integrated using PASTE.

Example 7

PASTE for Integration of Multiple Genes

The PASTE technique for site-specific integration of multiple genes into a cell is facilitated with the use of orthogonal attB and attP sites. Central dinucleotide can be changed to GA from GT, and only GA containing attB/attP sites can interact and do not cross react with GT containing sequences. A screen of dinucleotide combinations to find orthogonal attB/attP pairs for multiplexed PASTE editing can be performed. It has been shown that many orthogonal dinucleotide combinations can be found using a Bxb1 reporter system.

Figure 14A:
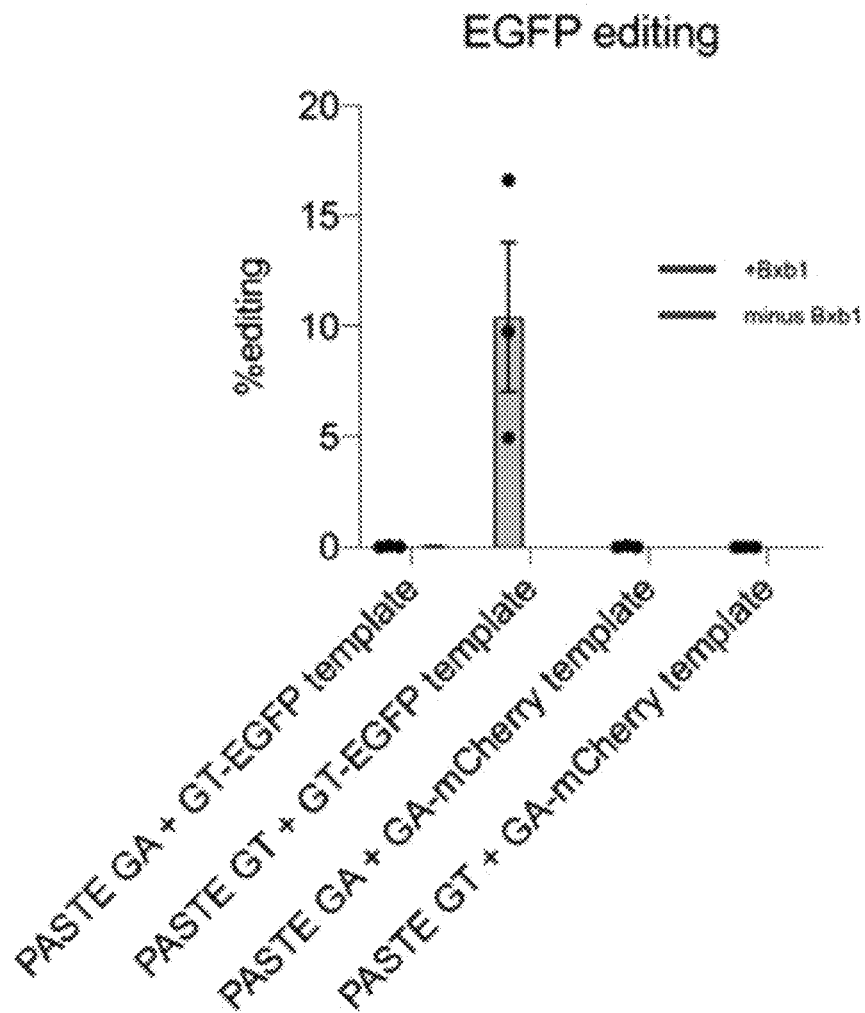
FIG. 14A shows a diagram of the orthogonal editing with the right GT-EGFP according to embodiments of the present teachings.
Figure 14B:
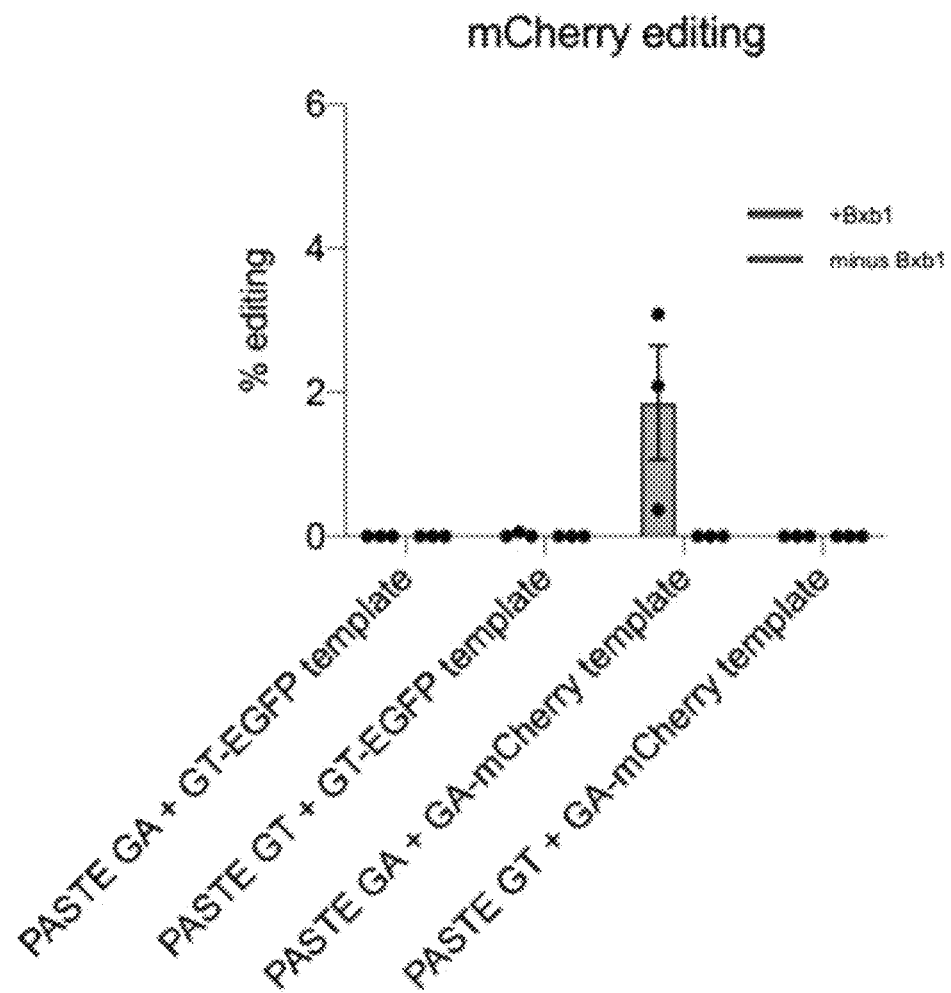
FIG. 14B shows a diagram of the orthogonal editing with the right GA-mCherry according to embodiments of the present teachings.

To test this, $attB^{GT}$ and $attB^{GA}$ dinucleotides for Bxb1 was added at a ACTB site by prime editing. A EGFP—$attP^{GT}$ DNA minicircle and a mCherry—$attP^{GA}$ DNA minicircle was introduced to test the percent EGFP and mCherry editing in the presence or absence of Bxb1. The results of EGFP and mCherry editing are shown in FIGS. 14A-14B.

Orthogonal editing with the right GT-EGFP and GA-mCherry pairs was achieved demonstrating the ability for multiplexed PASTE editing in cells.

Figure 15A:
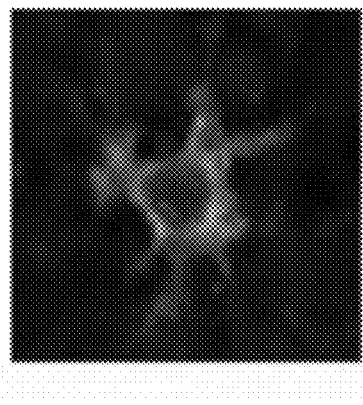
FIG. 15A shows a fluorescent image of a multiplexing of ACTB-EGFP and NOLC1-mCherry according to embodiments of the present teachings
Figure 15B:
FIG. 15B shows a fluorescent image of a multiplexing of ACTB-EGFP and LAMNB1-mCherry according to embodiments of the present teachings.

Two genes were introduced in the same cell using multiplexed PASTE to tag two different genes in a single reaction. EGFP and mCherry were tagged into the loci of ACTB and NOLC1 in a x cell line, in a single reaction. Further, EGFP and mCherry were tagged into the loci of ACTB and LAMNB1. The cells were visualized using fluorescence microscopy. FIGS. 15A-15B show the results of fluorescent microscopy for multiplexed PASTE.

Figure 16A:
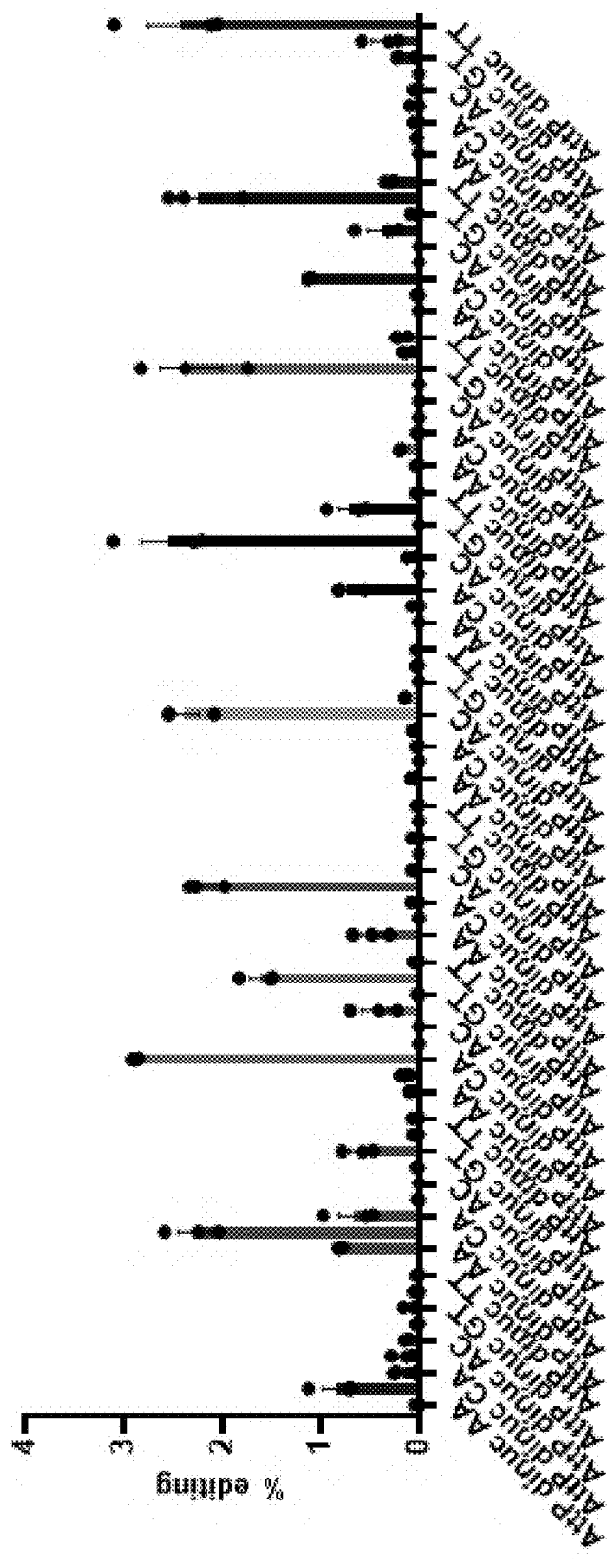
FIG. 16A shows next generation sequencing results of 9×9 attP and attB central dinucleotide variants and their edit percentage wherein the orthogonality of attB/attP combinations for potential multiplexing applications is shown according to embodiments of the present teachings.
Figure 16B:
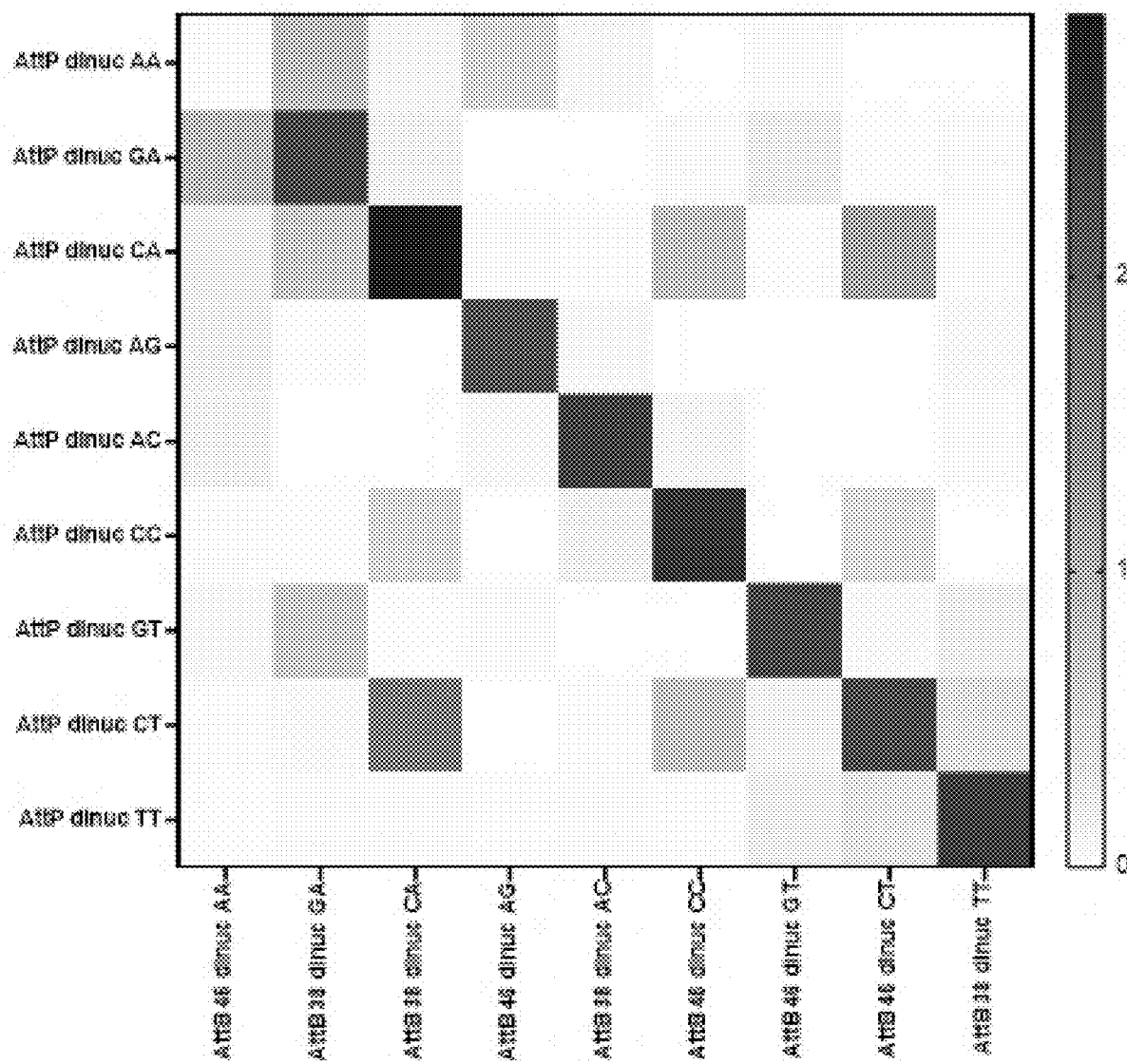
FIG. 16B shows an heatmap of 9×9 attP and attB central dinucleotide variants and their edit percentage according to embodiments of the present teachings.

The ability of multiplexing with 9-different attB and attP central dinucleotides—AA, GA, CA, AG, AC, CC, GT, CT and TT (SEQ ID NOs: 7, 8, 23, 24, 19, 20, 25, 26, 27, 28, 9, 10, 15, 16, 17, 18, 5 and 6)—in a 9×9 cross of attB and attP was tested. The edits were probed using next-generation sequencing. The results of the 9×9 cross of attB and attP central dinucleotides—AA, GA, CA, AG, AC, CC, GT, CT and TT—are shown in FIG. 16A. Only orthogonal pairs of attB and attP show the highest edit percentage. This result is also shown in the heat-map of FIG. 16B.

Example 8

Figure 17:
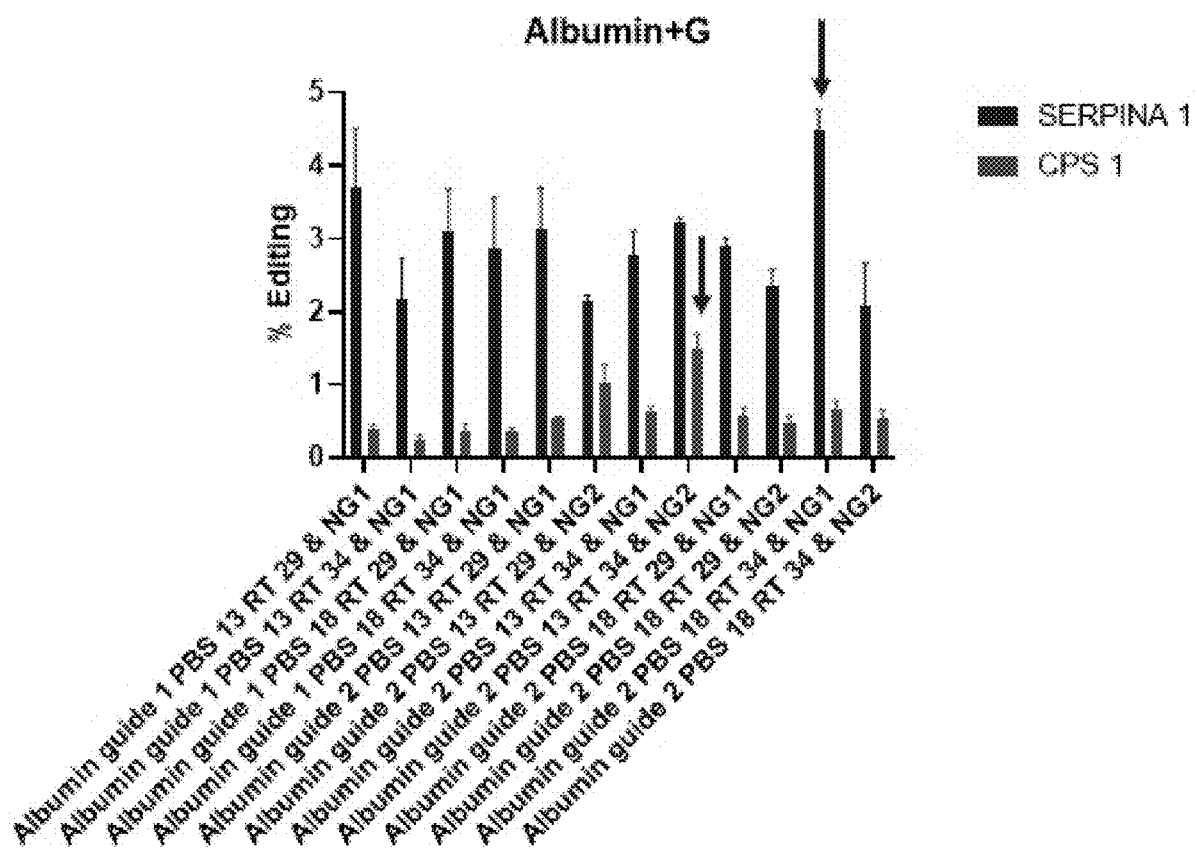
FIG. 17 shows integration of SERPINA and CPS1 into Albumin loci using Albumin guide-pegRNA in HEK293FT cells according to embodiments of the present teachings.

Integration of Albumin and CPS1 Into Albumin Locus 12 pegRNAs with albumin guide were linked to PBS and reverse transcriptase sequence of variable length, and different nicking guide RNAs were used to transfect HEK293FT cells. The percent editing in the albumin was probed using next-generation sequencing. The results of prime editing at the albumin locus are shown in FIG. 17. It was observed that SEQ ID NO: 79 showed the highest percent edits with SERPINA1 and SEQ ID NO: 80 showed the highest percent edits with CPS1.

Example 9

Engineering T-Cells

Figure 18:
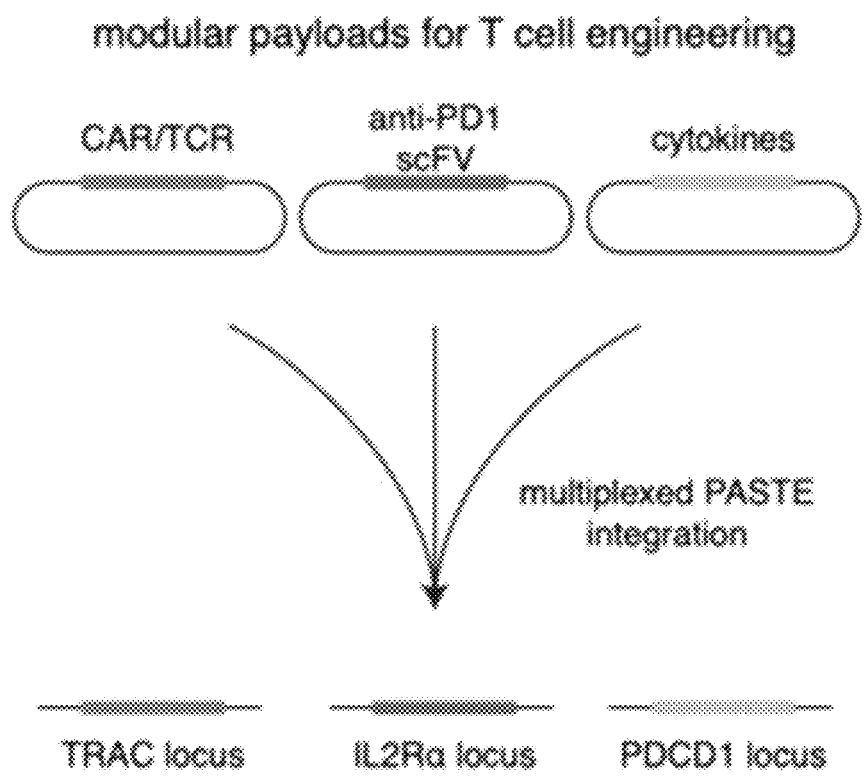
FIG. 18 shows schematics for different nucleic acids for engineering T-cells according to embodiments of the present teachings.

In order to engineer CD8+ T-cells, the efficiency of PASTE delivery and editing in T-cells can be evaluated (FIG. 18). ACTB targeting pegRNA can be used to insert an integration site with an EGFP insertion template. To deliver the PASTE components to CD8+ T-cells, electroporation can be used along with an optimized electroporation protocol for unstimulated T-cells. As multiple plasmids may reduce the efficiency of electroporation, the consolidated PASTE components that use fewer vectors can be applied.

Figure 19:
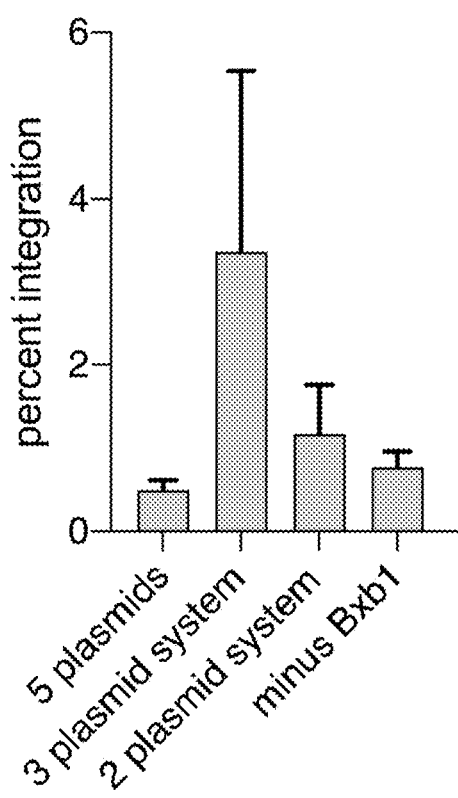
FIG. 19 shows the editing efficiency for EGFP integration at the ACTB locus in primary T-cells according to embodiments of the present teachings.
Figure 20:
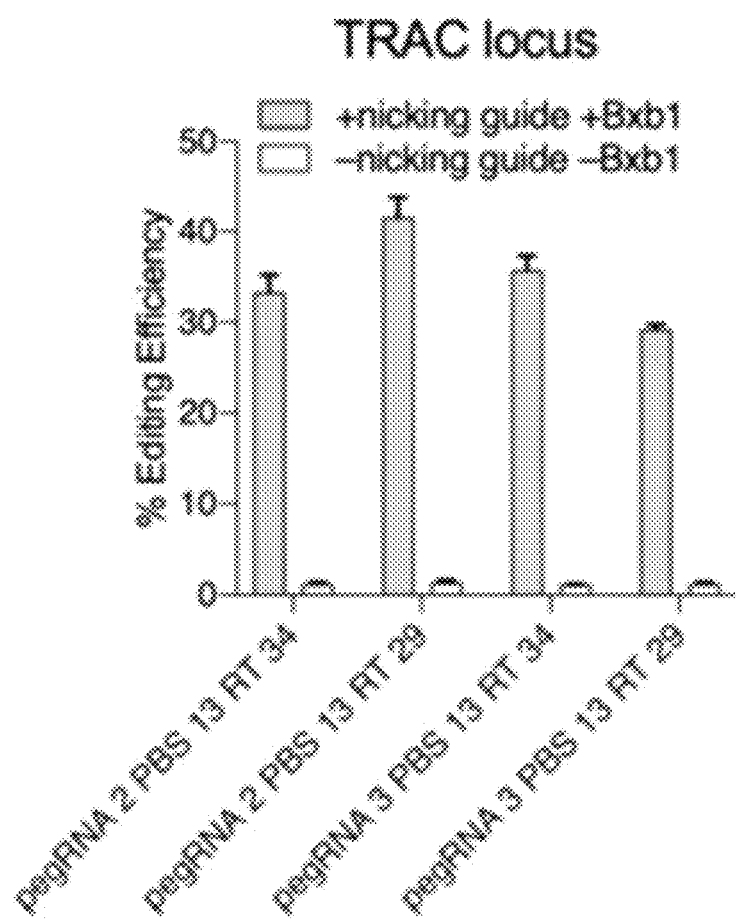
FIG. 20 shows editing in TRAC locus in HEK293FT with different pegRNA according to embodiments of the present teachings.

Five vectors, three vectors, and two vectors PASTE systems show that robust T-cell editing can be achieved with maximal editing using the three-vector approach (FIG. 19). Further, expanded sets of electroporation conditions, including the overall plasmid amounts, cell numbers, and voltage/amperage protocol can be tested. In addition, stimulation of T-cells may influence the efficiency of transduction and PASTE efficiency. Further, CD4+/CD8+ T cell mixtures stimulated with T-Activator CD3/CD28 ligands can have higher PASTE editing efficiency versus unstimulated cells. In order to separate efficiency of PASTE from the overall delivery rate, an mCherry expression cassette on PASTE vectors can be evaluated in order to sort successfully transfected T cells. Once optimized parameters are achieved, a panel of 10 insertion sites with PASTE in T cells, including the TRAC, IL2Rα, and PDCD1 loci, can be evaluated, using different insertions (e.g. EGFP, BFP, and YFP), both in single and multiplexed editing contexts. A tested subset of relevant sites in HEK293FT achieved greater than 40% editing for EGFP insertion (FIG. 20). The PASTE efficiency at TRAC locus with different TCR and CAR constructs can be evaluated. The T-cells can successfully be transfected to achieve insertion of CARs or TCRs.

Example 10

PASTE for CFTR

PASTE for the CFTR locus can be tested in HEK293FT cells to identify top performing pegRNA and nicking designs for human cells. Neuro-2A cells can also be tested to identify top performing pegRNA and nicking designs for mouse cells. The best constructs can be applied for testing in mouse air lung interface (ALI) organoids in vitro or for delivery in pre-clinical models of cystic fibrosis in mice. Table 12 shows the pegRNA, nicking guide and minicircle DNA characteristics for the CFTR gene modulation.

TABLE 12

| Variables | Characteristics |
|---|---|
| pegRNA | 38 bp shortened minimal attB and normal 46 bp attB sequence with:<br>a. PBS of 17, 13, and 9 nt length, and<br>b. RT of 20, 15, and 10 nt in length |
| Nicking guides | Nicking guide 1 +64 bp Nicking guide 2 +23 bp Nicking guide 3 −60 bp<br>Nicking guide 4 −78 bp (distance is calculated from cut site of pegRNA) |
| Minicircle template | A. CFTR coding sequence alone (~4,454 pb in size)<br>B. CFTR coding sequence plus 5' and 3' UTRs (~6,011 bp in size)<br>(Both minicircles have attP site on them for integration by Bxb1 and a bGH poly A signal) |

Example 11

AttB and EGPF Integration Using PASTE

Figure 21A:
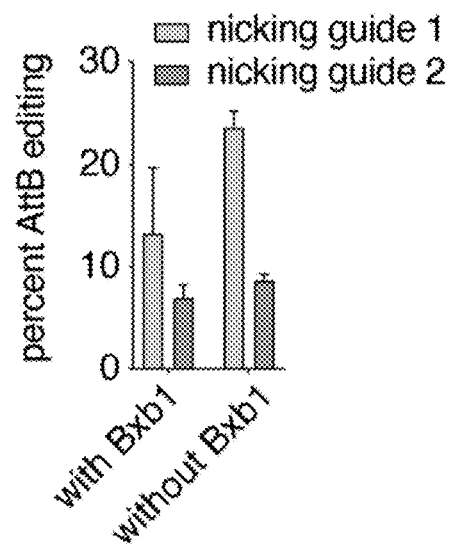
FIG. 21A shows the attB integration at the ACTB locus using nicking guides 1 and 2 according to embodiments of the present teachings.
Figure 21B:
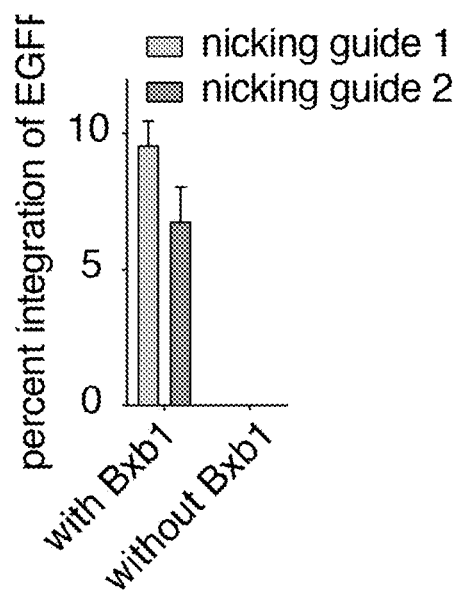
FIG. 21B shows the EGFP integration at the ACTB locus using nicking guides 1 and 2 according to embodiments of the present teachings.
Figure 21C:
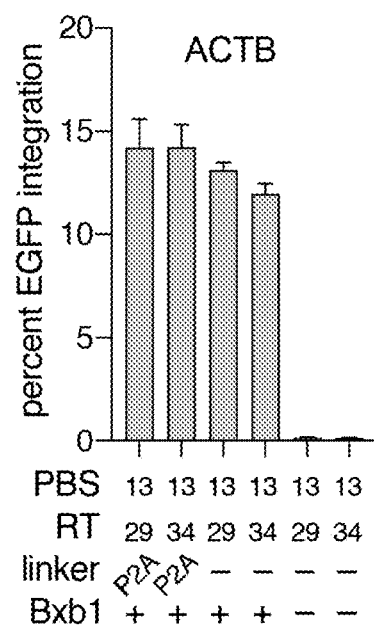
FIG. 21C shows the EGFP integration at an ACTB site according to embodiments of the present teachings.

The efficiency of the integration of attB and EGPF at the ACTB locus was evaluated (FIGS. 21A-21C). To investigate whether Bxb1 can add an EGFP template into this site, a delivery approach using a 5 plasmid system expressing each of the following component was deployed: 1) pegRNA expression, 2) nicking guide expression, 3) Prime expression (Cas9-RT), 4) Bxb1 expression and 5) the insertion template (in this case EGFP). This approach was found to yield editing efficiency of the attB site up to 24% and integration of EGFP ~10% in HEK293FT cells as measured by sequencing (FIGS. 21A-21B). Optimal activity is achieved in 3-4 days and can be performed as a single step transfection or electroporation of all components. Because the EGFP plasmid is designed as a minicircle, allowing removal of all undesired bacterial components, only the desired gene is inserted along with minimal scars from the Bxb1 recombined sites.

To make the tool simpler to use, the Bxb1 can be linked to Prime via a P2A linker to the Cas9-RT fusion, allowing for only a single plasmid to be used for PASTE protein expression rather than two. This optimization can maintain the same level of editing, making it easier to use the tool and deliver it (FIG. 21C).

Example 12

Programmable EGFP Integrations in Different Cell Types

Figure 22A:
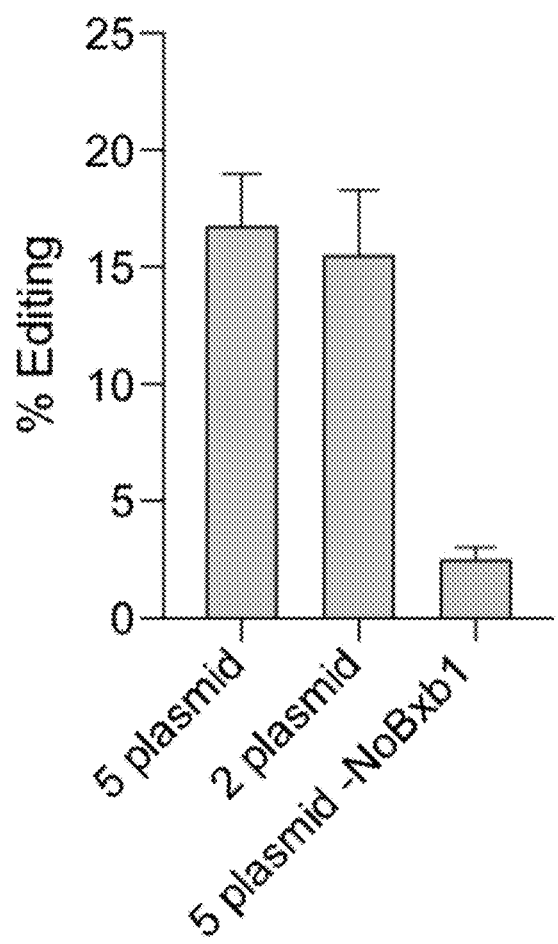
FIG. 22A shows PASTE editing in liver hepatocellular carcinoma cell line HEPG2 according to embodiments of the present teachings.
Figure 22B:
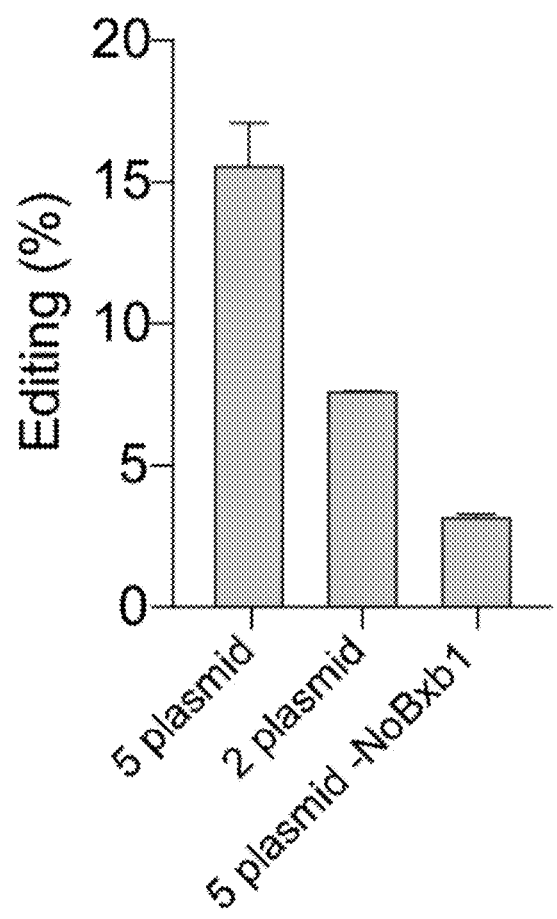
FIG. 22B shows PASTE editing of chronic myelogenous leukemia cell line K562 according to embodiments of the present teachings.

The programmable EGFP integration in liver hepatocellular carcinoma cell line HEPG2 (FIG. 22A) and chronic myelogenous leukemia cell line K562 (FIG. 22B) was evaluated. EGFP integration at the ACTB locus in K562 and HEPG2 cells of about 15% was observed, demonstrating robustness of the platform across cell types.

Example 13

Mutagenesis of Bxb1 for Enhanced PASTE Activity

Figure 23A:
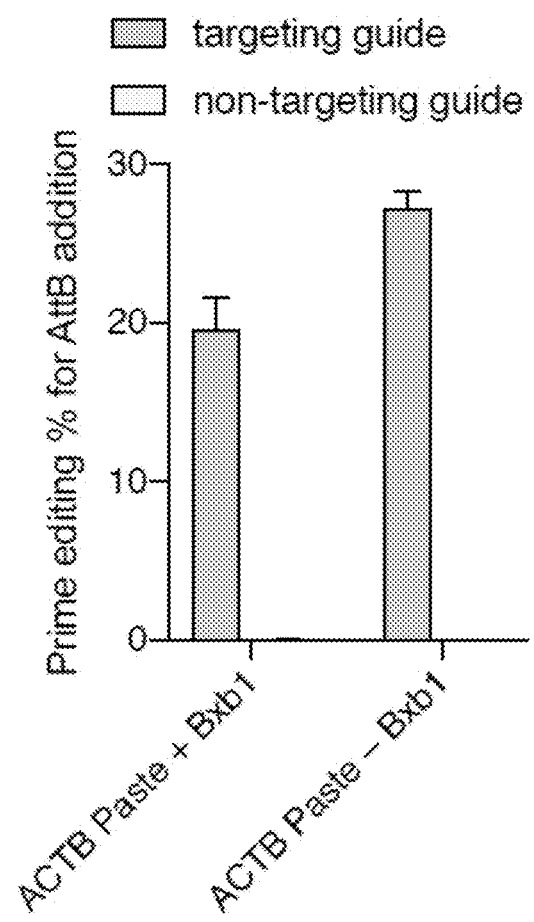
FIG. 23A shows the attB addition with targeting and non-targeting guides according to embodiments of the present teachings.
Figure 23B:
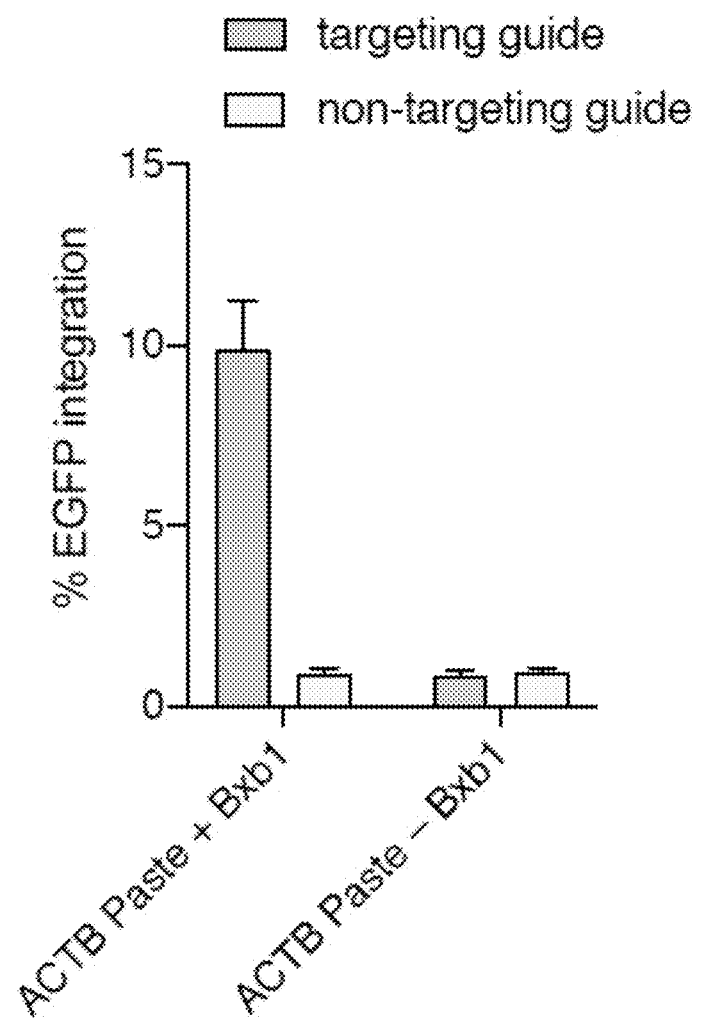
FIG. 23B shows the EGFP integration with targeting and non-targeting guides according to embodiments of the present teachings.
Figure 23C:
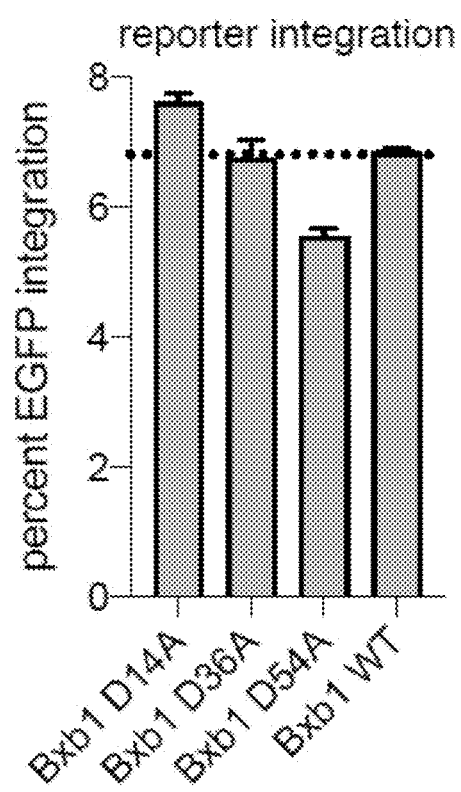
FIG. 23C shows the EGFP integration for mutagenized Bxb1 according to embodiments of the present teachings.

The mutagenesis of Bxb1 for enhanced PASTE activity was evaluated (FIGS. 23A-23C). Two levers for optimizing PASTE activity exist: 1) improving the activity of the integrase and 2) enhancing the Prime addition of the integration sequence. As illustrated in FIGS. 23A-23B, Bxb1 activity can be improved as only about 30% of Bxb1 attB sites that are added by PASTE are integrated into by Bxb1. This illustrates that if the Bxb1 efficiency can be improved, the PASTE can be improved. Furthermore, catalytic residues in the Bxb1 integrase were identified via conservation and structural analyses and Bxb1 mutants were generated to test as part of PASTE. As illustrated in FIG. 23B, the mutations can improve integration by about 20-30%.

Example 14

Figure 25A:
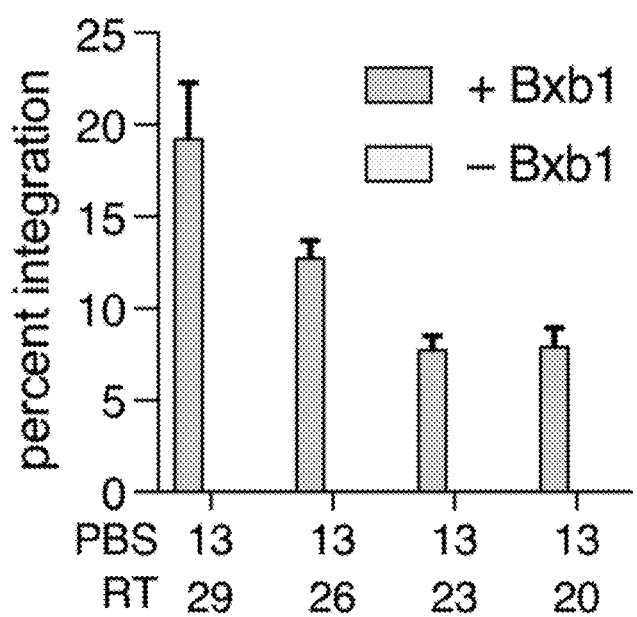
FIG. 25A shows the integration of EGFP at the ACTD locus with different PBS and RT lengths according to embodiments of the present teachings.
Figure 25B:
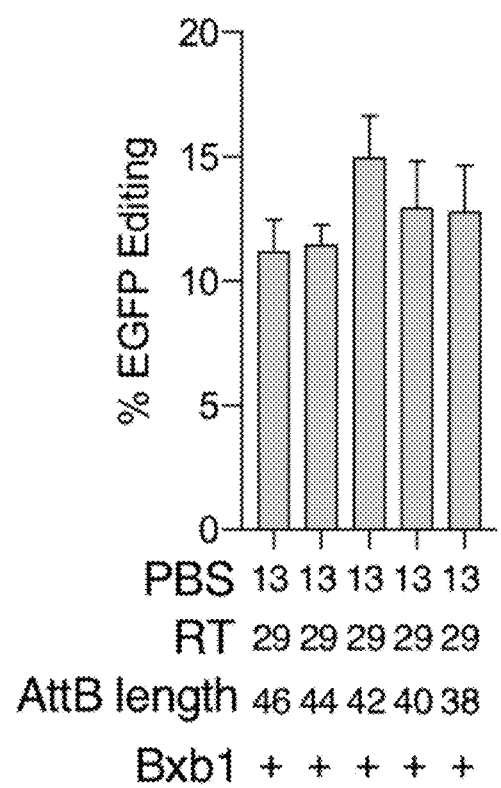
FIG. 25B shows the integration of EGFP at the LMNB1 loci with different PBS and RT lengths according to embodiments of the present teachings.
Figure 25C:
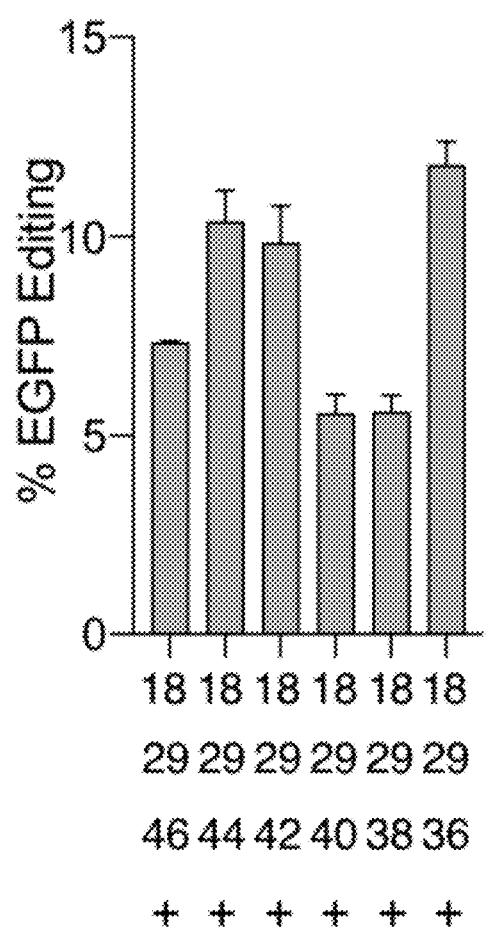
FIG. 25C shows the integration of EGFP at the NOLC1 loci with different PBS and RT lengths according to embodiments of the present teachings.
Figure 25D:
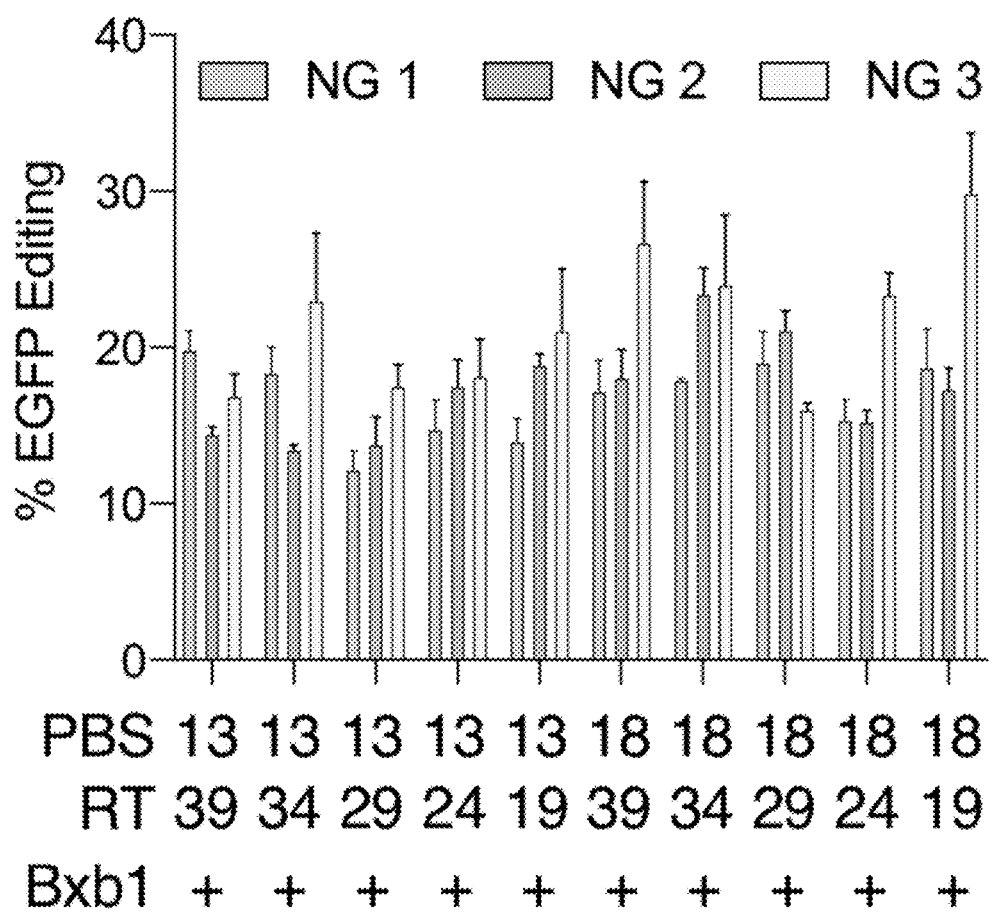
FIG. 25D shows the integration of EGFP at the GRSF1 locus with different PBS and RT lengths and different nicking guides according to embodiments of the present teachings.
Figure 25E:
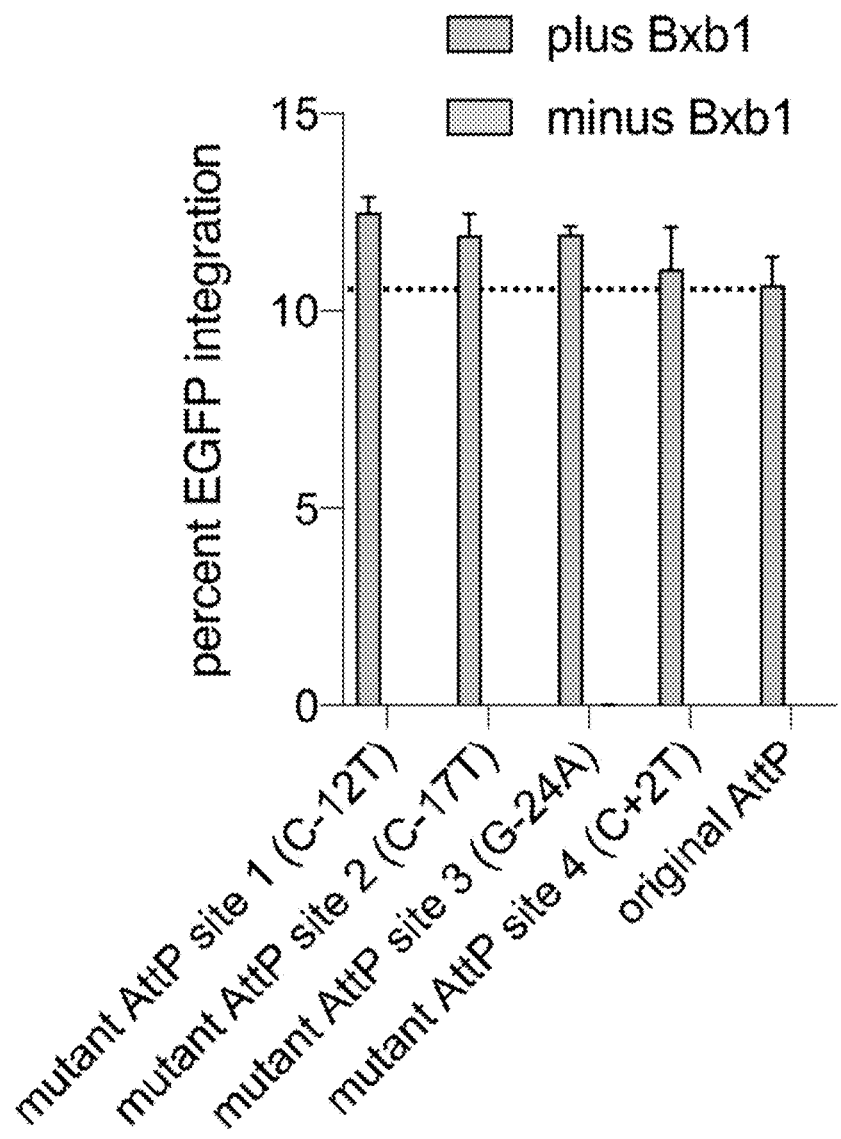
FIG. 25E shows EGFP integration with mutant attP sites according to embodiments of the present teachings.
Figure 25F:
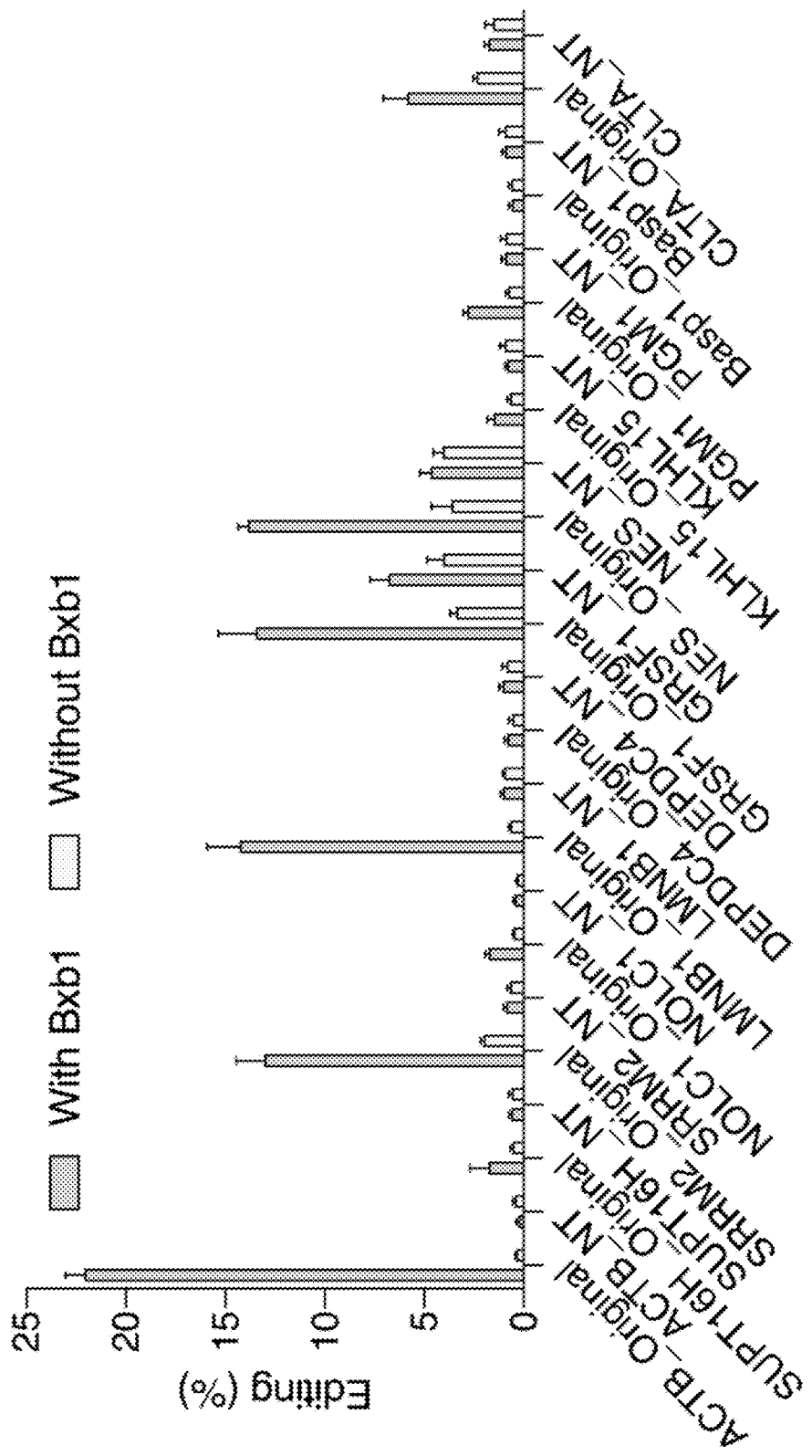
FIG. 25F shows the PASTE editing of an expanded panel of genes according to embodiments of the present teachings.

Effect of the pegRNA PBS and RT Lengths on the Prime Editing Integration Efficiency The effect of the pegRNA PBS and RT lengths on the prime editing integration efficiency was evaluated (FIGS. 25A-25F). It was found that PASTE can be optimized by tuning the PBS and RT lengths at the ACTB locus to achieve editing rates up to about 20% (FIG. 25A). It was found that shortening the attB site can help improve PASTE function as Prime is better at inserting shorter sequences. Further optimization of PBS, RT, and attB lengths showed that optimal designs can be found for insertion upstream of the LMNB1, NOLC1, and GRSF1 loci (FIGS. 25B, 25C, and 25D). Lengths as short as 36 nt for attB were found to be still functional for integration into a reporter plasmid (FIGS. 25B and 25C). It was found that the reverse complemented version of the attB sequence was better integrated via Prime editing, suggesting that the sequence of what Prime is inserting matters. EGFP integrations with attP site mutants showed that certain mutants can improve integration efficiency significantly (FIG. 25E). PASTE was also performed with a large panel of genes, inserting EGFP at the N-terminus of ACTB, LMNB1, SUPT16H, SRRM2, NOLC1, KLHL15, GRSF1, DEPDC4, NES, PGM1, CLTA, BASP1, and DNAJC18 (FIG. 25F). Editing rates that are about 5%-40% were found using digital droplet PCR (ddPCR).

Example 15

Comparison of PASTE and HITI On-Target and Off-Target Activities

Figure 26A:
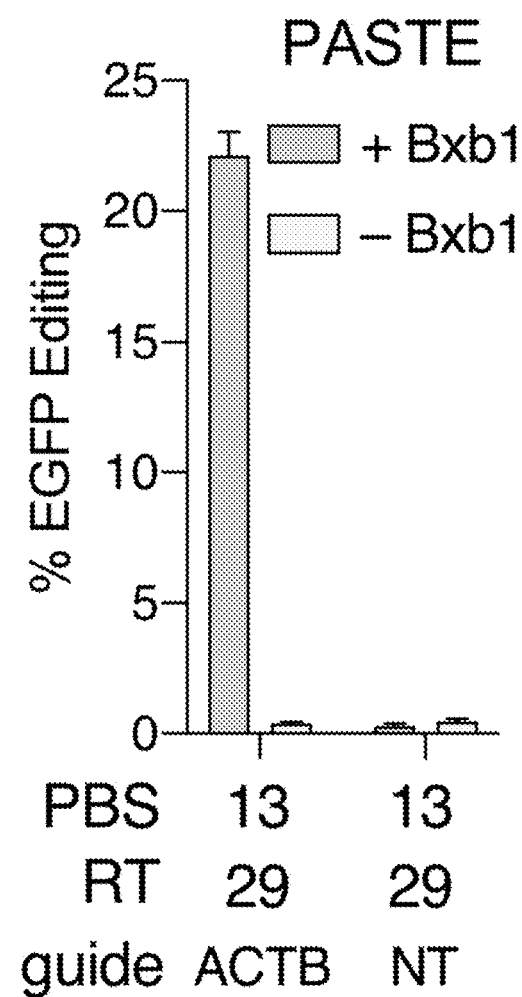
FIG. 26A shows the PASTE EGPF editing at the ACTB locus according to embodiments of the present teachings.
Figure 26B:
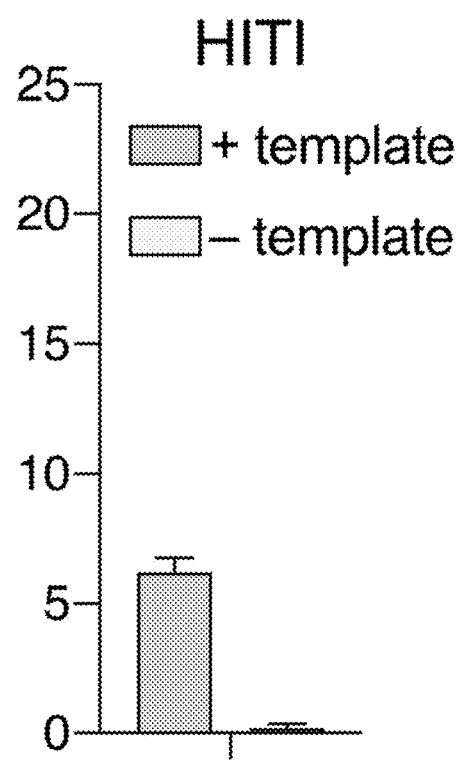
FIG. 26B shows the HITI EGPF editing at the ACTB locus according to embodiments of the present teachings.
Figure 26C:
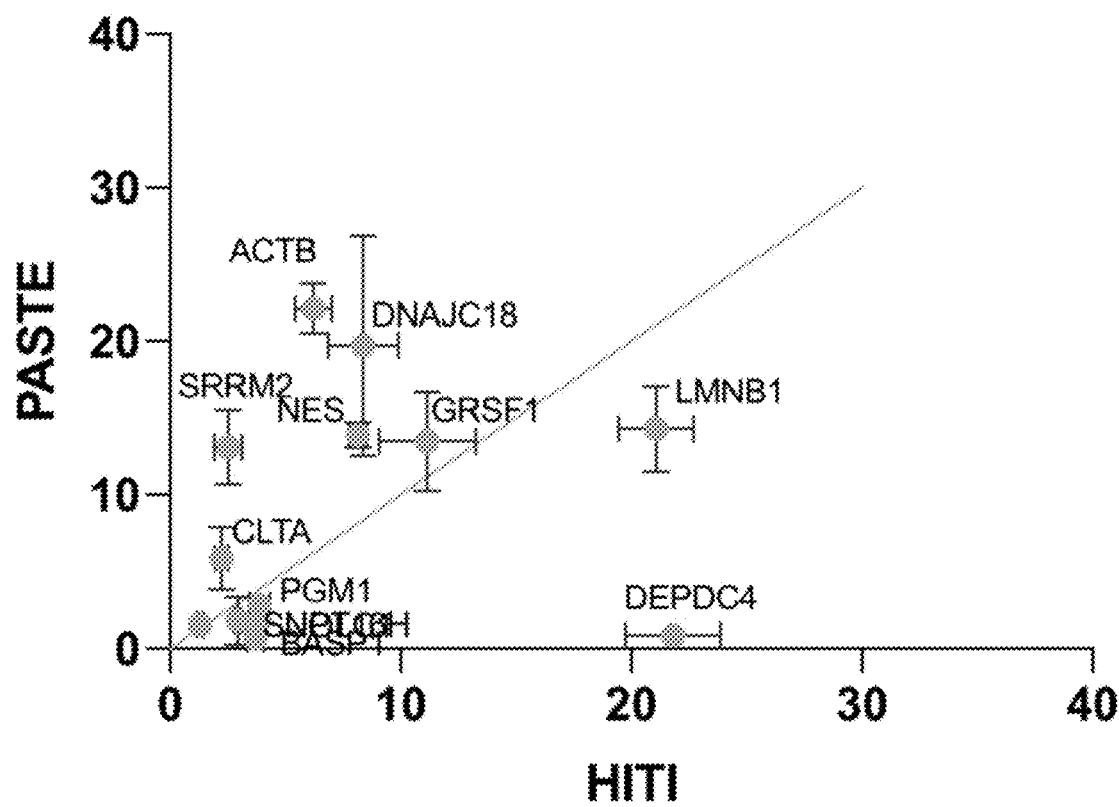
FIG. 26C shows the comparison between the PASTE and HITI editing a panel of 14 genes according to embodiments of the present teachings.
Figure 26D:
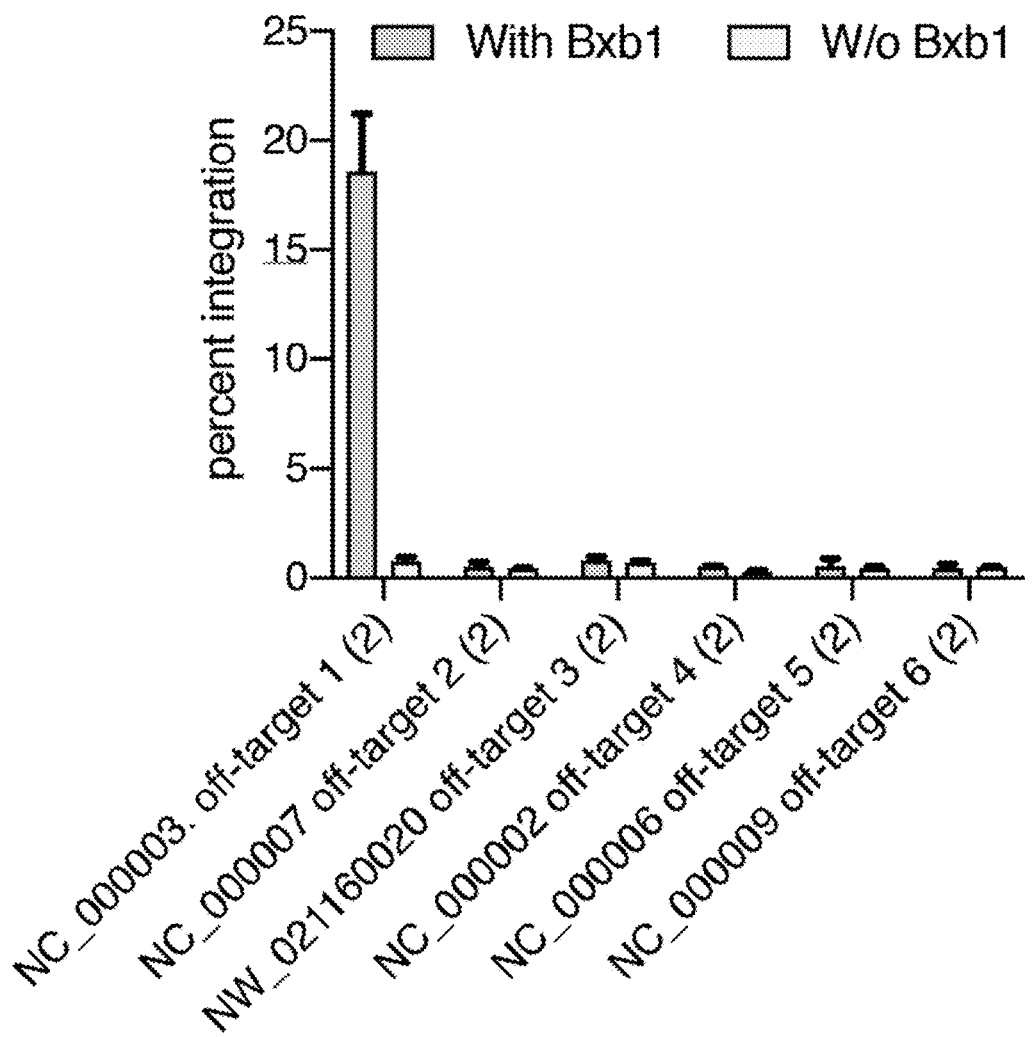
FIG. 26D shows PASTE Bxb1 off-target integrations according to embodiments of the present teachings.
Figure 26E:
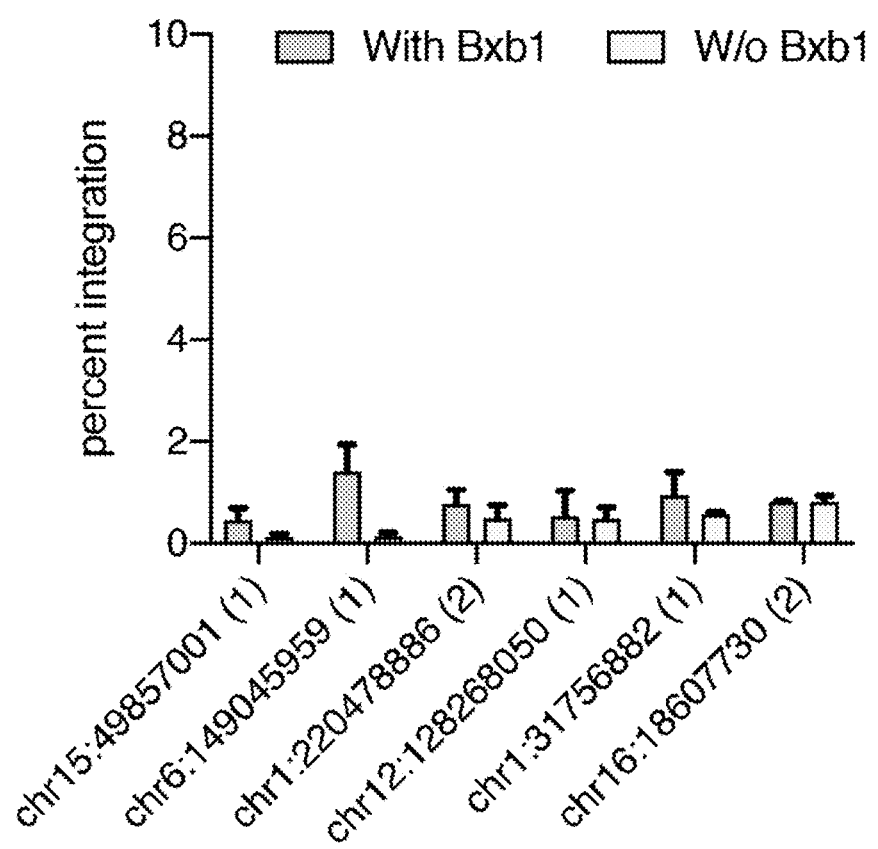
FIG. 26E shows PASTE Cas9 off-target integrations according to embodiments of the present teachings.
Figure 26F:
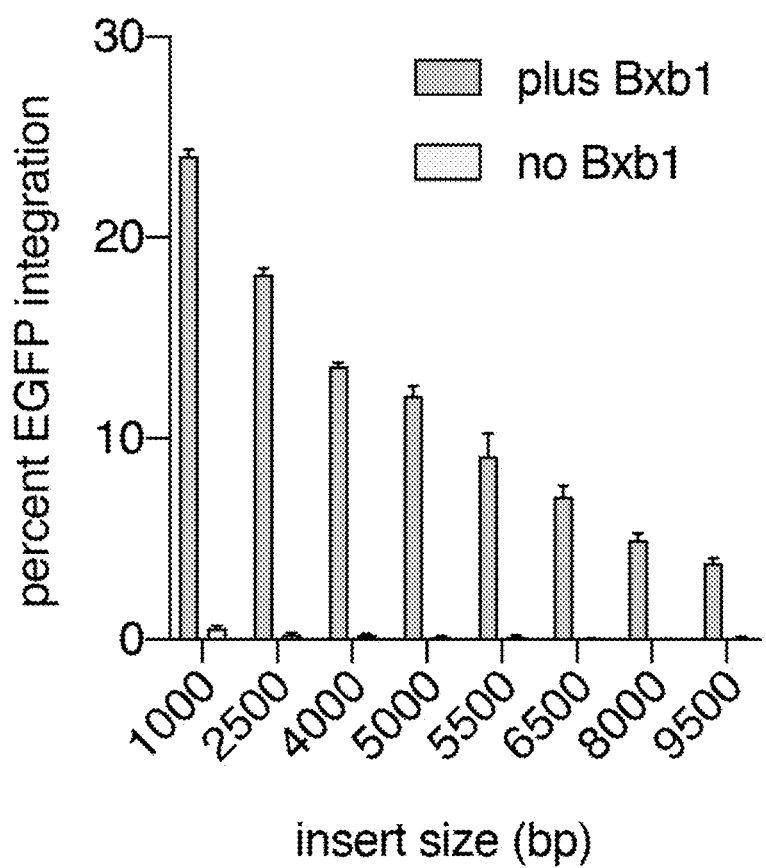
FIG. 26F shows the EGFP integration for gene inserts of different sizes according to embodiments of the present teachings.
Figure 27A:
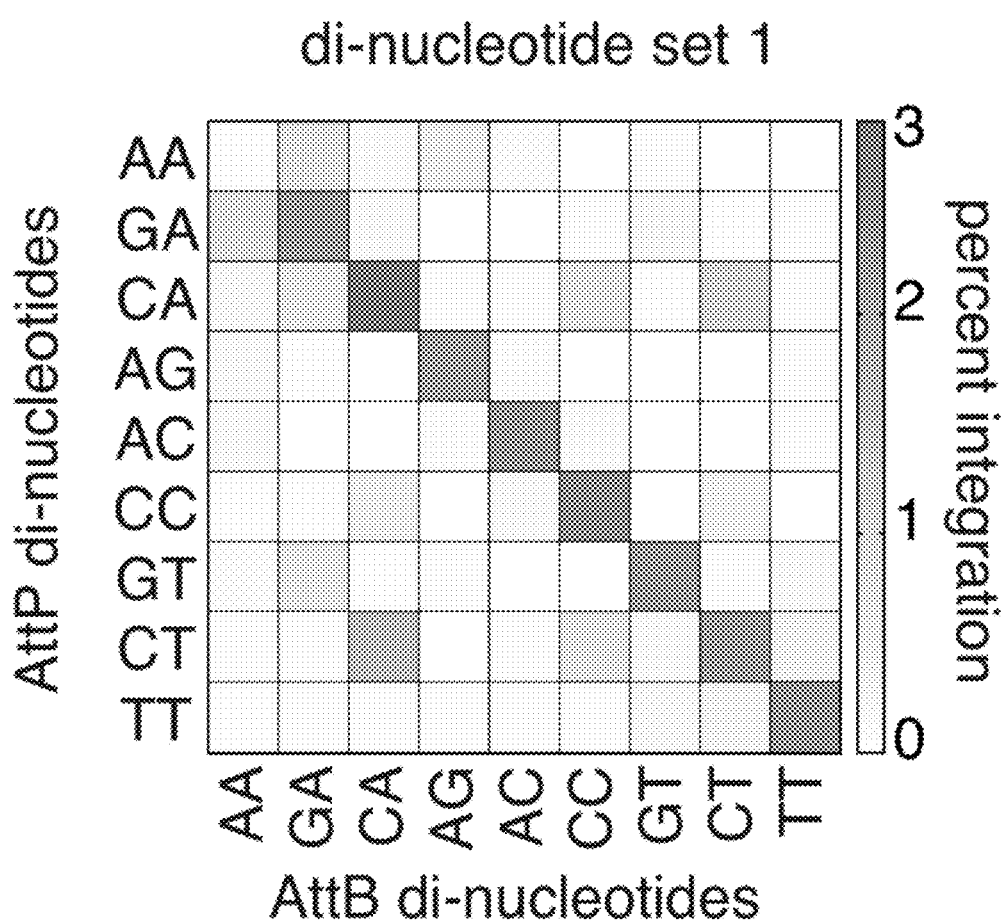
FIG. 27A shows the orthogonality between selected sets of attB and attP sites according to embodiments of the present teachings.
Figure 27B:
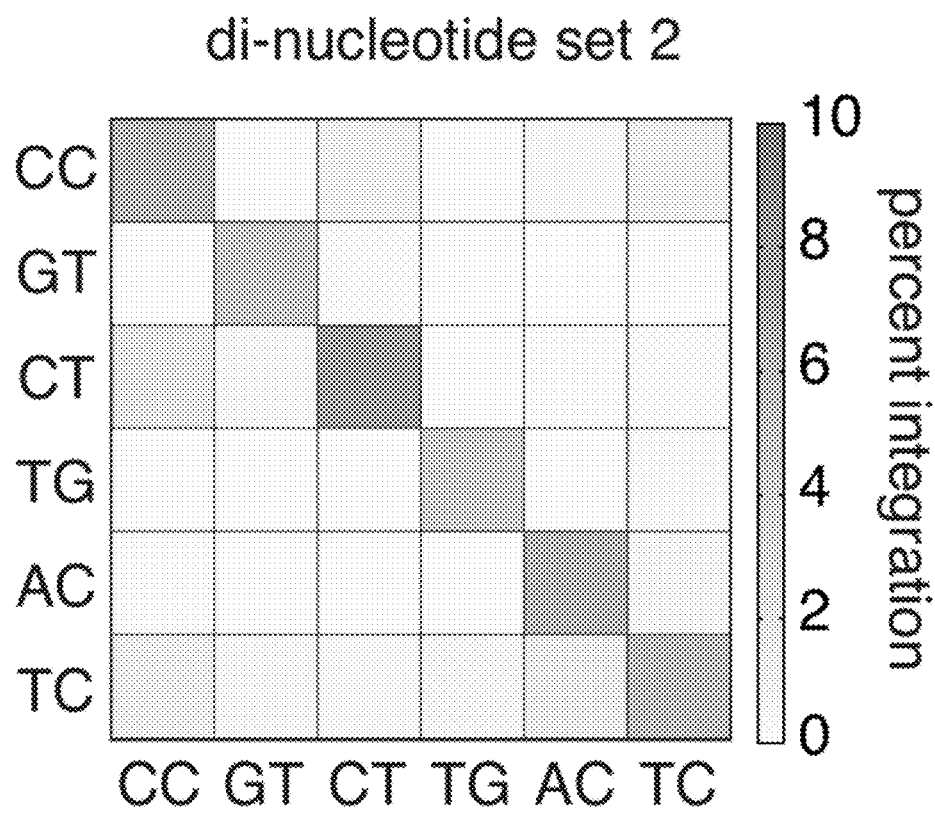
FIG. 27B shows the orthogonality between selected sets of attB and attP sites according to embodiments of the present teachings.
Figure 27C:
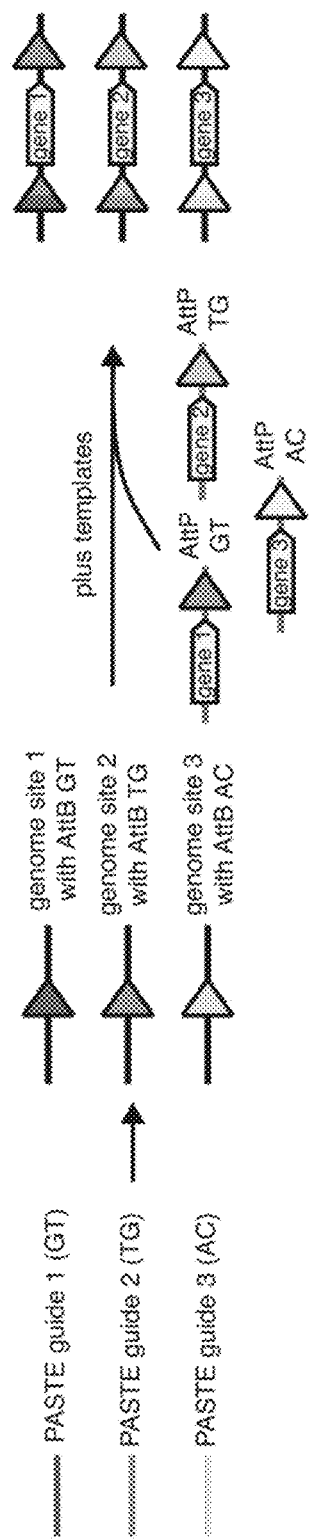
FIG. 27C shows a schematic for the orthogonal PASTE editing using engineered di-nucleotide combinations according to embodiments of the present teachings.

The PASTE and HITI on-target and off-target activities were compared (FIGS. 26A-26F). PASTE and HITI were found to have about 22% and 5% integration efficiencies respectively when using the same guide sequence (FIGS. 26A and 26B). PASTE was found to outperform HITI at most sites when analyzing the editing of 14 genes (FIG. 26C). Using a ddPCR based approach, it was found that PASTE was very specific with minimal off-target activity for Bxb1 off-targets integrations (FIG. 26D) and Cas9 off-targets integrations (FIG. 26E). The analysis of inserts of different sizes showed that PASTE can reliably insert sequences 1 kb-10 kb in size (FIG. 26F), revealing the wide range of sequence sizes PASTE is capable of working with. A decrease in insertion efficiency at larger sizes was also observed, which was likely due to the reduction in plasmid delivery to HEK293FT cells at larger plasmid sizes.

Example 16

Multiplexing with PASTE and Orthogonal Di-Nucleotide attB and attP Sites

Multiplexing with PASTE and orthogonal di-nucleotide attB and attP sites was evaluated (FIGS. 28A-28C). Multiple orthogonal combinations were found for mutants of the central di-nucleotide motif (FIGS. 28A and 28B). As illustrated in FIG. 28C, programmable multiplexed gene insertion can be achieved by using these orthogonal combinations with PASTE only delivering different pegRNAs and gene inserts while keeping the protein components the same (FIG. 8C).

Example 17

PASTE Multiplexed Integrations at Endogenous Sites

Figure 28D:
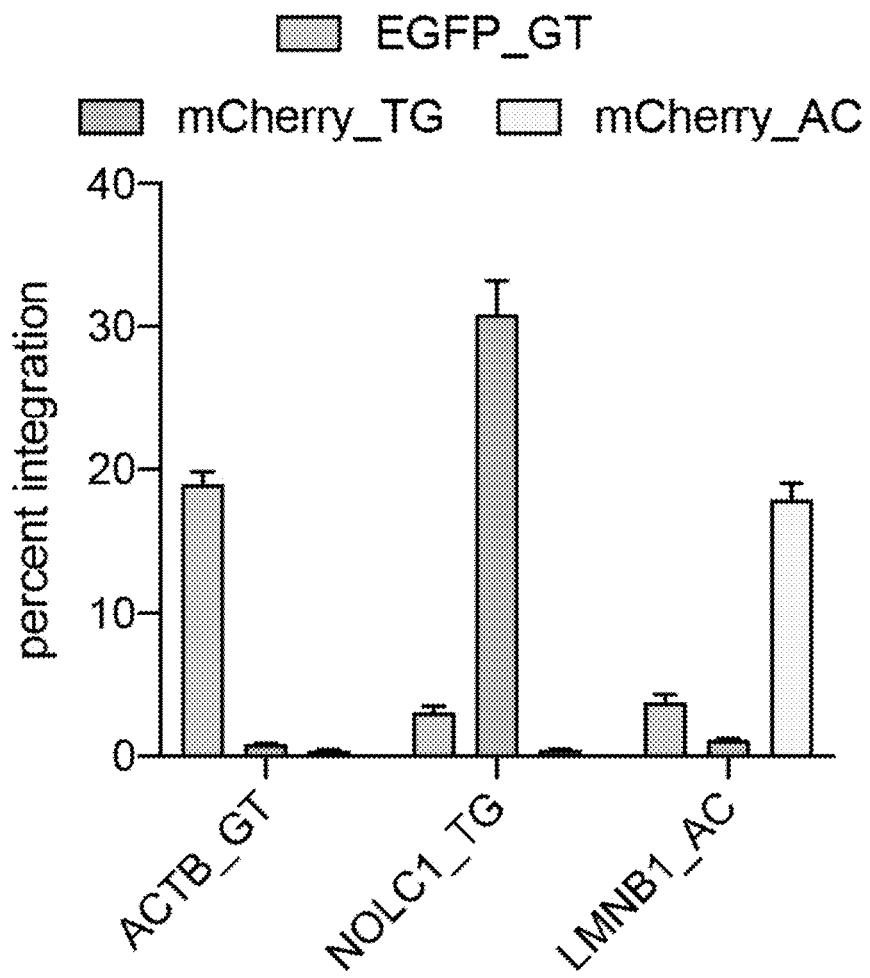
FIG. 28D shows the orthogonal gene integration at three endogenous sites with PASTE according to embodiments of the present teachings.
Figure 28E:
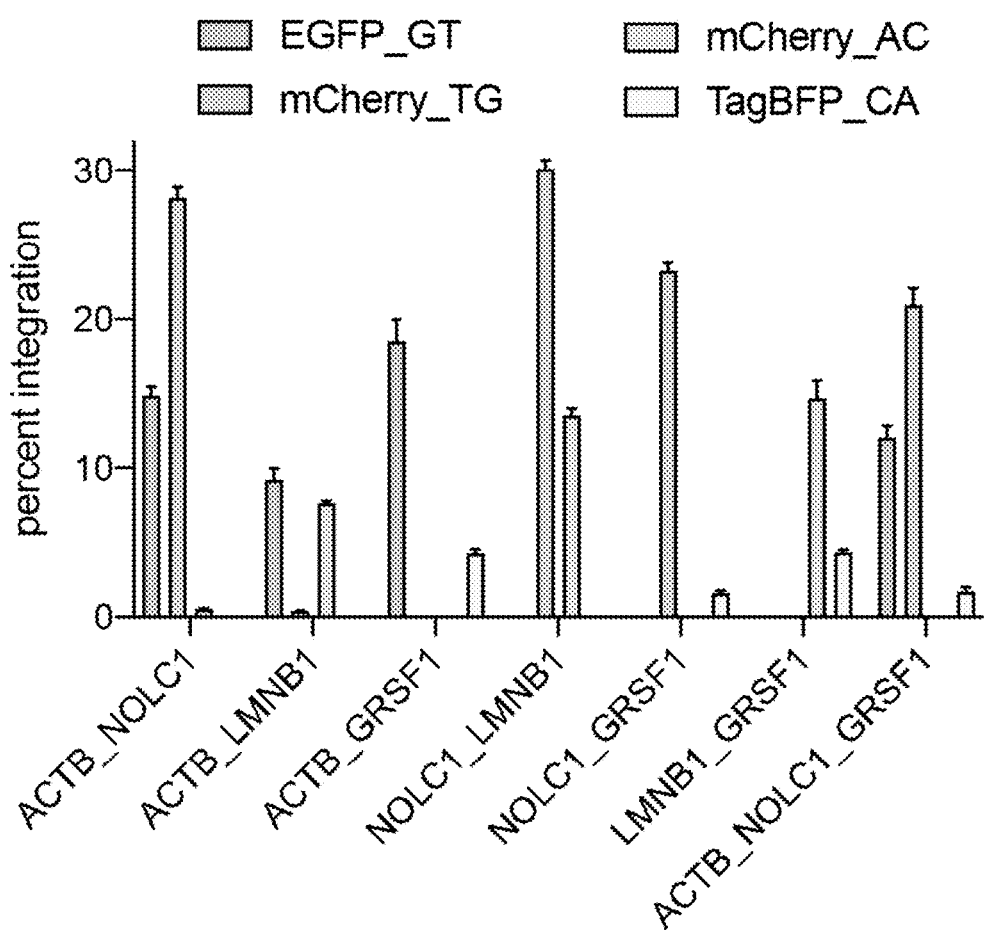
FIG. 28E shows the multiplexed insertion via one-plex, two-plex, and three-plex gene insertion at three endogenous sites via PASTE according to embodiments of the present teachings.

PASTE multiplexed integrations at endogenous sites were evaluated (FIGS. 28A-28G). A reading frame for the attR scar that is left post-integration by Bxb1 that is ideal for a protein linker due to the enrichment of glycines, serines, and prolines in the sequence (GLSGQPPRSPSSGSSG (SEQ ID NO: 426)) was identified. PegRNAs were designed using this linker frame for the resolution of the attR for tagging a number of genes at the N-terminus with EGFP (ACTB, NOLC1, LMNB1, SUPT16H, SRRM2, and DEPDC4). As these genes all have distinct protein localization appearances, microscopy can be used for ascertaining proper gene tagging. PASTE was found to be capable of high-efficiency gene tagging with protein localizations that match the reference images and expected localization of the proteins in the cells (FIGS. 28A-28C). Genes were also tagged in multiplexed fashion to demonstrate the orthogonality of the engineered integration sites. ACTB, LMNB1, NOLC1, and GRSF were targeted with orthogonal pegRNAs carrying GT, TG, AC, and CA, respectively in HEK293FT in groups of single, dual-plexing, and triple-plexing (FIGS. 28D-28E). These dinucleotides were paired with templates carrying EGFP, BFP, and mCherry to allow for multicolor imaging of these labeled genes. The efficiencies of integration for these multiplexing experiments were found to range from about 5%-32%, revealing efficient multiplex integration with PASTE. Using confocal microscopy of these multiplexed integration experiments, cells were found with simultaneous labeling of these different proteins (FIGS. 28F-28G).

Example 18

Combination of CRISPR-based Genome Editing and Site-specific Integration

The combination of CRISPR-based genome editing and site-specific integration was evaluated.

Figure 29A:
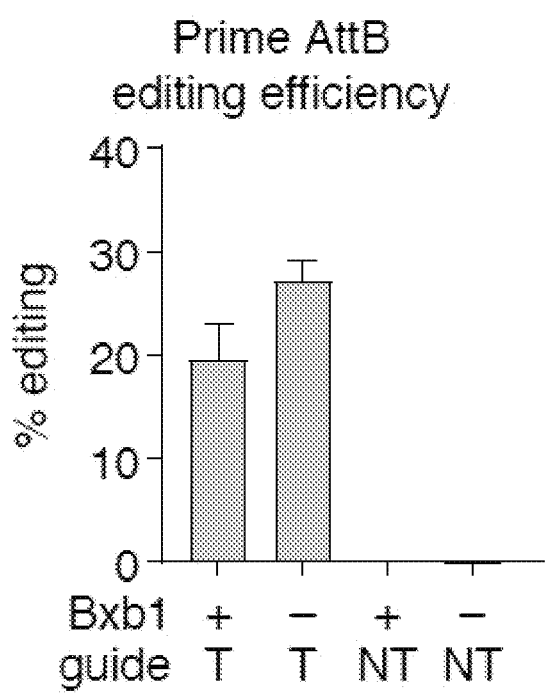
FIG. 29A shows the prime editing efficiency of Bxb1 attB site insertion at the ACTB locus according to embodiments of the present teachings.
Figure 29B:
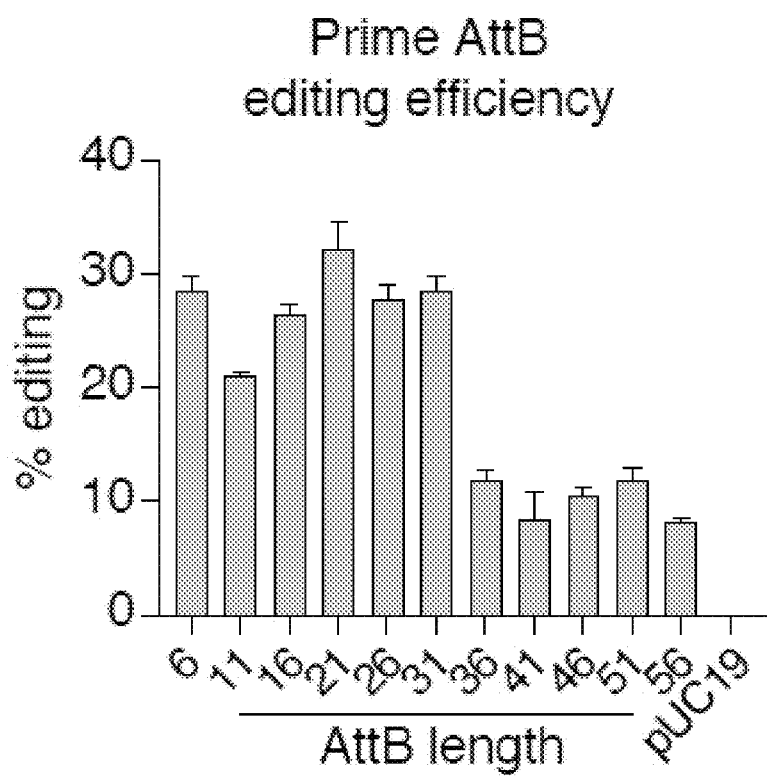
FIG. 29B shows the prime editing efficiency at inserting Bxb1 attB sites of different lengths at the ACTB locus according to embodiments of the present teachings.
Figure 29C:
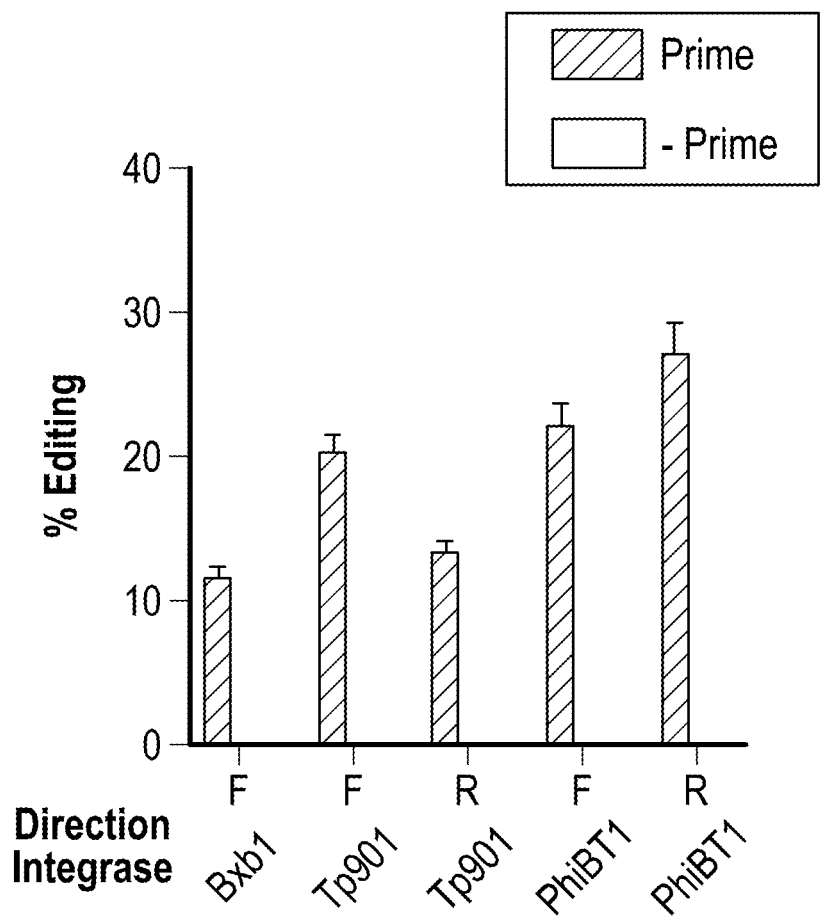
FIG. 29C shows the prime editing efficiency of inserting attB sequences from different integrases, wherein both orientations of landing sites are profiled (F, forward; and R, reverse) according to embodiments of the present teachings.
Figure 29D:
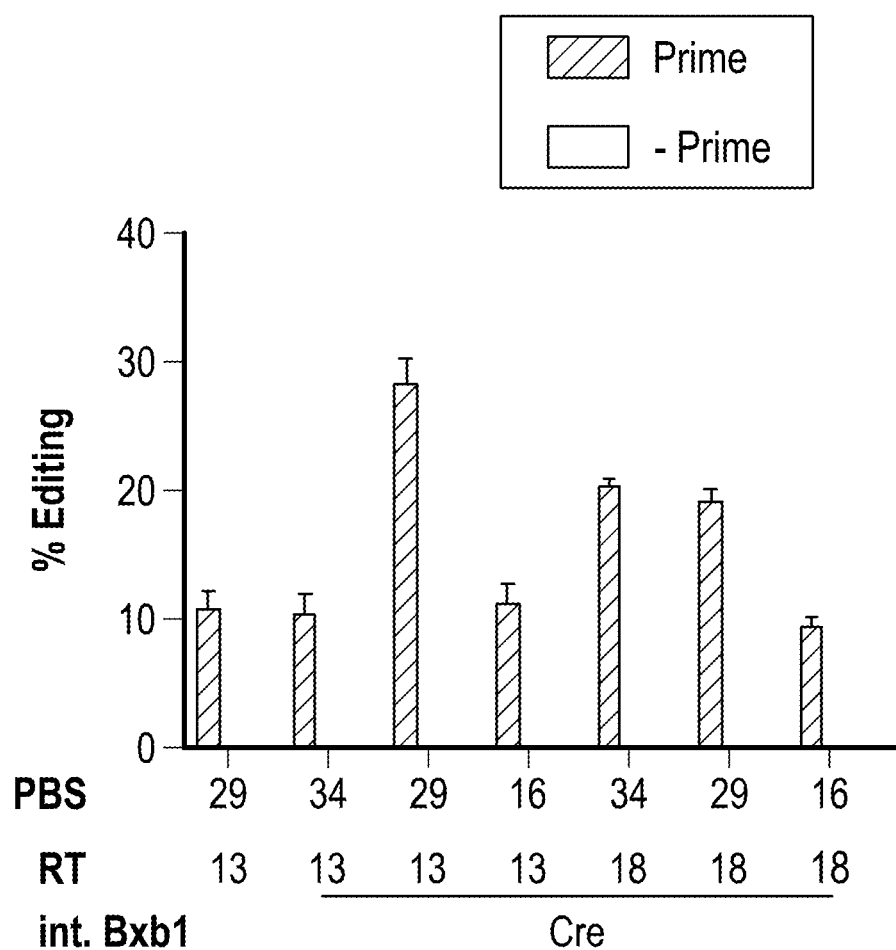
FIG. 29D shows the prime editing efficiency of inserting attB sequences from Bxb1 integrase and Cre recombinase, wherein both orientations of landing sites are profiled (F, forward; and R, reverse) according to embodiments of the present teachings.
Figure 29E:
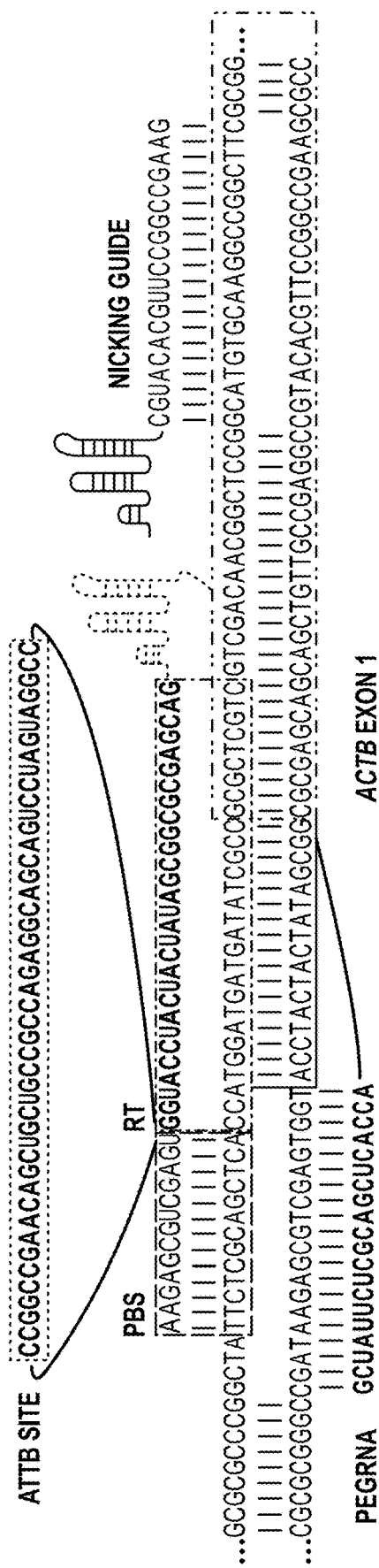
FIG. 29E shows a schematic of PASTE insertion at the ACTB locus showing guide and target sequences according to embodiments of the present teachings.
Figure 29F:
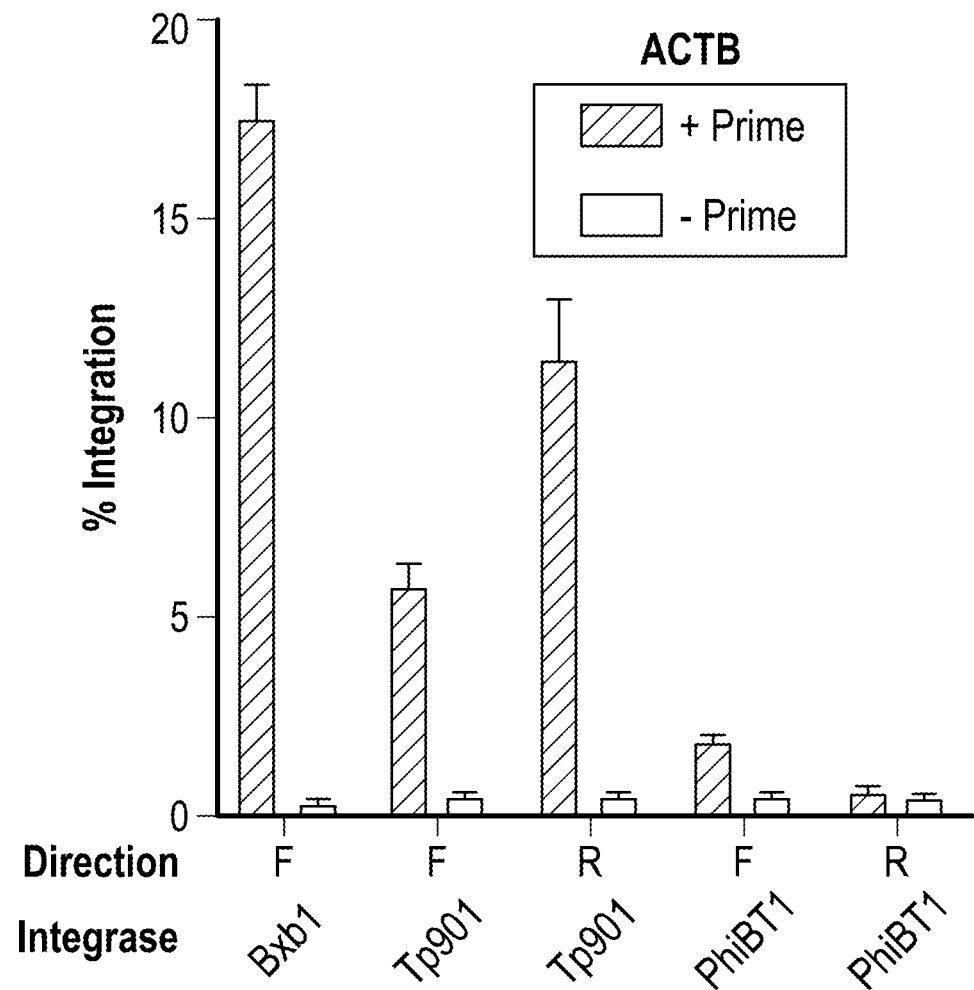
FIG. 29F shows a comparison of PASTE integration efficiency of GFP with a panel of integrases targeting the 5' end of the ACTB locus, wherein both orientations of landing sites are profiled (F, forward; and R, reverse) according to embodiments of the present teachings.
Figure 29G:
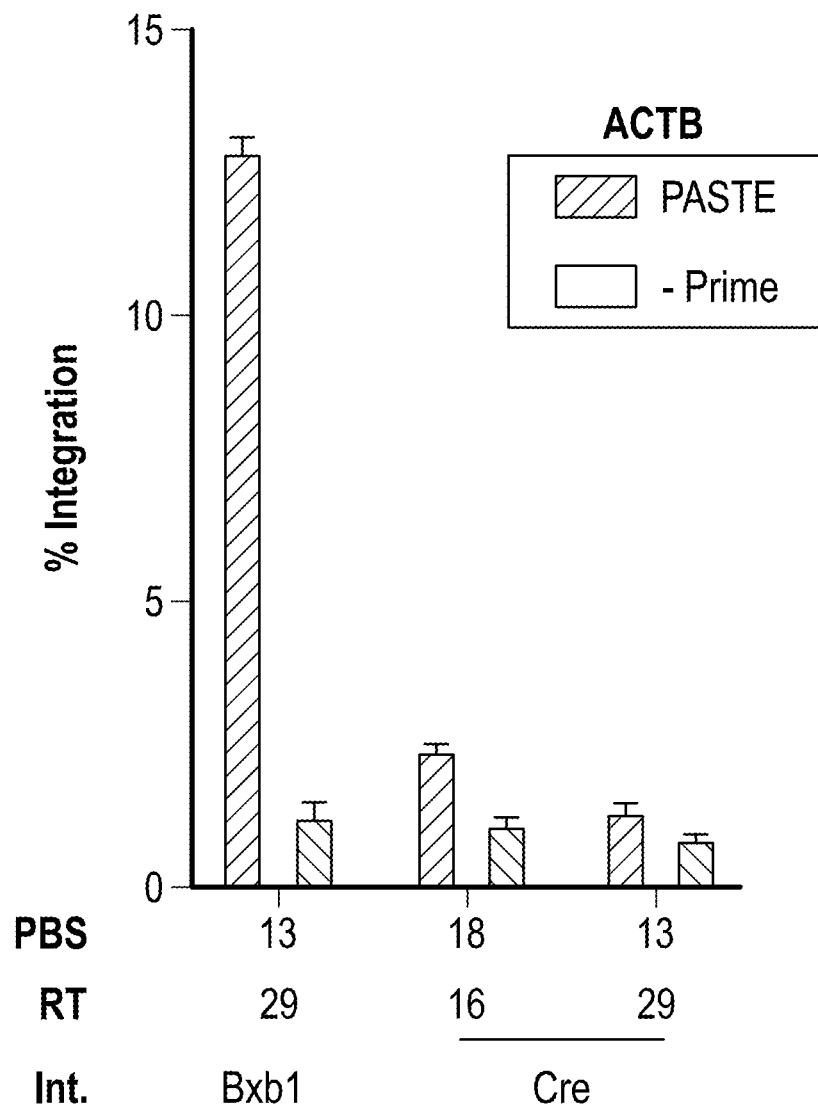
FIG. 29G shows a comparison of GFP cargo integration efficiency between Bxb1 integrases and Cre recombinase according to embodiments of the present teachings.
Figure 29H:
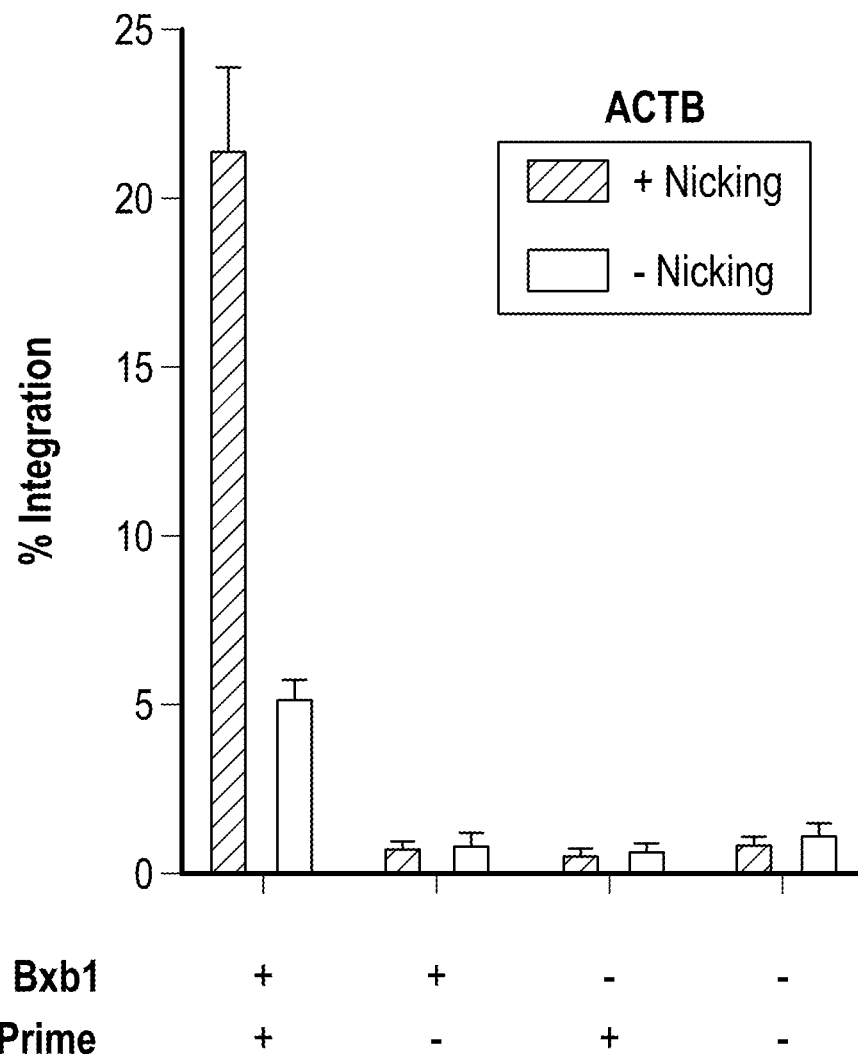
FIG. 29H shows the dependence of PASTE editing activity on different prime and integrase components according to embodiments of the present teachings.
Figure 29I:
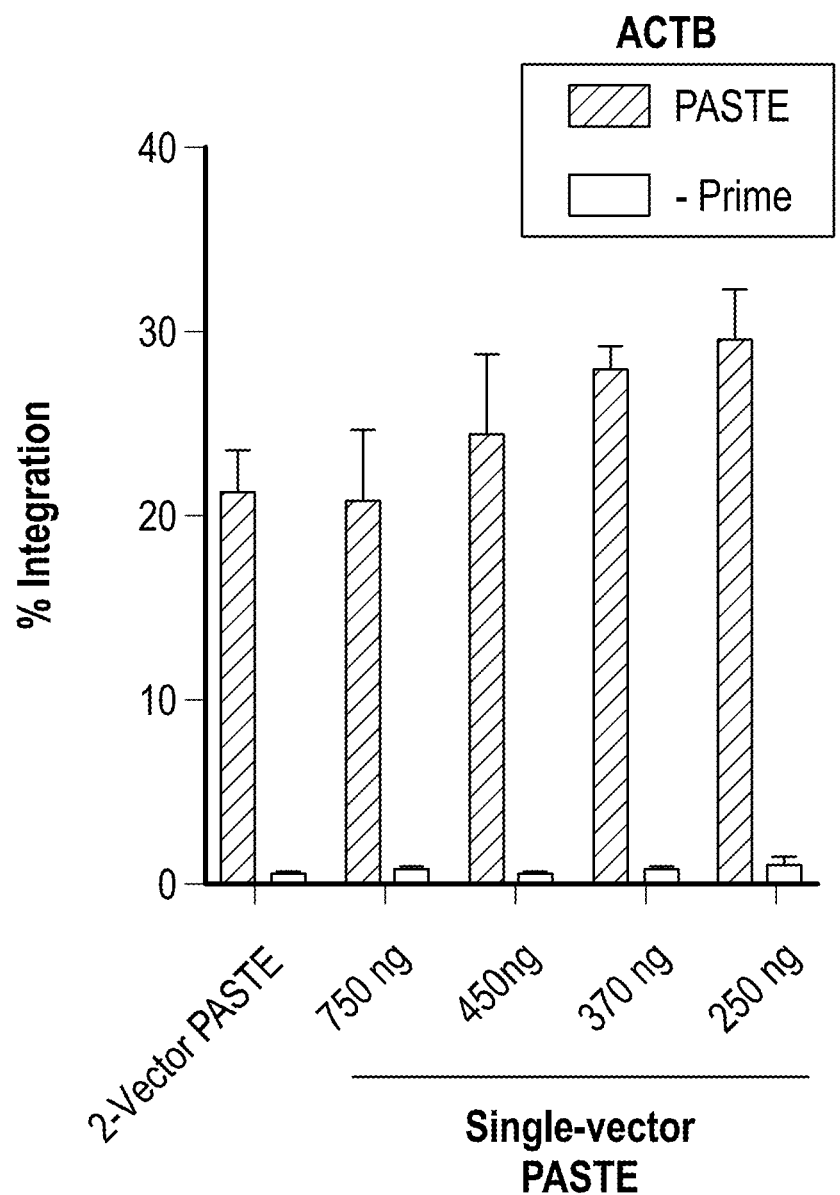
FIG. 29I shows a titration of a single vector PASTE system (SpCas9-RT-P2A-Bxb1) on integrase efficiency according to embodiments of the present teachings.
Figure 29J:
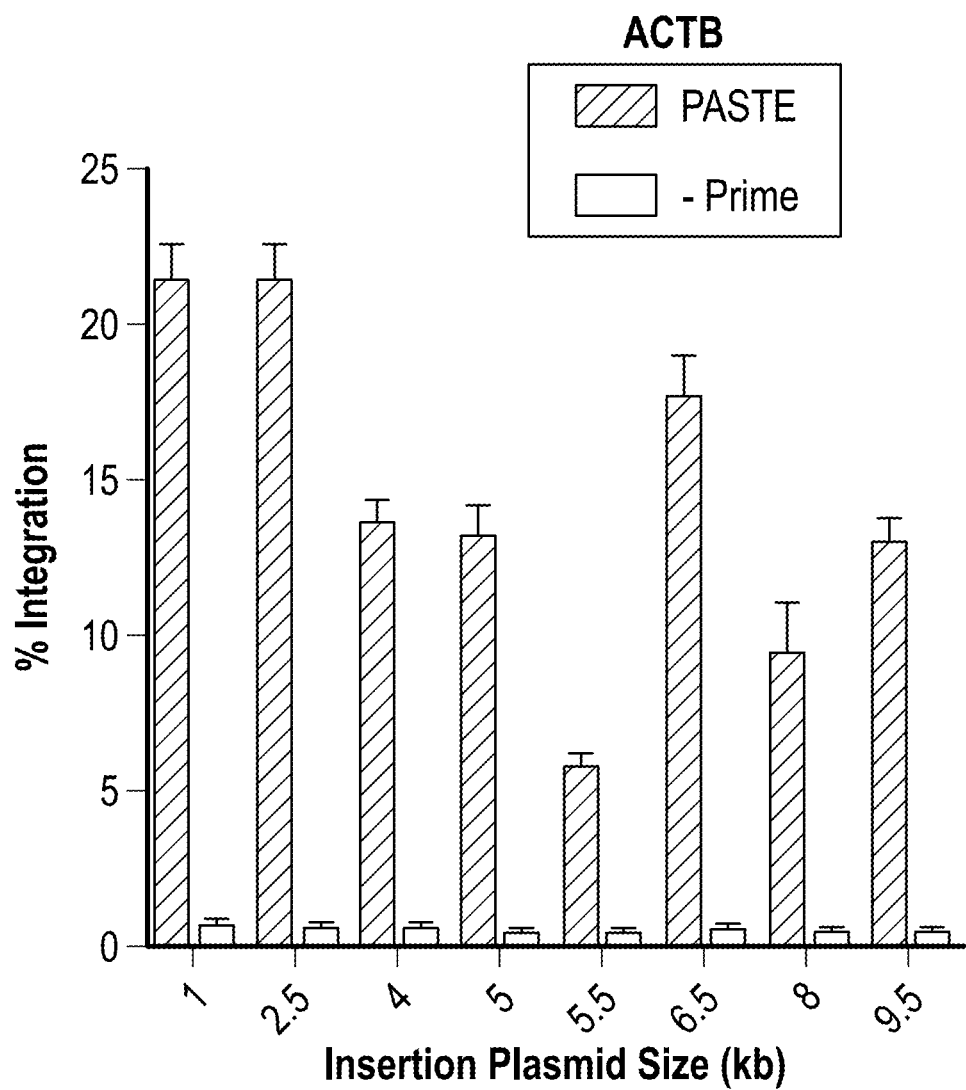
FIG. 29J shows the effect of cargo size on PASTE insertion efficiency at the endogenous ACTB target according to embodiments of the present teachings.
Figure 29K:
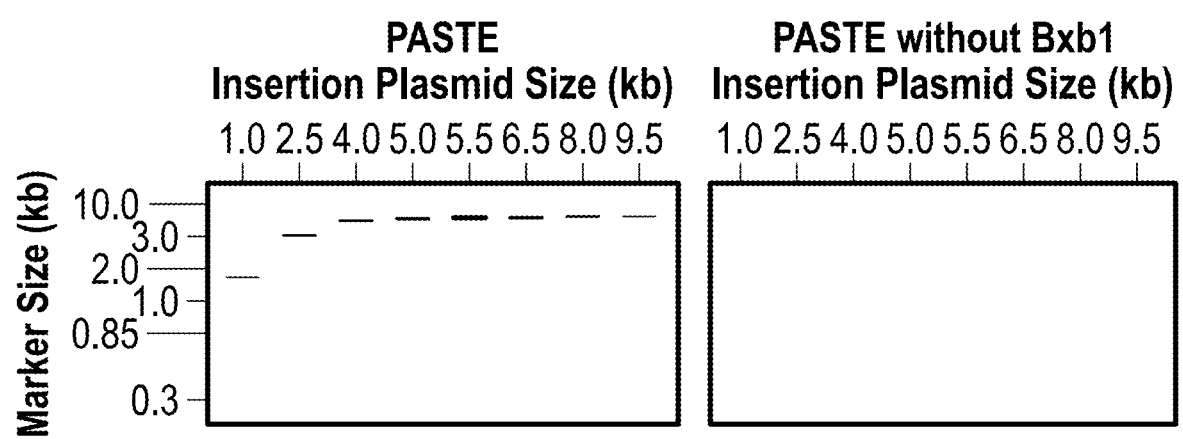
FIG. 29K shows a gel electrophoresis showing complete insertion by PASTE for multiple cargo sizes according to embodiments of the present teachings.
Figure 30A:
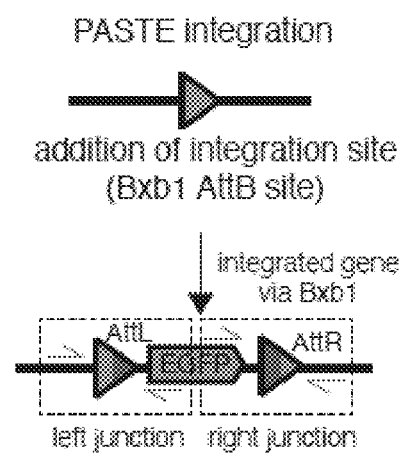
FIG. 30A shows a schematic of PASTE integration, including resulting attR and attL sites that are generated and PCR primers for assaying the integration junctions according to embodiments of the present teachings.
Figure 30B:
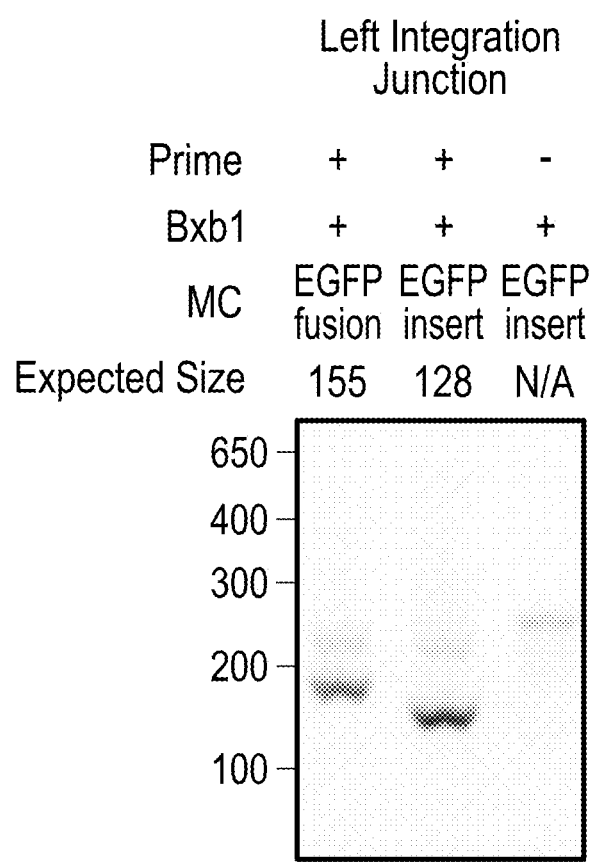
FIG. 30B shows a PCR and gel electrophoresis readout of left integration junction from PASTE insertion of GFP at the ACTB locus, wherein the insertion is analyzed for in-frame and out-of-frame GFP integration experiments as well as for a no prime control and expected sizes of the PCR fragments are shown using the primers shown in the schematic in subpanel FIG. 30A according to embodiments of the present teachings.
Figure 30C:
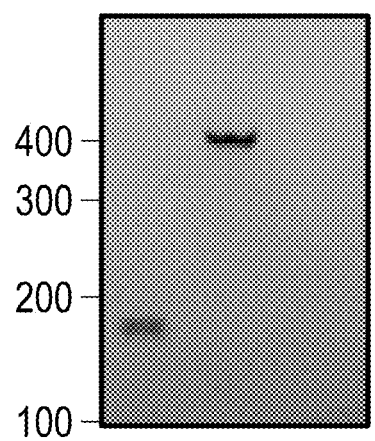
FIG. 30C shows a PCR and gel electrophoresis readout of right integration junction from PASTE insertion of GFP at the ACTB locus, wherein the insertion is analyzed for in-frame and out-of-frame GFP integration experiments as well as for a no prime control and the expected sizes of the PCR fragments are shown using the primers shown in the schematic in subpanel FIG. 30A according to embodiments of the present teachings.
Figure 30D:
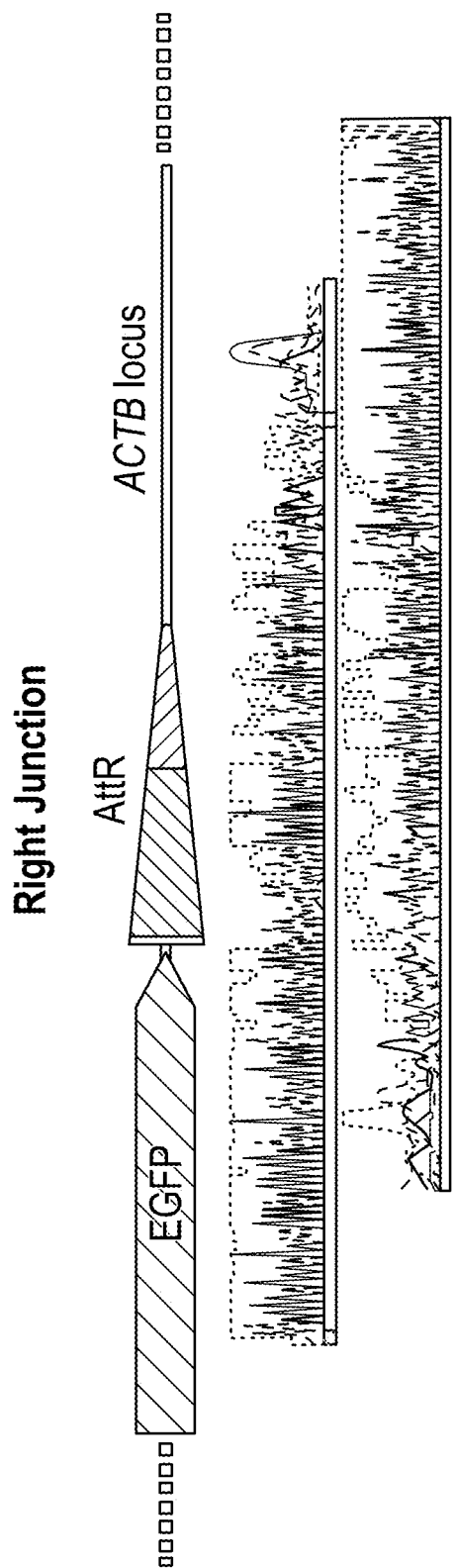
FIG. 30D shows a Sanger sequencing shown for the right integration junction for an in-frame fusion of GFP via PASTE to the N-terminus of ACTB according to embodiments of the present teachings.
Figure 30E:
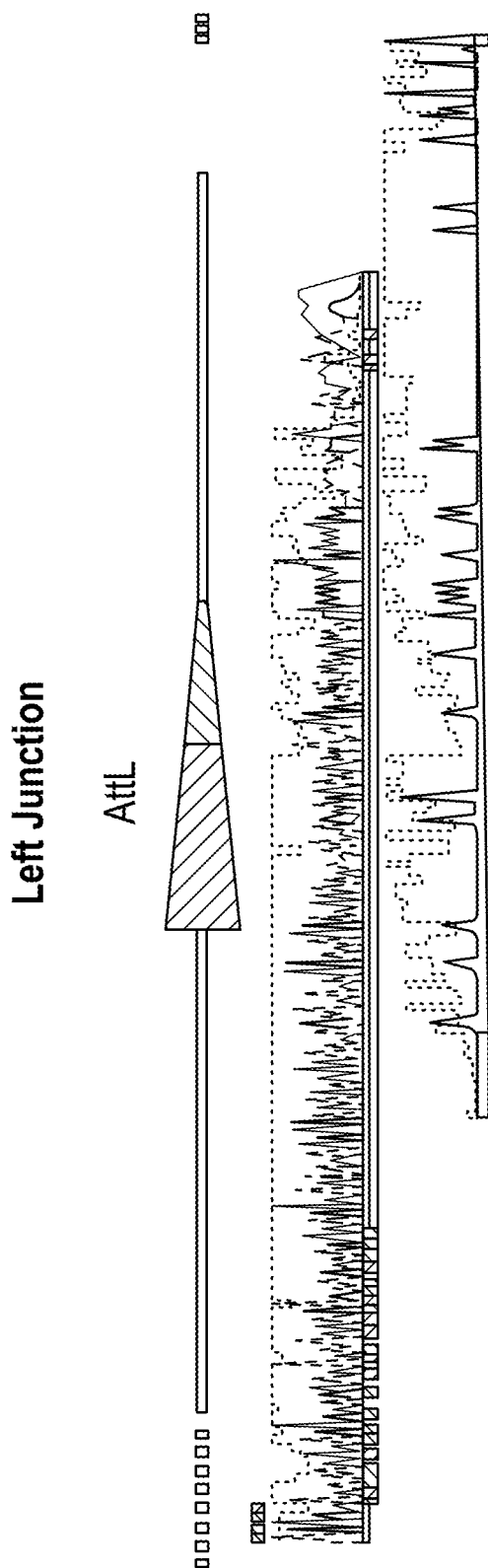
FIG. 30E shows a Sanger sequencing shown for the left integration junction for an in-frame fusion of GFP via PASTE to the N-terminus of ACTB according to embodiments of the present teachings.

PegRNAs containing different attB length truncations were assessed (FIG. 29A). Prime editing was found to be capable of inserting sequences up to 56 bp at the beta-actin (ACTB) gene locus, with higher efficiency at lengths below 31 bp (FIGS. 29A-B) The integration of cognate landing sites was tested for multiple insertion enzymes: Bxb1, TP901, and phiBT1 phage serine integrases and Cre recombinase. Prime editing successfully inserted all landing sites tested, with efficiencies between 10-30% (FIGS. 29C-D). To test the complete system, all components were combined and delivered in a single transfection: the prime editing vector, the landing site containing pegRNA, a nicking guide for stimulating prime editing, a mammalian expression vector for the corresponding integrase or recombinase and a 969 bp minicircle DNA cargo encoding green fluorescent protein (GFP) (FIG. 29E). GFP integration rates among the four integrases and recombinases were compared and Bxb1 integrase was found to have the highest integration rate (~20%) at the targeted ACTB locus and require the prime editing nicking guide for optimal performance (FIGS. 29F-H). Finally, to reduce the number of transfected components, Bxb1 was co-expressed with the SpCas9-M-MLV reverse transcriptase (PE2) fusion protein via a P2A protein cleavage site. This combination maintained high GFP insertion efficiency, up to 30% (FIG. 29E). The complete system, PASTE, achieved precise integration of templates as large as 9,500 bp with greater than 10% integration efficiency (FIGS. 29J-K and 26E), with complete integration of the full-length cargo confirmed by Sanger sequencing (FIG. 30A-E).

Example 19

Impact of Prime Editing and Integrase Parameters on PRIME Editing

The impact of prime editing and integrase parameters on the integration efficiency of PRIME editing was assessed.

Figure 31B:
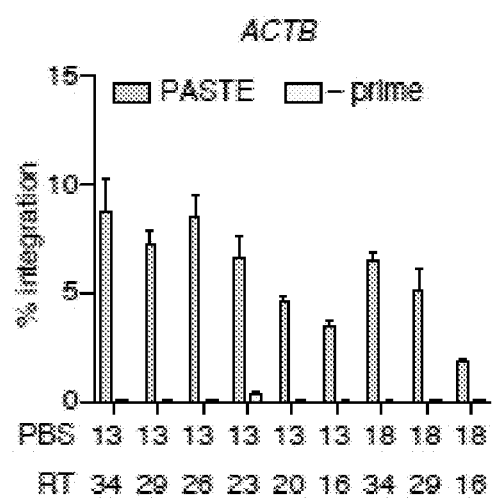
FIG. 31B shows the impact of PBS and RT length on PASTE integration of GFP at the ACTB locus according to embodiments of the present teachings.
Figure 31C:
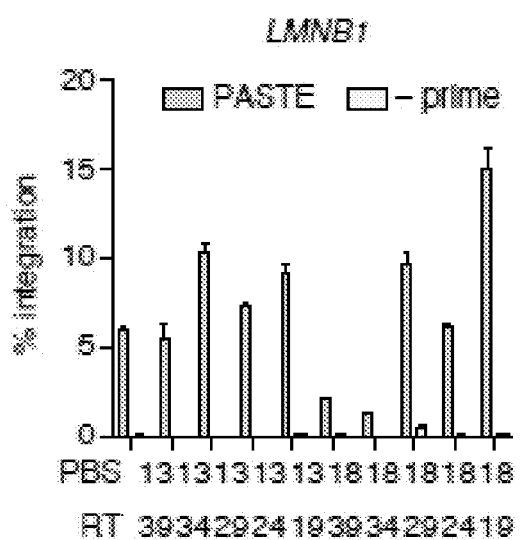
FIG. 31C shows the impact of PBS and RT length on PASTE integration of GFP at the LMNB1 locus according to embodiments of the present teachings.

Relevant pegRNA parameters for PASTE include the primer binding site (PBS), reverse transcription template (RT), and attB site lengths, as well as the relative locations and efficacy of the pegRNA spacer and nicking guide (FIG. 31A). A range of PBS and RT lengths were tested at two loci, ACTB and lamin B1 (LMNB1), and rules governing efficiency were found to vary between loci, with shorter PBS lengths and longer RT designs having higher editing at the ACTB locus (FIG. 31B) and longer PBS and shorter RT designs performing better at LMNB1 (FIG. 31C).

Figure 31D:
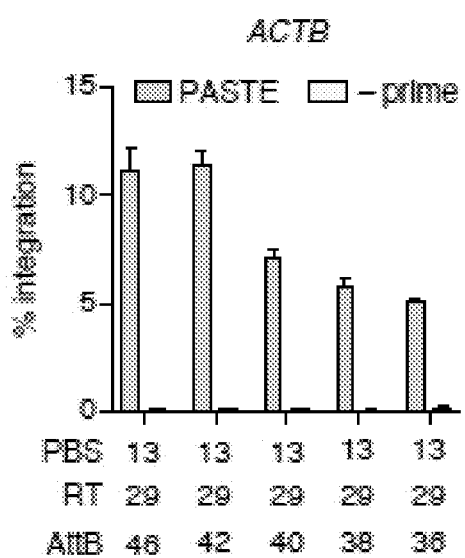
FIG. 31D shows the impact of attB length on PASTE integration of GFP at the ACTB locus according to embodiments of the present teachings.
Figure 31E:
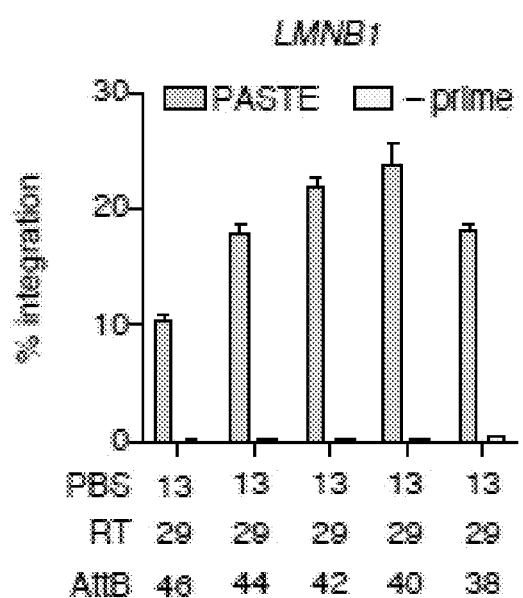
FIG. 31E shows the impact of attB length on PASTE integration of GFP at the LMNB1 locus according to embodiments of the present teachings.
Figure 31F:
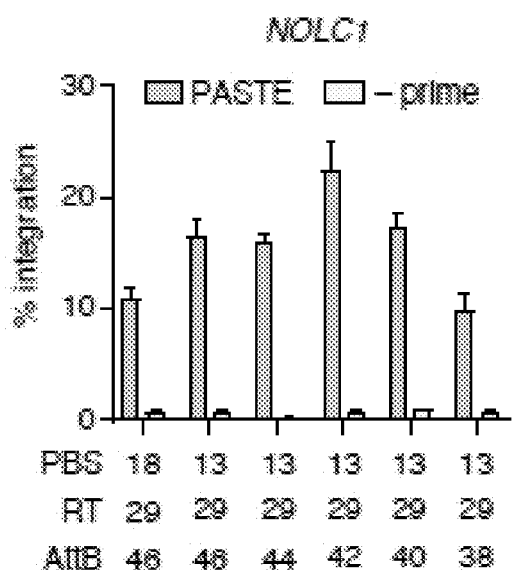
FIG. 31F shows the impact of attB length on PASTE integration of GFP at the NOLC1 locus according to embodiments of the present teachings.

The length of the attB landing site must balance two conflicting factors: the higher efficiency of prime editing for smaller inserts and reduced efficiency of Bxb1 integration at shorter attB lengths. AttB lengths were evaluated atACTB, LMNB1, and nucleolar phosphoprotein p130 (NOLC1), and the optimal attB length was found to be locus dependent. At the ACTB locus, long attB lengths could be inserted by prime editing (FIG. 29B) and overall PASTE efficiencies for the insertion of GFP were highest for long attB lengths (FIG. 31d). In contrast, intermediate attB lengths had higher overall integration efficiencies (>20%) at LMNB1 (FIG. 31E) and NOLC1 (FIG. 31F), indicating that the increased efficiency of installing shorter attB sequences overcame the reduction of Bxb1 integration at these sites.

Figure 32A:
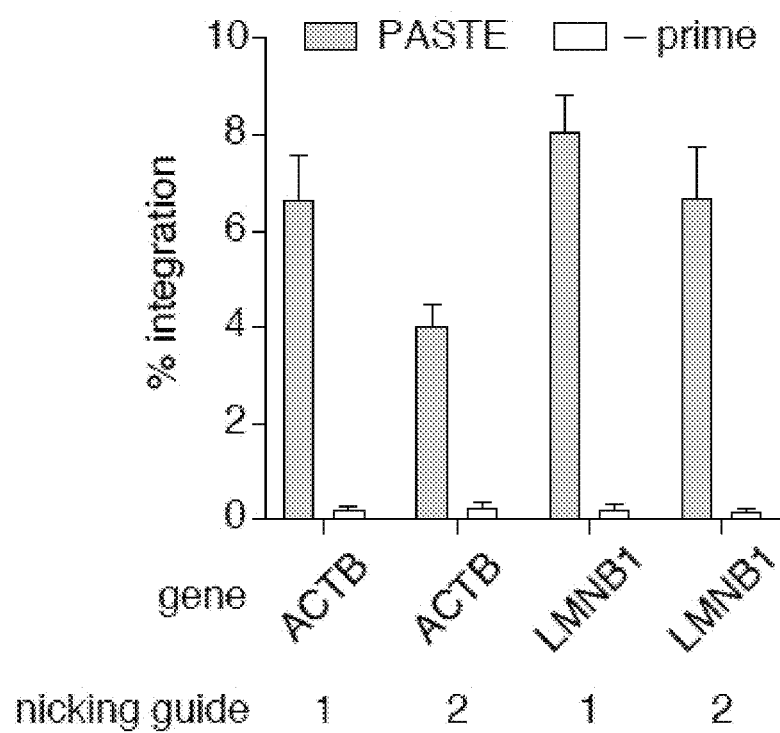
FIG. 32A shows the PASTE insertion efficiency at ACTB and LMNB1 loci with two different nicking guide designs according to embodiments of the present teachings.
Figure 32B:
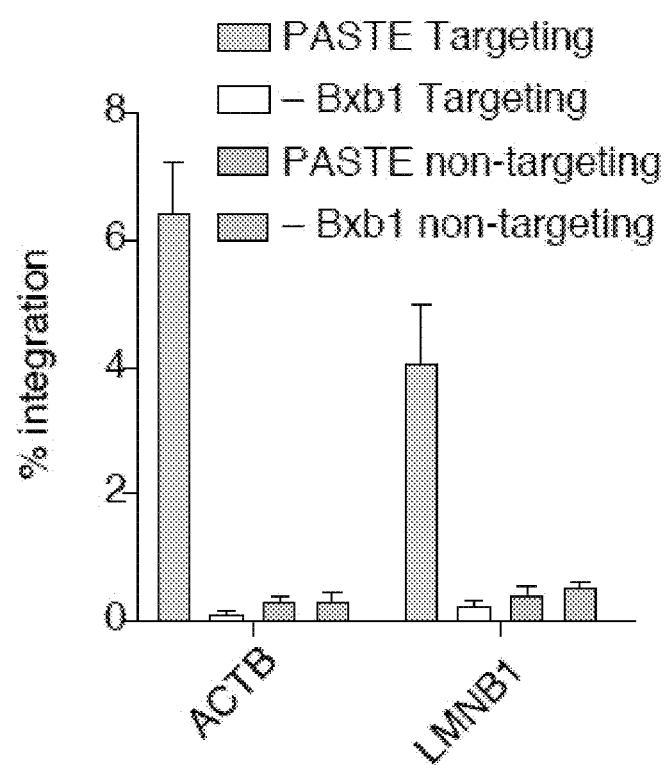
FIG. 32B shows the PASTE editing efficiency at ACTB and LMNB1 with target and non-targeting spacers and matched pegRNAs with and without Bxb1 expression according to embodiments of the present teachings.

The PE3 version of prime editing combines PE2 and an additional nicking guide to bias resolution of the flap intermediate towards insertion. To test the importance of nicking guide selection on PASTE editing, editing at ACTB and LMNB1 loci was tested with two nicking guide positions. Suboptimal nicking guide positions were found to reduce the PASTE efficiency up to 30% (FIG. 32A) in agreement with the 75% reduction of PASTE efficiency in the absence of nicking guide (FIG. 29G). The pegRNA spacer sequence was found to be necessary for PASTE editing, and substitution of the spacer sequence with a non-targeting guide was found to eliminate editing (FIG. 32B).

Figure 33A:
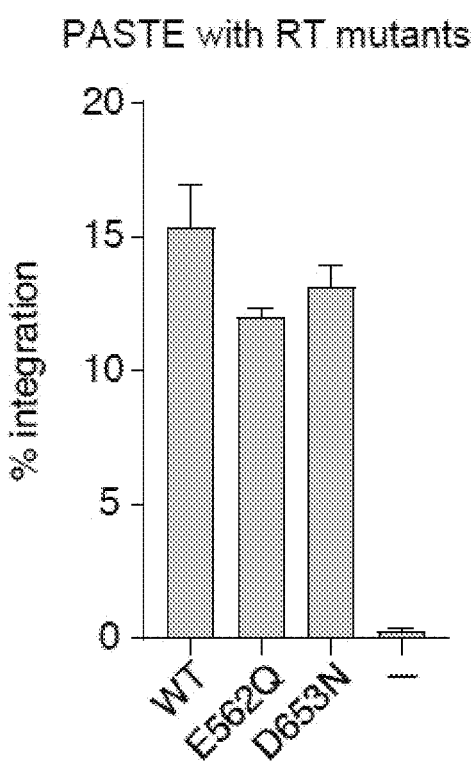
FIG. 33A shows the PASTE integration of GFP at the ACTB locus with different Bxb1 catalytic mutants according to embodiments of the present teachings.
Figure 33B:
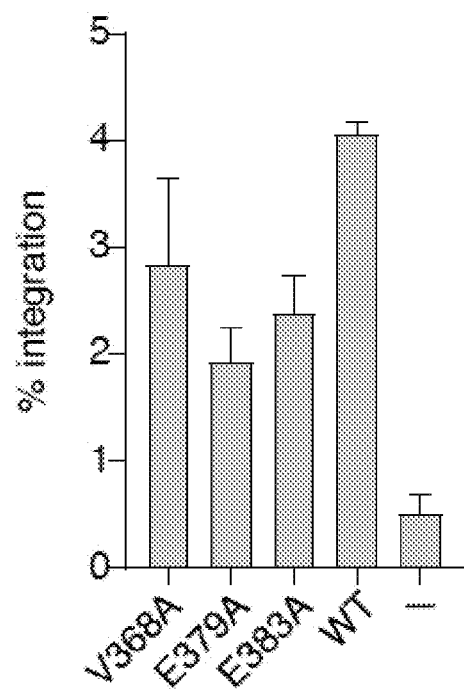
FIG. 33B shows the PASTE integration of GFP at the ACTB locus with different RT catalytic mutants according to embodiments of the present teachings.

Rational mutations were also introduced in both the Bxb1 integrase and reverse transcriptase domain of the PE2 construct to optimize PASTE further. While some of these mutations were well tolerated by PASTE (FIGS. 33A-B), none of them improved PASTE editing efficiency.

Figure 31G:
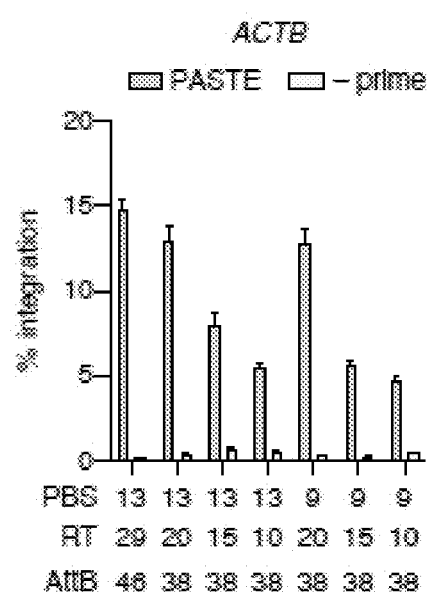
FIG. 31G shows the impact of minimal PBS, RT, and attB lengths on PASTE integration efficiency of GFP at the ACTB locus according to embodiments of the present teachings.
Figure 31H:
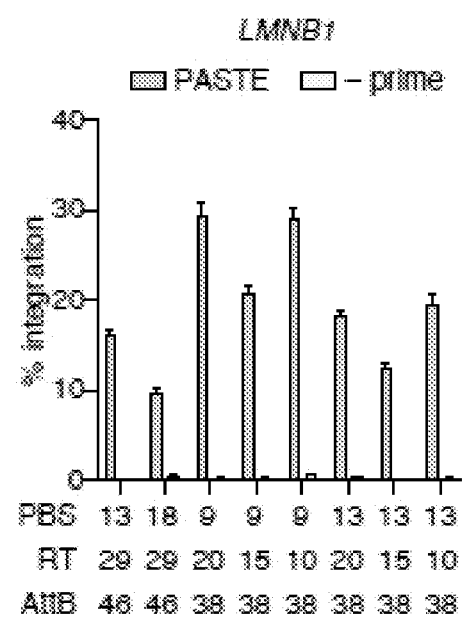
FIG. 31H shows the impact of minimal PBS, RT, and attB lengths on PASTE integration efficiency of GFP at the LMNB1 locus according to embodiments of the present teachings.
Figure 31I:
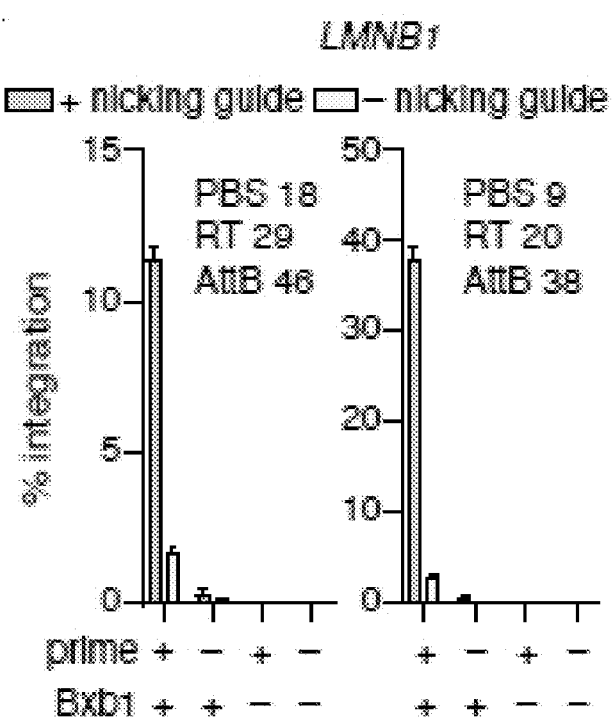
FIG. 31I shows the PASTE integration of GFP at the LMNB1 locus in the presence and absence of nicking guide, prime, and Bxb1 with a minimally compact pegRNA containing a 38 bp attB compared to a longer pegRNA design according to embodiments of the present teachings.

Short RT and PBS lengths can offer additional improvements for editing. A panel of shorter RT and PBS guides were tested at ACTB and LMNB1 loci and while shorter RT and PBS sequences did not increase editing at ACTB (FIG. 31G), it was found that they had improved editing at LMNB1 (FIG. 31H) with best performing guides reaching GFP insertion rates of ~40% (FIG. 31I).

Example 20

PASTE Tagging at Multiple Endogenous Genes

Figure 34A:
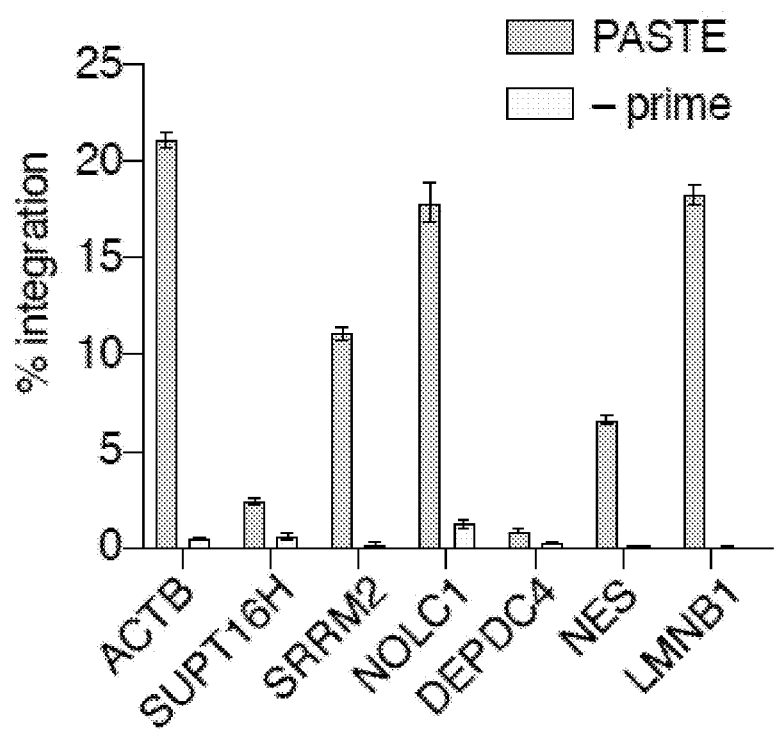
FIG. 34A shows the GFP integration by PASTE at a panel of endogenous genomic loci according to embodiments of the present teachings.
Figure 34B:
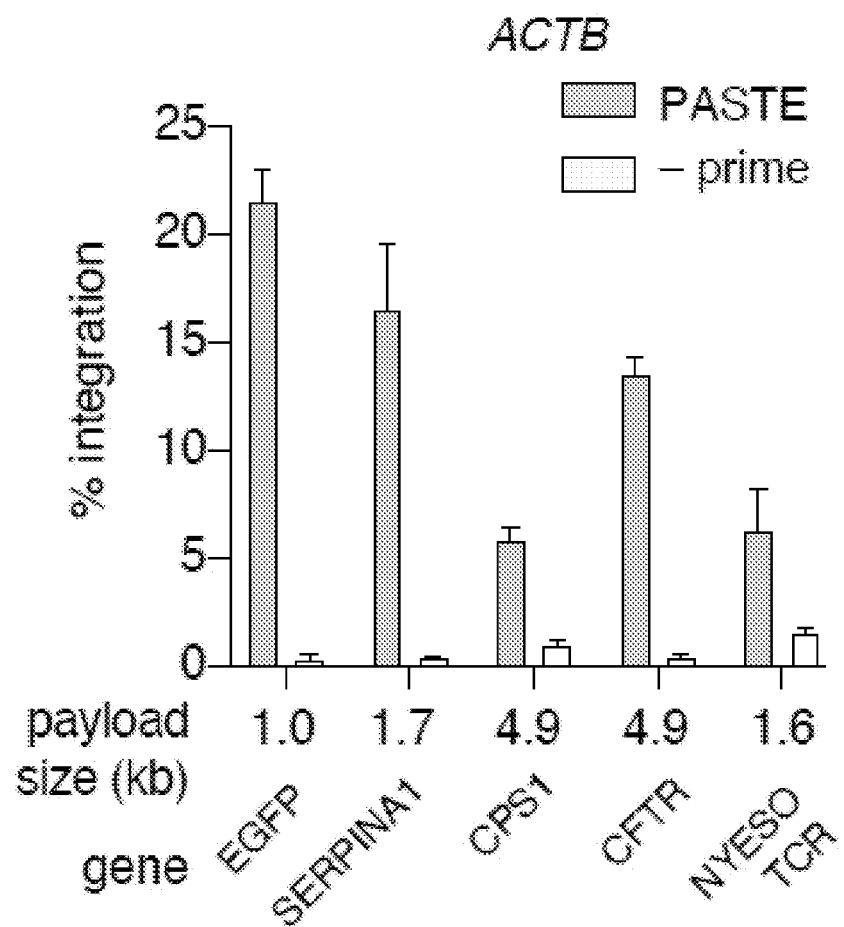
FIG. 34B shows the integration of a panel of different gene cargo at ACTB locus via PASTE according to embodiments of the present teachings.
Figure 34C:
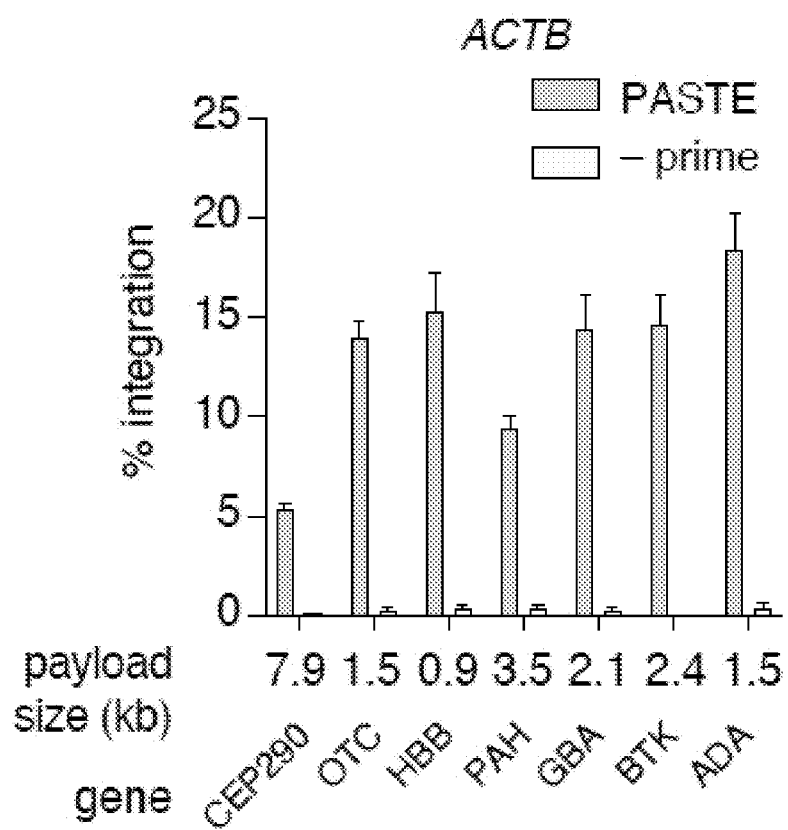
FIG. 34C shows the integration efficiency of therapeutically relevant genes at the ACTB locus according to embodiments of the present teachings.
Figure 35:
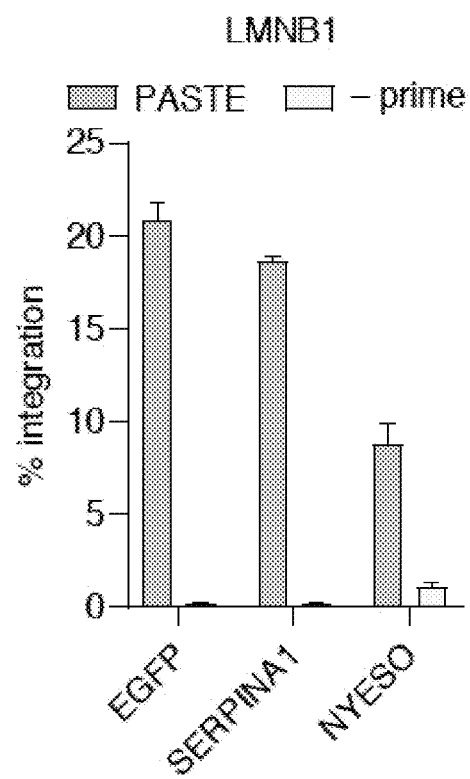
FIG. 35 shows the integration of a panel of different gene cargo at LMNB1 locus via PASTE according to embodiments of the present teachings.

GFP insertion efficiency was measured at seven different gene loci—ACTB, SUPT16H, SRRAM2, NOLC1, DEPDC4, NES, and LMNB1—to test the versatility of the PASTE programming. A range of integration rates up to 22% was found (FIG. 34A). Because PASTE does not require homology or sequence similarity on cargo plasmids, integration of diverse cargo sequences is modular and easily scaled across different loci. Six different gene cargos, varying in size from 969 bp to 4906 bp, were tested for insertion at ACTB and LMNB1 loci with PASTE. Integration frequencies between 5% and 22% depending on the gene and insertion locus were found (FIGS. 34B and 35). Additionally, a panel of seven common therapeutic genes, CEP290, OTC, HBB, PAH, GBA, BTK, and ADA was evaluated for insertion at the ACTB locus, and the efficient integration of these cargos were found between 5%-20% (FIG. 34C).

Figure 34D:
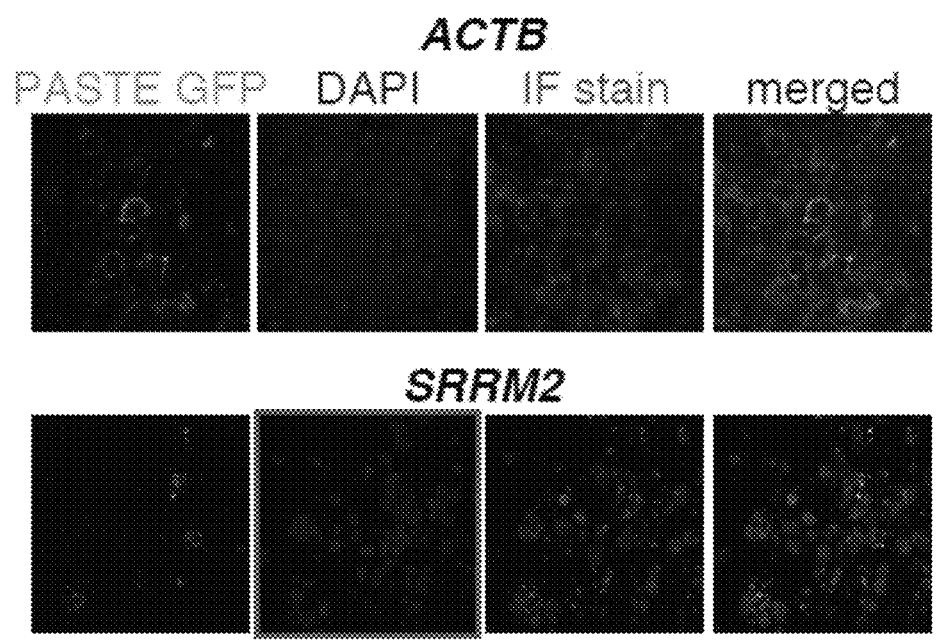
FIG. 34D shows the endogenous protein tagging with GFP via PASTE by in-frame endogenous gene tagging at the ACTB loci and SRRM2 loci according to embodiments of the present teachings.

The precise insertions of PASTE for in-frame protein tagging or expressing cargo without disruption of endogenous gene expression was assessed. As Bxb1 leaves residual sequences in the genome (termed attL and attR) after cargo integration, these genomic scars can serve as protein linkers. The frame of the attR sequence was positioned through strategic placement of the attP on the minicircle cargo, achieving a suitable protein linker, GGLSGQP-PRSPSSGSSG (SEQ ID NO: 427). Using this linker, four genes (ACTB, SRRM2, NOLC1, and LMNB1) were tagged with GFP using PASTE. To assess correct gene tagging, the subcellular location of GFP was compared with the tagged gene product by immunofluorescence. For all four targeted loci, GFP co-localized with the tagged gene product, indicating successful tagging (FIGS. 34D-E).

Example 21

Orthogonal Sequence Preferences for Bxb1 Integration

Figure 36A:
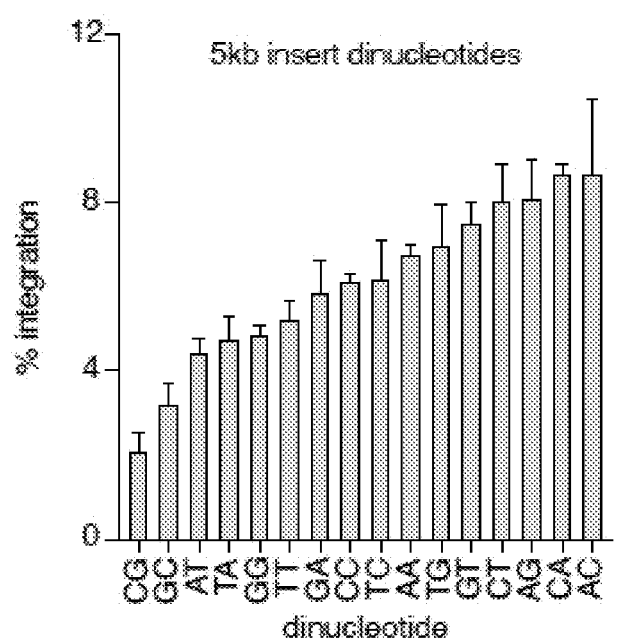
FIG. 36A shows the PASTE integration efficiency for all 16 central dinucleotide attB/attP sequence pairs with a 5 kb GFP template at the ACTB locus according to embodiments of the present teachings.

The central dinucleotide of Bxb1 is involved in the association of attB and attP sites for integration, and changing the matched central dinucleotide sequences can modify integrase activity and provide orthogonality for insertion of two genes. Expanding the set of attB/attP dinucleotides can enable multiplexed gene insertion with PASTE. The efficiency of GFP integration at the ACTB locus with PASTE across all 16 dinucleotide attB/attP sequence pairs was profiled to find optimal attB/attP dinucleotides for PASTE insertion. Several dinucleotides with integration efficiencies greater than the wild-type GT sequence were found (FIG. 36A). A majority of dinucleotides had 75% editing efficiency or greater compared to wild-type attB/attP efficiency, implying that these dinucleotides can be orthogonal channels for multiplexed gene insertion with PASTE.

Figure 36B:
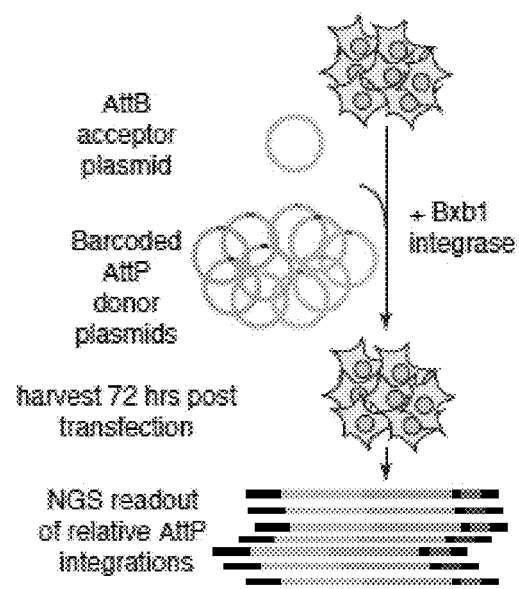
FIG. 36B shows a schematic of the pooled attB/attP dinucleotide orthogonality assay, wherein each attB dinucleotide sequence is co-transfected with a barcoded pool of all 16 attP dinucleotide sequences and Bxb1 integrase, relative integration efficiencies are determined by next generation sequencing of barcodes, and all 16 attB dinucleotides are profiled in an arrayed format with attP pools according to embodiments of the present teachings.
Figure 36C:
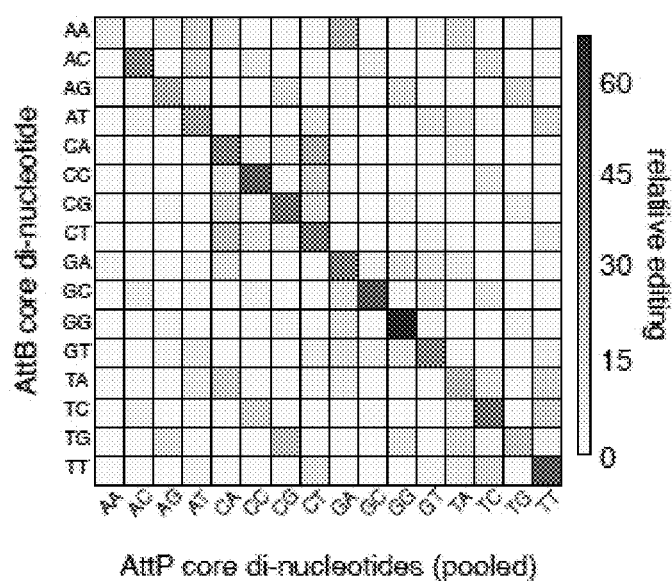
FIG. 36C shows the relative insertion preferences for all possible attB/attP dinucleotide pairs determined by the pooled orthogonality assay according to embodiments of the present teachings.
Figure 37:
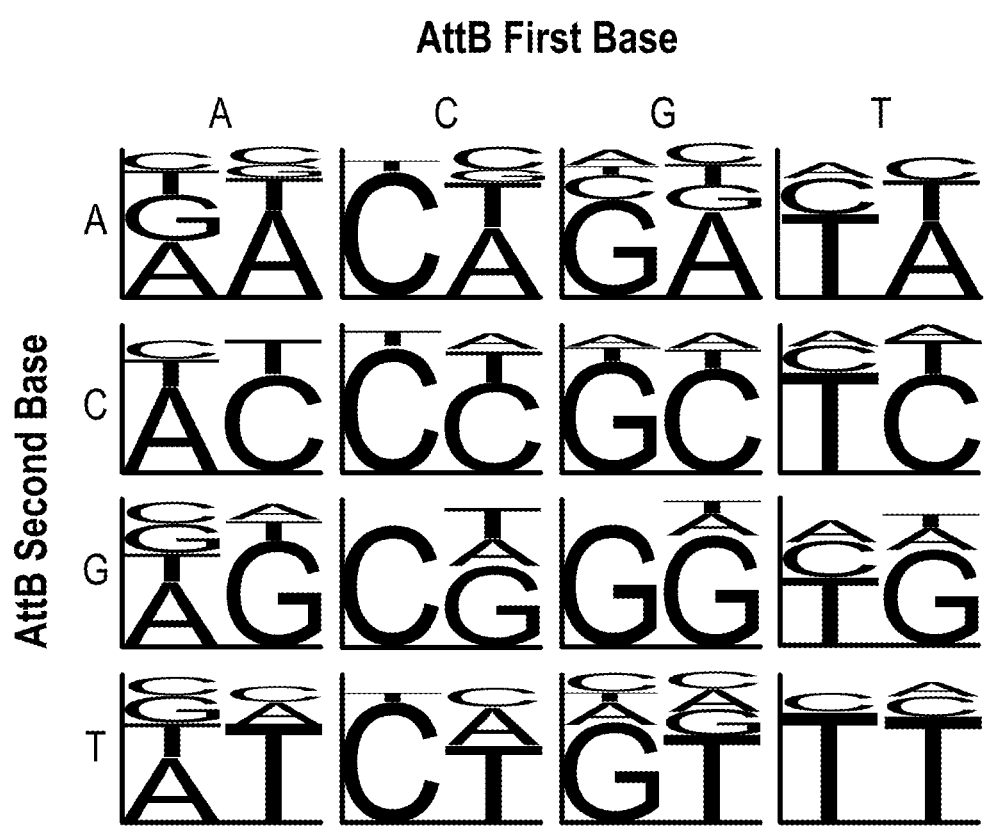
FIG. 37 shows the orthogonality of Bxb1 dinucleotides as measured by a pooled reporter assay, wherein each web logo motif shows the relative integration of different attP sequences in a pool at a denoted attB sequence with the listed dinucleotide according to embodiments of the present teachings.

The specificity of matched and unmatched attB/attP dinucleotide interactions was then assessed. The interactions between all dinucleotide combinations in a scalable fashion using a pooled assay to compare attB/attP integration were profiled (FIG. 36B). By barcoding 16 attP dinucleotide plasmids with unique identifiers, co-transfecting this attP pool with the Bxb1 integrase expression vector and a single attB dinucleotide acceptor plasmid, and sequencing the resulting integration products, the relative integration efficiencies of all possible attB/attP pairs were measured (FIG. 36C). Dinucleotide specificity was found to vary, with some dinucleotides (GG) exhibiting strong self-interaction with negligible crosstalk, and others (AA) showing minimal self-preference. Sequence logos of attP preferences (FIG. 37) revealed that dinucleotides with C or G in the first position have stronger preferences for attB dinucleotide sequences with shared first bases, while other attP dinucleotides, especially those with an A in the first position, have reduced specificity for the first attB base.

Figure 36D:
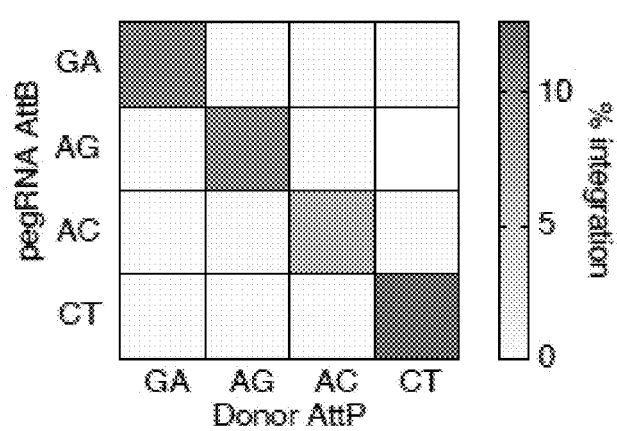
FIG. 36D shows the orthogonality of top 4 attB/attP dinucleotide pairs evaluated for GFP integration with PASTE at the ACTB locus according to embodiments of the present teachings.

GA, AG, AC, and CT dinucleotide pegRNAs were then tested for GFP integration at ACTB, either paired with their corresponding attP cargo or mispaired with the other three dinucleotide attP sequences. All four of the tested dinucleotides efficiently were found to integrate cargo only when paired with the corresponding attB/attP pair, with no detectable integration across mispaired combinations (FIG. 36D).

Example 22

Multiplex Gene Integration with PASTE

Figure 38A:
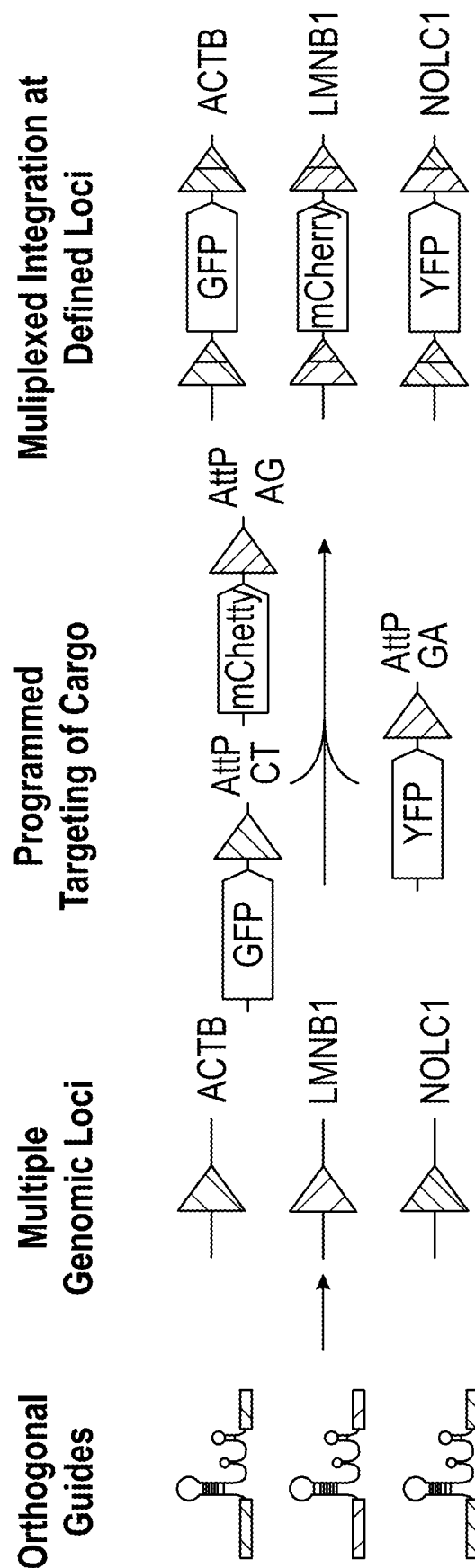
FIG. 38A shows a schematic of multiplexed integration of different cargo sets at specific genomic loci, wherein three fluorescent cargos (GFP, mCherry, and YFP) are inserted orthogonally at three different loci (ACTB, LMNB1, NOLC1) for in-frame gene tagging according to embodiments of the present teachings.
Figure 38B:
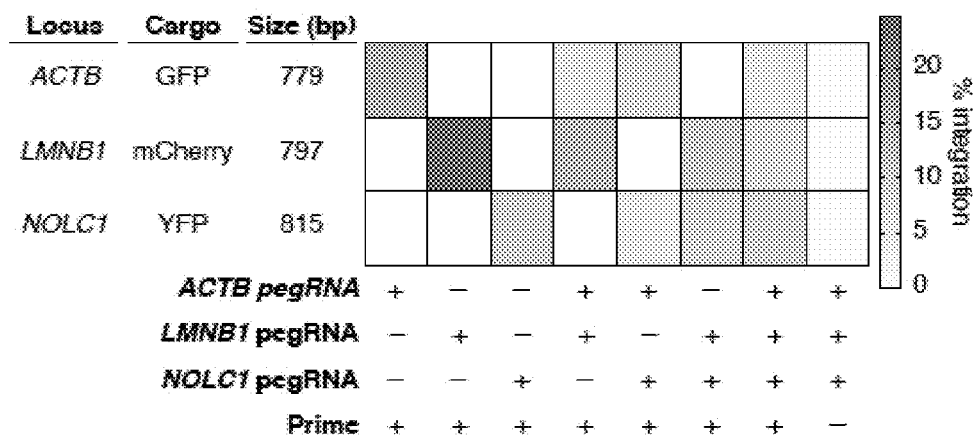
FIG. 38B shows the efficiency of multiplexed PASTE insertion of combinations of fluorophores at ACTB, LMNB1, and NOLC1 loci according to embodiments of the present teachings.

Multiplexing in cells by using orthogonal pegRNAs that direct a matched attP cargo to a specific site in the genome was assessed (FIG. 38A). Selecting the three top dinucleotide attachment site pairs (CT, AG, and GA), pegRNAs that target ACTB (CT), LMNB1 (AG), and NOLC1 (GA) and corresponding minicircle cargo containing GFP (CT), mCherry (AG), and YFP (GA) were designed. Upon co-delivering these reagents to cells, single-plex, dual-plex, and trip-plex editing of all possible combinations of these pegRNAs and cargo in the range of 5%-25% integration was found to be achieved (FIG. 38B).

An application for multiplexed gene integration is for labeling different proteins to visualize intracellular localization and interactions within the same cell. PASTE was used to simultaneously tag ACTB (GFP) and NOLC1 (mCherry) or ACTB (GFP) and LMNB1 (mCherry) in the same cell. No overlap of GFP and mCherry fluorescence was observed and tagged genes were confirmed to be visible in their appropriate cellular compartments, based on the known subcellular localizations of the ACTB, NOLC1 and LMNB1 protein products (FIGS. 15A-B).

Example 23

PASTE Efficiencies Compared With DSB-based Insertion Methods

PASTE efficiencies were found to exceed comparable DSB-based insertion methods.

Figure 39A:
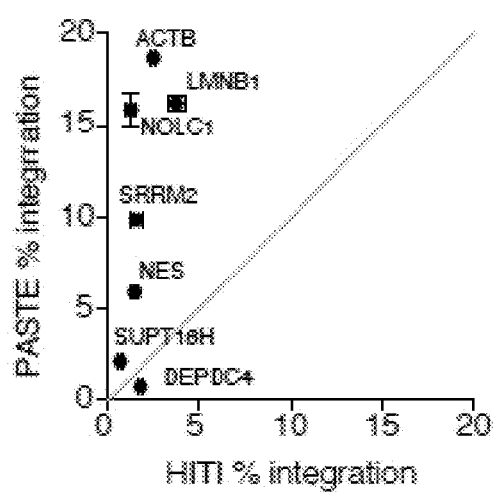
FIG. 39A shows the GFP integration efficiency at a panel of genomic loci by PASTE compared to insertion rates by homology-independent targeted integration (HITI) according to embodiments of the present teachings.
Figure 39B:
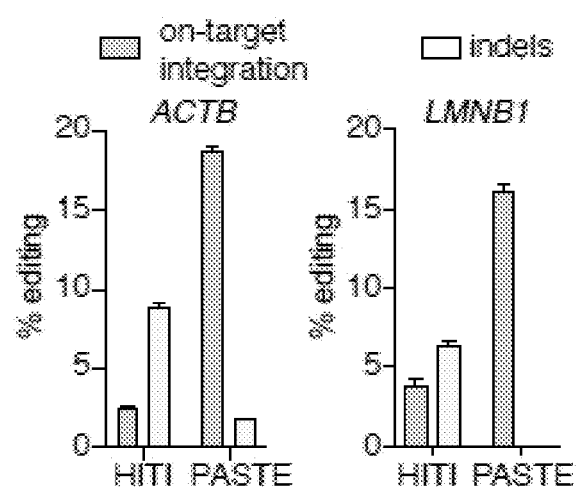
FIG. 39B shows a comparison of unintended indel generation by PASTE and HITI at the ACTB and LMNB1 target sites, wherein the on-target EGFP integration rate observed compared to unintended indels is shown according to embodiments of the present teachings.
Figure 39C:
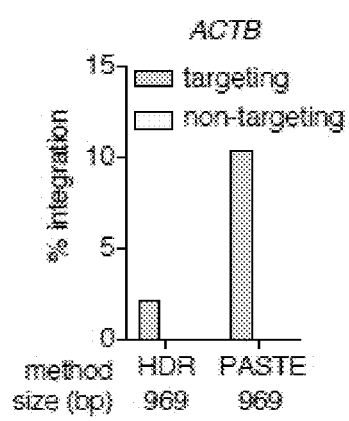
FIG. 39C shows the integration of a GFP template by PASTE at the ACTB locus compared to homology-directed repair (HDR) at the same target, wherein the quantification is by single-cell clone counting, wherein targeting and non-targeting guides were used for HDR insertion, and wherein for PASTE targeting and non-targeting refers to the presence or absence of the SpCas9-RT protein respectively according to embodiments of the present teachings.
Figure 39D:
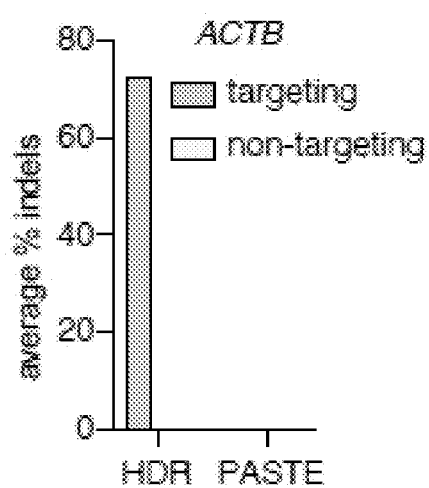
FIG. 39D shows the comparison of unintended indel generation by PASTE and HDR based EGFP insertion at the ACTB target site, wherein the average indel rate measured across all single-cell clones generated is showed according to embodiments of the present teachings.
Figure 40A:
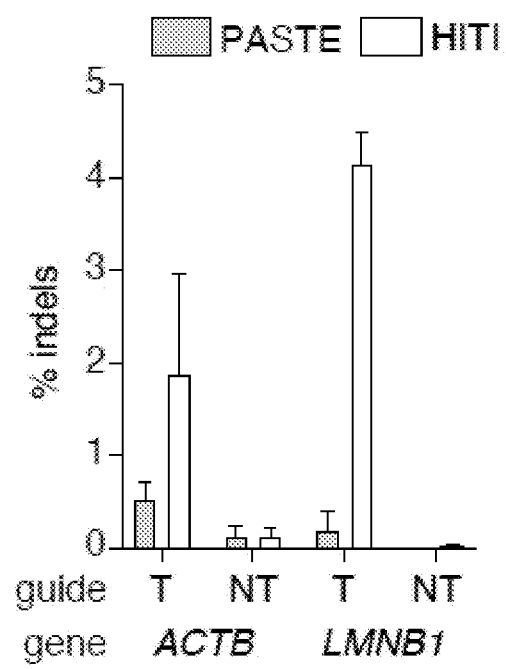
FIG. 40A shows a comparison of indel rates generated by PASTE and HITI mediated insertion of EGFP at the ACTB and LMNB1 loci in HepG2 cells according to embodiments of the present teachings.
Figure 40B:
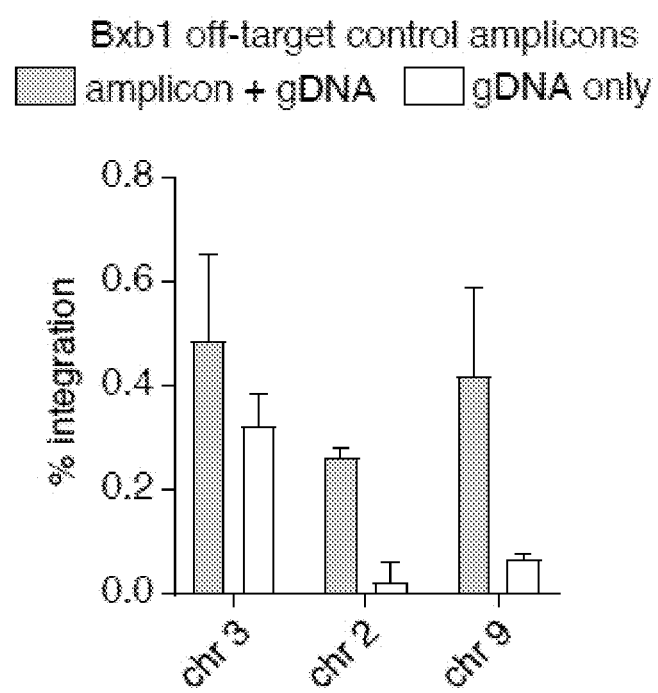
FIG. 40B shows the validation of ddPCR assays for detecting editing at predicted Bxb1 offtarget sites using synthetic amplicons according to embodiments of the present teachings.
Figure 40C:
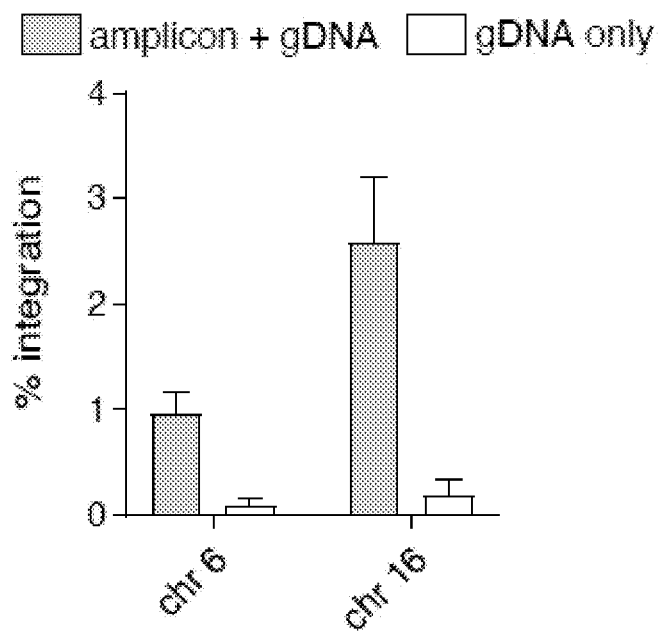
Figure 40D:
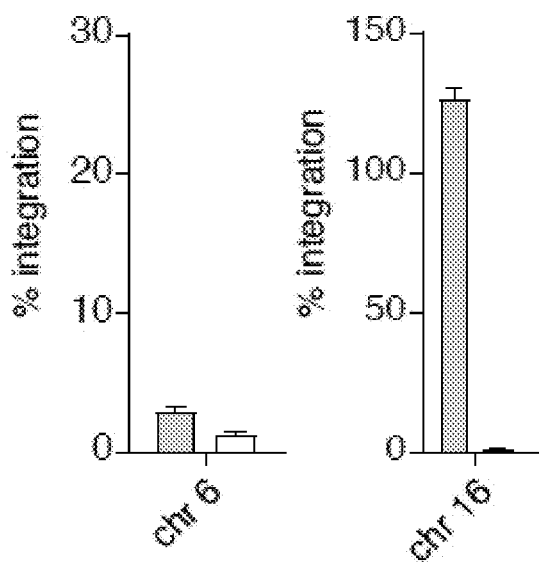

PASTE editing was assessed alongside DSB-dependent gene integration using either NHEJ (i.e., homology-independent targeted integration, HITI) or HDR pathways. PASTE had equivalent or better gene insertion efficiencies than either HITI (FIGS. 39A-B) or HDR (FIGS. 39C-D). On a panel of 7 different endogenous targets, PASTE exceeded HITI editing at 6 out of 7 genes, with similar efficiency for the 7th gene (FIG. 39A). As DSB generation can lead to insertions or deletions (indels) as an alternative and undesired editing outcome, the indel frequency of all three methods was assessed by next-generation sequencing, finding significantly fewer indels generated with PASTE than either HDR or HITI in both HEK293FT and HepG2 cells (FIGS. 39B, 39D and 40A), showcasing the high purity of gene integration outcomes with PASTE.

Example 24

Off-Target Characterization of PASTE and HITI Gene Integration

Figure 39E:
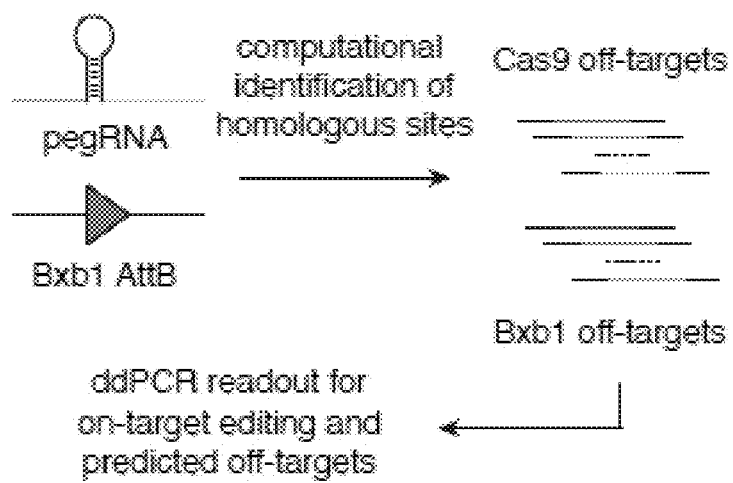
FIG. 39E shows a schematic for Bxb1 and Cas9 off-target identification and a detection assay according to embodiments of the present teachings.
Figure 39F:
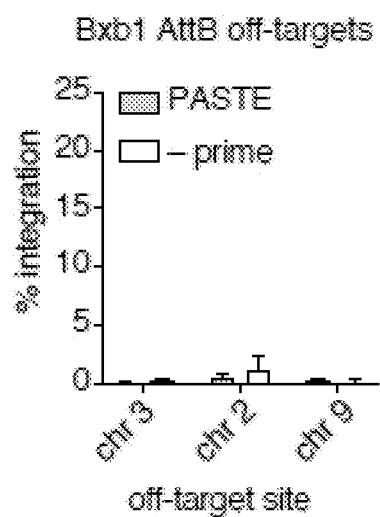
FIG. 39F shows the GFP integration activity at predicted Bxb1 off-target sites in the human genome according to embodiments of the present teachings.
Figure 39G:
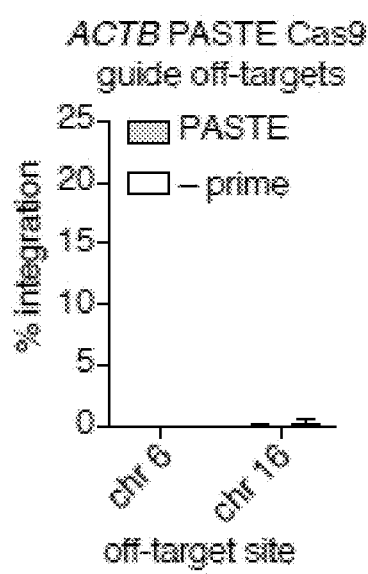
FIG. 39G shows the GFP integrations activity at predicted PASTE ACTB Cas9 guide off target sites according to embodiments of the present teachings.
Figure 39H:
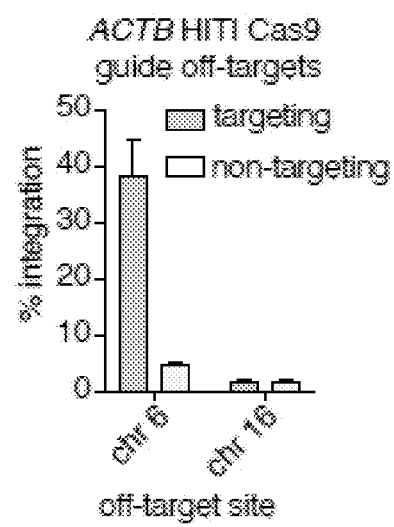
FIG. 39H shows the GFP integration activity at predicted HITI ACTB Cas9 guide off-target sites according to embodiments of the present teachings.

Off-target editing can be used in genome editing technologies. The specificity of PASTE at specific sites was assessed based on off-targets generated by Bxb1 integration into pseudo-attB sites in the human genome and off-targets generated via guide- and Cas9-dependent editing in the human genome (FIG. 39E). While Bxb1 lacks documented integration into the human genome at pseudo-attachment sites, potential sites with partial similarity to the natural Bxb1 attB core sequence were computationally identified. Bxb1 integration by ddPCR across these sites was tested and no off-target activity was found (FIGS. 39F and 40B-D). To assay Cas9 off-targets for the ACTB pegRNA, two potential off-target sites were identified via computational prediction and no off-target integration for PASTE was found (FIGS. 39G and 40A-D), but substantial off-target activity by HITI at one of the sites was found (FIGS. 39H and 40A-D).

Figure 39I:
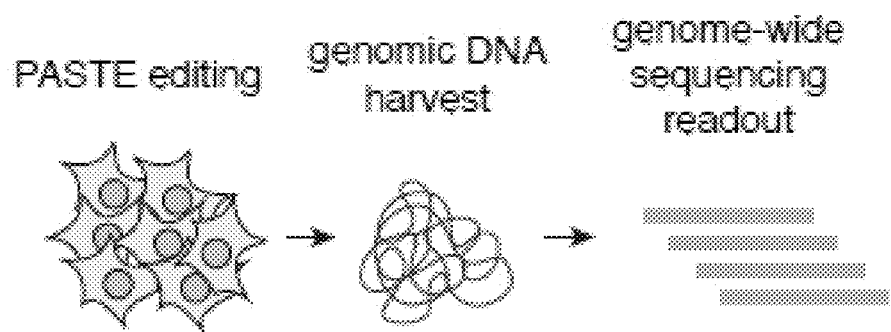
FIG. 39I shows a schematic of next-generation sequencing method to assay genome-wide off-target integration sites by PASTE according to embodiments of the present teachings.
Figure 39J:
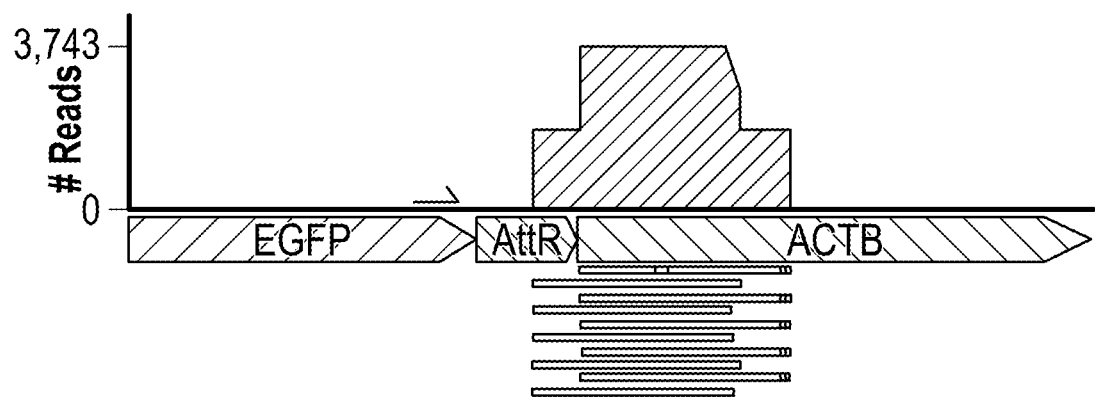
FIG. 39J shows the alignment of reads at the on-target ACTB site using a genome-wide integration assay, wherein expected on-target integration outcomes are shown according to embodiments of the present teachings.
Figure 39K:
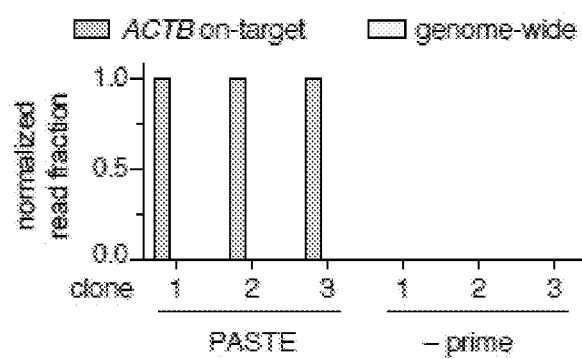
FIG. 39K shows the analysis of on-target and off-target integration events across 3 single-cell clones for PASTE and 3 single-cell clones for no prime condition according to embodiments of the present teachings.
Figure 39L:
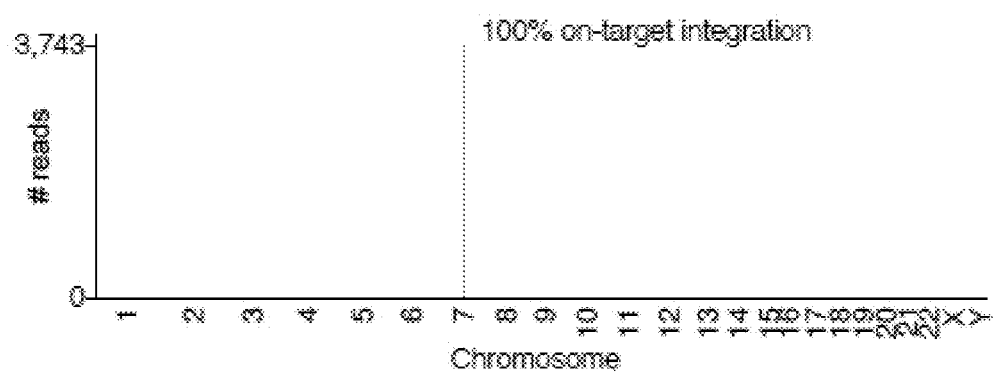
FIG. 39L shows a Manhattan plot of integration events for a representative single-cell clone with PASTE editing, wherein the on-target site is at the ACTB gene on chromosome 7 according to embodiments of the present teachings.

Genome-wide off-targets due to either Cas9 or Bxb1 through tagging and PCR amplification of insert-genomic junctions were additionally assessed (FIG. 39I). Single cell clones were isolated for conditions with PASTE editing and negative controls missing PE2, and deep sequencing of insert genomic junctions from these clones showed all reads aligning to the on-target ACTB site, confirming no off-target genomic insertions (FIGS. 39J-L).

Expression of reverse transcriptases and integrases involved in PASTE can have detrimental effects on cellular health. The complete PASTE system, the corresponding guides and cargo with only PE2, and the corresponding guides and cargo with only Bxb1 were transfected and compared to both GFP control transfections and guides without protein expression via transcriptome-wide RNA sequencing to determine the extent of these effects. While Bxb1 expression in the absence of Prime editing was found to have several significant off targets, the complete PASTE system had only one differentially regulated gene with more than a 1.5-fold change (FIGS. 41A-B). Genes upregulated by Bxb1 overexpression included stress response genes, such as TENT5C and DDIT3, but these changes were not seen in the expression of the PASTE system (FIG. 41C), potentially due to the decreased expression of Bxb1 from the P2A linker on the PASTE construct.

Example 25

PASTE Efficiency in Non-Dividing Cell

PASTE activity in non-dividing cells was assessed. Cas9 and HDR templates or PASTE were transfected into HEK293FT cells and cell division was arrested via aphidicolin treatment (FIG. 42A). In this model of blocked cell division, PASTE was found to maintain a GFP gene integration activity greater than 20% at the ACTB locus whereas HDR-mediated integration was abolished (FIGS. 42B and 43A).

Example 26

Production and Secretion of Therapeutic Transgene

PASTE with larger transgenes and in additional cell lines were assessed.

To evaluate the size limits for therapeutic transgenes, insertion of cargos up to 13.3 kb in length in both dividing and aphidicolin treated cells was assessed. Insertion efficiency greater than 10% was found (FIG. 42C), enabling insertion of ~99.7% of all full-length human cDNA transgenes. To overcome reduction of large insert delivery to cells because of delivery inefficiencies, delivering larger DNA amounts of insert was found to significantly improve gene integration efficiency (FIG. 43B). PASTE editing to additional cell types such as PASTE in the K562 lymphoblast line and in primary human T cells were also assessed. Both PE2-P2A-Bxb1 (PASTE) and separate delivery of PE2 and Bxb1 were found to result in efficient editing in both cell types (FIGS. 42D-E). Lastly, as therapeutic delivery of PASTE in vivo might require viral delivery of the DNA cargo, whether AAV could deliver an attP containing payload that could be integrated into the genome via Bxb1 was evaluated. Targeting the ACTB locus, AAV was found to be capable of delivering the appropriate template for integrase mediated insertion with rates up to 4% in a dose dependent fashion (FIGS. 42F and 43C).

To improve the efficiency of PASTE, PE2* NLS was incorporated for prime editing and improved PASTE integration at multiple loci was found (FIG. 44A). Furthermore, PE2* resulted in more robust integration at lower titrations of cargo plasmid, demonstrating integration at amounts as low as 8 ng of plasmid (FIG. 44B). To combat reductions in PASTE efficiency due to incomplete plasmid delivery, a puromycin resistance gene was co-delivered and found to increase the PASTE efficiency in the presence of drug selection (FIG. 45).

Programmable gene integration provides a modality for expression of therapeutic protein products, and protein production was assessed for therapeutically relevant proteins Alpha-1 antitrypsin (encoded by SERPINA1) and Carbamoyl phosphate synthetase I (encoded by CPS1), involved in the diseases Alpha-1 antitrypsin deficiency and CPS1 deficiency, respectively. By tagging gene products with the luminescent protein subunit HiBiT, the transgene production and secretion were assessed independently in response to PASTE treatment (FIG. 42G). PASTE was transfected with SERPINA1 or CPS1 cargo in HEK293FT cells and a human hepatocellular carcinoma cell line (HepG2) and efficient integration at the ACTB locus was found (FIG. 42H-I). This integration resulted in robust protein expression, intracellular accumulation of transgene products (FIGS. 42J and 46A-B), and secretion of proteins into the media (FIG. 42K).

Example 27

Optimized PASTE Constructs

To optimize complex activity, a panel of protein modifications were screened, including alternative reverse transcriptase fusions and mutations, various linkers between the reverse transcriptase domain and integrase and between the Cas9 and reverse transcriptase domain, and reverse transcriptase and BxbINT domain mutants (FIG. 47A and FIG. 49C-FIG. 49F). A number of protein modifications, including a 48 residue XTEN linker between the Cas9 and reverse transcriptase and the fusion of MMuLV to the Sto7d DNA binding domain (Oscorbin et al. FEBS Lett. 594. 4338-4356. 2020) improved editing efficiency (FIG. 47A and FIG. 49C-FIG. 49D). When these top modifications were combined with a GGGGS linker (SEQ ID NO: 420) between the reverse transcriptase-Sto7d domain and the BxbINT, they produced ~55% gene integration, highlighting the importance of directly recruiting the integrase to the target site (FIG. 47A). This optimized construct was referred to as SpCas9-(XTEN-48)-RT-Sto7d-(GGGGS)-BxbINT. The optimized contruct achieved precise integration of templates as large as ~36,000 bp with ~20% integration efficiency (FIG. 47A), with complete integration of the full-length cargo confirmed by Sanger sequencing.

Additionally, pegRNAs containing different AttB length truncations were tested and found that prime editing was capable of inserting sequences up to 56 bp at the beta-actin (ACTB) gene locus, with higher efficiency at lengths below 31 bp (FIG. 48A-FIG. 48B). A panel of multiple enzymes was evaluated, including Bxb1 (i.e., BxbINT), TP901 (i.e., Tp9INT), and phiBT1 (i.e., Bt1INT) phage serine integrases. Prime editing successfully inserted all landing sites tested, with efficiencies between 10-30% (FIG. 48C-FIG. 48D)

Example 28

Viral Delivery & In Vivo Editing

In order to package the complete PASTE system in viral vectors, an AdV vector was utilized (FIG. 50B). Adenovirus was evaluated for if it could deliver a suitable template for BxbINT-mediated insertion along with plasmids for SpCas9-RT-BxbINT and guide expression, or AdV delivery of guides and BxbINT with plasmid delivery of SpCas9-RT, finding that 10-20% integration of the ~36 kb adenovirus genome carrying EGFP in HEK293FT and HepG2 cells was achieved (FIG. 50C). Upon packaging and delivering the cargo and PASTE system components across 3 AdV vectors, the complete PASTE system (Cas9-reverse transcriptase, integrase and guide RNAs, or cargo) could be substituted by adenoviral delivery, with integration of up to ~50-60% with viral-only delivery in HEK293FT and HepG2 cells (FIG. 50D).

To further demonstrate PASTE would be amenable for in vivo delivery, an mRNA version of the PASTE protein components was developed as well as chemically-modified synthetic atgRNA and nicking guide against the LMNB1 target (FIG. 50E). Electroporation of the mRNA and guides along with delivery of the template via adenovirus or plasmid yielded high efficiency integration up to ~23% (FIG. 50E-FIG. 50F). More sustained BxbINT expression could allow for integration into newly placed AttB sites in the genome, so circular mRNA expression was tested and found to boost the efficiency of integration to ~30% (FIG. 50G-FIG. 50I).

Example 29

Simultaneous Deletion & Insertion With PASTE

The PASTE system was used to simultaneously delete one sequence and insert another. 130 bp and 385 bp deletions of first exon of LMNB1 with combined insertion of AttB nucleic acid sequence was performed (FIG. 51A). This data shows that it is possible to replace DNA sequence using the PASTE system.

A130 bp deletion of the first exon of LMNB1 with combined insertion of a 967 bp cargo using the PASTE system was also performed.

One of two attP sequences were inserted using the mini circle template that has mutated AttP, as described above. This AttP mutants shows better integration kinetics and efficiency, especially for the shorter AttBs (38-44 bp). The LMNB1 AttB used in this experiment is 38 bp (FIG. 51B).

What is claimed is:

1. A system capable of site-specifically integrating an exogenous nucleic acid into a mammalian cell genome at a desired target site, wherein the system comprises, concurrently within the mammalian cell:
   (a) a nucleic acid encoding a DNA binding nickase domain linked to a reverse transcriptase domain, wherein the linked nickase-RT domains are further linked to a serine integration enzyme via a linker selected from P2A, (GGGS)₃, GGGGS, PAPAP, (EAAAK)₃, XTEN, (GGS)₆, and EAAAK;
   (b) a guide RNA or a nucleic acid encoding a guide RNA (gRNA), the guide RNA comprising, from 3' to 5',
      i. a primer binding sequence,
      ii. a sequence complementary to one strand of an AttB or AttP integration recognition sequence, and
      iii. a target binding sequence,
   wherein the gRNA is capable of guiding the linked nickase-reverse transcriptase domains to the genomic target site;
   (c) an exogenous nucleic acid linked to a sequence that is an integration cognate of the integration recognition sequence,
   whereby the system site specifically integrates the exogenous nucleic acid into the mammalian cell genome at the desired target site.

2. The system of claim 1, wherein the DNA binding nickase domain is linked to the reverse transcriptase domain by in-frame fusion.

3. The system of claim 1, wherein the DNA binding nickase domain is linked to the reverse transcriptase domain by a linker.

4. The system of claim 3, wherein the linker is a peptide fused in-frame between the nickase and reverse transcriptase domains.

5. The system of claim 1, wherein the DNA binding nickase domain is selected from Cas9-D10A, Cas9-H840A, and Cas12a/b nickase.

6. The system of claim 1, wherein the reverse transcriptase domain is selected from the group consisting of Moloney Murine Leukemia Virus (M-MLV) reverse transcriptase domain, transcription xenopolymerase (RTX), avian myeloblastosis virus reverse transcriptase (AMV-RT), and Eubacterium rectale maturase RT.

7. The system of claim 6, wherein the reverse transcriptase domain is a M-MLV reverse transcriptase domain.

8. The system of claim 6, wherein the M-MLV reverse transcriptase domain comprises one or more mutations selected from the group consisting of D200N, T306K, W313F, T330P, and L603W.

9. The system of claim 1, wherein the exogenous nucleic acid is a minicircle, a plasmid, a mRNA, or a linear DNA.

10. The system of claim 8, wherein exogenous nucleic acid is a minicircle.

11. The system of claim 10, wherein the minicircle does not comprise a sequence of a bacterial origin.

12. The system of claim 1, wherein the serine integration enzyme is selected from the group consisting of Bxb1, φC31, RDF, φBT1, R1, R2, R3, R4, RS, TP901-1, A118, φFC1, φC1, MR11, TG1, φ370.1, Wβ, BL3, SPBc, K38, Peaches, Veracruz, Rebeuca, Theia, Benedict, KSSJEB, PattyP, Doom, Scowl, Lockley, Switzer, Bob3, Troube, Abrogate, Anglerfish, Sarfire, SkiPole, ConceptII, Museum, Severus, Airmid, Benedict, Hinder, ICleared, Sheen, Mundrea, BxZ2, and φRV.

13. The system of claim 12, wherein the serine integration enzyme is Bxb1.

14. The system of claim 1, wherein the exogenous nucleic acid encodes:

a reporter gene;
a degradation tag for programmable knockdown of proteins in the presence of small molecules;
a T-cell receptor (TCR), a chimeric antigen receptor (CAR), an interleukin, a cytokine, or an immune checkpoint gene and the mammalian cell is a T-cell or natural killer (NK) cell;
a beta hemoglobin (HBB) gene and the mammalian cell is a hematopoietic stem cell (HSC);
a metabolic gene; or
a gene involved in an inherited disease or syndrome.

15. The system of claim 1, wherein the exogenous nucleic acid is between 1000 bp and 36,000 bp in length.

16. The system of claim 1, wherein the exogenous nucleic acid is more than 36,000 bp in length.

17. The system of claim 1, wherein the exogenous nucleic acid is less than 1000 bp in length.

18. The system of claim 14, wherein the inherited disease is cystic fibrosis, familial hypercholesterolemia, adenosine deaminase (ADA) deficiency, X-linked SCID (X-SCID), Wiskott-Aldrich syndrome (WAS), hemochromatosis, Tay-Sachs, fragile X syndrome, Huntington's disease, Marfan syndrome, phenylketonuria, or muscular dystrophy.

19. The system of claim 1, further comprising a nicking gRNA.

20. The system of claim 1, wherein (a)-(c) are introduced into the mammalian cell as an adeno-associated virus (AAV) or an adenovirus (AdV).

21. The system of claim 1, wherein (a)-(c) are delivered in a single transfection.

22. The system of claim 1, wherein (a)-(c) are co-expressed.

23. The system of claim 1, wherein the linker comprises P2A.

* * * * *

UNITED STATES PATENT AND TRADEMARK OFFICE
CERTIFICATE OF CORRECTION

| | |
|---|---|
| PATENT NO. | : 12,195,733 B2 |
| APPLICATION NO. | : 18/487610 |
| DATED | : January 14, 2025 |
| INVENTOR(S) | : Abudayyeh et al. |

Page 1 of 1

It is certified that error appears in the above-identified patent and that said Letters Patent is hereby corrected as shown below:

In the Specification

In Column 1, Line 18, after paragraph "CROSS REFERENCE TO RELATED APPLICATIONS" insert heading & paragraph:
--GOVERNMENT SUPPORT
This invention was made with government support under EB031957 awarded by the National Institutes of Health. The government has certain rights in the invention.--

Signed and Sealed this
Eleventh Day of November, 2025

John A. Squires
*Director of the United States Patent and Trademark Office*

SEQUENCE LISTING

```
Sequence total quantity: 431
SEQ ID NO: 1            moltype = DNA  length = 34
FEATURE                 Location/Qualifiers
misc_feature            1..34
                        note = Description of Artificial Sequence: Synthetic
                        oligonucleotide
misc_feature            1..34
                        note = Lox71
source                  1..34
                        mol_type = other DNA
                        organism = synthetic construct
SEQUENCE: 1
ataacttcgt ataatgtatg ctatacgaac ggta                                34

SEQ ID NO: 2            moltype = DNA  length = 34
FEATURE                 Location/Qualifiers
misc_feature            1..34
                        note = Description of Artificial Sequence: Synthetic
                        oligonucleotide
misc_feature            1..34
                        note = Lox66
source                  1..34
                        mol_type = other DNA
                        organism = synthetic construct
SEQUENCE: 2
taccgttcgt ataatgtatg ctatacgaag ttat                                34

SEQ ID NO: 3            moltype = DNA  length = 46
FEATURE                 Location/Qualifiers
misc_feature            1..46
                        note = Description of Artificial Sequence: Synthetic
                        oligonucleotide
misc_feature            1..46
                        note = AttB
source                  1..46
                        mol_type = other DNA
                        organism = synthetic construct
SEQUENCE: 3
ggccggcttg tcgacgacgg cggtctccgt cgtcaggatc atccgg                   46

SEQ ID NO: 4            moltype = DNA  length = 46
FEATURE                 Location/Qualifiers
misc_feature            1..46
                        note = Description of Artificial Sequence: Synthetic
                        oligonucleotide
misc_feature            1..46
                        note = AttP
source                  1..46
                        mol_type = other DNA
                        organism = synthetic construct
SEQUENCE: 4
ccggatgatc ctgacgacgg agaccgccgt cgtcgacaag ccggcc                   46

SEQ ID NO: 5            moltype = DNA  length = 38
FEATURE                 Location/Qualifiers
misc_feature            1..38
                        note = Description of Artificial Sequence: Synthetic
```

```
                                oligonucleotide
misc_feature                    1..38
                                note = AttB-TT
source                          1..38
                                mol_type = other DNA
                                organism = synthetic construct
SEQUENCE: 5
ggcttgtcga cgacggcgtt ctccgtcgtc aggatcat                             38

SEQ ID NO: 6            moltype = DNA  length = 52
FEATURE                 Location/Qualifiers
misc_feature            1..52
                        note = Description of Artificial Sequence: Synthetic
                            oligonucleotide
misc_feature            1..52
                        note = AttP-TT
source                  1..52
                        mol_type = other DNA
                        organism = synthetic construct
SEQUENCE: 6
gtggtttgtc tggtcaacca ccgcgttctc agtggtgtac ggtacaaacc ca             52

SEQ ID NO: 7            moltype = DNA  length = 38
FEATURE                 Location/Qualifiers
misc_feature            1..38
                        note = Description of Artificial Sequence: Synthetic
                            oligonucleotide
misc_feature            1..38
                        note = AttB-AA
source                  1..38
                        mol_type = other DNA
                        organism = synthetic construct
SEQUENCE: 7
ggcttgtcga cgacggcgaa ctccgtcgtc aggatcat                             38

SEQ ID NO: 8            moltype = DNA  length = 52
FEATURE                 Location/Qualifiers
misc_feature            1..52
                        note = Description of Artificial Sequence: Synthetic
                            oligonucleotide
misc_feature            1..52
                        note = AttP-AA
source                  1..52
                        mol_type = other DNA
                        organism = synthetic construct
SEQUENCE: 8
gtggtttgtc tggtcaacca ccgcgaactc agtggtgtac ggtacaaacc ca             52

SEQ ID NO: 9            moltype = DNA  length = 38
FEATURE                 Location/Qualifiers
misc_feature            1..38
                        note = Description of Artificial Sequence: Synthetic
                            oligonucleotide
misc_feature            1..38
                        note = AttB-CC
source                  1..38
                        mol_type = other DNA
                        organism = synthetic construct
SEQUENCE: 9
ggcttgtcga cgacggcgcc ctccgtcgtc aggatcat                             38

SEQ ID NO: 10           moltype = DNA  length = 52
FEATURE                 Location/Qualifiers
misc_feature            1..52
                        note = Description of Artificial Sequence: Synthetic
                            oligonucleotide
misc_feature            1..52
                        note = AttP-CC
source                  1..52
                        mol_type = other DNA
                        organism = synthetic construct
SEQUENCE: 10
gtggtttgtc tggtcaacca ccgcgccctc agtggtgtac ggtacaaacc ca             52

SEQ ID NO: 11           moltype = DNA  length = 38
FEATURE                 Location/Qualifiers
misc_feature            1..38
                        note = Description of Artificial Sequence: Synthetic
                            oligonucleotide
```

```
misc_feature            1..38
                        note = AttB-GG
source                  1..38
                        mol_type = other DNA
                        organism = synthetic construct
SEQUENCE: 11
ggcttgtcga cgacggcggg ctccgtcgtc aggatcat                              38

SEQ ID NO: 12           moltype = DNA  length = 52
FEATURE                 Location/Qualifiers
misc_feature            1..52
                        note = Description of Artificial Sequence: Synthetic
                         oligonucleotide
misc_feature            1..52
                        note = AttP-GG
source                  1..52
                        mol_type = other DNA
                        organism = synthetic construct
SEQUENCE: 12
gtggtttgtc tggtcaacca ccgcgggctc agtggtgtac ggtacaaacc ca              52

SEQ ID NO: 13           moltype = DNA  length = 38
FEATURE                 Location/Qualifiers
misc_feature            1..38
                        note = Description of Artificial Sequence: Synthetic
                         oligonucleotide
misc_feature            1..38
                        note = AttB-TG
source                  1..38
                        mol_type = other DNA
                        organism = synthetic construct
SEQUENCE: 13
ggcttgtcga cgacggcgtg ctccgtcgtc aggatcat                              38

SEQ ID NO: 14           moltype = DNA  length = 52
FEATURE                 Location/Qualifiers
misc_feature            1..52
                        note = Description of Artificial Sequence: Synthetic
                         oligonucleotide
misc_feature            1..52
                        note = AttP-TG
source                  1..52
                        mol_type = other DNA
                        organism = synthetic construct
SEQUENCE: 14
gtggtttgtc tggtcaacca ccgcgtgctc agtggtgtac ggtacaaacc ca              52

SEQ ID NO: 15           moltype = DNA  length = 38
FEATURE                 Location/Qualifiers
misc_feature            1..38
                        note = Description of Artificial Sequence: Synthetic
                         oligonucleotide
misc_feature            1..38
                        note = AttB-GT
source                  1..38
                        mol_type = other DNA
                        organism = synthetic construct
SEQUENCE: 15
ggcttgtcga cgacggcggt ctccgtcgtc aggatcat                              38

SEQ ID NO: 16           moltype = DNA  length = 52
FEATURE                 Location/Qualifiers
misc_feature            1..52
                        note = Description of Artificial Sequence: Synthetic
                         oligonucleotide
misc_feature            1..52
                        note = AttP-GT
source                  1..52
                        mol_type = other DNA
                        organism = synthetic construct
SEQUENCE: 16
gtggtttgtc tggtcaacca ccgcggtctc agtggtgtac ggtacaaacc ca              52

SEQ ID NO: 17           moltype = DNA  length = 38
FEATURE                 Location/Qualifiers
misc_feature            1..38
                        note = Description of Artificial Sequence: Synthetic
                         oligonucleotide
misc_feature            1..38
```

```
                        note = AttB-CT
source                  1..38
                        mol_type = other DNA
                        organism = synthetic construct
SEQUENCE: 17
ggcttgtcga cgacggcgct ctccgtcgtc aggatcat                              38

SEQ ID NO: 18           moltype = DNA  length = 52
FEATURE                 Location/Qualifiers
misc_feature            1..52
                        note = Description of Artificial Sequence: Synthetic
                        oligonucleotide
misc_feature            1..52
                        note = AttP-CT
source                  1..52
                        mol_type = other DNA
                        organism = synthetic construct
SEQUENCE: 18
gtggtttgtc tggtcaacca ccgcgctctc agtggtgtac ggtacaaacc ca              52

SEQ ID NO: 19           moltype = DNA  length = 38
FEATURE                 Location/Qualifiers
misc_feature            1..38
                        note = Description of Artificial Sequence: Synthetic
                        oligonucleotide
misc_feature            1..38
                        note = AttB-CA
source                  1..38
                        mol_type = other DNA
                        organism = synthetic construct
SEQUENCE: 19
ggcttgtcga cgacggcgca ctccgtcgtc aggatcat                              38

SEQ ID NO: 20           moltype = DNA  length = 52
FEATURE                 Location/Qualifiers
misc_feature            1..52
                        note = Description of Artificial Sequence: Synthetic
                        oligonucleotide
misc_feature            1..52
                        note = AttP-CA
source                  1..52
                        mol_type = other DNA
                        organism = synthetic construct
SEQUENCE: 20
gtggtttgtc tggtcaacca ccgcgcactc agtggtgtac ggtacaaacc ca              52

SEQ ID NO: 21           moltype = DNA  length = 38
FEATURE                 Location/Qualifiers
misc_feature            1..38
                        note = Description of Artificial Sequence: Synthetic
                        oligonucleotide
misc_feature            1..38
                        note = AttB-TC
source                  1..38
                        mol_type = other DNA
                        organism = synthetic construct
SEQUENCE: 21
ggcttgtcga cgacggcgtc ctccgtcgtc aggatcat                              38

SEQ ID NO: 22           moltype = DNA  length = 52
FEATURE                 Location/Qualifiers
misc_feature            1..52
                        note = Description of Artificial Sequence: Synthetic
                        oligonucleotide
misc_feature            1..52
                        note = AttP-TC
source                  1..52
                        mol_type = other DNA
                        organism = synthetic construct
SEQUENCE: 22
gtggtttgtc tggtcaacca ccgcgtcctc agtggtgtac ggtacaaacc ca              52

SEQ ID NO: 23           moltype = DNA  length = 38
FEATURE                 Location/Qualifiers
misc_feature            1..38
                        note = Description of Artificial Sequence: Synthetic
                        oligonucleotide
misc_feature            1..38
                        note = AttB-GA
```

```
source                  1..38
                        mol_type = other DNA
                        organism = synthetic construct
SEQUENCE: 23
ggcttgtcga cgacggcgga ctccgtcgtc aggatcat                              38

SEQ ID NO: 24           moltype = DNA  length = 52
FEATURE                 Location/Qualifiers
misc_feature            1..52
                        note = Description of Artificial Sequence: Synthetic
                        oligonucleotide
misc_feature            1..52
                        note = AttP-GA
source                  1..52
                        mol_type = other DNA
                        organism = synthetic construct
SEQUENCE: 24
gtggtttgtc tggtcaacca ccgcggactc agtggtgtac ggtacaaacc ca              52

SEQ ID NO: 25           moltype = DNA  length = 38
FEATURE                 Location/Qualifiers
misc_feature            1..38
                        note = Description of Artificial Sequence: Synthetic
                        oligonucleotide
misc_feature            1..38
                        note = AttB-AG
source                  1..38
                        mol_type = other DNA
                        organism = synthetic construct
SEQUENCE: 25
ggcttgtcga cgacggcgag ctccgtcgtc aggatcat                              38

SEQ ID NO: 26           moltype = DNA  length = 52
FEATURE                 Location/Qualifiers
misc_feature            1..52
                        note = Description of Artificial Sequence: Synthetic
                        oligonucleotide
misc_feature            1..52
                        note = AttP-AG
source                  1..52
                        mol_type = other DNA
                        organism = synthetic construct
SEQUENCE: 26
gtggtttgtc tggtcaacca ccgcgagctc agtggtgtac ggtacaaacc ca              52

SEQ ID NO: 27           moltype = DNA  length = 38
FEATURE                 Location/Qualifiers
misc_feature            1..38
                        note = Description of Artificial Sequence: Synthetic
                        oligonucleotide
misc_feature            1..38
                        note = AttB-AC
source                  1..38
                        mol_type = other DNA
                        organism = synthetic construct
SEQUENCE: 27
ggcttgtcga cgacggcgac ctccgtcgtc aggatcat                              38

SEQ ID NO: 28           moltype = DNA  length = 52
FEATURE                 Location/Qualifiers
misc_feature            1..52
                        note = Description of Artificial Sequence: Synthetic
                        oligonucleotide
misc_feature            1..52
                        note = AttP-AC
source                  1..52
                        mol_type = other DNA
                        organism = synthetic construct
SEQUENCE: 28
gtggtttgtc tggtcaacca ccgcgacctc agtggtgtac ggtacaaacc ca              52

SEQ ID NO: 29           moltype = DNA  length = 38
FEATURE                 Location/Qualifiers
misc_feature            1..38
                        note = Description of Artificial Sequence: Synthetic
                        oligonucleotide
misc_feature            1..38
                        note = AttB-AT
source                  1..38
```

```
                        mol_type = other DNA
                        organism = synthetic construct
SEQUENCE: 29
ggcttgtcga cgacggcgat ctccgtcgtc aggatcat                                38

SEQ ID NO: 30           moltype = DNA  length = 52
FEATURE                 Location/Qualifiers
misc_feature            1..52
                        note = Description of Artificial Sequence: Synthetic
                         oligonucleotide
misc_feature            1..52
                        note = AttP-AT
source                  1..52
                        mol_type = other DNA
                        organism = synthetic construct
SEQUENCE: 30
gtggtttgtc tggtcaacca ccgcgatctc agtggtgtac ggtacaaacc ca               52

SEQ ID NO: 31           moltype = DNA  length = 38
FEATURE                 Location/Qualifiers
misc_feature            1..38
                        note = Description of Artificial Sequence: Synthetic
                         oligonucleotide
misc_feature            1..38
                        note = AttB-GC
source                  1..38
                        mol_type = other DNA
                        organism = synthetic construct
SEQUENCE: 31
ggcttgtcga cgacggcggc ctccgtcgtc aggatcat                                38

SEQ ID NO: 32           moltype = DNA  length = 52
FEATURE                 Location/Qualifiers
misc_feature            1..52
                        note = Description of Artificial Sequence: Synthetic
                         oligonucleotide
misc_feature            1..52
                        note = AttP-GC
source                  1..52
                        mol_type = other DNA
                        organism = synthetic construct
SEQUENCE: 32
gtggtttgtc tggtcaacca ccgcggcctc agtggtgtac ggtacaaacc ca               52

SEQ ID NO: 33           moltype = DNA  length = 38
FEATURE                 Location/Qualifiers
misc_feature            1..38
                        note = Description of Artificial Sequence: Synthetic
                         oligonucleotide
misc_feature            1..38
                        note = AttB-CG
source                  1..38
                        mol_type = other DNA
                        organism = synthetic construct
SEQUENCE: 33
ggcttgtcga cgacggcgcg ctccgtcgtc aggatcat                                38

SEQ ID NO: 34           moltype = DNA  length = 52
FEATURE                 Location/Qualifiers
misc_feature            1..52
                        note = Description of Artificial Sequence: Synthetic
                         oligonucleotide
misc_feature            1..52
                        note = AttB-CG
source                  1..52
                        mol_type = other DNA
                        organism = synthetic construct
SEQUENCE: 34
gtggtttgtc tggtcaacca ccgcgcgctc agtggtgtac ggtacaaacc ca               52

SEQ ID NO: 35           moltype = DNA  length = 38
FEATURE                 Location/Qualifiers
misc_feature            1..38
                        note = Description of Artificial Sequence: Synthetic
                         oligonucleotide
misc_feature            1..38
                        note = AttB-TA
source                  1..38
                        mol_type = other DNA
```

```
                            organism = synthetic construct
SEQUENCE: 35
ggcttgtcga cgacggcgta ctccgtcgtc aggatcat                              38

SEQ ID NO: 36               moltype = DNA   length = 52
FEATURE                     Location/Qualifiers
misc_feature                1..52
                            note = Description of Artificial Sequence: Synthetic
                              oligonucleotide
misc_feature                1..52
                            note = AttP-TA
source                      1..52
                            mol_type = other DNA
                            organism = synthetic construct
SEQUENCE: 36
gtggtttgtc tggtcaacca ccgcgtactc agtggtgtac ggtacaaacc ca              52

SEQ ID NO: 37               moltype = DNA   length = 45
FEATURE                     Location/Qualifiers
misc_feature                1..45
                            note = Description of Artificial Sequence: Synthetic
                              oligonucleotide
misc_feature                1..45
                            note = C-31-B
source                      1..45
                            mol_type = other DNA
                            organism = synthetic construct
SEQUENCE: 37
tgcgggtgcc agggcgtgcc cttgggctcc ccgggcgcgt actcc                      45

SEQ ID NO: 38               moltype = DNA   length = 42
FEATURE                     Location/Qualifiers
misc_feature                1..42
                            note = Description of Artificial Sequence: Synthetic
                              oligonucleotide
misc_feature                1..42
                            note = C31-P
source                      1..42
                            mol_type = other DNA
                            organism = synthetic construct
SEQUENCE: 38
gtgccccaac tggggtaacc tttgagttct ctcagttggg gg                         42

SEQ ID NO: 39               moltype = DNA   length = 57
FEATURE                     Location/Qualifiers
misc_feature                1..57
                            note = Description of Artificial Sequence: Synthetic
                              oligonucleotide
misc_feature                1..57
                            note = R4-B
source                      1..57
                            mol_type = other DNA
                            organism = synthetic construct
SEQUENCE: 39
gcgcccaagt tgcccatgac catgccgaag cagtggtaga agggcaccgg cagacac         57

SEQ ID NO: 40               moltype = DNA   length = 70
FEATURE                     Location/Qualifiers
misc_feature                1..70
                            note = Description of Artificial Sequence: Synthetic
                              oligonucleotide
misc_feature                1..70
                            note = R4-P
source                      1..70
                            mol_type = other DNA
                            organism = synthetic construct
SEQUENCE: 40
aggcatgttc cccaaagcga taccacttga agcagtggta ctgcttgtgg gtacactctg      60
cgggtgatga                                                             70

SEQ ID NO: 41               moltype = DNA   length = 60
FEATURE                     Location/Qualifiers
misc_feature                1..60
                            note = Description of Artificial Sequence: Synthetic
                              oligonucleotide
misc_feature                1..60
                            note = BT1-B
source                      1..60
                            mol_type = other DNA
```

```
                        organism = synthetic construct
SEQUENCE: 41
gtccttgacc aggtttttga cgaaagtgat ccagatgatc cagctccaca ccccgaacgc    60

SEQ ID NO: 42           moltype = DNA  length = 63
FEATURE                 Location/Qualifiers
misc_feature            1..63
                        note = Description of Artificial Sequence: Synthetic
                        oligonucleotide
misc_feature            1..63
                        note = BT1-P
source                  1..63
                        mol_type = other DNA
                        organism = synthetic construct
SEQUENCE: 42
ggtgctgggt tgttgtctct ggacagtgat ccatgggaaa ctactcagca ccaccaatgt    60
tcc                                                                  63

SEQ ID NO: 43           moltype = DNA  length = 50
FEATURE                 Location/Qualifiers
misc_feature            1..50
                        note = Description of Artificial Sequence: Synthetic
                        oligonucleotide
misc_feature            1..50
                        note = Bxb-B
source                  1..50
                        mol_type = other DNA
                        organism = synthetic construct
SEQUENCE: 43
tcggccggct tgtcgacgac ggcggtctcc gtcgtcagga tcatccgggc               50

SEQ ID NO: 44           moltype = DNA  length = 58
FEATURE                 Location/Qualifiers
misc_feature            1..58
                        note = Description of Artificial Sequence: Synthetic
                        oligonucleotide
misc_feature            1..58
                        note = Bxb-P
source                  1..58
                        mol_type = other DNA
                        organism = synthetic construct
SEQUENCE: 44
gtcgtggttt gtctggtcaa ccaccgcggt ctcagtggtg tacggtacaa accccgac      58

SEQ ID NO: 45           moltype = DNA  length = 46
FEATURE                 Location/Qualifiers
misc_feature            1..46
                        note = Description of Artificial Sequence: Synthetic
                        oligonucleotide
misc_feature            1..46
                        note = TG1-B
source                  1..46
                        mol_type = other DNA
                        organism = synthetic construct
SEQUENCE: 45
gatcagctcc gcgggcaaga ccttctcctt cacggggtgg aaggtc                   46

SEQ ID NO: 46           moltype = DNA  length = 67
FEATURE                 Location/Qualifiers
misc_feature            1..67
                        note = Description of Artificial Sequence: Synthetic
                        oligonucleotide
misc_feature            1..67
                        note = TG1-P
source                  1..67
                        mol_type = other DNA
                        organism = synthetic construct
SEQUENCE: 46
tcaaccccgt tccagcccaa cagtgttagt ctttgctctt acccagttgg gcgggatagc    60
ctgcccg                                                              67

SEQ ID NO: 47           moltype = DNA  length = 57
FEATURE                 Location/Qualifiers
misc_feature            1..57
                        note = Description of Artificial Sequence: Synthetic
                        oligonucleotide
misc_feature            1..57
                        note = C1-B
source                  1..57
```

```
                        mol_type = other DNA
                        organism = synthetic construct
SEQUENCE: 47
aacgattttc aaaggatcac tgaatcaaaa gtattgctca tccacgcgaa attttc          57

SEQ ID NO: 48           moltype = DNA  length = 57
FEATURE                 Location/Qualifiers
misc_feature            1..57
                        note = Description of Artificial Sequence: Synthetic
                         oligonucleotide
misc_feature            1..57
                        note = C1-P
source                  1..57
                        mol_type = other DNA
                        organism = synthetic construct
SEQUENCE: 48
aatatttag gtatatgatt ttgtttatta gtgtaaataa cactatgtac ctaaaat          57

SEQ ID NO: 49           moltype = DNA  length = 53
FEATURE                 Location/Qualifiers
misc_feature            1..53
                        note = Description of Artificial Sequence: Synthetic
                         oligonucleotide
misc_feature            1..53
                        note = C370-B
source                  1..53
                        mol_type = other DNA
                        organism = synthetic construct
SEQUENCE: 49
tgtaaaggag actgataatg gcatgtacaa ctatactcgt cggtaaaaag gca             53

SEQ ID NO: 50           moltype = DNA  length = 52
FEATURE                 Location/Qualifiers
misc_feature            1..52
                        note = Description of Artificial Sequence: Synthetic
                         oligonucleotide
misc_feature            1..52
                        note = C370-P
source                  1..52
                        mol_type = other DNA
                        organism = synthetic construct
SEQUENCE: 50
taaaaaaata cagcgttttt catgtacaac tatactagtt gtagtgccta aa              52

SEQ ID NO: 51           moltype = DNA  length = 56
FEATURE                 Location/Qualifiers
misc_feature            1..56
                        note = Description of Artificial Sequence: Synthetic
                         oligonucleotide
misc_feature            1..56
                        note = K38-B
source                  1..56
                        mol_type = other DNA
                        organism = synthetic construct
SEQUENCE: 51
gagcgccgga tcagggagtg gacggcctgg gagcgctaca cgctgtggct gcggtc          56

SEQ ID NO: 52           moltype = DNA  length = 56
FEATURE                 Location/Qualifiers
misc_feature            1..56
                        note = Description of Artificial Sequence: Synthetic
                         oligonucleotide
misc_feature            1..56
                        note = K38-P
source                  1..56
                        mol_type = other DNA
                        organism = synthetic construct
SEQUENCE: 52
ccctaatacg caagtcgata actctcctgg gagcgttgac aacttgcgca ccctga          56

SEQ ID NO: 53           moltype = DNA  length = 68
FEATURE                 Location/Qualifiers
misc_feature            1..68
                        note = Description of Artificial Sequence: Synthetic
                         oligonucleotide
misc_feature            1..68
                        note = RB-B
source                  1..68
                        mol_type = other DNA
```

```
                                organism = synthetic construct
SEQUENCE: 53
tctcgtggtg gtggaaggtg ttggtgcggg gttggccgtg gtcgaggtgg ggtggtggta    60
gccattcg                                                             68

SEQ ID NO: 54           moltype = DNA  length = 69
FEATURE                 Location/Qualifiers
misc_feature            1..69
                        note = Description of Artificial Sequence: Synthetic
                         oligonucleotide
misc_feature            1..69
                        note = RV-P
source                  1..69
                        mol_type = other DNA
                        organism = synthetic construct
SEQUENCE: 54
gcacaggtgt agtgtatctc acaggtccac ggttggccgt ggactgctga agaacattcc    60
acgccagga                                                            69

SEQ ID NO: 55           moltype = DNA  length = 65
FEATURE                 Location/Qualifiers
misc_feature            1..65
                        note = Description of Artificial Sequence: Synthetic
                         oligonucleotide
misc_feature            1..65
                        note = SPBC-B
source                  1..65
                        mol_type = other DNA
                        organism = synthetic construct
SEQUENCE: 55
agtgcagcat gtcattaata tcagtacaga taaagctgta tctcctgtga acacaatggg    60
tgcca                                                                65

SEQ ID NO: 56           moltype = DNA  length = 55
FEATURE                 Location/Qualifiers
misc_feature            1..55
                        note = Description of Artificial Sequence: Synthetic
                         oligonucleotide
misc_feature            1..55
                        note = SPBC-P
source                  1..55
                        mol_type = other DNA
                        organism = synthetic construct
SEQUENCE: 56
aaagtagtaa gtatcttaaa aaacagataa agctgtatat taagatactt actac         55

SEQ ID NO: 57           moltype = DNA  length = 54
FEATURE                 Location/Qualifiers
misc_feature            1..54
                        note = Description of Artificial Sequence: Synthetic
                         oligonucleotide
misc_feature            1..54
                        note = TP901-B
source                  1..54
                        mol_type = other DNA
                        organism = synthetic construct
SEQUENCE: 57
tgataattgc caacacaatt aacatctcaa tcaaggtaaa tgcttttcg tttt            54

SEQ ID NO: 58           moltype = DNA  length = 54
FEATURE                 Location/Qualifiers
misc_feature            1..54
                        note = Description of Artificial Sequence: Synthetic
                         oligonucleotide
misc_feature            1..54
                        note = TP901-P
source                  1..54
                        mol_type = other DNA
                        organism = synthetic construct
SEQUENCE: 58
aattgcgagt ttttatttcg tttatttcaa ttaaggtaac taaaaaactc cttt           54

SEQ ID NO: 59           moltype = DNA  length = 68
FEATURE                 Location/Qualifiers
misc_feature            1..68
                        note = Description of Artificial Sequence: Synthetic
                         oligonucleotide
misc_feature            1..68
                        note = Wbeta-B
```

```
source                  1..68
                        mol_type = other DNA
                        organism = synthetic construct
SEQUENCE: 59
aaggtagcgt caacgatagg tgtaactgtc gtgtttgtaa cggtacttcc aacagctggc    60
gtttcagt                                                             68

SEQ ID NO: 60           moltype = DNA   length = 68
FEATURE                 Location/Qualifiers
misc_feature            1..68
                        note = Description of Artificial Sequence: Synthetic
                         oligonucleotide
misc_feature            1..68
                        note = Wbeta-P
source                  1..68
                        mol_type = other DNA
                        organism = synthetic construct
SEQUENCE: 60
tagttttaaa gttggttatt agttactgtg atatttatca cggtacccaa taaccaatga    60
atatttga                                                             68

SEQ ID NO: 61           moltype = DNA   length = 57
FEATURE                 Location/Qualifiers
misc_feature            1..57
                        note = Description of Artificial Sequence: Synthetic
                         oligonucleotide
misc_feature            1..57
                        note = A118-B
source                  1..57
                        mol_type = other DNA
                        organism = synthetic construct
SEQUENCE: 61
tgtaactttt tcggatcaag ctatgaagga cgcaaagagg gaactaaaca cttaatt       57

SEQ ID NO: 62           moltype = DNA   length = 57
FEATURE                 Location/Qualifiers
misc_feature            1..57
                        note = Description of Artificial Sequence: Synthetic
                         oligonucleotide
misc_feature            1..57
                        note = A118-P
source                  1..57
                        mol_type = other DNA
                        organism = synthetic construct
SEQUENCE: 62
ttgtttagtt cctcgttttc tctcgttgga agaagaagaa acgagaaact aaaatta       57

SEQ ID NO: 63           moltype = DNA   length = 63
FEATURE                 Location/Qualifiers
misc_feature            1..63
                        note = Description of Artificial Sequence: Synthetic
                         oligonucleotide
misc_feature            1..63
                        note = BL3-B
source                  1..63
                        mol_type = other DNA
                        organism = synthetic construct
SEQUENCE: 63
caacctgttg acatgtttcc acagacaact cacgtggagg tagtcacggc ttttacgtta    60
gtt                                                                  63

SEQ ID NO: 64           moltype = DNA   length = 61
FEATURE                 Location/Qualifiers
misc_feature            1..61
                        note = Description of Artificial Sequence: Synthetic
                         oligonucleotide
misc_feature            1..61
                        note = BL3-P
source                  1..61
                        mol_type = other DNA
                        organism = synthetic construct
SEQUENCE: 64
gagaatactg ttgaacaatg aaaaactagg catgtagaag ttgtttgtgc actaacttta    60
a                                                                    61

SEQ ID NO: 65           moltype = DNA   length = 120
FEATURE                 Location/Qualifiers
misc_feature            1..120
                        note = Description of Artificial Sequence: Synthetic
```

```
                           polynucleotide
misc_feature               1..120
                           note = MR11-B
source                     1..120
                           mol_type = other DNA
                           organism = synthetic construct
SEQUENCE: 65
acaggtcaac acatcgcagt tatcgaacaa tcttcgaaaa tgtatggagg cacttgtatc   60
aatataggat gtataccttc gaagacactt gtacatgatg gattagaagg caaatccttt  120

SEQ ID NO: 66              moltype = DNA  length = 120
FEATURE                    Location/Qualifiers
misc_feature               1..120
                           note = Description of Artificial Sequence: Synthetic
                           polynucleotide
misc_feature               1..120
                           note = MR11-P
source                     1..120
                           mol_type = other DNA
                           organism = synthetic construct
SEQUENCE: 66
caaaataaaa aacattgatt tttattaact tcttttgtgc ggaactacga acagttcatt   60
aatacgaagt gtacaaactt ccatacaaaa ataaccacga caattaagac gtggtttcta  120

SEQ ID NO: 67              moltype = DNA  length = 17
FEATURE                    Location/Qualifiers
misc_feature               1..17
                           note = Description of Artificial Sequence: Synthetic
                           oligonucleotide
misc_feature               1..17
                           note = AttL
source                     1..17
                           mol_type = other DNA
                           organism = synthetic construct
SEQUENCE: 67
attatttctc accctga                                                  17

SEQ ID NO: 68              moltype = DNA  length = 17
FEATURE                    Location/Qualifiers
misc_feature               1..17
                           note = Description of Artificial Sequence: Synthetic
                           oligonucleotide
misc_feature               1..17
                           note = AttR
source                     1..17
                           mol_type = other DNA
                           organism = synthetic construct
SEQUENCE: 68
atcatctccc acccgga                                                  17

SEQ ID NO: 69              moltype = DNA  length = 34
FEATURE                    Location/Qualifiers
misc_feature               1..34
                           note = Description of Artificial Sequence: Synthetic
                           oligonucleotide
misc_feature               1..34
                           note = Vox
source                     1..34
                           mol_type = other DNA
                           organism = synthetic construct
SEQUENCE: 69
aataggtctg agaacgccca ttctcagacg tatt                               34

SEQ ID NO: 70              moltype = DNA  length = 34
FEATURE                    Location/Qualifiers
misc_feature               1..34
                           note = Description of Artificial Sequence: Synthetic
                           oligonucleotide
misc_feature               1..34
                           note = FRT
source                     1..34
                           mol_type = other DNA
                           organism = synthetic construct
SEQUENCE: 70
gaagttccta tactttctag agaataggaa cttc                               34

SEQ ID NO: 71              moltype = DNA  length = 5881
FEATURE                    Location/Qualifiers
misc_feature               1..5881
```

|  | note = Description of Artificial Sequence: Synthetic polynucleotide |  |
| --- | --- | --- |
| misc_feature | 1..5881 | |
|  | note = Cre Recombinase Expression Plasmid | |
| source | 1..5881 | |
|  | mol_type = other DNA | |
|  | organism = synthetic construct | |

SEQUENCE: 71

```
ggtcgacatt gattattgac tagttattaa tagtaatcaa ttacggggtc attagttcat    60
agcccatata tggagttccg cgttacataa cttacggtaa atggcccgcc tggctgaccg   120
cccaacgacc cccgcccatt gacgtcaata atgacgtatg ttcccatagt aacgccaata   180
gggactttcc attgacgtca atgggtggag tatttacggt aaactgccca cttggcagta   240
catcaagtgt atcatatgcc aagtacgccc cctattgacg tcaatgacgg taaatggccc   300
gcctggcatt atgcccagta catgacctta tgggactttc ctacttggca gtacatctac   360
gtattagtca tcgctattac catggtcgag gtgagcccca cgttctgctt cactctcccc   420
atctcccccc cctccccacc cccaattttg tatttattta tttttaatt attttgtgca   480
gcgatggggg cggggggggg ggggcgcgc gccaggcggg ggggggggg ggggggggg   540
ggggggggg gggcggcggc agccaatcag agcggcgcgc tccgaaagtt   600
tccttttatg gcgaggcggc ggcggcggcg gccctataaa aagcgaagcg cgcggcgggc   660
gggagtcgct gcgcgctgcc ttcgccccgt gccccgctcc gccgccgcct cgcgccgccc   720
gccccggctc tgactgaccg cgttactccc acaggtgagc gggcgggacg gcccttctcc   780
tccgggctgt aattagcgct tggtttaatg acggcttgtt tcttttctgt ggctgcgtga   840
aagccttgag gggctccggg agggcccttt gtgcggggga agcggctcgg ggggtgcgtg   900
cgtgtgtgtg tgcgtgggga gcgccgcgtg cggctccgcg ctgccggcg gctgtgagcg   960
ctgcgggcgc ggcgcgggc tttgtgcgct ccgcagtgtg cgcgagggga gcgcggccgg  1020
gggcggtgcc ccgcggtgcg gggggggctg cgaggggaac aaaggctgcg tgcggggtgt  1080
gtgcgtgggg gggtgagcag ggggtgtggg cgcgtcggtc gggctgcaac ccccctgca  1140
cccccctccc cgagttgctg agcacggcc ggcttcgggt gcggggctcc gtacggggcg  1200
tggcgcgggg ctcgccgtgc cgggcggggg gtggcggcag gtggggtgc cgggcgggc  1260
ggggccgcct cgggccgggg agggctcggg ggagggcgc ggcggcccccc ggagcgcggc  1320
cggctgtcga ggcgcggcga gccgcagcca ttgcctttta tggtaatcgt gcgagagggc  1380
gcagggactt cctttgtccc aaatctgtgc ggagccgaaa tctgggaggc gccgccgcac  1440
cccctctagc gggcgcgggg cgaagcgtg cggcgccggc aggaaggaaa tgggcgggga  1500
gggccttcgt gcgtcgccgc gccgccgtcc ccttctccct ctccagcctc ggggctgtcc  1560
gcggggggac ggctgccttc gggggggacg gggcagggcg gggttcggct tctggcgtgt  1620
gaccggcggc tctagagcct ctgctaacca tgttcatgcc ttcttctttt tcctacagct  1680
cctgggcaac gtgctggtta ttgtgctgtc tcatcatttt ggcaaagaat tctgagccgc  1740
caccatggcc aatttactga ccgtacacca aaatttgcct gcattaccgg tcgatgcaac  1800
gagtgatgag gttcgcaaga acctgatgga catgttcagg gatcgccagg cgttttctga  1860
gcatacctgg aaaatgcttc tgtccgtttc ccggtcgtgg gcggcatggt gcaagttgaa  1920
taaccggaaa tggtttcccg cagaacctga agatgttcgc gattatcttc tatatcttca  1980
ggcgcgcggt ctggcagtaa aaactatcca gcaacatttg ggccagctaa acatgcttca  2040
tcgtcgtgtcc gggctgccac gaccaagtga cagcaatgct gtttcactgg ttatgcggcg  2100
gatccgaaaa gaaaacgttg atgccggtga acgtgcaaaa caggctctag cgttcgaacg  2160
cactgatttc gaccaggttc gttcactcat ggaaaatagc gatcgctgcc aggatatacg  2220
taatctggca tttctgggga ttgcttataa caccctgtta cgtatagccg aaattgccag  2280
gatcagggtt aaagatatct cacgtactga cggtgggaga atgttaatc atattgcag  2340
aacgaaaacg ctggttagca ccgcaggtgt agagaaggca cttagcctgg gggtaactaa  2400
actggtcgag cgatggattt ccgtctctgg tgtagctgat gatccgaata actacctgtt  2460
ttgccgggtc agaaaaaatg gtgttgccgc gccatctgcc accagccagc tatcaactcg  2520
cgccctgaa gggatttttg aagcaactca tcgattgatt tacggcgcta aggatgactc  2580
tggtcagaga tacctggcct ggtctggaca cagtgcccgt gtcggagccg cgcgagatat  2640
ggcccgcgct ggagtttcaa taccggagat catgcaagct ggtggctgga ccaatgtaaa  2700
tattgtcatg aactatatcc gtaacctgga tagtgaaaca ggggcaatgg tgcgcctgct  2760
ggaagatggc gatggaccgg tggaacaaaa acttatttcc gaagaagatc tgtgatagcg  2820
gccgcactcc tcaggtgcag gctgcctatc agaaggtggt ggctggtgtg gccaatgccc  2880
tggctcacaa ataccactga gatcttttc cctctgccaa aaattatggg gacatcatga  2940
agccccttga gcatctgact tctggctaat aaaggaaatt tatttcatt gcaatagtgt  3000
gttggaattt tttgtgtctc tcactcggaa ggacatatgg gagggcaaat catttaaaac  3060
atcagaatga gtatttggtt tagagtttgg caacatatgc ccatatgctg gctgccatga  3120
acaaaggttg gctataaaga ggtcatcagt atatgaaaca gccccctgct gtccattcct  3180
tattccatag aaaagccttg acttgaggtt agatttttt tatattttgt tttgtgttat  3240
tttttctttt aacatcccta aaattttcct tacatgtttt actagccaga ttttttcctcc  3300
tctcctgact actcccagtc atagctgtcc ctcttctctt atggagatcc ctcgacctgc  3360
agcccaagct tggcgtaatc atggtcatag ctgtttcctg tgtgaaattg ttatccgctc  3420
acaattccac acaacatacg agccggaagc ataaagtgta aagcctgggg tgcctaatga  3480
gtgagctaac tcacattaat tgcgttgcgc tcactgcccg ctttccagtc gggaaacctg  3540
tcgtgccagc ggatccgcat ctcaattagt cagcaaccat agtcccgcc ctaactccg  3600
ccatccccgc cctaactccg cccagttccg cccattctcc gccccatggc tgactaattt  3660
ttttatttta tgcagaggcc gaggccgcct cggcctctga gctattccag aagtagtgag  3720
gaggctttt tggaggccta ggcttttgca aaaagctaac ttgtttattg cagcttataa  3780
tggttacaaa taaagcaata gcatcacaaa tttcacaaat aaagcatttt ttcactgca  3840
ttctagttgt ggtttgtcca aactcatcaa tgtatcttat catgtctgga tccgctgcat  3900
taatgaatcg gccaacgcgc ggggagaggc ggtttgcgta ttgggcgctc ttccgcttcc  3960
tcgctcactg actcgctgcg ctcggtcgtt cggctgcggc gagcggtatc agctcactca  4020
aaggcggtaa tacggttatc cacagaatca ggggataacg caggaaagaa catgtgagca  4080
aaaggccagc aaaaggccag gaaccgtaaa aaggccgcgt tgctggcgtt tttccatagg  4140
ctccgccccc ctgacgagca tcacaaaaat cgacgctcaa gtcagaggtg gcgaaaccccg  4200
acaggactat aaagatacca ggcgtttccc cctggaagct ccctcgtgcg ctctcctgtt  4260
```

```
ccgaccctgc cgcttaccgg atacctgtcc gcctttctcc cttcgggaag cgtggcgctt    4320
tctcatagct cacgctgtag gtatctcagt tcggtgtagg tcgttcgctc caagctgggc    4380
tgtgtgcacg aaccccccgt tcagcccgac cgctgcgcct tatccggtaa ctatcgtctt    4440
gagtccaacc cggtaagaca cgacttatcg ccactggcag cagccactgg taacaggatt    4500
agcagagcga ggtatgtagg cggtgctaca gagttcttga agtggtggcc taactacggc    4560
tacactagaa gaacagtatt tggtatctgc gctctgctga agccagttac cttcggaaaa    4620
agagttggta gctcttgatc cggcaaacaa accaccgctg gtagcggtgg ttttttttgtt    4680
tgcaagcagc agattacgcg cagaaaaaaa ggatctcaag aagatccttt gatcttttct    4740
acggggtctg acgctcagtg gaacgaaaac tcacgttaag ggattttggt catgagatta    4800
tcaaaaagga tcttcaccta gatcctttta aattaaaaat gaagttttaa atcaatctaa    4860
agtatatatg agtaaacttg gtctgacagt taccaatgct taatcagtga ggcacctatc    4920
tcagcgatct gtctatttcg ttcatccata gttgcctgac tccccgtcgt gtagataact    4980
acgatacggg agggcttacc atctggcccc agtgctgcaa tgataccgcg agacccacgc    5040
tcaccggctc cagatttatc agcaataaac cagcagccag gaagggccga gcgcagaagt    5100
ggtcctgcaa ctttatccgc ctccatccag tctattaatt gttgccggga agctagagta    5160
agtagttcgc cagttaatag tttgcgcaac gttgttgcca ttgctacagg catcgtggtg    5220
tcacgctcgt cgtttggtat ggcttcattc agctccggtt cccaacgatc aaggcgagtt    5280
acatgatccc ccatgttgtg caaaaaagcg gttagctcct tcggtcctcc gatcgttgtc    5340
agaagtaagt tggccgcagt gttatcactc atggttatgg cagcactgca taattctctt    5400
actgtcatgc catccgtaag atgcttttct gtgactggtg agtactcaac caagtcattc    5460
tgagaatagt gtatgcggcg accgagttgc tcttgcccgg cgtcaatacg ggataatacc    5520
gcgccacata gcagaacttt aaaagtgctc atcattggaa aacgttcttc ggggcgaaaa    5580
ctctcaagga tcttaccgct gttgagatcc agttcgatgt aacccactcg tgcacccaac    5640
tgatcttcag catcttttac tttcaccagc gtttctgggt gagcaaaaac aggaaggcaa    5700
aatgccgcaa aaaagggaat aagggcgaca cggaaatgtt gaatactcat actcttcctt    5760
tttcaatatt attgaagcat ttatcagggt tattgtctca tgagcggata catatttgaa    5820
tgtatttaga aaaataaaca aataggggtt ccgcgcacat ttccccgaaa agtgccacct    5880
g                                                                    5881

SEQ ID NO: 72         moltype = DNA  length = 4915
FEATURE               Location/Qualifiers
misc_feature          1..4915
                      note = Description of Artificial Sequence: Synthetic
                      polynucleotide
misc_feature          1..4915
                      note = GFP-Lox66-Cre expression plasmid
source                1..4915
                      mol_type = other DNA
                      organism = synthetic construct
SEQUENCE: 72
agctctgatc aagagacagg atgaggatcg tttcgcatga ttgaacaaga tggattgcac      60
gcaggttctc cggccgcttg ggtggagagg ctattcggct atgactgggc acaacagaca     120
atcggctgct ctgatgccgc cgtgttccgg ctgtcagcga ggggcgcccc ggttcttttt     180
gtcaagaccg acctgtccgg tgccctgaat gaactgcaag acgaggcagc gcggctatcg     240
tggctggcca cgacgggcgt tccttgcgca gctgtgctcg acgttgtcac tgaagcggga     300
agggactggc tgctattggg cgaagtgccg gggcaggatc tcctgtcat ctacaccttg     360
ctcctgccga gaaagtatcc atcatggctg atgcaatgcg gcggctgcat acgcttgatc     420
cggctacctg cccattcgac caccaagcga aacatcgcat cgagcgagca cgtactcgga     480
tggaagccgg tcttgtcgat caggatgatc tggacgaaga gcatcagggg ctcgcgccag     540
ccgaactgtt cgccaggctc aaggcgagca tgcccgacgg cgaggatctc gtcgtgaccc     600
atggcgatgc ctgcttgccg aatatcatgg tggaaaatgg ccgcttttct ggattcatcg     660
actgtggccg gctgggtgtg gcggaccgct atcaggacat agcgttggct acccgtgata     720
ttgctgaaga gcttggcggc gaatgggctg accgcttcct cgtgctttac ggtatcgccg     780
ctcccgattc gcagcgcatc gccttctatc gccttcttga cgagttcttc tgaattatta     840
actgagatc cactagagtg tggcggccgc attcttataa tcagcatcat gatgtggtac     900
cacatcatga tgctgattac ccccaactga gagaactcaa aggttacccc agttggggc     960
ggcccacaaa taaagcaata gcatcacaaa tttcacaaat aaagcatttt ttcactgca    1020
ttctagttgt ggtttgtcca aactcatcga gctcgagatc tggcgaaggc gatggggtc    1080
ttgaaggcgt gctggtactc cacgatgccc agctcggtgt tgctgtgcag ctcctccacg    1140
cggcggaagg cgaacatggg gcccccgttc tgcaggatgc tgggggtgat ggcgctcttg    1200
aagtgcatgt ggctgtccac cacgaagctg tagtagccgc cgtcgcgcag gctgaaggtg    1260
cgggcgaagc tgcccaccag cacgttatcg cccatggggt gcaggtgctc cacggtggcg    1320
ttgctgcgga tgatcttgtc ggtgaagatc acgctgtcct cggggaagcc ggtgcccacc    1380
accttgaagt cgccgatcac gcggccggcc tcgtagcggt agtcgaagct cacgtgcagc    1440
acgccgccgt cctcgtactt ctcgatgcgg gtgttggtgt agccgccgtt gttgatggcc    1500
tgcaggaagg ggttctcgta gccgctgggg taggtgccga agtggtagaa gccgtagccc    1560
atcacgtggc tcagcaggta ggggctgaag gtcagggcgc ctttggtgct cttcatcttg    1620
ttggtcatgc ggccctgctc gggggtgccc tctccgccgc ccaccagctc gaactccacg    1680
ccgttcaggg tgccggtgat gcggcactcg atcttcatgg cggaccggtt ggcgaccggt    1740
agcgctagcg gcttcggata acttcgtata gcatacatta tacgaacggt aagcgctacc    1800
gccggcatac ccaagtgaag ttgctcgcag cttatagtcg cgcccgggga gcccaagggc    1860
acgccctggc accgcggccg ctgagtctcg accatcatca tcatcatcat tgagtttatc    1920
tgggataaca gggtaatgtc atctagggat aacagggtat gtcatctggg ataacagggt    1980
aatgtatcta gggataacag ggtaatgtca tctgggataa cagggtaatg tcatctaggg    2040
ataacagggt atgtcatctg gataacagg gtaatgtatc tagggataac agggtaatgt    2100
catctgggat aacagggtaa tgtcatctag ggataacagg gtatgtcatc tgggataaca    2160
gggtaatgta tctagggata acagggtaat gtcatctggg ataacagggt aatgtcatct    2220
agggataaca gggtatgtca tctggggataa cagggtaatg tatctaggga taacagggta    2280
atgtcatctg gataacagg gtaatgtcat ctagggataa caggtgtgt catctgggat    2340
```

```
aacagggtaa tgtatctagg gataacaggg taatgtcatc tgggataaca gggtaatgtc  2400
atctagggat aacagggtat gtcatctggg ataacagggt aatgtatcta gggataacag  2460
ggtaatgtca tctgggataa cagggtaatg tcatctaggg ataacagggt aaatgtcatc  2520
tagggataac agggtaatgt catctaggga taacagggta atgtcatctg gataacagg   2580
gtaatgtcat ctagggataa cagggtaatg tatcgccagc gtcgcacagc atgtttgctt  2640
gtcgccgtcg cgtctgtcac atcttttccg ccagcagtta gggattagcg tcttaagctg  2700
gcgcgaggac caacgtatca gccaggcgaa gctgcttttg agcaccaccc ggatgcctat  2760
cgccaccgtc ggtcgcaatg ttggttttga cgatcaactc tatttctcgc gggtatttaa  2820
aaaatgcacc ggggccagcc cgagcgagtt ccgtgccggt tgtgaagaaa aagtgaatga  2880
tgtagccgtc aagttgtcat aattggtaac gaatcagaca attgacggct tgacggagta  2940
gcatagggtt tgcagaatcc ctgcttcgtc catttgacag gcacattatg catgccgctt  3000
cgccttcgcg cgcgaattga tctgctgcct cgcgcgtttc ggtgatgacg gtgaaaacct  3060
ctgacacatg cagctcccgg agacggtcac agcttgtctg taagcggatg ccgggagcag  3120
acaagcccgt cagggcgcgt cagcgggtgt tggcgggtgt cggggcgcag ccatgaccca  3180
gtcacgtagc gatagcggag tgtatactgg cttaactatg cggcatcaga gcagattgta  3240
ctgagagtgc accatatgcg gtgtgaaata ccgcacagat gcgtaaggag aaaataccgc  3300
atcaggcgct cttccgcttc ctcgctcact gactcgctgc gctcggtcgt tcggctgcgg  3360
cgagcggtat cagctcactc aaaggcggta atacggttat ccacagaatc aggggataac  3420
gcaggaaaga acatgtgagc aaaaggccag caaaaggcca ggaaccgtaa aaaggccgcg  3480
ttgctggcgt ttttccatag gctccgcccc cctgacgagc atcacaaaaa tcgacgctca  3540
agtcagaggt ggcgaaaccc gacaggacta taaagatacc aggcgtttcc ccctggaagc  3600
tccctcgtgc gctctcctgt tccgaccctg ccgcttaccg gatacctgtc cgcctttctc  3660
ccttcgggaa gcgtggcgct ttctcatagc tcacgctgta ggtatctcag ttcggtgtag  3720
gtcgttcgct ccaagctggg ctgtgtgcac gaaccccccg ttcagcccga ccgctgcgcc  3780
ttatccggta actatcgtct tgagtccaac ccggtaagac acgacttatc gccactggca  3840
gcagccactg gtaacaggat tagcagagcg aggtatgtag gcggtgctac agagttcttg  3900
aagtggtggc ctaactacgg ctacactaga aggacagtat ttggtatctg cgctctgctg  3960
aagccagtta ccttcggaaa aagagttggt agctcttgat ccggcaaaca aaccaccgct  4020
ggtagcggtg gtttttttgt ttgcaagcag cagattacgc gcagaaaaaa aggatctcaa  4080
gaagatcctt tgatcttttc tacggggtct gacgctcagt ggaacgaaaa ctcacgttaa  4140
gggattttgg tcatgagcgg atacatattt gaatgtattt agaaaaataa acaaaagagt  4200
ttgtagaaac gcaaaaaggc catccgtcag gatggccttc tgcttaattt gatgcctggc  4260
agtttatggc gggcgtcctg cccgccaccc tccgggccgt tgcttcgcaa cgttcaaatc  4320
cgctcccggc ggatttgtcc tactcaggag agcgttcacc gacaaacaac agataaaacg  4380
aaaggcccag tctttcgact gagcctttcg ttttatttga tgcctggcag ttccctactc  4440
tcgcatgggg agaccccaca ctaccatcgg cgctacggcg tttcacttct gagttcggca  4500
tggggtcagg tgggaccacc gcgctactgc cgccaggcaa attctgtttt atcagaccgc  4560
ttctgcgttc tgatttaatc tgtatcaggc tgaaaatctt ctctcatccg ccaaaacagc  4620
caagctggag accgtttggc cccctcgag cacgtagaaa gccagtccgc agaaacggtg  4680
ctgaccccgg atgaatgtca gctactgggc tatctggaca agggaaaacg caagcgcaaa  4740
gagaaagcag gtagcttgca gtgggcttac atgcgcatag ctagactggg cggttttatg  4800
gacagcaagc gaaccggaat tgccagctgg ggcgccctct ggtaaggttg ggaagccctg  4860
caaagtaaac tggatggctt tctcgccgcc aaggatctga tggcgcaggg gatca       4915
```

SEQ ID NO: 73            moltype = DNA    length = 10815
FEATURE                 Location/Qualifiers
misc_feature         1..10815
                         note = Description of Artificial Sequence: Synthetic
                         polynucleotide
misc_feature         1..10815
                         note = pCMV-PE2-P2A-Cre
source                  1..10815
                         mol_type = other DNA
                         organism = synthetic construct
SEQUENCE: 73

```
acgcgttgac attgattatt gactagttat taatagtaat caattacggg gtcattagtt    60
catagcccat atatggagtt ccgcgttaca taacttacgg taaatggccc gcctggctga   120
ccgcccaacg acccccgccc attgacgtca ataatgacgt atgttcccat agtaacgcca   180
atagggactt tccattgacg tcaatgggtg gagtatttac ggtaaactgc ccacttggca   240
gtacatcaag tgtatcatat gccaagtacg ccccctattg acgtcaatga cggtaaatgg   300
cccgcctggc attatgccca gtacatgacc ttatgggact ttcctacttg gcagtacatc   360
tacgtattag tcatcgctat taccatggtg atgcggtttt ggcagtacat caatgggcgt   420
ggatagcggt ttgactcacg gggatttcca agtctccacc ccattgacgt caatgggagt   480
ttgttttggc accaaaatca acgggacttt ccaaaatgtc gtaacaactc cgccccattg   540
acgcaaatgg gcggtaggcg tgtacggtgg gaggtctata taagcagagc tggtttagtg   600
aaccgtcaga tccgctagag atccgcggcc gctaatacga ctcactatag ggagagccgc   660
caccatgaaa cggacagccg acggaagcga gttcgagtca ccaaagaaga agcggaaagt   720
cgacaagaag tacagcatcg gcctggacat cggcaccaac tctgtgggct gggccgtgat   780
caccgacgag tacaaggtgc ccagcaagaa attcaaggtg ctgggcaaca ccgaccggca   840
cagcatcaag aagaacctga tcggagccct gctgttcgac agcggcgaaa cagccgaggc   900
cacccggctg aagagaaccg ccagaagaag ataccaccag cggaagaacc ggatctgcta   960
tctgcaagag atcttcagca acgagatggc caaggtggac gacagcttct ccacagactt  1020
ggaagagtcc ttcctggtgg aagaggataa gaagcacgag cggcacccca tcttcggcaa  1080
catcgtggac gaggtggcct accacgagaa gtacccaacc atctaccacc tgagaaagaa  1140
actggtggac agcaccgaca aggccgacct gcgcctgatc tatctggccc tggcccacat  1200
gatcaagttc cggggccact tcctgatcga gggcgacctg aaccccgaca acagcgacgt  1260
ggacaagctg ttcatccagc tggtgcagac ctacaaccag ctgttcgagg aaaaccccat  1320
caacgccagc ggcgtggacg ccaaggccat cctgtctgcc agactgagca gagcagacg   1380
gctggaaaat ctgatcgccc agctgcccgg cgagaagaag aatggcctgt tcggaaacct  1440
```

```
gattgccctg agcctgggcc tgaccccaa cttcaagagc aacttcgacc tggccgagga   1500
tgccaaactg cagctgagca aggacaccta cgacgacgac ctggacaacc tgctggccca   1560
gatcggcgac cagtacgccg acctgtttct ggccgccaag aacctgtccg acgccatcct   1620
gctgagcgac atcctgagag tgaacaccga gatcaccaag gcccccctga cgcctctat    1680
gatcaagaga tacgacgagc accaccaagga cctgaccctg ctgaaagctc tcgtgcggca   1740
gcagctgcct gagaagtaca aagagatttt cttcgaccag agcaagaacg gctacgccgg   1800
ctacattgac ggcggagcca gccaggaaga gttctacaag ttcatcaagc ccatcctgga   1860
aaagatggac ggcaccgagg aactgctcgt gaagctgaac agagaggacc tgctgcggaa   1920
gcagcggacc ttcgacaacg gcagcatccc ccaccagatc cacctgggag agctgcacgg   1980
cattctgcgg cggcaggaag attttttacc attcctgaag gacaaccggg aaaagatcga   2040
gaagatcctg accttccgca tcccctacta cgtgggccct ctggccaggg aaacagcag    2100
attcgcctgg atgaccagaa agagcgagga aaccatcacc ccctggaact tcgaggaagt   2160
ggtggacaag ggcgcttccg cccagagctt catcgagcgg atgaccaact tcgataagaa   2220
cctgcccaac gagaaggtgc tgcccaagca cagcctgctc tacgagtact tcaccgtgta   2280
taacgagctg accaaagtga aatacgtgac cgagggaatg agaaagcccg ccttcctgag   2340
cggcgagcag aaaaaggcca tcgtggacct gctgttcaag accaaccgga aagtgaccgt   2400
gaagcagctg aaagaggact acttcaagaa aatcgagtgc ttcgactccg tggaaatctc   2460
cggcgtggaa gatcggttca acgcctccct gggcacatac cacgatctgc tgaaaattat   2520
caaggacaag gacttcctgg acaatgagga aaacgaggac attctggaag atatcgtgct   2580
gaccctgaca ctgtttgagg acagagagat gatcgaggaa cggctgaaaa cctatgccca   2640
cctgttcgac gacaaagtga tgaagcagct gaagcggcgg agatacaccg gctggggcag   2700
gctgagccgg aagctgatca acggcatccg ggacaagcag tccggcaaga caatcctgga   2760
tttcctgaag tccgacggct tcgccaacag aaacttcatg cagctgatcc acgacgacag   2820
cctgaccttt aaagaggaca tccagaaagc ccaggtgtcc ggccaggcg ataggcctgca   2880
cgagcacatt gccaatctgg ccggcagccc cgccattaag aagggcatcc tgcagacagt   2940
gaaggtggtg gacgagctcg tgaaagtgat gggccgcaac aagcccgaga acatcgtgat   3000
cgaaatggcc agagagaacc agaccaccca gaagggacaa agaacagcc gcgagagaat   3060
gaagcggatc gaagagggca tcaaagagct gggcagccag atcctgaaag aacaccccgt   3120
ggaaaacacc cagctgcaga acgagaagct gtacctgtac tacctgcaga atgggcggga   3180
tatgtacgtg gaccaggaac tggacatcaa ccggctgtcc gactacgatg tggacgctat   3240
cgtgcctcag agctttctga aggacgactc catcgacaac aaggtgctga ccagaagcga   3300
caagaaccgg ggcaagagcg acaacgtgcc ctccgaagag gtcgtgaaga agatgaagaa   3360
ctactggcgg cagctgctga acgccaagct gattacccag agaaagttcg acaatctgac   3420
caaggccgag agaggcggcc tgagcgaact ggataaggcc ggcttcatca agagacagct   3480
ggtgaaaacc cggcagatca caaagcacgt ggcacagatc ctggactccc ggatgaacac   3540
taagtacgac gagaatgaca agctgatccg ggaagtgaaa gtgatcaccc tgaagtccaa   3600
gctggtgtcc gatttccgga aggatttcca gttttacaaa gtgcgcgaga tcaacaacta   3660
ccaccacgcc cacgacgcct acctgaacgc cgtcgtggga accgccctga tcaaaaagta   3720
ccctaagctg gaaagcgagt tcgtgtacgg cgactacaag gtgtacgacg tgcggaagat   3780
gatcgccaag agcgagcagg aaatcggcaa ggctaccgcc aagtacttct tctacagcaa   3840
catcatgaac ttttttcaaga ccgagattac cctggccaac ggcgagatcc ggaagcggcc   3900
tctgatcgag acaaacggcg aaaccgggga gatcgtgtgg gataagggcc gggattttgc   3960
caccgtgcgg aaagtgctga gcatgcccca agtgaatatc gtgaaaaaga ccgaggtgca   4020
gacaggcggc ttcagcaaag agtctatcct gcccaagagg aacagcgata gctgatcgc    4080
cagaaagaag gactgggacc ctaagaagta cggcggcttc gacagcccca ccgtggccta   4140
ttctgtgctg gtggtggcca aagtggaaaa gggcaagtcc aagaaactga agagtgtgaa   4200
agagctgctg gggatcacca tcatggaaag aagcagcttc gagaagaatc ccatcgactt   4260
tctggaagcc aagggctaca aagaagtgaa aaaggacctg atcatcaagc tgcctaagta   4320
ctccctgttc gagctggaaa acggccggaa gagaatgctg gcctctgccg gcgaactgca   4380
gaagggaaac gaactggccc tgccctccaa atatgtgaac ttcctgtacc tggccagcca   4440
ctatgaaaag ctgaagggct cccccgagga taatgagcag aaacagctgt ttgtggaaga   4500
gcacaagcac tacctggacg agatcatcga gcagatcagc gagttctcca agagagtgat   4560
cctggccgac gctaatctgg acaaagtgct gtccgcctac aacaagcacc gggataagcc   4620
catcagagag caggccgaga atatcatcca cctgtttacc ctgaccaatc tgggagcccc   4680
tgccgccttc aagtactttg acaccaccat cgaccggaag aggtacacca gcaccaaaga   4740
ggtgctggac gccaccctga tccaccagag catcaccggc ctgtacgaga cacggatcga   4800
cctgtctcag ctgggaggtg actctggagg atctagcgga ggatcctctg cagcgagac    4860
accaggaaca agcgagtcag caacaccaga gagcagtggc ggcagcagcg gcggcagcag   4920
cacccctaaat atagaagatg agtatcggct acatgacacc tcaaaaagac cagatgtttc   4980
tctagggtcc acatggctgt ctgatttttcc tcaggcctgg gcggaaaccg ggggcatggg   5040
actggcagtt cgccaagctc ctctgatcat acctctgaaa gcaacctcta cccccgtgtc   5100
cataaaacaa taccccatgt cacaagaagc cagactgggg atcaagcccc acatacagag   5160
actgttggac cagggaatac tggtaccctg ccagtccccc tggaacacgc ccctgctacc   5220
cgttaagaaa ccagggacta atgattatag gcctgtccga gatctgagag aagtcaacaa   5280
gcggtggaa gacatccacc ccaccgtgcc caacccttac aacctcttga gcgggctccc    5340
accgtcccac cagtggtaca ctgtgcttga tttaaaggat gccttttttct gcctgagact   5400
ccacccacc agtcagcctc tcttcgcctt tgagtggaga gatccagaga tgggaatctc    5460
aggacaattg acctggacca gactcccaca gggtttcaaa acagtccca ccctgttttaa    5520
tgaggcactg cacagagacc tagcagactt ccggatccag cacccagatt tgatcctgct   5580
acagtacgtg gatgacttac tgctggccgc cacttctgag ctagactgcc aacaaggtac   5640
tcgggccctg ttacaaaccc tagggaacct cgggtatcgg gcctcggcca agaaagccca   5700
aatttgccag aaacaggtca agtatctggg gtatcttcta aaagagggtc agagatggct   5760
gactgaggcc agaaaagaga ctgtgatggg gcagcctact ccgaagaccc ctcgacaact   5820
taggggagttc ctagggaagg caggcttctg tcgcctcttc atccctgggt ttgcagaaat   5880
ggcagccccc ctgtaccctc tcaccaaacc ggggactctg tttaattggg gcccagacca   5940
acaaaaggcc tatcaagaaa tcaagcaagc tcttctaact gccccagccc tggggttgcc   6000
agatttgact aagccctttg aactctttgt cgacgagaag cagggctacg ccaaaggtgt   6060
cctaacgcaa aaactgggac cttggcgtcg gccggtggcc tacctgtcca aaaagctaga   6120
cccagtagca gctgggtggc cccctgcct acggatggta gcagccattg ccgtactgac   6180
```

-continued

```
aaaggatgca ggcaagctaa ccatgggaca gccactagtc attctggccc cccatgcagt    6240
agaggcacta gtcaaacaac cccccgaccg ctggctttcc aacgcccgga tgactcacta    6300
tcaggccttg cttttggaca cggaccgggt ccagttcgga ccggtggtag ccctgaaccc    6360
ggctacgctg ctcccactgc ctgaggaagg gctgcaacac aactgccttg atatcctggc    6420
cgaagcccac ggaacccgac ccgacctaac ggaccagccg ctcccagacg cgaccacac    6480
ctggtacacg gatggaagca gtctcttaca agagggacag cgtaaggcgg gagctgcggt    6540
gaccaccgag accgaggtaa tctgggctaa agccctgcca gccgggacat ccgctcagcg    6600
ggctgaactg atagcactca cccaggccct aaagatggca gaaggtaaga agctaaatgt    6660
ttatactgat agccgttatg cttttgctac tgcccatatc catggagaaa tatacagaag    6720
gcgtgggtgg ctcacatcag aaggcaaaga gatcaaaaat aaagacgaga tcttggccct    6780
actaaaagcc ctctttctgc ccaaaagact tagcataatc cattgtccag gacatcaaaa    6840
gggacacagc gccgaggcta gaggcaaccg gatggctgac caagcggccc gaaaggcagc    6900
catcacagag actccagaca cctctaccct cctcatagaa aattcatcac cctctggcgg    6960
ctcaaaaaga accgccgacg gcagcgaatt cgagcccaag aagaagagga aagtcggaag    7020
cggagctact aacttcagcc tgctgaagca ggctggcgac gtggaggaga accctggacc    7080
taatttactg accgtacacc aaaatttgcc tgcattaccg gtcgatgcaa cgagtgatga    7140
ggttcgcaag aacctgatgg acatgttcag ggatcgccag gcgttttctg agcatacctg    7200
gaaaatgctt ctgtccgttt gccggtcgtg ggcggcatgg tgcaagttga ataaccggaa    7260
atggtttccc gcagaacctg aagatgttcg cgattatctt ctatatcttc aggcgcgcgg    7320
tctggcagta aaaactatcc agcaacattt gggccagcta acatgcttc atcgtcggtc    7380
cgggctgcca cgaccaagtg acagcaatgc tgtttcactg gttatgcggc ggatccgaaa    7440
agaaaacgtt gatgccggtg aacgtgcaaa acaggctcta gcgttcgaac gcactgattt    7500
cgaccaggtt cgttcactca tggaaaatag cgatcgctgc caggatatac gtaatctggc    7560
atttctgggg attgcttata acaccctgtt acgtatagcc gaaattgcca ggatcagggt    7620
taaagatatc tcacgtactg acggtgggag aatgttaatc catattggca gaacgaaaac    7680
gctggttagc accgcaggtg tagagaaggc acttagcctg ggggtaacta aactggtcga    7740
gcgatggatt tccgtctctg gtgtagctga tgatccgaat aactaccgt tttgccgggt    7800
cagaaaaaat ggtgttgccg cgccatctgc caccagccag ctatcaactc gcgccctgga    7860
agggattttt gaagcaactc atcgattgat ttacggcgct aaggatgact ctggtcagag    7920
atacctggcc tggtctggac acagtgcccg tgtcggagcc gcgcagaata tggcccgcgc    7980
tggagtttca ataccggaga tcatgcaagc tggtggctgg accaatgtaa atattgtcat    8040
gaactatatc cgtaacctgg atagtgaaac aggggcaatg gtgcgcctgc tggaagatgg    8100
cgattaattt aaacccgctg atcagcctcg actgtgcctt ctagttgcca gccatctgtt    8160
gtttgcccct cccccgtgcc ttccttgacc ctggaaggtg ccactcccac tgtcctttcc    8220
taataaaatg agaaaattgc atcgcattgt ctgagtaggt gtcattctat tctgggggt    8280
ggggtgggc aggacagcaa gggggaggat tgggaagaca atagcaggca tgctggggat    8340
gcggtgggct ctatggcttc tgaggcggaa agaaccagct ggggctcgat accgtcgacc    8400
tctagctaga gcttggcgta atcatggtca tagctgtttc ctgtgtgaaa ttgttatccg    8460
ctcacaattc cacacaacat acgagccgga agcataaagt gtaaagcctg gggtgcctaa    8520
tgagtgagct aactcacatt aattgcgttg cgctcactgc ccgctttcca gtcgggaaac    8580
ctgtcgtgcc agctgcatta atgaatcggc caacgcgcgg ggagaggcgg tttgcgtatt    8640
gggcgctctt ccgcttcctc gctcactgac tcgctgcgct cggtcgttcg gctgcggcga    8700
gcggtatcag ctcactcaaa ggcggtaata cggttatcca cagaatcagg ggataacgca    8760
ggaaagaaca tgtgagcaaa aggccagcaa aaggccagga accgtaaaaa ggccgcgttg    8820
ctggcgtttt tccataggct ccgcccccct gacgagcatc acaaaaatcg acgctcaagt    8880
cagaggtggc gaaacccgac aggactataa agataccagg cgtttccccc tggaagctcc    8940
ctcgtgcgct ctcctgttcc gaccctgccg cttaccggat acctgtccgc ctttctccct    9000
tcggaagcg tggcgctttc tcatagctca cgctgtaggt atctcagttc ggtgtaggtc    9060
gttcgctcca agctgggctg tgtgcacgaa ccccccgttc agcccgaccg ctgcgcctta    9120
tccggtaact atcgtcttga gtccaacccg gtaagacacg acttatcgcc actggcagca    9180
gccactggta acaggattag cagagcgagg tatgtaggcg gtgctacaga gttcttgaag    9240
tggtggccta actacggcta cactagaaga acagtatttg gtatctgcgc tctgctgaag    9300
ccagttacct tcggaaaaag agttggtagc tcttgatccg gcaaacaaac caccgctggt    9360
agcggtggtt ttttgtttg caagcagcag attacgcgca gaaaaaagg atctcaagaa    9420
gatcctttga tcttttctac ggggtctgac gctcagtgga acgaaaactc acgttaaggg    9480
attttggtca tgagattatc aaaaaggatc ttcacctaga tccttttaaa ttaaaaatga    9540
agttttaaat caatctaaag tatatatgag taaacttggt ctgacagtta ccaatgctta    9600
atcagtgagg cacctatctc agcgatctgt ctatttcgtt catccatagt tgcctgactc    9660
cccgtcgtgt agataactac gatacgggag ggcttaccat ctggccccag tgctgcaatg    9720
ataccgcgag acccacgctc accggctcca gatttatcga caataaacca gccagccgga    9780
agggccgagc gcagaagtgg tcctgcaact ttatccgcct ccatccagtc tattaattgt    9840
tgccgggaag ctagagtaag tagttcgcca gttaatagtt tgcgcaacgt tgttgccatt    9900
gctacaggca tcgtggtgtc acgctcgtcg tttggtatgg cttcattcag ctccggttcc    9960
caacgatcaa ggcgagttac atgatccccc atgttgtgca aaaaagcggt tagctccttc    10020
ggtcctccga tcgttgtcag aagtaagttg gccgcagtgt tatcactcat ggttatggca    10080
gcactgcata attctcttac tgtcatgcca tccgtaagat gcttttctgt gactggtgag    10140
tactcaacca agtcattctg agaatagtgt atgcggcgac cgagttgctc ttgcccggcg    10200
tcaatacggg ataataccgc gccacatagc agaactttaa aagtgctcat cattggaaaa    10260
cgttcttcgg ggcgaaaact ctcaaggatc ttaccgctgt tgagatccag ttcgatgtaa    10320
cccactcgtg cacccaactg atcttcagca tcttttactt tcaccagcgt ttctgggtga    10380
gcaaaaacag gaaggcaaaa tgccgcaaaa aagggaataa gggcgacacg gaaatgttga    10440
atactcatac tcttcctttt tcaatattat tgaagcattt atcagggtta ttgtctcatg    10500
agcggataca tatttgaatg tatttagaaa aataaacaaa taggggttcc gcgcacattt    10560
ccccgaaaag tgccacctga cgtcgacgga tcgggagagc gttcccgagg gcctcgatat    10620
tcgactctca gtacaatctg ctctgatgcc gcatagttaa gccagtatct gctccctgct    10680
tgtgtgttgg aggtcgctga gtagtgcgcg agcaaaattt aagctacaac aaggcaaggc    10740
ttgaccgaca attgcatgaa gaatctgctt agggttaggc gttttgcgct gcttcgcgat    10800
gtacgggcca gatat                                                    10815
```

```
SEQ ID NO: 74             moltype = DNA   length = 20
FEATURE                   Location/Qualifiers
misc_feature              1..20
                          note = Description of Artificial Sequence: Synthetic
                          oligonucleotide
misc_feature              1..20
                          note = +90ngRNA guide sequence
source                    1..20
                          mol_type = other DNA
                          organism = synthetic construct
SEQUENCE: 74
gtcaaccagt atcccggtgc                                                 20

SEQ ID NO: 75             moltype = DNA   length = 96
FEATURE                   Location/Qualifiers
misc_feature              1..96
                          note = Description of Artificial Sequence: Synthetic
                          oligonucleotide
misc_feature              1..96
                          note = +90ngRNA
source                    1..96
                          mol_type = other DNA
                          organism = synthetic construct
SEQUENCE: 75
gtcaaccagt atcccggtgc gttttagagc tagaaatagc aagttaaaat aaggctagtc     60
cgttatcaac ttgaaaaagt ggcaccgagt cggtgc                               96

SEQ ID NO: 76             moltype = DNA   length = 4968
FEATURE                   Location/Qualifiers
misc_feature              1..4968
                          note = Description of Artificial Sequence: Synthetic
                          polynucleotide
misc_feature              1..4968
                          note = GFP minicircle template (before cleavage)
source                    1..4968
                          mol_type = other DNA
                          organism = synthetic construct
SEQUENCE: 76
tgatccctg cgccatcaga tccttggcgg cgagaaagcc atccagttta ctttgcaggg      60
cttcccaacc ttaccagagg gcgccccagc tggcaattcc ggttcgcttg ctgtccataa    120
aaccgcccga tctagctatc gccatgtaag cccactgcaa gctacctgct ttctctttgc    180
gcttgcgttt tcccttgtcc agatagccca gtagctgaca ttcatccggg gtcagcaccg    240
tttctgcgga ctggctttct acgtgctcga gggggcaa acggtctcca gcttggctgt     300
tttggcggat gagagaagat tttcagcctg atacagatta aatcagaacg cagaagcggt    360
ctgataaaac agaatttgcc tggcggcagt agcgcggtgg tcccacctga ccccatgccg    420
aactcagaag tgaaacgccg tagcgccgat ggtagtgtgg ggtctcccca tgcgagagta    480
gggaactgcc aggcatcaaa taaaacgaaa ggctcagtcg aaagactggg cctttcgttt    540
tatctgttgt ttgtcggtga acgctctcct gagtaggaca aatccgccgg gagcggattt    600
gaacgttgcg aagcaacggc ccggagggtg cgggcagga cgcccgccat aaactgccag    660
gcatcaaatt aagcagaagg ccatcctgac ggatggcctt tttgcgtttc tacaaactct    720
tttgtttatt tttctaaata cattcaaata tgtatccgct catgaccaaa atcccttaac    780
gtgagttttc gttccactga gcgtcagacc ccgtagaaaa gatcaaagga tcttcttgag    840
atccttttt tctgcgcgta atctgctgct tgcaaacaaa aaaaccaccg ctaccagcgg    900
tggtttgttt gccggatcaa gagctaccaa ctctttttcc gaaggtaact ggcttcagca    960
gagcgcagat accaaatact gtccttctag tgtagccgta gttaggccac cacttcaaga   1020
actctgtagc accgcctaca tacctcgctc tgctaatcct gttaccagtg gctgctgcca   1080
gtggcgataa gtcgtgtctt accgggttgg actcaagacg atagttaccg gataaggcgc   1140
agcggtcggg ctgaacgggg ggttcgtgca cacagcccag cttggagcga acgacctaca   1200
ccgaactgag atacctacag cgtgagctat gagaaagcgc cacgcttccc gaagggagaa   1260
aggcggacag gtatccggta agcggcaggg tcggaacagg agagcgcacg agggagcttc   1320
cagggggaaa cgcctggtat ctttatagtc ctgtcgggtt cgccacctc tgacttgagc    1380
gtcgatttt tgtgatgctcg tcagggggc ggagcctatg gaaaaacgcc agcaacgcgg   1440
ccttttacg gttcctggcc ttttgctggc cttttgctca catgttcttt cctgcgttat   1500
ccctgattc tgtggataac cgtattaccg cctttgagtg agctgatacc gctcgccgca   1560
gccgaacgac cgagcgcagc gagtcagtga gcgaggaagc ggaagagcgc ctgatgcggt   1620
attttctcct tacgcatctg tgcggtattt cacaccgcat atggtgcact ctcagtacaa   1680
tctgctctga tgccgcatag ttaagccagt atacactccg ctatcgctac gtgactgggt   1740
catggctgcg ccccgacacc cgccaacacc cgctgacgcg ccctgacggg cttgtctgct   1800
cccggcatcc gcttacagac aagctgtgac cgtctccggg agctgcatgt gtcagaggtt   1860
ttcaccgtca tcaccgaaac gcgcgaggca gcagatcaat tcgcgcgcga aggcgaagcg   1920
gcatgcataa tgtgcctgtc aaatggacga agcagggatt ctgcaaaccc tatgctactc   1980
cgtcaagccg tcaattgtct gattcgttac caattatgac aacttgacgg ctacatcatt   2040
cactttttct tcacaaccgg cacgaactc gctcgggctg gccccggtgc attttttaaa    2100
tacccgcgag aaatagagtt gatcgtcaaa accaacattg cgaccgacgg tggcgatagg   2160
catccgggtg gtgctcaaaa gcagcttcgc ctggctgata cgttggtcct cgcgccagct   2220
taagacgcta atccctaact gctggcgaa aagatgtgac agacgcgacg gcgacaagca    2280
aacatgctgt gcgacgctgg cgatacatta cctgttatc cctagatgac attccctgt    2340
tatcccgat gacattaccc tgttatccct agatgacatt accctgttat ccctagatga   2400
catttaccct gttatcccta gatgacatta ccctgttatc cagatgaca ttaccctgtt    2460
```

```
atccctagat acattaccct gttatcccag atgacatacc ctgttatccc tagatgacat  2520
taccctgtta tcccagatga cattaccctg ttatccctag atacattacc ctgttatccc  2580
agatgacata ccctgttatc cctagatgac attaccctgt tatcccagat gacattaccc  2640
tgttatccct agatacatta ccctgttatc ccagatgaca tacccTgtta tcccTagatg  2700
acattaccct gttatcccag atgacattac ctagatacat taccctgtta  2760
tcccagatga catacccTgt tatccctaga tgacattacc ctgttatccc agatgacatt  2820
accctgttat ccctagatac attaccctgt tatcccagat gacatacccT gttatcccta  2880
gatgacatta ccctgttatc ccagatgaca ttaccctgtt atcccTagat acattaccct  2940
gttatcccag atgacatacc ctgttatccc tagatgacat taccctgtta tcccagataa  3000
actcaatgat gatgatgatg atggTcgaga ctcagcggcc gcggTgccag ggcgTgccct  3060
tgggctcccc gggcgcgact ataagctgcg agcaacttca cttgggtatg ccggcggtag  3120
cgcttaccgt tcgtataatg tatgctatac gaagttatcc gaagccgcta gcggtggttt  3180
gtctggtcaa ccaccgcggt ctcagtggtg tacggtacaa cccagctac cggtcgccac  3240
catgcccgcc atgaagatcg agtgccgcat caccggcacc ctgaacggcg tggagttcga  3300
gctggtgggc ggcggagagg gcaccccga gcagggccgc atgaccaaca agatgaagag  3360
caccaaaggc gccctgacct tcagccccta cctgctgagc cacgtgatgg gctacggctt  3420
ctaccacttc ggcacctacc ccagcggcta cgagaacccc ttcctgcacg ccatcaacaa  3480
cggcggctac accaacaccc gcatcgagaa gtacgaggac ggcggcgtgc tgcacgtgag  3540
cttcagctac cgctacgagg ccggccgcgt gatcggcgac ttcaaggtgg tgggcaccgg  3600
cttccccgag gacagcgtga tcttcaccga caagatcatc cgcagcaacg ccaccgtgga  3660
gcacctgcac cccatgggcg ataacgtgct ggtgggcagc ttcgcccgca ccttcagcct  3720
gcgcgacggc ggctactaca gcttcgtggt ggacagccac atgcacttca gagcgccat  3780
ccaccccagc atcctgcaga acgggggccc catgttcgcc ttccgccgcg tggaggagct  3840
gcacagcaac accgagctgg gcatcgtgga gtaccagcac gccttcaaga cccccatcgc  3900
cttcgccaga tctcgagctc gatgagtttg acaaaccac aactagaatg cagtgaaaaa  3960
aatgctttat ttgtgaaatt tgtgatgcta ttgctttatt tgtgggcccg ccccaactgg  4020
ggtaaccttt gagttctctc agttgggggt aatcagcatc atgatgTggt accacatcat  4080
gatgctgatt ataagaatgc ggccgccaca ctctagtgga tctcgagtta ataattcaga  4140
agaactcgtc aagaaggcga tagaaggcga tgcgctgcga atcgggagcg cgataccgt  4200
aaagcacgag gaagcggtca gcccattcgc cgccaagctc ttcagcaata tcacgggtag  4260
ccaacgctat gtcctgatag cggtccgcca cacccagccg ccacagtcg atgaatccag  4320
aaaagcggcc attttccacc atgatattcg gcaagcaggc atcgccatgg gtcacgacga  4380
gatcctcgcc gtcgggcatg ctcgccttga gcctggcgaa cagttcggct ggcgcgagcc  4440
cctgatgctc ttcgtccaga tcatcctgat cgacaagacc ggcttccatc cgagtacgtg  4500
ctcgctcgat gcgatgttTc gcttggtggt cgaatgggca ggtagccgga tcaagcgtat  4560
gcagccgccg cattgcatca gccatgatgg atactttctc ggcaggagca aggtgtagat  4620
gacatggaga tcctgccccg gcacttcgcc caatagcagc cagtcccttc ccgcttcagt  4680
gacaacgtcg agcacagctg cgcaaggaac gcccgtcgtg gccagccacg atagccgcgc  4740
tgcctcgtct tgcagttcat tcagggcacc ggacaggtcg gtcttgacaa aagaaccgg  4800
gcgcccctgc gctgacagcc ggaacacggc ggcatcagag cagccgattg tctgttgtgc  4860
ccagtcatag ccgaatagcc tctccaccca agcggccgga gaacctgcgt gcaatccatc  4920
ttgttcaatc atgcgaaacg atcctcatcc tgtctcttga tcagagct                4968

SEQ ID NO: 77           moltype = DNA   length = 4855
FEATURE                 Location/Qualifiers
misc_feature            1..4855
                        note = Description of Artificial Sequence: Synthetic
                         polynucleotide
misc_feature            1..4855
                        note = GLuc minicircle template
source                  1..4855
                        mol_type = other DNA
                        organism = synthetic construct
SEQUENCE: 77
tgatccctg cgccatcaga tccttggcgg cgagaaagcc atccagttta ctttgcaggg    60
cttcccaacc ttaccagagg gcgccccagc tggcaattcc ggttcgcttg ctgtccataa   120
aaccgcccag tctagctatc gccatgtaag cccactgcaa gctacctgct ttctctttgc   180
gcttgcgttt tcccttgtcc agatagccca gtagctgaca ttcatccggg gtcagcaccg   240
tttctgcgga ctggctttct acgtgctcga gggggcaga acggtctcca gcttggctgt   300
tttggcggat gagagaagat tttcagcctg atacagatta aatcagaacg cagaagcggt   360
ctgataaaac agaatttgcc tggcggcagt agcgcggtgg tcccacctga ccccatgccg   420
aactcagaag tgaaacgccg tagcgccgat ggtagtgtgg ggtctcccca tgcgagagta   480
gggaactgcc aggcatcaaa taaaacgaaa ggctcagtcg aaagactggg cctttcgttt   540
tatctgttgt ttgtcggtga acgctctcct gagtaggaca atccgccctg gagcggattt   600
gaacgttgcg aagcaacggc ccggagggtg cgggcagga cccgccat aaactgccag     660
gcatcaaatt aagcagaagg ccatcctgac ggatggcctt tttgcgttc tacaaactct   720
tttgtttatt tttctaaata cattcaaata tgtatccgct catgaccaaa atccctttaac  780
gtgagttttc gttccactga gcgtcagacc ccgtagaaaa gatcaaagga tcttcttgag  840
atccttttt tctgcgcgta atctgctgct tgcaaacaaa aaaaccaccg ctaccagcgg   900
tggtttgttt gccggatcaa gagctaccaa ctctttttcc gaaggtaact ggcttcagca   960
gagcgcagat accaaatact gtccttctag tgtagccgta gttaggccac acttcaaga  1020
actctgtagc accgcctaca tacctcgctc tgctaatcct gttaccagtg gctgctgcca  1080
gtggcgataa gtcgtgtctt accgggttgg actcaagacg atagttaccg gataaggcgc  1140
agcggtcggg ctgaacgggg ggttcgtgca cacaccca cttggagcga acgacctaca  1200
ccgaactgag atacctacag cgtgagctat gagaaagcgc cacgcttccc gaagggagaa  1260
aggcggacag gtatccggta agcggcaggg tcggaacagg agagcgcacg agggagcttc  1320
cagggggaaa cgcctggtat ctttatagtc ctgtcgggtt tcgccacctc tgacttgagc  1380
gtcgatttt gtgatgctcg tcagggggc ggagcctatg gaaaaacgcc agcaacgcgg   1440
ccttttacg gttcctggcc ttttgctggc cttttgctca catgttcttt cctgcgttat  1500
```

```
cccctgattc tgtggataac cgtattaccg cctttgagtg agctgatacc gctcgccgca 1560
gccgaacgac cgagcgcagc gagtcagtga gcgaggaagc ggaagagcgc ctgatgcggt 1620
attttctcct tacgcatctg tgcggtattt cacaccgcat atggtgcact ctcagtacaa 1680
tctgctctga tgccgcatag ttaagccagt atacactccg ctatcgctac gtgactgggt 1740
catggctgcg ccccgacacc cgccaacacc cgctgacgcg ccctgacggg cttgtctgct 1800
cccggcatcc gcttacagac aagctgtgac cgtctccggg agctgcatgt gtcagaggtt 1860
ttcaccgtca tcaccgaaac gcgcgaggca gcagatcaat tcgcgcgcga aggcgaagcg 1920
gcatgcataa tgtgcctgtc aaatggacga agcagggatt ctgcaaaccc tatgctactc 1980
cgtcaagccg tcaattgtct gattcgttac caattatgac aacttgacgg ctacatcatt 2040
cacttttttct tcacaaccgg cacggaactc gctcgggctg gccccggtgc attttttaaa 2100
tacccgcgag aaatagagtt gatcgtcaaa accaacattg cgaccgacgg tggcgatagg 2160
catccgggtg gtgctcaaaa gcagcttcgc ctggctgata cgttggtcct cgcgccagct 2220
taagacgcta atccctaact gctggcgaaa aagatgtgac agacgcgacg gcgacaagca 2280
aacatgctgt gcgacgctgg cgatacatta ccctgttatc cctagatgaa gccgacaaga 2340
tatcccagat gacattaccc tgttatccct agatgacatt accctgttat ccctagatga 2400
catttaccct gttatcccta gatgacatta ccctgttatc ccagatgaca ttaccctgtt 2460
atccctagat acattaccct gttatcccag atgacatacc ctgttatccc tagatgacat 2520
taccctgtta tcccagatga cattacccctg ttatcccctag atacattaccc ctgttatccc 2580
agatgacata ccctgttatc cctagatgac attaccctgt tatcccagat gacattaccc 2640
tgttatccct agatacatta ccctgttatc cagatgacat acccctgtta tccctagatg 2700
acattaccct gttatcccag atgacattac cctgttatcc ctagatacat accctgtta 2760
tcccagatga catacccctgt tatccctaga tgacattacc ctgttatccc agatgacatt 2820
accctgttat cccctagatac attaccctgt tatcccagat gacataccct gttatcccta 2880
gatgacatta ccctgttatc cagatgaca ttaccctgtt atccctagat acattaccct 2940
gttatcccag atgacatacc ctgttatccc tagatgacat accctgtta tcccagataa 3000
actcaatgat gatgatgatg atggtcgaga ctcagccgcc gcggtgccag ggcgtgccct 3060
tgggctcccc gggcgcgact ataagctgcg agcaacttca cttgggtatg ccggcggtag 3120
cgcttaccgt tcgtataatg tatgctatac gaagttatcc gaagccgcta gcggtggttt 3180
gtctggtcaa ccaccgcggt ctcagtggtg tacggtacaa acccactacc ggtcgccacc 3240
atgggagtca aagttctgtt tgccctgatc tgcatcctg tggccgaggc caagcccacc 3300
gagaacaacg aagacttcaa catcgtggcc gtgccagca acttcgcgac cacggatctc 3360
gatgctgacc gcgggaagtt gccccggcaag aagctgccgc tggaggtgct caaagagatg 3420
gaagccaatg cccggaaagc tggctgcacc aggggctgtc tgatctgcct gtcccacatc 3480
aagtgcacgc ccaagatgaa gaagttcatc ccaggacgct gccacaccta cgaaggcgac 3540
aaagagtccg cacagggcgg cataggcgag gcgatcgtcg acattcctga gattcctgcg 3600
ttcaaggact tggagcccat ggagcagttc atccgcacagg tcgatctgtg tgtggactgc 3660
acaactgtgct gcctcaaagg gcttgccaac gtgcagtgtt ctgacctgct caagaagtgg 3720
ctgccgcaac gctgtgcgac ctttgccagc aagatccagg gccaggtgga caagatcaag 3780
ggggccggtg gtgactaagc ggagctcgat gagtttgaac aaaccacaac tagaatgcag 3840
tgaaaaaaat gctttatttg tgaaatttgt gatgctattg cttatttgt gggcccgccc 3900
caactggggt aacctttgag ttctctcagt tgggggtaat cagcatcatg atgtggtacc 3960
acatcatgat gctgattata agaatgcggc cgccacactc tagtggatct cgagttaata 4020
attcagaaga actcgtcaag aaggcgatag aaggcgatgc gctgcgaatc ggagcggcga 4080
ataccgtaaa gcacgaggaa gcggtcagcc cattcgccgc caagctcttc agcaatatca 4140
cgggtagcca acgctatgtc ctgatagcgg tccgccacac ccagccggcc acagtcgatg 4200
aatccagaaa agcggccatt ttccaccatg atattcggca agcaggcatc gccatgggtc 4260
acgacgagat cctcgccgtc gggcatgctc gccttgagcc tggcgaacag ttcggctggc 4320
gcgagcccct gatgctcttc gtccagatca tcctgatcga caagaccggc ttccatccga 4380
gtacgtgctc gctcgatgcg atgtttcgct tggtggtcga atgggcaggt agccggatca 4440
agcgtatgca gccgccgcat tgcatcagcc atgatggata tttctcggc aggagcaagg 4500
tgtagatgac atggagatcc tgccccggca cttcgcccaa tagcagccag tcccttcccg 4560
cttcagtgac aacgtcgagc acagctgcgc aaggaacgcc cgtcgtggcc agccacgata 4620
gccgcgctgc ctcgtcttgc agttcattca gggcaccgga caggtcggtc ttgacaaaaa 4680
gaaccgggcg cccctgcgct gacagccgga acacggcggc atcagagcag ccgattgtct 4740
gttgtgccca gtcatagccg aatagcctct cacccaagc ggccggagaa cctgcgtgca 4800
atccatcttg ttcaatcatg cgaaacgatc ctcatcctgt ctcttgatca gagct 4855

SEQ ID NO: 78         moltype = DNA   length = 38
FEATURE               Location/Qualifiers
misc_feature          1..38
                      note = Description of Artificial Sequence: Synthetic
                      oligonucleotide
misc_feature          1..38
                      note = pseudo-attP
source                1..38
                      mol_type = other DNA
                      organism = synthetic construct
SEQUENCE: 78
ccccaactgg ggtaaccttt gagttctctc agttggggg                            38

SEQ ID NO: 79         moltype = DNA   length = 194
FEATURE               Location/Qualifiers
misc_feature          1..194
                      note = Description of Artificial Sequence: Synthetic
                      polynucleotide
misc_feature          1..194
                      note = Albumin-pegRNA-SERPIN
source                1..194
                      mol_type = other DNA
```

```
                            organism = synthetic construct
SEQUENCE: 79
gactgaaact tcacagaata gttttagagc tagaaatagc aagttaaaat aaggctagtc   60
cgttatcaac ttgaaaaagt ggcaccgagt cggtgcttgg gatagttatg aattcaatct  120
tcaaccctat ccggatgatc ctgacgacgg agaccgccgt cgtcgacaag ccggcctctg  180
tgaagtttca gtca                                                    194

SEQ ID NO: 80               moltype = DNA  length = 189
FEATURE                     Location/Qualifiers
misc_feature                1..189
                            note = Description of Artificial Sequence: Synthetic
                             polynucleotide
misc_feature                1..189
                            note = Albumin-pegRNA-CPS1
source                      1..189
                            mol_type = other DNA
                            organism = synthetic construct
SEQUENCE: 80
gactgaaact tcacagaata gttttagagc tagaaatagc aagttaaaat aaggctagtc   60
cgttatcaac ttgaaaaagt ggcaccgagt cggtgcttgg gatagttatg aattcaatct  120
tcaaccctat ccggatgatc ctgacgacgg agaccgccgt cgtcgacaag ccggcctctg  180
tgaagtttc                                                          189

SEQ ID NO: 81               moltype = DNA  length = 177
FEATURE                     Location/Qualifiers
misc_feature                1..177
                            note = Description of Artificial Sequence: Synthetic
                             polynucleotide
misc_feature                1..177
                            note = 34bp lox71 pegRNA
source                      1..177
                            mol_type = other DNA
                            organism = synthetic construct
SEQUENCE: 81
ggcccagact gagcacgtga gttttagagc tagaaatagc aagttaaaat aaggctagtc   60
cgttatcaac ttgaaaaagt ggcaccgagt cggtgctgga ggaagcaggg cttcctttcc  120
tctgccatca taccgttcgt atagcataca ttatacgaag ttatcgtgct cagtct      177

SEQ ID NO: 82               moltype = DNA  length = 177
FEATURE                     Location/Qualifiers
misc_feature                1..177
                            note = Description of Artificial Sequence: Synthetic
                             polynucleotide
misc_feature                1..177
                            note = 34bp lox66 pegRNA
source                      1..177
                            mol_type = other DNA
                            organism = synthetic construct
SEQUENCE: 82
ggcccagact gagcacgtga gttttagagc tagaaatagc aagttaaaat aaggctagtc   60
cgttatcaac ttgaaaaagt ggcaccgagt cggtgctgga ggaagcaggg cttcctttcc  120
tctgccatca ataacttcgt atagcataca ttatacgaac ggtacgtgct cagtct      177

SEQ ID NO: 83               moltype = DNA  length = 20
FEATURE                     Location/Qualifiers
misc_feature                1..20
                            note = Description of Artificial Sequence: Synthetic
                             oligonucleotide
misc_feature                1..20
                            note = gRNA2
source                      1..20
                            mol_type = other DNA
                            organism = synthetic construct
SEQUENCE: 83
ggcccagact gagcacgtga                                               20

SEQ ID NO: 84               moltype = DNA  length = 184
FEATURE                     Location/Qualifiers
misc_feature                1..184
                            note = Description of Artificial Sequence: Synthetic
                             polynucleotide
source                      1..184
                            mol_type = other DNA
                            organism = synthetic construct
SEQUENCE: 84
gctattctcg cagctcacca gttttagagc tagaaatagc aagttaaaat aaggctagtc   60
cgttatcaac ttgaaaaagt ggcaccgagt cggtgcgacg agcgcggcga tatcatcatc  120
catgccggga tgatcctgac gacggagacc gccgtcgtcg acaagccggc ctgagctgcg  180
agaa                                                               184
```

```
SEQ ID NO: 85          moltype = DNA   length = 179
FEATURE                Location/Qualifiers
misc_feature           1..179
                       note = Description of Artificial Sequence: Synthetic
                       polynucleotide
source                 1..179
                       mol_type = other DNA
                       organism = synthetic construct
SEQUENCE: 85
gctattctcg cagctcacca gttttagagc tagaaatagc aagttaaaat aaggctagtc   60
cgttatcaac ttgaaaaagt ggcaccgagt cggtgcgagt cggtgcgacg agcgcggcga  120
tatcatcatc catggcacaa ttaacatctc aatcaaggta aatgcttgag ctgcgagaa   179

SEQ ID NO: 86          moltype = DNA   length = 179
FEATURE                Location/Qualifiers
misc_feature           1..179
                       note = Description of Artificial Sequence: Synthetic
                       polynucleotide
source                 1..179
                       mol_type = other DNA
                       organism = synthetic construct
SEQUENCE: 86
gctattctcg cagctcacca gttttagagc tagaaatagc aagttaaaat aaggctagtc   60
cgttatcaac ttgaaaaagt ggcaccgagt cggtgcgagt cggtgcgacg agcgcggcga  120
tatcatcatc catggagcat ttaccttgat tgagatgtta attgtgtgag ctgcgagaa   179

SEQ ID NO: 87          moltype = DNA   length = 182
FEATURE                Location/Qualifiers
misc_feature           1..182
                       note = Description of Artificial Sequence: Synthetic
                       polynucleotide
source                 1..182
                       mol_type = other DNA
                       organism = synthetic construct
SEQUENCE: 87
gctattctcg cagctcacca gttttagagc tagaaatagc aagttaaaat aaggctagtc   60
cgttatcaac ttgaaaaagt ggcaccgagt cggtgcgagt cggtgcgacg agcgcggcga  120
tatcatcatc catggcaggt ttttgacgaa agtgatccag atgatccagt gagctgcgag  180
aa                                                                 182

SEQ ID NO: 88          moltype = DNA   length = 182
FEATURE                Location/Qualifiers
misc_feature           1..182
                       note = Description of Artificial Sequence: Synthetic
                       polynucleotide
source                 1..182
                       mol_type = other DNA
                       organism = synthetic construct
SEQUENCE: 88
gctattctcg cagctcacca gttttagagc tagaaatagc aagttaaaat aaggctagtc   60
cgttatcaac ttgaaaaagt ggcaccgagt cggtgcgagt cggtgcgacg agcgcggcga  120
tatcatcatc catggctgga tcatctggat cactttcgtc aaaaacctgt gagctgcgag  180
aa                                                                 182

SEQ ID NO: 89          moltype = DNA   length = 96
FEATURE                Location/Qualifiers
misc_feature           1..96
                       note = Description of Artificial Sequence: Synthetic
                       oligonucleotide
source                 1..96
                       mol_type = other DNA
                       organism = synthetic construct
SEQUENCE: 89
gaagccggcc ttgcacatgc gttttagagc tagaaatagc aagttaaaat aaggctagtc   60
cgttatcaac ttgaaaaagt ggcaccgagt cggtgc                             96

SEQ ID NO: 90          moltype = DNA   length = 164
FEATURE                Location/Qualifiers
misc_feature           1..164
                       note = Description of Artificial Sequence: Synthetic
                       polynucleotide
source                 1..164
                       mol_type = other DNA
                       organism = synthetic construct
SEQUENCE: 90
gaagccggcc ttgcacatgc gttttagagc tagaaatagc aagttaaaat aaggctagtc   60
cgttatcaac ttgaaaaagt ggcaccgagt cggtgcatat catcatccat ggtaccgttc  120
gtatagcata cattatacga agttattgag ctgcgagaat agcc                   164
```

```
SEQ ID NO: 91            moltype = DNA   length = 172
FEATURE                  Location/Qualifiers
misc_feature             1..172
                         note = Description of Artificial Sequence: Synthetic
                          polynucleotide
source                   1..172
                         mol_type = other DNA
                         organism = synthetic construct
SEQUENCE: 91
gaagccggcc ttgcacatgc gttttagagc tagaaatagc aagttaaaat aaggctagtc   60
cgttatcaac ttgaaaaagt ggcaccgagt cggtgcgacg agcgcggcga tatcatcatc  120
catggtaccg ttcgtatagc atacattata cgaagttatt gagctgcgag aa          172

SEQ ID NO: 92            moltype = DNA   length = 189
FEATURE                  Location/Qualifiers
misc_feature             1..189
                         note = Description of Artificial Sequence: Synthetic
                          polynucleotide
source                   1..189
                         mol_type = other DNA
                         organism = synthetic construct
SEQUENCE: 92
gctattctcg cagctcacca gttttagagc tagaaatagc aagttaaaat aaggctagtc   60
cgttatcaac ttgaaaaagt ggcaccgagt cggtgctcga cgacgagcgc ggcgatatca  120
tcatccatgg ccggatgatc ctgacgacgg agaccgccgt cgtcgacaag ccggcctgag  180
ctgcgagaa                                                           189

SEQ ID NO: 93            moltype = DNA   length = 181
FEATURE                  Location/Qualifiers
misc_feature             1..181
                         note = Description of Artificial Sequence: Synthetic
                          polynucleotide
source                   1..181
                         mol_type = other DNA
                         organism = synthetic construct
SEQUENCE: 93
gctattctcg cagctcacca gttttagagc tagaaatagc aagttaaaat aaggctagtc   60
cgttatcaac ttgaaaaagt ggcaccgagt cggtgcgagc gcggcgatat catcatccat  120
ggccggatga tcctgacgac ggagaccgcc gtcgtcgaca agccggcctg agctgcgaga  180
a                                                                   181

SEQ ID NO: 94            moltype = DNA   length = 178
FEATURE                  Location/Qualifiers
misc_feature             1..178
                         note = Description of Artificial Sequence: Synthetic
                          polynucleotide
source                   1..178
                         mol_type = other DNA
                         organism = synthetic construct
SEQUENCE: 94
gctattctcg cagctcacca gttttagagc tagaaatagc aagttaaaat aaggctagtc   60
cgttatcaac ttgaaaaagt ggcaccgagt cggtgccgcg gcgatatcat catccatggc  120
cggatgatcc tgacgacgga gaccgccgtc gtcgacaagc cggcctgagc tgcgagaa    178

SEQ ID NO: 95            moltype = DNA   length = 175
FEATURE                  Location/Qualifiers
misc_feature             1..175
                         note = Description of Artificial Sequence: Synthetic
                          polynucleotide
source                   1..175
                         mol_type = other DNA
                         organism = synthetic construct
SEQUENCE: 95
gctattctcg cagctcacca gttttagagc tagaaatagc aagttaaaat aaggctagtc   60
cgttatcaac ttgaaaaagt ggcaccgagt cggtgcggcg atatcatcat ccatggccgg  120
atgatcctga cgacggagac cgccgtcgtc gacaagccgg cctgagctgc gagaa       175

SEQ ID NO: 96            moltype = DNA   length = 171
FEATURE                  Location/Qualifiers
misc_feature             1..171
                         note = Description of Artificial Sequence: Synthetic
                          polynucleotide
source                   1..171
                         mol_type = other DNA
                         organism = synthetic construct
SEQUENCE: 96
gctattctcg cagctcacca gttttagagc tagaaatagc aagttaaaat aaggctagtc   60
cgttatcaac ttgaaaaagt ggcaccgagt cggtgcatat catcatccat ggccggatga  120
```

```
tcctgacgac ggagaccgcc gtcgtcgaca agccggcctg agctgcgaga a         171

SEQ ID NO: 97            moltype = DNA   length = 194
FEATURE                  Location/Qualifiers
misc_feature             1..194
                         note = Description of Artificial Sequence: Synthetic
                         polynucleotide
source                   1..194
                         mol_type = other DNA
                         organism = synthetic construct
SEQUENCE: 97
gctattctcg cagctcacca gttttagagc tagaaatagc aagttaaaat aaggctagtc  60
cgttatcaac ttgaaaaagt ggcaccgagt cggtgctcga cgacgagcgc ggcgatatca 120
tcatccatgg ccggatgatc ctgacgacgg agaccgccgt cgtcgacaag ccggcctgag 180
ctgcgagaat agcc                                                  194

SEQ ID NO: 98            moltype = DNA   length = 189
FEATURE                  Location/Qualifiers
misc_feature             1..189
                         note = Description of Artificial Sequence: Synthetic
                         polynucleotide
source                   1..189
                         mol_type = other DNA
                         organism = synthetic construct
SEQUENCE: 98
gctattctcg cagctcacca gttttagagc tagaaatagc aagttaaaat aaggctagtc  60
cgttatcaac ttgaaaaagt ggcaccgagt cggtgcgacg agcgcggcga tcatcatcatc 120
catggccgga tgatcctgac gacggagacc gccgtcgtcg acaagccggc ctgagctgcg 180
agaatagcc                                                        189

SEQ ID NO: 99            moltype = DNA   length = 176
FEATURE                  Location/Qualifiers
misc_feature             1..176
                         note = Description of Artificial Sequence: Synthetic
                         polynucleotide
source                   1..176
                         mol_type = other DNA
                         organism = synthetic construct
SEQUENCE: 99
gctattctcg cagctcacca gttttagagc tagaaatagc aagttaaaat aaggctagtc  60
cgttatcaac ttgaaaaagt ggcaccgagt cggtgcatat catcatccat ggccggatga 120
tcctgacgac ggagaccgcc gtcgtcgaca agccggcctg agctgcgaga atagcc    176

SEQ ID NO: 100           moltype = DNA   length = 194
FEATURE                  Location/Qualifiers
misc_feature             1..194
                         note = Description of Artificial Sequence: Synthetic
                         polynucleotide
source                   1..194
                         mol_type = other DNA
                         organism = synthetic construct
SEQUENCE: 100
gctgtctccg ccgcccgcca gttttagagc tagaaatagc aagttaaaat aaggctagtc  60
cgttatcaac ttgaaaaagt ggcaccgagt cggtgcctgc ccatccgcgg cggcacgggg 120
gtcgcagtcg ccatgccgga tgatcctgac gacggagacc gccgtcgtcg acaagccggc 180
ccgggcggcg gaga                                                  194

SEQ ID NO: 101           moltype = DNA   length = 189
FEATURE                  Location/Qualifiers
misc_feature             1..189
                         note = Description of Artificial Sequence: Synthetic
                         polynucleotide
source                   1..189
                         mol_type = other DNA
                         organism = synthetic construct
SEQUENCE: 101
gctgtctccg ccgcccgcca gttttagagc tagaaatagc aagttaaaat aaggctagtc  60
cgttatcaac ttgaaaaagt ggcaccgagt cggtgccatc gcggcggca cggggtcgc  120
agtcgccatg ccggatgatc ctgacgacgg agaccgccgt cgtcgacaag ccggcccggg 180
cggcggaga                                                        189

SEQ ID NO: 102           moltype = DNA   length = 184
FEATURE                  Location/Qualifiers
misc_feature             1..184
                         note = Description of Artificial Sequence: Synthetic
                         polynucleotide
source                   1..184
                         mol_type = other DNA
                         organism = synthetic construct
```

```
SEQUENCE: 102
gctgtctccg ccgcccgcca gttttagagc tagaaatagc aagttaaaat aaggctagtc    60
cgttatcaac ttgaaaaagt ggcaccgagt cggtgcgcgg cggcacgggg gtcgcagtcg   120
ccatgccgga tgatcctgac gacggagacc gccgtcgtcg acaagccggc ccgggcggcg   180
gaga                                                                184

SEQ ID NO: 103              moltype = DNA   length = 179
FEATURE                     Location/Qualifiers
misc_feature                1..179
                            note = Description of Artificial Sequence: Synthetic
                              polynucleotide
source                      1..179
                            mol_type = other DNA
                            organism = synthetic construct
SEQUENCE: 103
gctgtctccg ccgcccgcca gttttagagc tagaaatagc aagttaaaat aaggctagtc    60
cgttatcaac ttgaaaaagt ggcaccgagt cggtgcggca cggggtcgc agtcgccatg    120
ccggatgatc ctgacgacgg agaccgccgt cgtcgacaag ccgcccggg cggcggaga    179

SEQ ID NO: 104              moltype = DNA   length = 174
FEATURE                     Location/Qualifiers
misc_feature                1..174
                            note = Description of Artificial Sequence: Synthetic
                              polynucleotide
source                      1..174
                            mol_type = other DNA
                            organism = synthetic construct
SEQUENCE: 104
gctgtctccg ccgcccgcca gttttagagc tagaaatagc aagttaaaat aaggctagtc    60
cgttatcaac ttgaaaaagt ggcaccgagt cggtgcgggg gtcgcagtcg ccatgccgga   120
tgatcctgac gacggagacc gccgtcgtcg acaagccggc ccgggcggcg gaga          174

SEQ ID NO: 105              moltype = DNA   length = 199
FEATURE                     Location/Qualifiers
misc_feature                1..199
                            note = Description of Artificial Sequence: Synthetic
                              polynucleotide
source                      1..199
                            mol_type = other DNA
                            organism = synthetic construct
SEQUENCE: 105
gctgtctccg ccgcccgcca gttttagagc tagaaatagc aagttaaaat aaggctagtc    60
cgttatcaac ttgaaaaagt ggcaccgagt cggtgcctgc ccatccgcgg cggcacgggg   120
gtcgcagtcg ccatgccgga tgatcctgac gacggagacc gccgtcgtcg acaagccggc   180
ccgggcggcg gagacagcg                                                199

SEQ ID NO: 106              moltype = DNA   length = 194
FEATURE                     Location/Qualifiers
misc_feature                1..194
                            note = Description of Artificial Sequence: Synthetic
                              polynucleotide
source                      1..194
                            mol_type = other DNA
                            organism = synthetic construct
SEQUENCE: 106
gctgtctccg ccgcccgcca gttttagagc tagaaatagc aagttaaaat aaggctagtc    60
cgttatcaac ttgaaaaagt ggcaccgagt cggtgccatc cgcggcggca cggggtcgc    120
agtcgccatg ccggatgatc ctgacgacgg agaccgccgt cgtcgacaag ccggcccggg   180
cggcggagac agcg                                                     194

SEQ ID NO: 107              moltype = DNA   length = 189
FEATURE                     Location/Qualifiers
misc_feature                1..189
                            note = Description of Artificial Sequence: Synthetic
                              polynucleotide
source                      1..189
                            mol_type = other DNA
                            organism = synthetic construct
SEQUENCE: 107
gctgtctccg ccgcccgcca gttttagagc tagaaatagc aagttaaaat aaggctagtc    60
cgttatcaac ttgaaaaagt ggcaccgagt cggtgcgcgg cggcacgggg gtcgcagtcg   120
ccatgccgga tgatcctgac gacggagacc gccgtcgtcg acaagccggc ccgggcggcg   180
gagacagcg                                                           189

SEQ ID NO: 108              moltype = DNA   length = 184
FEATURE                     Location/Qualifiers
misc_feature                1..184
                            note = Description of Artificial Sequence: Synthetic
                              polynucleotide
```

```
source                  1..184
                        mol_type = other DNA
                        organism = synthetic construct
SEQUENCE: 108
gctgtctccg ccgcccgcca gttttagagc tagaaatagc aagttaaaat aaggctagtc   60
cgttatcaac ttgaaaaagt ggcaccgagt cggtgcggca cggggtcgc agtcgccatg   120
ccggatgatc ctgacgacgg agaccgccgt cgtcgacaag ccggcccggg cggcggagac  180
agcg                                                              184

SEQ ID NO: 109          moltype = DNA   length = 179
FEATURE                 Location/Qualifiers
misc_feature            1..179
                        note = Description of Artificial Sequence: Synthetic
                         polynucleotide
source                  1..179
                        mol_type = other DNA
                        organism = synthetic construct
SEQUENCE: 109
gctgtctccg ccgcccgcca gttttagagc tagaaatagc aagttaaaat aaggctagtc   60
cgttatcaac ttgaaaaagt ggcaccgagt cggtgcgggg gtcgcagtcg ccatgccgga  120
tgatcctgac gacggagacc gccgtcgtcg acaagccggc ccgggcggcg gagacagcg   179

SEQ ID NO: 110          moltype = DNA   length = 96
FEATURE                 Location/Qualifiers
misc_feature            1..96
                        note = Description of Artificial Sequence: Synthetic
                         oligonucleotide
source                  1..96
                        mol_type = other DNA
                        organism = synthetic construct
SEQUENCE: 110
gcgtggtggg gccgccagcg gttttagagc tagaaatagc aagttaaaat aaggctagtc   60
cgttatcaac ttgaaaaagt ggcaccgagt cggtgc                            96

SEQ ID NO: 111          moltype = DNA   length = 180
FEATURE                 Location/Qualifiers
misc_feature            1..180
                        note = Description of Artificial Sequence: Synthetic
                         polynucleotide
source                  1..180
                        mol_type = other DNA
                        organism = synthetic construct
SEQUENCE: 111
gctattctcg cagctcacca gttttagagc tagaaatagc aagttaaaat aaggctagtc   60
cgttatcaac ttgaaaaagt ggcaccgagt cggtgcgacg agcgcggcga tatcatcatc  120
catggggatg atcctgacga cggagaccgc cgtcgtcgac aagccggtga gctgcgagaa  180

SEQ ID NO: 112          moltype = DNA   length = 178
FEATURE                 Location/Qualifiers
misc_feature            1..178
                        note = Description of Artificial Sequence: Synthetic
                         polynucleotide
source                  1..178
                        mol_type = other DNA
                        organism = synthetic construct
SEQUENCE: 112
gctattctcg cagctcacca gttttagagc tagaaatagc aagttaaaat aaggctagtc   60
cgttatcaac ttgaaaaagt ggcaccgagt cggtgcgacg agcgcggcga tatcatcatc  120
catgggatga tcctgacgac ggagaccgcc gtcgtcgaca agccgtgagc tgcgagaa    178

SEQ ID NO: 113          moltype = DNA   length = 176
FEATURE                 Location/Qualifiers
misc_feature            1..176
                        note = Description of Artificial Sequence: Synthetic
                         polynucleotide
source                  1..176
                        mol_type = other DNA
                        organism = synthetic construct
SEQUENCE: 113
gctattctcg cagctcacca gttttagagc tagaaatagc aagttaaaat aaggctagtc   60
cgttatcaac ttgaaaaagt ggcaccgagt cggtgcgacg agcgcggcga tatcatcatc  120
catggatgat cctgacgacg gagaccgccg tcgtcgacaa gcctgagctg cgagaa      176

SEQ ID NO: 114          moltype = DNA   length = 174
FEATURE                 Location/Qualifiers
misc_feature            1..174
                        note = Description of Artificial Sequence: Synthetic
                         polynucleotide
source                  1..174
```

```
                            mol_type = other DNA
                            organism = synthetic construct
SEQUENCE: 114
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catggtgatc ctgacgacgg agaccgccgt cgtcgacaag ctgagctgcg agaa         174

SEQ ID NO: 115              moltype = DNA   length = 182
FEATURE                     Location/Qualifiers
misc_feature                1..182
                            note = Description of Artificial Sequence: Synthetic
                             polynucleotide
source                      1..182
                            mol_type = other DNA
                            organism = synthetic construct
SEQUENCE: 115
gctgtctccg ccgcccgcca gttttagagc tagaaatagc aagttaaaat aaggctagtc    60
cgttatcaac ttgaaaaagt ggcaccgagt cggtgcgcgg cggcacgggg gtcgcagtcg   120
ccatgcggat gatcctgacg acggagaccg ccgtcgtcga caagccggcc gggcggcgga   180
ga                                                                  182

SEQ ID NO: 116              moltype = DNA   length = 180
FEATURE                     Location/Qualifiers
misc_feature                1..180
                            note = Description of Artificial Sequence: Synthetic
                             polynucleotide
source                      1..180
                            mol_type = other DNA
                            organism = synthetic construct
SEQUENCE: 116
gctgtctccg ccgcccgcca gttttagagc tagaaatagc aagttaaaat aaggctagtc    60
cgttatcaac ttgaaaaagt ggcaccgagt cggtgcgcgg cggcacgggg gtcgcagtcg   120
ccatgggatg atcctgacga cggagaccgc cgtcgtcgac aagccggcgg cggcggaga    180

SEQ ID NO: 117              moltype = DNA   length = 178
FEATURE                     Location/Qualifiers
misc_feature                1..178
                            note = Description of Artificial Sequence: Synthetic
                             polynucleotide
source                      1..178
                            mol_type = other DNA
                            organism = synthetic construct
SEQUENCE: 117
gctgtctccg ccgcccgcca gttttagagc tagaaatagc aagttaaaat aaggctagtc    60
cgttatcaac ttgaaaaagt ggcaccgagt cggtgcgcgg cggcacgggg gtcgcagtcg   120
ccatggatga tcctgacgac ggagaccgcc gtcgtcgaca agccgcgggc ggcggaga     178

SEQ ID NO: 118              moltype = DNA   length = 176
FEATURE                     Location/Qualifiers
misc_feature                1..176
                            note = Description of Artificial Sequence: Synthetic
                             polynucleotide
source                      1..176
                            mol_type = other DNA
                            organism = synthetic construct
SEQUENCE: 118
gctgtctccg ccgcccgcca gttttagagc tagaaatagc aagttaaaat aaggctagtc    60
cgttatcaac ttgaaaaagt ggcaccgagt cggtgcgcgg cggcacgggg gtcgcagtcg   120
ccatgatgat cctgacgacg gagaccgccg tcgtcgacaa gcccgggcgg cggaga       176

SEQ ID NO: 119              moltype = DNA   length = 189
FEATURE                     Location/Qualifiers
misc_feature                1..189
                            note = Description of Artificial Sequence: Synthetic
                             polynucleotide
source                      1..189
                            mol_type = other DNA
                            organism = synthetic construct
SEQUENCE: 119
gcgtattgcc tggaggatgg gttttagagc tagaaatagc aagttaaaat aaggctagtc    60
cgttatcaac ttgaaaaagt ggcaccgagt cggtgcgaac cacgcggcga atgccggcgt   120
ccgcccggga tgatcctgac gacggagacc gccgtcgtcg acaagccggc ctcctccagg   180
caatacgcg                                                           189

SEQ ID NO: 120              moltype = DNA   length = 184
FEATURE                     Location/Qualifiers
misc_feature                1..184
                            note = Description of Artificial Sequence: Synthetic
                             polynucleotide
```

```
source                          1..184
                                mol_type = other DNA
                                organism = synthetic construct
SEQUENCE: 120
gcgtattgcc tggaggatgg gttttagagc tagaaatagc aagttaaaat aaggctagtc    60
cgttatcaac ttgaaaaagt ggcaccgagt cggtgcgaac cacgcggcga atgccggcgt   120
ccgccccgga tgatcctgac gacggagacc gccgtcgtcg acaagccggc ctcctccagg   180
caat                                                                184

SEQ ID NO: 121                  moltype = DNA   length = 182
FEATURE                         Location/Qualifiers
misc_feature                    1..182
                                note = Description of Artificial Sequence: Synthetic
                                 polynucleotide
source                          1..182
                                mol_type = other DNA
                                organism = synthetic construct
SEQUENCE: 121
gcgtattgcc tggaggatgg gttttagagc tagaaatagc aagttaaaat aaggctagtc    60
cgttatcaac ttgaaaaagt ggcaccgagt cggtgcgaac cacgcggcga atgccggcgt   120
ccgcccggat gatcctgacg acggagaccg ccgtcgtcga caagccggct cctccaggca   180
at                                                                  182

SEQ ID NO: 122                  moltype = DNA   length = 180
FEATURE                         Location/Qualifiers
misc_feature                    1..180
                                note = Description of Artificial Sequence: Synthetic
                                 polynucleotide
source                          1..180
                                mol_type = other DNA
                                organism = synthetic construct
SEQUENCE: 122
gcgtattgcc tggaggatgg gttttagagc tagaaatagc aagttaaaat aaggctagtc    60
cgttatcaac ttgaaaaagt ggcaccgagt cggtgcgaac cacgcggcga atgccggcgt   120
ccgccggatg atcctgacga cggagaccgc cgtcgtcgac aagccggtcc tccaggcaat   180

SEQ ID NO: 123                  moltype = DNA   length = 178
FEATURE                         Location/Qualifiers
misc_feature                    1..178
                                note = Description of Artificial Sequence: Synthetic
                                 polynucleotide
source                          1..178
                                mol_type = other DNA
                                organism = synthetic construct
SEQUENCE: 123
gcgtattgcc tggaggatgg gttttagagc tagaaatagc aagttaaaat aaggctagtc    60
cgttatcaac ttgaaaaagt ggcaccgagt cggtgcgaac cacgcggcga atgccggcgt   120
ccgccgatga tcctgacgac ggagaccgcc gtcgtcgaca agccgtcctc caggcaat    178

SEQ ID NO: 124                  moltype = DNA   length = 176
FEATURE                         Location/Qualifiers
misc_feature                    1..176
                                note = Description of Artificial Sequence: Synthetic
                                 polynucleotide
source                          1..176
                                mol_type = other DNA
                                organism = synthetic construct
SEQUENCE: 124
gcgtattgcc tggaggatgg gttttagagc tagaaatagc aagttaaaat aaggctagtc    60
cgttatcaac ttgaaaaagt ggcaccgagt cggtgcgaac cacgcggcga atgccggcgt   120
ccgccatgat cctgacgacg gagaccgccg tcgtcgacaa gcctcctcca ggcaat      176

SEQ ID NO: 125                  moltype = DNA   length = 97
FEATURE                         Location/Qualifiers
misc_feature                    1..97
                                note = Description of Artificial Sequence: Synthetic
                                 oligonucleotide
source                          1..97
                                mol_type = other DNA
                                organism = synthetic construct
SEQUENCE: 125
gagccgagca cgaggggata cgttttagag ctagaaatag caagttaaaa taaggctagt    60
ccgttatcaa cttgaaaaag tggcaccgag tcggtgc                             97

SEQ ID NO: 126                  moltype = DNA   length = 167
FEATURE                         Location/Qualifiers
misc_feature                    1..167
                                note = Description of Artificial Sequence: Synthetic
                                 polynucleotide
```

```
                     source          1..167
                                     mol_type = other DNA
                                     organism = synthetic construct
SEQUENCE: 126
gctattctcg cagctcacca gttttagagc tagaaatagc aagttaaaat aaggctagtc   60
cgttatcaac ttgaaaaagt ggcaccgagt cggtgcggcg atatcatcat ccatggatga  120
tcctgacgac ggagaccgcc gtcgtcgaca agcctgagct gcgagaa               167

SEQ ID NO: 127          moltype = DNA  length = 162
FEATURE                 Location/Qualifiers
misc_feature            1..162
                        note = Description of Artificial Sequence: Synthetic
                         polynucleotide
source                  1..162
                        mol_type = other DNA
                        organism = synthetic construct
SEQUENCE: 127
gctattctcg cagctcacca gttttagagc tagaaatagc aagttaaaat aaggctagtc   60
cgttatcaac ttgaaaaagt ggcaccgagt cggtgctatc atcatccatg gatgatcctg  120
acgacggaga ccgccgtcgt cgacaagcct gagctgcgag aa                    162

SEQ ID NO: 128          moltype = DNA  length = 157
FEATURE                 Location/Qualifiers
misc_feature            1..157
                        note = Description of Artificial Sequence: Synthetic
                         polynucleotide
source                  1..157
                        mol_type = other DNA
                        organism = synthetic construct
SEQUENCE: 128
gctattctcg cagctcacca gttttagagc tagaaatagc aagttaaaat aaggctagtc   60
cgttatcaac ttgaaaaagt ggcaccgagt cggtgctcat ccatggatga tcctgacgac  120
ggagaccgcc gtcgtcgaca agcctgagct gcgagaa                          157

SEQ ID NO: 129          moltype = DNA  length = 163
FEATURE                 Location/Qualifiers
misc_feature            1..163
                        note = Description of Artificial Sequence: Synthetic
                         polynucleotide
source                  1..163
                        mol_type = other DNA
                        organism = synthetic construct
SEQUENCE: 129
gctattctcg cagctcacca gttttagagc tagaaatagc aagttaaaat aaggctagtc   60
cgttatcaac ttgaaaaagt ggcaccgagt cggtgcggcg atatcatcat ccatggatga  120
tcctgacgac ggagaccgcc gtcgtcgaca agcctgagct gcg                   163

SEQ ID NO: 130          moltype = DNA  length = 158
FEATURE                 Location/Qualifiers
misc_feature            1..158
                        note = Description of Artificial Sequence: Synthetic
                         polynucleotide
source                  1..158
                        mol_type = other DNA
                        organism = synthetic construct
SEQUENCE: 130
gctattctcg cagctcacca gttttagagc tagaaatagc aagttaaaat aaggctagtc   60
cgttatcaac ttgaaaaagt ggcaccgagt cggtgctatc atcatccatg gatgatcctg  120
acgacggaga ccgccgtcgt cgacaagcct gagctgcg                         158

SEQ ID NO: 131          moltype = DNA  length = 153
FEATURE                 Location/Qualifiers
misc_feature            1..153
                        note = Description of Artificial Sequence: Synthetic
                         polynucleotide
source                  1..153
                        mol_type = other DNA
                        organism = synthetic construct
SEQUENCE: 131
gctattctcg cagctcacca gttttagagc tagaaatagc aagttaaaat aaggctagtc   60
cgttatcaac ttgaaaaagt ggcaccgagt cggtgctcat ccatggatga tcctgacgac  120
ggagaccgcc gtcgtcgaca agcctgagct gcg                              153

SEQ ID NO: 132          moltype = DNA  length = 167
FEATURE                 Location/Qualifiers
misc_feature            1..167
                        note = Description of Artificial Sequence: Synthetic
                         polynucleotide
source                  1..167
```

```
                        mol_type = other DNA
                        organism = synthetic construct
SEQUENCE: 132
gctgtctccg ccgcccgcca gttttagagc tagaaatagc aagttaaaat aaggctagtc    60
cgttatcaac ttgaaaaagt ggcaccgagt cggtgccggg ggtcgcagtc gccatgatga   120
tcctgacgac ggagaccgcc gtcgtcgaca agcccgggcg gcggaga                 167

SEQ ID NO: 133          moltype = DNA   length = 162
FEATURE                 Location/Qualifiers
misc_feature            1..162
                        note = Description of Artificial Sequence: Synthetic
                         polynucleotide
source                  1..162
                        mol_type = other DNA
                        organism = synthetic construct
SEQUENCE: 133
gctgtctccg ccgcccgcca gttttagagc tagaaatagc aagttaaaat aaggctagtc    60
cgttatcaac ttgaaaaagt ggcaccgagt cggtgcgtcg cagtcgccat gatgatcctg   120
acgacggaga ccgccgtcgt cgacaagccc gggcggcgga ga                      162

SEQ ID NO: 134          moltype = DNA   length = 157
FEATURE                 Location/Qualifiers
misc_feature            1..157
                        note = Description of Artificial Sequence: Synthetic
                         polynucleotide
source                  1..157
                        mol_type = other DNA
                        organism = synthetic construct
SEQUENCE: 134
gctgtctccg ccgcccgcca gttttagagc tagaaatagc aagttaaaat aaggctagtc    60
cgttatcaac ttgaaaaagt ggcaccgagt cggtgcagtc gccatgatga tcctgacgac   120
ggagaccgcc gtcgtcgaca agcccgggcg gcggaga                            157

SEQ ID NO: 135          moltype = DNA   length = 163
FEATURE                 Location/Qualifiers
misc_feature            1..163
                        note = Description of Artificial Sequence: Synthetic
                         polynucleotide
source                  1..163
                        mol_type = other DNA
                        organism = synthetic construct
SEQUENCE: 135
gctgtctccg ccgcccgcca gttttagagc tagaaatagc aagttaaaat aaggctagtc    60
cgttatcaac ttgaaaaagt ggcaccgagt cggtgccggg ggtcgcagtc gccatgatga   120
tcctgacgac ggagaccgcc gtcgtcgaca agcccgggcg gcg                     163

SEQ ID NO: 136          moltype = DNA   length = 158
FEATURE                 Location/Qualifiers
misc_feature            1..158
                        note = Description of Artificial Sequence: Synthetic
                         polynucleotide
source                  1..158
                        mol_type = other DNA
                        organism = synthetic construct
SEQUENCE: 136
gctgtctccg ccgcccgcca gttttagagc tagaaatagc aagttaaaat aaggctagtc    60
cgttatcaac ttgaaaaagt ggcaccgagt cggtgcgtcg cagtcgccat gatgatcctg   120
acgacggaga ccgccgtcgt cgacaagccc gggcggcg                           158

SEQ ID NO: 137          moltype = DNA   length = 153
FEATURE                 Location/Qualifiers
misc_feature            1..153
                        note = Description of Artificial Sequence: Synthetic
                         polynucleotide
source                  1..153
                        mol_type = other DNA
                        organism = synthetic construct
SEQUENCE: 137
gctgtctccg ccgcccgcca gttttagagc tagaaatagc aagttaaaat aaggctagtc    60
cgttatcaac ttgaaaaagt ggcaccgagt cggtgcagtc gccatgatga tcctgacgac   120
ggagaccgcc gtcgtcgaca agcccgggcg gcg                                153

SEQ ID NO: 138          moltype = DNA   length = 180
FEATURE                 Location/Qualifiers
misc_feature            1..180
                        note = Description of Artificial Sequence: Synthetic
                         polynucleotide
source                  1..180
                        mol_type = other DNA
```

```
                        organism = synthetic construct
SEQUENCE: 138
gagaagcggc gtccggggct agttttagag ctagaaatag caagttaaaa taaggctagt    60
ccgttatcaa cttgaaaaag tggcaccgag tcggtgctct tgtccagag tcacagccat    120
accggatgat cctgacgacg gagaccgccg tcgtcgacaa gccggccccc cggacgccgc   180

SEQ ID NO: 139          moltype = DNA   length = 179
FEATURE                 Location/Qualifiers
misc_feature            1..179
                        note = Description of Artificial Sequence: Synthetic
                         polynucleotide
source                  1..179
                        mol_type = other DNA
                        organism = synthetic construct
SEQUENCE: 139
gggcacgggg ccatgtacaa gttttagagc tagaaatagc aagttaaaat aaggctagtc    60
cgttatcaac ttgaaaaagt ggcaccgagt cggtgcggcg tcggcagccc gatcccgttg   120
ccggatgatc ctgacgacgg agaccgccgt cgtcgacaag ccggcctaca tggcccgt    179

SEQ ID NO: 140          moltype = DNA   length = 185
FEATURE                 Location/Qualifiers
misc_feature            1..185
                        note = Description of Artificial Sequence: Synthetic
                         polynucleotide
source                  1..185
                        mol_type = other DNA
                        organism = synthetic construct
SEQUENCE: 140
gtgtcaggtg gggcggggct agttttagag ctagaaatag caagttaaaa taaggctagt    60
ccgttatcaa cttgaaaaag tggcaccgag tcggtgcgct ggctcctccc ctggcaccat   120
accggatgat cctgacgacg gagaccgccg tcgtcgacaa gccggccccc cgccccacct   180
gacac                                                                185

SEQ ID NO: 141          moltype = DNA   length = 184
FEATURE                 Location/Qualifiers
misc_feature            1..184
                        note = Description of Artificial Sequence: Synthetic
                         polynucleotide
source                  1..184
                        mol_type = other DNA
                        organism = synthetic construct
SEQUENCE: 141
gagtgggtca gacgagcagg agttttagag ctagaaatag caagttaaaa taaggctagt    60
ccgttatcaa cttgaaaaag tggcaccgag tcggtgcgat ggagggctgc atggggagg   120
agtcgccgga tgatcctgac gacggagacc gccgtcgtcg acaagccggc ctgctcgtct   180
gacc                                                                 184

SEQ ID NO: 142          moltype = DNA   length = 97
FEATURE                 Location/Qualifiers
misc_feature            1..97
                        note = Description of Artificial Sequence: Synthetic
                         oligonucleotide
source                  1..97
                        mol_type = other DNA
                        organism = synthetic construct
SEQUENCE: 142
gcagccaccc gctctcggcc cgttttagag ctagaaatag caagttaaaa taaggctagt    60
ccgttatcaa cttgaaaaag tggcaccgag tcggtgc                             97

SEQ ID NO: 143          moltype = DNA   length = 97
FEATURE                 Location/Qualifiers
misc_feature            1..97
                        note = Description of Artificial Sequence: Synthetic
                         oligonucleotide
source                  1..97
                        mol_type = other DNA
                        organism = synthetic construct
SEQUENCE: 143
gtgtagtcag gccgctcacc cgttttagag ctagaaatag caagttaaaa taaggctagt    60
ccgttatcaa cttgaaaaag tggcaccgag tcggtgc                             97

SEQ ID NO: 144          moltype = DNA   length = 97
FEATURE                 Location/Qualifiers
misc_feature            1..97
                        note = Description of Artificial Sequence: Synthetic
                         oligonucleotide
source                  1..97
                        mol_type = other DNA
                        organism = synthetic construct
```

```
SEQUENCE: 144
gctgacaagt ctacggaacc tgttttagag ctagaaatag caagttaaaa taaggctagt    60
ccgttatcaa cttgaaaaag tggcaccgag tcggtgc                             97

SEQ ID NO: 145          moltype = DNA  length = 96
FEATURE                 Location/Qualifiers
misc_feature            1..96
                        note = Description of Artificial Sequence: Synthetic
                        oligonucleotide
source                  1..96
                        mol_type = other DNA
                        organism = synthetic construct
SEQUENCE: 145
gctcctccag cgccttgacc gttttagagc tagaaatagc aagttaaaat aaggctagtc    60
cgttatcaac ttgaaaaagt ggcaccgagt cggtgc                              96

SEQ ID NO: 146          moltype = DNA  length = 20
FEATURE                 Location/Qualifiers
misc_feature            1..20
                        note = Description of Artificial Sequence: Synthetic
                        oligonucleotide
source                  1..20
                        mol_type = other DNA
                        organism = synthetic construct
SEQUENCE: 146
gctattctcg cagctcacca                                                20

SEQ ID NO: 147          moltype = DNA  length = 20
FEATURE                 Location/Qualifiers
misc_feature            1..20
                        note = Description of Artificial Sequence: Synthetic
                        oligonucleotide
source                  1..20
                        mol_type = other DNA
                        organism = synthetic construct
SEQUENCE: 147
agaagcggcg tccggggcta                                                20

SEQ ID NO: 148          moltype = DNA  length = 20
FEATURE                 Location/Qualifiers
misc_feature            1..20
                        note = Description of Artificial Sequence: Synthetic
                        oligonucleotide
source                  1..20
                        mol_type = other DNA
                        organism = synthetic construct
SEQUENCE: 148
gggcacgggg ccatgtacaa                                                20

SEQ ID NO: 149          moltype = DNA  length = 20
FEATURE                 Location/Qualifiers
misc_feature            1..20
                        note = Description of Artificial Sequence: Synthetic
                        oligonucleotide
source                  1..20
                        mol_type = other DNA
                        organism = synthetic construct
SEQUENCE: 149
gcgtattgcc tggaggatgg                                                20

SEQ ID NO: 150          moltype = DNA  length = 20
FEATURE                 Location/Qualifiers
misc_feature            1..20
                        note = Description of Artificial Sequence: Synthetic
                        oligonucleotide
source                  1..20
                        mol_type = other DNA
                        organism = synthetic construct
SEQUENCE: 150
tgtcaggtgg ggcggggcta                                                20

SEQ ID NO: 151          moltype = DNA  length = 20
FEATURE                 Location/Qualifiers
misc_feature            1..20
                        note = Description of Artificial Sequence: Synthetic
                        oligonucleotide
source                  1..20
                        mol_type = other DNA
                        organism = synthetic construct
```

```
SEQUENCE: 151
agtgggtcag acgagcagga                                              20

SEQ ID NO: 152          moltype = DNA  length = 20
FEATURE                 Location/Qualifiers
misc_feature            1..20
                        note = Description of Artificial Sequence: Synthetic
                        oligonucleotide
source                  1..20
                        mol_type = other DNA
                        organism = synthetic construct
SEQUENCE: 152
gctgtctccg ccgcccgcca                                              20

SEQ ID NO: 153          moltype = DNA  length = 96
FEATURE                 Location/Qualifiers
misc_feature            1..96
                        note = Description of Artificial Sequence: Synthetic
                        oligonucleotide
source                  1..96
                        mol_type = other DNA
                        organism = synthetic construct
SEQUENCE: 153
gctattctcg cagctcacca gttttagagc tagaaatagc aagttaaaat aaggctagtc  60
cgttatcaac ttgaaaaagt ggcaccgagt cggtgc                            96

SEQ ID NO: 154          moltype = DNA  length = 184
FEATURE                 Location/Qualifiers
misc_feature            1..184
                        note = Description of Artificial Sequence: Synthetic
                        polynucleotide
misc_difference         148..149
                        note = CG, GC, AT, TA, GG, TT, GA, AG, CC, TC, CT, AA, TG,
                        GT, CA, or AC
source                  1..184
                        mol_type = other DNA
                        organism = synthetic construct
SEQUENCE: 154
gctattctcg cagctcacca gttttagagc tagaaatagc aagttaaaat aaggctagtc  60
cgttatcaac ttgaaaaagt ggcaccgagt cggtgcgacg agcgcggcga tatcatcatc 120
catggccgga tgatcctgac gacggagnnc gccgtcgtcg acaagccggc ctgagctgcg 180
agaa                                                              184

SEQ ID NO: 155          moltype = DNA  length = 183
FEATURE                 Location/Qualifiers
misc_feature            1..183
                        note = Description of Artificial Sequence: Synthetic
                        polynucleotide
source                  1..183
                        mol_type = other DNA
                        organism = synthetic construct
SEQUENCE: 155
gctattctcg cagctcacca gttttagagc tagaaatagc aagttaaaat aaggctagtc  60
cgttatcaac ttgaaaaagt ggcaccgagt cggtgcgacg agcgcggcga tatcatcatc 120
catgccggat gatcctgacg acggagaccc cgtcgtcga caagccggcc tgagctgcga 180
gaa                                                               183

SEQ ID NO: 156          moltype = DNA  length = 183
FEATURE                 Location/Qualifiers
misc_feature            1..183
                        note = Description of Artificial Sequence: Synthetic
                        polynucleotide
source                  1..183
                        mol_type = other DNA
                        organism = synthetic construct
SEQUENCE: 156
gctattctcg cagctcacca gttttagagc tagaaatagc aagttaaaat aaggctagtc  60
cgttatcaac ttgaaaaagt ggcaccgagt cggtgcgacg agcgcggcga tatcatcatc 120
catgccggat gatcctgacg acggagagcg ccgtcgtcga caagccggcc tgagctgcga 180
gaa                                                               183

SEQ ID NO: 157          moltype = DNA  length = 189
FEATURE                 Location/Qualifiers
misc_feature            1..189
                        note = Description of Artificial Sequence: Synthetic
                        polynucleotide
source                  1..189
                        mol_type = other DNA
                        organism = synthetic construct
```

```
SEQUENCE: 157
gcgtattgcc tggaggatgg gttttagagc tagaaatagc aagttaaaat aaggctagtc    60
cgttatcaac ttgaaaaagt ggcaccgagt cggtgcgaac cacgcggcga atgccggcgt   120
ccgcccgga tgatcctgac gacggagtcc gccgtcgtcg acaagccggc ctcctccagg    180
caatacgcg                                                           189

SEQ ID NO: 158          moltype = DNA   length = 189
FEATURE                 Location/Qualifiers
misc_feature            1..189
                        note = Description of Artificial Sequence: Synthetic
                        polynucleotide
source                  1..189
                        mol_type = other DNA
                        organism = synthetic construct
SEQUENCE: 158
gctgtctccg ccgcccgcca gttttagagc tagaaatagc aagttaaaat aaggctagtc    60
cgttatcaac ttgaaaaagt ggcaccgagt cggtgcgcgg cggcacgggg gtcgcagtcg   120
ccatgccgga tgatcctgac gacggagctc gccgtcgtcg acaagccggc ccgggcggcg   180
gagacagcg                                                           189

SEQ ID NO: 159          moltype = DNA   length = 20
FEATURE                 Location/Qualifiers
misc_feature            1..20
                        note = Description of Artificial Sequence: Synthetic
                        oligonucleotide
source                  1..20
                        mol_type = other DNA
                        organism = synthetic construct
SEQUENCE: 159
gtcacctcca atgactaggg                                                20

SEQ ID NO: 160          moltype = DNA   length = 20
FEATURE                 Location/Qualifiers
misc_feature            1..20
                        note = Description of Artificial Sequence: Synthetic
                        oligonucleotide
source                  1..20
                        mol_type = other DNA
                        organism = synthetic construct
SEQUENCE: 160
gggcaaccac aaacccacga                                                20

SEQ ID NO: 161          moltype = DNA   length = 194
FEATURE                 Location/Qualifiers
misc_feature            1..194
                        note = Description of Artificial Sequence: Synthetic
                        polynucleotide
source                  1..194
                        mol_type = other DNA
                        organism = synthetic construct
SEQUENCE: 161
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catggctatg ccggatgatc ctgacgacgg agtccgccgt cgtcgacaag ccggccctag   180
ctgagctgcg agaa                                                     194

SEQ ID NO: 162          moltype = DNA   length = 189
FEATURE                 Location/Qualifiers
misc_feature            1..189
                        note = Description of Artificial Sequence: Synthetic
                        polynucleotide
source                  1..189
                        mol_type = other DNA
                        organism = synthetic construct
SEQUENCE: 162
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catggtgccg gatgatcctg acgacggagt ccgccgtcgt cgacaagccg gccctatgag   180
ctgcgagaa                                                           189

SEQ ID NO: 163          moltype = DNA   length = 184
FEATURE                 Location/Qualifiers
misc_feature            1..184
                        note = Description of Artificial Sequence: Synthetic
                        polynucleotide
source                  1..184
                        mol_type = other DNA
                        organism = synthetic construct
SEQUENCE: 163
```

```
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catggccgga tgatcctgac gacggagtcc gccgtcgtcg acaagccggc ctgagctgcg   180
agaa                                                                184

SEQ ID NO: 164         moltype = DNA   length = 179
FEATURE                Location/Qualifiers
misc_feature           1..179
                       note = Description of Artificial Sequence: Synthetic
                         polynucleotide
source                 1..179
                       mol_type = other DNA
                       organism = synthetic construct
SEQUENCE: 164
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catgggatg atcctgacga cggagtccgc cgtcgtcgac aagccgtgag ctgcgagaa    179

SEQ ID NO: 165         moltype = DNA   length = 174
FEATURE                Location/Qualifiers
misc_feature           1..174
                       note = Description of Artificial Sequence: Synthetic
                         polynucleotide
source                 1..174
                       mol_type = other DNA
                       organism = synthetic construct
SEQUENCE: 165
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catggtgatc ctgacgacgg agtccgccgt cgtcgacaag ctgagctgcg agaa         174

SEQ ID NO: 166         moltype = DNA   length = 169
FEATURE                Location/Qualifiers
misc_feature           1..169
                       note = Description of Artificial Sequence: Synthetic
                         polynucleotide
source                 1..169
                       mol_type = other DNA
                       organism = synthetic construct
SEQUENCE: 166
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catggatcct gacgacggag tccgccgtcg tcgactgag ctgcgagaa                169

SEQ ID NO: 167         moltype = DNA   length = 164
FEATURE                Location/Qualifiers
misc_feature           1..164
                       note = Description of Artificial Sequence: Synthetic
                         polynucleotide
source                 1..164
                       mol_type = other DNA
                       organism = synthetic construct
SEQUENCE: 167
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catggcctga cgacggagtc cgccgtcgtc gtgagctgcg agaa                    164

SEQ ID NO: 168         moltype = DNA   length = 159
FEATURE                Location/Qualifiers
misc_feature           1..159
                       note = Description of Artificial Sequence: Synthetic
                         polynucleotide
source                 1..159
                       mol_type = other DNA
                       organism = synthetic construct
SEQUENCE: 168
gctattctcg cagctcacca gttttagagc tagaaatagc aagttaaaat aaggctagtc    60
cgttatcaac ttgaaaaagt ggcaccgagt cggtgcgacg agcgcggcga tatcatcatc   120
catggtgacg acggagtccg ccgtcgtgag ctgcgagaa                          159

SEQ ID NO: 169         moltype = DNA   length = 154
FEATURE                Location/Qualifiers
misc_feature           1..154
                       note = Description of Artificial Sequence: Synthetic
                         polynucleotide
source                 1..154
                       mol_type = other DNA
                       organism = synthetic construct
SEQUENCE: 169
```

```
gctattctcg cagctcacca gttttagagc tagaaatagc aagttaaaat aaggctagtc   60
cgttatcaac ttgaaaaagt ggcaccgagt cggtgcgacg agcgcggcga tatcatcatc  120
catggacgac ggagtccgcc gtgagctgcg agaa                              154

SEQ ID NO: 170           moltype = DNA   length = 149
FEATURE                  Location/Qualifiers
misc_feature             1..149
                         note = Description of Artificial Sequence: Synthetic
                         polynucleotide
source                   1..149
                         mol_type = other DNA
                         organism = synthetic construct
SEQUENCE: 170
gctattctcg cagctcacca gttttagagc tagaaatagc aagttaaaat aaggctagtc   60
cgttatcaac ttgaaaaagt ggcaccgagt cggtgcgacg agcgcggcga tatcatcatc  120
catgggacgg agtccgtgag ctgcgagaa                                    149

SEQ ID NO: 171           moltype = DNA   length = 144
FEATURE                  Location/Qualifiers
misc_feature             1..144
                         note = Description of Artificial Sequence: Synthetic
                         polynucleotide
source                   1..144
                         mol_type = other DNA
                         organism = synthetic construct
SEQUENCE: 171
gctattctcg cagctcacca gttttagagc tagaaatagc aagttaaaat aaggctagtc   60
cgttatcaac ttgaaaaagt ggcaccgagt cggtgcgacg agcgcggcga tatcatcatc  120
catggcggag ttgagctgcg agaa                                         144

SEQ ID NO: 172           moltype = DNA   length = 182
FEATURE                  Location/Qualifiers
misc_feature             1..182
                         note = Description of Artificial Sequence: Synthetic
                         polynucleotide
source                   1..182
                         mol_type = other DNA
                         organism = synthetic construct
SEQUENCE: 172
gaagccggcc ttgcacatgc gttttagagc tagaaatagc aagttaaaat aaggctagtc   60
cgttatcaac ttgaaaaagt ggcaccgagt cggtgctcga cgacgagcgc ggcgatatca  120
tcatccatgg taccgttcgt atagcataca ttatacgaag ttattgagct gcgagaatag  180
cc                                                                 182

SEQ ID NO: 173           moltype = DNA   length = 177
FEATURE                  Location/Qualifiers
misc_feature             1..177
                         note = Description of Artificial Sequence: Synthetic
                         polynucleotide
source                   1..177
                         mol_type = other DNA
                         organism = synthetic construct
SEQUENCE: 173
gaagccggcc ttgcacatgc gttttagagc tagaaatagc aagttaaaat aaggctagtc   60
cgttatcaac ttgaaaaagt ggcaccgagt cggtgcgacg agcgcggcga tatcatcatc  120
catggtaccg ttcgtatagc atacattata cgaagttatt gagctgcgag aatagcc     177

SEQ ID NO: 174           moltype = DNA   length = 177
FEATURE                  Location/Qualifiers
misc_feature             1..177
                         note = Description of Artificial Sequence: Synthetic
                         polynucleotide
source                   1..177
                         mol_type = other DNA
                         organism = synthetic construct
SEQUENCE: 174
gaagccggcc ttgcacatgc gttttagagc tagaaatagc aagttaaaat aaggctagtc   60
cgttatcaac ttgaaaaagt ggcaccgagt cggtgctcga cgacgagcgc ggcgatatca  120
tcatccatgg taccgttcgt atagcataca ttatacgaag ttattgagct gcgagaa     177

SEQ ID NO: 175           moltype = DNA   length = 159
FEATURE                  Location/Qualifiers
misc_feature             1..159
                         note = Description of Artificial Sequence: Synthetic
                         polynucleotide
source                   1..159
                         mol_type = other DNA
                         organism = synthetic construct
SEQUENCE: 175
```

```
gaagccggcc ttgcacatgc gttttagagc tagaaatagc aagttaaaat aaggctagtc    60
cgttatcaac ttgaaaaagt ggcaccgagt cggtgcatat catcatccat ggtaccgttc   120
gtatagcata cattatacga agttattgag ctgcgagaa                          159

SEQ ID NO: 176          moltype = DNA   length = 96
FEATURE                 Location/Qualifiers
misc_feature            1..96
                        note = Description of Artificial Sequence: Synthetic
                        oligonucleotide
source                  1..96
                        mol_type = other DNA
                        organism = synthetic construct
SEQUENCE: 176
ccccacgatg gaggggaaga gttttagagc tagaaatagc aagttaaaat aaggctagtc    60
cgttatcaac ttgaaaaagt ggcaccgagt cggtgc                              96

SEQ ID NO: 177          moltype = DNA   length = 96
FEATURE                 Location/Qualifiers
misc_feature            1..96
                        note = Description of Artificial Sequence: Synthetic
                        oligonucleotide
source                  1..96
                        mol_type = other DNA
                        organism = synthetic construct
SEQUENCE: 177
ccttctcctg gagccgcgac gttttagagc tagaaatagc aagttaaaat aaggctagtc    60
cgttatcaac ttgaaaaagt ggcaccgagt cggtgc                              96

SEQ ID NO: 178          moltype = DNA   length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 178
gtggtttgtc tggtcaacca ccgcggtctc agtggtgtac ggtacaaacc ca             52

SEQ ID NO: 179          moltype = DNA   length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 179
tgggtttgta ccgtacacca ctgagaccgc ggtggttgac cagacaaacc ac             52

SEQ ID NO: 180          moltype = DNA   length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 180
gtggtttgtc tggtcaacca ccgcgcgctc agtggtgtac ggtacaaacc ca             52

SEQ ID NO: 181          moltype = DNA   length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 181
tgggtttgta ccgtacacca ctgagcgcgc ggtggttgac cagacaaacc ac             52

SEQ ID NO: 182          moltype = DNA   length = 52
FEATURE                 Location/Qualifiers
misc_feature            1..52
                        note = Description of Artificial Sequence: Synthetic
                        oligonucleotide
source                  1..52
                        mol_type = other DNA
```

```
                         organism = synthetic construct
SEQUENCE: 182
gtggtttgtc tggtcaacca ccgcggcctc agtggtgtac ggtacaaacc ca           52

SEQ ID NO: 183          moltype = DNA  length = 52
FEATURE                 Location/Qualifiers
misc_feature            1..52
                        note = Description of Artificial Sequence: Synthetic
                          oligonucleotide
source                  1..52
                        mol_type = other DNA
                        organism = synthetic construct
SEQUENCE: 183
tgggtttgta ccgtacacca ctgaggccgc ggtggttgac cagacaaacc ac           52

SEQ ID NO: 184          moltype = DNA  length = 52
FEATURE                 Location/Qualifiers
misc_feature            1..52
                        note = Description of Artificial Sequence: Synthetic
                          oligonucleotide
source                  1..52
                        mol_type = other DNA
                        organism = synthetic construct
SEQUENCE: 184
gtggtttgtc tggtcaacca ccgcgatctc agtggtgtac ggtacaaacc ca           52

SEQ ID NO: 185          moltype = DNA  length = 52
FEATURE                 Location/Qualifiers
misc_feature            1..52
                        note = Description of Artificial Sequence: Synthetic
                          oligonucleotide
source                  1..52
                        mol_type = other DNA
                        organism = synthetic construct
SEQUENCE: 185
tgggtttgta ccgtacacca ctgagatcgc ggtggttgac cagacaaacc ac           52

SEQ ID NO: 186          moltype = DNA  length = 52
FEATURE                 Location/Qualifiers
misc_feature            1..52
                        note = Description of Artificial Sequence: Synthetic
                          oligonucleotide
source                  1..52
                        mol_type = other DNA
                        organism = synthetic construct
SEQUENCE: 186
gtggtttgtc tggtcaacca ccgcgtactc agtggtgtac ggtacaaacc ca           52

SEQ ID NO: 187          moltype = DNA  length = 52
FEATURE                 Location/Qualifiers
misc_feature            1..52
                        note = Description of Artificial Sequence: Synthetic
                          oligonucleotide
source                  1..52
                        mol_type = other DNA
                        organism = synthetic construct
SEQUENCE: 187
tgggtttgta ccgtacacca ctgagtacgc ggtggttgac cagacaaacc ac           52

SEQ ID NO: 188          moltype = DNA  length = 52
FEATURE                 Location/Qualifiers
misc_feature            1..52
                        note = Description of Artificial Sequence: Synthetic
                          oligonucleotide
source                  1..52
                        mol_type = other DNA
                        organism = synthetic construct
SEQUENCE: 188
gtggtttgtc tggtcaacca ccgcgggctc agtggtgtac ggtacaaacc ca           52

SEQ ID NO: 189          moltype = DNA  length = 52
FEATURE                 Location/Qualifiers
misc_feature            1..52
                        note = Description of Artificial Sequence: Synthetic
                          oligonucleotide
source                  1..52
                        mol_type = other DNA
                        organism = synthetic construct
SEQUENCE: 189
```

```
tgggtttgta ccgtacacca ctgagcccgc ggtggttgac cagacaaacc ac          52

SEQ ID NO: 190          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 190
gtggtttgtc tggtcaacca ccgcgttctc agtggtgtac ggtacaaacc ca          52

SEQ ID NO: 191          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 191
tgggtttgta ccgtacacca ctgagaacgc ggtggttgac cagacaaacc ac          52

SEQ ID NO: 192          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 192
gtggtttgtc tggtcaacca ccgcggactc agtggtgtac ggtacaaacc ca          52

SEQ ID NO: 193          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 193
tgggtttgta ccgtacacca ctgagtccgc ggtggttgac cagacaaacc ac          52

SEQ ID NO: 194          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 194
gtggtttgtc tggtcaacca ccgcgagctc agtggtgtac ggtacaaacc ca          52

SEQ ID NO: 195          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 195
tgggtttgta ccgtacacca ctgagctcgc ggtggttgac cagacaaacc ac          52

SEQ ID NO: 196          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 196
gtggtttgtc tggtcaacca ccgcgccctc agtggtgtac ggtacaaacc ca          52
```

```
SEQ ID NO: 197           moltype = DNA   length = 52
FEATURE                  Location/Qualifiers
misc_feature             1..52
                         note = Description of Artificial Sequence: Synthetic
                         oligonucleotide
source                   1..52
                         mol_type = other DNA
                         organism = synthetic construct
SEQUENCE: 197
tgggtttgta ccgtacacca ctgagggcgc ggtggttgac cagacaaacc ac              52

SEQ ID NO: 198           moltype = DNA   length = 52
FEATURE                  Location/Qualifiers
misc_feature             1..52
                         note = Description of Artificial Sequence: Synthetic
                         oligonucleotide
source                   1..52
                         mol_type = other DNA
                         organism = synthetic construct
SEQUENCE: 198
gtggtttgtc tggtcaacca ccgcgtcctc agtggtgtac ggtacaaacc ca              52

SEQ ID NO: 199           moltype = DNA   length = 52
FEATURE                  Location/Qualifiers
misc_feature             1..52
                         note = Description of Artificial Sequence: Synthetic
                         oligonucleotide
source                   1..52
                         mol_type = other DNA
                         organism = synthetic construct
SEQUENCE: 199
tgggtttgta ccgtacacca ctgaggacgc ggtggttgac cagacaaacc ac              52

SEQ ID NO: 200           moltype = DNA   length = 52
FEATURE                  Location/Qualifiers
misc_feature             1..52
                         note = Description of Artificial Sequence: Synthetic
                         oligonucleotide
source                   1..52
                         mol_type = other DNA
                         organism = synthetic construct
SEQUENCE: 200
gtggtttgtc tggtcaacca ccgcgctctc agtggtgtac ggtacaaacc ca              52

SEQ ID NO: 201           moltype = DNA   length = 52
FEATURE                  Location/Qualifiers
misc_feature             1..52
                         note = Description of Artificial Sequence: Synthetic
                         oligonucleotide
source                   1..52
                         mol_type = other DNA
                         organism = synthetic construct
SEQUENCE: 201
tgggtttgta ccgtacacca ctgagagcgc ggtggttgac cagacaaacc ac              52

SEQ ID NO: 202           moltype = DNA   length = 52
FEATURE                  Location/Qualifiers
misc_feature             1..52
                         note = Description of Artificial Sequence: Synthetic
                         oligonucleotide
source                   1..52
                         mol_type = other DNA
                         organism = synthetic construct
SEQUENCE: 202
gtggtttgtc tggtcaacca ccgcgaactc agtggtgtac ggtacaaacc ca              52

SEQ ID NO: 203           moltype = DNA   length = 52
FEATURE                  Location/Qualifiers
misc_feature             1..52
                         note = Description of Artificial Sequence: Synthetic
                         oligonucleotide
source                   1..52
                         mol_type = other DNA
                         organism = synthetic construct
SEQUENCE: 203
tgggtttgta ccgtacacca ctgagttcgc ggtggttgac cagacaaacc ac              52

SEQ ID NO: 204           moltype = DNA   length = 52
FEATURE                  Location/Qualifiers
```

```
misc_feature              1..52
                          note = Description of Artificial Sequence: Synthetic
                             oligonucleotide
source                    1..52
                          mol_type = other DNA
                          organism = synthetic construct
SEQUENCE: 204
gtggtttgtc tggtcaacca ccgcgcactc agtggtgtac ggtacaaacc ca        52

SEQ ID NO: 205            moltype = DNA  length = 52
FEATURE                   Location/Qualifiers
misc_feature              1..52
                          note = Description of Artificial Sequence: Synthetic
                             oligonucleotide
source                    1..52
                          mol_type = other DNA
                          organism = synthetic construct
SEQUENCE: 205
tgggtttgta ccgtacacca ctgagtgcgc ggtggttgac cagacaaacc ac        52

SEQ ID NO: 206            moltype = DNA  length = 52
FEATURE                   Location/Qualifiers
misc_feature              1..52
                          note = Description of Artificial Sequence: Synthetic
                             oligonucleotide
source                    1..52
                          mol_type = other DNA
                          organism = synthetic construct
SEQUENCE: 206
gtggtttgtc tggtcaacca ccgcgacctc agtggtgtac ggtacaaacc ca        52

SEQ ID NO: 207            moltype = DNA  length = 52
FEATURE                   Location/Qualifiers
misc_feature              1..52
                          note = Description of Artificial Sequence: Synthetic
                             oligonucleotide
source                    1..52
                          mol_type = other DNA
                          organism = synthetic construct
SEQUENCE: 207
tgggtttgta ccgtacacca ctgaggtcgc ggtggttgac cagacaaacc ac        52

SEQ ID NO: 208            moltype = DNA  length = 52
FEATURE                   Location/Qualifiers
misc_feature              1..52
                          note = Description of Artificial Sequence: Synthetic
                             oligonucleotide
source                    1..52
                          mol_type = other DNA
                          organism = synthetic construct
SEQUENCE: 208
gtggtttgtc tggtcaacca ccgcgtgctc agtggtgtac ggtacaaacc ca        52

SEQ ID NO: 209            moltype = DNA  length = 52
FEATURE                   Location/Qualifiers
misc_feature              1..52
                          note = Description of Artificial Sequence: Synthetic
                             oligonucleotide
source                    1..52
                          mol_type = other DNA
                          organism = synthetic construct
SEQUENCE: 209
tgggtttgta ccgtacacca ctgagcacgc ggtggttgac cagacaaacc ac        52

SEQ ID NO: 210            moltype = DNA  length = 46
FEATURE                   Location/Qualifiers
misc_feature              1..46
                          note = Description of Artificial Sequence: Synthetic
                             oligonucleotide
source                    1..46
                          mol_type = other DNA
                          organism = synthetic construct
SEQUENCE: 210
ggccggcttg tcgacgacgg cggtctccgt cgtcaggatc atccgg              46

SEQ ID NO: 211            moltype = DNA  length = 46
FEATURE                   Location/Qualifiers
misc_feature              1..46
                          note = Description of Artificial Sequence: Synthetic
```

```
                              oligonucleotide
source                        1..46
                              mol_type = other DNA
                              organism = synthetic construct
SEQUENCE: 211
ccggatgatc ctgacgacgg agaccgccgt cgtcgacaag ccggcc            46

SEQ ID NO: 212          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 212
ggccggcttg tcgacgacgg cgaactccgt cgtcaggatc atccgg            46

SEQ ID NO: 213          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 213
ccggatgatc ctgacgacgg agttcgccgt cgtcgacaag ccggcc            46

SEQ ID NO: 214          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 214
ggccggcttg tcgacgacgg cggactccgt cgtcaggatc atccgg            46

SEQ ID NO: 215          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 215
ccggatgatc ctgacgacgg agtccgccgt cgtcgacaag ccggcc            46

SEQ ID NO: 216          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 216
ggccggcttg tcgacgacgg cgcactccgt cgtcaggatc atccgg            46

SEQ ID NO: 217          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 217
ccggatgatc ctgacgacgg agtgcgccgt cgtcgacaag ccggcc            46

SEQ ID NO: 218          moltype = DNA   length = 46
FEATURE                 Location/Qualifiers
misc_feature            1..46
                        note = Description of Artificial Sequence: Synthetic
                        oligonucleotide
source                  1..46
```

```
                        mol_type = other DNA
                        organism = synthetic construct
SEQUENCE: 218
ggccggcttg tcgacgacgg cgtactccgt cgtcaggatc atccgg              46

SEQ ID NO: 219          moltype = DNA  length = 46
FEATURE                 Location/Qualifiers
misc_feature            1..46
                        note = Description of Artificial Sequence: Synthetic
                          oligonucleotide
source                  1..46
                        mol_type = other DNA
                        organism = synthetic construct
SEQUENCE: 219
ccggatgatc ctgacgacgg agtacgccgt cgtcgacaag ccggcc              46

SEQ ID NO: 220          moltype = DNA  length = 46
FEATURE                 Location/Qualifiers
misc_feature            1..46
                        note = Description of Artificial Sequence: Synthetic
                          oligonucleotide
source                  1..46
                        mol_type = other DNA
                        organism = synthetic construct
SEQUENCE: 220
ggccggcttg tcgacgacgg cgagctccgt cgtcaggatc atccgg              46

SEQ ID NO: 221          moltype = DNA  length = 46
FEATURE                 Location/Qualifiers
misc_feature            1..46
                        note = Description of Artificial Sequence: Synthetic
                          oligonucleotide
source                  1..46
                        mol_type = other DNA
                        organism = synthetic construct
SEQUENCE: 221
ccggatgatc ctgacgacgg agctcgccgt cgtcgacaag ccggcc              46

SEQ ID NO: 222          moltype = DNA  length = 46
FEATURE                 Location/Qualifiers
misc_feature            1..46
                        note = Description of Artificial Sequence: Synthetic
                          oligonucleotide
source                  1..46
                        mol_type = other DNA
                        organism = synthetic construct
SEQUENCE: 222
ggccggcttg tcgacgacgg cgggctccgt cgtcaggatc atccgg              46

SEQ ID NO: 223          moltype = DNA  length = 46
FEATURE                 Location/Qualifiers
misc_feature            1..46
                        note = Description of Artificial Sequence: Synthetic
                          oligonucleotide
source                  1..46
                        mol_type = other DNA
                        organism = synthetic construct
SEQUENCE: 223
ccggatgatc ctgacgacgg agcccgccgt cgtcgacaag ccggcc              46

SEQ ID NO: 224          moltype = DNA  length = 46
FEATURE                 Location/Qualifiers
misc_feature            1..46
                        note = Description of Artificial Sequence: Synthetic
                          oligonucleotide
source                  1..46
                        mol_type = other DNA
                        organism = synthetic construct
SEQUENCE: 224
ggccggcttg tcgacgacgg cgcgctccgt cgtcaggatc atccgg              46

SEQ ID NO: 225          moltype = DNA  length = 46
FEATURE                 Location/Qualifiers
misc_feature            1..46
                        note = Description of Artificial Sequence: Synthetic
                          oligonucleotide
source                  1..46
                        mol_type = other DNA
                        organism = synthetic construct
```

```
SEQUENCE: 225
ccggatgatc ctgacgacgg agcgcgccgt cgtcgacaag ccggcc        46

SEQ ID NO: 226          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 226
ggccggcttg tcgacgacgg cgtgctccgt cgtcaggatc atccgg        46

SEQ ID NO: 227          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 227
ccggatgatc ctgacgacgg agcacgccgt cgtcgacaag ccggcc        46

SEQ ID NO: 228          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 228
ggccggcttg tcgacgacgg cgacctccgt cgtcaggatc atccgg        46

SEQ ID NO: 229          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 229
ccggatgatc ctgacgacgg aggtcgccgt cgtcgacaag ccggcc        46

SEQ ID NO: 230          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 230
ggccggcttg tcgacgacgg cggcctccgt cgtcaggatc atccgg        46

SEQ ID NO: 231          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 231
ccggatgatc ctgacgacgg aggccgccgt cgtcgacaag ccggcc        46

SEQ ID NO: 232          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 232
ggccggcttg tcgacgacgg cgccctccgt cgtcaggatc atccgg        46
```

```
SEQ ID NO: 233          moltype = DNA  length = 46
FEATURE                 Location/Qualifiers
misc_feature            1..46
                        note = Description of Artificial Sequence: Synthetic
                         oligonucleotide
source                  1..46
                        mol_type = other DNA
                        organism = synthetic construct
SEQUENCE: 233
ccggatgatc ctgacgacgg agggcgccgt cgtcgacaag ccggcc              46

SEQ ID NO: 234          moltype = DNA  length = 46
FEATURE                 Location/Qualifiers
misc_feature            1..46
                        note = Description of Artificial Sequence: Synthetic
                         oligonucleotide
source                  1..46
                        mol_type = other DNA
                        organism = synthetic construct
SEQUENCE: 234
ggccggcttg tcgacgacgg cgtcctccgt cgtcaggatc atccgg              46

SEQ ID NO: 235          moltype = DNA  length = 46
FEATURE                 Location/Qualifiers
misc_feature            1..46
                        note = Description of Artificial Sequence: Synthetic
                         oligonucleotide
source                  1..46
                        mol_type = other DNA
                        organism = synthetic construct
SEQUENCE: 235
ccggatgatc ctgacgacgg aggacgccgt cgtcgacaag ccggcc              46

SEQ ID NO: 236          moltype = DNA  length = 46
FEATURE                 Location/Qualifiers
misc_feature            1..46
                        note = Description of Artificial Sequence: Synthetic
                         oligonucleotide
source                  1..46
                        mol_type = other DNA
                        organism = synthetic construct
SEQUENCE: 236
ggccggcttg tcgacgacgg cgatctccgt cgtcaggatc atccgg              46

SEQ ID NO: 237          moltype = DNA  length = 46
FEATURE                 Location/Qualifiers
misc_feature            1..46
                        note = Description of Artificial Sequence: Synthetic
                         oligonucleotide
source                  1..46
                        mol_type = other DNA
                        organism = synthetic construct
SEQUENCE: 237
ccggatgatc ctgacgacgg agatcgccgt cgtcgacaag ccggcc              46

SEQ ID NO: 238          moltype = DNA  length = 46
FEATURE                 Location/Qualifiers
misc_feature            1..46
                        note = Description of Artificial Sequence: Synthetic
                         oligonucleotide
source                  1..46
                        mol_type = other DNA
                        organism = synthetic construct
SEQUENCE: 238
ggccggcttg tcgacgacgg cgctctccgt cgtcaggatc atccgg              46

SEQ ID NO: 239          moltype = DNA  length = 46
FEATURE                 Location/Qualifiers
misc_feature            1..46
                        note = Description of Artificial Sequence: Synthetic
                         oligonucleotide
source                  1..46
                        mol_type = other DNA
                        organism = synthetic construct
SEQUENCE: 239
ccggatgatc ctgacgacgg agagcgccgt cgtcgacaag ccggcc              46

SEQ ID NO: 240          moltype = DNA  length = 46
```

```
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 240
ggccggcttg tcgacgacgg cgttctccgt cgtcaggatc atccgg            46

SEQ ID NO: 241          moltype = DNA   length = 46
FEATURE                 Location/Qualifiers
misc_feature            1..46
                        note = Description of Artificial Sequence: Synthetic
                        oligonucleotide
source                  1..46
                        mol_type = other DNA
                        organism = synthetic construct
SEQUENCE: 241
ccggatgatc ctgacgacgg agaacgccgt cgtcgacaag ccggcc            46

SEQ ID NO: 242          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 242
ggcttgtcga cgacggcggt ctccgtcgtc aggatcat                     38

SEQ ID NO: 243          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 243
atgatcctga cgacggagac cgccgtcgtc gacaagcc                     38

SEQ ID NO: 244          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 244
ggcttgtcga cgacggcgaa ctccgtcgtc aggatcat                     38

SEQ ID NO: 245          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 245
atgatcctga cgacggagtt cgccgtcgtc gacaagcc                     38

SEQ ID NO: 246          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 246
ggcttgtcga cgacggcgga ctccgtcgtc aggatcat                     38

SEQ ID NO: 247          moltype = DNA   length = 38
FEATURE                 Location/Qualifiers
misc_feature            1..38
```

-continued

```
                        note = Description of Artificial Sequence: Synthetic
                            oligonucleotide
source                  1..38
                        mol_type = other DNA
                        organism = synthetic construct
SEQUENCE: 247
atgatcctga cgacggagtc cgccgtcgtc gacaagcc                                  38

SEQ ID NO: 248          moltype = DNA  length = 38
FEATURE                 Location/Qualifiers
misc_feature            1..38
                        note = Description of Artificial Sequence: Synthetic
                            oligonucleotide
source                  1..38
                        mol_type = other DNA
                        organism = synthetic construct
SEQUENCE: 248
ggcttgtcga cgacggcgca ctccgtcgtc aggatcat                                  38

SEQ ID NO: 249          moltype = DNA  length = 38
FEATURE                 Location/Qualifiers
misc_feature            1..38
                        note = Description of Artificial Sequence: Synthetic
                            oligonucleotide
source                  1..38
                        mol_type = other DNA
                        organism = synthetic construct
SEQUENCE: 249
atgatcctga cgacggagtg cgccgtcgtc gacaagcc                                  38

SEQ ID NO: 250          moltype = DNA  length = 38
FEATURE                 Location/Qualifiers
misc_feature            1..38
                        note = Description of Artificial Sequence: Synthetic
                            oligonucleotide
source                  1..38
                        mol_type = other DNA
                        organism = synthetic construct
SEQUENCE: 250
ggcttgtcga cgacggcgta ctccgtcgtc aggatcat                                  38

SEQ ID NO: 251          moltype = DNA  length = 38
FEATURE                 Location/Qualifiers
misc_feature            1..38
                        note = Description of Artificial Sequence: Synthetic
                            oligonucleotide
source                  1..38
                        mol_type = other DNA
                        organism = synthetic construct
SEQUENCE: 251
atgatcctga cgacggagta cgccgtcgtc gacaagcc                                  38

SEQ ID NO: 252          moltype = DNA  length = 38
FEATURE                 Location/Qualifiers
misc_feature            1..38
                        note = Description of Artificial Sequence: Synthetic
                            oligonucleotide
source                  1..38
                        mol_type = other DNA
                        organism = synthetic construct
SEQUENCE: 252
ggcttgtcga cgacggcgag ctccgtcgtc aggatcat                                  38

SEQ ID NO: 253          moltype = DNA  length = 38
FEATURE                 Location/Qualifiers
misc_feature            1..38
                        note = Description of Artificial Sequence: Synthetic
                            oligonucleotide
source                  1..38
                        mol_type = other DNA
                        organism = synthetic construct
SEQUENCE: 253
atgatcctga cgacggagct cgccgtcgtc gacaagcc                                  38

SEQ ID NO: 254          moltype = DNA  length = 38
FEATURE                 Location/Qualifiers
misc_feature            1..38
                        note = Description of Artificial Sequence: Synthetic
                            oligonucleotide
```

```
source               1..38
                     mol_type = other DNA
                     organism = synthetic construct
SEQUENCE: 254
ggcttgtcga cgacggcggg ctccgtcgtc aggatcat                      38

SEQ ID NO: 255       moltype = DNA   length = 38
FEATURE              Location/Qualifiers
misc_feature         1..38
                     note = Description of Artificial Sequence: Synthetic
                     oligonucleotide
source               1..38
                     mol_type = other DNA
                     organism = synthetic construct
SEQUENCE: 255
atgatcctga cgacggagcc cgccgtcgtc gacaagcc                      38

SEQ ID NO: 256       moltype = DNA   length = 38
FEATURE              Location/Qualifiers
misc_feature         1..38
                     note = Description of Artificial Sequence: Synthetic
                     oligonucleotide
source               1..38
                     mol_type = other DNA
                     organism = synthetic construct
SEQUENCE: 256
ggcttgtcga cgacggcgcg ctccgtcgtc aggatcat                      38

SEQ ID NO: 257       moltype = DNA   length = 38
FEATURE              Location/Qualifiers
misc_feature         1..38
                     note = Description of Artificial Sequence: Synthetic
                     oligonucleotide
source               1..38
                     mol_type = other DNA
                     organism = synthetic construct
SEQUENCE: 257
atgatcctga cgacggagcg cgccgtcgtc gacaagcc                      38

SEQ ID NO: 258       moltype = DNA   length = 38
FEATURE              Location/Qualifiers
misc_feature         1..38
                     note = Description of Artificial Sequence: Synthetic
                     oligonucleotide
source               1..38
                     mol_type = other DNA
                     organism = synthetic construct
SEQUENCE: 258
ggcttgtcga cgacggcgtg ctccgtcgtc aggatcat                      38

SEQ ID NO: 259       moltype = DNA   length = 38
FEATURE              Location/Qualifiers
misc_feature         1..38
                     note = Description of Artificial Sequence: Synthetic
                     oligonucleotide
source               1..38
                     mol_type = other DNA
                     organism = synthetic construct
SEQUENCE: 259
atgatcctga cgacggagca cgccgtcgtc gacaagcc                      38

SEQ ID NO: 260       moltype = DNA   length = 38
FEATURE              Location/Qualifiers
misc_feature         1..38
                     note = Description of Artificial Sequence: Synthetic
                     oligonucleotide
source               1..38
                     mol_type = other DNA
                     organism = synthetic construct
SEQUENCE: 260
ggcttgtcga cgacggcgac ctccgtcgtc aggatcat                      38

SEQ ID NO: 261       moltype = DNA   length = 38
FEATURE              Location/Qualifiers
misc_feature         1..38
                     note = Description of Artificial Sequence: Synthetic
                     oligonucleotide
source               1..38
                     mol_type = other DNA
```

```
                            organism = synthetic construct
SEQUENCE: 261
atgatcctga cgacggaggt cgccgtcgtc gacaagcc                                 38

SEQ ID NO: 262          moltype = DNA  length = 38
FEATURE                 Location/Qualifiers
misc_feature            1..38
                        note = Description of Artificial Sequence: Synthetic
                            oligonucleotide
source                  1..38
                        mol_type = other DNA
                        organism = synthetic construct
SEQUENCE: 262
ggcttgtcga cgacggcggc ctccgtcgtc aggatcat                                 38

SEQ ID NO: 263          moltype = DNA  length = 38
FEATURE                 Location/Qualifiers
misc_feature            1..38
                        note = Description of Artificial Sequence: Synthetic
                            oligonucleotide
source                  1..38
                        mol_type = other DNA
                        organism = synthetic construct
SEQUENCE: 263
atgatcctga cgacggaggc cgccgtcgtc gacaagcc                                 38

SEQ ID NO: 264          moltype = DNA  length = 38
FEATURE                 Location/Qualifiers
misc_feature            1..38
                        note = Description of Artificial Sequence: Synthetic
                            oligonucleotide
source                  1..38
                        mol_type = other DNA
                        organism = synthetic construct
SEQUENCE: 264
ggcttgtcga cgacggcgcc ctccgtcgtc aggatcat                                 38

SEQ ID NO: 265          moltype = DNA  length = 38
FEATURE                 Location/Qualifiers
misc_feature            1..38
                        note = Description of Artificial Sequence: Synthetic
                            oligonucleotide
source                  1..38
                        mol_type = other DNA
                        organism = synthetic construct
SEQUENCE: 265
atgatcctga cgacggaggg cgccgtcgtc gacaagcc                                 38

SEQ ID NO: 266          moltype = DNA  length = 38
FEATURE                 Location/Qualifiers
misc_feature            1..38
                        note = Description of Artificial Sequence: Synthetic
                            oligonucleotide
source                  1..38
                        mol_type = other DNA
                        organism = synthetic construct
SEQUENCE: 266
ggcttgtcga cgacggcgtc ctccgtcgtc aggatcat                                 38

SEQ ID NO: 267          moltype = DNA  length = 38
FEATURE                 Location/Qualifiers
misc_feature            1..38
                        note = Description of Artificial Sequence: Synthetic
                            oligonucleotide
source                  1..38
                        mol_type = other DNA
                        organism = synthetic construct
SEQUENCE: 267
atgatcctga cgacggagga cgccgtcgtc gacaagcc                                 38

SEQ ID NO: 268          moltype = DNA  length = 38
FEATURE                 Location/Qualifiers
misc_feature            1..38
                        note = Description of Artificial Sequence: Synthetic
                            oligonucleotide
source                  1..38
                        mol_type = other DNA
                        organism = synthetic construct
SEQUENCE: 268
```

```
ggcttgtcga cgacggcgat ctccgtcgtc aggatcat                               38

SEQ ID NO: 270          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 269
atgatcctga cgacggagat cgccgtcgtc gacaagcc                               38

SEQ ID NO: 270          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 270
ggcttgtcga cgacggcgct ctccgtcgtc aggatcat                               38

SEQ ID NO: 271          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 271
atgatcctga cgacggagag cgccgtcgtc gacaagcc                               38

SEQ ID NO: 272          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 272
ggcttgtcga cgacggcgtt ctccgtcgtc aggatcat                               38

SEQ ID NO: 273          moltype = DNA   length = 38
FEATURE                 Location/Qualifiers
misc_feature            1..38
                        note = Description of Artificial Sequence: Synthetic
                        oligonucleotide
source                  1..38
                        mol_type = other DNA
                        organism = synthetic construct
SEQUENCE: 273
atgatcctga cgacggagaa cgccgtcgtc gacaagcc                               38

SEQ ID NO: 274          moltype = DNA   length = 34
FEATURE                 Location/Qualifiers
misc_feature            1..34
                        note = Description of Artificial Sequence: Synthetic
                        oligonucleotide
source                  1..34
                        mol_type = other DNA
                        organism = synthetic construct
SEQUENCE: 274
taccgttcgt ataatgtatg ctatacgaag ttat                                   34

SEQ ID NO: 275          moltype = DNA   length = 34
FEATURE                 Location/Qualifiers
misc_feature            1..34
                        note = Description of Artificial Sequence: Synthetic
                        oligonucleotide
source                  1..34
                        mol_type = other DNA
                        organism = synthetic construct
SEQUENCE: 275
ataacttcgt atagcataca ttatacgaac ggta                                   34
```

| | | |
|---|---|---|
| SEQ ID NO: 276 | moltype = DNA   length = 34 | |
| FEATURE | Location/Qualifiers | |
| misc_feature | 1..34<br>note = Description of Artificial Sequence: Synthetic<br>oligonucleotide | |
| source | 1..34<br>mol_type = other DNA<br>organism = synthetic construct | |
| SEQUENCE: 276 | | |
| ataacttcgt ataatgtatg ctatacgaac ggta | | 34 |
| | | |
| SEQ ID NO: 277 | moltype = DNA   length = 34 | |
| FEATURE | Location/Qualifiers | |
| misc_feature | 1..34<br>note = Description of Artificial Sequence: Synthetic<br>oligonucleotide | |
| source | 1..34<br>mol_type = other DNA<br>organism = synthetic construct | |
| SEQUENCE: 277 | | |
| taccgttcgt atagcataca ttatacgaag ttat | | 34 |
| | | |
| SEQ ID NO: 278 | moltype = DNA   length = 27 | |
| FEATURE | Location/Qualifiers | |
| misc_feature | 1..27<br>note = Description of Artificial Sequence: Synthetic<br>oligonucleotide | |
| source | 1..27<br>mol_type = other DNA<br>organism = synthetic construct | |
| SEQUENCE: 278 | | |
| tttaccttga ttgagatgtt aattgtg | | 27 |
| | | |
| SEQ ID NO: 279 | moltype = DNA   length = 27 | |
| FEATURE | Location/Qualifiers | |
| misc_feature | 1..27<br>note = Description of Artificial Sequence: Synthetic<br>oligonucleotide | |
| source | 1..27<br>mol_type = other DNA<br>organism = synthetic construct | |
| SEQUENCE: 279 | | |
| cacaattaac atctcaatca aggtaaa | | 27 |
| | | |
| SEQ ID NO: 280 | moltype = DNA   length = 50 | |
| FEATURE | Location/Qualifiers | |
| misc_feature | 1..50<br>note = Description of Artificial Sequence: Synthetic<br>oligonucleotide | |
| source | 1..50<br>mol_type = other DNA<br>organism = synthetic construct | |
| SEQUENCE: 280 | | |
| gcgagttttt atttcgttta tttcaattaa ggtaactaaa aaactcesttt | | 50 |
| | | |
| SEQ ID NO: 281 | moltype = DNA   length = 50 | |
| FEATURE | Location/Qualifiers | |
| misc_feature | 1..50<br>note = Description of Artificial Sequence: Synthetic<br>oligonucleotide | |
| source | 1..50<br>mol_type = other DNA<br>organism = synthetic construct | |
| SEQUENCE: 281 | | |
| aaaggagttt ttagttacc ttaattgaaa taaacgaaat aaaaactcgc | | 50 |
| | | |
| SEQ ID NO: 282 | moltype = DNA   length = 34 | |
| FEATURE | Location/Qualifiers | |
| misc_feature | 1..34<br>note = Description of Artificial Sequence: Synthetic<br>oligonucleotide | |
| source | 1..34<br>mol_type = other DNA<br>organism = synthetic construct | |
| SEQUENCE: 282 | | |
| ctggatcatc tggatcactt tcgtcaaaaa cctg | | 34 |
| | | |
| SEQ ID NO: 283 | moltype = DNA   length = 34 | |
| FEATURE | Location/Qualifiers | |

```
misc_feature           1..34
                       note = Description of Artificial Sequence: Synthetic
                          oligonucleotide
source                 1..34
                       mol_type = other DNA
                       organism = synthetic construct
SEQUENCE: 283
caggtttttg acgaaagtga tccagatgat ccag                              34

SEQ ID NO: 284         moltype = DNA  length = 57
FEATURE                Location/Qualifiers
misc_feature           1..57
                       note = Description of Artificial Sequence: Synthetic
                          oligonucleotide
source                 1..57
                       mol_type = other DNA
                       organism = synthetic construct
SEQUENCE: 284
ttcgggtgct gggttgttgt ctctggacag tgatccatgg gaaactactc agcacca     57

SEQ ID NO: 285         moltype = DNA  length = 57
FEATURE                Location/Qualifiers
misc_feature           1..57
                       note = Description of Artificial Sequence: Synthetic
                          oligonucleotide
source                 1..57
                       mol_type = other DNA
                       organism = synthetic construct
SEQUENCE: 285
tggtgctgag tagtttccca tggatcactg tccagagaca caacccagc acccgaa      57

SEQ ID NO: 286         moltype = DNA  length = 24
FEATURE                Location/Qualifiers
misc_feature           1..24
                       note = Description of Artificial Sequence: Synthetic
                          oligonucleotide
source                 1..24
                       mol_type = other DNA
                       organism = synthetic construct
SEQUENCE: 286
aaaagtgtgg gctgcaggat ctga                                         24

SEQ ID NO: 287         moltype = DNA  length = 22
FEATURE                Location/Qualifiers
misc_feature           1..22
                       note = Description of Artificial Sequence: Synthetic
                          oligonucleotide
source                 1..22
                       mol_type = other DNA
                       organism = synthetic construct
SEQUENCE: 287
ggagctggca gctgtcaatg cc                                           22

SEQ ID NO: 288         moltype = DNA  length = 21
FEATURE                Location/Qualifiers
misc_feature           1..21
                       note = Description of Artificial Sequence: Synthetic
                          oligonucleotide
source                 1..21
                       mol_type = other DNA
                       organism = synthetic construct
SEQUENCE: 288
agtcaatgcc gctctcgtgg a                                            21

SEQ ID NO: 289         moltype = DNA  length = 21
FEATURE                Location/Qualifiers
misc_feature           1..21
                       note = Description of Artificial Sequence: Synthetic
                          oligonucleotide
source                 1..21
                       mol_type = other DNA
                       organism = synthetic construct
SEQUENCE: 289
cagcgggctc agctgatagc a                                            21

SEQ ID NO: 290         moltype = DNA  length = 21
FEATURE                Location/Qualifiers
misc_feature           1..21
                       note = Description of Artificial Sequence: Synthetic
```

```
                    oligonucleotide
source              1..21
                    mol_type = other DNA
                    organism = synthetic construct
SEQUENCE: 290
cggatggcta accaagcggc c                                              21

SEQ ID NO: 291      moltype = DNA   length = 17
FEATURE             Location/Qualifiers
misc_feature        1..17
                    note = Description of Artificial Sequence: Synthetic primer
source              1..17
                    mol_type = other DNA
                    organism = synthetic construct
SEQUENCE: 291
cccggcttcc tttgtcc                                                   17

SEQ ID NO: 292      moltype = DNA   length = 17
FEATURE             Location/Qualifiers
misc_feature        1..17
                    note = Description of Artificial Sequence: Synthetic primer
source              1..17
                    mol_type = other DNA
                    organism = synthetic construct
SEQUENCE: 292
gaactccacg ccgttca                                                   17

SEQ ID NO: 293      moltype = DNA   length = 17
FEATURE             Location/Qualifiers
misc_feature        1..17
                    note = Description of Artificial Sequence: Synthetic primer
source              1..17
                    mol_type = other DNA
                    organism = synthetic construct
SEQUENCE: 293
cccggcttcc tttgtcc                                                   17

SEQ ID NO: 294      moltype = DNA   length = 22
FEATURE             Location/Qualifiers
misc_feature        1..22
                    note = Description of Artificial Sequence: Synthetic primer
source              1..22
                    mol_type = other DNA
                    organism = synthetic construct
SEQUENCE: 294
aaccacaact agaatgcagt ga                                             22

SEQ ID NO: 295      moltype = DNA   length = 17
FEATURE             Location/Qualifiers
misc_feature        1..17
                    note = Description of Artificial Sequence: Synthetic primer
source              1..17
                    mol_type = other DNA
                    organism = synthetic construct
SEQUENCE: 295
cccggcttcc tttgtcc                                                   17

SEQ ID NO: 296      moltype = DNA   length = 17
FEATURE             Location/Qualifiers
misc_feature        1..17
                    note = Description of Artificial Sequence: Synthetic primer
source              1..17
                    mol_type = other DNA
                    organism = synthetic construct
SEQUENCE: 296
gaactccacg ccgttca                                                   17

SEQ ID NO: 297      moltype = DNA   length = 17
FEATURE             Location/Qualifiers
misc_feature        1..17
                    note = Description of Artificial Sequence: Synthetic primer
source              1..17
                    mol_type = other DNA
                    organism = synthetic construct
SEQUENCE: 297
cccggcttcc tttgtcc                                                   17

SEQ ID NO: 298      moltype = DNA   length = 22
FEATURE             Location/Qualifiers
```

-continued

| | | |
|---|---|---|
| misc_feature | 1..22 | |
| | note = Description of Artificial Sequence: Synthetic primer | |
| source | 1..22 | |
| | mol_type = other DNA | |
| | organism = synthetic construct | |
| SEQUENCE: 298 | | |
| aaccacaact agaatgcagt ga | | 22 |
| | | |
| SEQ ID NO: 299 | moltype = DNA   length = 17 | |
| FEATURE | Location/Qualifiers | |
| misc_feature | 1..17 | |
| | note = Description of Artificial Sequence: Synthetic primer | |
| source | 1..17 | |
| | mol_type = other DNA | |
| | organism = synthetic construct | |
| SEQUENCE: 299 | | |
| cccggcttcc tttgtcc | | 17 |
| | | |
| SEQ ID NO: 300 | moltype = DNA   length = 17 | |
| FEATURE | Location/Qualifiers | |
| misc_feature | 1..17 | |
| | note = Description of Artificial Sequence: Synthetic primer | |
| source | 1..17 | |
| | mol_type = other DNA | |
| | organism = synthetic construct | |
| SEQUENCE: 300 | | |
| gaactccacg ccgttca | | 17 |
| | | |
| SEQ ID NO: 301 | moltype = DNA   length = 21 | |
| FEATURE | Location/Qualifiers | |
| misc_feature | 1..21 | |
| | note = Description of Artificial Sequence: Synthetic primer | |
| source | 1..21 | |
| | mol_type = other DNA | |
| | organism = synthetic construct | |
| SEQUENCE: 301 | | |
| tccttatcac ggtcccgctc g | | 21 |
| | | |
| SEQ ID NO: 302 | moltype = DNA   length = 17 | |
| FEATURE | Location/Qualifiers | |
| misc_feature | 1..17 | |
| | note = Description of Artificial Sequence: Synthetic primer | |
| source | 1..17 | |
| | mol_type = other DNA | |
| | organism = synthetic construct | |
| SEQUENCE: 302 | | |
| gaactccacg ccgttca | | 17 |
| | | |
| SEQ ID NO: 303 | moltype = DNA   length = 17 | |
| FEATURE | Location/Qualifiers | |
| misc_feature | 1..17 | |
| | note = Description of Artificial Sequence: Synthetic primer | |
| source | 1..17 | |
| | mol_type = other DNA | |
| | organism = synthetic construct | |
| SEQUENCE: 303 | | |
| cgtcgacaac ggtagtg | | 17 |
| | | |
| SEQ ID NO: 304 | moltype = DNA   length = 17 | |
| FEATURE | Location/Qualifiers | |
| misc_feature | 1..17 | |
| | note = Description of Artificial Sequence: Synthetic primer | |
| source | 1..17 | |
| | mol_type = other DNA | |
| | organism = synthetic construct | |
| SEQUENCE: 304 | | |
| gaactccacg ccgttca | | 17 |
| | | |
| SEQ ID NO: 305 | moltype = DNA   length = 18 | |
| FEATURE | Location/Qualifiers | |
| misc_feature | 1..18 | |
| | note = Description of Artificial Sequence: Synthetic primer | |
| source | 1..18 | |
| | mol_type = other DNA | |
| | organism = synthetic construct | |
| SEQUENCE: 305 | | |
| tcgcgtgatt ctcggaac | | 18 |
| | | |
| SEQ ID NO: 306 | moltype = DNA   length = 17 | |

-continued

```
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 306
gaactccacg ccgttca                                                         17

SEQ ID NO: 307          moltype = DNA  length = 20
FEATURE                 Location/Qualifiers
misc_feature            1..20
                        note = Description of Artificial Sequence: Synthetic primer
source                  1..20
                        mol_type = other DNA
                        organism = synthetic construct
SEQUENCE: 307
gggcggtaag tggttagttt                                                      20

SEQ ID NO: 308          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 308
gaactccacg ccgttca                                                         17

SEQ ID NO: 309          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 309
aagaggcgga gccagta                                                         17

SEQ ID NO: 310          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 310
gaactccacg ccgttca                                                         17

SEQ ID NO: 311          moltype = DNA  length = 19
FEATURE                 Location/Qualifiers
misc_feature            1..19
                        note = Description of Artificial Sequence: Synthetic primer
source                  1..19
                        mol_type = other DNA
                        organism = synthetic construct
SEQUENCE: 311
ctcccttctc ccggtgccc                                                       19

SEQ ID NO: 312          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 312
gaactccacg ccgttca                                                         17

SEQ ID NO: 313          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 313
cccggcttcc tttgtcc                                                         17
```

```
SEQ ID NO: 314           moltype = DNA   length = 17
FEATURE                  Location/Qualifiers
misc_feature             1..17
                         note = Description of Artificial Sequence: Synthetic primer
source                   1..17
                         mol_type = other DNA
                         organism = synthetic construct
SEQUENCE: 314
gaactccacg ccgttca                                                         17

SEQ ID NO: 315           moltype = DNA   length = 20
FEATURE                  Location/Qualifiers
misc_feature             1..20
                         note = Description of Artificial Sequence: Synthetic primer
source                   1..20
                         mol_type = other DNA
                         organism = synthetic construct
SEQUENCE: 315
gggcggtaag tggttagttt                                                      20

SEQ ID NO: 316           moltype = DNA   length = 17
FEATURE                  Location/Qualifiers
misc_feature             1..17
                         note = Description of Artificial Sequence: Synthetic primer
source                   1..17
                         mol_type = other DNA
                         organism = synthetic construct
SEQUENCE: 316
gaactccacg ccgttca                                                         17

SEQ ID NO: 317           moltype = DNA   length = 17
FEATURE                  Location/Qualifiers
misc_feature             1..17
                         note = Description of Artificial Sequence: Synthetic primer
source                   1..17
                         mol_type = other DNA
                         organism = synthetic construct
SEQUENCE: 317
cgtcgacaac ggtagtg                                                         17

SEQ ID NO: 318           moltype = DNA   length = 17
FEATURE                  Location/Qualifiers
misc_feature             1..17
                         note = Description of Artificial Sequence: Synthetic primer
source                   1..17
                         mol_type = other DNA
                         organism = synthetic construct
SEQUENCE: 318
gaactccacg ccgttca                                                         17

SEQ ID NO: 319           moltype = DNA   length = 17
FEATURE                  Location/Qualifiers
misc_feature             1..17
                         note = Description of Artificial Sequence: Synthetic primer
source                   1..17
                         mol_type = other DNA
                         organism = synthetic construct
SEQUENCE: 319
aagaggcgga gccagta                                                         17

SEQ ID NO: 320           moltype = DNA   length = 17
FEATURE                  Location/Qualifiers
misc_feature             1..17
                         note = Description of Artificial Sequence: Synthetic primer
source                   1..17
                         mol_type = other DNA
                         organism = synthetic construct
SEQUENCE: 320
gaactccacg ccgttca                                                         17

SEQ ID NO: 321           moltype = DNA   length = 19
FEATURE                  Location/Qualifiers
misc_feature             1..19
                         note = Description of Artificial Sequence: Synthetic primer
source                   1..19
                         mol_type = other DNA
                         organism = synthetic construct
SEQUENCE: 321
ctcccttctc ccggtgccc                                                       19
```

```
SEQ ID NO: 322           moltype = DNA  length = 17
FEATURE                  Location/Qualifiers
misc_feature             1..17
                         note = Description of Artificial Sequence: Synthetic primer
source                   1..17
                         mol_type = other DNA
                         organism = synthetic construct
SEQUENCE: 322
gaactccacg ccgttca                                                        17

SEQ ID NO: 323           moltype = DNA  length = 21
FEATURE                  Location/Qualifiers
misc_feature             1..21
                         note = Description of Artificial Sequence: Synthetic primer
source                   1..21
                         mol_type = other DNA
                         organism = synthetic construct
SEQUENCE: 323
tccttatcac ggtcccgctc g                                                   21

SEQ ID NO: 324           moltype = DNA  length = 17
FEATURE                  Location/Qualifiers
misc_feature             1..17
                         note = Description of Artificial Sequence: Synthetic primer
source                   1..17
                         mol_type = other DNA
                         organism = synthetic construct
SEQUENCE: 324
gaactccacg ccgttca                                                        17

SEQ ID NO: 325           moltype = DNA  length = 17
FEATURE                  Location/Qualifiers
misc_feature             1..17
                         note = Description of Artificial Sequence: Synthetic primer
source                   1..17
                         mol_type = other DNA
                         organism = synthetic construct
SEQUENCE: 325
cccggcttcc tttgtcc                                                        17

SEQ ID NO: 326           moltype = DNA  length = 18
FEATURE                  Location/Qualifiers
misc_feature             1..18
                         note = Description of Artificial Sequence: Synthetic primer
source                   1..18
                         mol_type = other DNA
                         organism = synthetic construct
SEQUENCE: 326
ggcctgccag caggagga                                                       18

SEQ ID NO: 327           moltype = DNA  length = 17
FEATURE                  Location/Qualifiers
misc_feature             1..17
                         note = Description of Artificial Sequence: Synthetic primer
source                   1..17
                         mol_type = other DNA
                         organism = synthetic construct
SEQUENCE: 327
cccggcttcc tttgtcc                                                        17

SEQ ID NO: 328           moltype = DNA  length = 25
FEATURE                  Location/Qualifiers
misc_feature             1..25
                         note = Description of Artificial Sequence: Synthetic primer
source                   1..25
                         mol_type = other DNA
                         organism = synthetic construct
SEQUENCE: 328
ggtgtgcagt cacattggta aagcc                                               25

SEQ ID NO: 329           moltype = DNA  length = 17
FEATURE                  Location/Qualifiers
misc_feature             1..17
                         note = Description of Artificial Sequence: Synthetic primer
source                   1..17
                         mol_type = other DNA
                         organism = synthetic construct
SEQUENCE: 329
```

-continued

```
cccggcttcc tttgtcc                                                        17

SEQ ID NO: 330          moltype = DNA  length = 22
FEATURE                 Location/Qualifiers
misc_feature            1..22
                        note = Description of Artificial Sequence: Synthetic primer
source                  1..22
                        mol_type = other DNA
                        organism = synthetic construct
SEQUENCE: 330
gatgggtcta gtccagctaa ag                                                  22

SEQ ID NO: 331          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 331
cccggcttcc tttgtcc                                                        17

SEQ ID NO: 332          moltype = DNA  length = 18
FEATURE                 Location/Qualifiers
misc_feature            1..18
                        note = Description of Artificial Sequence: Synthetic primer
source                  1..18
                        mol_type = other DNA
                        organism = synthetic construct
SEQUENCE: 332
gagagacaag gctgcaca                                                       18

SEQ ID NO: 333          moltype = DNA  length = 26
FEATURE                 Location/Qualifiers
misc_feature            1..26
                        note = Description of Artificial Sequence: Synthetic primer
source                  1..26
                        mol_type = other DNA
                        organism = synthetic construct
SEQUENCE: 333
ccaggtgaga gtcagggtag tgttca                                              26

SEQ ID NO: 334          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 334
gaactccacg ccgttca                                                        17

SEQ ID NO: 335          moltype = DNA  length = 23
FEATURE                 Location/Qualifiers
misc_feature            1..23
                        note = Description of Artificial Sequence: Synthetic primer
source                  1..23
                        mol_type = other DNA
                        organism = synthetic construct
SEQUENCE: 335
agggaccttt gcctgtgtga gtc                                                 23

SEQ ID NO: 336          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 336
gaactccacg ccgttca                                                        17

SEQ ID NO: 337          moltype = DNA  length = 21
FEATURE                 Location/Qualifiers
misc_feature            1..21
                        note = Description of Artificial Sequence: Synthetic primer
source                  1..21
                        mol_type = other DNA
                        organism = synthetic construct
```

-continued

```
SEQUENCE: 337
tcagctctgt gctgaggcga a                                                  21

SEQ ID NO: 338         moltype = DNA   length = 17
FEATURE                Location/Qualifiers
misc_feature           1..17
                       note = Description of Artificial Sequence: Synthetic primer
source                 1..17
                       mol_type = other DNA
                       organism = synthetic construct
SEQUENCE: 338
gaactccacg ccgttca                                                       17

SEQ ID NO: 339         moltype = DNA   length = 32
FEATURE                Location/Qualifiers
misc_feature           1..32
                       note = Description of Artificial Sequence: Synthetic primer
source                 1..32
                       mol_type = other DNA
                       organism = synthetic construct
SEQUENCE: 339
aagccatctc ccagaatatc tgcttagaaa tg                                      32

SEQ ID NO: 340         moltype = DNA   length = 17
FEATURE                Location/Qualifiers
misc_feature           1..17
                       note = Description of Artificial Sequence: Synthetic primer
source                 1..17
                       mol_type = other DNA
                       organism = synthetic construct
SEQUENCE: 340
gaactccacg ccgttca                                                       17

SEQ ID NO: 341         moltype = DNA   length = 25
FEATURE                Location/Qualifiers
misc_feature           1..25
                       note = Description of Artificial Sequence: Synthetic primer
source                 1..25
                       mol_type = other DNA
                       organism = synthetic construct
SEQUENCE: 341
gagaggagca acagtgagca tgatg                                              25

SEQ ID NO: 342         moltype = DNA   length = 17
FEATURE                Location/Qualifiers
misc_feature           1..17
                       note = Description of Artificial Sequence: Synthetic primer
source                 1..17
                       mol_type = other DNA
                       organism = synthetic construct
SEQUENCE: 342
gaactccacg ccgttca                                                       17

SEQ ID NO: 343         moltype = DNA   length = 32
FEATURE                Location/Qualifiers
misc_feature           1..32
                       note = Description of Artificial Sequence: Synthetic primer
source                 1..32
                       mol_type = other DNA
                       organism = synthetic construct
SEQUENCE: 343
aagccatctc ccagaatatc tgcttagaaa tg                                      32

SEQ ID NO: 344         moltype = DNA   length = 17
FEATURE                Location/Qualifiers
misc_feature           1..17
                       note = Description of Artificial Sequence: Synthetic primer
source                 1..17
                       mol_type = other DNA
                       organism = synthetic construct
SEQUENCE: 344
gaactccacg ccgttca                                                       17

SEQ ID NO: 345         moltype = DNA   length = 25
FEATURE                Location/Qualifiers
misc_feature           1..25
                       note = Description of Artificial Sequence: Synthetic primer
source                 1..25
                       mol_type = other DNA
```

```
                        organism = synthetic construct
SEQUENCE: 345
gagaggagca acagtgagca tgatg                                              25

SEQ ID NO: 346          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 346
gaactccacg ccgttca                                                       17

SEQ ID NO: 347          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 347
cccggcttcc tttgtcc                                                       17

SEQ ID NO: 348          moltype = DNA  length = 22
FEATURE                 Location/Qualifiers
misc_feature            1..22
                        note = Description of Artificial Sequence: Synthetic primer
source                  1..22
                        mol_type = other DNA
                        organism = synthetic construct
SEQUENCE: 348
ggctatgaac taatgacccc gt                                                 22

SEQ ID NO: 349          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 349
cccggcttcc tttgtcc                                                       17

SEQ ID NO: 350          moltype = DNA  length = 18
FEATURE                 Location/Qualifiers
misc_feature            1..18
                        note = Description of Artificial Sequence: Synthetic primer
source                  1..18
                        mol_type = other DNA
                        organism = synthetic construct
SEQUENCE: 350
ggcctgccag caggagga                                                      18

SEQ ID NO: 351          moltype = DNA  length = 17
FEATURE                 Location/Qualifiers
misc_feature            1..17
                        note = Description of Artificial Sequence: Synthetic primer
source                  1..17
                        mol_type = other DNA
                        organism = synthetic construct
SEQUENCE: 351
cccggcttcc tttgtcc                                                       17

SEQ ID NO: 352          moltype = DNA  length = 25
FEATURE                 Location/Qualifiers
misc_feature            1..25
                        note = Description of Artificial Sequence: Synthetic primer
source                  1..25
                        mol_type = other DNA
                        organism = synthetic construct
SEQUENCE: 352
ggtgtgcagt cacattggta aagcc                                              25

SEQ ID NO: 353          moltype = DNA  length = 52
FEATURE                 Location/Qualifiers
misc_feature            1..52
                        note = Description of Artificial Sequence: Synthetic
                        oligonucleotide
```

```
                    source          1..52
                                    mol_type = other DNA
                                    organism = synthetic construct
SEQUENCE: 353
acactctttc cctacacgac gctcttccga tctccgacct cggctcacag cg           52

SEQ ID NO: 354          moltype = DNA   length = 53
FEATURE                 Location/Qualifiers
misc_feature            1..53
                        note = Description of Artificial Sequence: Synthetic
                           oligonucleotide
source                  1..53
                        mol_type = other DNA
                        organism = synthetic construct
SEQUENCE: 354
acactctttc cctacacgac gctcttccga tctaccgacc tcggctcaca gcg          53

SEQ ID NO: 355          moltype = DNA   length = 54
FEATURE                 Location/Qualifiers
misc_feature            1..54
                        note = Description of Artificial Sequence: Synthetic
                           oligonucleotide
source                  1..54
                        mol_type = other DNA
                        organism = synthetic construct
SEQUENCE: 355
acactctttc cctacacgac gctcttccga tctgaccgac ctcggctcac agcg         54

SEQ ID NO: 356          moltype = DNA   length = 55
FEATURE                 Location/Qualifiers
misc_feature            1..55
                        note = Description of Artificial Sequence: Synthetic
                           oligonucleotide
source                  1..55
                        mol_type = other DNA
                        organism = synthetic construct
SEQUENCE: 356
acactctttc cctacacgac gctcttccga tcttgaccga cctcggctca cagcg        55

SEQ ID NO: 357          moltype = DNA   length = 56
FEATURE                 Location/Qualifiers
misc_feature            1..56
                        note = Description of Artificial Sequence: Synthetic
                           oligonucleotide
source                  1..56
                        mol_type = other DNA
                        organism = synthetic construct
SEQUENCE: 357
acactctttc cctacacgac gctcttccga tctctgaccg acctcggctc acagcg       56

SEQ ID NO: 358          moltype = DNA   length = 57
FEATURE                 Location/Qualifiers
misc_feature            1..57
                        note = Description of Artificial Sequence: Synthetic
                           oligonucleotide
source                  1..57
                        mol_type = other DNA
                        organism = synthetic construct
SEQUENCE: 358
acactctttc cctacacgac gctcttccga tctactgacc gacctcggct cacagcg      57

SEQ ID NO: 359          moltype = DNA   length = 58
FEATURE                 Location/Qualifiers
misc_feature            1..58
                        note = Description of Artificial Sequence: Synthetic
                           oligonucleotide
source                  1..58
                        mol_type = other DNA
                        organism = synthetic construct
SEQUENCE: 359
acactctttc cctacacgac gctcttccga tcttactgac cgacctcggc tcacagcg     58

SEQ ID NO: 360          moltype = DNA   length = 59
FEATURE                 Location/Qualifiers
misc_feature            1..59
                        note = Description of Artificial Sequence: Synthetic
                           oligonucleotide
source                  1..59
                        mol_type = other DNA
```

```
                      organism = synthetic construct
SEQUENCE: 360
acactctttc cctacacgac gctcttccga tctgtactga ccgacctcgg ctcacagcg        59

SEQ ID NO: 361          moltype = DNA  length = 51
FEATURE                 Location/Qualifiers
misc_feature            1..51
                        note = Description of Artificial Sequence: Synthetic
                        oligonucleotide
source                  1..51
                        mol_type = other DNA
                        organism = synthetic construct
SEQUENCE: 361
gtgactggag ttcagacgtg tgctcttccg atctccaccc agccagctcc c                51

SEQ ID NO: 362          moltype = DNA  length = 51
FEATURE                 Location/Qualifiers
misc_feature            1..51
                        note = Description of Artificial Sequence: Synthetic
                        oligonucleotide
source                  1..51
                        mol_type = other DNA
                        organism = synthetic construct
SEQUENCE: 362
acactctttc cctacacgac gctcttccga tctccggtgg cgcattgcca c                51

SEQ ID NO: 363          moltype = DNA  length = 52
FEATURE                 Location/Qualifiers
misc_feature            1..52
                        note = Description of Artificial Sequence: Synthetic
                        oligonucleotide
source                  1..52
                        mol_type = other DNA
                        organism = synthetic construct
SEQUENCE: 363
acactctttc cctacacgac gctcttccga tctaccggtg gcgcattgcc ac               52

SEQ ID NO: 364          moltype = DNA  length = 53
FEATURE                 Location/Qualifiers
misc_feature            1..53
                        note = Description of Artificial Sequence: Synthetic
                        oligonucleotide
source                  1..53
                        mol_type = other DNA
                        organism = synthetic construct
SEQUENCE: 364
acactctttc cctacacgac gctcttccga tctgaccggt ggcgcattgc cac              53

SEQ ID NO: 365          moltype = DNA  length = 54
FEATURE                 Location/Qualifiers
misc_feature            1..54
                        note = Description of Artificial Sequence: Synthetic
                        oligonucleotide
source                  1..54
                        mol_type = other DNA
                        organism = synthetic construct
SEQUENCE: 365
acactctttc cctacacgac gctcttccga tcttgaccgg tggcgcattg ccac             54

SEQ ID NO: 366          moltype = DNA  length = 55
FEATURE                 Location/Qualifiers
misc_feature            1..55
                        note = Description of Artificial Sequence: Synthetic
                        oligonucleotide
source                  1..55
                        mol_type = other DNA
                        organism = synthetic construct
SEQUENCE: 366
acactctttc cctacacgac gctcttccga tctctgaccg gtggcgcatt gccac            55

SEQ ID NO: 367          moltype = DNA  length = 56
FEATURE                 Location/Qualifiers
misc_feature            1..56
                        note = Description of Artificial Sequence: Synthetic
                        oligonucleotide
source                  1..56
                        mol_type = other DNA
                        organism = synthetic construct
SEQUENCE: 367
```

```
acactctttc cctacacgac gctcttccga tctactgacc ggtggcgcat tgccac      56

SEQ ID NO: 368         moltype = DNA  length = 57
FEATURE                Location/Qualifiers
misc_feature           1..57
                       note = Description of Artificial Sequence: Synthetic
                           oligonucleotide
source                 1..57
                       mol_type = other DNA
                       organism = synthetic construct
SEQUENCE: 368
acactctttc cctacacgac gctcttccga tcttactgac cggtggcgca ttgccac     57

SEQ ID NO: 369         moltype = DNA  length = 58
FEATURE                Location/Qualifiers
misc_feature           1..58
                       note = Description of Artificial Sequence: Synthetic
                           oligonucleotide
source                 1..58
                       mol_type = other DNA
                       organism = synthetic construct
SEQUENCE: 369
acactctttc cctacacgac gctcttccga tctgtactga ccggtggcgc attgccac    58

SEQ ID NO: 370         moltype = DNA  length = 54
FEATURE                Location/Qualifiers
misc_feature           1..54
                       note = Description of Artificial Sequence: Synthetic
                           oligonucleotide
source                 1..54
                       mol_type = other DNA
                       organism = synthetic construct
SEQUENCE: 370
gtgactggag ttcagacgtg tgctcttccg atctcagagt ccagcttggg ccca        54

SEQ ID NO: 371         moltype = DNA  length = 20
FEATURE                Location/Qualifiers
misc_feature           1..20
                       note = Description of Artificial Sequence: Synthetic
                           oligonucleotide
source                 1..20
                       mol_type = other DNA
                       organism = synthetic construct
SEQUENCE: 371
gatattttcc cagctcacca                                              20

SEQ ID NO: 372         moltype = DNA  length = 20
FEATURE                Location/Qualifiers
misc_feature           1..20
                       note = Description of Artificial Sequence: Synthetic
                           oligonucleotide
source                 1..20
                       mol_type = other DNA
                       organism = synthetic construct
SEQUENCE: 372
tctattctcc cagctcccca                                              20

SEQ ID NO: 373         moltype = DNA  length = 40
FEATURE                Location/Qualifiers
misc_feature           1..40
                       note = Description of Artificial Sequence: Synthetic
                           oligonucleotide
source                 1..40
                       mol_type = other DNA
                       organism = synthetic construct
SEQUENCE: 373
agcggcttct gtctctgtga gtgagctggc ggtctccgtc                        40

SEQ ID NO: 374         moltype = DNA  length = 43
FEATURE                Location/Qualifiers
misc_feature           1..43
                       note = Description of Artificial Sequence: Synthetic
                           oligonucleotide
source                 1..43
                       mol_type = other DNA
                       organism = synthetic construct
SEQUENCE: 374
gactagccca cgctccggtt ctgagccgcg acggcggtct ccg                    43
```

```
SEQ ID NO: 375              moltype = DNA  length = 41
FEATURE                     Location/Qualifiers
misc_feature                1..41
                            note = Description of Artificial Sequence: Synthetic
                            oligonucleotide
source                      1..41
                            mol_type = other DNA
                            organism = synthetic construct
SEQUENCE: 375
cccagggtcc catgcgctcc ccggccctga cggcggtctc c                            41

SEQ ID NO: 376              moltype = AA  length = 2560
FEATURE                     Location/Qualifiers
REGION                      1..2560
                            note = Description of Artificial Sequence: Synthetic
                            polypeptide
source                      1..2560
                            mol_type = protein
                            organism = synthetic construct
SEQUENCE: 376
MKRTADGSEF ESPKKKRKVD KKYSIGLDIG TNSVGWAVIT DEYKVPSKKF KVLGNTDRHS  60
IKKNLIGALL FDSGETAEAT RLKRTARRRY TRRKNRICYL QEIFSNEMAK VDDSFFHRLE  120
ESFLVEEDKK HERHPIFGNI VDEVAYHEKY PTIYHLRKKL VDSTKADLR LIYLALAHMI  180
KFRGHFLIEG DLNPDNSDVD KLFIQLVQTY NQLFEENPIN ASGVDAKAIL SARLSKSRRL  240
ENLIAQLPGE KKNGLFGNLI ALSLGLTPNF KSNFDLAEDA KLQLSKDTYD DDLDNLLAQI  300
GDQYADLFLA AKNLSDAILL SDILRVNTEI TKAPLSASMI KRYDEHHQDL TLLKALVRQQ  360
LPEKYKEIFF DQSKNGYAGY IDGGASQEEF YKFIKPILEK MDGTEELLVK LNREDLLRKQ  420
RTFDNGSIPH QIHLGELHAI LRRQEDFYPF LKDNREKIEK ILTFRIPYYV GPLARGNSRF  480
AWMTRKSEET ITPWNFEEVV DKGASAQSFI ERMTNFDKNL PNEKVLPKHS LLYEYFTVYN  540
ELTKVKYVTE GMRKPAFLSG EQKKAIVDLL FKTNRKVTVK QLKEDYFKKI ECFDSVEISG  600
VEDRFNASLG TYHDLLKIIK DKDFLDNEEN EDILEDIVLT LTLFEDREMI EERLKTYAHL  660
FDDKVMKQLK RRRYTGWGRL SRKLINGIRD KQSGKTILDF LKSDGFANRN FMQLIHDDSL  720
TFKEDIQKAQ VSGQGDSLHE HIANLAGSPA IKKGILQTVK VVDELVKVMG RHKPENIVIE  780
MARENQTQK GQKNSRERMK RIEEGIKELG SQILKEHPVE NTQLQNEKLY LYYLQNGRDM  840
YVDQELDINR LSDYDVDAIV PQSFLKDDSI DNKVLTRSDK NRGKSDNVPS EEVVKKMKNY  900
WRQLLNAKLI TQRKFDNLTK AERGGLSELD KAGFIKRQLV ETRQITKHVA QILDSRMNTK  960
YDENDKLIRE VKVITLKSKL VSDFRKDFQF YKVREINNYH HAHDAYLNAV VGTALIKKYP  1020
KLESEFVYGD YKVYDVRKMI AKSEQEIGKA TAKYFFYSNI MNFFKTEITL ANGEIRKRPL  1080
IETNGETGEI VWDKGRDFAT VRKVLSMPQV NIVKKTEVQT GGFSKESILP KRNSDKLIAR  1140
KKDWDPKKYG GFDSPTVAYS VLVVAKVEKG KSKKLKSVKE LLGITIMERS SFEKNPIDFL  1200
EAKGYKEVKK DLIIKLPKYS LFELENGRKR MLASAGELQK GNELALPSKY VNFLYLASHY  1260
EKLKGSPEDN EQKQLFVEQH KHYLDEIIEQ ISEFSKRVIL ADANLDKVLS AYNKHRDKPI  1320
REQAENIIHL FTLTNLGAPA AFKYFDTTID RKRYTSTKEV LDATLIHQSI TGLYETRIDL  1380
SQLGGDSGGS SGGSSGSETP GTSESATPES SGSETPGTSE SATPESSGSE TPGTSESATP  1440
ESSGGSSGGS STLNIEDEYR LHETSKEPDV SLGSTWLSDF PQAWAETGGM GLAVRQAPLI  1500
IPLKATSTPV SIKQYPMSQE ARLGIKPHIQ RLLDQGILVP CQSPWNTPLL PVKKPGTNDY  1560
RPVQDLREVN KRVEDIHPTV PNPYNLLSGP PPSHQWYTVL DLKDAFFCLR LHPTSQPLFA  1620
FEWRDPEMGI SGQLTWTRLP QGFKNSPTLF NEALHRDLAD FRIQHPDLIL LQYVDDLLLA  1680
ATSELDCQQG TRALLQTLGN LGYRASAKKA QICQKQVKYL GYLLKEGQRW LTEARKETVM  1740
GQPTPKTPRQ LREFLGKAGF CRLFIPGFAE MAAPLYPLTK PGTLFNWGPD QQKAYQEIKQ  1800
ALLTAPALGL PDLTKPFELF VDEKQGYAKG VLTQKLGPWR RPVAYLSKKL DPVAAGWPPC  1860
LRMVAAIAVL TKDAGKLTMG QPLVILAPHA VEALVKQPPD RWLSNARMTH YQALLLDTDR  1920
VQFGPVVALN PATLLPLPEE GLQHNCLDGT GGGGVTVKFK YKGEELEVDI SKIKKVWRVG  1980
KMISFTYDDN GKTGRGAVSE KDAPKELLQM LEKSGKKSGG SKRTADGSEF EPKKKRKVGG  2040
GGSPKKKRKV YPYDVPDYAG SRALVVIRLS RVTDATTSPE RQLESCQQLC AQRGWDVVGV  2100
AEDLDVSGAV DPFDRKRRPN LARWLAFEEQ PFDVIVAYRV DRLTRSIRHL QQLVHWAEDH  2160
KKLVVSATEA HFDTTTPFAA VVIALMGTVA QMELEAIKER NRSAAHFNIR AGKYRGSLPP  2220
WGYLPTRVDG EWRLVPDPVQ RERILEVYHR VVDNHEPLHL VAHDLNRRGV LSPKDYFAQL  2280
QGREPQGREW SATALKRSMI SEAMLGYATL NGKTVRDDDG APLVRAEPIL TREQLEALRA  2340
ELVKTSRAKP AVSTPSLLLR VLFCAVCGEP AYKFAGGGRK HPRYRCRSMG FPKHCGNGTV  2400
AMAEWDAFCE EQVLDLLGDA ERLEKVWVAG SDSAVELAEV NAELVDLTSL IGSPAYRAGS  2460
PQREALDARI AALAARQEEL EGLEARPSGW EWRETGQRFG DWWREQDTAA KNTWLRSMNV  2520
RLTFDVRGGL TRTIDFGDLQ EYEQHLRLGS VVERLHTGMS                       2560

SEQ ID NO: 377              moltype = DNA  length = 7680
FEATURE                     Location/Qualifiers
misc_feature                1..7680
                            note = Description of Artificial Sequence: Synthetic
                            polynucleotide
source                      1..7680
                            mol_type = other DNA
                            organism = synthetic construct
SEQUENCE: 377
atgaaacgga cagccgacgg aagcgagttc gagtcaccaa agaagaagcg gaaagtcgac  60
aagaagtaca gcatcggcct ggacatcggc accaactctg tgggctgggc cgtgatcacc  120
gacgagtaca aggtgcccag caagaaattc aaggtgctgg gcaacaccga ccggcacagc  180
atcaagaaga acctgatcgg agccctgctg ttcgacagcg gcgaaacagc cgaggccacc  240
cggctgaaga gaaccgccag aagaagatac accagacgga gaaccggat ctgctatctg  300
caagagatct tcagcaacga gatggccaag gtggacgaca gcttcttcca cagactggaa  360
```

```
gagtccttcc tggtggaaga ggataagaag cacgagcggc accccatctt cggcaacatc    420
gtggacgagg tggcctacca cgagaagtac cccaccatct accacctgag aaagaaactg    480
gtggacagca ccgacaaggc cgacctgcgg ctgatctatc tggccctggc ccacatgatc    540
aagttccggg gccacttcct gatcgagggc gacctgaacc ccgacaacag cgacgtggac    600
aagtcgttca tccagctggt gcagacctac aaccagctgt tcgaggaaaa ccccatcaac    660
gccagcggcg tggacgccaa ggccatcctg tctgccagac tgagcaagag cagacgcctg    720
gaaaatctga tcgcccagct gcccggcgag aagaagaatg gcctgttcgg aaacctgatt    780
gccctgagcc tgggcctgac ccccaacttc aagagcaact cgacctggcc cgaggatgcc    840
aaactgcagc tgagcaagga cacctacgac gacgacctgg acaacctgct ggcccagatc    900
ggcgaccagt acgccgacct gtttctggcc gccaagaacc tgtccgacgc catcctgctg    960
agcgacatcc tgagagtgaa caccgagatc accaaggccc ccctgagcgc ctctatgatc   1020
aagagatacg acgagcacca ccaggacctg accctgctga agctctcgt gcggcagcag   1080
ctgcctgaga agtacaaaga gattttcttc gaccagagca agaacggcta cgccggctac   1140
attgacggcg gagccagcca ggaagagttc tacaagttca tcaagcccat cctgaaaag   1200
atggacggca ccgaggaact gctcgtgaag ctgaacagag aggacctgct gcggaagcag   1260
cggaccttcg acaacggcag catcccccac cagatccacc tgggagagct gcacgccatt   1320
ctgcggcggc aggaagattt ttacccattc tgaaggaca accgggaaaa gatcgagaag   1380
atcctgacct tccgcatccc tactacgtg ggccctctgg ccaggggaaa cagcagattc   1440
gcctggatga ccagaaagag cgaggaaacc atcacccct ggaacttcga ggaagtggtg   1500
gacaagggcg cttccgccca gagcttcatc gagcggatga ccaacttcga taagaacctg   1560
cccaacgaga aggtgctgcc caagcacagc ctgctgtacg agtacttcac cgtgtataac   1620
gagctgacca aagtgaaata cgtgaccgag ggaatgagaa agcccgcctt cctgagcggc   1680
gagcagaaaa aggccatcgt ggacctgctg ttcaagacca accggaaagt gaccgtgaag   1740
cagctgaaag aggactactt caagaaaatc gagtgcttcg actccgtgga aatctccggc   1800
gtggaagatc ggttcaacgc ctccctgggc acataccacg atctgctgaa aattatcaag   1860
gacaaggact tcctggacaa tgaggaaaac gaggacattc tggaagatat cgtgctgacc   1920
ctgacactgt ttgaggacag agagatgatc gaggaacggc tgaaaaccta tgcccacctg   1980
ttcgacgaca aagtgatgaa gcagctgaag cggcggagat acaccggctg gggcaggctg   2040
agccggaagc tgatcaacgg catccgggac aagcagtccg gcaagacaat cctggatttc   2100
ctgaagtccg acggcttcgc caacagaaac ttcatgcagc tgatccacga cgacagcctg   2160
acctttaaag aggacatcca gaaagcccag gtgtccggcc agggcgatag cctgcacgag   2220
cacattgcca atctgccggg cagccccgcc attaagaagg gcatcctgca gacagtgaag   2280
gtggtggacg agctcgtgaa agtgatgggc cggcacaagc ccgagaacat cgtgatcgaa   2340
atggccagag agaaccagac cacccagaag ggacagaaga acagccgcga gagaatgaag   2400
cggatcgaag agggcatcaa agagctgggg agccagatcc tgaaagaaca ccccgtggaa   2460
aacacccagc tgcagaacga gaagctgtac ctgtactacc tgcagaatgg gcgggatatg   2520
tacgtggacc aggaactgga catcaaccgg ctgtccgact acgatgtgga cgctatcgtg   2580
cctcagagct ttctgaagga cgactccatc gacaacaagg tgctgaccag aagcgacaag   2640
aaccggggca agagcgacaa cgtgccctcc aagaggtcg tgaagaagat gaagaactac   2700
tggcggcagc tgctgaacgc caagctgatt acccagagaa agttcgacaa tctgaccaag   2760
gccgagagag cggcctgag cgaactggat aaggccggct tcatcaagag acagctggtg   2820
gaaacccggc agatcacaaa gcacgtgca cagatcctgg actcccggat gaacactaag   2880
tacgacgaga atgacaagct gatccggaag gtgaaagtga tcacccctga gtccaagctg   2940
gtgtccgatt tccggaagga tttccagttt tacaaagtgc gcgagatcaa caactaccac   3000
cacgcccacg acgcctacct gaacgccgtc gtgggaaccg ccctgatcaa aaagtaccct   3060
aagctggaaa gcgagttcgt gtacggcgac tacaaggtgt acgacgtgcg gaagatgatc   3120
gccaagagcg agcaggaaat cggcaaggct accgccagac acttcttcta cagcaacatc   3180
atgaacttt tcaagaccga gattaccctg gccaacggcg agatccgaa gcggcctctg   3240
atcgagacaa acggcgaaac cggggagatc gtgtgggata agggccggga ttttgccacc   3300
gtgcggaaag tgctgagcat gccccaagtg aatatcgtga aaagaccga ggtgcagaca   3360
ggcggcttca gcaaagagtc tatcctgccc aagaggaaca gcgataagct gatcgccaga   3420
aagaaggact gggaccctaa gaagtacggc ggcttcgaca gccccaccgt ggcctattct   3480
gtgctggtgg tggccaaagt ggaaaagggc aagtccaaga aactgaagag tgtgaaagag   3540
ctgctgggga tcaccatcat ggaaagaagc agcttcgaga gaatcccat cgactttctg   3600
gaagccaagg gctacaaaga agtgaaaaag gacctgatca tcaagctgcc taagtactcc   3660
ctgttcgagc tggaaaacgg ccggaagaga atgctggcct ctgccggcga actgcagaag   3720
ggaaacgaac tggcccctgcc ctccaaatat gtgaacttcc tgtacctggc cagccactat   3780
gagaagctga agggctcccc cgaggataat gagcagaaac agctgtttgt ggaacagcac   3840
aagcactacc tggacgagat catcgagcag atcagcgagt tctccaagag agtgatcctg   3900
gccgacgcta atctggacaa agtgctgtcc gcctacaaca agcaccggga taagcccatc   3960
agagagcagg ccgagaatat catccacctg tttaccctga ccaatctggg agcccctgcc   4020
gccttcaagt actttgacac caccatcgac cggaagaggt acaccagcac caaagaggtg   4080
ctggacgcca ccctgatcca ccagagcatc accggcctgt acgagacacg gatcgacctg   4140
tctcagctgg gaggtgactc tggaagatct agcggaggat cctctggcga cagacacca   4200
ggaacaagcg agtcagcaac accagagagc tctggtagcg agacaccgg taccagtgaa   4260
agcgccacgc cagaaagcag tgggagtgag actccggta catctgaatc agcgacaccg   4320
gaatcaagtg gcggcagcag cggcggcagc agcaccctaa atatagaaga tgagtatcgg   4380
ctacatgaga cctcaaaaga gccagatgtt tctctaggt ccacatggct gtctgatttt   4440
cctcaggcct gggcggaaac cggggcatg ggactggtga ttcgccaagc tcctctgatc   4500
atacctctga aagcaacctc tacccccgtg tccataaaac aataccccat gtcacaagaa   4560
gccagactgg ggatcaagcc ccacatacag agactgttgg accagggaat actggtaccc   4620
tgccagtccc cctggaacac gccctgcta cccgttaaga aaccaggac taatgattat   4680
aggcctgtcc aggatctgag agaagtcaac aagcgggtgg aagacatcca ccccaccgtg   4740
cccaaccctt acaacctctt gagcgggcc ccaccgtcc accagtggta cactgtgctt   4800
gatttaaagg atgccttttt ctgcctgaga ctccacccca ccagtcagcc tctcttcgcc   4860
tttgagtgga gagatccaga gatgggaatc tcaggacaat tgacctggac cagactccca   4920
cagggtttca aaaacagtcc caccctgttt aatgaggcac tgcacagaga cctagcagac   4980
ttccggatcc agcacccaga cttgatcctg ctacagtacg tggatgactt actgctggcc   5040
gccacttctg agctagactg ccaacaaggt actcgggccc tgttacaaac cctagggaac   5100
```

```
ctcgggtatc gggcctcggc caagaaagcc caaatttgcc agaaacaggt caagtatctg    5160
gggtatcttc taaaagaggg tcagagatgg ctgactgagg ccagaaaaga gactgtgatg    5220
gggcagccta ctccgaagac ccctcgacaa ctaagggagt tcctagggaa ggcaggcttc    5280
tgtcgcctct tcatccctgg gtttgcagaa atggcagccc cctgtaccc tctcaccaaa     5340
ccggggactc tgtttaattg gggcccagac caacaaaagg cctatcaaga aatcaagcaa    5400
gctcttctaa ctgccccagc cctggggttg ccagatttga ctaagcccct tgaactcttt    5460
gtcgacgaga agcagggcta cgccaaaggt gtcctaacgc aaaaactggg accttggcgt    5520
cggccggtgg cctacctgtc caaaaagcta gacccagtag cagctgggtg gccccttgc     5580
ctacggatgg tagcagccat tgccgtactg acaaaggatg caggcaagct aaccatggga    5640
cagccactag tcattctggc ccccatgca gtagaggcac tagtcaaaca accccccgac     5700
cgctggcttt ccaacgcccg gatgactcac tatcaggcct tgcttttgga cacggaccgg    5760
gtccagttcg gaccggtggt agccctgaac ccggctacgc tgctcccact gcctgaggaa    5820
gggctgcaac acaactgcct tgatgggaca ggtggcggtg tgtgcaccgt caagttcaag    5880
tacaagggtg aggaacttga agttgatatt agcaaaatca agaaggtttg gcgcgttggt    5940
aaaatgatat ctttttactta tgacgacaac ggcaagacag gtagaggggc agtgtctgag    6000
aaagacgccc ccaaggagct gttgcaaatg ttggaaaagt ctgggaaaaa gtctggcggc    6060
tcaaaaagaa ccgccgacgg cagcgaattc gagcccaaga agaagaggaa agtcggaggt    6120
ggcggaagcc caaaaaagaa aagaaaagtg tatccctatg atgtccccga ttatgccggt    6180
tcaagagccc tggtcgtgat tagactgagc cgagtgacga acgccaccac aagtcccgag    6240
agacagctgg aatcatgcca gcagctctgt gctcagcggg gttgggatgt ggtcggcgtg    6300
gcagaggatc tggacgtgag cggggccgtc gatccattcg acagaaagag gaggcccaac    6360
ctggcaagat ggctcgcttt cgaggaacag ccctttgatg tgatcgtcgc ctacagagtg    6420
gaccggctga cccgctcaat tcgacatctc cagcagctgg tgcattgggc tgaggaccac    6480
aagaaactgg tggtcagcgc aacagaagcc cacttcgata ctaccacacc ttttgccgct    6540
gtggtcatcg cactgatggg cactgtggcc cagatggagc tcgaagctat caaggagcga    6600
aacaggaagcg cagcccattt caatattagg gccggtaaat acagaggctc cctgccccct    6660
tggggatatc tccctaccag ggtggatggg gagtggagac tggtgccaga cccccgtccag   6720
agagagcgga ttctggaagt gtaccacaga gtggtcgata ccaccgaacc actccatctg    6780
gtggcacacg acctgaatag acgcggcgtg ctctctccaa aggattattt tgctcagctg    6840
cagggaagag agccacaggg aagagaatgg agtgctactg cactgaagag atctatgatc    6900
agtgaggcta tgctgggtta cgcaacactc aatggcaaaa ctgtccggga cgatgacgga    6960
gcccctctgg tgagggctga gccattctc accagagagc agctcgaagc tctgcgggca    7020
gaactggtca agactagtcg cgccaaacct gccgtgagca cccaagcct gctcctgagg     7080
gtgctgttct gcgccgtctg tggagagcca gcatacaagt ttgcggcgg agggcgcaaa    7140
catccccgct atcgatgcag gagcatgggg ttccctaagc actgtggaaa cgggacagtg    7200
gccatggctg agtgggacgc cttttgcgag gaacaggtgc tggatctcct gggtgacgct    7260
gagcggctga aaaagtgtg gtggcagga tctgactccg ctgtggagct ggcagaagtc      7320
aatgccgagc tcgtggatct gacttccctc atcggatctc ctgcatatag agctgggtcc    7380
ccacagagag aagctctgga cgcacgaatt gctgcactcg ctgctagaca gggaactg      7440
gagggcctgg aggccaggcc ctctggatgg gagtggcgag aaaccggaca gaggtttggg    7500
gattggtgga gggagcagga caccgcagcc aagaacacat ggctgagatc catgaatgtc    7560
cggctcacat tcgacgtgcg cggtggcctg actcgaacca tcgattttgg cgacctgcag    7620
gagtatgaac agcacctgag actggggtcc gtggtcgaaa gactgcacac tgggatgtcc    7680
```

SEQ ID NO: 378         moltype = AA   length = 1367
FEATURE                Location/Qualifiers
REGION                 1..1367
                       note = Description of Artificial Sequence: Synthetic
                       polypeptide
source                 1..1367
                       mol_type = protein
                       organism = synthetic construct
SEQUENCE: 378
DKKYSIGLDI GTNSVGWAVI TDEYKVPSKK FKVLGNTDRH SIKKNLIGAL LFDSGETAEA    60
TRLKRTARRR YTRRKNRICY LQEIFSNEMA KVDDSFFHRL EESFLVEEDK KHERHPIFGN    120
IVDEVAYHEK YPTIYHLRKK LVDSTDKADL RLIYLALAHM IKFRGHFLIE GDLNPDNSDV    180
DKLFIQLVQT YNQLFEENPI NASGVDAKAI LSARLSKSRR LENLIAQLPG EKKNGLFGNL    240
IALSLGLTPN FKSNFDLAED AKLQLSKDTY DDDLDNLLAQ IGDQYADLFL AAKNLSDAIL    300
LSDILRVNTE ITKAPLSASM IKRYDEHHQD LTLLKALVRQ QLPEKYKEIF FDQSKNGYAG    360
YIDGGASQEE FYKFIKPILE KMDGTEELLV KLNREDLLRK QRTFDNGSIP HQIHLGELHA    420
ILRRQEDFYP FLKDNREKIE KILTFRIPYY VGPLARGNSR FAWMTRKSEE TITPWNFEEV    480
VDKGASAQSF IERMTNFDKN LPNEKVLPKH SLLYEYFTVY NELTKVKYVT EGMRKPAFLS    540
GEQKKAIVDL LFKTNRKVTV KQLKEDYFKK IECFDSVEIS GVEDRFNASL GTYHDLLKII    600
KDKDFLDNEE NEDILEDIVL TLTLFEDREM IEERLKTYAH LFDDKVMKQL KRRRYTGWGR    660
LSRKLINGIR DKQSGKTILD FLKSDGFANR NFMQLIHDDS LTFKEDIQKA QVSGQGDSLH    720
EHIANLAGSP AIKKGILQTV KVVDELVKVM GRHKPENIVI EMARENQTTQ KGQKNSRERM    780
KRIEEGIKEL GSQILKEHPV ENTQLQNEKL YLYYLQNGRD MYVDQELDIN RLSDYDVDAI    840
VPQSFLKDDS IDNKVLTRSD KNRGKSDNVP SEEVVKKMKN YWRQLLNAKL ITQRKFDNLT    900
KAERGGLSEL DKAGFIKRQL VETRQITKHV AQILDSRMNT KYDENDKLIR EVKVITLKSK    960
LVSDFRKDFQ FYKVREINNY HHAHDAYLNA VVGTALIKKY PKLESEFVYG DYKVYDVRKM    1020
IAKSEQEIGK ATAKYFFYSN IMNFFKTEIT LANGEIRKRP LIETNGETGE IVWDKGRDFA    1080
TVRKVLSMPQ VNIVKKTEVQ TGGFSKESIL PKRNSDKLIA RKKDWDPKKY GGFDSPTVAY    1140
SVLVVAKVEK GKSKKLKSVK ELLGITIMER SSFEKNPIDF LEAKGYKEVK KDLIIKLPKY    1200
SLFELENGRK RMLASAGELQ KGNELALPSK YVNFLYLASH YEKLKGSPED NEQKQLFVEQ    1260
HKHYLDEIIE QISEFSKRVI LADANLDKVL SAYNKHRDKP IREQAENIIH LFTLTNLGAP    1320
AAFKYFDTTI DRKRYTSTKE VLDATLIHQS ITGLYETRID LSQLGGD                  1367

SEQ ID NO: 379         moltype = AA   length = 576
FEATURE                Location/Qualifiers

```
REGION                    1..576
                          note = Description of Artificial Sequence: Synthetic
                           polypeptide
source                    1..576
                          mol_type = protein
                          organism = synthetic construct
SEQUENCE: 379
LNIEDEYRLH ETSKEPDVSL GSTWLSDFPQ AWAETGGMGL AVRQAPLIIP LKATSTPVSI   60
KQYPMSQEAR LGIKPHIQRL LDQGILVPCQ SPWNTPLLPV KKPGTNDYRP VQDLREVNKR  120
VEDIHPTVPN PYNLLSGPPP SHQWYTVLDL KDAFFCLRLH PTSQPLFAFE WRDPEMGISG  180
QLTWTRLPQG FKNSPTLFNE ALHRDLADFR IQHPDLILLQ YVDDLLLAAT SELDCQQGTR  240
ALLQTLGNLG YRASAKKAQI CQKQVKYLGY LLKEGQRWLT EARKETVMGQ PTPKTPRQLR  300
EFLGKAGFCR LFIPGFAEMA APLYPLTKPG TLFNWGPDQQ KAYQEIKQAL LTAPALGLPD  360
LTKPFELFVD EKQGYAKGVL TQKLGPWRRP VAYLSKKLDP VAAGWPPCLR MVAAIAVLTK  420
DAGKLTMGQP LVILAPHAVE ALVKQPPDRW LSNARMTHYQ ALLLDTDRVQ FGPVVALNPA  480
TLLPLPEEGL QHNCLDGTGG GGVTVKFKYK GEELEVDISK IKKVWRVGKM ISFTYDDNGK  540
TGRGAVSEKD APKELLQMLE KSGKKSGGSK RTADGS                            576

SEQ ID NO: 380            moltype = AA  length = 500
FEATURE                   Location/Qualifiers
REGION                    1..500
                          note = Description of Artificial Sequence: Synthetic
                           polypeptide
source                    1..500
                          mol_type = protein
                          organism = synthetic construct
SEQUENCE: 380
SRALVVIRLS RVTDATTSPE RQLESCQQLC AQRGWDVVGV AEDLDVSGAV DPFDRKRRPN   60
LARWLAFEEQ PFDVIVAYRV DRLTRSIRHL QQLVHWAEDH KKLVVSATEA HFDTTTPFAA  120
VVIALMGTVA QMELEAIKER NRSAAHFNIR AGKYRGSLPP WGYLPTRVDG EWRLVPDPVQ  180
RERILEVYHR VVDNHEPLHL VAHDLNRRGV LSPKDYFAQL QGREPQGREW SATALKRSMI  240
SEAMLGYATL NGKTVRDDDG APLVRAEPIL TREQLEALRA ELVKTSRAKP AVSTPSLLLR  300
VLFCAVCGEP AYKFAGGGRK HPRYRCRSMG FPKHCGNGTV AMAEWDAFCE EQVLDLLGDA  360
ERLEKVWVAG SDSAVELAEV NAELVDLTSL IGSPAYRAGS PQREALDARI AALAARQEEL  420
EGLEARPSGW EWRETGQRFG DWWREQDTAA KNTWLRSMNV RLTFDVRGGL TRTIDFGDLQ  480
EYEQHLRLGS VVERLHTGMS                                             500

SEQ ID NO: 381            moltype = DNA  length = 11344
FEATURE                   Location/Qualifiers
misc_feature              1..11344
                          note = Description of Artificial Sequence: Synthetic
                           polynucleotide
source                    1..11344
                          mol_type = other DNA
                          organism = synthetic construct
SEQUENCE: 381
ccgaaaagtg ccacctgacg tcgacggatc gggagatcga tctcccgatc ccctagggtc   60
gactctcagt acaatctgct ctgatgccgc atagttaagc cagtatctgc tccctgcttg  120
tgtgttggag gtcgctgagt agtgcgcgag caaaatttaa gctacaacaa ggcaaggctt  180
gaccgacaat tgcatgaaga atctgcttag ggttaggcgt tttgcgctgc ttcgcgatgt  240
acgggccaga tatacgcgtt gacattgatt attgactagt tattaatagt aatcaattac  300
ggggtcatta gttcatagcc catatatgga gttccgcgtt acataactta cggtaaatgg  360
cccgcctggc tgaccgccca acgacccccg cccattgacg tcaataatga cgtatgttcc  420
catagtaacg ccaataggga cttccattg acgtcaatgg gtggagtatt tacggtaaac  480
tgcccacttg gcagtacatc aagtgtatca tatgccaagt acgccccta ttgacgtcaa  540
tgacggtaaa tggcccgcct ggcattatgc ccagtacatg accttatggg actttcctac  600
ttggcagtac atctacgtat tagtcatcgc tattaccatg gtgatgcggt tttggcagta  660
catcaatggg cgtggatagc ggtttgactc acggggattt ccaagtctcc accccattga  720
cgtcaatggg agtttgtttt ggcaccaaaa tcaacgggac tttccaaaat gtcgtaacaa  780
ctccgcccca ttgacgcaaa tgggcggtag cgtgtacgg tgggaggtct atataagcag  840
agctggttta gtgaaccgtc agatccgcta gagatccgcg gccgctaata cgactcacta  900
tagggagagc cgccaccatg aaacggacag ccgacggaag cgagttcgag tcaccaaaga  960
agaagcggaa agtcgacaag aagtacagca tcggcctgga catcggcacc aactctgtgg 1020
gctgggccgt gatcacggac gagtacaagg tgcccagcaa gaaattcaag gtgctgggca 1080
acaccgaccg gcacagcatc aagaagaacc tgatcggagc cctgctgttc gacagcggcg 1140
aaacagccga ggccacccgg ctgaagagaa ccgccagaag aagatacacc agacggaaga 1200
accggatctg ctatctgcaa gagatcttca gcaacgagat ggccaaggtg gacgacagct 1260
tcttccacag actggaagag tccttcctgg tggaagagga taagaagcac gagcggcacc 1320
ccatcttcgg caacatcgtg gacgaggtgg cctaccacga gaagtacccc accatctacc 1380
acctgagaaa gaaactggtg gacagcaccg acaaggccga cctgcggctg atctatctgg 1440
ccctggccca catgatcaag ttccggggcc acttcctgat cgaggcgac ctgaaccccg 1500
acaacagcga cgtggacaag ctgttcatcc agctggtgca gacctacaac cagctgttcg 1560
aggaaaaccc catcaacgcc agcggcgtgg acgccaaggc catcctgtct gccagactga 1620
gcaagagcag aaggctggaa aatctgatcg cccagctgcc cggcgagaag aagaatggcc 1680
tgttcggaaa cctgattgcc ctgagcctgg gcctgacccc caacttcaag agcaacttcg 1740
acctggccga ggatgccaaa ctgcagctga gcaaggacac ctacgacgac gacctggaca 1800
acctgctggc ccagatcggc gaccagtacg ccgacctgtt tctggccgcc aagaacctgt 1860
ccgacgccat cctgctgagc gacatcctga gagtgaacac cgagatcacc aaggcccccc 1920
tgagcgcctc tatgatcaag agatacgacg agcaccacca ggacctgacc ctgctgaaag 1980
```

```
ctctcgtgcg gcagcagctg cctgagaagt acaaagagat tttcttcgac cagagcaaga  2040
acggctacgc cggctacatt gacgcggag ccagccagga agagttctac aagttcatca   2100
agcccatcct ggaaaagatg gacggcaccg aggaactgct cgtgaagctg aacagagagg   2160
acctgctgcg gaagcagcgg accttcgaca acggcagcat ccccaccag atccacctgg    2220
gagagctgca cgccattctg cggcggcagg aagattttta cccattcctg aaggacaacc   2280
gggaaaagat cgagaagatc ctgaccttcc gcatcccta ctacgtgggc cctctggcca    2340
ggggaaacag cagattcgcc tggatgacca gaaagagcga ggaaaccatc accccctgga   2400
acttcgagga agtggtggac aagggcgctt ccgcccagag cttcatcgag cggatgacca   2460
acttcgataa gaacctgccc aacgaaggg tgctgcccaa gcacagcctg ctgtacgagt    2520
acttcaccgt gtataacgag ctgaccaaag tgaaatacgt gaccgaggga atgagaaagc   2580
ccgccttcct gagcggcgag cagaaaaagg ccatcgtgga cctgctgttc aagaccaacc   2640
ggaaagtgac cgtgaagcag ctgaaagagg actacttcaa gaaaatcgag tgcttcgact   2700
ccgtggaaat ctccggcgtg gaagatcggt tcaacgcctc cctgggcaca taccacgatc   2760
tgctgaaaat tatcaaggac aaggacttcc tggacaatga gaaaacgag gacattctgg   2820
aagatatcgt gctgacctg acactgtttg aggacagaga gatgatcgag aacggctga    2880
aaacctatgc ccacctgttc gacgacaaag tgatgaagca gctgaagcgg cggagataca   2940
ccggctgggg caggctgagc cggaagctga tcaacgcat ccgggacaag cagtccggca    3000
agacaatcct ggatttcctg aagtccgacg gcttcgccaa cagaaacttc atgcagctga   3060
tccacgacga cagcctgacc tttaaagagg acatccagaa agcccaggtg tccggccagg   3120
gcgatagcct gcacgagcac attgccaatc tggccggcag ccccgccatt aagaagggca   3180
tcctgcagac agtgaaggtg gtggacgagc tcgtgaaagt gatgggccgg cacaagcccg   3240
agaacatcgt gatcgaaatg gccagagaa accagaccac ccagaaggga cagaagaaca    3300
gccgcgagag aatgaagcgg atcgaagagg gcatcaaaga gctgggcagc cagatcctga   3360
aagaacaccc cgtggaaaac acccagctgc agaacgagaa gctgtacctg tactacctgc   3420
agaatgggcg ggatatgtac gtggaccagg aactggacat caaccggctg tccgactacg   3480
atgtggacgc tatcgtgcct cagagcttc tgaaggacga ctccatcgac aacaaggtgc   3540
tgaccagaag cgacaagaac cggggcaaga gcgacaacgt gccctccgaa gaggtcgtga   3600
agaagatgaa gaactactgg cggcagctgc tgaacgccaa gctgattacc cagagaaagt   3660
tcgacaatct gaccaaggcc gagagaggcg gcctgagcga actggataag gccggcttca   3720
tcaagagaca gctggtggaa acccggcaga tcacaaagca cgtggcacag atcctggact   3780
cccggatgaa cactaagtac gacgagaatg acaagctgat ccgggaagtg aaagtgatca   3840
ccctgaagtc caagcggtg tccgatttcc ggaaggattt ccagttttac aaagtgcgcg   3900
agatcaacaa ctaccaccac gcccacgacg cctacctgaa cgccgtcgtg ggaaccgccc   3960
tgatcaaaaa gtaccctaag ctggaaagcg agttcgtgta cggcgactac aaggtgtacg   4020
acgtgcggaa gatgatcgcc aagagcgagc aggaaatcgg caaggctacc gccaagtact   4080
tcttctacag caacatcatg aacttttca agaccgagat taccctggcc aacggcgaga    4140
tccggaagcg gcctctgatc gagacaaacg gcgaaaccgg ggagatcgtg tgggataagg   4200
gccgggattt tgccaccgtg cggaaagtgc tgagcatgcc ccaagtgaat atcgtgaaaa   4260
agaccgaggt gcagacaggc ggcttcagca aagagtctat cctgcccaag aggaacagcg   4320
ataagctgat cgccagaaag aaggactggg accctaagaa gtacggcggc ttcgacagcc   4380
ccaccgtggc ctattctgtg ctggtggtgg ccaaagtgga aaagggcaag tccaagaaac   4440
tgaagagtgt gaaagagctg ctggggatca ccatcatgga agaagcagc ttcgagaaga    4500
atcccatcga ctttctggaa gccaagggct acaaagaagt ctgatcatca              4560
agctgcctaa gtactccctg ttcgagctgg aaaacggccg gaagagaatg ctggcctctg   4620
ccggcgaact gcagaaggga aacgaactgg ccctgccctc caaatatgtg aacttcctgt   4680
acctggccca ccactatgag aagctgaagg ctcccccga ggataatgag cagaaacagc     4740
tgtttgtgga acagcacaag cactacctgg acgagatcat cgagcagatc agcgagttct   4800
ccaagagagt gatcctggcc gacgctaatc tggacaaagt gctgtccgcc tacaacaagc   4860
accgggataa gcccatcaga gagcaggccg agaatatcat ccacctgttt accctgacca   4920
atctgggagc ccctgccgcc ttcaagtact ttgacaccac catcgaccgg aagaggtaca   4980
ccagcaccaa agaggtgctg gacgccaccc tgatccacca gagcatcacc ggcctgtacg   5040
agacacggat cgacctgtct cagctgggag gtgactctgg aggatctagc ggaggatcct   5100
ctggcagcga gacaccagga acaagcgagt cagcaacacc agagagcagt ggcggcagca   5160
gcggcggcag cagcaccta aatatagaag atgagtatcg gctacatgag acctcaaaag    5220
agccagatgt ttctctaggg tccacatggc tgtctgattt tcctcaggcc tgggcggaaa   5280
ccgggggcat gggactggca gttcgccaag ctcctctgat catacctctg aaagcaacct   5340
ctaccccccgt gtccataaaa caatacccca tgtcacaaga agccagactg gggatcaagc   5400
cccacataca gagactgttg gaccaggaa tactggtacc ctgccagtcc ccctggaaca    5460
cgccctgct acccgttaag aaaccaggga ctaatgatta taggcctgtc caggatctga   5520
gagaagtcaa caagcgggtg gaagacatcc accccaccgt gcccaaccct tacaacctct   5580
tgagcggct cccaccgtcc caccagtggt acactgtgct tgatttaaag gatgcctttt   5640
tctgcctgag actccacccc accagtcagc ctctcttcgc ctttgagtgg agagatccag   5700
agatgggaat ctcaggacaa ttgacctgga ccagactccc acagggttc aaaaacagtc    5760
ccaccctgtt taatgaggca ctgcacagag acctagcaga cttccggatc cagcacccag   5820
acttgatcct gctacagtac gtggatgact tactgctggc cgccacttct gagctagact   5880
gccaacaagg tactcgggcc ctgttacaaa ccctaggaa cctcgggtat cgggcctcgg    5940
ccaagaaagc ccaaatttgc cagaaacagg tcaagtatct ggggtatctt ctaaaagagg   6000
gtcagagatg gctgactgag gccagaaaag agactgtgat ggggcagctc actccgaaga   6060
cccctcgaca actaagggag ttcctaggga aggcaggctt ctgtcgcctc ttcatcccag   6120
ggtttgcaga aatggcagcc cccctgtacc ctctccaccaa accggggact ctgtttaatt   6180
ggggcccaga ccaacaaaag gcctatcaag aaatcaagca agctcttcta actgcccag    6240
ccctggggtt gccagatttg actaagccct ttgaactctt tgtcgacgag aagcagggct   6300
acgccaaagg tgtcctaacg caaaaactgg gaccttggcg tcggcggtg gcctacctgt    6360
ccaaaagct agaccccagta gcagtgggt ggccccttg cctacggatg gtagcagcca     6420
ttgccgtact gacaaaggat gcaggcaagc taaccatggg acagccacta gtcattctgg   6480
cccccatgc agtagaggca ctagtcaaac aaccccccga ccgctggctt tccaacgccc    6540
ggatgactca ctatcaggcc ttgcttttgg acacggaccg ggtccagttc ggaccggtgg   6600
tagccctgaa cccggctacg ctgctcccac tgcctgagga agggctgcaa cacaactgcc   6660
ttgatatcct ggccgaagcc cacggaaccc gacccgacct aacggaccag ccgctcccag   6720
```

```
acgccgacca cacctggtac acggatggaa gcagtctctt acaagaggga cagcgtaagg   6780
cgggagctgc ggtgaccacc gagaccgagg taatctgggc taaagccctg ccagccggga   6840
catccgctca gcgggctgaa ctgatagcac tcacccaggc cctaaagatg gcagaaggta   6900
agaagctaaa tgtttatact gatagccgtt atgcttttgc tactgcccat atccatggag   6960
aaatatacag aaggcgtggg tggctcacat cagaaggcaa agagatcaaa aataaagacg   7020
agatcttggc cctactaaaa gccctctttc tgcccaaaag acttagcata atccattgtc   7080
caggacatca aaagggacac agcgccgagg ctagaggcaa ccggatggct gaccaagcgg   7140
cccgaaaggc agccatcaca gagactccag acacctctac cctcctcata gaaaattcat   7200
caccctctcg cggctcaaaa agaacccgcc acggcagcga attcgagccc aagaagaaga   7260
ggaaagtcgg aagcggagct actaacttca gcctgctgaa gcaggctggc gacgtggagg   7320
agaaccctgg acctccaaaa aagaaaagaa aagtgtatcc ctatgatgtc ccgattatg    7380
ccggttcaag agccctggtc gtgattagac tgagccgagt gacagacgcc accacaagtc   7440
ccgagagaca gctggaatca tgccagcagc tctgtgctca gcggggttgg gatgtggtcg   7500
gcgtggcaga ggatctggac gtgagcgggg ccgtcgatcc attcgacaga aagaggaggc   7560
ccaacctggc aagatggctc gctttcgagg aacagccctt tgatgtgatc gtcgcctaca   7620
gagtggaccg gctgacccgc tcaattcgac atctccagca gctggtgcat gggctgagg   7680
accacaagaa actggtggtc agcgcaacag aagcccactc cgatactacc acaccttttg   7740
ccgctgtggt catcgcactg atgggcactg tggcccagat ggcctcgaa gctatcaagg   7800
agcgaaacag gagcgcagcc catttcaata ttagggccgg taaatacaga ggctccctgc   7860
cccccttggg atatctccct accagggtgg atggggagtg gagactggtg ccagaccccg   7920
tccagagaga gcggattctg gaagtgtacc acagagtggt cgataaccac gaaccactcc   7980
atctggtggc cacgaccctg aatagacgcg gcgtgctctc tccaaaggat tattttgctc   8040
agctgcaggg aagagagcca cagggaagag aatggagtgc tactgcactg aagagatcta   8100
tgatcagtga ggctatgctg ggttacgcaa cactcaatgg caaaactgtc cgggacgatg   8160
acggagcccc tctggtgagg gctgagccta ttctcaccag agagcagctc gaagctctgc   8220
gggcagaact ggtcaagact agtcgcgcca aacctgccgt gagcaccca agcctgctcc   8280
tgagggtgct gttctgcgcc gtctgtggag agccagcata caagtttgcc ggcgagggc   8340
gcaaacatcc ccgctatcga tgcaggagca tggggttccc taagcactgt ggaaacggga   8400
cagtggccat ggctgagtgg gacgccttt gcgaggaaca ggtgctggat ctcctgggtg   8460
acgctgagcg gctggaaaaa gtgtgggtgg caggatctga ctccgctgtg gagctggcag   8520
aagtcaatgc cgagctcgtg gatctgactt ccctcatcgg atctcctgca tatagagctg   8580
ggtccccaca gagagaagct ctggacgcac gaattgctgc actcgctgct agacaggagg   8640
aactggaggg cctggaggcc aggccctctg gatgggagtg gcgagaaacc ggacagaggt   8700
ttgggggattg gtggaagggag caggacaccg cagccaagaa cacatggctg agatcctga   8760
atgtccggct cacattcgac gtgcgcggtg gcctgactcg aaccatcgat tttggcgacc   8820
tgcaggagta tgaacagcac ctgagactgg ggtccgtggt cgaaagactg cacactggga   8880
tgtcctaggt ttaaacccgc tgatcagcct cgactgtgcc ttctagttgc cagccatctg   8940
ttgtttgccc ctccccgtg ccttcctga ccctggaagg tgccactccc actgtccttt    9000
cctaataaaa tgaaaattt gcatcgcatt gtctgagtag tgtcattct attctgggg     9060
gtgggggtggg gcaggacagc aaggggggagg attgggaaga caatagcagg catgctgggg   9120
atgcggtggg ctctatggct tctgaggcgg aaagaaccag ctgggctcg ataccgtcga   9180
cctctagcta gagcttggcg taatcatggt catagctgtt tcctgtgtga aattgttatc   9240
cgctcacaat tccacacaac atacgagccg gaagcataaa gtgtaaagcc tagggtgcct   9300
aatgagtgag ctaactcaca ttaattgcgt tgcgctcact gcccgctttc cagtcgggaa   9360
acctgtcgtg ccagctgcat taatgaatcg gccaacgcgc ggggagaggc ggtttgcgta   9420
ttgggcgctc ttccgcttcc tcgctcactg actcgctgcg ctcggtcgtt cggctgcggc   9480
gagcgtgatc agctcactca aaggcggtaa tacggttatc cacagaatca ggggataacg   9540
caggaaagaa catgtgagca aaaggccagc aaaaggccag gaaccgtaaa aaggccgcgt   9600
tgctggcgtt tttccatagg ctccgcccc ctgacgagca tcacaaaaat cgacgctcaa    9660
gtcagaggtg gcgaaacccg acaggactat aaagatacca ggcgtttccc cctggaagct   9720
ccctcgtgcg ctctcctgtt ccgaccctgc cgcttaccgg atacctgtcc gcctttctcc   9780
cttcgggaag cgtggcgctt tctcatagct cacgctgtag gtatctcagt tcggtgtagg   9840
tcgttcgctc caagctgggc tgtgtgcacg aaccccccgt tcagcccgac cgctgcgcct   9900
tatccggtaa ctatcgtctt gagtccaacc cggtaagaca cgacttatcg ccactggcag   9960
cagccactgg taacaggatt agcagagcga ggtatgtagg cggtgctaca gagttcttga  10020
agtggtggcc taactacggc tacactagaa gaacagtatt tggtatctgc gctctgctga  10080
agccagttac cttcggaaaa agagttggta gctcttgatc cggcaaacaa accaccgctg  10140
gtagcggtgg ttttttttgtt tgcaagcagc agattacgcg cagaaaaaaa ggatctcaag  10200
aagatccttt gatcttttct acggggtctg acgctcagtg gaacgaaaac tcacgttaag  10260
ggattttggt catgagatta tcaaaaagga tcttcaccta gatccttta aattaaaaat  10320
gaagttttaa atcaatctaa agtatatatg agtaaacttg gtctgacagt taccaatgct  10380
taatcagtga ggcacctatc tcagcgatct gtctatttcg ttcatccata gttgcctgac  10440
tccccgtcgt gtagataact acgatacggg agggcttacc atctggcccc agtgctgcaa  10500
tgataccgcg agacccacgc tcaccggctc cagatttatc agcaataaac cagccagccg  10560
gaagggccga gcgcagaagt ggtcctgcaa ctttatccgc ctccatccag tctattaatt  10620
gttgccggga agctagagta agtagttcgc cagttaatag tttgcgcaac gttgttgcca  10680
ttgctacagg catcgtggtg tcacgctcgt cgtttggtat ggcttcattc agctccggtt  10740
cccaacgatc aaggcgagtt acatgatccc ccatgttgtg caaaaaagcg gttagctcct  10800
tcggtcctcc gatcgttgtc agaagtaagt tggccgcagt gttatcactc atggttatgg  10860
cagcactgca taattctctt actgtcatgc catccgtaag atgcttttct gtgactggtg  10920
agtactcaac caagtcattc tgagaatagt gtatgcggcg accgagttgc tcttgcccgg  10980
cgtcaatacg ggataatacc gcgccacata gcagaacttt aaaagtgctc atcattggaa  11040
aacgttcttc ggggcgaaaa ctctcaagga tcttaccgct gttgagatcc agttcgatgt  11100
aacccactcg tgcacccaac tgatcttcag catctttttac tttcaccagc gtttctgggt  11160
gagcaaaaac aggaaggcaa aatgccgcaa aaaagggaat aagggcgaca cggaaatgtt  11220
gaatactcat actcttcctt tttcaatatt attgaagcat ttatcagggt tattgtctca  11280
tgagcggata catatttgaa tgtatttaga aaaataaaca ataggggtt ccgcgcacat   11340
ttcc                                                               11344
```

```
SEQ ID NO: 382         moltype = DNA   length = 9753
FEATURE                Location/Qualifiers
misc_feature           1..9753
                       note = Description of Artificial Sequence: Synthetic
                       polynucleotide
source                 1..9753
                       mol_type = other DNA
                       organism = synthetic construct
SEQUENCE: 382
ccgaaaagtg ccacctgacg tcgacggatc gggagatcga tctcccgatc cctagggtc    60
gactctcagt acaatctgct ctgatgccgc atagttaagc cagtatctgc tccctgcttg  120
tgtgttggag gtcgctgagt agtgcgcgag caaaatttaa gctacaacaa ggcaaggctt  180
gaccgacaat tgcatgaaga atctgcttag ggttaggcgt tttgcgctgc ttcgcgatgt  240
acgggccaga tatacgcgtt gacattgatt attgactagt tattaatagt aatcaattac  300
ggggtcatta gttcatagcc catatatgga gttccgcgtt acataactta cggtaaatgg  360
cccgcctggc tgaccgccca acgacccccg cccattgacg tcaataatga cgtatgttcc  420
catagtaacg ccaatagggα ctttccattg acgtcaatgg gtggagtatt tacgtaaac   480
tgcccacttg gcagtacatc aagtgtatca tatgccaagt acgccccta ttgacgtcaa   540
tgacggtaaa tggcccgcct ggcattatgc ccagtacatg accttatggg actttcctac  600
ttggcagtac atctacgtat tagtcatcgc tattaccatg gtgatgcggt tttggcagta  660
catcaatggg cgtggatagc ggtttgactc acggggattt ccaagtctcc accccattga  720
cgtcaatggg agtttgtttt ggcaccaaaa tcaacgggac tttccaaaat gtcgtaacaa  780
ctccgcccca ttgacgcaaa tgggcggtag gcgtgtacgg tgggaggtct atataagcag  840
agctggttta gtgaaccgtc agatccgcta gagatccgcg gccgctaata cgactcacta  900
tagggagagc cgccaccatg aaacggacag ccgacggaag cgagttcgag tcaccaaaga  960
agaagcggaa agtcgacaag aagtacagca tcggcctgga catcggcacc aactctgtgg 1020
gctgggccgt gatcaccgac gagtacaagg tgcccagcag gaaattcaag gtgctgggca 1080
acaccgaccg gcacagcatc aagaagaacc tgatcggagc cctgctgttc gacagcggcg 1140
aaacagccga ggccacccgg ctgaagagaa ccgccagaag aagatacacc agacggaaga 1200
accggatctg ctatctgcaa gagatcttca gcaacgagat ggccaaggtg gacgacagct 1260
tcttccacag actggaagag tccttcctgg tggaagagga taagaagcac gagcggcacc 1320
catcttcgg caacatcgtg gacgaggtgg cctaccacga gaagtacccc accatctacc 1380
acctgagaaa gaaactggtg gacagcaccg acaaggccga cctgcggctg atctatctgg 1440
ccctggccca catgatcaag ttccggggcc acttcctgat cgagggcgac ctgaacccg  1500
acaacagcga cgtggacaag ctgttcatcc agctggtgca gacctacaac cagcgtttcg 1560
aggaaaaccc catcaacgcc agcggcgtgg acgccaaggc catcctgtct gccagactga 1620
gcaagagcag acggctggaa aatctgatcg cccagctgcc cggcgagaag aagaatggcc 1680
tgttcggaaa cctgattgcc ctgagcctgg gcctgacccc caacttcaag agcaacttcg 1740
acctggccga ggatgccaaa ctgcagctga gcaaggacac ctacgacgac gacctggaca 1800
acctgctggc ccagatcggc gaccagtacg ccgacctgtt tctggccgcc aagaacctgt 1860
ccgacgccat cctgctgagc gacatcctga gagtgaacac cgagatcacc aaggcccccc 1920
tgagcgcctc tatgatcaag agatacgacg agcaccacca ggacctgacc ctgctgaaag 1980
ctctcgtgcg gcagcagctg cctgagaagt acaaagagat tttcttcgac cagagcaaga 2040
acggctacgc cggctacatt gacggcgag ccagccagga agagttctac aagttcatca 2100
agcccatcct ggaaaagatg gacggcaccg aggaactgct cgtgaagctg aacagagagg 2160
acctgctgcg gaagcagcgg accttcgaca acggcagcat ccccaccag atccacctgg 2220
gagagctgca cgccattctg cggcgccagg aagattttta cccattcctg aaggacaacc 2280
gggaaaagat cgagaagatc ctgaccttcc gcatcccta ctacgtgggc cctctgcca  2340
ggggaaacag cagattcgcc tggatgacca gaaagagcga ggaaaccatc accccctgga 2400
acttcgagga agtggtggac aagggcgctt ccgcccagag cttcatcgag cggatgacca 2460
acttcgataa gaacctgccc aacgagaagg tgctgccaaa gcacagcctg ctgtacgagt 2520
acttcaccgt gtataacgag ctgaccaaag tgaaatacgt gaccgaggga atgagaaagc 2580
ccgccttcct gagcggcgag cagaaaaagg ccatcgtgga cctgctgttc aagaccaacc 2640
ggaaagtgac cgtgaagcag ctgaaagagg actacttcaa gaaaatcgag tgcttcgact 2700
ccgtggaaat ctccgtgtg gaagatcggt tcaacgcctc cctgggcaca taccacgatc 2760
tgctgaaaat tatcaaggac aaggacttcc tggacaatga ggaaacagag gacattctgg 2820
aagatatcgt gctgaccctg acactgtttg aggacagaga gatgatcgag gaacggctga 2880
aaacctatgc ccacctgttc gacgacaaag tgatgaagca gctgaagcgg cggagataca 2940
ccggctgggg caggctgagc cggaagctga tcaacggat cctcaacag cagtccggca 3000
agacaatcct ggatttcctg aagtccgacg gcttcgccaa cagaaacttc atgcagctga 3060
tccacgacga cagcctgacc tttaaagagg catccagaa agcccaggtg tccgccagg  3120
gcgatagcct gcacgagcac attgccaatc tggccggcag ccccgccatt aagaagggca 3180
tcctgcagac agtgaaggtg gtggacgagc tcgtgaaagt gatgggccgg cacaagccg  3240
agaacatcgt gatcgaaatg gccagagaga accagacca ccagaaggaa cagaagaaca 3300
gccgcgagag aatgaagcgg atcgaagagg gcatcaaaga gctgggcagc cagatcctga 3360
aagaacaccc cgtggaaaac acccagctgc agaacgagaa gctgtacctg tactacctgc 3420
agaatgggcg ggatatgtac gtggaccagg aactggacat caaccggctg tccgactacg 3480
atgtggacgc tatcgtgcct cagagctttc tgaaggacga ctccatcgac aacaaggtgc 3540
tgaccagaag cgacaagaac cggggcaaga gcgacaacgt gcctccgaa gaggtcgtga 3600
agaagatgaa gaactactgg cggcagctgc tgaacgccaa gctgattacc cagagaaagt 3660
tcgacaatct gaccaaggcc gagagaggcg gcctgagcga actggataag gccggcttca 3720
tcaagagaca gctggtggaa accggcaga tcacaaagca cgtggcacag atcctggact 3780
cccggatgaa cactaagtac gacgagaatg acaagctgat ccgggaagtg aaagtgatca 3840
cctgaagtc caagctggtg tccgatttcc ggaaggattt ccagttttac aaagtgcgcg 3900
agatcaacaa ctaccaccac gcccacgacg cctacctgaa cgccgtcgtg ggaaccgccc 3960
tgatcaaaaa gtaccctaag ctggaaagcg agttcgtgta cggcgactac aaggtgtacg 4020
acgtgcggaa gatgatcgcc aagagcgagc aggaaatcgg caaggctacc gccaagtact 4080
tcttctacag caacatcatg aactttttca agaccgagat taccctggcc aacggcgaga 4140
tccggaagcg gcctctgatc gagacaaacg gcgaaaccgg ggagatcgtg tgggataagg 4200
```

```
gccgggattt tgccaccgtg cggaaagtgc tgagcatgcc ccaagtgaat atcgtgaaaa  4260
agaccgaggt gcagacaggc ggcttcagca aagagtctat cctgcccaag aggaacagcg  4320
ataagctgat cgccagaaag aaggactggg accctaagaa gtacggcggc ttcgacagcc  4380
ccaccgtggc ctattctgtg ctggtggtgg ccaaagtgga aaagggcaag tccaagaaac  4440
tgaagagtgt gaaagagctg ctggggatca ccatcatgga aagaagcagc ttcgagaaga  4500
atcccatcga ctttctggaa gccaagggct acaaagaagt gaaaaaggac ctgatcatca  4560
agctgcctaa gtactccctg ttcgagctgg aaaacggccg gaagagaatg ctggcctctg  4620
ccggcgaact gcagaaggga aacgaactgg ccctgccctc caaatatgtg aacttcctgt  4680
acctggccag ccactatgag aagctgaagg gctcccccga ggataatgag cagaaacagc  4740
tgtttgtgga acagcacaag cactacctgg acgagatcat cgagcagatc agcgagttct  4800
ccaagagagt gatcctggcc gacgctaatc tggacaaagt gctgtccgcc tacaacaagc  4860
accgggataa gcccatcaga gagcaggccg agaatatcat ccacctgttt accctgacca  4920
atctgggagc ccctgccgcc ttcaagtact tgacaccac catcgaccgg aagaggtaca  4980
ccagcaccaa agaggtgctg gacgccaccc tgatccacca gagcatcacc ggcctgtacg  5040
agacacggat cgacctgtct cagctgggag gtgactctgg aggatctagc ggaggatcct  5100
ctggcagcga gacaccagga acaagcgagt cagcaacacc agagagcagt ggcggcagca  5160
gcggcggcag cagcacccta aatatagaag atgagtatcg gctacatgag acctcaaaag  5220
agccagatgt ttctctaggg tccacatggc tgtctgattt tcctcaggcc tgggcggaaa  5280
ccgggggcat gggactggca gttcgccaag ctcctctgat catacctctg aaagcaacct  5340
ctaccccgt gtccataaaa caatacccca tgtcacaaga agcagactg gggatcaagc  5400
cccacataca gagactgttg gaccaggaa tactggtacc ctgccagtcc cctggaacaa  5460
cgccctgct acccgttaag aaaccaggga ctaatgatta taggcctgtc caggatctga  5520
gagaagtcaa caagcgggtg aagacatcc accccaccgt gcccaaccct tacaacctct  5580
tgagcgggct cccaccgtcc caccagtggt acactgtgct tgatttaaag gatgccttt  5640
tctgcctgag actccacccc accagtcagc ctctcttcgc ctttgagtgg agagatccag  5700
agatggaat ctcaggacaa ttgacctgga ccagactccc acagggtttc aaaaacagtc  5760
ccaccctgtt taatgaggca ctgcacagag acctagcaga cttccggatc cagcacccag  5820
acttgatcct gctacagtac gtggatgact tactgctggc cgccacttct gagctagact  5880
gccaacaagg tactcgggcc ctgttacaaa ccctagggaa cctcgggtat cgggcctcgg  5940
ccaagaaagc ccaaatttgc cagaaacagg tcaagtatct ggggtatctt ctaaaagagg  6000
gtcagagatg gctgactgag gccagaaaag agactgtgat ggggcagcct actccgaaga  6060
ccctcgaca actaagggag ttcctaggga aggcaggctt ctgtcgcctc ttcatccctg  6120
ggtttgcaga aatggcagcc ccctgtacc ctctcaccaa accggggact ctgtttaatt  6180
ggggcccaaa ccaacaaaag gcctatcaag aaatcaagca agctcttta actgcccag  6240
cctgggtt gccagatttg actaagcct ttgaactctt tgtcgacgag aagcagggct  6300
acgccaaagg tgtcctaacg caaaaactgg accttggcg tcggccggtg gcctaccgt  6360
ccaaaaagct agaccagta gcagctgggt ggccccttg cctacggatg gtagcagcca  6420
ttgccgtact gacaaaggat gcaggcaagc taaccatggg acagccacta gtcattctgg  6480
ccccccatgc agtagaggca ctagtcaaac aacccccgc ccgctggctt tccaacgccg  6540
ggatgactca ctatcaggcc ttgcttttgc acacggaccg ggtccagttc ggaccggtgg  6600
tagccctgaa cccggctacg ctgctcccac tgcctgagga agggctgcaa cacaactgcc  6660
ttgatatcct ggccgaagcc cacggaaccc gacccgacct aacggaccag ccgctcccag  6720
acgccgacca cacctggtac acaggatgaa gcagtctctt acaagaggga cagcgtaagg  6780
cgggagctgc ggtgaccacc gagaccgagg taatctgggc taaagccctg ccagccggga  6840
catccgctca gcgggctgaa ctgatagcac tcacccaggc cctaaagatg gcagaaggta  6900
agaagctaaa tgtttatact gatagccgtt atgcttttgc tactgcccat atccatgag  6960
aaatatacag aaggcgtggg tggctcacat cagaaggcaa agagatcaaa aataaagacg  7020
agatcttggc cctactaaaa gcccctcttt tgcccaaaag acttagcata atccattgtc  7080
caggacatca aaagggacac agcgccgagg ctagaggcaa ccggatggct gaccaagcgg  7140
cccgaaaggc agccatcaca gagactccag acacctctac cctcctcata gaaaattcat  7200
caccctctgg cggctcaaaa agaaccgccg acggcagcga attcgagccc aagaagaaga  7260
ggaaagtcta accggtcatc atcaccatca ccattgagtt taaacccgct gatcagcctc  7320
gactgtgcct tctagttgcc agccatctgt tgtttgcccc tcccccgtgc cttccttgac  7380
cctggaaggt gccactccca ctgtcctttc ctaataaaat gagaaaattg catcgcattg  7440
tctgagtagg tgtcattcta ttctggggg tggggtgggg caggacagca aggggagga  7500
ttgggaagac aatagcaggc atgctgggga tgcggtgggc tctatggctt ctgaggcgga  7560
aagaaccagc tggggctcga taccgtcgac ctctagctag agcttggcgt aatcatggtc  7620
atagctgttt cctgtgtgaa attgttatcc gctcacaatt ccacacaaca tacgagccgg  7680
aagcataaag tgtaaagcct agggtgccta atgagtgagc taactcacat taattgcgtt  7740
gcgctcactg cccgctttcc agtcgggaaa cctgtcgtgc cagctgcatt aatgaatcgg  7800
ccaacgcgcg gggagaggcg gtttgcgtat tgggcgctct tccgcttcct cgctcactga  7860
ctcgctgcgc tcggtcgttc ggctgcggcg agcggtatca gctcactcaa aggcggtaat  7920
acggttatcc acagaatcag gggataacgc aggaaagaac atgtgagcaa aaggccagca  7980
aaaggccagg aaccgtaaaa aggccgcgtt gctggcgttt ttccataggc tccgcccccc  8040
tgacgagcat cacaaaaatc gacgctcaag tcagaggtgg cgaaacccga caggactata  8100
aagataccag gcgtttcccc ctggaagctc cctcgtgcgc tctcctgttc cgaccctgcc  8160
gcttaccgga tacctgtccg cctttctccc ttcgggaagc gtggcgcttt ctcatagctc  8220
acgctgtagg tatctcagtt cggtgtaggt cgttcgctcc aagctgggct gtgtgcacga  8280
accccccgtt cagcccgacc gctgcgcctt atccggtaac tatcgtcttg agtccaaccc  8340
ggtaagacac gacttatcgc cactggcagc agccactggt aacaggatta gcagagcgag  8400
gtatgtaggc ggtgctacag agttcttgaa gtggtggcct aactacggct acactagaag  8460
aacagtattt ggtatctgcg ctctgctgaa gccagttacc ttcggaaaaa gagttggtag  8520
ctcttgatcc ggcaaacaaa ccaccgctgg tagcggtggt ttttttgttt gcaagcagca  8580
gattacgcgc agaaaaaaag gatctcaaga atcttttcta cggggtctga cggggtctga  8640
cgctcagtgg aacgaaaact cacgttaagg gattttggtc atgagattat caaaaaggat  8700
cttcacctag atccttttaa attaaaaatg aagttttaaa tcaatctaaa gtatatatga  8760
gtaaacttgg tctgacagtt accaatgctt aatcagtgag gcacctatct cagcgatctg  8820
tctatttcgt tcatccatag ttgcctgact ccccgtcgtg tagataacta cgatacggga  8880
gggcttacca tctggcccca gtgctgcaat gataccgcga gacccacgct caccggctcc  8940
```

```
agatttatca gcaataaacc agccagccgg aagggccgag cgcagaagtg gtcctgcaac   9000
tttatccgcc tccatccagt ctattaattg ttgccgggaa gctagagtaa gtagttcgcc   9060
agttaatagt ttgcgcaacg ttgttgccat tgctacaggc atcgtggtgt cacgctcgtc   9120
gtttggtatg gcttcattca gctccggttc ccaacgatca aggcgagtta catgatcccc   9180
catgttgtgc aaaaaagcgg ttagctcctt cggtcctccg atcgttgtca gaagtaagtt   9240
ggccgcagtg ttatcactca tggttatggc agcactgcat aattctctta ctgtcatgcc   9300
atccgtaaga tgcttttctg tgactggtga gtactcaacc aagtcattct gagaatagtg   9360
tatgcggcga ccgagttgct cttgcccggc gtcaatacgg gataataccg cgccacatag   9420
cagaacttta aaagtgctca tcattggaaa acgttcttcg gggcgaaaac tctcaaggat   9480
cttaccgctg ttgagatcca gttcgatgta acccactcgt gcacccaact gatcttcagc   9540
atcttttact ttcaccagcg tttctgggtg agcaaaaaca ggaaggcaaa atgccgcaaa   9600
aaagggaata agggcgacac ggaaatgttg aatactcata ctcttccttt tcaatatta   9660
ttgaagcatt tatcagggtt attgtctcat gagcggatac atatttgaat gtatttagaa   9720
aaataaacaa ataggggttc cgcgcacatt tcc                                9753

SEQ ID NO: 383        moltype = DNA  length = 11433
FEATURE               Location/Qualifiers
misc_feature          1..11433
                      note = Description of Artificial Sequence: Synthetic
                      polynucleotide
source                1..11433
                      mol_type = other DNA
                      organism = synthetic construct
SEQUENCE: 383
ccgaaaagtg ccacctgacg tcgacggatc gggagatcga tctcccgatc ccctagggtc   60
gactctcagt acaatctgct ctgatgccgc atagttaagc cagtatctgc tccctgcttg   120
tgtgttggag gtcgctgagt agtgcgcgag caaaatttaa gctacaacaa ggcaaggctt   180
gaccgacaat tgcatgaaga atctgcttag ggttaggcgt tttgcgctgc ttcgcgatgt   240
acgggccaga tatacgcgtt gacattgatt attgactagt tattaatagt aatcaattac   300
ggggtcatta gttcatagcc catatatgga gttccgcgtt acataactta cggtaaatgg   360
cccgcctggc tgaccgccca acgacccccg cccattgacg tcaataatga cgtatgttcc   420
catagtaacg ccaataggga ctttccattg acgtcaatgg gtggagtatt tacggtaaac   480
tgcccacttg gcagtacatc aagtgtatca tatgccaagt acgccccta ttgacgtcaa   540
tgacggtaaa tggcccgcct ggcattatgc ccagtacatg acctaggg actttcctac   600
ttggcagtac atctacgtat tagtcatcgc tattaccatg gtgatgcggt tttggcagta   660
catcaatggg cgtggatagc ggtttgactc acggggattt ccaagtctcc accccattga   720
cgtcaatggg agtttgtttt ggcaccaaaa tcaacgggac tttccaaaat gtcgtaacaa   780
ctccgcccca ttgacgcaaa tgggcggtag gcgtgtacgg tgggaggtct atataagcag   840
agctggttta gtgaaccgtc agatccgcta gagatccgcg gctaata cgactcacta   900
tagggagagc cgccaccatg cccgcggcta gagggtgaa gcttgacggt ggaaaacgga   960
cagccgacgg aagcgagttc gagtcaccaa agaagaagcg gaaagtcgac aagaagtaca   1020
gcatcggcct ggacatcggc accaactctg tgggctgggc cgtgatcacc gacgagtaca   1080
aggtgcccaa gaaaatttc aaggtgctgg gcaacaccga tcaagaaga                1140
acctgatcgg agccctgctg ttcgacagcg gcgaaacagc cgaggccacc cggctgaaga   1200
gaaccgccag aagaagatac accagacgga gaaccggat ctgctatctg caagagatct   1260
tcagcaacga gatggccaag gtggacgaca gcttcttcca cagactggaa gagtccttcc   1320
tggtggaaga ggataagaag cacgagcggc accccatctt cggcaacatc gtggacgagg   1380
tggcctacca cgagaagtac cccaccatct accacctgag aaagaaactg gtggacagca   1440
ccgacaaggc cgacctgcgg ctgatctatc tggccctggc ccacatgatc aagttccggg   1500
gccacttcct gatcgagggc gacctgaacc cggacaacag cgacgtggac aagctgttca   1560
tccagctggt gcagacctac aaccagctgt tcgaggaaaa ccccatcaac gccagccgag   1620
tggacgccaa ggccatcctg tctgccagac tgagcaagag cagacggctg gaaaatctga   1680
tcgcccagct gcccggcgag aagaagaatg gcctgttcgg aaacctgatt gccctgagcc   1740
tgggcctgac cccaacttc aagagcaact tcgacctggc cgaggatgcc aaactgcagc   1800
tgagcaagga cacctacgac gacgacctgg acaacctgct ggcccagatc ggcgaccagt   1860
acgccgacct gtttctggcc gccaagaacc tgtccgacgc catcctgctg agcgacatcc   1920
tgagagtgaa caccgagatc accaaggccc ctgagcgc ctctatgatc aagagatacg   1980
acgagcacca ccaggacctg accctgctga aagctctcgt gcggcagcag ctgcctgaga   2040
agtacaaaga gatttttctt gaccagagca agaaggccta cgccggctac attgacggcg   2100
gagccagcca ggaagagttc tacaagttca tcaagcccat cctggaaaag atggacggca   2160
ccgaggaact gctcgtgaag ctgaacagag aggacctgct gcgcaagcag cggaccttcg   2220
acaacggcag catcccccac cagatccacc tgggagagct gcacgccatt ctgcggcggc   2280
aggaagattt ttacccattc ctgaaggaca accgggaaaa gatcgagaag atcctgacct   2340
tccgcatccc ctactacgtg ggccctctgg cgagggaaa cagcagattc gcctggatga   2400
ccagaaagag cgaggaaacc atcaccccct ggaacttcga ggaagtggtg gacaagggcc   2460
cttccgccca gagcttcatc gagcggatga ccaacttcga taagaacctg cccaacgaga   2520
aggtgctgcc caagcacagc ctgctgtacg agtacttcac cgtgtataac gagctgacca   2580
aagtgaaata cgtgaccgag ggaatgagaa agcccgcctt cctgagcggc gagcagaaaa   2640
aggccatcgt ggacctgctg ttcaagacca accggaaagt gaccgtgaaa                2700
aggactactt caagaaaatc gagtgcttcg actccgtgga atctccggc gtggaagatc   2760
ggttcaacgc ctccctgggc acataccacg atctgctgaa aattatcaag gacaaggact   2820
tcctggacaa tgaggaaaac gaggacattc tggaagatat cgtgctgacc ctgacactgt   2880
ttgaggacag agagatgatc gaggaacggc tgaaaaccta tgcccacctg ttcgacgaca   2940
aagtgatgaa acagctgaag cggcggagat acaccggctg gggcaggctg agccgggaac   3000
tgatcaacgg catccgggac aagcagtccg gcaagacaat cctggatttc ctgaagtccg   3060
acggcttcgc caacagaaac ttcatgcagc tgatccacga cgacagcctg accttttaag   3120
aggacatcca gaaagcccag gtgtccggcc agggcgatag cctgcacgag cacattgcca   3180
atctggccgg cagccccgcc attaagaagg gcatcctgca gacagtgaag gtggtggacg   3240
agctcgtgaa agtgatgggc cggcacaagc ccgagaacat cgtgatcgaa atggccgaga   3300
```

```
agaaccagac cacccagaag ggacagaaga acagccgcga gagaatgaag cggatcgaag   3360
agggcatcaa agagctgggc agccagatcc tgaaagaaca cccgtggaa aacacccagc    3420
tgcagaacga gaagctgtac ctgtactacc tgcagaatgg gcgggatatg tacgtggacc   3480
aggaactgga catcaaccgg ctgtccgact acgatgtgga cgctatcgtg cctcagagct   3540
ttctgaagga cgactccatc gacaacaagg tgctgaccag aagcgacaag aaccggggca   3600
agagcgacaa cgtgccctcc gaagaggtcg tgaagaagat gaagaactac tggcggcagc   3660
tgctgaacgc caagctgatt acccagaaga agttcgacaa tctgaccaag gccgagagag   3720
gcggcctgag cgaactggat aaggccggct tcatcaagag acagctggtg gaaacccggc   3780
agatcacaaa gcacgtggca cagatcctgg actcccggat gaacactaag tacgacgaga   3840
atgacaagct gatccgggaa gtgaaagtga tcacccgtga gtccaagctg tgtccgatt    3900
tccggaagga tttccagttt tacaaagtgc gcgagatcaa caactaccac cacgcccacg   3960
acgcctacct gaacgccgtc gtgggaaccg ccctgatcaa aaagtaccct aagctggaaa   4020
gcgagttcgt gtacggcgac tacaaggtgt acgacgtgcg gaagatgatc gccaagagcg   4080
agcaggaaat cggcaaggct accgccaagt acttcttcta cagcaacatc atgaacttt    4140
tcaagaccga gattaccctg gccaacggcg agatccggaa gcggcctctg atcgagacaa   4200
acggcgaaac cggggagatc gtgtgggata agggccggga ttttgccacc gtgcggaaag   4260
tgctgagcat gccccaagtg aatatcgtga aaaagaccgg ggtgcagaca ggcggcttca   4320
gcaaagagtc tatcctgccc aagaggaaca gcgataagct gatcgccaga aagaaggact   4380
gggaccctaa gaagtacggc ggcttcgaca gccccaccgt ggcctattct gtgctggtgg   4440
tggccaaagt ggaaaagggc aagtccaaga aactgaagag tgtgaaagag ctgctgggga   4500
tcaccatcat ggaagaagc agcttcgaga agaatcccat cgactttctg gaagccaagg   4560
gctacaaaga agtgaaaaag gacctgatca tcaagctgcc taagtactcc ctgttcgagc   4620
tggaaaacgg ccggaagaga atgctggcct ctgccggcga actgcagaag ggaaacgaac   4680
tggccctgcc ctccaaatat gtgaacttcc tgtacctggc cagccactat gagaagctga   4740
agggctcccc cgaggataat gagcagaaac agctgtttgt ggaacagcac aagcactacc   4800
tggacgagat catcgagcag atcagcgagt tctccaagag agtgatcctg gccgacgcta   4860
atctggacaa agtgctgtcc gcctacaaca gcaccgggta taagcccatc agagcaggg    4920
ccgagaatat catccacctg tttaccctga ccaatctggg agccctgcc gccttcaagt    4980
actttgacac caccatcgac cggaagaggt acaccagcac caaagaggtg ctggacgcca   5040
ccctgatcca ccagagcatc accggcctgt acgagacacg gatcgacctg tctcagctgg   5100
gaggtgactc tggaggatct agcggaggat cctctggcga cgagacacca ggaacaagcg   5160
agtcagcaac accagagagc agtggcggca gcagcggcgg cagcagcacc ctaaatatag   5220
aagatgagta tcggctacat gagacctcaa agagccagaa tgtttctcta gggtccacat   5280
ggctgtctga ttttcctcag gcctgggcgg aaaccggggg catgggactg gcagttcgca   5340
aagctcctct gatcatacct ctgaaagcaa cctctaccca cgtgtccata aaacaatacc   5400
ccatgtcaca agaagccaga ctggggatca agccccacat acagagactg tttggaccagg  5460
gaatatggta ccctgccagt ccccctggaa cacgccctg ctacccgtta agaaaccagg    5520
gactaatgat tataggcctg tccaggatct gagagaagtc aacaagcggg tggaagacat   5580
ccacccgcac cgtgcccaacc cttacaacct cttgagcggg ctcccaccgg cccaccagtg   5640
gtacactgtg cttgatttaa aggatgcctt tttctgcctg agactccacc ccaccagtca   5700
gcctctcttc gcctttgagt ggagagatcc agagatggga atctcaggac aattgacctg   5760
gaccagactc ccacagggtt tcaaaaacag tcccaccctg tttaatgagg cactgcacag   5820
agacctagca gacttccgga tccagcaccc agacttgatc ctgctacagt acgtggatga   5880
cttactgctg gccgccactt ctgagctaga ctgccaacag ggtactcggg ccctgttaca   5940
aaccctaggg aacctcgggt atcgggcctc ggccaagaaa gcccaaattt gccagaaaca   6000
ggtcaagtat ctgggggtatc ttctaaaaga gggtcagaga tggctgactg aggccagaaa   6060
agagactgtg atggggcagc ctactccgaa gaccccctga caactaaggg agttcctagg   6120
gaaggcaggc ttctgtcgcc tcttcatccc tgggttgca gaaatggcag cccccctgta    6180
ccctctcacc aaaccgggga ctctgtttaa ttggggccca gaccaacaaa aggcctatca   6240
agaaatcaag caagctcttc taactgcccc agccctgggg ttgccagatt tgactaagcc   6300
ctttgactc tttgtcgacg agaagcaggg ctacgccaaa ggtgtcctaa cgcaaaaact    6360
gggaccttgg cgtcggccgg tggcctacct gtccaaaaag ctagacccag tagcagctgg   6420
gtggccccct tgcctacgga tggtagcagc cattgccgta ctgacaaagg atgcaggcaa   6480
gctaaccatg ggacagccac tagtcattct ggcccccat gcagtagagg cactagtcaa    6540
acaacccccc gaccgctggc tttccaacgc ccggatgact cactatcagg ccttgcttt    6600
ggacacggac cgggtccagt tcggaccggt ggtagccctg aacccggcta cgctgctccc   6660
actgcctgag gaagggctgc aacacaactg ccttgatatc ctggccgaag cccacggaac   6720
ccgacccgac ctaacggacc agccgctccc agacgccgac cacacctggt acacggatgg   6780
aagcagtctc ttacaagagg gacagcgtaa ggcgggagct gcggtgacca ccgagaccga   6840
ggtaatctgg gctaaagccc tgccagccgg gacatccgct cagcgggctg aactgatagc   6900
actcacccag gccctaaaga tggcagaagg taagaagcta aatgtttata ctgatagccg   6960
ttatgctttt gctactgccc atatccatgg agaaatatac agaaggcgtg ggtggctcac   7020
atcagaaggc aaagagatca aaaataaaga cgagatcttg gccctactaa aagcctctt    7080
tctgcccaaa agacttagca taatccattg tccaggacat caaaagggac acagcgccga   7140
ggctagaggc aaccgatgg ctgaccaagc ggcccgaaag gcagccatca cagagactcc    7200
agacacctct accctcctca tagaaaattc atcaccctct ggcggctcaa aaagaaccgc   7260
cgacggcagc gaaaaagaa ccgctgactc tcaacattcc acacctccaa aaaccaagcg    7320
aaaagtggaa ttcgagccca agaagaagag gaaagtcgga agcggagcta ctaacttcag   7380
cctgctgaag caggctggcg acgtggagga gaacccggga cctccaaaaa agaaaagaa    7440
agtgtatccc tatgatgtcc ccgattatgc cggttcaaga gccctggtcg tgattagact   7500
gagccgagtg acagacgcca ccacaagtcc cgagagacag ctggaatcat gccagcagct   7560
ctgtgctcag cgggttggg atgtggtcgg cgtggcagga gatctggacg tgagcgggc    7620
cgtcgatcca ttcgacagaa agaggaggcc caacctggca agatggctcg ctttcgagga   7680
acagccctt gatgtgatcg tcgcctacag agtgaccccg ct caattcgaca             7740
tctccagcag ctggtgcatt gggctgagga ccacaagaaa ctggtggtca gcgcaacaga   7800
agcccacttc gatactacca caccttttgc cgctgtggtc atcgcactga tgggcactgt   7860
ggcccagatg gagctcgaag ctatcaagga gcgaacagg agcgcagccc atttcaatat    7920
tagggccggt aaatacagag ctccctgcc cccttgggga tatctcccta ccagggtgga   7980
tggggagtgg agactggtgc cagaccccgt ccagagagag cggattctgg aagtgtacca   8040
```

```
cagagtggtc gataaccacg aaccactcca tctggtggca cacgacctga atagacgcgg   8100
cgtgctctct ccaaaggatt attttgctca gctgcaggga agagagccac agggaagaga   8160
atggagtgct actgcactga agagatctat gatcagtgag gctatgctgg gttacgcaac   8220
actcaatggc aaaactgtcc gggacgatga cggagcccct ctggtgaggg ctgagcctat   8280
tctcaccaga gagcagctcg aagctctgcg ggcagaactg gtcaagacta gtcgcgccaa   8340
acctgccgtg agcaccccaa gcctgctcct gagggtgctg ttctgcgccg tctgtggaga   8400
gccagcatac aagtttgccg gcggagggcg caaacatccc cgctatcgat gcaggagcat   8460
ggggttccct aagcactgtg gaaacgggac agtggccatg gctgagtggg acgcctttg    8520
cgaggaacag gtgctggatc tcctgggtga cgctgagcgg ctggaaaaag tgtgggtggc   8580
aggatctgac tccgctgtgg agctggcaga agtcaatgcc gagctcgtgg atctgacttc   8640
cctcatcgga tctcctgcat atagagctgg gtcccacag agagaagctc tggacgcacg    8700
aattgctgca ctcgctgcta gacaggagga actggagggc ctggaggcca ggccctctgg   8760
atgggagtgg cgagaaaccg gacagaggtt tggggattgg tggagggagc aggacaccgc   8820
agccaagaac acatggctga gatccatgaa gtccggctca acattcgacg tgcgcggtgg   8880
cctgactcga accatcgatt ttggcgacct gcaggagtat gaacagcacc tgagactggg   8940
gtccgtggtc gaaagactgc acactgggat gtcctaggtt taaacccgct gatcagcctc   9000
gactgtgcct tctagttgcc agccatctgt tgtttgcccc tcccccgtgc cttccttgac   9060
cctggaaggt gccactccca ctgtcctttc ctaataaaat gaggaaattg catcgcattg   9120
tctgagtagg tgtcattcta ttctgggggg tggggtgggg caggacagca ggggggagga   9180
ttgggaagac aatagcaggc atgctgggga tgcggtgggc tctatggctt ctgaggcgga   9240
aagaaccagc tggggctcga taccgtcgac ctctagctag agcttggcgt aatcatggtc   9300
atagctgttt cctgtgtgaa attgttatcc gctcacaatt ccacacaaca tacgagccgg   9360
aagcataaag tgtaaagcct agggtgccta atgagtgagc taactcacat taattgcgtt   9420
gcgctcactg cccgctttcc agtcgggaaa cctgtcgtgc cagctgcatt aatgaatcgg   9480
ccaacgcgcg gggagaggcg gtttgcgtat gggcgctct ccgcttcct cgctcactga     9540
ctcgctgcgc tcggtcgttc ggctgcggcg agcggtatca gctcactcaa aggcggtaat   9600
acggttatcc acagaatcag gggataacgc aggaaagaac atgtgagcaa aaggccagca   9660
aaaggccagg aaccgtaaaa aggccgcgtt gctggcgttt ttccataggc tccgcccccc   9720
tgacgagcat cacaaaaatc gacgctcaag tcagaggtgg cgaaacccga caggactata   9780
aagataccag gcgtttcccc ctggaagctc cctcgtgcgc tctcctgttc cgaccctgcc   9840
gcttaccgga tacctgtccg cctttctccc ttcgggaagc gtggcgcttt ctcatagctc   9900
acgctgtagg tatctcagtt cggtgtaggt cgttcgctcc aagctgggct gtgtgcacga   9960
accccccgtt cagcccgacc gctgcgcctt atccggtaac tatcgtcttg agtccaaccc   10020
ggtaagacac gacttatcgc cactggcagc agccactggt aacaggatta gcagagcgag   10080
gtatgtaggc ggtgctacag agttcttgaa gtggtggcct aactacggct acactagaag   10140
aacagtattt ggtatctgcg ctctgctgaa gccagttacc ttcggaaaaa gagttggtag   10200
ctcttgatcc ggcaaacaaa ccaccgctgg tagcggtggt ttttttgttt gcaagcagca   10260
gattacgcgc agaaaaaaag gatctcaaga agatcctttg atcttttcta cggggtctga   10320
cgctcagtgg aacgaaaact cacgttaagg gattttggtc atgagattat caaaaaggat   10380
cttcacctag atccttttaa attaaaaatg aagttttaaa tcaatctaaa gtatatatga   10440
gtaaacttgg tctgacagtt accaatgctt aatcagtgag gcacctatct cagcgatctg   10500
tctatttcgt tcatccatag ttgcctgact ccccgtcgtg tagataacta cgatacggga   10560
gggcttacca tctggcccca gtgctgcaat gataccgcga gacccacgct caccggctcc   10620
agatttatca gcaataaacc agccagccgg aagggccgag cgcagaagtg gtcctgcaac   10680
tttatccgcc tccatccagt ctattaattg ttgccgggaa gctagagtaa gtagttcgcc   10740
agttaatagt ttgcgcaacg ttgttgccat tgctacaggc atcgtggtgt cacgctcgtc   10800
gtttggtatg gcttcattca gctccggttc ccaacgatca aggcgagtta catgatcccc   10860
catgttgtgc aaaaaagcgg ttagctcctt cggtcctccg atcgttgtca gaagtaagtt   10920
ggccgcagtg ttatcactca tggttatggc agcactgcat aattctctta ctgtcatgcc   10980
atccgtaaga tgcttttctg tgactggtga gtactcaacc aagtcattct gagaatagtg   11040
tatgcggcga ccgagttgct cttgcccggc gtcaatacgg gataataccg cgccacatag   11100
cagaacttta aaagtgctca tcattggaaa acgttcttcg gggcgaaaac tctcaaggat   11160
cttaccgctg ttgagatcca gttcgatgta acccactcgt gcacccaact gatcttcagc   11220
atcttttact ttcaccagcg tttctgggtg agcaaaaaca ggaaggcaaa atgccgcaaa   11280
aaagggaata agggcgacac ggaaatgttg aatactcata ctcttccttt ttcaatatta   11340
ttgaagcatt tatcagggtt attgtctcat gagcggatac atatttgaat gtatttagaa   11400
aaataaacaa atagggggttc cgcgcacatt tcc                               11433

SEQ ID NO: 384         moltype = DNA   length = 11056
FEATURE                Location/Qualifiers
misc_feature           1..11056
                       note = Description of Artificial Sequence: Synthetic
                       polynucleotide
source                 1..11056
                       mol_type = other DNA
                       organism = synthetic construct
SEQUENCE: 384
ccgaaaagtg ccacctgacg tcgacggatc gggagatcga tctcccgatc ccctagggtc   60
gactctcagt acaatctgct ctgatgccgc atagttaagc cagtatctgc tccctgcttg   120
tgtgttggag gtcgctgagt agtgcgcgag caaaatttaa gctacaacaa ggcaaggctt   180
gaccgacaat gcatgaaga atctgcttag ggttaggcgt tttgcgctgc ttcgcgatgt    240
acgggccaga tatacgcgtt gacattgatt attgactagt tattaatagt aatcaattac   300
ggggtcatta gttcatagcc catatatgga gttccgcgtt acataactta cggtaaatgg   360
cccgcctggc tgaccgccca acgacccccg cccattgacg tcaataatga cgtatgttcc   420
catagtaacg ccaataggga ctttccattg acgtcaatgg gtggagtatt tacggtaaac   480
tgcccacttg gcagtacatc aagtgtatca tatgccaagt acgccccta ttgacgtcaa    540
tgacggtaaa tggcccgcct ggcattatgc ccagtacatg accttatggg actttcctac   600
ttggcagtac atctacgtat tagtcatcgc tattaccatg gtgatgcggt tttggcagta   660
catcaatggg cgtggatagc ggtttgactc acggggattt ccaagtctcc accccattga   720
```

```
cgtcaatggg agtttgtttt ggcaccaaaa tcaacgggac tttccaaaat gtcgtaacaa    780
ctccgcccca ttgacgcaaa tgggcggtag gcgtgtacgg tgggaggtct atataagcag    840
agctggttta gtgaaccgtc agatccgcta gagatccgcg ccgctaata cgactcacta    900
tagggagagc cgccaccatg aaacggacag ccgacgaag cgagttcgag tcaccaaaga    960
agaagcggaa agtcgacaag aagtacagca tcggcctgga catcggcacc aactctgtgg   1020
gctgggccgt gatcaccgac gagtacaagg tgcccagcaa gaaattcaag gtgctgggca   1080
acaccgaccg gcacagcatc aagaagaacc tgatcggagc cctgctgttc gacagcggcg   1140
aaacagccga ggccacccgg ctgaagagaa ccgccgagaa aagatacacc agacggaaga   1200
accggatctg ctatctgcaa gagatcttca gcaacgagat ggccaaggtg gacgacagct   1260
tcttccacag actggaagag tccttcctgg tggaagagga taagaagcac gagcggcacc   1320
ccatcttcgg caacatcgtg gacgaggtgg cctaccacga gaagtacccc accatctacc   1380
acctgagaaa gaaactggtg gacagcaccg acaaggccga cctgcggctg atctatctgg   1440
ccctggccca catgatcaag ttccggggcc acttcctgat cgaggcgac ctgaaccccg   1500
acaacagcga cgtggacaag ctgttcatcc agctggtgca gacctacaac cagctgttcg   1560
aggaaaaccc catcaacgcc agcggcgtgg acgccaaggc catcctgtct gccagactga   1620
gcaagagcag acggctggaa aatctgatcg cccagctgcc cggcgagaag aagaatggcc   1680
tgttcggaaa cctgattgcc ctgagcctgg cctgacccc caacttcaag agcaacttcg   1740
acctggccga ggatgccaaa ctgcagctga caaggacac ctacgacgag gacctggaca   1800
acctgctggc ccagatcggc gaccagtacg ccgacctgtt tctggccgcc aagaacctgt   1860
ccgacgccat cctgctgagc gacatcctga gagtgaacac cgagatcacc aaggcccccc   1920
tgagcgcctc tatgatcaag agatacgacg agcaccacca ggacctgacc ctgctgaaag   1980
ctctcgtgcg gcagcagctg cctgaagagt acaaagagat tttcttcgac cagagcaaga   2040
acggctacgc cggctacatt gacggcgag ccagccagga agagttctac aagttcatca   2100
agcccatcct ggaaaagatg gacggcaccg aggaactgct cgtgaagctg aacagagagg   2160
acctgctgcg gaagcagcgg accttcgaca acggcagcat ccccaccag atccacctgg   2220
gagagctgca cgccattctg cggcggcagg aagattttta cccattcctg aaggacaacc   2280
gggaaaagat cgagaagatc ctgaccttcc gcatcccta ctacgtgggc cctctggcca   2340
ggggaaacag cagattcgcc tggatgacca gaaagagcga ggaaaccatc accccctgga   2400
acttcgagga agtggtggac aagggcgctt ccgcccagag cttcatcgag cggatgacca   2460
acttcgataa gaacctgccc aacgagaagg tgctgcccaa gcacagcctg ctgtacgagt   2520
acttcaccgt gtataacgag ctgaccaaag tgaaatacgt gaccgaggga atgagaaagc   2580
ccgccttcct gagcggcgag cagaaaaagg ccatcgtgga cctgctgttc aagaccaacc   2640
ggaaagtgac cgtgaagcag ctgaaagagg actacttcaa gaaaatcgag tgcttcgact   2700
ccgtggaaat ctccggcgtg gaagatcggt tcaacgcctc cctgggcaca taccacgatc   2760
tgctgaaaat tatcaaggac aaggacttcc tggacaatga agaaaacgag gacattctgg   2820
aagatatcgt gctgaccctg acactgtttg aggacagaga gatgatcgag aacggctga   2880
aaacctatgc ccacctgttc gacgacaaag tgatgaagca gctgaagcgg cggagataca   2940
ccggctgggg caggctgagc cggaagctga tcaacggcat ccgggacaag cagtccggca   3000
agacaatcct ggatttcctg aagtccgacg gcttcgccaa cagaaacttc atgcagctga   3060
tccacgacga cagcctgacc tttaaagagg acatccagaa agcccaggtg tccggccagg   3120
gcgatagcct gcacgagcac attgccaatc tggccggcag ccccgccatt aagaagggca   3180
tcctgcagac agtgaaggtg gtggacgagc tcgtgaaagt gatgggccgg cacaagcccg   3240
agaacatcgt gatcgaaatg gccagagaga accagaccac ccagaaggga cagaagaaca   3300
gccgcgagag aatgaagcgg atcgaagagg gcatcaaaga gctgggcagc cagatcctga   3360
aagaacaccc cgtggaaaac acccagctgc agaacgagaa gctgtacctg tactacctgc   3420
agaatggcgc ggatatgtac gtggaccagg aactggacat caaccggctg tccgactacg   3480
atgtggacca tatcgtgcct cagagctttc tgaaggacga ctccatcgac aacaaggtga   3540
tgaccagaag cgacaagaac cggggcaaga gcgacaacgc gccctccgaa gaggtcgtga   3600
agaagatgaa gaactactgg cggcagctgc tgaacgccaa gctgattacc cagagaaagt   3660
tcgacaatct gaccaaggcc gagagaggcg gcctgagcga actggataag gccggcttca   3720
tcaagagaca gctggtggaa acccggcaga tcacaaagca cgtggcacag atcctggatt   3780
cccggatgaa cactaagtac gacgagaatg acaagctgat ccgggaagtg aaagtgatca   3840
ccctgaagtc caagctggtg tccgatttcc ggaaggattt ccagttttac aaagtgcgcg   3900
agatcaacaa ctaccaccac gcccacgacg cctacctgaa cgccgtcgtg ggaaccgccc   3960
tgatcaaaaa gtaccctaag ctggaaagcg agttcgtgta cggcgactac aaggtgtacg   4020
acgtgcggaa gatgatcgcc aagagcgagc aggaaatcgg caaggctacc gccaagtact   4080
tcttctacag caacatcatg aacttttca agaccgagat taccctggcc aacggcgaga   4140
tccgaagcg gcctctgatc gagacaaacg gcgaaccgg ggagatcgtg tgggataagg   4200
gccgggattt tgccaccgtg cggaaagtgc tgagcatgcc ccaagtgaat atcgtgaaa   4260
agaccgaggt gcagacaggc ggcttcagca aagagtctat cctgcccaag aggaacagcg   4320
ataagctgat cgccagaaag aaggactggg accctaagaa gtacggcggc ttcgacagcc   4380
ccaccgtggc ctattctgtg ctggtggtgg ccaaagtgga aaaggcaag tccaagaaac   4440
tgaagagtgt gaaagagctg ctggggatca ccatcatgga aagaagcagc ttcgagaaga   4500
atcccatcga cttcctggaa gccaagggct acaaaaggac ctgatcatca   4560
agctgcctaa gtactccctg ttcgagctgg aaaacggccg gaagagaatg ctggcctctg   4620
ccggcgaact gcagaaggga acgaactgg ccctgccctc caaatatgtg aacttcctgt   4680
acctggccag ccactatgag aagctgaagg ctcccccga ggataatgag cagaaacagc   4740
tgtttgtgga acagcacaag cactacctgg acgagatcat cgagcagatc agcgagttct   4800
ccaagagagt gatcctggcc gacgctaatc tggacaaagt gctgtccgcc tacaacaagc   4860
accgggataa gcccatcaga gagcaggccg agaatatcat ccacctgttt accctgacca   4920
atctgggagc ccctgccgcc ttcaagtact ttgacaccac catcgaccgg aagaggtaca   4980
ccagcaccaa agaggtgctg gacgccaccc tgatccacca gagcatcacc ggcctgtacg   5040
agacacggat cgacctgtct cagctgggag gtgactctgg aggatctagc ggaggatcct   5100
ctggcagcga gacaccagga acaagcgagt cagcaacaga gcggtagcgaa   5160
cacccggtac cagtgaaagc gccacgccaa aaagcagtgg gagtgagact ccgggtacat   5220
ctgaatcagc gacaccggaa tcaagtggcg gcagcagcgg cggcagcagc acctaaata   5280
tagaagatga gtatcggcta catgagacct caaaagagcc agatgtttct ctagggtcca   5340
catggctgtc tgatttccct caggcctggg cggaaaccgg gggcatggga ctggcagttc   5400
gccaagctcc tctgatcata cctctgaaag caacctctac ccccgtgtcc ataaaacaat   5460
```

```
acccccatgtc acaagaagcc agactgggga tcaagcccca catacagaga ctgttggacc   5520
agggaatact ggtaccctgc cagtcccct ggaacacgcc cctgctaccc gttaagaaac    5580
cagggactaa tgattatagg cctgtccagg atctgagaga agtcaacaag cgggtggaag   5640
acatccaccc caccgtgccc aaccttaca acctcttgag cgggcccca ccgtcccacc     5700
agtggtacac tgtgcttgat ttaaaggatg ccttttttctg cctgagactc caccccacca  5760
gtcagcctct cttcgccttt gagtggagag atccagagat gggaatctca ggacaattga   5820
cctggaccag actcccacag ggtttcaaaa acagtcccac cctgtttaat gaggcactgc   5880
acagagacct agcagacttc cggatccagc acccagactt gatcctgcta cagtacgtgg   5940
atgacttact gctggccgcc acttctgagc tagactgaca acaaggtact cgggccctgt   6000
tacaaacct agggaacctc gggtatcggg cctcggccaa gaaagcccaa atttgccaga    6060
aacaggtcaa gtatctgggg tatcttctaa aagagggtca gagatggctg actgaggcca   6120
gaaaagagac tgtgatgggg cagcctactc cgaagacccc tcgacaacta agggagttcc   6180
tagggaaggc aggcttctgt cgcctcttca tccctgggtt tgcagaaatg gcagccccc    6240
tgtaccctct caccaaaccg gggactctgt ttaattgggg cccagaccaa caaaaggcct   6300
atcaagaaat caagcaagct cttctaactg ccccagccct ggggttgcca gatttgacta   6360
agcccttga actctttgtc gacgagaagc agggctacgc caaaggtgtc ctaacgcaaa    6420
aactgggacc ttggcgtcgg ccggtggcct acctgtccaa aaagctagac ccagtagcag   6480
ctgggtggcc cccttgccta cggatggtag cagccattgc cgtactgaca aaggatgcag   6540
gcaagctaac catgggacag ccactagtca ttctggcccc ccatgcagta gaggcactag   6600
tcaaacaacc ccccgaccgc tggctttcca acgcccggat gactcactat caggccttgc   6660
ttttggacac ggaccgggtc cagttcggac cggtggtagc cctgaacccg gctacgctgc   6720
tcccactgcc tgaggaaggg ctgcaacaca actgccttga tgggacaggt ggcggtggtg   6780
tcaccgtcaa gttcaagtac aagggtgagg aacttgaagt tgatattagc aaaatcaaga   6840
aggtttggcg cgttggtaaa atgatatctt ttacttatga cgacaacggc aagacaggta   6900
gaggggcagt gtctgagaaa gacgccccca aggagctgtt gcaaatgttg gaaaagtctg   6960
ggaaaaagtc tggcggctca aaaagaaccg ccgacggcag cgaattcgag cccaagaaga   7020
agaggaaagt cggaggtggc gggagcccaa aaaagaaaag aaaagtgtat ccctatgatg   7080
tccccgatta tgccggttca agagccctgg tcgtgattag actgagccga gtgacagacg   7140
ccaccacaag tcccgagaga cagctggaat catgccagca gctctgtgct cagcggggtt   7200
gggatgtggt cggcgtggca gaggatctgg acgtgagcgg ggcgtcgat ccattcgaca    7260
gaaagaggag gcccaacctg gcaagatggc tcgctttcga ggaacagccc tttgatgtga   7320
tcgtcgccta cagtggac cggctgaccc gctcaattcg acatctccag cagctggtgc     7380
attgggctga ggaccacaag aaactggtgg tcagcgcaac agaagcccac ttcgatacta   7440
ccacaccttt tgccgctgtg gtcatcgcac tgatggcac tgtggccag atggagctgg     7500
aagctatcaa ggagcgaaac aggagcgcag cccatttcaa tattagggcg ggtaaataca   7560
gaggctccct gccccttgg ggatatctcc ctaccaggt ggatgggag tggagactgg       7620
tgccagaccc cgtccagaga gagcggattc tggaagtgta ccacagagtg gtcgataacc   7680
acgaaccact ccatctggtg gcacacgacc tgaatagacg cggcgtgctc tctccaaagg   7740
attattttgc tcagctgcag ggaagagagc cacagggaag agaatggagt gctactgcac    7800
tgaagagatc tatgatcagt gaggctatgc tgggttacgc aacactcaat ggcaaaactg   7860
tccgggacga tgacggagcc cctctggtga gggctgagcc tattctcacc agagagcagc   7920
tcgaagctct gcgggcagaa ctggtcaaga ctagtcgcgc caaacctgcc gtgagcaccc   7980
caagcctgct cctgagggtg ctgttctgcg ccgtctgtgg agagccagca tacaagtttg   8040
ccggcgagg gcgcaaacat ccccgctatc gatgcaggag catgggggttc cctaagcact   8100
gtggaaacgg gacagtggcc atggctgagt gggacgcctt ttgcgaggaa caggtgctgg   8160
atctcctggg tgacgctgag cggctggaaa aagtgtgggt ggcaggatct gactccgctg   8220
tggagctggc agaagtcaat gccgagctcg tggatctgac ttccctcatc ggatctcctg   8280
catatagagc tgggtcccca cagagagaag ctctgacgc acgaattgct gcactgctg    8340
ctagacagga ggaactggag ggcctggagg ccaggccctc tggatgggag tggcagaaa    8400
ccggacagag gtttggggat tggtggaggg agcaggacac cgcagccaag aacacatggc   8460
tgagatccat gaatgtccgg ctcacattcg acgtgcgcgg tggcctgact cgaaccatcg   8520
attttggcga cctgcaggag tatgaacagc acctgagact ggggtccgtg gtcgaaagac   8580
tgcacactgg gatgtcctag gtttaaaccc gctgatcagc ctcgactgtg ccttctagtt   8640
gccagccatc tgttgtttgc ccctcccccg tgccttcctt gaccctggaa ggtgccactc    8700
ccactgtcct ttcctaataa aatgagaaaa ttgcatcgca ttgtctgagt aggtgtcatt   8760
ctattctggg gggtggggtg gggcaggaca gcaaggggga ggattgggaa gacaatagca   8820
ggcatgctgg ggatgcggtg ggctctatgg cttctgaggc ggaaagaacc agctggggct   8880
cgataccgtc gacctctagc tagagcttgg cgtaatcatg gtcatagctg tttcctgtgt   8940
gaaattgtta tccgctcaca attccacaca acatacgagc cggaagcata aagtgtaaag   9000
cctagggtgc ctaatgagtg agctaactca cattaattgc gttgcgctca ctgcccgctt   9060
tccagtcggg aaacctgtcg tgccagctgc attaatgaat cggccaacgc gcggggagag   9120
gcggtttgcg tattgggcgc tcttccgctt cctcgctcac tgactcgctg cgctcggtcg   9180
ttcggctgcg gcgagcggta tcagctcact caaaggcggt aatacggtta ccacagaat    9240
cagggataa cgcaggaaa acatgtgag caaaaggcca ggaaccgta                  9300
aaaaggccgc gttgctggcg ttttcccata ggctccgccc cctgacgag catcacaaaa    9360
atcgacgctc aagtcagagg tggcgaaacc cgacaggact ataaagatac caggcgttc    9420
cccctggaag ctccctcgtg cgctctcctg ttccgaccct gccgcttacc ggatacctgt   9480
ccgcctttct cccttcggga agcgtggcgc tttctcatag ctcacgctgt aggtatctca   9540
gttcgtgta ggtcgttcgc tccaagctgg gctgtgtgca cgaacccccc gttcagccccg   9600
accgctgcgc cttatccggt aactatcgtc ttgagtccaa cccggtaaga cacgacttat   9660
cgccactggc agcagccact ggtaacagga ttagcagagc gaggtatgta ggcggtgcta   9720
cagagttctt gaagtggtgg cctaactacg gctacactag aagaacagta tttggtatct   9780
gcgctctgct gaagccagtt accttcggaa aaagagttgg tagctcttga tccggcaaac   9840
aaaccaccgc tggtagcggt ggttttttgt ttgcaagca gcagattacg cgcagaaaaa    9900
aaggatctca agaagatcct ttgatctttt ctacggggtc tgacgctcag tggaacgaaa   9960
actcacgtta agggattttg gtcatgagat tatcaaaaag gatcttcacc tagatccttt  10020
taaattaaaa atgaagtttt aaatcaatct aaagtatata tgagtaaact tggtctgaca   10080
gttaccaatg cttaatcagt gaggcaccta tctcagcgat ctgtctattt cgttcatcca   10140
tagttgcctg actcccccgtc gtgtagataa ctacgatacg ggagggctta ccatctggcc   10200
```

```
ccagtgctgc aatgataccg cgagacccac gctcaccggc tccagattta tcagcaataa    10260
accagccagc cggaagggcc gagcgcagaa gtggtcctgc aactttatcc gcctccatcc    10320
agtctattaa ttgttgccgg gaagctagag taagtagttc gccagttaat agtttgcgca    10380
acgttgttgc cattgctaca ggcatcgtgg tgtcacgctc gtcgtttggt atggcttcat    10440
tcagctccgg ttcccaacga tcaaggcgag ttacatgatc ccccatgttg tgcaaaaaag    10500
cggttagctc cttcggtcct ccgatcgttg tcagaagtaa gttggccgca gtgttatcac    10560
tcatggttat ggcagcactg cataattctc ttactgtcat gccatccgta agatgctttt    10620
ctgtgactgg tgagtactca accaagtcat tctgagaata gtgtatgcgg cgaccgagtt    10680
gctcttgccc ggcgtcaata cgggataata ccgcgccaca tagcagaact ttaaaagtgc    10740
tcatcattgg aaaacgttct tcggggcgaa aactctcaag gatcttaccg ctgttgagat    10800
ccagttcgat gtaacccact cgtgcaccca actgatcttc agcatctttt actttcacca    10860
gcgtttctgg gtgagcaaaa acaggaaggc aaaatgccgc aaaaaaggga ataagggcga    10920
cacggaaatg ttgaatactc atactcttcc ttttcaata ttattgaagc atttatcagg    10980
gttattgtct catgagcgga tacatatttg aatgtattta gaaaaataaa caataggggg    11040
ttccgcgcac atttcc                                                   11056

SEQ ID NO: 385          moltype = DNA  length = 2367
FEATURE                 Location/Qualifiers
misc_feature            1..2367
                        note = Description of Artificial Sequence: Synthetic
                        polynucleotide
source                  1..2367
                        mol_type = other DNA
                        organism = synthetic construct
SEQUENCE: 385
tgttgagatc cagttcgatg taacccactc gtgcacccaa ctgatcttca gcatctttta    60
ctttcaccag cgtttctggg tgagcaaaaa caggaaggca aaatgccgca aaaaagggaa    120
taagggcgac acggaaatgt tgaatactca tactcttcct ttttcaatat tattgaagca    180
tttatcaggg ttattgtctc atgagcggat acatatttga atgtatttag aaaaataaac    240
aataggggt tccgcgcaca tttccccgaa aagtgccacc tgacgtcgct agctgtacaa    300
aaaagcaggc tttaaaggaa ccaattcagt cgactggatc cggtaccaag gtcgggcagg    360
aagagggcct atttcccatg attccttcat atttgcatat acgatacaag gctgttagag    420
agataattag aattaatttg actgtaaaca caagatatt agtacaaaat acgtgacgta    480
gaaagtaata atttcttggg tagtttgcag ttttaaaatt atgtttaaa atggactatc    540
atatgcttac cgtaacttga aagtatttcg atttcttggc tttatatatc ttgtgaaag    600
gacgaaacac cgctattctc gcagctcacc agttttagag ctagaaatag caagttaaaa    660
taaggctagt ccgttatcaa cttgaaaaag tggcaccgag tcgtgcgac gagcgcggcg    720
atatcatcat ccatggccgg atgatcctga cgacggagac cgccgtcgtc gacaagccgg    780
cctgagctgc gagaattttt ttaagcttgg gccgctcgag gtacctctct acatatgcaa    840
tgtgagcaaa aggccagcaa aaggccagga accgtaaaaa ggccgcgttg ctggcgtttt    900
tccataggct ccgcccccct gacgagcatc acaaaaatcg acgctcaagt cagaggtggc    960
gaaacccgac aggactataa agataccagg cgtttcccc tggaagctcc ctcgtgcgct    1020
ctcctgttcc gaccctgccg cttaccggat acctgtccgc ctttctccct tcgggaagcg    1080
tggcgctttc tcatagctca cgctgtaggt atctcagttc ggtgtaggtc gttcgctcca    1140
agctgggctg tgtgcacgaa ccccccgttc agcccgaccg ctgcgcctta tccggtaact    1200
atcgtcttga gtccaacccg gtaagacacg acttatcgcc actggcagca gccactggta    1260
acaggattag cagagcgagg tatgtaggcg gtgctacaga gttcttgaag tggtggccta    1320
actacggcta cactagaaga acagtatttg gtatctgcgc tctgctgaag ccagttacct    1380
tcggaaaaag agttggtagc tcttgatccg gcaaacaaac caccgctggt agcggtggtt    1440
tttttgtttg caagcagcag attacgcgca gaaaaaaagg atctcaagaa gatcctttga    1500
tcttttctac ggggtctgac gctcagtgga acgaaaactc acgttaaggg attttggtca    1560
tgagattatc aaaaaggatc ttcacctaga tccttttaaa ttaaaaatga agttttaaat    1620
caatctaaag tatatatgag taaacttggt ctgacagtta ccaatgctta atcagtgagg    1680
cacctatctc agcgatctgt ctatttcgtt catccatagt tgcctgactc cccgtcgtgt    1740
agataactac gatacgggag ggcttaccat ctggccccag tgctgcaatg ataccgcgag    1800
atccacgctc accggctcca gatttatcag caataaacca gccagccgga agggccgagc    1860
gcagaagtgg tcctgcaact ttatccgcct ccatccagtc tattaattgt tgccgggaag    1920
ctagagtaag tagttcgcca gttaatagtt tgcgcaacgt tgttgccatt gctacaggca    1980
tcgtggtgtc acgctcgtcg tttggtatgg cttcattcag ctccggttcc caacgatcaa    2040
ggcgagttac atgatccccc atgttgtgca aaaaagcggt tagctccttc ggtcctccga    2100
tcgttgtcag aagtaagttg gccgcagtgt tatcactcat ggttatggca gcactgcata    2160
attctcttac tgtcatgcca tccgtaagat gcttttctgt gactggtgag tactcaacca    2220
agtcattctg agaatagtgt atgcggcgac cgagttgctc ttgcccggcg tcaatacggg    2280
ataatacccgc gccacatagc agaactttaa aagtgctcat cattggaaaa cgttcttcgg    2340
ggcgaaaact ctcaaggatc ttaccgc                                        2367

SEQ ID NO: 386          moltype = DNA  length = 2280
FEATURE                 Location/Qualifiers
misc_feature            1..2280
                        note = Description of Artificial Sequence: Synthetic
                        polynucleotide
source                  1..2280
                        mol_type = other DNA
                        organism = synthetic construct
SEQUENCE: 386
ctccatccag tctattaatt gttgccggga agctagagta agtagttcgc cagttaatag    60
tttgcgcaac gttgttgcca ttgctacagg catcgtggtg tcacgctcgt cgtttggtat    120
ggcttcattc agctccggtt cccaacgatc aaggcgagtt acatgatccc catgttgtg    180
caaaaaagcg gttagctcct tcggtcctcc gatcgttgtc agaagtaagt tggccgcagt    240
```

```
gttatcactc atggttatgg cagcactgca taattctctt actgtcatgc catccgtaag  300
atgcttttct gtgactggtg agtactcaac caagtcattc tgagaatagt gtatgcggcg  360
accgagttgc tcttgcccgg cgtcaatacg ggataatacc gcgccacata gcagaacttt  420
aaaagtgctc atcattggaa aacgttcttc ggggcgaaaa ctctcaagga tcttaccgct  480
gttgagatcc agttcgatgt aacccactcg tgcacccaac tgatcttcag catctttttac  540
tttcaccagc gtttctgggt gagcaaaaac aggaaggcaa aatgccgcaa aaaagggaat  600
aagggcgaca cggaaatgtt gaatactcat actcttcctt tttcaatatt attgaagcat  660
ttatcagggt tattgtctca tgagcggata catatttgaa tgtatttaga aaataaaca  720
aataggggtt ccgcgcacat ttccccgaaa agtgccacct gacgtcgcta gctgtacaaa  780
aaagcaggct ttaaaggaac caattcagtc gactggatcc ggtaccaagg tcgggcagga  840
agagggccta tttcccatga ttccttcata tttgcatata cgatacaagg ctgttagaga  900
gataattaga attaatttga ctgtaaacac aaagatatta gtacaaaata cgtgacgtag  960
aaagtaataa tttcttgggt agtttgcagt tttaaaatta tgttttaaaa tggactatca 1020
tatgcttacc gtaacttgaa agtatttcga tttcttggct ttatatatct tgtggaaagt 1080
acgaaacacc gaagccggcc ttgcacatgc gttttagagc tagaaatagc aagttaaaat 1140
aaggctagtc cgttatcaac ttgaaaaagt ggcaccgagt cggtgcgttt ttttaagctt 1200
gggccgctcg aggtacctct ctacatatga catgtgagca aaaggccagc aaaaggccag 1260
gaaccgtaaa aaggccgcgt tgctggcgtt tttccatagg ctccgccccc ctgacgagca 1320
tcacaaaaat cgacgctcaa gtcagaggtg gcgaaacccg acaggactat aaagatacca 1380
ggcgtttccc cctggaagct ccctcgtgcg ctctcctgtt ccgaccctgc cgcttaccgg 1440
atacctgtcc gcctttctcc cttcgggaag cgtggcgctt tctcatagct cacgctgtag 1500
gtatctcagt tcggtgtagg tcgttcgctc caagctgggc tgtgtgcacg aaccccccgt 1560
tcagcccgac cgctgcgcct tatccggtaa ctatcgtctt gagtccaacc cggtaagaca 1620
cgacttatcg ccactggcag cagccactgg taacaggatt agcagagcga ggtatgtagg 1680
cggtgctaca gagttcttga agtggtggcc taactacggc tacactagaa gaacagtatt 1740
tggtatctgc gctctgctga agccagttac cttcggaaaa agagttggta gctcttgatc 1800
cggcaaacaa accaccgctg gtagcggtgg ttttttttgtt tgcaagcagc agattacgcg 1860
cagaaaaaaa ggatctcaag aagatccttt gatcttttct acggggtctg acgctcagtg 1920
gaacgaaaac tcacgttaag ggattttggt catgagatta tcaaaaagga tcttcaccta 1980
gatccttttta aattaaaaat gaagttttaa atcaatctaa agtatatatg agtaaacttg 2040
gtctgacagt taccaatgct taatcagtga ggcacctatc tcagcgatct gtctatttcg 2100
ttcatccata gttgcctgac tccccgtcgt gtagataact acgatacggg agggcttacc 2160
atctggcccc agtgctgcaa tgataccgcg agatccacgc tcaccggctc cagatttatc 2220
agcaataaac cagccagccg gaagggccga gcgcagaagt ggtcctgcaa ctttatccgc 2280
```

SEQ ID NO: 387           moltype = DNA   length = 6386
FEATURE                  Location/Qualifiers
misc_feature             1..6386
                         note = Description of Artificial Sequence: Synthetic
                         polynucleotide
source                   1..6386
                         mol_type = other DNA
                         organism = synthetic construct
SEQUENCE: 387

```
tgagcgcaac gcaattaatg tgagttagct cactcattag gcaccccagg ctttacactt   60
tatgcttccg gctcgtatgt tgtgtggaat tgtgagcgga taacaatttc acacaggaaa  120
cagctatgac catgagggcg gccggattcg acattgatta ttgactagtt attaatagta  180
atcaattacg gggtcattag ttcatagccc atatatggag ttccgcgtta caaacttac  240
ggtaaatggc ccgcctggct gaccgcccaa cgacccccgc ccattgacgt caataatgac  300
gtatgttccc atagtaacgc caatagggac tttccattga cgtcaatggg tggagtattt  360
acggtaaact gcccacttgg cagtacatca agtgtatcat atgccaagta cgccccctat  420
tgacgtcaat gacggtaaat ggcccgcctg gcattatgcc cagtacatga cctttatggga  480
cttttcctact tggcagtaca tctacgtatt agtcatcgct attaccatgg tcgaggtgag  540
ccccacgttc tgcttcactc tccccatctc ccccccctcc cacccccaa ttttgtattt  600
atttttttt taattatttt gtgcagcgat gggggcgggg ggggggggggg ggcgcgcgcc  660
rggsggggsg gggsgggsg rgggsgggg sgggsgagg cggagaggtg cggcggcagc  720
caatcagagc ggcgcgctcc gaaagtttcc ttttatggcg aggcggcggc ggcggcggcc  780
ctataaaaag cgaagcgcgc ggcgggcggg agtcgctgcg cgctgccttc gccccgtgcc  840
ccgctccgcc gccgcctcgc gccgcccgcc ccggctctga ctgaccgcgt tactcccaca  900
ggtgagcggg cgggacggcc cttctcctcc gggctgtaat tagcgcttgg tttaatgacg  960
gcttgttttc tttctgtggc tgcgtgaaag ccttgagggg ctccgggagg ccctttgtg  1020
cggggggagc ggctcggggg gtgcgtgcgt gtgtgtgtgc gtggggagcg ccgcgtgcgg 1080
ctccgcgctg cccggcggct gtgagcgctg cgggcgcggc gcgggctttt gtgcgctccg 1140
cagtgtgcgc gaggggagcg cggccggggg ccgtgccccg cggtgccccg gggcctgcgg 1200
ggggaacaaa ggctgcgtgc ggggtgtgtg cgtggggggg tgagcagggg gtgtgggcgc 1260
gtcggtcggg ctgcaacccc ccctgcaccc ccctccccga gttgctgagc acggcccggc 1320
ttcgggtgcg ggctccgta cggggcgtgg cgcggggctc gccgtgccgg gcgggggtg 1380
gcggcaggtg ggggtgccgg gcggggcggg gccgcctcgg gccggggagg gctcgggga 1440
gggcgcggc ggccccggc ggccggcggg ctgtcgaggc gcggcagcc gcagccattg 1500
ccttttatgg taatcgtgcg agagggcgca gggacttcct ttgtcccaaa tctgtgcgga 1560
gccgaaatct gggaggcgcc gccgcacccc tctagcgggg cgcggggcga agcggtgcgg 1620
cgccggcagg aaggaaatgg gcgggagggc cttcgtgcgt cgccgcgcc gcgtccct 1680
tctccctctc cagcctcggg gctgtccgcg ggggacggc tgcctccggg gggacgggg 1740
caggcgggg ttcggcttct ggcgtgtgac cggcggctct agagcctctg ctaaccatgt 1800
tcatgccttc ttctttttcc tacagatcct taattaataa tacgactcac tatagggggt 1860
cgacccgcca ccatgccaaa aaagaaaaga aagtgtatc cctatgatgt cccgattat 1920
gccggttcaa gagccctggt cgtgattaga ctgagccgag tgcagacgc caccacaagt 1980
cccgagagac agctggaatc atgccagcag ctctgtgctc agcggggttg ggatgtggtc 2040
ggcgtggcag aggatctgga cgtgagcggg gccgtcgatc cattcgacag aaagaggagg 2100
```

```
cccaacctgg caagatggct cgctttcgag gaacagccct ttgatgtgat cgtcgcctac 2160
agagtggacc ggctgacccg ctcaattcga catctccagc agctggtgca ttgggctgag 2220
gaccacaaga aactggtggt cagcgcaaca gaagcccact tcgatactac cacaccttt  2280
gccgctgtgg tcatcgcact gatgggcact gtggcccaga tggagctcga agctatcaag 2340
gagcgaaaca ggagcgcagc ccatttcaat attagggccg gtaaatacag aggctccctg 2400
cccccttggg gatatctccc taccaggggtg gatggggagt ggagactggt gccagacccc 2460
gtccagagag agcggattct ggaagtgtac cacagagtgg tcgataacca cgaaccactc 2520
catctggtgg cacacgacct gaatagacgc ggcgtgctct ctccaaagga ttattttgct 2580
cagctgcagg gaagagagcc acagggaaga gaatgcagtg ctactgcact gaagagatct 2640
atgatcagtg aggctatgct gggttacgca acactcaatg gcaaaactgt ccgggacgat 2700
gacggagccc ctctggtgag ggctgagcct attctcacca gagagcagct cgaagctctg 2760
cgggcagaac tggtcaagac tagtcgcgcc aaacctgccg tgagcacccc aagcctgctc 2820
ctgagggtgc tgttctgcgc cgtctgtgga gagccagcat acaagtttgc cggcggaggg 2880
cgcaaacatc cccgctatcg atgcaggagc atgggggttcc ctaagcactg tggaaacggg 2940
acagtggcca tggctgagtg ggacgccttt tgcgaggaac aggtgctgga tctcctgggt 3000
gacgctgagc ggctggaaaa agtgtgggtg caggatctg actccgctgt ggagctggca 3060
gaagtcaatg ccgagctcgt ggatctgact tccctcatcg gatctcctgc atatagagct 3120
gggtccccac agagagaagc tctggacgca cgaattgctg cactcgctgc tagacaggag 3180
gaactggagg gcctggaggc caggccctct ggatgggagt ggcgagaaac cggacagagg 3240
tttgggggatt ggtggaggga gcaggacacc gcagccaaga acacatggct gagatccatg 3300
aatgtccggc tcacattcga cgtgcgcggt ggcctgactc gaaccatcga ttttggcgac 3360
ctgcaggagt atgaacagca cctgagactg gggtccgtgg tcgaaagact gcacactggg 3420
atgtcctagg tcagagctcg ctgatcagcc tcgactgtgc cttctagttg ccagccatct 3480
gttgtttgcc cctcccccgt gccttccttg accctggaag gtgccactcc cactgtcctt 3540
tcctaataaa atgaggaaat tgcatcgcat tgtctgagta ggtgtcattc tattctgggg 3600
ggtggggtgg ggcaggacag caaggggggag gattgggaag acaatagcag gcatgctggg 3660
gatgcggtgg gctctatggc ttctgaggcg gaaagaacca gctggggctc gagatccact 3720
agttctagcc tcgaggctag agcggccgcc actggccgtc gttttacaac gtcgtgactg 3780
ggaaaaccct ggcgttaccc aacttaatcg ccttgcagca catccccctt tcgccagctg 3840
gcgtaatagc gaagaggccc gcaccgatcg cccttcccaa cagttgcgca gcctgaatgg 3900
cgaatgggac gcgccctgta gcggcgcatt aagcgcggcg ggtgtggtgg ttacgcgcag 3960
cgtgaccgct acacttgcca gcgccctagc gcccgctcct ttcgctttct tcccttcctt 4020
tctcgccacg ttcgccggct ttccccgtca gctctaaat cggggggctcc ctttagggtt 4080
ccgatttagt gctttacggc acctcgaccc caaaaaactt gattagggtg atggttcacg 4140
tagtgggcca tcgccctgat agacggtttt tcgccctttg acgttggagt ccacgttctt 4200
taatagtgga ctcttgttcc aaactggaac aacactcaac cctatctcgg tctattcttt 4260
tgatttataa gggattttgc cgatttcggc ctattggtta aaaaatgagc tgatttaaca 4320
aaaatttaac gcgaatttta acaaaatatt aacgcttacr mktymsrtks smcwttymgg 4380
sgaaatgtgc gcggaacccc tatttgttta tttttcttaaa tacattcaaa tatgtatccg 4440
ctcatgagac aataaccctg ataaatgctt caataatatt gaaaaaggaa gagtatgagt 4500
attcaacatt tccgtgtcgc ccttattccc ttttttgcgg cattttgcct tcctgttttt 4560
gctcacccag aaacgctggt gaaagtaaaa gatgctgaag atcagttggg tgcacgagtg 4620
ggttacatcg aactggatct caacagcggt aagatcttg agagttttcg ccccgaagaa 4680
cgttttccaa tgatgagcac ttttaaagtt ctgctatgtg gcgcggtatt atcccgtatt 4740
gacgccgggc aagagcaact cggtcgccgc atacactatt ctcagaatga cttggttgag 4800
tactcaccag tcacagaaaa gcatcttacg gatggcatga cagtaagaga attatgcagt 4860
gctgccataa ccatgagtga taacactgcg gccaacttac ttctgacaac gatcggagga 4920
ccgaaggagc taaccgcttt tttgcacaac atgggggatc atgtaactcg ccttgatcgt 4980
tgggaaccgg agctgaatga agccatacca aacgacgagc gtgacaccac gatgcctgta 5040
gcaatggcaa caacgttgcg caaactatta actggcgaac tacttactct agcttcccgg 5100
caacaattaa tagactggat ggaggcggat aaagttgcag gaccacttct gcgctcgccc 5160
cttccggctg gctggtttat tgctgataaa tctggagccg gtgagcgtgg gtctcgcggt 5220
atcattgcag cactggggcc agatggtaag ccctcccgta tcgtagttat ctacacgacg 5280
gggagtcagg caactatgga tgaacgaaat agacagatcg ctgagatagg tgcctcactg 5340
attaagcatt ggtaactgtc agaccaagtt tactcatata tactttagat tgatttaaaa 5400
cttcattttt aatttaaaag gatctaggtg aagatccttt ttgataatct catgaccaaa 5460
atcccttaac gtgagttttc gttccactga gcgtcagacc ccgtagaaaa gatcaaagga 5520
tcttcttgag atcctttttt tctgcgcgta atctgctgct tgcaaacaaa aaaaccaccg 5580
ctaccagcgg tggtttgttt gccggatcaa gagctaccaa ctcttttttcc gaaggtaact 5640
ggcttcagca gagcgcagat accaaatact gttcttctag tgtagccgta gttaggccac 5700
cacttcaaga actctgtagc accgcctaca tacctcgctc tgctaatcct gttaccagtg 5760
gctgctgcca gtggcgataa gtcgtgtctt accgggttgg actcaagacg atagttaccg 5820
gataaggcgc agcggtcggg ctgaacgggg gttcgtgcac acagcccag cttggagcga 5880
acgacctaca ccgaactgag atacctacag cgtgagctat gagaaagcgc cacgcttccc 5940
gaagggagaa aggcggacag gtatccggta agcggcaggg tcggaacagg agagcgcacg 6000
agggagcttc caggggggaaa cgcctggtat ctttatagtc ctgtcgggtt cgccacctc  6060
tgacttgagc gtcgattttt gtgatgctcg tcagggggggc ggagcctatg gaaaaacgcc 6120
agcaacgcgg cctttttacg gttcctggcc ttttgctggc cttttgctca catgttcttt 6180
cctgcgttat cccctgattc tgtggataac cgtattaccg cctttgagtg agctgatacc 6240
gctcgccgca gccgaacgac cgagcgcagc gagtcagtga gcgaggaagc ggaagagcgc 6300
ccaatacgca aaccgcctct ccccgcgcgt tggccgattc attaatgcag ctggcacgac 6360
aggtttcccg actggaaagc gggcag                                      6386

SEQ ID NO: 388      moltype = DNA  length = 6317
FEATURE             Location/Qualifiers
misc_feature        1..6317
                    note = Description of Artificial Sequence: Synthetic
                    polynucleotide
source              1..6317
```

```
                mol_type = other DNA
                organism = synthetic construct
SEQUENCE: 388
gattcgacat tgattattga ctagttatta atagtaatca attacggggt cattagttca    60
tagcccatat atggagttcc gcgttacata acttacggta aatggcccgc ctggctgacc   120
gcccaacgac ccccgcccat tgacgtcaat aatgacgtat gttcccatag taacgccaat   180
agggactttc cattgacgtc aatgggtgga gtatttacgg taaactgccc acttggcagt   240
acatcaagtg tatcatatgc caagtacgcc ccctattgac gtcaatgacg gtaaatggcc   300
cgcctggcat tatgcccagt acatgacctt atgggacttt cctacttggc agtacatcta   360
cgtattagtc atcgctatta ccatggtcga ggtgagcccc acgttctgct tcactctccc   420
catctccccc cctcccccac cccaatttt gtatttattt attttttaat tattttgtgc   480
agcgatgggg gcggggggg gggggggcg cgcgccrggs ggggsggggs ggggsgrggg   540
gsggggsggg gsgaggcgga gaggtgcggc ggcagccaat cagagcggcg cgctccgaaa   600
gttttccttt atggcgaggc ggcggccggcg gcggcccctat aaaaagcgaa gcgcgcggcg   660
ggcgggagtc gctgcgcgct gccttcgccc cgtgccccgc tccgccgccg cctcgccgcc   720
cccgccccgg ctctgactga ccgcgttact cccacaggtg agcgggcggg acggcccttc   780
tcctccgggc tgtaattagc gcttggttta atgacggctt gtttcttttc tgtggctgcg   840
tgaaagcctt gagggggtcc gggaggggcc tttgtgcggg ggagcggct cgggggtgc   900
gtgcgtgtgt gtgtgcgtgg ggagcgccgc gtgcggctcc gcgctgcccg cggctgtga   960
gcgctgcggg cgcggcgcgg ggctttgtgc gctccgcagt gtgcgcgagg ggagcgcggc  1020
cggggcggt gccccgcggt gcgggggggg ctgcgagggg aacaaaggct gcgtgcgggg  1080
tgtgtgcgtg gggggtgag cagggggtgt gggcgcgtcg gtcgggctgc aacccccct   1140
gcaccccct ccccgagttg ctgagcacgg cccggcttcg ggtgcggggc tccgtacggg  1200
gcgtggcgcg gggctcgccg tgccgggcgg ggggtgcgg caggtggggg tgccgggcgg  1260
ggcggggccg cctcggccg gggagggctc ggggagggg cgcggcggcc cccggagcgc  1320
cggcggctgt cgaggcgcgg cgagccgcag ccattgcctt ttatggtaat cgtgcgagag  1380
ggcgcaggga cttcctttgt cccaaatctg tgccgagccg aaatctggga ggcgccgccg  1440
cacccctct agcgggcgcg gggcgaagcg gtgcggcgcc ggcaggaagg aaatgggcgg  1500
ggagggcctt cgtgcgtcgc cgcgccgccg tccccttctc cctctccagc ctcggggctg  1560
tccgcgggg gacggctgcc ttcggggggg acggggcagg gcggggtttcg gcttctggcg  1620
tgtgaccggc ggctctagag cctctgctaa ccatgttcat gccttcttct ttttcctaca  1680
gatccttaat taataatacg actcactata ggggtcgac ccgccaccat gacagccgca  1740
aagaaaaaga ggaaggtcat gaccaagaaa gtggccatct atactagagt gagcacaacg  1800
aatcaggccg aggaggggtt ctctattgac gagcaaatca atcgtctgac caagtacgcg  1860
gaagcaatgg gctggcaagt cagcgacact tacaccgatg ctgggttctc cggcgccaaa  1920
ctggaaaggc ctgccatgca gcggctgatt aacgacattg agaacaaggc ctttgataca  1980
gtgctcgtat acaagctcga caggctcagc cgatctgtgc gggacacgct ttacctcgta  2040
aaggatgttt tcactaagaa taaaatcgac ttcattagcc tgaacgaatc cattgacacc  2100
agctcagcta tgggctctct gttcctgacc atcctgacg ctatcaatga gtttgagagg  2160
gagaatataa aggagcgcat gacaatggga aagctgggta gagcgaagtc cgggaaatct  2220
atgatgtgga ccaagaccgc ttttggatac taccacaata ggaagacggg cattctggag  2280
atcgtgccct tgcaggcaac catcgttgag cagatcttca ccgactacct gagcggaata  2340
tctctcacga agttgcgaga taagctgaat gagagcgaac acattggcaa ggatattcct  2400
tggtcatata gaaccctccg ccaaactctg gataatccgg tgtactgcgg ttacatcaag  2460
ttcaaagaca gcctcttcga gggaatgcat aaacctatca ttccatacga gacatacctg  2520
aaagtccaaa aggaactcga agagcgccag caacagactt acgaacggaa taataatccc  2580
aggcctttcc aggccaaata tatgctgtcc ggcatgcaga gatgcggata ctgcggggca  2640
ccactcaaga ttgtgcttgg ccataaacg aaggatggaa gcagaaccat gaaatatcac  2700
tgcgcaaacc gctttccaag gaaaacgaag gggattaccg tgtacaatga caacaaaaaa  2760
tgtgatagcg gaacctacga tctgtccaac ttggaaaaca ccgtcattga caatttaatt  2820
ggatttcagg aaaataatga cagccttctg aagattatca aaccgaacaa tcagccgatt  2880
ctggacactt catcttcaa aaaacagatc tctcagattg ataagaaaat tcagaaaaat  2940
tccgatttat acctcaatga tttcataacg atggatgagc tgaaggaccg gaccgacagt  3000
ttgcaggcca agaagaaact gctgaaagca aagatctccg agaacaagtt caatgacagt  3060
accgatgtct tcgagttggt gaagaccag ctgggtagta tcccaatcaa cgagttgagc  3120
tatgacaata gaagaagat tgttaataac ctggtgagca aagtggacgt gaccgctgat  3180
aacgtggata ttatcttcaa gttccagctg gcctgagtca gagctcgctg atcagcctcg  3240
actgtgcctt ctagttgcca gccatctgtt gtttgcccct ccccgtgcc ttccttgacc  3300
ctggaaggtg ccactccac tgtcctttcc taataaaatg aggaaattgc atcgcattgt  3360
ctgagtaggt gtcattctat tctgggggt ggggtggggc aggacagcaa gggggaggat  3420
tgggaagaca atagcaggca tgctgggat gcgtgggct ctatggcttc tgaggcggaa  3480
agaaccagct ggggctcgag atccactagt tctagcctcg aggctagagc ggcgccact  3540
ggccgtcgtt ttacaacgtc gtgactggga aaaccctggc gttacccaac ttaatcgcct  3600
tgcagcacat ccccctttcg ccagctggcg taatagcgaa gaggcccgca ccgatcgccc  3660
ttcccaacag ttgcgcagcc tgaatggcga atgggacgcg ccctgtagcg gcgcattaag  3720
cgcggcgggt gtggtggtta cgcgcagcgt gaccgctaca cttgccagcg ccctagcgcc  3780
cgctcctttc gctttcttcc cttcctttct cgccacgttc gccggctttc cccgtcaagc  3840
tctaaatcgg gggctccctt tagggttccg atttagtgct ttacggcacc tcgaccccaa  3900
aaaacttgat tagggtgatg gttcacgtag tgggccatcg ccctgataga cggtttttcg  3960
cccctttgacg ttggagtcca cgttctttaa tagtggactc ttgttccaaa ctggaacaac  4020
actcaaccct atctcggtct attctttga tttataaggg attttgccga tttcggccta  4080
ttggttaaaa aatgagctga tttaacaaaa atttaacgcg aattttaaca aaatattaac  4140
gcttacrmkt ymsrtkssmc wttymggsga aatgtgcgcg gaacccctat ttgtttattt  4200
ttctaaatac attcaaatat gtatccgctc atgagacaat aaccctgata aatgcttcaa  4260
taatattgaa aaaggaagag tatgagtatt caacatttcc gtgtcgccct tattcccttt  4320
tttgcgcat tttgccttcc tgttttgct cacccagaaa cgctggtgaa agtaaaagat  4380
gctgaagatc agttgggtgc acgagtgggt tacatcgaac tggatctcaa cagcggtaag  4440
atccttgaga gttttcgccc cgaagaacgt tttccaatga tgagcacttt taagttctg  4500
ctatgtggcg cggtattatc ccgtattgac gccgggcaag agcaactcgg tcgccgcata  4560
```

```
cactattctc agaatgactt ggttgagtac tcaccagtca cagaaaagca tcttacggat   4620
ggcatgacag taagagaatt atgcagtgct gccataacca tgagtgataa cactgcggcc   4680
aacttacttc tgacaacgat cggaggaccg aaggagctaa ccgcttttt gcacaacatg    4740
ggggatcatg taactcgcct tgatcgttgg aaccggagc tgaatgaagc cataccaaac    4800
gacgagcgtg acaccacgat gcctgtagca atggcaacaa cgttgcgcaa actattaact   4860
ggcgaactac ttactctagc ttcccggcaa caattaatag actggatgga ggcggataaa   4920
gttgcaggac cacttctgcg ctcggccctt ccggctggct ggtttattgc tgataaatct   4980
ggagccggtg agcgtgggtc tcgcggtatc attgcagcac tggggccaga tggtaagccc   5040
tcccgtatcg tagttatcta cacgacgggg agtcaggcaa ctatggatga acgaaataga   5100
cagatcgctg agataggtgc ctcactgatt aagcattggt aactgtcaga ccaagtttac   5160
tcatatatac tttagattga tttaaaactt cattttaat ttaaaaggat ctaggtgaag    5220
atccttttg ataatctcat gaccaaaatc ccttaacgtg agttttcgtt ccactgagcg    5280
tcagacccg tagaaaagat caaaggatct tcttgagatc ctttttttct gcgcgtaatc    5340
tgctgcttgc aaacaaaaaa accaccgcta ccagcggtgg tttgtttgcc ggatcaagag   5400
ctaccaactc ttttccgaa ggtaactggc ttcagcagag cgcagatacc aaatactgtt    5460
cttctagtgt agccgtagtt aggccaccac ttcaagaact ctgtagcacc gcctacatac   5520
ctcgctctgc taatcctgtt accagtggct gctgccagtg gcgataagtc gtgtcttacc   5580
gggttggact caagacgata gttaccggat aaggcgcagc ggtcgggctg aacgggggt    5640
tcgtgcacac agcccagctt ggagcgaacg acctacaccg aactgagata cctacagcgt   5700
gagctatgag aaagcgccac gcttcccgaa gggagaaagg cggacaggta tccggtaagc   5760
ggcagggtcg gaacaggaga gcgcacgagg gagcttccag ggggaaacgc ctggtatctt   5820
tatagtcctg tcgggtttcg ccacctctga cttgagcgtc gatttttgtg atgctcgtca   5880
gggggggcgga gcctatgaa aaacgccagc aacgcggcct ttttacggtt cctggccttt   5940
tgctggcctt ttgctcacat gttctttcct gcgttatccc ctgattctgt ggataaccgt   6000
attaccgcct ttgagtgagc tgataccgct cgccgcagcc gaacgaccga gcgcagcgag   6060
tcagtgagcg aggaagcgga agagcgccca atacgcaaac cgcctctccc cgcgcgttgg   6120
ccgattcatt aatgcagctg gcacgacagg tttcccgact ggaaagcggg cagtgagcgc   6180
aacgcaatta atgtgagtta gctcactcat taggcacccc aggctttaca ctttatgctt   6240
ccggctcgta tgttgtgtgg aattgtgagc ggataacaat ttcacacagg aaacagctat   6300
gaccatgagg cgcgccg                                                  6317
```

SEQ ID NO: 389          moltype = DNA   length = 6638
FEATURE                 Location/Qualifiers
misc_feature            1..6638
                        note = Description of Artificial Sequence: Synthetic
                         polynucleotide
source                  1..6638
                        mol_type = other DNA
                        organism = synthetic construct
SEQUENCE: 389

```
gattcgacat tgattattga ctagttatta atagtaatca attacggggt cattagttca    60
tagcccatat atggagttcc gcgttacata acttacggta aatggcccgc ctggctgacc   120
gcccaacgac ccccgcccat tgacgtcaat aatgacgtat gttcccatag taacgccaat   180
agggactttc cattgacgtc aatgggtgga gtatttacgg taaactgccc acttggcagt   240
acatcaagtg tatcatatgc caagtacgcc ccctattgac gtcaatgacg gtaaatggcc   300
cgcctggcat tatgcccagt acatgacctt atgggacttt cctacttggc agtacatcta   360
cgtattagtc atcgctatta ccatggtcga ggtgagcccc acgttctgct tcactctccc   420
catctccccc cctcccac ccccaatttt gtatttattt attttttaat tattttgtgt       480
agcgatgggg gcggggggg gggggggcg cgcgccrggs ggggsgggs gggsrggg         540
gsgggsggg gsgaggcgga gaggtgcggc ggcagccaat cagagcggcg cgctccgaaa    600
gtttccttt atggcgaggc ggcggcggcg gcggccctat aaaaagcgaa gcgcgcggcg    660
ggcgggagtc gctgcgcgct gccttcgccc cgtgccccgc tccgccgccg cctcgcgccg   720
cccgcccgg ctctgactga ccgcgttact cccacaggtg agcgggcggg acggcccttc    780
tcctccggc tgtaattagc gcttggttta atgacggctt gtttcttttc tgtggctgcg    840
tgaaagcctt gaggggctcc gggagggccc ttttgtgggg gagcggctt cgggggtgc     900
gtgcgtgtgt gtgtgcgtgg ggagcgccgc gtgcggctcc gcgctgcccg gcggctgtga   960
gcgctgcggg cgcggcgcgg ggctttgtgc gctccgcagt gtgcgcgagg ggagcgcggc  1020
cggggggcggt gccccgcggt gcgggggggg ctgcgagggg aacaaaggct gcgtgcgggg  1080
tgtgtgcgtg ggggggtgag cagggggtgt gggcgcgtcg gtcgggctgc aacccccct   1140
gcaccccct cccgagttg ctgagcacgg cccggcttcg ggtgcggtgc tccgtacggg    1200
gcgtggcgcg gggctcgccg tgccgggcgg ggggtggcgg caggtggggg tgccgggcgg  1260
ggcggggccg cctcgggccg gggagggctc ggggagggg cgcggcggcc ccggagcgc    1320
cggcggctgt cgaggcgcgg cgagccgcag ccattgcctt ttatggtaat cgtgcgagag  1380
ggcgcaggga cttccttgt cccaaatctg tgcggagccg aaatctggga gccgctgctgc 1440
caccccctct agcggggcg gggcgaagcg gtgcggcgcc ggcaggaagg aaatgggcgg  1500
ggagggcctt cgtgcgtcgc cgcgccgccg tcccttctc cctctccagc ctcggggctg  1560
tccgcgggg gacggctgcc ttcggggggg acggggcagg gcggggttcg gcttctggcg  1620
tgtgaccggc ggctctagag cctctgctaa ccatgttcat gccttcttct tttccctaca  1680
gatccttaat taataatacg actcactata ggggtcgac ccgccaccat gcccaagaag   1740
aaacggaaag tgatgagccc ctttatcgcc ccggacgtgc ccgagcacct cctggacact  1800
gtgcgcgtct ttctgtacgc ccgtcagagt aaaggacggt cagatggatc tgacgtgtcc  1860
accgaagcac agctcgctgc cggacgggcc cttgttgcct caagaaacgc acaaggggga  1920
gctagatggg tggtggcggg cgaattcgtg gatgtgggca gatcagggtg ggacccgaat  1980
gtgacacgcg ccgacttcga aagaatgatg ggcagacgta gggagacgta                2040
gtggtggtta atgaactgag tcgccttacg aggaagggcg cccacgacgc tctgagatc    2100
gataacgaac tcaaaaaaca cggtgtgcgg ttcatgagcg tgctggaacc attcctggat  2160
accagcaccc caatcggtgt cgcgatcttt gccctgattg ccgcgctcgc taaacaggat  2220
tcagaccta aagctgagcg gctgaagggg gctaaagatg agatcgctgc cttgggggt    2280
gtgcacagct catctgcgcc attcggcatg agggcggtca gaagagaagt ggataacctg  2340
```

```
gtcatatctg ttctggagcc tgatgaggac aacccggacc acgttgagct tgtggaacgg   2400
atggctaaga tgtctttcga aggcgtcagc gataacgcaa ttgccacaac atttgagaag   2460
gagaaaatcc cctctccggg gatggctgag agacgagcca cggagaagag gcttgcttct   2520
attaaggcac ggaggctcaa tggcgccgaa aagccgatca tgtggcgggc gcagacagtt   2580
agatggattc ttaaccatcc cgcgattggt ggattcgcat tcgagcgggt gaaacacgga   2640
aaagcccaca tcaacgtgat acgaagagat cccggcggca aaccccttac ccctcacact   2700
ggtatcctgt ctggatccaa gtggttgaaa ctccaggaga agagaagcgg gaaaaatctc   2760
tccgaccgca aaccaggtgc cgaagtggaa cctacgctgc tttccgggtg gagatttctg   2820
ggatgtcgga tatgcggtgg gtcaatgggc cagtcccaag ggggccgtaa gaggaatggg   2880
gacttggctg agggcaatta catgtgtgca aacccaaagg ggcacggcgg tctgagcgtc   2940
aagaggtctg agcttgatga attcgtggca tcaaaagtct gggccaggtt gcgcacggct   3000
gacatggagg atgaacatga ccaagcatgg attgcagctg cagctgaacg gtttgctttg   3060
cagcacgacc tggcggggt agctgacgag cgacgggagc aacaagctca cctggataac   3120
gttcggagat caataaaaga tctccaggcg gataggaagg caggtctcta cgtgggacgc   3180
gaagaactgg agacctggcg cagtaccgtc ctgcaatata ggagctacga ggctgagtgt   3240
actactaggt tggctgagct ggatgaaaaa atgaatggat ccacccgggt gccttcagaa   3300
tggtttagcg gcgaggaccc aaccgcgaaa ggaggcatat gggcgagctg gatgtctat   3360
gagcgccggg agtttctcag cttttttttg gactccgtaa tggttgacag gggcagacat   3420
cctgaaacca agaaatatat accattgaaa gaccgggtga ccttaaagtg ggcggagctg   3480
ttaaaggaag aggatgaagc aagcgaggcc acagaacggg agctggcagc tctttaggtc   3540
agagctcgct gatcagcctc gactgtgcct tctagttgcc agccatcgt tgtttgcccc   3600
tccccgtgc cttccttgac cctggaaggt gccactccca ctgtcctttc ctaataaaat   3660
gaggaaattg catcgcattg tctgagtagg tgtcattcta ttctgggggg tggggtgggg   3720
caggacagca agggggagga ttgggaagac aatagcaggc atgctgggga tgcggtgggc   3780
tctatggctt ctgaggcgga aagaaccagc tggggctcga gatccactag ttctagcctc   3840
gaggctagag cggccgccac tggccgtcgt tttacaacgt cgtgactggg aaaaccctgg   3900
cgttacccaa cttaatcgcc ttgcagcaca tccccctttc gccagctggc gtaatagcga   3960
agaggcccgc accgatcgcc cttcccaaca gttgcgcagc ctgaatggcg aatgggacgc   4020
gccctgtagc ggcgcattaa gcgcggcggg tgtggtggtt acgcgcagcg tgaccgctac   4080
acttgccagc gccctagcgc ccgctccttt cgctttcttc ccttcctttc tcgccacgtt   4140
cgccggcttt ccccgtcaag ctctaaatcg ggggctccct ttagggttcc gatttagtgc   4200
tttacgcac ctcgaccca aaaaacttga ttagggtgat ggttcacgta gtgggccatc   4260
gccctgatag acggttttc gccctttgac gttggagtcc acgttcttta atagtggact   4320
cttgttccaa actggaacaa cactcaaccc tatctcggtc tattcttttg atttataagg   4380
gattttgccg atttcggcct attggttaaa aaatgagctg atttaacaaa aatttaacgc   4440
gaattttaac aaaatattaa cgcttacrmk tymsrtkssm cwttymggsg aaatgtgcgc   4500
ggaacccta tttgtttatt tttctaaata cattcaaata tgtatccgct catgagacaa   4560
taaccctgat aaatgcttca ataatattga aaaaggaaga gtatgagtat tcaacatttc   4620
cgtgtcgccc ttattccctt ttttgcggca ttttgccttc ctgttttgc tcacccagaa   4680
acgctggtga agtaaaaga tgctgaagat cagttgggtg cacgagtggg ttacatcgaa   4740
ctggatctca acagcggtaa gatccttgag agttttcgcc ccgaagaacg ttttccaatg   4800
atgagcactt ttaaagttct gctatgtggc gcggtattat cccgtattga cgccgggcaa   4860
gagcaactcg gtcgccgcat acactattct cagaatgact tggttgagta ctcaccagtc   4920
acagaaaagc atcttacgga tggcatgaca gtaagagaat tatgcagtgc tgccataacc   4980
atgagtgata acactgcggc caacttactt ctgacaacga tcggaggacc gaaggagcta   5040
accgcttttt tgcacaacat ggggatcat gtaactcgcc ttgatcgttg gaaccggag   5100
ctgaatgaag ccataccaaa cgacgagcgt gacaccacga tgcctgtagc aatggcaaca   5160
acgttgcgca aactattaac tggcgaacta cttactctag cttcccggca acaattaata   5220
gactggatga aggcggataa agttgcagga ccacttctgc gctcggccct tccggctggc   5280
tggtttattg ctgataaatc tggagccggt gagcgtgggt ctcgcggtat cattgcagca   5340
ctggggccag atggtaagcc ctcccgtatc gtagttatct acacgacggg gagtcaggca   5400
actatgatg aacgaaatag acagatcgct gagataggtg cctcactgat taagcattgg   5460
taactgtcag accaagttta ctcatatata ctttagattg atttaaaact tcattttaa   5520
tttaaagga tctaggtgaa gatcctttt gataatctca tgaccaaaat cccttaacgt   5580
gagttttcgt tccactgagc gtcagacccc gtagaaaaga tcaaaggatc ttcttgagat   5640
cctttttttc tgcgcgtaat ctgctgcttg caaacaaaaa aaccaccgct accagcggtg   5700
gtttgtttgc cggatcaaga gctaccaact cttttccga aggtaactgg cttcagcaga   5760
gcgcagatac caaatactgt tcttctagtg tagccgtagt taggccacca cttcaagaac   5820
tctgtagcac cgcctacata cctcgctctg ctaatcctgt taccagtggc tgctgccagt   5880
ggcgataagt cgtgtcttac cgggttggac tcaagacgat agttaccgga taaggcgcag   5940
cggtcgggct gaacggggg ttcgtgcaca cagcccagct tggagcgaac gacctacacc   6000
gaactgagat acctacagcg tgagctatga gaaagcgcca cgcttcccga agggagaaag   6060
gcggacaggt atccggtaag cggcagggtc ggaacaggag agcgcacgag ggagcttcca   6120
gggggaaacg cctggtatct ttatagtcct gtcgggtttc gccacctctg acttgagcgt   6180
cgatttttgt gatgctcgtc aggggggcgg agcctatgga aaaacgccag caacgcggcc   6240
tttttacggt tcctggcctt ttgctggcct tttgctcaca tgttctttcc tgcgttatcc   6300
cctgattctg tggataaccg tattaccgcc tttgagtgag ctgataccgc tcgccgcagc   6360
cgaacgaccg agcgcagcga gtcagtgagc gaggaagcgg aagagcgccc aatacgcaaa   6420
ccgcctctcc ccgcgcgttg gccgattcat taatgcagct ggcacgacag gtttcccgac   6480
tggaaagcgg gcagtgagcg caacgcaatt aatgtgagtt agctcactca ttaggcaccc   6540
caggctttac actttatgct tccggctcgt atgttgtgtg gaattgtgag cggataacaa   6600
tttcacacag gaaacagcta tgaccatgag gcgcgccg                          6638
```

SEQ ID NO: 390        moltype = DNA   length = 9530
FEATURE              Location/Qualifiers
misc_feature      1..9530
                       note = Description of Artificial Sequence: Synthetic
                       polynucleotide
source               1..9530

```
                mol_type = other DNA
                organism = synthetic construct
SEQUENCE: 390
taatcagcat catgatgtgg taccacatca tgatgctgat tataagaatg cggccgccac   60
actctagtgg atctcgagtt aataattcag aagaactcgt caagaaggcg atagaaggcg  120
atgcgctgcg aatcgggagc ggcgatacgc taaagcacga ggaagcggtc agcccattcg  180
ccgccaagct cttcagcaat atcacgggta gccaacgcta tgtcctgata gcggtccgcc  240
acacccagcc ggccacagtc gatgaatcca gaaaagcggc cattttccac catgatattc  300
ggcaagcagg catcgccatg ggtcacgacg agatcctcgc cgtcgggcat gctcgccttg  360
agcctggcga acagttcggc tggcgcgagc ccctgatgct cttcgtccag atcatcctga  420
tcgacaagac cggcttccat ccgagtacgt gctcgctcga tgcgatgttt cgcttggtgg  480
tcgaatgggc aggtagccgg atcaagcgta tgcagccgcc gcattgcatc agccatgatg  540
gatactttct cggcaggagc aaggtgtaga tgacatggaa atcctgcccc ggcacttcgc  600
ccaatagcag ccagtccctt cccgcttcag tgacaacgtc gagcacagct gcgcaaggaa  660
cgcccgtcgt ggccagccac gatagccgcg ctgcctcgtc ttgcagttca ttcagggcac  720
cggacaggtc ggtcttgaca aaaagaaccg ggcgcccctg cgctgacagc cggaacacgg  780
cggcatcaga gcagccgatt gtctgttgtg cccagtcata gccgaatagc ctctccaccc  840
aagcggccgg agaacctgcg tgcaatccat cttgttcaat catgcgaaac gatcctcatc  900
ctgtctcttg atcagagctt gatccctgc gccatcagat ccttggcggc gagaaagcca  960
tccagttac tttgcagggc ttcccaacct taccagaggg cgcccagct ggcaattccg 1020
gttcgcttgc tgtccataaa accgcccagt ctagctatcg ccatgtaagc ccactgcaag 1080
ctacctgctt tctctttgcg cttgcgtttt cccttgtcca gatagcccag tagctgacat 1140
tcatccgggg tcagcaccgt ttctgcggac tggctttcta cgtgctcgag ggggccaaa 1200
cggtctccag cttggctgtt ttgcggatg agagaagatt ttcagcctga tacagattaa 1260
atcagaacga agaagcggtc tgataaaaca gaatttgcct ggcggcagta gcgcggtggt 1320
cccacctgac cccatgccga actcagaagt gaaacgccgt agcgccgatg gtagtgtggg 1380
gtctccccat gcgagagtag ggaactgcca ggcatcaaat aaaacgaaag gctcagtcga 1440
aagactgggc ctttcgtttt atctgttgtt tgtcggtgaa cgctctcctg agtaggacaa 1500
atccgccggg agcggatttg aacgttgcga agcaacggcc cggagggtgg cgggcaggac 1560
gcccgccata aactgccagg catcaaatta agcagaaggc catcctgacg gatggccttt 1620
ttgcgtttct acaaactctt ttgttttattt ttctaaatac attcaaatat gtatccgctc 1680
atgaccaaaa tcccttaacg tgagttttcg ttccactgag cgtcagaccc cgtagaaaag 1740
atcaaaggat cttcttgaga tcctttttttt ctgcgcgtaa tctgctgctt gcaaacaaaa 1800
aaaccaccgc taccagcggt ggtttgtttg ccggatcaag agctaccaac tcttttttccg 1860
aaggtaactg gcttcagcag agcgcagata ccaaatactg tccttctagt gtagccgtag 1920
ttaggccacc acttcaagaa ctctgtagca ccgcctacat acctcgctct gctaatcctg 1980
ttaccagtgg ctgctgccag tggcgataag tcgtgtctta ccgggttgga ctcaagacga 2040
tagttaccgg ataaggcgca gcggtcgggc tgaacggggg gttcgtgcac acagcccagc 2100
ttggagcgaa cgacctacac cgaactgaga tacctacagc gtgagctatg agaaagcgcc 2160
acgcttcccg aagggagaaa ggcggacagg tatccggtaa gcggcagggt cggaacagga 2220
gagcgcacga gggagcttcc agggggaaac gcctggtatc tttatagtcc tgtcgggttt 2280
cgccacctct gacttgagcg tcgatttttg tgatgctcgt caggggggcg gagcctatgg 2340
aaaaacgcca gcaacgcggc cttttttacgg ttcctggcct tttgctgcgg 2400
atgttctttc ctgcgttatc ccctgattct gtggataacc gtattaccgc ctttgagtga 2460
gctgataccg ctcgccgcag ccgaacgacc gagcgcagcg agtcagtgag cgaggaagcg 2520
gaagagcgcc tgatgcggta ttttctcctt acgcatctgt gcggtatttc acaccgcata 2580
tggtgcactc tcagtacaat ctgctctgat gccgcatagt taagccagta tacactccgc 2640
tatcgctacg tgactgggtc atggctgcgc cccgacaccc gccaacaccc gctgacgcgc 2700
cctgacgggc ttgtctgctc ccggcatccg cttacagaca agctgtgacc gtctccggga 2760
gctgcatgtg tcagaggttt tcaccgtcat caccgaaacg cgcgaggcag cagatcaatt 2820
cgcgcgcgaa ggcgaagcgg catgcataat gtgcctgtca aatgacgaaa gcagggattc 2880
tgcaaaccct atgctactcc gtcaagccgt caattgtctg attcgttacc aattatgaca 2940
acttgacggc tacatcattc acttttttctt cacaaccggc acggaactcg ctcgggctgg 3000
ccccggtgca tttttttaaat acccgcgaga aatagagttg atcgtcaaaa ccaacattgc 3060
gaccgacggt ggcgataggc atccgggtgg tgctcaaaag cagcttcgcc tggctgatac 3120
gttggtcctc gcgccagctt aagacgctaa tccctaactg ctggcggaaa agatgtgaca 3180
gacgcgacgg cgacaagcaa acatgctgtg cgacgctggc gatacattac cctgttatcc 3240
ctagatgaca ttaccctgtt atcccagatg acattaccct gttatcccta gatgacatta 3300
ccctgttatc cctagatgac atttaccctg ttatccctag atgacattac cctgttatcc 3360
cagatgacat taccctgtta tccctagata cattaccctg tatcccaga tgacataccc 3420
tgttatccct agatgacatt accctgttat cccagatgac attaccctgt tatccctaga 3480
tacattaccc tgttatccca gatgacatac cctgttatcc ctagatgaca ttaccctgtt 3540
atcccagatg acattaccct gttatcccta gatacattac cctgttatcc cagatgacat 3600
taccctgtta tccctagatga cattaccctg ttatccccaga ctgttatcc 3660
tagatacatt accctgttat cccagatgac ataccctgtt atccctagat gacattaccc 3720
tgttatccca gatgacatta ccctgttatc cctagataca ttaccctgtt atcccagatg 3780
acataccctg ttatccctag atgacattac cctgttatcc cagatgacat taccctgtta 3840
tccctagata cattaccctg ttatcccaga tgacatacc tgttatccct agatgacatt 3900
accctgttat cccagataaa ctcaatgatg atgatgatga tggtcgagac tcagcggccg 3960
cggtgccagg gcgtgccctt gggctcccgg ggcgcgacta taagctgcga gcaacttcac 4020
ttgggtatgc cggcggtagc gctgagggcc tatttcccat gattccttca tatttgcata 4080
tacgatacaa ggctgttaga gagataattg gaattaattt gactgtaaac acaaagatat 4140
tagtacaaaa tacgtgacgt agaaagtaat aatttcttgg gtagtttgca gttttaaaat 4200
tatgttttaa aatgactat catatgctta ccgtaacttg aaagtatttc gatttcttgg 4260
ctttatatat cttgtggaaa ggacgaaaca ccgggtcttc gagaagacct gttttagagc 4320
tagaaatcgt ggttcgcacc gactcggtgc cacagcaagt taaaataagg ctagtccgtt 4380
atcaacttga aaaagtggca ccgagtcggt gcttttttga attcgctagc taggtcttga 4440
aaggagtggg aattggctcc ggtgcccgtc agtgggcaga gcgcacatcg cccacagtcc 4500
ccgagaagtt gggggggaggg gtcggcaatt gatccggtgc ctagagaagg tggcgcgggg 4560
```

-continued

```
taaactggga aagtgatgtc gtgtactggc tccgccttt tcccgagggt gggggagaac  4620
cgtatataag tgcagtagtc gccgtgaacg ttctttttcg caacgggttt gccgccagaa  4680
cacaggaccg gttctagagc gctgccacca tggacaagaa gtacagcatc ggcctggaca  4740
tcggcaccaa ctctgtgggc tgggccgtga tcaccgacga gtacaaggtg cccagcaaga  4800
aattcaaggt gctgggcaac accgaccggc acagcatcaa gaagaacctg atcggagccc  4860
tgctgttcga cagcggcgaa acagccgagg ccaccggct gaagagaacc gccagaagaa  4920
gatacaccag acggaagaac cggatctgct atctgcaaga gatcttcagc aacgagatgg  4980
ccaaggtgga cgacagcttc ttccacagac tggaagagtc cttcctggtg gaagaggata  5040
agaagcacga gcggcacccc atcttcggca acatcgtgga cgaggtggcc taccacgaga  5100
agtaccccac catctaccac ctgagaaaga aactggtgga cagcaccgac aaggccgacc  5160
tgcggctgat ctatctggcc ctgcccaca tgatcaagtt ccgggccac ttcctgatcg  5220
agggcgacct gaaccccgac aacagcgacg tggacaagct gttcatccag ctggtgcaga  5280
cctacaacca gctgttcgag aaaaccccca tcaacgccag cggcgtggac gccaaggcca  5340
tcctgtctgc cagactgagc aagagcagac ggctggaaaa tctgatcgcc cagctgcccg  5400
gcgagaagaa gaatggcctg ttcggaaacc tgattgccct gagcctgggc ctgacccca  5460
acttcaagag caacttcgac ctggccgagg atgccaaact gcagctgagc aaggacacct  5520
acgacgacga cctggacaac ctgctggccc agatcggcga ccagtacgcc gacctgtttc  5580
tggccgccaa gaacctgtcc gacgccatcc tgctgagcga catcctgaga gtgaacaccg  5640
agatcaccaa ggcccccctg agcgcctcta tgatcaagag atacgacgag caccaccagg  5700
acctgaccct gctgaaagct ctcgtgcggc agcagctgcc tgagaagtac aaagagattt  5760
tcttcgacca gagcaagaac ggctacgccg gctacattga cggcggagcc agccaggaag  5820
agttctacaa gttcatcaag cccatcctgg aaaagatgga cggcaccgag gaactgctcg  5880
tgaagctgaa cagagaggac ctgctgcgga agcagcggac cttcgacaac ggcagcatcc  5940
cccaccagat ccacctggga gagctgcacg ccattctgcg gcgcaggaa gattttacc  6000
cattcctgaa ggacaaccgg aaaagatcg agaagatcct gaccttccgc atccctact  6060
acgtgggcc tctggccagg ggaaacagca gattcgctgg gatgaccaga aagagcgagg  6120
aaaccatcac cccctggaac ttcgaggaag tggtggacaa gggcgcttcc gcccagagct  6180
tcatcgagcg gatgaccaac ttcgataaga acctgcccaa cgagaaggtg ctgcccaagc  6240
acagcctgct gtacgagtac ttcaccgtgt ataacgagtc gaccaaagtg aaatacgtga  6300
ccgagggat gagaaagccc gccttcctga gcggcgaaca gaaaaagccc atcgtggacc  6360
tgctgttcaa gaccaaccgg aaagtgaccg tgaagcagct gaaagaggac tacttcaaga  6420
aaatcgagtg cttcgactcc gtggaaatct ccggcgtgga agatcggttc aacgcctccc  6480
tgggcacata ccacgatctg ctgaaaatta tcaaggacaa ggacttcctg gacaatgagg  6540
aaaacgagga cattctggaa gatatcgtgc tgaccctgac actgtttgag gacagagaga  6600
tgatcgagga acggctgaaa acctatgccc acctgttcga cgacaaagtg atgaagcagc  6660
tgaagcggcg gagatacacc ggctgggca ggctgagccg gaagctgatc aacggcatcc  6720
gggacaagca gtccggcaag acaatcctgg atttcctgaa gtccgacggc ttcgccaaca  6780
gaaacttcat gcagctgatc cacgacgaca gcctgacctt taaagaggac atccagaaag  6840
cccaggtgtc cggccagggc gatagcctgc acgagcacat tgccaatctg gccggcagcc  6900
ccgccattaa gaagggcatc ctgcagacag tgaaggtggt ggacgagctc gtgaaagtga  6960
tgggccggca aagcccgag aacatcgtga tcgaaatggc cagagagaac cagaccaccc  7020
agaagggaca gaagaacagc cgcgagagaa tgaagcggat cgaagagggc atcaaagagc  7080
tgggccgcca gatcctgaaa gaacaccccg tggaaaacac ccagctgcag aacgagaagc  7140
tgtacctgta ctacctgcag aatgggcggg atatgtacgt ggaccaggaa ctggacatca  7200
accggctgtc cgactacgat gtggaccata tcgtgcctca gagctttctg aaggacgact  7260
ccatcgacaa caaggtgctg accagaagcg acaagaaccg gggcaagagc gacaacgtgc  7320
cctccgaaga ggtcgtgaag aagatgaaga actactggcg tcagctgctg aacgccaagc  7380
tgattaccca gagaaagttc gacaatctga ccaaggccga gagaggcggc ctgagcgaac  7440
tggataaggc cggcttcatc aagagacagc tggtggaaac ccggcagatc acaaagcacg  7500
tggcacagat cctggactcc cggatgaaca ctaagtacga cgagaatgac aagctgatcc  7560
gggaagtgaa agtgatcacc ctgaagtcca agctggtgtc cgatttccgg aaggatttcc  7620
agttttacaa agtgcgcgag atcaacaact accaccacgc ccacgacgcc tacctgaacg  7680
ccgtcgtggg aaccgccctg atcaaaaagt accctaagct ggaaagcgag ttcgtgtacg  7740
gcgactacaa ggtgtacgac gtgcggaaga tgatcgccaa gagcgagcag gaaatcggca  7800
aggctaccgc caagtacttc ttctacagca acatcatgaa cttttttcaag accgagatta  7860
ccctggccaa cggcgagatc cggaagcggc ctctgatcga gacaaacggc gaaaccgggg  7920
agatcgtgtg ggataaggc cgggattttg ccaccgtgcg gaaagtgctg agcatgcccc  7980
aagtgaatat cgtgaaaaag accgaggtgc agacaggcgg cttcagcaaa gagtctatcc  8040
tgcccaagag gaacagcgat aagctgatcg ccagaaagaa ggactgggac cctaagaagt  8100
acggcggctt cgacagcccc accgtggcct attctgtgc ggtggtggcc aaagtggaaa  8160
agggcaagtc caagaaactg aagagtgtga aagagctgct ggggatcacc atcatggaaa  8220
gaagcagctt cgagaagaat cccatcgact tctggaagc aagggctac aaagaagtga  8280
aaaaggacct gatcatcaag ctgcctaagt actccctgtt cgagctggaa aacggccgga  8340
agagaatgct ggcctctgcc ggcgaactgc agaagggaaa cgaactgccc tgccctgtca  8400
aatatgtgaa cttcctgtac ctggccagcc actatgagaa gctgaagggc tcccccgagg  8460
ataatgagca gaaacagctg tttgtggaac agcacaagca ctacctggac gagatcatcg  8520
agcagatcag cgagttctcc aagagagtga tcctggccga cgctaatctg gacaaagtgc  8580
tgtccgccta caacaagcac agggataagc ccatcagaga gcagccgag aatatcatcc  8640
acctgtttac cctgaccaat ctgggagccc ctgccgcctt caagtactt gacaccacca  8700
tcgaccggaa gaggtacacc agcaccaaag aggtgctgga cgccaccctg atccaccaga  8760
gcatcaccgg cctgtacgag acacggatcg acctgtctca gctgggaggc gacaagcgac  8820
ctgccgccac aaagaaggct ggacaggcta agaagaagaa agattacaaa gacgatgacg  8880
ataagtaact agagctcgct gatcagcctc gactgtgcct tctagttgcc agccatctgt  8940
tgtttgccc tccccgtgc cttccttgac cctgaaggt gccactccca ctgtccttc  9000
ctaataaaat gaggaaattg catcgcattg tctgagtagg tgtcattcta ttctgggggg  9060
tggggtgggg caggacagca aggggagga ttgggaagaa aatagcaggc atgctgggga  9120
ctgaggcgga aagaaccagc tgtggaatgt gtgtcagtta gggtgtggaa agtccccagg  9180
ctccccagca ggcagaagta tgcaaagcat gcatctcaat tagtcagcaa ccaggtgtgg  9240
aaagtcccca ggctccccag caggcagaag tatgcaaagc atgcatctca attagtcagc  9300
```

```
aaccatagtc ccgcccctaa ctccgcccat cccgcccta actccgccca gttccgccca  9360
ttctccgccc catggctgac taatttttt tatttatgca gaggccgagg ccgcctcggc  9420
ctctgagcta ttccagaagt agtgaggagg ctttttggga ggcctaggct tttgcaaaaa  9480
gcttgggccc gccccaactg gggtaacctt tgagttctct cagttggggg              9530

SEQ ID NO: 391          moltype = DNA   length = 5722
FEATURE                 Location/Qualifiers
misc_feature            1..5722
                        note = Description of Artificial Sequence: Synthetic
                        polynucleotide
source                  1..5722
                        mol_type = other DNA
                        organism = synthetic construct
SEQUENCE: 391
tgatccctg cgccatcaga tccttggcgg cgagaaagcc atccagttta ctttgcaggg    60
cttcccaacc ttaccagagg gcgcccagc tggcaattcc ggttcgcttg ctgtccataa    120
aaccgcccag tctagctatc gccatgtaag cccactgcaa gctacctgct ttctctttgc    180
gcttgcgttt tcccttgtcc agatagccca gtagctgaca ttcatccggg gtcagcaccg    240
tttctgcgga ctggctttct acgtgctcga ggggggccaa acggtctcca gcttggctgt    300
tttggcggat gagagaagat tttcagcctg atacagatta aatcagaacg cagaagcggt    360
ctgataaaac agaatttgcc tggcggcagt agcgcggtgg tcccacctga ccccatgccg    420
aactcagaag tgaaacgccg tagcgccgat ggtagtgtgg gtctccccca tgcgagagta    480
gggaactgcc aggcatcaaa taaaacgaaa ggctcagtcg aaagactggg cctttcgttt    540
tatctgttgt ttgtcggtga acgctctcct gagtaggaca aatccgccgg gagcggattt    600
gaacgttgcg aagcaacggc ccggagggtg gcggcagga cgcccgccat aaactgccag    660
gcatcaaatt aagcagaagg ccatcctgac ggatggcctt tttgcgtttc tacaaactct    720
tttgtttatt tttctaaata cattcaaata tgtatccgct catgaccaaa atcccttaac    780
gtgagttttc gttccactga gcgtcagacc ccgtagaaaa gatcaaagga tcttcttgag    840
atcctttttt tctgcgcgta atctgctgct tgcaaacaaa aaaaccaccg ctaccagcgg    900
tggtttgttt gccggatcaa gagctaccaa ctctttttcc gaaggtaact ggcttcagca    960
gagcgcagat accaaatact gtccttctag tgtagccgta gttaggccac cacttcaaga   1020
actctgtagc accgcctaca tacctcgctc tgctaatcct gttaccagtg gctgctgcca   1080
gtggcgataa gtcgtgtctt accgggttgg actcaagacg atagttaccg gataaggcgc   1140
agcggtcggg ctgaacgggg ggttcgtgca cacagcccag cttggagcga acgacctaca   1200
ccgaactgag atacctacag cgtgagctat gagaaagcgc cacgcttccc gaagggagaa   1260
aggcggacag gtatccggta agcggcaggg tcggaacagg agagcgcacg agggagcttc   1320
cagggggaaa cgcctggtat ctttatagtc ctgtcgggtt tcgccacctc tgacttgagc   1380
gtcgatttt gtgatgctcg tcaggggggc ggagcctatg gaaaaacgcc agcaacgcgg   1440
cctttttacg gttcctggcc tttgctggc cttttgctca catgttcttt cctgcgttat   1500
cccctgattc tgtggataac cgtattaccg cctttgagtg agctgatacc gctcgccgca   1560
gccgaacgac cgagcgcagc gagtcagtga gcgaggaagc ggaagagcgc ctgatgcggt   1620
attttctcct tacgcatctg tgcggtattt cacaccgcat atggtgcact ctcagtacaa   1680
tctgctctga tgccgcatag ttaagccagt atacactccg ctatcgctac gtgactgggt   1740
catggctgcg ccccgacacc cgccaacacc cgctgacgcg ccctgacggg cttgtctgct   1800
cccggcatcc gcttacagac aagctgtgac cgtctccggg agctgcatgt gtcagaggtt   1860
ttcaccgtca tcaccgaaac gcgcgaggca gcagatcaat tcgcgcgcga aggcgaagcg   1920
gcatgcataa tgtgcctgtc aaatggacga agcagggatt ctgcaaaccc tatgctactc   1980
cgtcaagccg tcaattgtct gattcgttac caattatgac aacttgacgg ctacatcatt   2040
cactttttct tcacaaccgg cacgaactc gctcgggctg gccccggtgc atttttaaa   2100
tacccgcgag aaatagagtt gatcgtcaaa accaacattg cgaccgacgg tggcgatagg   2160
catccgggtg gtgctcaaaa gcagcttcgc ctggctgata cgttggtcct cgcgccagct   2220
taagacgcta atccctaact gctgcgcgaa aagatgtgac agacgcgacg gcgacaagca   2280
aacatgctgt gcgacgctgg cgatacatta ccctgttatc cctagatgac attaccctgt   2340
tatcccagat gacattaccc tgttatccct agatgacatt accctgttat ccctagatga   2400
catttaccct gttatcccta gatgacatta cccctgttaa ttaccctgtt   2460
atccctagat acattaccct gttatccag atgacatacc ctgttatccc tagatgacat   2520
taccctgtta tccagatga cattaccctg ttatccctag atacattacc ctgttatccc   2580
agatgacata cccctgttatc cctagatgac attaccctgt tatcccagat gacattaccc   2640
tgttatccct agatacatta ccctgttatc cagatgaca taccctgtta tccctagatg   2700
acattaccct gttatcccag atgacattac cctgttatcc ctagatacat accctgtta   2760
tcccagatga cataccctgt tatccctaga tgacattacc ctgttatccc agatgacatt   2820
accctgttat cccctagatac attaccctgt tatcccagat gacatacct gttatcccta   2880
gatgacatta cccctgttatc ccagatgaca ttaccctgtt atcccctagat acattaccct   2940
gttatcccag atgacatacc ctgttatccc tagatgacat taccctgtta tcccagataa   3000
actcaatgat gatgatgatg atggtcgaga ctcagcggcc gcggtgccag ggcgtgccct   3060
tgggctcccc gggcgcggtc ctttgggcgc taactgcgtg cgcgctggga attggcgcta   3120
attgcgcgtg cgcgctggga ctcaaggcgc taactgcgcg tgcgttctgg ggcccggggt   3180
gccgcggcct gggctgggc gaaggcgggc tcggccggaa ggggtgggt cgccgcgct   3240
cccggggcgt tgcgcgcact tcctgcccga gccgctgccc ggccgaggtg gccgcgctg   3300
cgtgcgcgcg gccgacccg cgcgtgtttg aaccggcgg aggcgggct ggcgccggt    3360
tgggaggggg ttggggcctg gcttcctgcc gcgccgcgcg gggacgcctc cgaccagtgt   3420
ttgccttttta tggtaataac gcggccgcc cggcttcctt tgtccccaat ctgggcgcgc   3480
gccggcgccc cctggcggcc taaggactcg gcgcgccgga agtggccagg gcggggggcga   3540
cctcggtca cagccgcgcc ggctattcct gcagctcgac accatgcatg catgaagat   3600
cgagtgccgc atcaccggca ccctgaacgg cgtggagttc gagctggtgg gcggcggaga   3660
gggcacccc gagcagggcc gcatgaccaa caagatgaag agcaccaaag cgccctgac   3720
cttcagcccc tacctgctga gccacgtgat gggctacggc ttctaccact cggcacctta   3780
ccccagcggc tacgagaacc ccttcctgca cgccatcaac acggcggct acaccaacac   3840
ccgcatcgag aagtacgagg acggcggcgt gctgcacgtg agcttcagct accgctacga   3900
```

```
ggccggccgc gtgatcggcg acttcaaggt ggtgggcacc ggcttccccg aggacagcgt  3960
gatcttcacc gacaagatca tccgcagcaa cgccaccgtg gagcacctgc acccccatggg  4020
cgataacgtg ctggtgggca gcttcgcccg caccttcagc ctgcgcgacg gcggctacta  4080
cagcttcgtg gtggacagcc acatgcactt caagagcgcc atccacccca gcatcctgca  4140
gaacggggggc cccatgttcg ccttccgccg cgtggaggga ctgcacagca cacccgagct  4200
gggcatcgtg gagtaccagc acgccttcaa gaccccccatc gccttcgcca gatctcgagc  4260
tcgaaccatg gatgatgata tcgccgcgct cgtcgtcgac aacggctccg gcatgtgcaa  4320
ggccggcttc gcgggcgacg atgccccccg ggccgtcttc ccctccatcg tggggcgccc  4380
caggcaccag gtaggggagc tggctgggtg gggcagcccc gggagcgggc gggaggcaag  4440
ggcgctttct ctgcacagga gcctcccggt ttccggggtg gggggctgcgc ccgtgctcag  4500
ggcttcttgt cctttccttc ccagggcgtg atggtgggca tgggtcagaa ggattcctat  4560
gtgggcgacag aggcccagag caagagaggc atcctcaccc tgaagtaccc catcgagcac  4620
ggcatcgtca ccaactggga cgacatggag aaaatctggc accacacctt ctacaatgag  4680
ctgcgtgtgg ctcccgagga gcaccccgtg ctgctgaccg aggcccccct gaaccccaag  4740
gccaaccgcg agaagatgac ccagcccccaa ctggggtaac ctttgagttc tctcagttgg  4800
gggtaatcag catcatgatg tggtaccaca tcatgatgct gattataaga atgcggccgc  4860
cacactctag tggatctcga gttaataatt cagaagaact cgtcaagaag gcgatagaag  4920
gcgatgcgct gcgaatcggg agcggcgata ccgtaaagca cgaggaagcg gtcagccgcat  4980
tcgccgccaa gctcttcagc aatatcacgg gtagccaacg ctatgtcctg atagcggtcc  5040
gccacaccca gccggccaca gtcgatgaat ccagaaaagc ggccattttc caccatgata  5100
ttcggcaagc aggcatcgcc atgggtcacg acgagatcct cgccgtcggg catgctcgcc  5160
ttgagcctgg cgaacagttc cggctggcgcg agcccctgat gctcttcgtc cagatcatcc  5220
tgatcgacaa gaccggcttc catccgagta cgtgctcgct cgatgcgatg tttcgcttgg  5280
tggtcgaatg gcaggtagc cggatcaagc gtatgcagcc gccgcattgc atcagccatg  5340
atggatactt tctcggcagg agcaaggtgt agatgacatg gagatcctgc cccggcactt  5400
cgcccaatag cagccagtcc cttcccgctt cagtgacaac gtcgagcaca gctgcgcaag  5460
gaacgcccgt cgtggccagc cacgatagcc gcgctgcctc gtcttgcagt tcattcaggg  5520
caccggacag gtcggtcttg acaaaaagaa ccgggcgccc ctgcgctgac agccggaaca  5580
cggcggcatc agagcagccg attgtctgtt gtgcccagtc atagccgaat agcctctcca  5640
cccaagcggc cggagaacct gcgtgcaatc catcttgttc aatcatgcga aacgatcctc  5700
atcctgtctc ttgatcagag ct                                            5722
```

SEQ ID NO: 392        moltype = DNA  length = 15424
FEATURE               Location/Qualifiers
misc_feature       1..15424
                      note = Description of Artificial Sequence: Synthetic
                      polynucleotide
source                1..15424
                      mol_type = other DNA
                      organism = synthetic construct

```
SEQUENCE: 392
tcgacggtat cgataagctt gatatcgaat tcctgcagcc cggggggatcc actagttcta   60
gagcggccgc caccgcggtg gagctccagc ttttgttccc tttagtgagg gttaatttcg  120
agcttggcgt aatcatggtc atagctgttt cctgtgtgaa attgttatcc gctcacaatt  180
ccacacaaca tacgagccgg aagcataaag tgtaaagcct ggggtgccta atgagtgagc  240
taactcacat taattgcgtt gcgctcactg cccgctttcc agtcgggaaa cctgtcgtgc  300
cagctgcatt aatgaatcgg ccaacgcgcg gggagaggcg gtttgcgtat tgggcgctct  360
tccgcttcct cgctcactga ctcgctgcgc tcggtcgttc ggctgcggcg agcggtatca  420
gctcactcaa aggcggtaat acggttatcc acagaatcag gggataacgc aggaaagaac  480
atgtgagcaa aaggccagca aaaggccagg aaccgtaaaa aggccgcgtt gctggcgttt  540
ttccataggc tccgcccccc tgacgagcat cacaaaaatc gacgctcaag tcagaggtgg  600
cgaaacccga caggactata agataccagg cgtttccccc tggaagctcc ctcgtgcgc  660
tctcctgttc cgaccctgcc gcttaccgga tacctgtccg cctttctccc ttcgggaagc  720
gtggcgcttt ctcatagctc acgctgtagg tatctcagtt cggtgtaggt cgttcgctcc  780
aagctgggct gtgtgcacga accccccgtt cagcccgacc gctgcgcctt atccggtaac  840
tatcgtcttg agtccaaccc ggtaagacac gacttatcgc cactggcagc agccactggt  900
aacaggatta gcagagcgag gtatgtaggc ggtgctacag agttcttgaa gtggtggcct  960
aactacggct acactagaag gacagtattt ggtatctgcg ctctgctgaa gccagttacc 1020
ttcggaaaaa gagttggtag ctcttgatcc ggcaaacaaa ccaccgctgg tagcggtggt 1080
tttttttgttt gcaagcagca gattacgcgc agaaaaaaag gatctcaaga agatccttt 1140
atctttctc cggggtctga cgctcagtgg aacgaaaact cacgttaagg gattttggtc 1200
atgagattat caaaaaggat cttcacctag atccttttaa attaaaaatg aagttttaaa 1260
tcaatctaaa gtatatatga gtaaacttgg tctgacagtt accaatgctt aatcagtgag 1320
gcacctatct cagcgatctg tctatttcgt tcatccatag ttgcctgact ccccgtcgtg 1380
tagataacta cgatacggga gggcttacca tctggcccca gtgctgcaat gataccgcga 1440
gacccacgct caccggctcc agatttatca gcaataaacc agccagccgg aagggccgag 1500
cgcagaagtg gtcctgcaac tttatccgcc tccatccagt ctattaattg ttgccggaa 1560
gctagagtaa gtagttcgcc agttaatagt ttgcgcaacg ttgttgccat tgctacaggc 1620
atcgtggtgt cacgctcgtc gtttggtatg gcttcattca gctccggttc ccaacgatca 1680
aggcgagtta catgatcccc catgttgtgc aaaaaagcgg ttagctcctt cggtcctccg 1740
atcgttgtca gaagtaagtt ggccgcagtg ttatcactca tggttatggc agcactgcat 1800
aattctctta ctgtcatgcc atccgtaaga tgcttttctg tgactggtga gtactcaacc 1860
aagtcattct gagaatagtg tatgcggcga ccgagttgct cttgcccggc gtcaatacgg 1920
gataataccg cgccacatag cagaactta aagtgctca tcattgaaaa acgttctgtg 1980
gggcgaaaac tctcaaggat cttaccgctg ttgagatcca gttcgatgta acccactcgt 2040
gcacccaact gatcttcagc atcttttact ttcaccagcg tttctgggtg agcaaaaaca 2100
ggaaggcaaa atgccgcaaa aaagggaata agggcgacac ggaaatgttg aatactcata 2160
ctcttccttt ttcaatatta ttgaagcatt tatcagggtt attgtctcat gagcggatac 2220
atatttgaat gtatttagaa aaataaacaa ataggggttc cgcgcacatt tccccgaaaa 2280
```

```
gtgccacctg acgtctaaga aaccattatt atcatgacat taacctataa aaataggcgt  2340
atcacgaggc cctttcgtct tcaagaattc tcatgtttga cagcttatca tcgataagct  2400
ttaatgcggt agtttatcac agttaaattg ctaacgcagt caggcaccgt gtatgaaatc  2460
taacaatgcg ctcatcgtca tcctcggcac cgtcaccctg gatgctgtag cataggctt   2520
ggttatgccg gtactgccgg gcctcttgcg ggatatcgtc cattccgaca gcatcgccag  2580
tcactatggc gtgctgctag cgctatatgc gttgatgcaa tttctatgcg caccgttct   2640
cggagcactg tccgaccgct ttggccgccg cccagtcctg ctcgcttcgc tacttggagc  2700
cactatcgac tacgcgatca tggcgaccac acccgtcctg tggatccggc gcacaccaaa  2760
aacgtcactt ttgccacatc cgtcgcttac atgtgttccg ccacacttgc aacatcacac  2820
ttccgccaca ctactacgtc acccgccccg ttcccacgcc ccgcgccacg tcacaaactc  2880
cacccctca ttatcatatt ggcttcaatc caaaataaat catcaataat ataccttatt   2940
ttggattgaa gccaatatga taatgagggg gtggagtttg tgacgtggcg cggggcgtgg  3000
gaacggggcg ggtgacgtag gttttagggc ggagtaactt gtatgtgttg ggaattgtag  3060
ttttcttaaa atgggaagtt acgtaacgtg ggaaaacgga agtgacgatt tgaggaagtt  3120
gtgggttttt tggctttcgt ttctgggcgt aggttcgcgt gcggttttct gggtgttttt  3180
tgtgacttt aaccgttacg tcatttttta gtcctatata tactcgctct gcacttggcc   3240
ctttttaca ctgtgactga ttgagctggt gccgtgtcga gtggtgtttt tttaataggt   3300
tttcttttt actggtaagg ctgactgtta ggctgccgct gtgaagcgct gtatgttgtt   3360
ctggagcggg agggtgctat tttgcctagg caggagggtt tttcaggtgt ttatgtgttt  3420
ttctctccta ttaattttgt tatacctcct atggggctg taatgttgtc tctacgcctg   3480
cgggtatgta ttccccgggg ctatttcggt cgctttttag cactgaccga tgaatcaacc  3540
tgatgtgttt accgagtctt acattatgac tccgacatg accgaggagc tgtcggtggt  3600
gcttttaat cacggtgacc agttttttta cggtcacgcc ggcatggccg tagtccgtct   3660
tatgcttata agggttgttt ttcctgttgt aagacaggct tctaatgttt aaatgttttt  3720
ttgttatttt attttgtgtt tatgcagaaa cccgcagaca tgtttgagag aaaaatggtg  3780
tcttttttctg tggtggttcc ggagcttacc tgcctttatc tgcatgagca tgactacgat  3840
gtgctttctt ttttgcgcga ggctttgcct gattttttga gcagcacctt gcatttttata 3900
tcgccgccca tgcaacaaag cttacatcgg ggctacgctg gttagcatag ctccgagtat  3960
gcgtgtcata atcagtgtgg gttcttttgt caaggttcct ggcggggaag tggccgcgct  4020
ggtccgtgca gacctgcacg attatgttca gctggccctg cgaagggacc tacgggatcg  4080
cggtattttt gttaatgttc cgcttttgaa tcttatacag gtctgtgagg aacctgaatt  4140
tttgcaatca tgattcgctg cttgaggctg aaggtggagg gcgctctgga gcagattttt  4200
acaatggccg gacttaatat tcgggatttg cttagagata tattgagaag gtggcgagat  4260
gagaattatt tgggcatggt tgaaggtgct ggaatgttta tagaggagat tcaccctgaa  4320
gggtttagcc tttacgtcca cttggacgtg agggccgttt gccttttgga agccattgtc  4380
caacatctta caaatgccat tatctgttct ttggctgtag agtttgacca cgccaccgga  4440
ggggagcgcg ttcacttaat agatcttcat tttgaggttt tggataatct tttgaataa   4500
aaaaaaaaac atggttcttc cagctcttcc cgctcctccc gtgtgtgact cgcagaacga  4560
atgtgtaggt tggctgggtg tggcttattc tgccgtgggtg gatgttatca gggcagcggc  4620
gcatgaagga gttacatag aacccgaagc caggggcgc ctggatgctt tgagagagtg   4680
gatatactac aactactaca cagagcgatc taagcggcga gaccgagac gcagatctgt   4740
ttgtcacgcc cgcacctggt tttgcttcag gaaatatgac tacgtccggc gttccatttg  4800
gcatgacact acgaccaaca cgatctcggt tgtctcggcg cactccgtac agtagggatc  4860
gtctacctcc ttttgagaca gaaacccgcg ctaccatact ggaggatcat ccgctgctgc  4920
ccgaatgtaa cactttgaca atgcacaacg tgagttacgt gcgaggtctt ccctgcagtg  4980
tgggatttac gctgattcag gaatggggttg ttccctggga tatggttcta acgcgggagg  5040
agcttgtaat cctgaggaag tgtatgcacg tgtgcctgtg ttgtgccaac attgatatca  5100
tgacgagcat gatgatccat ggttacgagt cctgggctct ccactgtcat tgttccagtc  5160
ccggttccct gcagtgtata gccggcgggc aggttttggc cagctggttt aggatggtgg  5220
tggatggcgc catgtttaat cagaggttta tatggtaccg ggaggtggtg aattacaaca  5280
tgccaaaaga ggtaatgttt atgtccaacg tgtttatgag gggtcgccac ttaatctacc  5340
tgcgcttgtg gtatgatggc cacgtgggtt ctgtggtccc cgccatgagc tttggataca  5400
gcgccttgca ctgtgggatt ttgaacaata ttgtggtgct gtgctgcagt tactgtgctg  5460
atttaagtga gatcagggtg cgctgctgtg cccggaggac aaggcgcctt atgctgcggg  5520
cggtgcgaat catcgctgag gagaccactg ccatgttgta ttcctgcagg acggagcggc  5580
ggcggcagca gtttattcgc gcgctgctgc agcaccaccg ccctatcctg atgcacgatt  5640
atgactctac ccccatgtag gcgtggactt ctccttcgcc gcccgttaag caaccgcaag  5700
ttggacagca gcctgtggct cagcagctgg acagcgacat gaacttaagt gagctgcccg  5760
gggagtttat taatatcact gatgagcgtt tggctcgaca ggaaaccgtg tggaatataa  5820
cacctaagaa tatgtctgtt acccatgata tgatgctttt taaggccagc cggggagaaa  5880
ggactgtgta ctctgtgtgt tgggaggggag gtggcaggtt gaatactagg gttctgtgag  5940
tttgattaag gtacggtgat ctgtataagc tatgtggtgg tggggctata ctactgaatg  6000
aaaaatgact tgaaattttc tgcaattgaa aaataaaaac gttgaaacat aacacaaacg  6060
attctttatt cttgggcaat gtatgaaaaa gtgtaaggag atgtggcaaa tatttcatta  6120
atgtagttgt ggccagacca gtcccatgaa aatgacatag agtatgcact tggagttgtg  6180
tctcctgttt cctgtgtacc gttagtgta atggttagtg ttacaggttt agttttgtct   6240
ccgtttaagt aaacttgact gacaatgtta cttttgcag ttttaccgtg agattttgga    6300
taagctgata ggttaggcat aaatccaaca gcgtttgtat aggtgtgcc ttcagtaaga    6360
tctccatttc taaagttcca atatttgtgg tccaggaagg aattgtttag tagcactcca   6420
ttttcgtcaa atcttataat aagatgagca ctttgaactg ttccagatat tggagccaaa  6480
ctgccttttaa cagccaaaac tgaaactgta gcaagtattt gactgccaca ttttgttaag  6540
accaaagtga gtttagcatc tttctctgca tttagtctac agttaggaga tggagctggt  6600
gtggtccaca aagttagctt atcattattt ttgttttccta ctgtaatggc acctgtgctg  6660
tcaaaactaa ggccagttcc tagtttagga accatgactt tgtttgaatc aaattctaag  6720
ccatggccaa ttttttgttt gaggggatt tgtttggtg cattaggtga accaaattca    6780
agcccatctc ctgcattaat ggctatggct gtagcgtcaa acatcaaccc cttggcagtg  6840
cttaggttaa cctcaagctt tttggaattg tttgaagctg taaacaagta aaggcctttg  6900
ttgtagttaa tatccaagtt gtgggctgag tttataaaaa gagggccctg tcctagtctt   6960
agatttagtt ggttttgagc atcaaacgga taactaacat caagtataag gcgtctgttt   7020
```

```
tgagaatcaa tccttagtcc tcctgctaca ttaagttgca tattgccttg tgaatcaaaa   7080
cccaaggctc cagtaacttt agtttgcaag gaagtattat taatagtcac acctggacca   7140
gttgctacgg tcaaagtgtt taggtcgtct gttacatgca aaggagcccc gtactttagt   7200
cctagttttc cattttgtgt ataaatgggc tctttcaagt caatgcccaa gctaccagtg   7260
gcagtagtta gaggggtga ggcagtgata gtaagggtac tgctatcggt ggtggtgagg   7320
gggcctgatg tttgcagggc tagctttcct tctgacactg tgaggggtcc ttgggtggca   7380
atgctaagtt tggagtcgtg cacggttagc ggggcctgtg attgcatggt gagtgtgttg   7440
cccgcgacca ttagaggtgc ggcggcagcc acagttaggg cttctgaggt aactgtgagg   7500
ggtgcagata tttccaggtt tatgtttgac ttggtttttt tgagaggtgg gctcacagtg   7560
gttacatttt gggaggtaag gttgccggcc tcgtccagag agaggccgtt gcccattttg   7620
agcgcaagca tgccattgga ggtaactaga ggttcggata ggcgcaaaga gagtaccca    7680
gggggactct cttgaaaccc attggggat acaaagggag gagtaagaaa aggcacagtt    7740
ggaggaccgg tttccgtgtc atatggatac acggggttga aggtatcttc agacggtctt   7800
gcgcgcttca tctgcaacaa catgaagata gtgggtgccg atggacagga acaggaggaa   7860
actgacattc catttagatt gtggagaaag tttgcagcca ggaggaagct gcaataccag   7920
agctgggagg agggcaagga ggtgctgctg aataaactgg acagaaattt gctaactgat   7980
tttaagtaag tgatgcttta ttatttttt ttattagtta aagggaataa gatccccggg    8040
tactctagtt aattaactag aggatcttga tgtaatccaa ggttaggaca gttgcaaatc   8100
acagtgagaa cacagggtcc cctgtcccgc tcaactagca gggggcgctg ggtaaactcc   8160
cgaatcaggc tacgggcaag ctctccctgg gcggtaagcc ggacgccgtg cgccgggccc   8220
tcgatatgat cctcgggcaa ttcaaagtag caaaactcac cggagtcgcg ggcaaagcac   8280
tgtgtggcgag gacagtggac caggtgtttc aggcgcagtt gctctgcctc tccacttaac   8340
attcagtcgt agccgtccgc cgagtccttt accgcgctcaa agttaggaat aaattgatcc   8400
ggatagtggc cgggaggtcc cgagaagggg ttaaagtaga ccgatggcac aaactcctca   8460
ataaattgca gagttccaat gcctccagag cgcggctcag aggacgaggt ctgcagagtt   8520
aggattgcct gacgaggcgt gaatgaagga cggccgatctg aaatgtcccg   8580
tccggacgga gaccaagcga ggagctcacc gactcgtcgt tgagctgaat acctcgccct   8640
ctgattgtca ggtgagttat accctgcccg ggcgaccgca ccctgtgacg aaagccgccc   8700
gcaagctgcg cccctgagtt agtcatctga acttcggcct gggcgtctct gggaagtacc   8760
acagtggtgg gagcgggact ttcctggtac accagggcag cgggccaact acggggatta   8820
aggttattac gaggtgtggt ggtaatagcc gcctgttcca agagaattcg gtttcggtcg   8880
gcgcggattc cgttgacccg ggatatcatg tggggtcccg cgctcatgta gtttattcgg   8940
gttgagtagt cttgggcagc tccagccgca agtcccattt gtggctggta actccacatg   9000
tagggcgtgg gaatttcctt gctcataatg gcgctgacga caggtgctgg cgccgggtgt   9060
ggccgctgga gatgacgtag ttttcgcgct taaatttgag aaagggcgcg aaactagtcc   9120
ttaagagtca gcgcgcagta tttactgaag agagcctccg cgtcttccag cgtgcgccga   9180
agctgatctt cgcttttgtg atacaggcag ctgcgggtga gggatcgcag agacctgttt   9240
ttattttca gctcttgttc ttggcccctg ctctgttgaa atatagcata cagagtggga   9300
aaaatcctgt ttctaagctc gcgggtcgat acgggttcgt tgggcgccag acgcagcgct   9360
cctcctcctg ctgctgccgc cgctgtggat tccttgggct ttgtcagagt cttgctatcc   9420
ggtcgccttt gcttctgtgt ggccgctgct gttgctgccg ctgccgctgc cgccggtgca   9480
gtatgggctg tagagatgac ggtagtaatg caggatgtta cggggggaagg ccacgccgtg   9540
atggtagaga agaaagcggc ggggcgaagga gatgttgccc ccacagtctt gcaagcaagc   9600
aactatggcg ttcttgtgcc cgcgccatga gcggtagcct tggcgctgtt gttgctcttg   9660
ggctaacggc ggcggctgct tggacttacc ggccctggtt ccagtggtgt cccatctacg   9720
gttgggtcgg cgaacgggca gtgccggcgg cgcctgagga gcggaggttg tagccatgct   9780
ggaaccggtt gccgatttct ggggcgccgg cgagggggaat cgaccgagg gtgacggtgt   9840
ttcgtctgac acctcttcga cctcggaagc ttcctcgtct aggctctccc agtcttccat   9900
catgtcctcc tcctcctcgt ccaaaacctc tctgcctga ctgtcccagt attcctcctc    9960
gtccgtgggt ggcggcggca gctgcagctt ctttttgggt gccatcctgg gaagcaaggg   10020
cccgcgctc ctgctgatag ggctgcggcg gcgggggaat tgggttgagc tcctcgccgg    10080
actgggggtc caagtaaacc ccccgtccct ttcgtagcag aaaactcttgg cgggctttgt   10140
tgatggcttg caattggcca agaatgtggc cctgggtaat gacgcaggcg gtaagctccg   10200
catttggcgt gcgggattgg tcttcgtaga acctaatctc gtgggcgtgg tagtcctcag   10260
gtacaaattt gcgaaggtaa gccgacgtcc acagcccccg agtgagtttc aaccccggag   10320
ccgcggactt ttcgtcaggc gagggaccct gcagctcaaa ggtaccgata atttgacttt   10380
cgttaagcag ctgcgaattg caaaccaggg agccggtgcgg ggtgcatagg ttgcagcgac   10440
agtgacactc cagtagaccg tcaccgctca cgtcttccat tatgtcagag tggtaggcaa   10500
ggtagttggc tagctgcaga aggtagcagt ggccccaaag cggcggaggg cattcgcggt   10560
acttaatggg cacaaagtcg ctaggaagtg cacagcaggt gggggcaaa attcctgagc    10620
gctctaggat aaagttccta aagttctgca acatgctttg actggtgaag tctggcagac   10680
cctgttgcag ggttttaagc aggcgttcgg ggaaaatgat gtccgccagg tgcgcggcca   10740
cggagcgctc gttgaaggcc gtccataggt ccttcaagtt ttgctttagc agtttctgca   10800
gctccttgag gttgcactcc tccaagcact gctgccaaac cctgccatgg cctctgccagg   10860
tgtagcatag aaataagtaa acgcagtcgc ggacgtagtc gcggcgcgcc tcgcccttga   10920
gcgtggaatg aagcacgttt tgcccaaggc ggttttcgtg caaaattcca aggtaggaga   10980
ccaggttgca gagctccacg ttggagatct tgcaggcctg gcgtacgtag ccctgtcgaa   11040
aggtgtagtg caatgtttcc tctagcttgc gctgcatctc cgggtcagca aagaaccgct   11100
gcatgcactc aagctccacg gtaacgagca ctgccggcat cattagtttg cgtcgctcct   11160
ccaagtcggc aggctcgcgc gtttgaagcc agccgcgctag ctgctcgtcg ccaactgcgg   11220
gtaggccctc ctctgtttgt tcttgcaaat ttgcatccct ctccagggc tgcgcacggc    11280
gcacgatcag ctcactcatg actgtgctca tgaccttggg gggtaggtta agtgccgggt   11340
aggcaaagtg ggtgacctcg atgctgcgtt ttagtacggc taggcgcgcg ttgtcaccct   11400
gcgttccac caacactcca gagtgacttt cattttccgt gttttcctgt tgcagagcgt   11460
ttgccgcgcg cttctcgtcg cgtccaagac cctcaaagat ttttggcact tcgttgagcg   11520
aggcgatatc aggtatgaca gcgccctgcc gcaaggccag ctgcttgtcc gctcggctgc   11580
ggttggcacg gcaggatagg ggtatcttgc agttttggaa aaagatgtga taggtggcaa   11640
gcacctctgg cacggcaaat acggggtaga agttgaggcg cggggttgggc tcgcatgtgc   11700
cgttttcttg gcgtttgggg ggtacgcgcg gtgagaatag gtggcgttcg taggcaaggc   11760
```
tgacatccgc tatggcgagg ggcacatcgc tgcgctcttg caacgcgtcg cagataatgg  11820
cgcactggcg ctgcagatgc ttcaacagca cgtcgtctcc cacatctagg tagtcgccat  11880
gcctttcgtc cccccgcccg acttgttcct cgtttgcctc tgcgttgtcc tggtcttgct  11940
ttttatcctc tgttggtact gagcggtcct cgtcgtcttc gcttacaaaa cctgggtcct  12000
gctcgataat cacttcctcc tcctcaagcg ggggtgcctc acggggaagg gtggtaggcg  12060
cgttggcggc atcggtggag gcggtggtgg cgaactcaga gggggcggtt aggctgtcct  12120
tcttctcgac tgactccatg atctttttct gcctatagga gaaggaaatg gccagtcggg  12180
aagaggagca gcgcgaaacc accccgagc gcggacgcgg tgcggcgcga cgtcccccaa  12240
ccatggagga cgtgtcgtcc ccgtcccgt cgccgccgcc tccccgggcg cccccaaaaa  12300
agcggatgag gcggcgtatc gagtccgagg acgaggaaga ctcatcacaa gacgcgctgg  12360
tgccgcgcac acccagcccg cggccatcga cctcggcggc ggatttggcc attgcgccca  12420
agaagaaaaa gaagcgccct tctcccaagc ccgagcgccc gccatcacca gaggtaatcg  12480
tggacagcga ggaagaaaga gaagatgtgg cgctacaaat ggtgggtttc agcaaccac  12540
cggtgctaat caagcatggc aaaggaggta agcgcacagt gcggcggctg aatgaagacg  12600
acccagtggc gcgtgtatg cggacgcaag aggaagagga agagcccagc gaagcggaaa  12660
gtgaaattac ggtgatgaac ccgctgagtg tgccgatcgt gtctgcgtgg gagaagggca  12720
tggaggctgc gcgcgcgctg atggacaagt accacgtgga taacgatcta aaggcgaact  12780
tcaaactact gcctgaccaa gtggaagctc tggcggccgt atgcaagacc tggctgaacg  12840
aggagcaccg cggggttgcag ctgaccttca ccagcaacaa gacctttgtg acgatgatgg  12900
ggcgattcct gcaggcgtac ctgacagtcgt ttgcagaggt gacctacaag catcacgagc  12960
ccacgggctg cgcgttgtgg ctgcaccgct gcgctgagat cgaaggcgag cttaagtgtc  13020
tacacggaag cattatgata aataaggagc acgtgattga aatggatgtg acgagcgaaa  13080
acgggcagcg cgcgctgaag gagcagtcta gcaaggccaa gatcgtgaag aaccggtggg  13140
gccgaaatgt ggtgcagatc tccaacaccg acgcaaggtg ctgcgtgcac gacgcggcct  13200
gtccggccaa tcagttttcc ggcaagtctt gcggcatgtt cttctctgaa ggcgcaaagg  13260
ctcaggtggc ttttaagcag atcaaggctt ttatgcagcg gctgtatcct aacgcccaga  13320
ccgggcacgg tcacctttg atgccactac ggtgcgagtg caactcaaag cctgggcacg  13380
cgcccttttt gggaaggcag ctaccaaagt tgactccgtt cgccctgagc aacgcggagg  13440
acctggacgc ggatcgtgatc tccgacaaga gcgtgctggc cagcgtgcac cacccggcgc  13500
tgatagtgtt ccagtgctgc aaccctgtgt atccgcaactc gcgcgcagg gcggaggcc  13560
ccaactgcga cttcaagata tcggcgcccg acctgctaaa cgcgttggtg atggtgcgca  13620
gcctgtggag tgaaaacttc accgagctgc cgcggatggt tgtgcctgag tttaagtgga  13680
gcactaaaca ccagtatcgc aacgtgtccc tgccagtggc gcatagcgat gcgcggcaga  13740
accccttga ttttaaacg gcgcagacgg caagggtggg ggtaaataat caccccgagg  13800
tgtacaaata aaagcatttg cctttattga aagtgtctct agtacattat ttttacatgt  13860
ttttcaagtg acaaaagaa gtggcgctcc taatctgcgc actgtggctg cggaagtagg  13920
gcgagtggcg ctccaggaag ctgtagagct gttcctggtt gcgacgcagg gtgggctgta  13980
cctgggactg gttgagcatg gagttgggta ccccggtaat aaggttcatg gtggggtgt  14040
gatccatggg agtttgggc cagttggcaa aggcgtggaa aaacatgcag cagaatgtc  14100
cacaggcggc cgagttgggc ccctgtacgc tttgggtgga cttttccagc gttatacagc  14160
ggtcggggga agaagcaatg gcgctacggc gcaggagtga ctcgtactca aactggtaaa  14220
cctgcttgag tcgctggtca gaaaagccaa agggctcaaa gaggtagcat gttttttgagt  14280
gcgggttcca ggcaaaggcc atccagtgta cgccccagt ctcggtccga gactcgaacg  14340
gggggtcccg cgactcaacc cttggaaaat aaccctccgg ctacagggag cgagccactt  14400
aatgctttcg ctttccagcc taaccgctta cgctgcgcgc ggccagtggc caaaaaagct  14460
agcgcagcag ccgccgcgcc tggaaggaag ccaaaaggag cactccccg ttgtctgacg  14520
tcgcacacct gggttcgaca cgcggcggt aaccgcatgg atcacggcgg acggccggat  14580
acggggctcg aaccccggtc gtccgccatg ataccttgc gaatttatcc accagaccac  14640
ggaagagtgc ccgcttacag gctctccttt tgcacggtag agcgtcaacg attgcgcgcg  14700
cctgaccgga cagagcgtcc cgaccatgga gcacttttg ccgctgcgca acatctgaa  14760
ccgcgtccgc gactttccgc gcgcctccac caccgccgcg ggcatcacct ggatgtccag  14820
gtacatctac ggatatccatc gccttatgtt ggaagatctc gccccggag ccccggccac  14880
cctacgctgg cccctctacc gccagccgcc gccgcacttt ttggtgggat accagtacct  14940
ggtgcggact tgcaacgact acgtatttga ctcgagggct tactcgcgtc tcaggtacac  15000
cgagctctcg cagccgggtc accagaccgt taactggtcc gttatggcca actgcactta  15060
caccatcaac acgggcgcat accaccgctt tgtggacatg gatgacttcc agtctaccct  15120
cacgcaggtg cagcaggcca tattagccga gcgcgttgtc gccgacctag ccctgcttca  15180
gccgatgagg ggcttcgggg tcacacgcat gggaggaaga gggcgccacc tacggccaaa  15240
ctccgccgcc gccgcagcga tagatgcaag agatgcagga caagaggaag gagaagaaga  15300
agtgccggta gaaaggctca tgcaagacta ctacaaagac ctgcgccgat gtcaaaacga  15360
agcctgggc atggccgacc gcctgcgcat tcagcaggcc ggacccaagg acatggtgct  15420
tctg                                                               15424

SEQ ID NO: 393         moltype = DNA   length = 3849
FEATURE                Location/Qualifiers
misc_feature           1..3849
                       note = Description of Artificial Sequence: Synthetic
                       polynucleotide
source                 1..3849
                       mol_type = other DNA
                       organism = synthetic construct
SEQUENCE: 393
cggcgtcaat acgggataat accgcgccac atagcagaac tttaaaagtg ctcatcattg   60
gaaaacgttc ttcggggcga aaactctcaa ggatcttacc gctgttgaga tccagttcga  120
tgtaacccac tcgtgcaccc aactgatctt cagcatcttt tactttcacc agcgtttctg  180
ggtgagcaaa aacaggaagg caaaatgccg caaaaaaggg aataagggcg acacggaaat  240
gttgaatact catactcttc cttttcaat attattgaag catttatcag ggttattgtc  300
tcatgagcgg atacatattt gaatgtattt agaaaaataa acaaataggg gttccgcgca  360
catttccccg aaaagtgcca cctaaattgt aagcgttaat attttgttaa aattcgcgtt  420

```
aaattttttgt taaatcagct catttttttaa ccaataggcc gaaatcggca aaatcccttta    480
taaatcaaaa gaatagaccg agataggggtt gagtgttgtt ccagtttgga acaagagtcc     540
actattaaag aacgtggact ccaacgtcaa agggcgaaaa accgtctatc agggcgatgg     600
cccactacg  gaaccatcac cctaatcaag ttttttgggg tcgaggtgcc gtaaagcact     660
aaatcggaac cctaaaggga gcccccgatt tagagcttga cggggaaagc cggcgaacgt     720
ggcgagaaag gaagggaaga aagcgaaagg agcgggcgct agggcgctgg caagtgtagc     780
ggtcacgctg cgcgtaacca ccacacccgc cgcgcttaat gcgccgctac agggcgcgtc     840
ccattcgcca ttcaggctgc gcaactgttg gaagggcga tcggtgcggg cctcttcgct      900
attacgccag ctgcgcgctc gctcgctcac tgaggccgcc cgggcaaagc ccgggcgtcg     960
ggcgaccttt ggtcgcccgg cctcagtgag cgagcgagcg cgcagagagg gagtggccaa    1020
ctccatcact aggggttcct tgtagttaat gattaacccg ccatgctact tatctacgta    1080
gccatgctct aggaagagta ccattgacgt caataatgac gtatgttccc atagtaacgc    1140
caatagggac tttccattga cgtcaatggg tggagtattt acggtaaact gcccacttgg    1200
cagtacatca agtgtatcag tggtttgtct ggtcaaccac cgcggtctca gtggtgtacg    1260
gtacaaaccc agctaccggt cgccaccatg cccgccatga agatcgagtg ccgcatcacc    1320
ggcaccctga acggcgtgga gttcgagctg gtgggcggcg agagggcac ccccgagcag     1380
ggccgcatga ccaacaagat gaagagcacc aaaggcgccc tgaccttcag cccctacctg    1440
ctgagccacg tgatgggcta cggcttctac cacttcggca cctaccccag cggctacgag    1500
aacccccttcc tgcacgccat caacaacggc ggctacacca acacccgcat cgagaagtac    1560
gaggacggcg gcgtgctgca cgtgagcttc agctaccgct acgaggccgg ccgcgtgatc    1620
ggcgacttca aggtggtggg caccggcttc cccgaggaca gcgtgatctt caccgacaag    1680
atcatccgca gcaacgccac cgtggagcac ctgcacccca tgggcgataa cgtgctggtg    1740
ggcagcttcg cccgcacctt cagcctgcgc gacggcggct actacagctt cgtggtggac    1800
agccacatgc acttcaagag cgccatccac cccagcatcc tgcagaacgg ggggcccatg    1860
ttcgccttcc gccgcgtgga ggagctgcac agcaacaccg agctgggcat cgtggagtac    1920
cagcacgcct tcaagacccc catcgccttc gccagatctc gagctcgatg agtttggaca    1980
aaccacaact agaatgcagt gaaaaaaatg ctttatttgt gaaatttgtg atgctattgc    2040
tttatttgtg ggcccgggat cttcctagag catggctacg tagataagta gcatggcggg    2100
ttaatcatta actacaagga accccctagtg atggagttgg ccactccctc tctgcgcgct    2160
cgctcgctca ctgaggccgg gcgaccaaag gtcgcccgac gcccgggctt tgcccgggcg    2220
gcctcagtga gcgagcgagc gcgcagctgc attaatgaat cggccaacgc gcggggagag    2280
gcggtttgcg tattgggcgc tcttccgctt cctcgctcac tgactcgctg cgctcggtcg    2340
ttcggctgcg gcgagcggta tcagctcact caaaggcggt aatacggtta ccacagaat    2400
caggggataa cgcaggaaag aacatgtgag caaaaggcca gcaaaaggcc aggaaccgta    2460
aaaaggccgc gttgctggcg ttttttccata ggctccgccc ccctgacgag catcacaaaa    2520
atcgacgctc aagtcagagg tggcgaaacc cgacaggact ataaagatac caggcgtttc    2580
cccctggaag ctccctcgtg cgctctcctg ttccgaccct gccgcttacc ggatacctgt    2640
ccgcctttct cccttcggga agcgtggcgc tttctcatag ctcacgctgt aggtatctca    2700
gttcggtgta ggtcgttcgc tccaagctgg gctgtgtgca cgaacccccc gttcagcccg    2760
accgctgcgc cttatccggt aactatcgtc ttgagtccaa cccggtaaga cacgacttat    2820
cgccactggc agcagccact ggtaacagga ttagcagagc gaggtatgta ggcggtgcta    2880
cagagttctt gaagtggtgg cctaactacg gctacactaa gaacagta tttggtatct      2940
gcgctctgct gaagccagtt accttcggaa aaagagttgg tagctcttga tccggcaaac    3000
aaaccaccgc tggtagcggt ggtttttttg tttgcaagca gcagattacg cgcagaaaaa    3060
aaggatctca agaagatcct ttgatctttt ctacggggtc tgacgctcag tggaacgaaa    3120
actcacgtta agggattttg gtcatgagat tatcaaaaag gatcttcacc tagatccttt    3180
taaattaaaa atgaagtttt aaatcaatct aaagtatata tgagtaaact tggtctgaca    3240
gttaccaatg cttaatcagt gaggcaccta tctcagcgat ctgtctattt cgttcatcca    3300
tagttgcctg actccccgtc gtgtagataa ctacgatacg ggagggctta ccatctggcc    3360
ccagtgctgc aatgataccg cgagacccac gctcaccggc tccagattta tcagcaataa    3420
accagccagc cggaagggcc gagcgcagaa gtggtcctgc aactttatcc gcctccatcc    3480
agtctattaa ttgttgccgg gaagctagag taagtagttc gccagttaat agtttgcgca    3540
acgttgttgc cattgctaca ggcatcgtgg tgtcacgctc gtcgtttggt atggcttcat    3600
tcagctccgg ttcccaacga tcaaggcgag ttacatgatc cccatgttg tgcaaaaaag     3660
cggttagctc cttcggtcct ccgatcgttg tcagaagtaa gttggccgca gtgttatcac    3720
tcatggttat ggcagcactg cataattctc ttactgtcat gccatccgta agatgctttt    3780
ctgtgactgg tgagtactca accaagtcat tctgagaata gtgtatgcgg cgaccgagtt    3840
gctcttgcc                                                            3849

SEQ ID NO: 394         moltype = DNA   length = 7336
FEATURE                Location/Qualifiers
misc_feature           1..7336
                       note = Description of Artificial Sequence: Synthetic
                       polynucleotide
source                 1..7336
                       mol_type = other DNA
                       organism = synthetic construct
SEQUENCE: 394
atgccggggt tttacgagat tgtgattaag gtccccagcg accttgacga gcatctgccc      60
ggcatttctg acagctttgt gaactggggtg gccgagaagg aatgggagtt gccgccagat    120
tctgacatgg atctgaatct gattgagcag gcacccctga ccgtggccga aagctgcag     180
cgcgactttc tgacggaatg gcgccgtgtg agtaaggccc cggaggctct tttctttgtg    240
caatttgaga agggagagag ctacttccac atgcacgtgc tcgtggaaac caccggggtg    300
aaatccggga ttttttgggacg tttcctgagt cagattcccg aaaaactgat tcagagaatt    360
taccggggga tcgagccgac tttgccaaac tggttcgcgg tcacaaagac cagaaatggc    420
gccggaggcg ggaacaaggt ggtggatgag tgctacatcc caattacttt gctccccaaa    480
acccagcctg agctccagtg ggcgtggact aatatggaac agtatttaag cgcctgtttg    540
aatctcacgg agcgtaaacg gttggtgcg cagcatctga cgcacgtgtc gcagacgcag     600
gagcagaaca aagagaatca gaatcccaat tctgatgcgc cggtgatcag atcaaaaact    660
```

```
tcagccaggt acatggagct ggtcgggtgg ctcgtggaca aggggattac ctcggagaag  720
cagtggatcc aggaggacca ggcctcatac atctccttca atgcggcctc caactcgcgg  780
tcccaaatca aggctgcctt ggacaatgcg ggaaagatta tgagcctgac taaaaccgcc  840
cccgactacc tggtgggcca gcagcccgtg gaggacattt ccagcaatcg gatttataaa  900
attttggaac taaacgggta cgatcccaa tatgcggctt ccgtctttct gggatgggcc  960
acgaaaaagt tcggcaagag gaacaccatc tggctgtttg gcctgcaac taccgggaag 1020
accaacatcg cggaggccat agcccacact gtgcccttct acgggtgcgt aaactggacc 1080
aatgagaact ttcccttcaa cgactgtgtc gacaagatgg tgatctggtg ggaggagggg 1140
aagatgaccg ccaaggtcgt ggagtcggcc aaagccattc tcggaggaag caaggtgcgc 1200
gtggaccaga aatgcaagtc ctcggcccag atagacccga ctcccgtgat cgtcacctcc 1260
aacaccaaca tgtgcgccgt gattgacggg aactcaacga ccttcgaaca ccagcagccg 1320
ttgcaagacc ggatgttcaa atttgaactc acccgccgtc tggatcatga ctttgggaag 1380
gtcaccaagc aggaagtcaa agacttttc cggtgggcaa aggatcacgt ggttgaggtg 1440
gagcatgaat tctacgtcaa aaagggtgga gccaagaaa gacccgcccc cagtgacgca 1500
gatataagtg agcccaaacg ggtgcgcgag tcagttgcgc agccatcgac gtcagacgcg 1560
gaagcttcga tcaactacgc agacaggtac caaaacaaat gttctcgtca cgtgggcatg 1620
aatctgatgc tgtttccctg cagacaatgc gagagaatga atcagaattc aaatatctgc 1680
ttcactcacg gacagaaaga ctgtttagag tgcttttccg tgtcagaatc tcaacccgtt 1740
tctgtcgtca aaaaggcgta tcagaaactg tgctacattc atcatatcat gggaaaggtg 1800
ccagacgctt gcactgcctg cgatctggtc aatgtggatt tggatgactg catctttgaa 1860
caataaatga tttaaatcag gtatggctgc cgatggttat cttccagatt ggctcgagga 1920
caacctctct gagggcattc gcgagtggtg ggcgctcaaa cctggaaccc cgaagcccaa 1980
agccaaccag caaaagcagg acgacggccg gggtctggtg cttcctggct acaagtacct 2040
cggacccttc aacggactcg acaaggggga gcccgtcaac gcggcggacg cagcggccct 2100
cgagcacgac aaggcctacg accagcagct gcaggcgggt gacaatccgt acctgcggta 2160
taaccacgcc gacgccgagt tcaggagcg tctgcaagaa gatacgtctt ttgggggcaa 2220
cctcgggcga gcagtcttcc aggccaagaa gcgggttctc gaacctctcg gtctggttga 2280
ggaaggcgct aagacggctc ctggaaaaga gagaccggta gagccatcac cccagcgttc 2340
tccagactcc tctacgggca tcggcaagaa aggccaacag cccgcagaa aaagactcaa 2400
ttttggtcag actggcgact cagagtcagt tccagaccct caacctctcg gagaacctcc 2460
agcagcgccc tctggtgtgg gacctaatac aatggctgca ggcggtggcg caccaatggc 2520
agacaataac gaaggcgccg acggagtggg tagttcctcg ggaaattggc attgcgattc 2580
cacatgactg ggcgacagag tcatcaccac cagcaccga acctgggccc tgcccaccta 2640
caacaaccac ctctacaagc aaatctccaa cgggacatcg ggaggagcca ccaacgacaa 2700
cacctactc ggctacagca ccccctgggg gtattttgac tttaacagat tccactgcca 2760
ctttttcacca cgtgactggc agcgactcat caacaacaac tggggattcc ggcccaagag 2820
actcagcttc aagctcttca acatccaggt caaggaggtc acgcagaatg aaggcaccaa 2880
gaccatcgcc aataaccctc cagcaccatt ccaggtgttt acggactcgg agtaccagct 2940
gccgtacgtt ctcggctctg cccaccaggg ctgcctgcct ccgttccggg cggacgtgtt 3000
catgattccc cagtacggct acctaacact caacaacgtt agtcaggccg tgggacgctc 3060
ctccttctac tgcctggaat actttccttc gcagatgctg agaaccggca acaacttcca 3120
gtttacttac accttcgagg acgtgccttt ccacagcagc tacgcccaca gcagagctt 3180
ggaccggctg atgaatcctc tgattgacca gtacctgtac tacttgtctc ggactcaaac 3240
aacaggaggc acggcaaata cgcagactct gggcttcagc caaggtgggc taatacaat 3300
ggccaatcag gcaaagaact ggctgccagg accctgttac cgccaacaac gcgtctcaac 3360
gacaaccggg caaaacaaca atagcaactt tgcctggact gctgggacca aataccatct 3420
gaatggaaga aattcattgg ctaatcctgg catcgctatg gcaacacaca aagacgacga 3480
ggagcgtttt tttcccagta acgggatcct gatttttggc aaacaaaatg ctgccagaga 3540
caatgcggat tacagcgatg tcatgctcac cagcgaggaa gaaatcaaaa ccactaaccc 3600
tgtggctaca gaggaatacg gtatcgtggc agataacttg cagcagcaaa acacggctcc 3660
tcaaattgga actgtcaaca gccaggggc cttacccggt atggtctggc agaaccggga 3720
cgtgtacctg caggtccca tctgggccaa gattcctcac acggacggca acttccaccg 3780
gtctccgctg atgggcggct ttggcctgaa acatcctccg cctcagatcc tgatcaagaa 3840
cacgcctgta cctgcggatc ctccgaccac cttcaaccag tcaaagctga actctttcat 3900
cacgcaatac agcaccggac aggtcagcgt ggaaattgaa tgggagctgc agaaggaaaa 3960
cagcaagcgc tggaaccccg agatccagta cacctccaac tactacaaat ctacaagtgt 4020
ggactttgct gttaatacag aaggcgtgta tctctgaaccc cgcccattg gcacccgtta 4080
cctcacccgt aatctgtaat tgcctgttaa tcaataaacc ggttgattcg tttcagttga 4140
actttggtct ctgcgaaggg cgaattcgtt taaacctgca ggactagagg tcctgtatta 4200
gaggtcacgt gagtgttttg cgacattttg cgacaccatg tggtcacgct gggtatttaa 4260
gcccgagtga gcacgcaggg tctccatttt gaagcgggag gtttgaacgc gcagccgcca 4320
agccgaattc tgcagatatc catcacactg gcggccgctc gactagagcg gccgcaccg 4380
cggtggagct ccagcttttg ttccctttag tgagggttaa ttgcgcgctt ggcgtaatca 4440
tggtcatagc tgtttcctgt gtgaaattgt tatccgctca caattccaca acaatacga 4500
gccgaagca taaagtgtaa agcctggggt gcctaatgag tgagctaact cacattaatt 4560
gcgttgcgct cactgcccgc tttccagtcg ggaaacctgt cgtgccagct gcattaatga 4620
atcggccaac gcgcggggag aggcggtttg cgtattgggc gctcttccgc ttcctcgctc 4680
actgactcgc tgcgctcggt cgttcggctg cggcgagcgg tatcagctc ctcaaaggcg 4740
gtaatacggt tatccacaga atcaggggat aacgcaggaa agaacatgtg agcaaaaggc 4800
cagcaaaagg ccaggaaccg taaaaaggcc gcgttgctgg cgtttttcca taggctccgc 4860
cccccctgacg agcatcacaa aaatcgacgc tcaagtcaga ggtggcgaaa cccgacagga 4920
ctataaagat accaggcgtt tccccctgga agctccctcg tgcgctctcc tgttccgacc 4980
ctgccgctta ccggatacct gtccgccttt ctcccttcgg gaagcgtggc gctttctcat 5040
agctcacgct gtaggtatct cagttcggtg taggtcgttc gctccaagct gggctgtgtg 5100
cacgaacccc ccgttcagcc cgaccgctgc gccttatccg gtaactatcg tcttgagtcc 5160
aacccggtaa gacacgactt atcgccactg gcagcagcca ctggtaacag gattagcaga 5220
gcgaggtatg taggcggtgc tacagagttc ttgaagtggt ggcctaacta cggctacact 5280
agaagaacag tatttggtat ctgcgctctg ctgaagccag ttaccttcgg aaaaagagtt 5340
ggtagctctt gatccggcaa acaaaccacc gctggtagcg tggttttttt tgtttgcaag 5400
```

-continued

```
cagcagatta cgcgcagaaa aaaggatct caagaagatc ctttgatctt ttctacgggg   5460
tctgacgctc agtggaacga aaactcacgt taagggattt tggtcatgag attatcaaaa   5520
aggatcttca cctagatcct tttaaattaa aaatgaagtt ttaaatcaat ctaaagtata   5580
tatgagtaaa cttggtctga cagttaccaa tgcttaatca gtgaggcacc tatctcagcg   5640
atctgtctat ttcgttcatc catagttgcc tgactcccg tcgtgtagat aactacgata    5700
cgggagggct taccatctgg ccccagtgct gcaatgatac cgcgagaccc acgctcaccg   5760
gctccagatt tatcagcaat aaaccagcca gccggaaggg ccgagcgcag aagtggtcct   5820
gcaactttat ccgcctccat ccagtctatt aattgttgcc gggaagctag agtaagtagt   5880
tcgccagtta atagtttgcg caacgttgtt gccattgcta gcagcatcgt ggtgtcacgc   5940
tcgtcgtttg gtatggcttc attcagctcc ggttcccaac gatcaaggcg agttacatga   6000
tcccccatgt tgtgcaaaaa agcggttagc tccttcggtc ctccgatcgt tgtcagaagt   6060
aagttggccg cagtgttatc actcatggtt atggcagcac tgcataattc tcttactgtc   6120
atgccatccg taagatgctt ttctgtgact ggtgagtact caaccaagtc attctgagaa   6180
tagtgtatgc ggcgaccgag ttgctcttgc ccggcgtcaa tacgggataa taccgcgcca   6240
catagcagaa ctttaaaagt gctcatcatt ggaaaacgtt cttcggggcg aaaactctca   6300
aggatcttac cgctgttgag atccagttcg atgtaaccca ctcgtgcacc caactgatct   6360
tcagcatctt ttactttcac cagcgtttct gggtgagcaa aaacaggaag gcaaaatgcc   6420
gcaaaaaagg gaataagggc gacacggaaa tgttgaatac tcatactctt ccttttttcaa  6480
tattattgaa gcatttatca gggttattgt ctcatgagcg gatacatatt tgaatgtatt   6540
tagaaaaata aacaaatagg ggttccgcgc acatttcccc gaaaagtgcc acctaaattg   6600
taagcgttaa tattttgtta aaattcgcgt taaattttg ttaaatcagc tcattttta     6660
accaataggc cgaaatcggc aaaatccctt ataaatcaaa agaatagacc gagataggt    6720
tgagtgttgt tccagtttgg aacaagagtc cactattaaa gaacgtggac tccaacgtca   6780
aagggcgaaa aaccgtctat cagggcgatg gcccactacg tgaaccatca ccctaatcaa   6840
gttttttggg gtcgaggtgc cgtaaagcac taaatcggaa ccctaaaggg agcccccgat   6900
ttagagcttg acggggaaag ccggcgaacg tggcgagaaa ggaagggaag aaagcgaaag   6960
gagcgggcgc tagggcgctg gcaagtgtag cggtcacgct gcgcgtaacc accacacccg   7020
ccgcgcttaa tgccgcgcta cagggcgcgt cccattcgcc attcaggctg cgcaactgtt   7080
gggaagggcg atcggtgcgg gcctcttcgc tattacgcca gctggcgaaa gggggatgtg   7140
ctgcaaggcg attaagttgg gtaacgccag ggttttccca gtcacgacgt tgtaaaacga   7200
cggccagtga gcgcgcgtaa tacgactcac tataggcga attgggtacc gggccccccc   7260
tcgatcgagg tcgacggtat cgggggagct cgcagggtct ccattttgaa gcgggaggtt   7320
tgaacgcgca gccgcc                                                   7336
```

SEQ ID NO: 395        moltype = DNA  length = 969
FEATURE                Location/Qualifiers
misc_feature       1..969
                       note = Description of Artificial Sequence: Synthetic
                       polynucleotide
source                  1..969
                       mol_type = other DNA
                       organism = synthetic construct
SEQUENCE: 395

```
ccccaactgg ggtaaccttt gggctccccg ggcgcgacta taagctgcga gcaacttcac    60
ttgggtatgc cggcggtagc gcttaccgtt cgtataatgt atgctatacg aagttatccg   120
aagccgctag cggtggtttg tctggtcaac caccgcggtc tcagtggtgt acggtacaaa   180
cccagctacc ggtcgccacc atgcccgcca tgaagatgca gtgccgcatc accggcaccc   240
tgaacggcgt ggagttcgag ctggtgggcg gcgagagggg cacccccgag cagggccgca   300
tgaccaacaa gatgaagagc accaaggcg ccctgacctt cagcccctac ctgctgagcc    360
acgtgatggg ctacgcttc taccacttcg gcacctaccc cagcggctac gagaaccct    420
tcctgcaccg catcaacaac ggcggctaca ccaacaccg catcgagaag tacgaggacg   480
gcggcgtgct gcacgtgagc ttcagctacc gctacgaggc cggccgcgtg atcggcgact   540
tcaaggtggt gggcaccggc ttccccgagg acagcgtgat cttcaccgac aagatcatcc   600
gcagcaacgc caccgtggag cacctgcacc ccatgggcga taacgtgctg gtgggcagct   660
tcgcccgcac cttcagcctg cgcgaggcg gctactacag cttcgtggtg gacagccaca   720
tgcacttcaa gagcgccatc cacccccagca tcctgcagaa cggggcccc atgttcgcct   780
tccgccgcgt ggaggagctg cacagcaaca ccgagctggg catcgtggag taccagcacg   840
ccttcaagac ccccatcgcc ttcgccagat ctcgagctcg atgagtttgg acaaaccaca   900
actagaatgc agtgaaaaaa atgctttatt tgtgaaattt gtgatgctat tgctttattt   960
gtgggcccg                                                           969
```

SEQ ID NO: 396        moltype = DNA  length = 4769
FEATURE                Location/Qualifiers
misc_feature       1..4769
                       note = Description of Artificial Sequence: Synthetic
                       polynucleotide
source                  1..4769
                       mol_type = other DNA
                       organism = synthetic construct
SEQUENCE: 396

```
tgatcccctg cgccatcaga tccttggcgg cgagaaagcc atccagttta ctttgcaggg    60
cttcccaacc ttaccagagg gcgccccagc tggcaattcc ggttcgcttg ctgtccataa   120
aaccgcccag tctagctatc gccatgtaag cccactgcaa gctacctgct ttctctttgc   180
gcttgcgttt tcccttgtcc agatagccca gtagctgaca ttcatccggg gtcagcaccg   240
tttctgcgga ctggctttct acgtgctcga gggggccaa acggtctcca gcttggctgt    300
tttggcggat gagagaagat tttcagcctg atacagatta aatcagaacg cagaagcggt   360
ctgataaaac agaatttgcc tggcggcagt agcgcggtgg tcccacctga ccccatgccg   420
aactcagaag tgaaacgccg tagcgccgat ggtagtgtgg ggtctcccca tgcgagagta   480
gggaactgcc aggcatcaaa taaaacgaaa ggctcagtcg aaagactggg cctttcgttt   540
```

```
tatctgttgt ttgtcggtga acgctctcct gagtaggaca aatccgccgg gagcggattt    600
gaacgttgcg aagcaacggc ccggagggtg gcgggcagga cgcccgccat aaactgccag    660
gcatcaaatt aagcagaagg ccatcctgac ggatggcctt tttgcgtttc tacaaactct    720
tttgtttatt tttctaaata cattcaaata tgtatccgct catgaccaaa atcccttaac    780
gtgagttttc gttccactga gcgtcagacc ccgtagaaaa gatcaaagga tcttcttgag    840
atccttttt tctgcgcgta atctgctgct tgcaaacaaa aaaaccaccg ctaccagcgg    900
tggtttgttt gccggatcaa gagctaccaa ctctttttcc gaaggtaact ggcttcagca    960
gagcgcagat accaaatact gtccttctag tgtagccgta gttaggccac cacttcaaga   1020
actctgtagc accgcctaca tacctcgctc tgctaatcct gttaccagtg gctgctgcca   1080
gtggcgataa gtcgtgtctt accgggttgg actcaagacg atagttaccg gataaggcgc   1140
agcggtcggg ctgaacgggg ggttcgtgca cacagcccag cttggagcga acgacctaca   1200
ccgaactgag atacctacag cgtgagctat gagaaagcgc cacgcttccc gaagggagaa   1260
aggcggacag gtatccggta agcggcaggg tcggaacagg agagcgcacg agggagcttc   1320
caggggggaaa cgcctggtat ctttatagtc ctgtcgggtt tcgccaccct tgacttgagc   1380
gtcgatttt gtgatgctcg tcaggggggc ggagcctatg gaaaaacgcc agcaacgcgg   1440
ccttttacg gttcctggcc ttttgctggc cttttgctca catgttcttt cctgcgttat   1500
cccctgattc tgtggataac cgtattaccg cctttgagtg agctgatacc gctcgccgca   1560
gccgaacgac cgagcgcagc gagtcagtga gcgaggaagc ggaagagcgc ctgatgcggt   1620
attttctcct tacgcatctg tgcggtattt cacaccgcat atggtgcact ctcagtacaa   1680
tctgctctga tgccgcatag ttaagccagt atacactccg ctatcgctac gtgactgggt   1740
catggctgcg ccccgacacc cgccaacacc cgctgacgcg ccctgacggg cttgtctgct   1800
cccggcatcc gcttacagac aagctgtgac cgtctccggg tcgtcatgt gtcagaggtt   1860
ttcaccgtca tcaccgaaac gcgcgaggca gcagatcaat tcgcgcgcga aggcgaagcg   1920
gcatgcataa tgtgcctgtc aaatggacga agcagggatt ctgcaaaccc tatgctactc   1980
cgtcaagccg tcaattgtct gattcgttac caattatgac aacttgacgg ctacatcatt   2040
cacttttct tcacaaccgg cacggaactc gctcgggctg gccccggtgc atttttaaa   2100
tacccgcgag aaatagagtt gatcgtcaaa accaacattg cgaccgacgg tggcgatagg   2160
catccgggtg gtgctcaaaa gcagcttcgc ctggctgata cgttggtcct cgcgccagct   2220
taagacgcta atccctaact gctggcgaa aagatgtgac agacgcgacg gcgacaagca   2280
aacatgctgt gcgacgctgg cgatacatta ccctgttatc cctagatgca ttaccctgt   2340
tatcccagat gacattaccc tgttatccct agatgacatt accctgttat ccctagatga   2400
catttaccct gttatcccta gatgacatta ccctgttatc ccagatgaca ttaccctgtt   2460
atccctagat acattaccct gttatcccag atgcatacc ctgttatccc tagatgacat   2520
taccctgtta tcccagatga cattaccctg ttatccctag atacattacc ctgttatccc   2580
agatgacata ccctgttatc cctagatgac attaccctgt tatcccagat gacattaccc   2640
tgttatccct agatacatta ccctgttatc cagatgaca taccctgtta tcccagatg   2700
acattaccct gttatcccag atgacattac cctgttatcc ctagatacat taccctgtta   2760
tcccagatga catacctgt tatccctaga tgacattacc ctgtatccc agatgacatt   2820
accctgttat ccctagatac attaccctgt tatcccagat gacataccct gttatcccta   2880
gatgacatta ccctgttatc ccagatgaca ttacccctgtt atccctagat acattaccct   2940
gttatcccag atgacatacc ctgttatccc tagatgacat accctgtta tcccagataa   3000
actcaatgat gatgatgatg atggtcgaga ctcagcggcc gcggtgccag ggcgtgccct   3060
tgggctcccc gggcgcgatg cccgccatga agatcgatg ccgcatcacc ggcaccctga   3120
acggcgtgga gttcgagctg gtgggcggcg agagggcac ccccgagcag ggccgcatga   3180
ccaacaagat gaagagcacc aaaggcgccc tgacccttcag cccctacctg ctgagccacg   3240
tgatgggcta cggcttctac cacttcggca cctaccccag cggctacgag aaccccttcc   3300
tgcacgccat caacaacggc ggctacacca caccccgcat cgagaagtac gaggacgggc   3360
gcgtgctgca cgtgagcttc agctaccgct acgaggccgg ccgcgtgatc ggcgacttca   3420
aggtggtggg caccggcttc cccgaggaca gcgtgatctt caccgacaag atcatccgca   3480
gcaacgccac cgtggagcac ctgcacccca tgggcgataa cgtgctggtg ggcagcttcg   3540
cccgcacctt cagcctgcgc gacggcggct actacagctt cgtggtggac agccacatgg   3600
acttcaagag cgccatccac cccagcatcc tgcagaacgg gcccccatg ttcgccttcc   3660
gccgcgtgga ggagctgcac agcaacaccg agctgggcat cgtggagtac cagcacgcct   3720
tcaagacccc catcgccttc gccagatctc gagctcgagg tggtttgtct ggtcaaccac   3780
cgcggtctca gtggtgtacg gtacaaaccc acccccaactg gggtaacctt tgagttctct   3840
cagttggggg taatcagcat catgatgtgg taccacatca tgatgctgat tataagaatg   3900
cggccgccac actctagtgg atctcgagtt aataattcag aagaactcgt caagaaggcg   3960
atagaaggcg atgcgctgcg aatcgggagc ggcgataccg taaagcacga ggaagcggtc   4020
agcccattcg ccgccaagct cttcagcaat atcacgggta gccaacgcta tgtcctgata   4080
gcggtccgcc acacccagcc ggccacagtc gatgaatcca gaaaagcggc cattttccac   4140
catgatattc ggcaagcagg catcgccatg ggtcacgacg agatcctcgc cgtcgggcat   4200
gctcgccttg agcctggcga acagttcggc tggcgcgagc ccctgatgct cttcgtccag   4260
atcatcctga tcgacaagac cggcttccat ccgagtacgt gctcgctcga tgcgatgttt   4320
cgcttggtgg tcgaatgggc aggtagccgg atcaagcgta tgcagccgcc gcattgcatc   4380
agccatgatg gatactttct cggcaggagc aaggtgtaga tgacatggag atcctgcccc   4440
ggcacttcgc ccaatagcag ccagtccctt cccgcttcag tgacaacgtc gagcacagct   4500
gcgcaaggaa cgcccgtcgt ggccagccac gatagccgcg ctgcctcgtc ttgcagttca   4560
ttcagggcac cggacaggtc ggtcttgaca aaaagaaccg ggcgcccctg cgctgacagc   4620
cggaacacgg cggcatcaga gcagccgatt gtctgttgtg cccagtcata gccgaatagc   4680
ctctccaccc aagcggccgg agaacctgcg tgcaatccat cttgttcaat catgcgaaac   4740
gatcctcatc ctgtctcttg atcagagct                                    4769
```

SEQ ID NO: 397          moltype = DNA   length = 797
FEATURE                 Location/Qualifiers
misc_feature            1..797
                        note = Description of Artificial Sequence: Synthetic
                        polynucleotide
source                  1..797
                        mol_type = other DNA

```
                        organism = synthetic construct
SEQUENCE: 397
ccccaactgg ggtaaccttt gggctccccg ggcgcgatgg tgagcaaggg cgaggaggat    60
aacatggcca tcatcaagga gttcatgcgc ttcaaggtgc acatggaggg ctccgtgaac   120
ggccacgagt tcgagatcga gggcgagggc gagggccgcc cctacgaggg cacccagacc   180
gccaagctga aggtgaccaa gggtggcccc ctgcccttcg cctgggacat cctgtcccct   240
cagttcatgt acggctccaa ggcctacgtg aagcaccccg ccgacatccc cgactacttg   300
aagctgtcct tccccgaggg cttcaagtgg gagcgcgtga tgaacttcga ggacggcggc   360
gtggtgaccg tgacccagga ctcctccctg caggacggcc agttcatcta caaggtgaag   420
ctgcgcggca ccaacttccc ctccgacggc cccgtaatgc agaagaagac catgggctgg   480
gaggcctcct ccgagcggat gtaccccgag gacggcgccc tgaagggcga gatcaagcag   540
aggctgaagc tgaaggacgg cggccactac gacgctgagg tcaagaccac ctacaaggcc   600
aagaagcccg tgcagctgcc cggcgcctac aacgtcaaca tcaagttgga catcacctcc   660
cacaacgagg actacaccat cgtggaacag tacgaacgcg ccgagggccg ccactccacc   720
ggcggcatgg acgagctgta caagggtggt ttgtctggtc aaccaccgcg agctcagtgg   780
tgtacggtac aaaccca                                                  797

SEQ ID NO: 398         moltype = DNA  length = 815
FEATURE                Location/Qualifiers
misc_feature           1..815
                        note = Description of Artificial Sequence: Synthetic
                        polynucleotide
source                  1..815
                        mol_type = other DNA
                        organism = synthetic construct
SEQUENCE: 398
ccccaactgg ggtaaccttt gggctccccg ggcgcggccg ccaccatggt gtccaagggt    60
gaggaacttt ttaccggagt ggtgccgata ctggtagagc tggatggcga cgtaaacggg   120
cacaagttca gtgtacgggg agagggcgag gcgacgcta cgaatgggaa attgactttg    180
aaatttattt gcaccacggg caaattgccg gtcccgtacg gtcctttggt tacgaccttg   240
acctatggcg ttcagtgttt ctcacggtac ccagaccaca tgaaacagca tgactttttt   300
aagtcagcga tgccggaggg atatgtcaa gaacggacta tctcatttaa agatgatggc   360
acatataaga caagagcgga agtcaaattc gaagggggaca ccctcgtcaa tcgaatagaa   420
ctcaagggaa tagacttcaa agaagatggt aatatactgg ggcacaaact cgaatacaat   480
ttcaacagtc ataacgtcta catcactgcc gacaaacaaa aaatgggat caaagcgaac   540
ttcaaaatcc gacataatgt cgaggatggg agcgtccaac tggcagacca ttaccagcaa   600
aatactccaa taggtgatgg tccagtgctt ttgccagata tcattatct tagctatcag   660
agcaagttga gtaaggatcc gaatgaaaag cgagatcaca tggtcttgct ggagtttgtt   720
acggcggctg gtatcacact tggtatggat gaattgtaca agggtggttt gtctggtcaa   780
ccaccgcgga ctcagtggtg tacggtacaa accca                              815

SEQ ID NO: 399         moltype = DNA  length = 1660
FEATURE                Location/Qualifiers
misc_feature           1..1660
                        note = Description of Artificial Sequence: Synthetic
                        polynucleotide
source                  1..1660
                        mol_type = other DNA
                        organism = synthetic construct
SEQUENCE: 399
ccccaactgg ggtaaccttt gggctccccg ggcgcggcca ccatgaaatg ggttactttc    60
atatctctgt tgttttgtt ttcctctagt tccagggcca tgccgtcttc tgtctcgtgg   120
ggcatcctcc tgctgcagg cctgtgctgc ctggtccctg tctccctggc tgaggatccc   180
cagggagatg ctgcccagaa gacagataca tcccaccatg atcaggatca cccaaccttc   240
aacaagatca ccccaaacct ggctgagttc gccttcagcc tataccgcca gctggcacac   300
cagtccaaca gcaccaatat cttcttctct ccagtgagca tcgctacagc ctttgcaatg   360
ctctcccctgg ggaccaaggc tgacactcac gatgaaatcc tggagggcct gaatttcaac   420
ctcacgaga ttccggaggc tcagatccat gaaggcttcc aggaactcct ccgtaccctc    480
aaccagccag acagccagct ccagctgacc accggcaatg gctgttcct cagcgagggc   540
ctgaagctag tggataagtt tttggaggat gttaaaaagt tgtaccactc agaagccttc    600
actgtcaact cggggacac gaagaggcc aagaaacaga tcaacgatta cgtggagaag    660
ggtactcaag gaaaattgt ggatttggtc aaggagcttg acagagacac agtttttgct    720
ctggtgaatt acatcttctt taaaggcaaa tgggagagac cctttgaagt caaggacacc    780
gaggaagagg acttccacgt ggaccaggtg accaccgtga aggtgcctat gatgaagcgt    840
ttaggcatgt taacatcca gcactgtaag aagctgtcca gctgggtgct gctgatgaaa    900
tacctgggca tgccaccgc catcttcttc ctgcctgatg aggggaaact acagcacctg    960
gaaaatgaac tcacccacga tatcatcacc aagttcctgg aaaatgaaga cagaaggtct   1020
gccagcttac atttacccaa actgtccatt actggaacct atgatctgaa gagcgtcctg    1080
ggtcaactgg gcatcactaa ggtcttcagc aatggggctg acctctccgg ggtcacagaa   1140
gaggcacccc tgaagctctc caaggccgtg cataaggctg tgctgaccat cgacgagaaa    1200
gggactgaag ctgctgggc catgttttta gaggccatac ccatgtctat ccccccgag    1260
gtcaagttca acaaaccctt tgtcttctta atgattgaac aaaataccaa gtctcccctc   1320
ttcatgggaa agtggtgaa tcccacccaa aataagaat tctaactaga gctcgctgat   1380
cagcctgac tgtgccttct agttgccagc catctgttgt ttgccctcc cccgtgcctt    1440
ccttgaccct ggaaggtgcc actcccactg tcctttccta ataaaatgag gaaattgcat    1500
cgcattgtct gagtaggtgt cattctattc tggggggtgg ggtggggcag gacagcaagg    1560
gggaggattg gaagagaat agcaggcatg ctggggagcg agctcgaggt ggtttgtctg    1620
gtcaaccacc gcggtctcag tggtgtacgg tacaaaccca                          1660
```

-continued

| SEQ ID NO: 400 | moltype = DNA   length = 4906 |
| --- | --- |
| FEATURE | Location/Qualifiers |
| misc_feature | 1..4906 |
| | note = Description of Artificial Sequence: Synthetic polynucleotide |
| source | 1..4906 |
| | mol_type = other DNA |
| | organism = synthetic construct |

SEQUENCE: 400

```
ccccaactgg ggtaaccttt gggctccccg ggcgcggcca ccatgaaatg ggttactttc   60
atatctctgt tgtttttgtt ttcctctagt tccagggcca tgacgaggat tttgacagct  120
ttcaaagtgt tgaggacact gaagactggt tttggcttta ccaatgtgac tgcacaccaa  180
aaatggaaat tttcaagacc tggcatcagg ctcctttctg tcaaggcaca gacagcacac  240
attgtcctgg aagatggaac taagatgaaa ggttactcct ttggccatcc atcctctgtt  300
gctggtgaag tggtttttaa tactggcctg ggagggtacc cagaagctat tactgaccct  360
gcctacaaag gacagattct cacaatggcc aaccctatta ttgggaatgg tggagctcct  420
gatactactg ctctggatga actgggactt agcaaatatt tggagtctaa tggaatcaag  480
gtttcaggtt tgctggtgct ggattatagt aaagactaca accactggct ggctaccaag  540
agtttagggc aatggctaca ggaagaaaag gttcctgcaa tttatggagt ggacacaaga  600
atgctgacta aataaattcg ggataagggt accatgcttg gaagattga atttgaaggt  660
cagcctgtgg attttgtgga tccaaataaa cagaatttga ttgctgaggt ttcaaccaag  720
gatgtcaaag tgtacggcaa aggaaacccc acaaaagtga tagctgtaga ctgtgggatt  780
aaaaacaatg taatccgcct gctagtaaag cgaggagctg aagtgcactt agttccctgg  840
aaccatgatt tcaccaagat ggagtatgat gggattttga tcgcgggagg accggggaac  900
ccagctcttg cagaaccact aattcagaat gtcagaaaga ttttggagag tgatcgcaag  960
gagccattgt ttggaatcag tacaggaaac ttaataacag gattggctgc tggtgccaaa 1020
acctacaaga tgtccatggc caacagaggg cagaatcagc ctgttttgaa tatcacaaac 1080
aaacaggctt tcattactgc tcagaatcat ggctatgcct tggacaacac cctccctgct 1140
ggctggaaac actttttgt gaatgtcaac gatcaaacaa tgaggggat tatgcatgag 1200
agcaaaccct tcttcgctgt gcagttccac ccagaggtca ccccgggcc aatagacact 1260
gagtacctgt ttgattcctt tttctcactg ataaagaaag gaaaagctac caccattaca 1320
tcagtcttac cgaagccagc actagttgca tctcggggttg aggtttccaa agtccttatt 1380
ctaggatcag gaggtctgtc cattggtcag gctggagaat tgattactc aggatctcaa 1440
gctgtaaaag ccatgaagga agaaaatgtc aaaactgttc tgataaaccc aaacattgca 1500
tcagtccaga ccaatgaggt gggcttaaag caagcggata ctgtctactt tcttcccatc 1560
acccctcagt ttgtcacaga ggtcatcaag gcagaacagc cagatgggtt aatttctgggc 1620
atgggtggcc agacagctct gaactgtgga gtggaactat tcaagagagg tgtgctcaag 1680
gaatatggtg tgaaagtcct gggaacttca gttgagtcca ttatggctac ggaagacagg 1740
cagctgtttt cagataaact aaatgagatc aatgaaaaga ttctccaag ttttgcagtg 1800
gaatcgattg aggatgcact gaaggcagca gacaccattg gctacccagt gatgatccgt 1860
tccgcctatg cactgggtgg gttaggctca ggcatctgtc ccaacagaga ctttgatg  1920
gacctcagca caaaggcctt tgctatgacc aaccaaattc tggtgagaa gtcagtgaca 1980
ggttggaaag aaatagaata tgaagtgtt cgagatgctg atgcaaattg tgtcactgtc 2040
tgtaacatgg aaaatgttga tgccatgggc gttcacacag gtgactcagt tgttgtggct 2100
cctgcccaga cactctccaa tgccgagttt cagatgttga gacgtacttc aatcaatgtt 2160
gttcgccact gggcattgt gggtgaatgc aacattcagt ttgcccttca tcctacctca 2220
atggaatact gcatcattga agtgaatgcc agactgtccc gaagctctgc tctggcctca 2280
aaagccactg gctacccatt ggcattcatt gctgcaaaga ttgccctagg aatcccactt 2340
ccagaaatta gaacgtcgt atccgggaag acatcagcct gttttgaacc tagcctggat 2400
tacatggtca ccaagattcc ccgctgggat cttaccgtt ttcatggaac atctagccga 2460
attggtagct ctatgaaaag tgtaggagag gtcatggctca ttggtcgtac ctttgaggag 2520
agtttccaga aagctttacg gatgtgccac ccatctatag aaggtttcac tcccgtctc 2580
ccaatgaaca aagaatggcc atcaatttta gatcttagaa aagagttgtc tgaaccaagc 2640
agcacgcgta tctatgccat tgccaaggcc attgatgaca catgtccct tgatgagatt 2700
gagaagctca catacattga caagtggttt gtataaga tgcgtgatat tttaaacatg 2760
gaaaagacac tgaaaggcct caacagtgag tccatgacag aagaaaccct gaaaagggca 2820
aaggagattg ggttctcaga taagcagatt caaaatgcc ttgggctcac tgaggcccag 2880
acaagggagc tgaggttaaa gaaaaacatc caccttgggg ttaaacagat tgatacactg 2940
gctgcagaat acccatcagt aacaaactat ctctatgtta cctacaatgg tcaggagcat 3000
gatgtcaatt ttgatgacca tggaatgatg gtgctaggct gtggtccata tcacattggc 3060
agcagtgtgg aatttgattg gtgtgctgtc tctagtatcc gcacactgcg tcaacttggc 3120
aagaagacgt tggtggtgaa ttgcaatcct gagactgtga gcacagactt tgatgagtgt 3180
gacaaactgt acttttgaaga gttgtccttg gagagaatcc tagacatcta ccatcaggag 3240
gcatgtggtg gctgcatcat atcagttgga ggcagattc caaacaacct gacagttcct 3300
ctatacaaga atggtgtcaa gatcatgggc acaagccccc tgcagatcga cagggctgag 3360
gatcgctcca tcttctcagc tgtcttggat gagctgaagg tggctcaggc accttggaaa 3420
gctgttaata ctttgaatga agcactggaa tttgcaaagt ctgtggacta ccctgcttg 3480
ttgaggcctt cctatgtttt gagtgggtct gctatgactg tggttattctc tgaggatgag 3540
atgaaaaaat tcctagaaga ggcgactaga gtttctcagg aaccaccagt ggtgctgaca 3600
aaatttgttg aagggccccg agaagtagaa atggacgctg ttggcaaaga tggaagggtt 3660
atctctcatg ccatctctga acatgttgaa gatgcaggtg tccactcggg agatgccact 3720
ctgatgctgc ccacacaaac catcagccaa ggggccattg aaaaggtgaa ggatgctacc 3780
cggaagattg caaaggcttt tgccatctct ggtccattca acgtcaatt tcttgtcaaa 3840
ggaaatgatg tcttggttga tgagtgtaac ttgagagctt ctccttttgt 3900
tccaagactc ttgggggttga cttcattgat gtgccacca aggtgatgat tggagagaat 3960
gttgatgaga acatcttcc aacattggac catcccataa ttcctgctga ctatgttgca 4020
attaaggctc ccatgttttc ctggccccgg ttgagggatg ctgacccat tctgagatgt 4080
gagatggctt ccactggaga ggtggcttgc tttggtgaag gtattcatac agccttccta 4140
aaggcaatgc tttccacagg atttaagata ccccagaaag gcatcctgat aggcatccag 4200
```

```
caatcattcc ggccaagatt ccttggtgtg gctgaacaat tacacaatga aggtttcaag  4260
ctgtttgcca cggaagccac atcagactgg ctcaacgcca acaatgtccc tgccacccca  4320
gtggcatggc cgtctcaaga aggacagaat cccagcctct cttccatcag aaaattgatt  4380
agagatggca gcattgacct agtgattaac cttcccaaca acaacactaa atttgtccat  4440
gataattatg tgattcggag gacagctgtt gatagtcgaa tccctctcct cactaatttt  4500
caggtgacca aacttttgc tgaagctgtg cagaaatctc gcaaggtgga ctccaagagt  4560
cttttccact acaggcagta cagtgctgga aaagcagcat aggaattcta actagagctc  4620
gctgatcagc ctcgactgtg ccttctagtt gccagccatc tgttgtttgc ccctcccccg  4680
tgccttcctt gaccctggaa ggtgccactc ccactgtcct ttcctaataa aatgaggaaa  4740
ttgcatcgca ttgtctgagt aggtgtcatt ctattctggg gggtggggtg gggcaggaca  4800
gcaaggggga ggattgggaa gagaaatagca ggcatgctgg ggagcgagct cgaggtggtt  4860
tgtctggtca accaccgcgg tctcagtggt gtacggtaca aaccca             4906
```

SEQ ID NO: 401  moltype = DNA length = 4882
FEATURE    Location/Qualifiers
misc_feature   1..4882
       note = Description of Artificial Sequence: Synthetic
       polynucleotide
source      1..4882
       mol_type = other DNA
       organism = synthetic construct
SEQUENCE: 401

```
ccccaactgg ggtaaccttt gggctccccg ggcgcgacta taagctgcga gcaacttcac   60
ttgggtatgc cggcggtagc gcttaccgtt cgtataatgt atgctatacg aagttatccg  120
aagccgctag cggtggtttg tctggtcaac caccgcggtc tcagtggtgt acggtacaaa  180
cccacccgag agaccatgca gaggtcgcct ctggaaaagg ccagcgttgt ctccaaactt  240
ttctttagct ggactagacc catccttcgt aaaggataca gacagcgcct ggaattgtca  300
gacatatacc aaatcccttc tgttgattct gctgacaatc tatctgaaaa attggaaaga  360
gaatgggata gagagctggc ttcaaagaaa atcctaaac tcattaatgc ccttcggcga  420
tgttttttct ggagatttat gttctatgga atctttttat atttaggtgga agtcaccaaa  480
gcagtacagc ctctcttact gggaagaatc atagcttcct atgacccgga taacaaggag  540
gaacgctcta tcgcgattta tctaggcata ggcttatgcc ttctctttat tgtgaggaca  600
ctgctcctac acccagccat ttttggcctt catcacattg aatgcagat gagaatagct  660
atgtttagtt tgatttataa agagacttta aagctgtcaa gccgtgttct agataaaata  720
agtattggac aacttgttag tctccttttcc aacaacctga acaaatttga tgaaggactt  780
gcattggcac atttcgtgtg gatcgctcct ttgcaagtgg cactcctcat ggggctaatc  840
tgggagttgt tacaggcgtc tgccttctgt ggacttggtt tcctgatagt ccttgccctt  900
tttcaggctg ggctagggag aatgatgatg aagtacagag atcagagagc tgggaagatc  960
agtgaaagac ttgtgattac ctcagaaatg attgaaaata tccaatctgt taaggcatac 1020
tgctgggaag aagcaatgga aaaatgatt gaaaacttaa gacaaacaga actgaaactg 1080
actcggaagg cagcctatgt gagatacttc aatagctcag ccttcttctt ctcagggttc 1140
tttgtggtgt ttttatctgt gcttcccat gcactaatca aaggaatcat cctccggaaa 1200
atattcacca ccatctcatt ctgcattgtt ctgcgcactg cggtcactcg gcaatttcca 1260
tgggctgtac aaacatggta tgactctctt ggagcaataa acaaaataca ggatttctta 1320
caaaagcaag aatataagac attggaatat aacttaacga ctacagaagt agtgatggag 1380
aatgtaacag ccttctggga ggagggattt ggggaattat ttgagaaagc aaaacaaaac 1440
aataacaata gaaaaacttc taatgtgat gacagcctct tcttcagtaa tttctcactt 1500
cttggtactc ctgtcctgaa agatattaat ttcaagatag aaagaggaca gttgttggcg 1560
gttgctggat ccactggagc aggcaagact tcacttctaa tggtgattat gggagaactg 1620
gagccttcag agggtaaaat taagcacagt ggaagaattt cattctgttc tcagtttttcc 1680
tggattatgc ctggcaccat taaagaaaat atcatctttg gtgtttccta tgatgaatat 1740
agatacagaa gcgtcatcaa agcatgccaa ctagaagagg acatctccaa gtttgcagag 1800
aaagacaata tagttcttgg agaaggtgga atcacactga gtggaggtca acgagcaaga 1860
atttctttag caagagcagt atacaaagat gctgatttgt atttattaga ctctcctttt 1920
ggatacctag acgtattgac tgagaaggag atcttcgagt cctgcgtttg caagcttatg 1980
gccaataaga caagaatcct ggttacaagt aagatggaga acctgaagaa ggccgataag 2040
attctgatcc tgcacgaggg atcttctac ttctacggca ctttcagcga gcttcagaac 2100
ttgcaacctg atttctctag caagcttatg ggctgcgact cctttgatca gttctctgcc 2160
gagcgtcgca actccattct gaccgaaaca ctgcataggt tttcccctcga gggcgacgca 2220
ccagtgtctt ggactgagac taagaagcag agcttcaagc aaaccggcga attcggtgag 2280
aagagaaaga acagtatcct gaaccccatt aattcaattc ggaagttcag tatcgttcag 2340
aaaacgcctc ttcagatgaa cgggattgag gaagactcag acgaaccgct gaaaggcga 2400
ctctcattgg ttcctgacag tgaacaaggg gaagctattc tcccccggat tcagtaatt 2460
tccacaggtc cgactctgca gcccaggaga agacaatccg tgttgaatct tatgacccat 2520
tccgtgaatc aggggcaaaa tatccataga aagactactg cctctacgag gaaggtatcc 2580
cttgcacccc aagccaatct gacggagctc gacatctact ctgccgcct gtcccaggag 2640
acaggactgg agattagcga ggagatcaat gaagaggatc tgaaagaatg tttcttcgac 2700
gacatggaat ccattccctgc cgtcacgacg tggaatacct atttgcgtta catcacggta 2760
cataaaagtc tgatattcgt cctgatctgg tgtcttgtga tcttcctcgc tgaagtcgaa 2820
gccagcctgg tcgttctttg gctgctcggg aataccccct gcaggataa gggaaactcc 2880
acccactctc ggaacaatag ttacgccgtc atcattactt ccacttcctc atactacgta 2940
ttctatatat atgtcggggt cgctgataca ctgctggcca tgggcttctt tcgcggcctt 3000
ccgctcgtcc acacgctgat aactgtctcc aagatcttgc atcataagat gctgcactca 3060
gtgctgcagg ctccaatgag tacactgaat actcttaagg cgggcggcat cctgaacctc 3120
tttagtaagg acatcgccat acttgacgat ctccttgccc tgacaatctt cgatttattt 3180
caactccttt tgatcgttat cggggcgatc gctgtggttg ctgtgttcag ccatatata 3240
ttcgtagcta ctgttcccgt catcgtgcgc ttcatcatgc tccgtgccta cttttctgcag 3300
acgtcccaac agctgaagca gctcgagagc gagggacggt cccccatatt tacgcacttg 3360
gtaactagtc tgaaggggct gtggactctg agagcatttg gtcgacaacc atatttcgag 3420
```

```
accctctttc ataaggccct caacctgcac accgcgaatt ggtttctgta tttgagtacg  3480
ttgcggtggt ttcagatgcg catcgagatg atattcgtga tattctttat cgcagtcaca  3540
tttatcagca tcctgactac gggcgaggga gagggtcgcg tgggcatcat actcacgctc  3600
gctatgaaca ttatgagcac cctgcaatgg gccgtgaata gctctatcga cgttgacagt  3660
cttatgcgat ctgtgagccg agtctttaag ttcattgaca tgccaacaga aggtaaacct  3720
accaagtcaa ccaaaccata caagaatggc caactctcga aagttatgat tattgagaat  3780
tcacacgtga agaaagatga catctggccc tcagggggcc aaatgactgt caaagatctc  3840
acagcaaaat acacagaagg tggaaatgcc atattagaga catttccttc tcaataagt  3900
cctggccaga gggtgggcct cttgggaaga actggatcag ggaagagtac tttgttatca  3960
gcttttttga gactactgaa cactgaagga gaaatccaga tcgatggtgt gtcttgggat  4020
tcaataactt tgcaacagtg gaggaaagcc tttggagtga taccacagaa agtatttatt  4080
ttttctggaa catttagaaa aaacttggat ccctatgaac agtggagtga tcaagaaata  4140
tggaaagttg cagatgaggt tgggctcaga tctgtgatag aacagtttcc tgggaagctt  4200
gactttgtcc ttgtggatgg gggctgtgtc ctaagccatg gccacaagca gttgatgtgc  4260
ttggctagat ctgttctcag taaggcgaag atcttgctgc ttgatgaacc cagtgctcat  4320
ttggatccag taacatacca aataattaga agaactctaa acaagcatt tgctgattgc  4380
acagtaattc tctgtgaaca caggatagaa gcaatgctga aatgccaaca atttttggtc  4440
atagaagaga acaaagtgcg gcagtacgat tccatccaga aactgctgaa cgagagggag  4500
ctcttccggc aagccatcag cccctccgac agggtgaagc tcttccccca ccggaactca  4560
agcaagtgca agtctaagcc ccagattgct gctctgaaag aggagacaga agaaggtg  4620
caagatacaa ggctttagac ccgctgatca gcctcgactg tgccttctag ttgccagcca  4680
tctgtttgttt gcccctcccc cgtgccttcc ttgaccctgg aagtgccac tcccactgtc  4740
ctttcctaat aaaatgagaa aattgcatcg cattgtctga gtaggtgtca ttctattctg  4800
gggggtgggg tggggcagga cagcaagggg gaggattggg aagacaatag caggcatgct  4860
ggggatgcgg tgggctctat gg                                          4882

SEQ ID NO: 402          moltype = DNA length = 1594
FEATURE                 Location/Qualifiers
misc_feature            1..1594
                        note = Description of Artificial Sequence: Synthetic
                        polynucleotide
source                  1..1594
                        mol_type = other DNA
                        organism = synthetic construct
SEQUENCE: 402
ccccaactgg ggtaaccttt gggctccccg ggcgcggttc cggatccgga gagggcaggg   60
gatctctcct tacttgtggc gacgtggagg agaaccccgg ccccatgagc atcggcctcc  120
tgtgctgtgc agccttgtct ctcctgtggg caggtccagt gaatgctggt gtcactcaga  180
ccccaaaatt ccaggtcctg aagacaggac agagcatgac actgcagtgt gcccaggata  240
tgaaccatga atacatgtcc tggtatcgac aagacccagg catggggctg aggctgattc  300
attactcagt tggtgctggt atcactgacc aaggagaagt cccccaatgg tacaatgtct  360
ccagatcaac cacagaggat ttcccgctca ggctgctgtc ggctgctccc tcccagacat  420
ctgtgtactt ctgtgccagc agttacgtcg ggaacacgtg ggagctgttt tttggagaag  480
gctctaggct gaccgtactg gaggacctga aaaacgtgtt cccacccgag gtcgctgtgt  540
tgagccatc agaagcagag atctcccaca cccaaaaggc cacactggta tgcctggcca  600
caggcttcta ccccgaccac gtggagctga gctggtgggt gaatgggaag gaggtgcaca  660
gtgggtcag cacagaccg cagccctca aggagcagcc cactctcaat gactccagat  720
actgcctgag cagccgcctg agggtctcgg ccaccttctg gcagaacccc cgcaaccact  780
tccgctgtca agtccagttc tacgggctct cggagaatga cgagtggacc caggataggg  840
ccaaacccgt cacccagatc gtcagcgccg aggcctgggg tagagcagac tgtggcttca  900
cctccgagtc ttaccagcaa gggtcctgtc tgccaccat cctctatgag atcttgctag  960
ggaaggccac cttgtatgcc gtgctggtca gtgcccctcgt gctgatggct atggtcaaga  1020
gaaaggattc cagaggccgg gccaagcggt ccggatccgg agccaccaac ttcagcctgc  1080
tgaagcaggc cggcgacgtg gaggagaacc ccggccccat ggagaccctc ttgggcctgc  1140
ttatcttttg gctgcagctg caatgggtga gcagcaaaca ggaggtgacg cagattcctg  1200
cagctctgag tgtcccagaa ggagaaaact tggttctcaa ctgcagtttc actgatagcg  1260
ctatttacaa cctccagtgg tttaggcagg accctgggaa aggtctcaca tctctgttgc  1320
ttattcagtc aagtcagaga gagcaaacaa gtggaagact taatgcctcg ctggataaat  1380
catcaggacg tagtactta tacattgcag ctttctcagcc tggtgactca gccacctacc  1440
tctgtgctgt gaggcccctg tacggaggaa gctacatacc tacatttgga agagaaccca  1500
gccttattgt tcatccgtat atccagaacc ctgaccctgc gggtggttg tctggtcaac  1560
caccgcggtc tcagtggtgt acggtacaaa ccca                             1594

SEQ ID NO: 403          moltype = DNA length = 19
FEATURE                 Location/Qualifiers
misc_feature            1..19
                        note = Description of Artificial Sequence: Synthetic
                        oligonucleotide
source                  1..19
                        mol_type = other DNA
                        organism = synthetic construct
SEQUENCE: 403
ttgagcgggc ccccaccgt                                                19

SEQ ID NO: 404          moltype = DNA length = 393
FEATURE                 Location/Qualifiers
misc_feature            1..393
                        note = Description of Artificial Sequence: Synthetic
                        polynucleotide
```

```
source                  1..393
                        mol_type = other DNA
                        organism = synthetic construct
SEQUENCE: 404
atgactcact atcaggcctt gcttttggac acggaccggg tccagttcgg accggtggta    60
gccctgaacc cggctacgct gctcccactg cctgaggaag ggctgcaaca caactgcctt   120
gatgggacag gtggcggtgg tgtcaccgtc aagttcaagt acaagggtga ggaacttgaa   180
gttgatatta gcaaaatcaa gaaggtttgg cgcgttggta aaatgatatc ttttacttat   240
gacgacaacg gcaagacagg tagaggggca gtgtctgaga aagacgcccc caaggagctg   300
ttgcaaatgt tggaaaagtc tgggaaaaag tctggcggct caaaaagaac cgccgacggc   360
agcgaattcg agcccaagaa gaagaggaaa gtc                                393

SEQ ID NO: 405          moltype = DNA  length = 11
FEATURE                 Location/Qualifiers
misc_feature            1..11
                        note = Description of Artificial Sequence: Synthetic probe
source                  1..11
                        mol_type = other DNA
                        organism = synthetic construct
SEQUENCE: 405
cgacgacggc g                                                         11

SEQ ID NO: 406          moltype = DNA  length = 16
FEATURE                 Location/Qualifiers
misc_feature            1..16
                        note = Description of Artificial Sequence: Synthetic probe
source                  1..16
                        mol_type = other DNA
                        organism = synthetic construct
SEQUENCE: 406
tttatttgtg ggcccg                                                    16

SEQ ID NO: 407          moltype = DNA  length = 15
FEATURE                 Location/Qualifiers
misc_feature            1..15
                        note = Description of Artificial Sequence: Synthetic probe
source                  1..15
                        mol_type = other DNA
                        organism = synthetic construct
SEQUENCE: 407
tcgagtgccg catca                                                     15

SEQ ID NO: 408          moltype = DNA  length = 17
FEATURE                 Location/Qualifiers
misc_feature            1..17
                        note = Description of Artificial Sequence: Synthetic probe
source                  1..17
                        mol_type = other DNA
                        organism = synthetic construct
SEQUENCE: 408
aaagtggtga ggacact                                                   17

SEQ ID NO: 409          moltype = DNA  length = 15
FEATURE                 Location/Qualifiers
misc_feature            1..15
                        note = Description of Artificial Sequence: Synthetic probe
source                  1..15
                        mol_type = other DNA
                        organism = synthetic construct
SEQUENCE: 409
aacccacccg agaga                                                     15

SEQ ID NO: 410          moltype = DNA  length = 66
FEATURE                 Location/Qualifiers
misc_feature            1..66
                        note = Description of Artificial Sequence: Synthetic
                        oligonucleotide
source                  1..66
                        mol_type = other DNA
                        organism = synthetic construct
SEQUENCE: 410
ggaagcggag ctactaactt cagcctgctg aagcaggctg gcgacgtgga ggagaaccct    60
ggacct                                                               66

SEQ ID NO: 411          moltype = DNA  length = 45
FEATURE                 Location/Qualifiers
misc_feature            1..45
                        note = Description of Artificial Sequence: Synthetic
                        oligonucleotide
```

```
source                  1..45
                        mol_type = other DNA
                        organism = synthetic construct
SEQUENCE: 411
gggggaggag gttctggagg cggaggctcc ggaggcggag ggtca            45

SEQ ID NO: 412          moltype = DNA  length = 15
FEATURE                 Location/Qualifiers
misc_feature            1..15
                        note = Description of Artificial Sequence: Synthetic
                        oligonucleotide
source                  1..15
                        mol_type = other DNA
                        organism = synthetic construct
SEQUENCE: 412
ggaggtggcg ggagc                                             15

SEQ ID NO: 413          moltype = DNA  length = 15
FEATURE                 Location/Qualifiers
misc_feature            1..15
                        note = Description of Artificial Sequence: Synthetic
                        oligonucleotide
source                  1..15
                        mol_type = other DNA
                        organism = synthetic construct
SEQUENCE: 413
cccgcaccag cgcct                                             15

SEQ ID NO: 414          moltype = DNA  length = 45
FEATURE                 Location/Qualifiers
misc_feature            1..45
                        note = Description of Artificial Sequence: Synthetic
                        oligonucleotide
source                  1..45
                        mol_type = other DNA
                        organism = synthetic construct
SEQUENCE: 414
gaggcagctg ccaaggaagc cgctgccaag gaggcggccg caaag            45

SEQ ID NO: 415          moltype = DNA  length = 48
FEATURE                 Location/Qualifiers
misc_feature            1..48
                        note = Description of Artificial Sequence: Synthetic
                        oligonucleotide
source                  1..48
                        mol_type = other DNA
                        organism = synthetic construct
SEQUENCE: 415
agtgggagcg agaccctgg gactagcgag tcagctacac ccgaaagc           48

SEQ ID NO: 416          moltype = DNA  length = 54
FEATURE                 Location/Qualifiers
misc_feature            1..54
                        note = Description of Artificial Sequence: Synthetic
                        oligonucleotide
source                  1..54
                        mol_type = other DNA
                        organism = synthetic construct
SEQUENCE: 416
gggggggtcag gtggatccgg cggaagtggc ggatccggtg gatctggcgg cagt  54

SEQ ID NO: 417          moltype = DNA  length = 15
FEATURE                 Location/Qualifiers
misc_feature            1..15
                        note = Description of Artificial Sequence: Synthetic
                        oligonucleotide
source                  1..15
                        mol_type = other DNA
                        organism = synthetic construct
SEQUENCE: 417
gaagctgctg ctaag                                             15

SEQ ID NO: 418          moltype = AA  length = 22
FEATURE                 Location/Qualifiers
REGION                  1..22
                        note = Description of Artificial Sequence: Synthetic peptide
source                  1..22
                        mol_type = protein
                        organism = synthetic construct
```

```
SEQUENCE: 418
GSGATNFSLL KQAGDVEENP GP                                                              22

SEQ ID NO: 419          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 419
GGGGSGGGGS GGGGS                                                                      15

SEQ ID NO: 420          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 420
GGGGS                                                                                 5

SEQ ID NO: 421          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 421
PAPAP                                                                                 5

SEQ ID NO: 422          moltype = AA  length = 15
FEATURE                 Location/Qualifiers
REGION                  1..15
                        note = Description of Artificial Sequence: Synthetic peptide
source                  1..15
                        mol_type = protein
                        organism = synthetic construct
SEQUENCE: 422
EAAAKEAAAK EAAAK                                                                      15

SEQ ID NO: 423          moltype = AA  length = 16
FEATURE                 Location/Qualifiers
REGION                  1..16
                        note = Description of Artificial Sequence: Synthetic peptide
source                  1..16
                        mol_type = protein
                        organism = synthetic construct
SEQUENCE: 423
SGSETPGTSE SATPES                                                                     16

SEQ ID NO: 424          moltype = AA  length = 18
FEATURE                 Location/Qualifiers
REGION                  1..18
                        note = Description of Artificial Sequence: Synthetic peptide
source                  1..18
                        mol_type = protein
                        organism = synthetic construct
SEQUENCE: 424
GGSGGSGGSG GSGGSGGS                                                                   18

SEQ ID NO: 425          moltype = AA  length = 5
FEATURE                 Location/Qualifiers
REGION                  1..5
                        note = Description of Artificial Sequence: Synthetic peptide
source                  1..5
                        mol_type = protein
                        organism = synthetic construct
SEQUENCE: 425
EAAAK                                                                                 5

SEQ ID NO: 426          moltype = AA  length = 16
FEATURE                 Location/Qualifiers
REGION                  1..16
                        note = Description of Artificial Sequence: Synthetic peptide
source                  1..16
                        mol_type = protein
```

-continued

```
                        organism = synthetic construct
SEQUENCE: 426
GLSGQPPRSP SSGSSG                                                   16

SEQ ID NO: 427          moltype = AA   length = 17
FEATURE                 Location/Qualifiers
REGION                  1..17
                        note = Description of Artificial Sequence: Synthetic peptide
source                  1..17
                        mol_type = protein
                        organism = synthetic construct
SEQUENCE: 427
GGLSGQPPRS PSSGSSG                                                  17

SEQ ID NO: 428          moltype = RNA   length = 88
FEATURE                 Location/Qualifiers
misc_feature            1..88
                        note = Description of Artificial Sequence: Synthetic
                          oligonucleotide
source                  1..88
                        mol_type = other RNA
                        organism = synthetic construct
SEQUENCE: 428
gacgagcgcg gcgatatcat catccatggc cggatgatcc tgacgacgga gaccgccgtc  60
gtcgacaagc cggcctgagc tgcgagaa                                      88

SEQ ID NO: 429          moltype = RNA   length = 20
FEATURE                 Location/Qualifiers
misc_feature            1..20
                        note = Description of Artificial Sequence: Synthetic
                          oligonucleotide
source                  1..20
                        mol_type = other RNA
                        organism = synthetic construct
SEQUENCE: 429
gaagccggcc ttgcacatgc                                               20

SEQ ID NO: 430          moltype = DNA   length = 95
FEATURE                 Location/Qualifiers
source                  1..95
                        mol_type = unassigned DNA
                        organism = Homo sapiens
SEQUENCE: 430
gcgcgcccgg ctattctcgc agctcaccat ggatgatgat atcgccgcgc tcgtcgtcga  60
caacggctcc ggcatgtgca aggccggctt cgcgg                              95

SEQ ID NO: 431          moltype = RNA   length = 20
FEATURE                 Location/Qualifiers
misc_feature            1..20
                        note = Description of Artificial Sequence: Synthetic
                          oligonucleotide
source                  1..20
                        mol_type = other RNA
                        organism = synthetic construct
SEQUENCE: 431
accactcgac gctcttatcg                                               20
```